(12) United States Patent
Parris et al.

(10) Patent No.: US 7,135,319 B2
(45) Date of Patent: Nov. 14, 2006

(54) CRYSTALS OF AN ACYL CARRIER PROTEIN SYNTHASE/ACYL CARRIER PROTEIN COMPLEX

(75) Inventors: Kevin Delos Parris, Auburndale, MA (US); William Stuart Somers, Cambridge, MA (US); Amy Szepui Tam, Medford, MA (US); Laura Long Lin, Weston, MA (US); Mark Lloyd Stahl, Lexington, MA (US)

(73) Assignee: Wyeth, Madison, NJ (US)

( * ) Notice: Subject to any disclaimer, the term of this patent is extended or adjusted under 35 U.S.C. 154(b) by 155 days.

(21) Appl. No.: 10/717,138

(22) Filed: Nov. 19, 2003

(65) Prior Publication Data

US 2004/0078147 A1    Apr. 22, 2004

Related U.S. Application Data

(62) Division of application No. 09/770,834, filed on Jan. 25, 2001, now Pat. No. 6,684,162.

(60) Provisional application No. 60/202,466, filed on May 8, 2000.

(51) Int. Cl.
    *C12N 9/10* (2006.01)
(52) U.S. Cl. ...................... 435/193; 530/300; 530/344
(58) Field of Classification Search .................. None
    See application file for complete search history.

(56) References Cited

U.S. PATENT DOCUMENTS 6,160,092 A    12/2000    Chen et al.

OTHER PUBLICATIONS

Kunst et al., The complete genome sequence of the Gram-positive bacterium *Bacillus subtilis*, 1997, Nature, vol. 390, pp. 249-266.*
GenBank Accession No. Z99106, 1997, pp. 1-2 and 36.*
Huang et al., Crystal structure of beta-ketoacyl-acyl carrier protein synthase II from *E. coli* reveals the molecular architecture of condensing enzymes, 1998, The EMBO Journal, vol. 17, No. 5, pp. 1183-1191.*
Giege et al., "Crystallogenesis of Biological Macromolecules: Facts and Perspectives", Jul. 1994, Acta Crystallographica Section D, vol. 50, pp. 339-350.*
McPherson et al., "The science of macromolecular crystallization", Aug. 1995, Structure, vol. 3, pp. 759-768.☐☐☐☐.*
GenBank Accession No. Z99112, 1997, pp. 1-2 and 25.*
Drenth, entitled "Principles of Protein X-ray Crystallography," Springer-Verlag, Second Edition, pp. 1-18, 1995.
Baldwin et al. "Isolation and Partial Characterization of ACV Synthetase from *Cephalosporium acremonium* and *Streptomyces clavuligerus* Evidence for the Presence of Phosphopantothenate in ACV Synthetase" *J. Antibiot.* 44(2):241-248 (1991).
Banerjee et al. "inhA, a Gene Encoding a Target for Isoniazid and Ethionamide in Mycobacterium tuberculosis" *Science* 263(5144):227-230 (1994).

(Continued)

*Primary Examiner*—Nashaat T. Nashed
(74) *Attorney, Agent, or Firm*—Fish & Richardson P.C.

(57) ABSTRACT

This invention is directed to the crystal structure of Acyl Carrier Protein Synthase (ACPS) complexed with Acyl Carrier Protein (ACP), the solution structure of *B. subtilis* ACP, and to the use of these structures in rational drug design methods to identify agents that may interact with active sites of ACPS and ACP, and to the testing of these agents to identify agents that may represent novel antibiotics.

22 Claims, 99 Drawing Sheets

ACP

```
              10          20          30          40
GPLGS   ADTLERVTKI  IVDRLGVDEA  DVKLEASFKE   DLGADSLDVV
              50          60          70          76
        ELVMELEDEF  DMEISDEDAE  KIATVGDAVN   YIQNQQ
```

ACPS

```
                10          20          30          40
        AYGIGLDIT   ELKRIASMAG  RQKRFAERIL   TRSELDQYYE
                50          60          70          80
        LSEKRKNEFL  AGRFAAKEAF  SKAFGTGIGR   QLSFQDIEIR
                90         100         110          120
        KDQNGKPYII  CTKLSQAAVH  VSITHTKEYA   AAQVVIERLS
               121
        S
```

OTHER PUBLICATIONS

Bergler et al. "Protein EnvM Is the NADH-dependent Enoyl-ACP Reductase (FabI) of *Escherichia coli*" *J. Biol. Chem.* 269(8):5493-5496 (1994).

Crump et al. "Solution Structure of the Actinorhodin Polyketide Synthase Acyl Carrier Protein from *Streptomyces coelicolor* A3(2)" *Biochem.* 36:6000-6008 (1997).

Dessen et al. "Crystal Structure and Function of the Isoniazid Target of Mycobacterium tuberculosis" *Science* 267(5204):1638-1641 (1995).

Elovson et al. "Acyl Carrier Protein" *J. Biol. Chem.* 243(13):3603-3611 (1968).

Fischl et al. "Isolation and Properties of Acyl Carrier Protein Phosphodiesterase of *Escherichia coli*" *J. Bacteriol.* 172(9):5445-5449 (1990).

Furukawa et al. "Thiolactomycin Resistance in *Escherichia coli* Is Associated with the Multidrug Resistance Efflux Pump Encoded by *emrAB*" *J. Bacteriol.* 175(12):3723-3729 (1993).

Geiger et al. "Isolation of the *Rhizobium leguminosarum* NodF Nodulation Protein: NodF carries a 4'-Phosphopantetheine Prosthetic Group" *J. Bacteriol.* 173(9):2872-2878 (1991).

Hill et al. "Overexpression, Purification, and Characterization of *Escherichia coli* Acyl Carrier Protein and Two Mutant Proteins" *Protein Expression and Purification* 6:394-400 (1995).

Holak et al. "Three-Dimensional Structure of Acyl Carrier Protein Determined by NMR Pseudoenergy and Distance Geometry Calculations" *Biochem.* 27:6135-6142 (1988).

Holak et al. "Three-dimensional structure of acyl carrier protein in solution determined by nuclear magnetic resonance and the combined use of dynamical simulated annealing and distance geometry" *Eur. J. Biochem.* 175:9-15 (1988).

Holak et al. "Improved strategies for the determination of protein structures from NMR data: the solution structure of acyl carrier protein" *FEBS Lett.* 242(2):218-224 (1989).

Hopwood et al. "Molecular Genetics of Polyketides and its Comparison to Fatty Acid Biosynthesis" *Annu. Rev. Genet.* 24:37-66 (1990).

Issartel et al. "Activation of *Escherichia coli* prohaemolysin to the mature toxin by acyl carrier protein-dependent fatty acylation" *Nature* 351:759-761 (1991).

Kleinkauf et al. "A nonribosomal systemp of peptide biosynthesis" *Eur. J. Biochem.* 236(2):335-351 (1996).

Lambalot et al. "A new enzyme superfamily—the phosphopantetheinyl transferases" *Chem. & Biol.* 3(11):923-936 (1996).

Lambalot et al. "Cloning, Overproduction, and Characterization of the *Escherichia coli* Holo-acyl Carrier Protein Synthase" *J. Biol. Chem.* 270(42):24658-24661 (1995).

Lynen "On the Structure of Fatty Acid Synthetase of Yeast" *Eur. J. Biochem.* 112:431-442 (1980).

Magnuson et al. "Regulation of Fatty Acid Biosynthesis of *Escherichia coli*" *Microbiol. Reviews* 57:522-542 (1993).

Majerus et al. "Fatty Acid Biosynthesis and the Role of the Acyl Carrier Protein" *Advan. Lipid Res.* 5:1-33 (1967).

Marahiel "Multidomain enzymes involved in peptide synthesis" *FEBS Lett.* 307(1):40-43 (1992).

Prescott et al. "Acyl Carrier Protein" *Advan Enzymol. Relat. Areas Mol. Biol.* 36:269-311 (1972).

Quémard et al. "Enzymatic Characterization of the Target for Isoniazid in *Mycobacterium tuberculosis*" *Biochem.* 34:8235-8241 (1995).

Reuter et al. "Crystal structure of the surfactin synthetase-activating enzyme Sfp: a prototype of the 4'-phosphopantetheinyl transferase superfamily" *The EMBO J.* 18(23):6823-6831 (1999).

Rock et al. "Improved Purification of Acyl Carrier Protein" *Anal. Biochem.* 102:362-364 (1980).

Rusnak et al. "Biosynthesis of the *Escherichia coli* Siderophore Enterobactin: Sequence of the *entF* Gene, Expression and Purification of EntF, and Analysis of Covalent Phosphopantetheine" *Biochem.* 30:2916-2927 (1991).

Sanyal et al. "Biosynthesis of Pimeloyl-CoA, a Biotin Precursor in *Escherichia coli*, Follows a Modified Fatty Acid Synthesis Pathway: $^{13}$C-Labeling Studies" *J. Am. Chem. Soc.* 116:2637-2638 (1994).

Shen et al. "Purification and Characterization of the Acyl Carrier Protein of the *Streptomyces glaucescens* Tetracenomycin C Polyketide Synthase" *J. Bacteriol.* 174(11):3818-3821 (1992).

Takiff et al. "Locating Essential *Escherichia coli* Genes by Using Mini-Tn10 Transposons: the *pdxJ* Operon" *J. Bacteriol.* 174(5):1544-1553 (1992).

Wakil et al. "Fatty Acids Synthesis and its Regulation" *Annu. Rev. Biochem.* 52:537-579 (1983).

White "Stoichiometry and Stereochemistry of Deuterium Incorporated into Fatty Acids by Cells of *Escherichia coli* Grown on [methyl-$^2$H$_3$]Acetate" *Biochemistry* 19:9-15 (1980).

Huang et al., "Crystal structure of β-ketoacyl-acyl carrier protein synthase II from *E. coli* reveals the molecular architecture of condensing enzymes" *EMBO J.* 17(5):1183-1191 (1998).

Meurer et al., "Functional Analysis of Putative β-Ketoacyl:Acyl Carrier Protein Synthase and Acyltransferase Active Site Motifs in a Type II Polyketide Synthase of *Streptomyces glaucescens*" *J. Bacteriology* 177(2):477-481 (1995).

Moche et al., "Structure of the Complex between the Antibiotic Cerulenin and Its Target, β-Ketoacyl-Acyl Carrier Protein Synthase" *J. Biol. Chem.* 274(10):6031-6034 (1999).

Olsen et al., "The X-ray structure of β-ketoacyl [acyl carrier protein] synthase I" *FEBS Letters* 460:46-52 (1999).

* cited by examiner

ACP

```
            10          20          30          40
GPLGS   ADTLERVTKI  IVDRLGVDEA  DVKLEASFKE  DLGADSLDVV
            50          60          70          76
        ELVMELEDEF  DMEISDEDAE  KIATVGDAVN  YIQNQQ
```

ACPS

```
            10          20          30          40
        AYGIGLDIT   ELKRIASMAG  RQKRFAERIL  TRSELDQYYE
            50          60          70          80
    LSEKRKNEFL  AGRFAAKEAF  SKAFGTGIGR  QLSFQDIEIR
            90          100         110         120
    KDQNGKPYII  CTKLSQAAVH  VSITHTKEYA  AAQVVIERLS
    121
    S
```

FIG. 1

```
Aquifex          1   ----MIGVDIVKNERIKDALERFGDKFLDRIYTKRELEYCY----AHCDFLPCLAARWAG
Chlamydophila    1   MEIIHIGTDIIEISRIREAIATHGNRLLNRIFTEAEQKYCL----EKTDPIPSFAGRFAG
Helicobacter     1   ----MIGIDIVSIARIEKCVKRFKMKFLERFLSPSEIVLCK----DKSS---SIAGFFAL
Staphylococcus   1   -MIHGIGVDLIEIDRIQALYSKQ-PKLVERILTKNEQHKFNN-FTHEQRKIEFLAGRFAT
Thermotoga       1   -MIVGVGIDVLEVERVP-------EKFAERILGESEKRLF---LTRKRRR-EFIAGRFAL
Escherichia      1   MAILGLGTDIVEIARIEAVIARSGDRLARRVLSDNEWAIWK---THHQPV-RFLAKRFAV
Rickettsia       1   -MLIGVGTDIVQIPRIEKILNIYQELFAKKILALKELKQFT--LLNKTNHATFLAKRFSA
Streptomyces     1   MSIIGVGIDVAEVERFGA-ALERTPALAGRLFLESELLLP----GGERRGVASLAARFAA
Treponema        1   -MIIGVGIDIVEIERFVS-WTHNVRLLR-RFFHQEEIVDF----FKNHMRAQFLATRFAA
Bacillus         1   -MIYGIGLDITELKRIAS-MAGRQKRFAERILTRSELDQYY--ELSEKRKNEFLAGRFAG
Bradyrhizobium   1   -MIIGIGSDLIDITRYGKVIERHGERFLDRIFTAAERAKAERRAKNEKMVVATYAKRFAA
Mycobacterium    1   MGIVGVGIDLVSIPDFAEQVSQPGTVFM-TIFTPGERRDAS---VKSSSAVCHLAARWAV
consensus              G D                        E                            A
                 1   1........10........20........30........40........50.........

Aquifex          53  KEAVLKAFYTEFKIFL------RFKEIEILGNRGRPPTVVINRE--GVEEILKNY----E
Chlamydophila    57  KEAVAKALGTGIGSVV------AWKDIEVFKVSHGPEVLLPS----HVYAKIGIS----K
Helicobacter     50  KEACSKALQVGIGKEL------SFLDIKISKSPKNAPLITLSK---EKMDYFNIQ----S
Staphylococcus   58  KEAFSKALGTGLGKHV------AFNDIDCYNDELGKPKI----------DYEGF-----I
Thermotoga       49  KEAFFKALGTGLNGH-------SFTDVEFLESN-GKPVLCVH------KDFGFFN----Y
Escherichia      57  KEAAAKAFGTGIRNGL------AFNQFEVFNDELGKPRLRLWGEALKLAEKLGVA----N
Rickettsia       58  KEAVSKAFGVGIGRGI------NFKDITILNDNLGKPTVEISS---HYTNKLAPF----N
Streptomyces     56  KEALAKALGAPAG--L------LWTDAEVWVEAGGRPRLRVTGTVAARAAELGVA----S
Treponema        54  KEAFGKALGTGLRN-M------ELRNIRVCQNGWGKPRLEVYGAAQAMLAATGGT----H
Bacillus         57  KEAFSKAFGTGIGRQL------SFQDIEIRKDQNGKPYIICT--------KLSQA----A
Bradyrhizobium   60  KEACSKALGTGIRRGV------WWRDMGVVNLPGGRPTMQLTGGALARLQALTPDGFEAR
Mycobacterium    57  KEAVIKAWSGSRFAQRPMLPENIHRDIEVVNDMWGRPRVRLTG---AIAKHLTDV----T
consensus        61  KEA   KA
                 61  61........70........80........90........100.......110........

Aquifex          101 VIVSLSHERDYSVAVAYIKKKS------------------------------
Chlamydophila    103 VILSISHCKEYATATAIALA--------------------------------
Helicobacter     97  LSASISHDAGFAIAVVVSSSNE------------------------------
Staphylococcus   97  VHVSISHTEHYAMSQVVLEK----------SAF-------------------
Thermotoga       91  AHVSLSH-DRFAVALVVLEKRKGDIIVEGDESFLRKRFEVLERSVEGWEIETSLPPFTLK
Escherichia      107 MHVTLADERHYACATVIIES--------------------------------
Rickettsia       105 IHLSLSDDYPICIAFAIIESNC------------------------------
Streptomyces     104 WHVSLSHDAGIASAVVIAEG--------------------------------
Treponema        103 IQVSLTHEREVASAIVIIEGEPL-----------------------------
Bacillus         99  VHVSITHTKEYAAAQVVIERLSS-----------------------------
Bradyrhizobium   114 IDVSITDDWPLAQAFVIISAVPLAKS--------------------------
Mycobacterium    110 IHVSLTHEGDIAAAVVILEVL-------------------------------
consensus        121
                 121 121......130.......140.......150.......160.......170........

Aquifex              --------------------
Chlamydophila        --------------------
Helicobacter         --------------------
Staphylococcus       --------------------
Thermotoga       150 KLLESSGCRLVRYGNILIGE
Escherichia          --------------------
Rickettsia           --------------------
Streptomyces         --------------------
Treponema            --------------------
Bacillus             --------------------
Bradyrhizobium       --------------------
Mycobacterium        --------------------
consensus        181
                 181 181......190........
```

| | | Atom Type | Residue | | X | Y | Z | OCC | B | MOL |
|---|---|---|---|---|---|---|---|---|---|---|
| ATOM | 1 | CB | ALA | 2 | 21.270 | 43.877 | 0.867 | 1.00 | 54.04 | A1 |
| ATOM | 2 | C | ALA | 2 | 21.146 | 41.525 | -0.081 | 1.00 | 53.17 | A1 |
| ATOM | 3 | O | ALA | 2 | 20.651 | 40.668 | 0.655 | 1.00 | 53.21 | A1 |
| ATOM | 4 | N | ALA | 2 | 19.058 | 42.876 | 0.195 | 1.00 | 54.07 | A1 |
| ATOM | 5 | CA | ALA | 2 | 20.526 | 42.932 | -0.136 | 1.00 | 53.98 | A1 |
| ATOM | 6 | N | TYR | 3 | 22.204 | 41.299 | -0.869 | 1.00 | 51.45 | A1 |
| ATOM | 7 | CA | TYR | 3 | 22.910 | 40.017 | -0.878 | 1.00 | 49.41 | A1 |
| ATOM | 8 | CB | TYR | 3 | 23.783 | 39.899 | -2.129 | 1.00 | 52.10 | A1 |
| ATOM | 9 | CG | TYR | 3 | 22.990 | 39.823 | -3.410 | 1.00 | 55.89 | A1 |
| ATOM | 10 | CD1 | TYR | 3 | 21.766 | 39.131 | -3.444 | 1.00 | 57.46 | A1 |
| ATOM | 11 | CE1 | TYR | 3 | 21.050 | 38.984 | -4.611 | 1.00 | 58.14 | A1 |
| ATOM | 12 | CD2 | TYR | 3 | 23.477 | 40.371 | -4.606 | 1.00 | 56.50 | A1 |
| ATOM | 13 | CE2 | TYR | 3 | 22.757 | 40.222 | -5.804 | 1.00 | 58.53 | A1 |
| ATOM | 14 | CZ | TYR | 3 | 21.536 | 39.525 | -5.785 | 1.00 | 58.85 | A1 |
| ATOM | 15 | OH | TYR | 3 | 20.764 | 39.383 | -6.913 | 1.00 | 60.32 | A1 |
| ATOM | 16 | C | TYR | 3 | 23.793 | 39.899 | 0.393 | 1.00 | 46.52 | A1 |
| ATOM | 17 | O | TYR | 3 | 24.622 | 40.790 | 0.704 | 1.00 | 45.60 | A1 |
| ATOM | 18 | N | GLY | 4 | 23.609 | 38.782 | 1.102 | 1.00 | 42.70 | A1 |
| ATOM | 19 | CA | GLY | 4 | 24.320 | 38.543 | 2.338 | 1.00 | 37.45 | A1 |
| ATOM | 20 | C | GLY | 4 | 24.041 | 37.193 | 2.962 | 1.00 | 33.70 | A1 |
| ATOM | 21 | O | GLY | 4 | 23.431 | 36.317 | 2.340 | 1.00 | 32.64 | A1 |
| ATOM | 22 | N | ILE | 5 | 24.512 | 37.019 | 4.197 | 1.00 | 30.10 | A1 |
| ATOM | 23 | CA | ILE | 5 | 24.326 | 35.759 | 4.880 | 1.00 | 27.52 | A1 |
| ATOM | 24 | CB | ILE | 5 | 25.660 | 34.841 | 4.938 | 1.00 | 25.29 | A1 |
| ATOM | 25 | CG2 | ILE | 5 | 26.176 | 34.529 | 3.511 | 1.00 | 25.87 | A1 |
| ATOM | 26 | CG1 | ILE | 5 | 26.785 | 35.531 | 5.686 | 1.00 | 23.40 | A1 |
| ATOM | 27 | CD1 | ILE | 5 | 28.015 | 34.655 | 5.920 | 1.00 | 20.98 | A1 |
| ATOM | 28 | C | ILE | 5 | 23.890 | 36.156 | 6.277 | 1.00 | 26.57 | A1 |
| ATOM | 29 | O | ILE | 5 | 24.113 | 37.278 | 6.689 | 1.00 | 24.85 | A1 |
| ATOM | 30 | N | GLY | 6 | 23.263 | 35.229 | 6.984 | 1.00 | 25.44 | A1 |
| ATOM | 31 | CA | GLY | 6 | 22.811 | 35.540 | 8.317 | 1.00 | 26.60 | A1 |
| ATOM | 32 | C | GLY | 6 | 22.852 | 34.284 | 9.166 | 1.00 | 26.44 | A1 |
| ATOM | 33 | O | GLY | 6 | 22.550 | 33.151 | 8.686 | 1.00 | 26.78 | A1 |
| ATOM | 34 | N | LEU | 7 | 23.239 | 34.472 | 10.421 | 1.00 | 26.41 | A1 |
| ATOM | 35 | CA | LEU | 7 | 23.319 | 33.374 | 11.363 | 1.00 | 26.97 | A1 |
| ATOM | 36 | CB | LEU | 7 | 24.764 | 33.021 | 11.639 | 1.00 | 27.07 | A1 |
| ATOM | 37 | CG | LEU | 7 | 24.948 | 31.919 | 12.694 | 1.00 | 25.72 | A1 |
| ATOM | 38 | CD1 | LEU | 7 | 24.329 | 30.596 | 12.115 | 1.00 | 24.08 | A1 |
| ATOM | 39 | CD2 | LEU | 7 | 26.486 | 31.751 | 12.993 | 1.00 | 24.38 | A1 |
| ATOM | 40 | C | LEU | 7 | 22.667 | 33.741 | 12.657 | 1.00 | 28.25 | A1 |
| ATOM | 41 | O | LEU | 7 | 22.874 | 34.834 | 13.154 | 1.00 | 28.97 | A1 |
| ATOM | 42 | N | ASP | 8 | 21.858 | 32.861 | 13.225 | 1.00 | 29.53 | A1 |
| ATOM | 43 | CA | ASP | 8 | 21.272 | 33.229 | 14.505 | 1.00 | 31.00 | A1 |
| ATOM | 44 | CB | ASP | 8 | 19.978 | 34.022 | 14.354 | 1.00 | 32.06 | A1 |
| ATOM | 45 | CG | ASP | 8 | 19.332 | 34.330 | 15.737 | 1.00 | 35.48 | A1 |
| ATOM | 46 | OD1 | ASP | 8 | 18.624 | 33.437 | 16.301 | 1.00 | 35.96 | A1 |
| ATOM | 47 | OD2 | ASP | 8 | 19.556 | 35.443 | 16.293 | 1.00 | 34.80 | A1 |
| ATOM | 48 | C | ASP | 8 | 20.994 | 32.043 | 15.374 | 1.00 | 31.76 | A1 |
| ATOM | 49 | O | ASP | 8 | 20.379 | 31.114 | 14.917 | 1.00 | 32.34 | A1 |

FIG. 3A-1

```
ATOM    50  N    ILE   9     21.471  32.072  16.618  1.00 32.83      A1
ATOM    51  CA   ILE   9     21.247  31.006  17.589  1.00 34.13      A1
ATOM    52  CB   ILE   9     22.570  30.453  18.178  1.00 34.00      A1
ATOM    53  CG2  ILE   9     22.296  29.317  19.164  1.00 33.87      A1
ATOM    54  CG1  ILE   9     23.444  29.887  17.067  1.00 34.24      A1
ATOM    55  CD1  ILE   9     24.893  29.598  17.566  1.00 35.11      A1
ATOM    56  C    ILE   9     20.398  31.673  18.684  1.00 35.95      A1
ATOM    57  O    ILE   9     20.706  32.779  19.152  1.00 35.83      A1
ATOM    58  N    THR   10    19.276  31.027  19.009  1.00 37.57      A1
ATOM    59  CA   THR   10    18.319  31.517  20.012  1.00 38.92      A1
ATOM    60  CB   THR   10    16.963  31.852  19.371  1.00 39.79      A1
ATOM    61  OG1  THR   10    17.071  33.055  18.597  1.00 42.44      A1
ATOM    62  CG2  THR   10    15.920  32.030  20.438  1.00 41.04      A1
ATOM    63  C    THR   10    18.074  30.409  21.053  1.00 38.98      A1
ATOM    64  O    THR   10    17.705  29.273  20.707  1.00 38.16      A1
ATOM    65  N    GLU   11    18.303  30.762  22.311  1.00 39.04      A1
ATOM    66  CA   GLU   11    18.128  29.873  23.458  1.00 39.06      A1
ATOM    67  CB   GLU   11    18.697  30.562  24.706  1.00 40.96      A1
ATOM    68  CG   GLU   11    20.091  31.151  24.425  1.00 44.69      A1
ATOM    69  CD   GLU   11    20.728  31.947  25.576  1.00 47.14      A1
ATOM    70  OE1  GLU   11    20.543  33.201  25.664  1.00 47.18      A1
ATOM    71  OE2  GLU   11    21.434  31.302  26.391  1.00 49.53      A1
ATOM    72  C    GLU   11    16.634  29.571  23.662  1.00 37.28      A1
ATOM    73  O    GLU   11    15.819  30.487  23.748  1.00 35.93      A1
ATOM    74  N    LEU   12    16.296  28.287  23.677  1.00 35.49      A1
ATOM    75  CA   LEU   12    14.929  27.816  23.913  1.00 36.05      A1
ATOM    76  CB   LEU   12    14.929  26.279  24.073  1.00 36.45      A1
ATOM    77  CG   LEU   12    14.421  25.319  23.017  1.00 37.15      A1
ATOM    78  CD1  LEU   12    14.235  23.997  23.690  1.00 37.38      A1
ATOM    79  CD2  LEU   12    13.096  25.759  22.439  1.00 37.94      A1
ATOM    80  C    LEU   12    14.254  28.379  25.179  1.00 35.86      A1
ATOM    81  O    LEU   12    13.059  28.765  25.161  1.00 36.02      A1
ATOM    82  N    ALA   13    14.998  28.370  26.289  1.00 35.85      A1
ATOM    83  CA   ALA   13    14.455  28.819  27.586  1.00 37.01      A1
ATOM    84  CB   ALA   13    15.543  28.726  28.723  1.00 37.35      A1
ATOM    85  C    ALA   13    13.903  30.209  27.518  1.00 37.53      A1
ATOM    86  O    ALA   13    12.893  30.486  28.116  1.00 37.21      A1
ATOM    87  N    ARG   14    14.550  31.087  26.772  1.00 38.91      A1
ATOM    88  CA   ARG   14    14.041  32.440  26.670  1.00 40.95      A1
ATOM    89  CB   ARG   14    15.044  33.320  25.940  1.00 41.35      A1
ATOM    90  CG   ARG   14    16.138  33.808  26.853  1.00 43.91      A1
ATOM    91  CD   ARG   14    16.385  35.294  26.635  1.00 44.07      A1
ATOM    92  NE   ARG   14    17.184  35.440  25.443  1.00 44.98      A1
ATOM    93  CZ   ARG   14    17.473  36.595  24.859  1.00 45.66      A1
ATOM    94  NH1  ARG   14    17.033  37.741  25.356  1.00 45.42      A1
ATOM    95  NH2  ARG   14    18.192  36.586  23.746  1.00 45.86      A1
ATOM    96  C    ARG   14    12.679  32.515  25.986  1.00 42.15      A1
ATOM    97  O    ARG   14    11.887  33.419  26.262  1.00 41.07      A1
ATOM    98  N    ILE   15    12.398  31.578  25.077  1.00 43.69      A1
ATOM    99  CA   ILE   15    11.088  31.604  24.409  1.00 45.37      A1
ATOM   100  CB   ILE   15    11.022  30.801  23.055  1.00 44.97      A1
ATOM   101  CG2  ILE   15     9.634  30.994  22.442  1.00 44.72      A1
ATOM   102  CG1  ILE   15    12.119  31.219  22.074  1.00 44.89      A1
ATOM   103  CD1  ILE   15    11.983  32.621  21.518  1.00 45.11      A1
ATOM   104  C    ILE   15    10.125  30.881  25.330  1.00 46.54      A1
ATOM   105  O    ILE   15     8.955  31.170  25.337  1.00 46.55      A1
ATOM   106  N    ALA   16    10.613  29.897  26.073  1.00 48.62      A1
```

FIG. 3A-2

| | | | | | | | | | |
|---|---|---|---|---|---|---|---|---|---|
| ATOM | 107 | CA | ALA | 16 | 9.710 | 29.148 | 26.928 | 1.00 51.99 | A1 |
| ATOM | 108 | CB | ALA | 16 | 10.375 | 27.891 | 27.447 | 1.00 51.52 | A1 |
| ATOM | 109 | C | ALA | 16 | 9.247 | 30.000 | 28.084 | 1.00 54.29 | A1 |
| ATOM | 110 | O | ALA | 16 | 8.119 | 29.878 | 28.544 | 1.00 55.04 | A1 |
| ATOM | 111 | N | SER | 17 | 10.122 | 30.877 | 28.545 | 1.00 56.66 | A1 |
| ATOM | 112 | CA | SER | 17 | 9.797 | 31.752 | 29.653 | 1.00 58.77 | A1 |
| ATOM | 113 | CB | SER | 17 | 11.064 | 32.402 | 30.169 | 1.00 58.15 | A1 |
| ATOM | 114 | OG | SER | 17 | 11.864 | 31.409 | 30.758 | 1.00 58.99 | A1 |
| ATOM | 115 | C | SER | 17 | 8.807 | 32.836 | 29.283 | 1.00 60.67 | A1 |
| ATOM | 116 | O | SER | 17 | 9.034 | 34.013 | 29.587 | 1.00 61.61 | A1 |
| ATOM | 117 | N | MET | 18 | 7.719 | 32.463 | 28.620 | 1.00 61.88 | A1 |
| ATOM | 118 | CA | MET | 18 | 6.711 | 33.457 | 28.252 | 1.00 63.20 | A1 |
| ATOM | 119 | CB | MET | 18 | 6.411 | 33.397 | 26.760 | 1.00 63.45 | A1 |
| ATOM | 120 | CG | MET | 18 | 7.629 | 33.473 | 25.982 | 1.00 63.73 | A1 |
| ATOM | 121 | SD | MET | 18 | 8.431 | 34.930 | 26.488 | 1.00 64.97 | A1 |
| ATOM | 122 | CE | MET | 18 | 8.882 | 35.588 | 24.735 | 1.00 64.08 | A1 |
| ATOM | 123 | C | MET | 18 | 5.434 | 33.205 | 28.994 | 1.00 63.31 | A1 |
| ATOM | 124 | O | MET | 18 | 4.815 | 34.127 | 29.506 | 1.00 63.03 | A1 |
| ATOM | 125 | N | ALA | 19 | 5.054 | 31.933 | 29.017 | 1.00 64.24 | A1 |
| ATOM | 126 | CA | ALA | 19 | 3.827 | 31.469 | 29.670 | 1.00 65.18 | A1 |
| ATOM | 127 | CB | ALA | 19 | 4.036 | 31.349 | 31.198 | 1.00 65.29 | A1 |
| ATOM | 128 | C | ALA | 19 | 2.685 | 32.425 | 29.352 | 1.00 65.24 | A1 |
| ATOM | 129 | O | ALA | 19 | 1.899 | 32.199 | 28.419 | 1.00 66.10 | A1 |
| ATOM | 130 | N | GLY | 20 | 2.606 | 33.507 | 30.110 | 1.00 64.64 | A1 |
| ATOM | 131 | CA | GLY | 20 | 1.548 | 34.460 | 29.857 | 1.00 64.00 | A1 |
| ATOM | 132 | C | GLY | 20 | 1.725 | 35.165 | 28.534 | 1.00 63.02 | A1 |
| ATOM | 133 | O | GLY | 20 | 0.789 | 35.248 | 27.741 | 1.00 64.04 | A1 |
| ATOM | 134 | N | ALA | 21 | 2.943 | 35.638 | 28.288 | 1.00 61.60 | A1 |
| ATOM | 135 | CA | ALA | 21 | 3.280 | 36.392 | 27.085 | 1.00 59.98 | A1 |
| ATOM | 136 | CB | ALA | 21 | 4.525 | 37.225 | 27.378 | 1.00 59.25 | A1 |
| ATOM | 137 | C | ALA | 21 | 3.453 | 35.663 | 25.725 | 1.00 59.06 | A1 |
| ATOM | 138 | O | ALA | 21 | 3.425 | 36.310 | 24.675 | 1.00 58.46 | A1 |
| ATOM | 139 | N | GLN | 22 | 3.612 | 34.339 | 25.722 | 1.00 57.78 | A1 |
| ATOM | 140 | CA | GLN | 22 | 3.861 | 33.642 | 24.461 | 1.00 56.31 | A1 |
| ATOM | 141 | CB | GLN | 22 | 4.120 | 32.160 | 24.707 | 1.00 56.11 | A1 |
| ATOM | 142 | CG | GLN | 22 | 4.701 | 31.498 | 23.464 | 1.00 54.61 | A1 |
| ATOM | 143 | CD | GLN | 22 | 5.154 | 30.063 | 23.674 | 1.00 54.11 | A1 |
| ATOM | 144 | OE1 | GLN | 22 | 4.417 | 29.108 | 23.357 | 1.00 52.66 | A1 |
| ATOM | 145 | NE2 | GLN | 22 | 6.384 | 29.901 | 24.212 | 1.00 52.51 | A1 |
| ATOM | 146 | C | GLN | 22 | 2.877 | 33.786 | 23.305 | 1.00 55.31 | A1 |
| ATOM | 147 | O | GLN | 22 | 3.279 | 33.751 | 22.136 | 1.00 54.38 | A1 |
| ATOM | 148 | N | LYS | 23 | 1.599 | 33.950 | 23.625 | 1.00 54.54 | A1 |
| ATOM | 149 | CA | LYS | 23 | 0.587 | 34.102 | 22.597 | 1.00 53.74 | A1 |
| ATOM | 150 | CB | LYS | 23 | -0.816 | 34.126 | 23.192 | 1.00 54.52 | A1 |
| ATOM | 151 | CG | LYS | 23 | -1.908 | 34.428 | 22.158 | 1.00 55.45 | A1 |
| ATOM | 152 | CD | LYS | 23 | -3.280 | 34.438 | 22.820 | 1.00 56.61 | A1 |
| ATOM | 153 | CE | LYS | 23 | -4.342 | 35.093 | 21.932 | 1.00 57.55 | A1 |
| ATOM | 154 | NZ | LYS | 23 | -4.631 | 34.292 | 20.715 | 1.00 58.20 | A1 |
| ATOM | 155 | C | LYS | 23 | 0.795 | 35.387 | 21.819 | 1.00 52.72 | A1 |
| ATOM | 156 | O | LYS | 23 | 0.775 | 35.377 | 20.578 | 1.00 52.28 | A1 |
| ATOM | 157 | N | ARG | 24 | 0.966 | 36.494 | 22.530 | 1.00 50.67 | A1 |
| ATOM | 158 | CA | ARG | 24 | 1.151 | 37.730 | 21.811 | 1.00 49.83 | A1 |
| ATOM | 159 | CB | ARG | 24 | 1.027 | 38.929 | 22.746 | 1.00 52.03 | A1 |
| ATOM | 160 | CG | ARG | 24 | -0.442 | 39.179 | 23.140 | 1.00 54.86 | A1 |
| ATOM | 161 | CD | ARG | 24 | -0.689 | 40.544 | 23.779 | 1.00 57.57 | A1 |
| ATOM | 162 | NE | ARG | 24 | -0.708 | 41.626 | 22.799 | 1.00 59.50 | A1 |
| ATOM | 163 | CZ | ARG | 24 | 0.284 | 42.496 | 22.638 | 1.00 60.97 | A1 |

FIG. 3A-3

| ATOM | 164 | NH1 | ARG | 24 | 1.378 | 42.411 | 23.403 | 1.00 | 61.46 | A1 |
| ATOM | 165 | NH2 | ARG | 24 | 0.179 | 43.448 | 21.714 | 1.00 | 61.28 | A1 |
| ATOM | 166 | C | ARG | 24 | 2.473 | 37.735 | 21.070 | 1.00 | 47.89 | A1 |
| ATOM | 167 | O | ARG | 24 | 2.596 | 38.349 | 20.014 | 1.00 | 47.33 | A1 |
| ATOM | 168 | N | PHE | 25 | 3.456 | 37.039 | 21.622 | 1.00 | 45.04 | A1 |
| ATOM | 169 | CA | PHE | 25 | 4.748 | 36.965 | 20.992 | 1.00 | 42.60 | A1 |
| ATOM | 170 | CB | PHE | 25 | 5.757 | 36.301 | 21.927 | 1.00 | 41.19 | A1 |
| ATOM | 171 | CG | PHE | 25 | 7.107 | 36.071 | 21.294 | 1.00 | 39.72 | A1 |
| ATOM | 172 | CD1 | PHE | 25 | 7.945 | 37.133 | 21.010 | 1.00 | 39.39 | A1 |
| ATOM | 173 | CD2 | PHE | 25 | 7.538 | 34.791 | 21.010 | 1.00 | 39.13 | A1 |
| ATOM | 174 | CE1 | PHE | 25 | 9.198 | 36.924 | 20.460 | 1.00 | 39.53 | A1 |
| ATOM | 175 | CE2 | PHE | 25 | 8.776 | 34.578 | 20.469 | 1.00 | 39.73 | A1 |
| ATOM | 176 | CZ | PHE | 25 | 9.616 | 35.648 | 20.187 | 1.00 | 39.05 | A1 |
| ATOM | 177 | C | PHE | 25 | 4.617 | 36.143 | 19.701 | 1.00 | 41.96 | A1 |
| ATOM | 178 | O | PHE | 25 | 5.236 | 36.459 | 18.664 | 1.00 | 40.61 | A1 |
| ATOM | 179 | N | ALA | 26 | 3.824 | 35.078 | 19.771 | 1.00 | 40.74 | A1 |
| ATOM | 180 | CA | ALA | 26 | 3.635 | 34.237 | 18.597 | 1.00 | 40.86 | A1 |
| ATOM | 181 | CB | ALA | 26 | 2.786 | 32.993 | 18.948 | 1.00 | 39.28 | A1 |
| ATOM | 182 | C | ALA | 26 | 2.965 | 35.034 | 17.463 | 1.00 | 40.94 | A1 |
| ATOM | 183 | O | ALA | 26 | 3.380 | 34.940 | 16.293 | 1.00 | 40.38 | A1 |
| ATOM | 184 | N | GLU | 27 | 1.940 | 35.802 | 17.821 | 1.00 | 40.51 | A1 |
| ATOM | 185 | CA | GLU | 27 | 1.198 | 36.598 | 16.870 | 1.00 | 41.68 | A1 |
| ATOM | 186 | CB | GLU | 27 | -0.003 | 37.269 | 17.537 | 1.00 | 44.31 | A1 |
| ATOM | 187 | CG | GLU | 27 | -1.076 | 36.311 | 18.027 | 1.00 | 49.27 | A1 |
| ATOM | 188 | CD | GLU | 27 | -2.143 | 36.968 | 18.903 | 1.00 | 52.19 | A1 |
| ATOM | 189 | OE1 | GLU | 27 | -1.939 | 38.106 | 19.431 | 1.00 | 53.39 | A1 |
| ATOM | 190 | OE2 | GLU | 27 | -3.196 | 36.314 | 19.081 | 1.00 | 54.05 | A1 |
| ATOM | 191 | C | GLU | 27 | 2.059 | 37.672 | 16.245 | 1.00 | 40.55 | A1 |
| ATOM | 192 | O | GLU | 27 | 1.819 | 38.065 | 15.125 | 1.00 | 41.26 | A1 |
| ATOM | 193 | N | ARG | 28 | 3.043 | 38.172 | 16.971 | 1.00 | 39.83 | A1 |
| ATOM | 194 | CA | ARG | 28 | 3.907 | 39.216 | 16.433 | 1.00 | 39.44 | A1 |
| ATOM | 195 | CB | ARG | 28 | 4.712 | 39.897 | 17.558 | 1.00 | 39.37 | A1 |
| ATOM | 196 | CG | ARG | 28 | 5.203 | 41.267 | 17.199 | 1.00 | 40.38 | A1 |
| ATOM | 197 | CD | ARG | 28 | 6.175 | 41.850 | 18.199 | 1.00 | 42.61 | A1 |
| ATOM | 198 | NE | ARG | 28 | 6.730 | 43.108 | 17.671 | 1.00 | 45.42 | A1 |
| ATOM | 199 | CZ | ARG | 28 | 6.148 | 44.304 | 17.774 | 1.00 | 46.09 | A1 |
| ATOM | 200 | NH1 | ARG | 28 | 4.980 | 44.429 | 18.417 | 1.00 | 46.55 | A1 |
| ATOM | 201 | NH2 | ARG | 28 | 6.699 | 45.370 | 17.184 | 1.00 | 46.78 | A1 |
| ATOM | 202 | C | ARG | 28 | 4.901 | 38.628 | 15.428 | 1.00 | 38.17 | A1 |
| ATOM | 203 | O | ARG | 28 | 5.202 | 39.233 | 14.423 | 1.00 | 37.71 | A1 |
| ATOM | 204 | N | ILE | 29 | 5.344 | 37.416 | 15.728 | 1.00 | 37.47 | A1 |
| ATOM | 205 | CA | ILE | 29 | 6.364 | 36.675 | 14.989 | 1.00 | 37.22 | A1 |
| ATOM | 206 | CB | ILE | 29 | 7.140 | 35.756 | 16.013 | 1.00 | 38.04 | A1 |
| ATOM | 207 | CG2 | ILE | 29 | 8.353 | 35.033 | 15.400 | 1.00 | 40.19 | A1 |
| ATOM | 208 | CG1 | ILE | 29 | 7.740 | 36.634 | 17.113 | 1.00 | 38.36 | A1 |
| ATOM | 209 | CD1 | ILE | 29 | 8.363 | 37.896 | 16.573 | 1.00 | 37.14 | A1 |
| ATOM | 210 | C | ILE | 29 | 5.937 | 35.851 | 13.804 | 1.00 | 35.77 | A1 |
| ATOM | 211 | O | ILE | 29 | 6.646 | 35.793 | 12.827 | 1.00 | 35.39 | A1 |
| ATOM | 212 | N | LEU | 30 | 4.760 | 35.243 | 13.883 | 1.00 | 35.34 | A1 |
| ATOM | 213 | CA | LEU | 30 | 4.285 | 34.351 | 12.846 | 1.00 | 33.85 | A1 |
| ATOM | 214 | CB | LEU | 30 | 3.627 | 33.129 | 13.464 | 1.00 | 33.02 | A1 |
| ATOM | 215 | CG | LEU | 30 | 4.509 | 32.589 | 14.575 | 1.00 | 33.23 | A1 |
| ATOM | 216 | CD1 | LEU | 30 | 3.813 | 31.411 | 15.244 | 1.00 | 32.55 | A1 |
| ATOM | 217 | CD2 | LEU | 30 | 5.894 | 32.205 | 13.972 | 1.00 | 32.98 | A1 |
| ATOM | 218 | C | LEU | 30 | 3.322 | 34.899 | 11.877 | 1.00 | 33.78 | A1 |
| ATOM | 219 | O | LEU | 30 | 2.576 | 35.820 | 12.199 | 1.00 | 34.57 | A1 |
| ATOM | 220 | N | THR | 31 | 3.338 | 34.325 | 10.678 | 1.00 | 33.02 | A1 |

FIG. 3A-4

| | | | | | | | | | |
|---|---|---|---|---|---|---|---|---|---|
| ATOM | 221 | CA | THR | 31 | 2.369 | 34.702 | 9.662 | 1.00 33.03 | A1 |
| ATOM | 222 | CB | THR | 31 | 2.847 | 34.320 | 8.247 | 1.00 31.42 | A1 |
| ATOM | 223 | OG1 | THR | 31 | 3.043 | 32.896 | 8.180 | 1.00 28.99 | A1 |
| ATOM | 224 | CG2 | THR | 31 | 4.120 | 35.093 | 7.903 | 1.00 28.16 | A1 |
| ATOM | 225 | C | THR | 31 | 1.108 | 33.863 | 9.996 | 1.00 33.87 | A1 |
| ATOM | 226 | O | THR | 31 | 1.130 | 33.022 | 10.924 | 1.00 32.70 | A1 |
| ATOM | 227 | N | ALA | 32 | 0.042 | 34.064 | 9.211 | 1.00 34.24 | A1 |
| ATOM | 228 | CA | ALA | 32 | -1.226 | 33.341 | 9.401 | 1.00 34.08 | A1 |
| ATOM | 229 | CB | ALA | 32 | -2.259 | 33.767 | 8.340 | 1.00 34.11 | A1 |
| ATOM | 230 | C | ALA | 32 | -1.056 | 31.816 | 9.352 | 1.00 33.63 | A1 |
| ATOM | 231 | O | ALA | 32 | -1.506 | 31.094 | 10.258 | 1.00 33.02 | A1 |
| ATOM | 232 | N | SER | 33 | -0.421 | 31.306 | 8.303 | 1.00 33.11 | A1 |
| ATOM | 233 | CA | SER | 33 | -0.279 | 29.854 | 8.239 | 1.00 32.41 | A1 |
| ATOM | 234 | CB | SER | 33 | 0.204 | 29.411 | 6.884 | 1.00 31.81 | A1 |
| ATOM | 235 | OG | SER | 33 | 1.557 | 29.762 | 6.706 | 1.00 33.87 | A1 |
| ATOM | 236 | C | SER | 33 | 0.675 | 29.300 | 9.296 | 1.00 32.48 | A1 |
| ATOM | 237 | O | SER | 33 | 0.516 | 28.143 | 9.700 | 1.00 32.22 | A1 |
| ATOM | 238 | N | GLU | 34 | 1.653 | 30.100 | 9.736 | 1.00 31.47 | A1 |
| ATOM | 239 | CA | GLU | 34 | 2.591 | 29.616 | 10.750 | 1.00 32.82 | A1 |
| ATOM | 240 | CB | GLU | 34 | 3.806 | 30.539 | 10.893 | 1.00 32.38 | A1 |
| ATOM | 241 | CG | GLU | 34 | 4.740 | 30.472 | 9.705 | 1.00 33.34 | A1 |
| ATOM | 242 | CD | GLU | 34 | 5.726 | 31.605 | 9.716 | 1.00 34.32 | A1 |
| ATOM | 243 | OE1 | GLU | 34 | 5.342 | 32.743 | 10.078 | 1.00 36.26 | A1 |
| ATOM | 244 | OE2 | GLU | 34 | 6.877 | 31.352 | 9.349 | 1.00 34.55 | A1 |
| ATOM | 245 | C | GLU | 34 | 1.893 | 29.482 | 12.104 | 1.00 32.92 | A1 |
| ATOM | 246 | O | GLU | 34 | 2.113 | 28.522 | 12.821 | 1.00 33.23 | A1 |
| ATOM | 247 | N | LEU | 35 | 1.042 | 30.445 | 12.407 | 1.00 33.04 | A1 |
| ATOM | 248 | CA | LEU | 35 | 0.296 | 30.458 | 13.639 | 1.00 34.42 | A1 |
| ATOM | 249 | CB | LEU | 35 | -0.535 | 31.724 | 13.721 | 1.00 35.37 | A1 |
| ATOM | 250 | CG | LEU | 35 | -0.151 | 33.010 | 14.442 | 1.00 36.15 | A1 |
| ATOM | 251 | CD1 | LEU | 35 | -1.425 | 33.899 | 14.346 | 1.00 34.90 | A1 |
| ATOM | 252 | CD2 | LEU | 35 | 0.223 | 32.778 | 15.929 | 1.00 34.49 | A1 |
| ATOM | 253 | C | LEU | 35 | -0.643 | 29.237 | 13.764 | 1.00 34.43 | A1 |
| ATOM | 254 | O | LEU | 35 | -0.785 | 28.684 | 14.855 | 1.00 33.54 | A1 |
| ATOM | 255 | N | ASP | 36 | -1.286 | 28.862 | 12.650 | 1.00 33.79 | A1 |
| ATOM | 256 | CA | ASP | 36 | -2.192 | 27.710 | 12.582 | 1.00 33.66 | A1 |
| ATOM | 257 | CB | ASP | 36 | -2.764 | 27.472 | 11.161 | 1.00 33.07 | A1 |
| ATOM | 258 | CG | ASP | 36 | -3.803 | 28.533 | 10.727 | 1.00 34.30 | A1 |
| ATOM | 259 | OD1 | ASP | 36 | -4.410 | 29.136 | 11.612 | 1.00 33.98 | A1 |
| ATOM | 260 | OD2 | ASP | 36 | -4.048 | 28.748 | 9.492 | 1.00 33.61 | A1 |
| ATOM | 261 | C | ASP | 36 | -1.397 | 26.468 | 12.935 | 1.00 34.25 | A1 |
| ATOM | 262 | O | ASP | 36 | -1.900 | 25.564 | 13.582 | 1.00 34.41 | A1 |
| ATOM | 263 | N | GLN | 37 | -0.152 | 26.398 | 12.494 | 1.00 35.24 | A1 |
| ATOM | 264 | CA | GLN | 37 | 0.652 | 25.202 | 12.793 | 1.00 36.17 | A1 |
| ATOM | 265 | CB | GLN | 37 | 1.939 | 25.189 | 11.972 | 1.00 35.40 | A1 |
| ATOM | 266 | CG | GLN | 37 | 1.671 | 25.154 | 10.533 | 1.00 38.15 | A1 |
| ATOM | 267 | CD | GLN | 37 | 2.956 | 25.046 | 9.717 | 1.00 40.58 | A1 |
| ATOM | 268 | OE1 | GLN | 37 | 3.812 | 24.195 | 10.009 | 1.00 43.09 | A1 |
| ATOM | 269 | NE2 | GLN | 37 | 3.095 | 25.889 | 8.696 | 1.00 37.84 | A1 |
| ATOM | 270 | C | GLN | 37 | 1.003 | 25.162 | 14.254 | 1.00 35.48 | A1 |
| ATOM | 271 | O | GLN | 37 | 1.002 | 24.095 | 14.874 | 1.00 35.73 | A1 |
| ATOM | 272 | N | TYR | 38 | 1.269 | 26.346 | 14.790 | 1.00 34.97 | A1 |
| ATOM | 273 | CA | TYR | 38 | 1.669 | 26.510 | 16.176 | 1.00 34.85 | A1 |
| ATOM | 274 | CB | TYR | 38 | 2.143 | 27.952 | 16.370 | 1.00 33.46 | A1 |
| ATOM | 275 | CG | TYR | 38 | 2.273 | 28.458 | 17.781 | 1.00 32.73 | A1 |
| ATOM | 276 | CD1 | TYR | 38 | 1.208 | 29.115 | 18.405 | 1.00 32.82 | A1 |
| ATOM | 277 | CE1 | TYR | 38 | 1.348 | 29.645 | 19.682 | 1.00 34.21 | A1 |

FIG. 3A-5

| ATOM | 278 | CD2 | TYR | 38 | 3.463 | 28.341 | 18.465 | 1.00 | 31.00 | A1 |
| --- | --- | --- | --- | --- | --- | --- | --- | --- | --- | --- |
| ATOM | 279 | CE2 | TYR | 38 | 3.620 | 28.873 | 19.744 | 1.00 | 33.46 | A1 |
| ATOM | 280 | CZ | TYR | 38 | 2.577 | 29.522 | 20.346 | 1.00 | 34.00 | A1 |
| ATOM | 281 | OH | TYR | 38 | 2.761 | 30.111 | 21.570 | 1.00 | 37.22 | A1 |
| ATOM | 282 | C | TYR | 38 | 0.564 | 26.117 | 17.130 | 1.00 | 36.15 | A1 |
| ATOM | 283 | O | TYR | 38 | 0.804 | 25.382 | 18.089 | 1.00 | 35.82 | A1 |
| ATOM | 284 | N | TYR | 39 | -0.662 | 26.546 | 16.849 | 1.00 | 37.88 | A1 |
| ATOM | 285 | CA | TYR | 39 | -1.782 | 26.204 | 17.725 | 1.00 | 39.63 | A1 |
| ATOM | 286 | CB | TYR | 39 | -3.037 | 27.013 | 17.357 | 1.00 | 39.03 | A1 |
| ATOM | 287 | CG | TYR | 39 | -2.913 | 28.438 | 17.829 | 1.00 | 39.74 | A1 |
| ATOM | 288 | CD1 | TYR | 39 | -2.533 | 28.713 | 19.154 | 1.00 | 40.42 | A1 |
| ATOM | 289 | CE1 | TYR | 39 | -2.338 | 30.051 | 19.600 | 1.00 | 41.11 | A1 |
| ATOM | 290 | CD2 | TYR | 39 | -3.108 | 29.523 | 16.956 | 1.00 | 39.84 | A1 |
| ATOM | 291 | CE2 | TYR | 39 | -2.923 | 30.852 | 17.384 | 1.00 | 39.73 | A1 |
| ATOM | 292 | CZ | TYR | 39 | -2.538 | 31.112 | 18.721 | 1.00 | 41.24 | A1 |
| ATOM | 293 | OH | TYR | 39 | -2.435 | 32.412 | 19.217 | 1.00 | 41.44 | A1 |
| ATOM | 294 | C | TYR | 39 | -2.062 | 24.720 | 17.762 | 1.00 | 40.63 | A1 |
| ATOM | 295 | O | TYR | 39 | -2.604 | 24.206 | 18.747 | 1.00 | 42.50 | A1 |
| ATOM | 296 | N | ALA | 40 | -1.665 | 24.017 | 16.716 | 1.00 | 41.27 | A1 |
| ATOM | 297 | CA | ALA | 40 | -1.847 | 22.573 | 16.649 | 1.00 | 41.86 | A1 |
| ATOM | 298 | CB | ALA | 40 | -1.759 | 22.100 | 15.196 | 1.00 | 41.73 | A1 |
| ATOM | 299 | C | ALA | 40 | -0.789 | 21.837 | 17.473 | 1.00 | 42.96 | A1 |
| ATOM | 300 | O | ALA | 40 | -0.908 | 20.618 | 17.703 | 1.00 | 43.10 | A1 |
| ATOM | 301 | N | LEU | 41 | 0.252 | 22.539 | 17.927 | 1.00 | 42.81 | A1 |
| ATOM | 302 | CA | LEU | 41 | 1.301 | 21.833 | 18.650 | 1.00 | 42.81 | A1 |
| ATOM | 303 | CB | LEU | 41 | 2.665 | 22.466 | 18.339 | 1.00 | 42.41 | A1 |
| ATOM | 304 | CG | LEU | 41 | 3.140 | 22.361 | 16.875 | 1.00 | 43.61 | A1 |
| ATOM | 305 | CD1 | LEU | 41 | 4.395 | 23.238 | 16.638 | 1.00 | 41.82 | A1 |
| ATOM | 306 | CD2 | LEU | 41 | 3.425 | 20.898 | 16.550 | 1.00 | 42.33 | A1 |
| ATOM | 307 | C | LEU | 41 | 1.126 | 21.698 | 20.170 | 1.00 | 42.93 | A1 |
| ATOM | 308 | O | LEU | 41 | 0.363 | 22.432 | 20.778 | 1.00 | 41.85 | A1 |
| ATOM | 309 | N | SER | 42 | 1.859 | 20.733 | 20.748 | 1.00 | 43.71 | A1 |
| ATOM | 310 | CA | SER | 42 | 1.885 | 20.488 | 22.188 | 1.00 | 44.05 | A1 |
| ATOM | 311 | CB | SER | 42 | 2.659 | 19.246 | 22.461 | 1.00 | 43.73 | A1 |
| ATOM | 312 | OG | SER | 42 | 4.019 | 19.536 | 22.239 | 1.00 | 44.18 | A1 |
| ATOM | 313 | C | SER | 42 | 2.684 | 21.644 | 22.763 | 1.00 | 44.62 | A1 |
| ATOM | 314 | O | SER | 42 | 3.416 | 22.292 | 22.028 | 1.00 | 44.29 | A1 |
| ATOM | 315 | N | GLU | 43 | 2.603 | 21.884 | 24.068 | 1.00 | 45.05 | A1 |
| ATOM | 316 | CA | GLU | 43 | 3.332 | 23.019 | 24.607 | 1.00 | 45.94 | A1 |
| ATOM | 317 | CB | GLU | 43 | 2.971 | 23.259 | 26.071 | 1.00 | 48.60 | A1 |
| ATOM | 318 | CG | GLU | 43 | 1.444 | 23.613 | 26.267 | 1.00 | 52.40 | A1 |
| ATOM | 319 | CD | GLU | 43 | 0.995 | 24.887 | 25.505 | 1.00 | 54.53 | A1 |
| ATOM | 320 | OE1 | GLU | 43 | 1.696 | 25.925 | 25.631 | 1.00 | 55.13 | A1 |
| ATOM | 321 | OE2 | GLU | 43 | -0.062 | 24.845 | 24.800 | 1.00 | 55.25 | A1 |
| ATOM | 322 | C | GLU | 43 | 4.848 | 23.048 | 24.432 | 1.00 | 44.63 | A1 |
| ATOM | 323 | O | GLU | 43 | 5.401 | 24.132 | 24.209 | 1.00 | 44.60 | A1 |
| ATOM | 324 | N | ALA | 44 | 5.523 | 21.902 | 24.531 | 1.00 | 43.03 | A1 |
| ATOM | 325 | CA | ALA | 44 | 6.981 | 21.880 | 24.350 | 1.00 | 42.00 | A1 |
| ATOM | 326 | CB | ALA | 44 | 7.581 | 20.509 | 24.772 | 1.00 | 42.03 | A1 |
| ATOM | 327 | C | ALA | 44 | 7.253 | 22.130 | 22.850 | 1.00 | 41.00 | A1 |
| ATOM | 328 | O | ALA | 44 | 8.188 | 22.836 | 22.483 | 1.00 | 40.92 | A1 |
| ATOM | 329 | N | ARG | 45 | 6.415 | 21.548 | 21.996 | 1.00 | 39.12 | A1 |
| ATOM | 330 | CA | ARG | 45 | 6.575 | 21.735 | 20.588 | 1.00 | 38.05 | A1 |
| ATOM | 331 | CB | ARG | 45 | 5.695 | 20.782 | 19.825 | 1.00 | 39.12 | A1 |
| ATOM | 332 | CG | ARG | 45 | 6.067 | 19.368 | 20.050 | 1.00 | 42.02 | A1 |
| ATOM | 333 | CD | ARG | 45 | 7.460 | 19.066 | 19.559 | 1.00 | 45.74 | A1 |
| ATOM | 334 | NE | ARG | 45 | 7.673 | 19.650 | 18.247 | 1.00 | 49.41 | A1 |

FIG. 3A-6

| ATOM | 335 | CZ | ARG | 45 | 8.773 | 19.489 | 17.522 | 1.00 | 51.27 | A1 |
|---|---|---|---|---|---|---|---|---|---|---|
| ATOM | 336 | NH1 | ARG | 45 | 9.776 | 18.733 | 17.986 | 1.00 | 52.41 | A1 |
| ATOM | 337 | NH2 | ARG | 45 | 8.884 | 20.129 | 16.351 | 1.00 | 51.44 | A1 |
| ATOM | 338 | C | ARG | 45 | 6.305 | 23.174 | 20.185 | 1.00 | 36.52 | A1 |
| ATOM | 339 | O | ARG | 45 | 6.871 | 23.626 | 19.211 | 1.00 | 35.97 | A1 |
| ATOM | 340 | N | LYS | 46 | 5.480 | 23.896 | 20.929 | 1.00 | 34.62 | A1 |
| ATOM | 341 | CA | LYS | 46 | 5.249 | 25.294 | 20.610 | 1.00 | 34.21 | A1 |
| ATOM | 342 | CB | LYS | 46 | 4.171 | 25.906 | 21.474 | 1.00 | 33.14 | A1 |
| ATOM | 343 | CG | LYS | 46 | 2.738 | 25.639 | 21.025 | 1.00 | 35.37 | A1 |
| ATOM | 344 | CD | LYS | 46 | 1.803 | 26.461 | 21.945 | 1.00 | 35.71 | A1 |
| ATOM | 345 | CE | LYS | 46 | 0.356 | 26.339 | 21.546 | 1.00 | 37.07 | A1 |
| ATOM | 346 | NZ | LYS | 46 | -0.432 | 27.391 | 22.270 | 1.00 | 37.31 | A1 |
| ATOM | 347 | C | LYS | 46 | 6.524 | 26.132 | 20.803 | 1.00 | 33.86 | A1 |
| ATOM | 348 | O | LYS | 46 | 6.812 | 27.016 | 20.004 | 1.00 | 32.48 | A1 |
| ATOM | 349 | N | ASN | 47 | 7.278 | 25.865 | 21.871 | 1.00 | 33.74 | A1 |
| ATOM | 350 | CA | ASN | 47 | 8.477 | 26.646 | 22.098 | 1.00 | 34.19 | A1 |
| ATOM | 351 | CB | ASN | 47 | 9.005 | 26.388 | 23.480 | 1.00 | 35.68 | A1 |
| ATOM | 352 | CG | ASN | 47 | 7.983 | 26.734 | 24.497 | 1.00 | 39.69 | A1 |
| ATOM | 353 | OD1 | ASN | 47 | 7.324 | 27.795 | 24.363 | 1.00 | 41.09 | A1 |
| ATOM | 354 | ND2 | ASN | 47 | 7.802 | 25.867 | 25.513 | 1.00 | 38.62 | A1 |
| ATOM | 355 | C | ASN | 47 | 9.553 | 26.396 | 21.065 | 1.00 | 32.89 | A1 |
| ATOM | 356 | O | ASN | 47 | 10.276 | 27.324 | 20.693 | 1.00 | 30.94 | A1 |
| ATOM | 357 | N | GLU | 48 | 9.656 | 25.138 | 20.629 | 1.00 | 31.98 | A1 |
| ATOM | 358 | CA | GLU | 48 | 10.642 | 24.769 | 19.638 | 1.00 | 32.98 | A1 |
| ATOM | 359 | CB | GLU | 48 | 10.629 | 23.269 | 19.413 | 1.00 | 35.91 | A1 |
| ATOM | 360 | CG | GLU | 48 | 11.585 | 22.498 | 20.276 | 1.00 | 41.51 | A1 |
| ATOM | 361 | CD | GLU | 48 | 11.124 | 21.078 | 20.397 | 1.00 | 44.62 | A1 |
| ATOM | 362 | OE1 | GLU | 48 | 10.860 | 20.463 | 19.319 | 1.00 | 45.75 | A1 |
| ATOM | 363 | OE2 | GLU | 48 | 11.009 | 20.603 | 21.568 | 1.00 | 46.32 | A1 |
| ATOM | 364 | C | GLU | 48 | 10.346 | 25.455 | 18.301 | 1.00 | 31.14 | A1 |
| ATOM | 365 | O | GLU | 48 | 11.241 | 26.036 | 17.676 | 1.00 | 31.58 | A1 |
| ATOM | 366 | N | PHE | 49 | 9.087 | 25.344 | 17.892 | 1.00 | 28.29 | A1 |
| ATOM | 367 | CA | PHE | 49 | 8.574 | 25.895 | 16.666 | 1.00 | 26.99 | A1 |
| ATOM | 368 | CB | PHE | 49 | 7.059 | 25.633 | 16.566 | 1.00 | 26.28 | A1 |
| ATOM | 369 | CG | PHE | 49 | 6.461 | 26.100 | 15.286 | 1.00 | 25.52 | A1 |
| ATOM | 370 | CD1 | PHE | 49 | 6.587 | 25.339 | 14.120 | 1.00 | 26.28 | A1 |
| ATOM | 371 | CD2 | PHE | 49 | 5.823 | 27.313 | 15.212 | 1.00 | 24.67 | A1 |
| ATOM | 372 | CE1 | PHE | 49 | 6.071 | 25.798 | 12.878 | 1.00 | 25.84 | A1 |
| ATOM | 373 | CE2 | PHE | 49 | 5.303 | 27.773 | 13.960 | 1.00 | 26.00 | A1 |
| ATOM | 374 | CZ | PHE | 49 | 5.440 | 26.994 | 12.800 | 1.00 | 24.44 | A1 |
| ATOM | 375 | C | PHE | 49 | 8.827 | 27.399 | 16.672 | 1.00 | 26.54 | A1 |
| ATOM | 376 | O | PHE | 49 | 9.327 | 27.949 | 15.700 | 1.00 | 24.86 | A1 |
| ATOM | 377 | N | LEU | 50 | 8.504 | 28.034 | 17.794 | 1.00 | 25.76 | A1 |
| ATOM | 378 | CA | LEU | 50 | 8.667 | 29.452 | 17.929 | 1.00 | 26.80 | A1 |
| ATOM | 379 | CB | LEU | 50 | 8.013 | 29.905 | 19.205 | 1.00 | 26.47 | A1 |
| ATOM | 380 | CG | LEU | 50 | 7.184 | 31.173 | 19.245 | 1.00 | 26.96 | A1 |
| ATOM | 381 | CD1 | LEU | 50 | 6.188 | 31.085 | 18.097 | 1.00 | 28.27 | A1 |
| ATOM | 382 | CD2 | LEU | 50 | 6.427 | 31.298 | 20.634 | 1.00 | 26.53 | A1 |
| ATOM | 383 | C | LEU | 50 | 10.132 | 29.899 | 17.920 | 1.00 | 27.42 | A1 |
| ATOM | 384 | O | LEU | 50 | 10.477 | 30.897 | 17.298 | 1.00 | 28.25 | A1 |
| ATOM | 385 | N | ALA | 51 | 11.008 | 29.164 | 18.577 | 1.00 | 26.72 | A1 |
| ATOM | 386 | CA | ALA | 51 | 12.399 | 29.586 | 18.589 | 1.00 | 26.62 | A1 |
| ATOM | 387 | CB | ALA | 51 | 13.161 | 28.786 | 19.583 | 1.00 | 24.82 | A1 |
| ATOM | 388 | C | ALA | 51 | 13.009 | 29.369 | 17.187 | 1.00 | 26.71 | A1 |
| ATOM | 389 | O | ALA | 51 | 13.871 | 30.115 | 16.785 | 1.00 | 26.84 | A1 |
| ATOM | 390 | N | GLY | 52 | 12.564 | 28.333 | 16.475 | 1.00 | 26.28 | A1 |
| ATOM | 391 | CA | GLY | 52 | 13.120 | 28.049 | 15.160 | 1.00 | 27.58 | A1 |

FIG. 3A-7

| ATOM | 392 | C | GLY | 52 | 12.723 | 29.141 | 14.167 | 1.00 | 27.43 | A1 |
| ATOM | 393 | O | GLY | 52 | 13.537 | 29.588 | 13.353 | 1.00 | 27.16 | A1 |
| ATOM | 394 | N | ARG | 53 | 11.468 | 29.577 | 14.259 | 1.00 | 27.33 | A1 |
| ATOM | 395 | CA | ARG | 53 | 10.963 | 30.626 | 13.382 | 1.00 | 28.47 | A1 |
| ATOM | 396 | CB | ARG | 53 | 9.416 | 30.743 | 13.508 | 1.00 | 28.93 | A1 |
| ATOM | 397 | CG | ARG | 53 | 8.635 | 29.550 | 12.916 | 1.00 | 31.06 | A1 |
| ATOM | 398 | CD | ARG | 53 | 8.966 | 29.452 | 11.454 | 1.00 | 33.23 | A1 |
| ATOM | 399 | NE | ARG | 53 | 7.949 | 28.823 | 10.619 | 1.00 | 34.72 | A1 |
| ATOM | 400 | CZ | ARG | 53 | 7.853 | 27.509 | 10.417 | 1.00 | 34.64 | A1 |
| ATOM | 401 | NH1 | ARG | 53 | 8.712 | 26.691 | 11.017 | 1.00 | 33.41 | A1 |
| ATOM | 402 | NH2 | ARG | 53 | 6.959 | 27.037 | 9.551 | 1.00 | 32.59 | A1 |
| ATOM | 403 | C | ARG | 53 | 11.647 | 31.989 | 13.724 | 1.00 | 27.67 | A1 |
| ATOM | 404 | O | ARG | 53 | 11.960 | 32.741 | 12.810 | 1.00 | 27.77 | A1 |
| ATOM | 405 | N | PHE | 54 | 11.847 | 32.294 | 15.011 | 1.00 | 25.56 | A1 |
| ATOM | 406 | CA | PHE | 54 | 12.470 | 33.544 | 15.395 | 1.00 | 25.41 | A1 |
| ATOM | 407 | CB | PHE | 54 | 12.419 | 33.737 | 16.937 | 1.00 | 25.84 | A1 |
| ATOM | 408 | CG | PHE | 54 | 13.035 | 35.038 | 17.412 | 1.00 | 26.15 | A1 |
| ATOM | 409 | CD1 | PHE | 54 | 14.326 | 35.068 | 17.855 | 1.00 | 25.57 | A1 |
| ATOM | 410 | CD2 | PHE | 54 | 12.335 | 36.247 | 17.285 | 1.00 | 27.42 | A1 |
| ATOM | 411 | CE1 | PHE | 54 | 14.962 | 36.279 | 18.163 | 1.00 | 27.84 | A1 |
| ATOM | 412 | CE2 | PHE | 54 | 12.931 | 37.477 | 17.589 | 1.00 | 27.70 | A1 |
| ATOM | 413 | CZ | PHE | 54 | 14.245 | 37.507 | 18.023 | 1.00 | 29.21 | A1 |
| ATOM | 414 | C | PHE | 54 | 13.918 | 33.499 | 14.883 | 1.00 | 25.07 | A1 |
| ATOM | 415 | O | PHE | 54 | 14.416 | 34.481 | 14.315 | 1.00 | 24.66 | A1 |
| ATOM | 416 | N | ALA | 55 | 14.589 | 32.354 | 15.061 | 1.00 | 24.76 | A1 |
| ATOM | 417 | CA | ALA | 55 | 15.960 | 32.232 | 14.566 | 1.00 | 24.79 | A1 |
| ATOM | 418 | CB | ALA | 55 | 16.565 | 30.896 | 14.966 | 1.00 | 23.37 | A1 |
| ATOM | 419 | C | ALA | 55 | 16.000 | 32.384 | 13.036 | 1.00 | 24.40 | A1 |
| ATOM | 420 | O | ALA | 55 | 16.761 | 33.188 | 12.506 | 1.00 | 25.92 | A1 |
| ATOM | 421 | N | ALA | 56 | 15.201 | 31.612 | 12.332 | 1.00 | 23.65 | A1 |
| ATOM | 422 | CA | ALA | 56 | 15.178 | 31.705 | 10.873 | 1.00 | 23.88 | A1 |
| ATOM | 423 | CB | ALA | 56 | 14.184 | 30.759 | 10.314 | 1.00 | 21.79 | A1 |
| ATOM | 424 | C | ALA | 56 | 14.885 | 33.113 | 10.391 | 1.00 | 24.13 | A1 |
| ATOM | 425 | O | ALA | 56 | 15.510 | 33.572 | 9.449 | 1.00 | 24.31 | A1 |
| ATOM | 426 | N | LYS | 57 | 13.974 | 33.816 | 11.060 | 1.00 | 24.20 | A1 |
| ATOM | 427 | CA | LYS | 57 | 13.613 | 35.168 | 10.647 | 1.00 | 25.22 | A1 |
| ATOM | 428 | CB | LYS | 57 | 12.217 | 35.576 | 11.224 | 1.00 | 25.77 | A1 |
| ATOM | 429 | CG | LYS | 57 | 11.047 | 34.738 | 10.632 | 1.00 | 24.59 | A1 |
| ATOM | 430 | CD | LYS | 57 | 9.646 | 35.359 | 10.830 | 1.00 | 24.83 | A1 |
| ATOM | 431 | CE | LYS | 57 | 8.552 | 34.359 | 10.417 | 1.00 | 25.92 | A1 |
| ATOM | 432 | NZ | LYS | 57 | 7.084 | 34.830 | 10.452 | 1.00 | 26.32 | A1 |
| ATOM | 433 | C | LYS | 57 | 14.633 | 36.214 | 11.026 | 1.00 | 26.40 | A1 |
| ATOM | 434 | O | LYS | 57 | 14.705 | 37.245 | 10.355 | 1.00 | 26.87 | A1 |
| ATOM | 435 | N | GLU | 58 | 15.351 | 36.000 | 12.147 | 1.00 | 26.28 | A1 |
| ATOM | 436 | CA | GLU | 58 | 16.384 | 36.941 | 12.581 | 1.00 | 26.02 | A1 |
| ATOM | 437 | CB | GLU | 58 | 16.871 | 36.639 | 13.992 | 1.00 | 27.63 | A1 |
| ATOM | 438 | CG | GLU | 58 | 15.889 | 37.012 | 15.062 | 1.00 | 30.56 | A1 |
| ATOM | 439 | CD | GLU | 58 | 15.832 | 38.528 | 15.219 | 1.00 | 32.92 | A1 |
| ATOM | 440 | OE1 | GLU | 58 | 16.876 | 39.092 | 15.600 | 1.00 | 34.30 | A1 |
| ATOM | 441 | OE2 | GLU | 58 | 14.775 | 39.151 | 14.929 | 1.00 | 33.64 | A1 |
| ATOM | 442 | C | GLU | 58 | 17.553 | 36.768 | 11.611 | 1.00 | 25.11 | A1 |
| ATOM | 443 | O | GLU | 58 | 18.159 | 37.739 | 11.168 | 1.00 | 24.66 | A1 |
| ATOM | 444 | N | ALA | 59 | 17.865 | 35.529 | 11.276 | 1.00 | 24.85 | A1 |
| ATOM | 445 | CA | ALA | 59 | 18.928 | 35.272 | 10.327 | 1.00 | 23.99 | A1 |
| ATOM | 446 | CB | ALA | 59 | 19.128 | 33.764 | 10.154 | 1.00 | 23.99 | A1 |
| ATOM | 447 | C | ALA | 59 | 18.606 | 35.912 | 8.952 | 1.00 | 24.17 | A1 |
| ATOM | 448 | O | ALA | 59 | 19.459 | 36.540 | 8.315 | 1.00 | 21.87 | A1 |

FIG. 3A-8

```
ATOM   449  N    PHE  60      17.370  35.737   8.505  1.00 24.88      A1
ATOM   450  CA   PHE  60      16.968  36.251   7.218  1.00 25.44      A1
ATOM   451  CB   PHE  60      15.521  35.895   6.879  1.00 24.96      A1
ATOM   452  CG   PHE  60      15.037  36.546   5.586  1.00 26.06      A1
ATOM   453  CD1  PHE  60      15.193  35.904   4.363  1.00 25.13      A1
ATOM   454  CD2  PHE  60      14.474  37.831   5.598  1.00 25.99      A1
ATOM   455  CE1  PHE  60      14.804  36.507   3.170  1.00 24.37      A1
ATOM   456  CE2  PHE  60      14.078  38.450   4.391  1.00 25.81      A1
ATOM   457  CZ   PHE  60      14.251  37.766   3.185  1.00 24.62      A1
ATOM   458  C    PHE  60      17.114  37.770   7.207  1.00 27.27      A1
ATOM   459  O    PHE  60      17.691  38.352   6.242  1.00 27.79      A1
ATOM   460  N    SER  61      16.627  38.413   8.260  1.00 27.40      A1
ATOM   461  CA   SER  61      16.721  39.846   8.294  1.00 29.82      A1
ATOM   462  CB   SER  61      16.005  40.461   9.533  1.00 29.61      A1
ATOM   463  OG   SER  61      16.679  40.092  10.727  1.00 31.10      A1
ATOM   464  C    SER  61      18.191  40.242   8.294  1.00 31.09      A1
ATOM   465  O    SER  61      18.517  41.316   7.832  1.00 31.02      A1
ATOM   466  N    LYS  62      19.071  39.389   8.819  1.00 32.53      A1
ATOM   467  CA   LYS  62      20.508  39.723   8.828  1.00 34.06      A1
ATOM   468  CB   LYS  62      21.307  38.729   9.698  1.00 35.23      A1
ATOM   469  CG   LYS  62      21.305  38.975  11.242  1.00 37.56      A1
ATOM   470  CD   LYS  62      22.349  38.019  11.845  1.00 41.31      A1
ATOM   471  CE   LYS  62      22.427  38.038  13.347  1.00 43.94      A1
ATOM   472  NZ   LYS  62      21.213  37.446  14.089  1.00 46.69      A1
ATOM   473  C    LYS  62      21.066  39.710   7.382  1.00 34.27      A1
ATOM   474  O    LYS  62      21.760  40.641   6.956  1.00 34.53      A1
ATOM   475  N    ALA  63      20.746  38.649   6.651  1.00 33.34      A1
ATOM   476  CA   ALA  63      21.177  38.496   5.297  1.00 33.47      A1
ATOM   477  CB   ALA  63      20.751  37.106   4.756  1.00 32.08      A1
ATOM   478  C    ALA  63      20.563  39.610   4.459  1.00 33.97      A1
ATOM   479  O    ALA  63      21.230  40.142   3.616  1.00 34.33      A1
ATOM   480  N    PHE  64      19.291  39.945   4.700  1.00 35.12      A1
ATOM   481  CA   PHE  64      18.585  40.987   3.955  1.00 35.58      A1
ATOM   482  CB   PHE  64      17.097  41.040   4.371  1.00 33.83      A1
ATOM   483  CG   PHE  64      16.211  41.767   3.393  1.00 32.65      A1
ATOM   484  CD1  PHE  64      15.901  41.190   2.164  1.00 32.40      A1
ATOM   485  CD2  PHE  64      15.671  43.012   3.708  1.00 32.51      A1
ATOM   486  CE1  PHE  64      15.073  41.824   1.274  1.00 32.68      A1
ATOM   487  CE2  PHE  64      14.826  43.682   2.829  1.00 32.56      A1
ATOM   488  CZ   PHE  64      14.517  43.085   1.593  1.00 33.86      A1
ATOM   489  C    PHE  64      19.259  42.334   4.236  1.00 36.82      A1
ATOM   490  O    PHE  64      19.007  43.330   3.554  1.00 37.04      A1
ATOM   491  N    GLY  65      20.092  42.350   5.265  1.00 38.68      A1
ATOM   492  CA   GLY  65      20.837  43.542   5.636  1.00 41.46      A1
ATOM   493  C    GLY  65      20.119  44.748   6.216  1.00 43.07      A1
ATOM   494  O    GLY  65      20.749  45.793   6.427  1.00 42.77      A1
ATOM   495  N    THR  66      18.821  44.628   6.487  1.00 44.10      A1
ATOM   496  CA   THR  66      18.062  45.767   7.032  1.00 45.54      A1
ATOM   497  CB   THR  66      16.769  46.091   6.194  1.00 45.56      A1
ATOM   498  OG1  THR  66      15.854  44.992   6.288  1.00 46.47      A1
ATOM   499  CG2  THR  66      17.093  46.322   4.730  1.00 45.39      A1
ATOM   500  C    THR  66      17.579  45.503   8.463  1.00 46.31      A1
ATOM   501  O    THR  66      17.262  46.453   9.195  1.00 45.86      A1
ATOM   502  N    GLY  67      17.509  44.221   8.857  1.00 46.67      A1
ATOM   503  CA   GLY  67      16.994  43.912  10.186  1.00 46.27      A1
ATOM   504  C    GLY  67      15.487  44.210  10.210  1.00 46.15      A1
ATOM   505  O    GLY  67      14.938  44.754   9.254  1.00 46.00      A1
```

FIG. 3A-9

| ATOM | 506 | N | ILE | 68 | 14.813 | 43.892 | 11.310 | 1.00 | 45.81 | A1 |
| ATOM | 507 | CA | ILE | 68 | 13.380 | 44.098 | 11.393 | 1.00 | 45.27 | A1 |
| ATOM | 508 | CB | ILE | 68 | 12.744 | 43.185 | 12.478 | 1.00 | 44.45 | A1 |
| ATOM | 509 | CG2 | ILE | 68 | 11.221 | 43.417 | 12.518 | 1.00 | 42.62 | A1 |
| ATOM | 510 | CG1 | ILE | 68 | 13.043 | 41.716 | 12.159 | 1.00 | 43.31 | A1 |
| ATOM | 511 | CD1 | ILE | 68 | 12.415 | 41.217 | 10.850 | 1.00 | 42.83 | A1 |
| ATOM | 512 | C | ILE | 68 | 12.989 | 45.544 | 11.650 | 1.00 | 45.87 | A1 |
| ATOM | 513 | O | ILE | 68 | 13.490 | 46.188 | 12.572 | 1.00 | 46.37 | A1 |
| ATOM | 514 | N | GLY | 69 | 12.065 | 46.047 | 10.843 | 1.00 | 45.69 | A1 |
| ATOM | 515 | CA | GLY | 69 | 11.643 | 47.426 | 10.988 | 1.00 | 45.78 | A1 |
| ATOM | 516 | C | GLY | 69 | 10.838 | 47.891 | 9.789 | 1.00 | 46.78 | A1 |
| ATOM | 517 | O | GLY | 69 | 9.977 | 47.182 | 9.252 | 1.00 | 46.20 | A1 |
| ATOM | 518 | N | ARG | 70 | 11.120 | 49.108 | 9.360 | 1.00 | 47.73 | A1 |
| ATOM | 519 | CA | ARG | 70 | 10.415 | 49.684 | 8.236 | 1.00 | 48.39 | A1 |
| ATOM | 520 | CB | ARG | 70 | 10.932 | 51.108 | 8.026 | 1.00 | 51.49 | A1 |
| ATOM | 521 | CG | ARG | 70 | 10.084 | 51.897 | 7.059 | 1.00 | 55.58 | A1 |
| ATOM | 522 | CD | ARG | 70 | 10.755 | 53.199 | 6.589 | 1.00 | 59.37 | A1 |
| ATOM | 523 | NE | ARG | 70 | 9.972 | 53.806 | 5.496 | 1.00 | 62.26 | A1 |
| ATOM | 524 | CZ | ARG | 70 | 9.714 | 55.111 | 5.385 | 1.00 | 63.78 | A1 |
| ATOM | 525 | NH1 | ARG | 70 | 8.985 | 55.551 | 4.353 | 1.00 | 64.14 | A1 |
| ATOM | 526 | NH2 | ARG | 70 | 10.181 | 55.975 | 6.303 | 1.00 | 63.87 | A1 |
| ATOM | 527 | C | ARG | 70 | 10.499 | 48.871 | 6.914 | 1.00 | 47.02 | A1 |
| ATOM | 528 | O | ARG | 70 | 9.480 | 48.606 | 6.250 | 1.00 | 46.19 | A1 |
| ATOM | 529 | N | GLN | 71 | 11.705 | 48.471 | 6.532 | 1.00 | 45.11 | A1 |
| ATOM | 530 | CA | GLN | 71 | 11.875 | 47.743 | 5.279 | 1.00 | 43.56 | A1 |
| ATOM | 531 | CB | GLN | 71 | 13.336 | 47.854 | 4.821 | 1.00 | 44.43 | A1 |
| ATOM | 532 | CG | GLN | 71 | 13.896 | 49.308 | 4.720 | 1.00 | 45.80 | A1 |
| ATOM | 533 | CD | GLN | 71 | 15.391 | 49.319 | 4.344 | 1.00 | 47.82 | A1 |
| ATOM | 534 | OE1 | GLN | 71 | 15.764 | 48.917 | 3.228 | 1.00 | 48.24 | A1 |
| ATOM | 535 | NE2 | GLN | 71 | 16.253 | 49.751 | 5.276 | 1.00 | 47.27 | A1 |
| ATOM | 536 | C | GLN | 71 | 11.483 | 46.275 | 5.387 | 1.00 | 42.01 | A1 |
| ATOM | 537 | O | GLN | 71 | 11.186 | 45.639 | 4.395 | 1.00 | 42.31 | A1 |
| ATOM | 538 | N | LEU | 72 | 11.425 | 45.743 | 6.601 | 1.00 | 39.83 | A1 |
| ATOM | 539 | CA | LEU | 72 | 11.117 | 44.324 | 6.779 | 1.00 | 38.04 | A1 |
| ATOM | 540 | CB | LEU | 72 | 12.420 | 43.528 | 6.713 | 1.00 | 36.85 | A1 |
| ATOM | 541 | CG | LEU | 72 | 12.382 | 42.017 | 6.775 | 1.00 | 35.82 | A1 |
| ATOM | 542 | CD1 | LEU | 72 | 11.605 | 41.559 | 5.607 | 1.00 | 36.04 | A1 |
| ATOM | 543 | CD2 | LEU | 72 | 13.812 | 41.440 | 6.753 | 1.00 | 35.98 | A1 |
| ATOM | 544 | C | LEU | 72 | 10.400 | 43.984 | 8.086 | 1.00 | 37.03 | A1 |
| ATOM | 545 | O | LEU | 72 | 10.920 | 44.215 | 9.166 | 1.00 | 36.11 | A1 |
| ATOM | 546 | N | SER | 73 | 9.214 | 43.406 | 7.980 | 1.00 | 36.72 | A1 |
| ATOM | 547 | CA | SER | 73 | 8.461 | 43.031 | 9.175 | 1.00 | 36.31 | A1 |
| ATOM | 548 | CB | SER | 73 | 7.003 | 43.440 | 9.032 | 1.00 | 36.91 | A1 |
| ATOM | 549 | OG | SER | 73 | 6.222 | 42.756 | 10.003 | 1.00 | 39.16 | A1 |
| ATOM | 550 | C | SER | 73 | 8.518 | 41.529 | 9.333 | 1.00 | 34.81 | A1 |
| ATOM | 551 | O | SER | 73 | 8.730 | 40.849 | 8.353 | 1.00 | 34.46 | A1 |
| ATOM | 552 | N | PHE | 74 | 8.368 | 41.023 | 10.565 | 1.00 | 33.65 | A1 |
| ATOM | 553 | CA | PHE | 74 | 8.342 | 39.578 | 10.825 | 1.00 | 31.90 | A1 |
| ATOM | 554 | CB | PHE | 74 | 7.948 | 39.298 | 12.282 | 1.00 | 30.13 | A1 |
| ATOM | 555 | CG | PHE | 74 | 9.046 | 39.532 | 13.283 | 1.00 | 29.47 | A1 |
| ATOM | 556 | CD1 | PHE | 74 | 10.153 | 38.660 | 13.341 | 1.00 | 27.35 | A1 |
| ATOM | 557 | CD2 | PHE | 74 | 8.983 | 40.633 | 14.167 | 1.00 | 28.21 | A1 |
| ATOM | 558 | CE1 | PHE | 74 | 11.195 | 38.867 | 14.254 | 1.00 | 28.79 | A1 |
| ATOM | 559 | CE2 | PHE | 74 | 10.021 | 40.878 | 15.100 | 1.00 | 28.83 | A1 |
| ATOM | 560 | CZ | PHE | 74 | 11.146 | 39.992 | 15.160 | 1.00 | 29.18 | A1 |
| ATOM | 561 | C | PHE | 74 | 7.240 | 38.948 | 9.935 | 1.00 | 32.18 | A1 |
| ATOM | 562 | O | PHE | 74 | 7.334 | 37.801 | 9.490 | 1.00 | 31.91 | A1 |

FIG. 3A-10

| ATOM | 563 | N | GLN | 75 | 6.168 | 39.704 | 9.731 | 1.00 | 32.36 | A1 |
| ATOM | 564 | CA | GLN | 75 | 5.018 | 39.257 | 8.956 | 1.00 | 32.59 | A1 |
| ATOM | 565 | CB | GLN | 75 | 3.847 | 40.223 | 9.188 | 1.00 | 34.01 | A1 |
| ATOM | 566 | CG | GLN | 75 | 3.335 | 40.256 | 10.616 | 1.00 | 36.12 | A1 |
| ATOM | 567 | CD | GLN | 75 | 2.919 | 38.876 | 11.112 | 1.00 | 38.23 | A1 |
| ATOM | 568 | OE1 | GLN | 75 | 3.282 | 38.496 | 12.227 | 1.00 | 39.11 | A1 |
| ATOM | 569 | NE2 | GLN | 75 | 2.148 | 38.118 | 10.290 | 1.00 | 37.65 | A1 |
| ATOM | 570 | C | GLN | 75 | 5.270 | 39.153 | 7.450 | 1.00 | 32.64 | A1 |
| ATOM | 571 | O | GLN | 75 | 4.418 | 38.625 | 6.744 | 1.00 | 32.25 | A1 |
| ATOM | 572 | N | ASP | 76 | 6.407 | 39.681 | 6.958 | 1.00 | 31.97 | A1 |
| ATOM | 573 | CA | ASP | 76 | 6.732 | 39.636 | 5.535 | 1.00 | 32.18 | A1 |
| ATOM | 574 | CB | ASP | 76 | 7.584 | 40.808 | 5.066 | 1.00 | 32.18 | A1 |
| ATOM | 575 | CG | ASP | 76 | 6.939 | 42.171 | 5.288 | 1.00 | 35.33 | A1 |
| ATOM | 576 | OD1 | ASP | 76 | 5.748 | 42.417 | 4.914 | 1.00 | 35.87 | A1 |
| ATOM | 577 | OD2 | ASP | 76 | 7.669 | 43.031 | 5.842 | 1.00 | 36.61 | A1 |
| ATOM | 578 | C | ASP | 76 | 7.530 | 38.395 | 5.203 | 1.00 | 32.20 | A1 |
| ATOM | 579 | O | ASP | 76 | 7.811 | 38.130 | 4.021 | 1.00 | 31.47 | A1 |
| ATOM | 580 | N | ILE | 77 | 7.901 | 37.632 | 6.229 | 1.00 | 31.49 | A1 |
| ATOM | 581 | CA | ILE | 77 | 8.744 | 36.421 | 6.006 | 1.00 | 31.71 | A1 |
| ATOM | 582 | CB | ILE | 77 | 10.005 | 36.477 | 6.882 | 1.00 | 30.86 | A1 |
| ATOM | 583 | CG2 | ILE | 77 | 10.951 | 35.376 | 6.513 | 1.00 | 29.76 | A1 |
| ATOM | 584 | CG1 | ILE | 77 | 10.629 | 37.868 | 6.771 | 1.00 | 31.47 | A1 |
| ATOM | 585 | CD1 | ILE | 77 | 11.497 | 38.255 | 7.981 | 1.00 | 30.84 | A1 |
| ATOM | 586 | C | ILE | 77 | 8.010 | 35.164 | 6.420 | 1.00 | 31.37 | A1 |
| ATOM | 587 | O | ILE | 77 | 7.504 | 35.095 | 7.534 | 1.00 | 33.09 | A1 |
| ATOM | 588 | N | GLU | 78 | 7.959 | 34.169 | 5.565 | 1.00 | 29.65 | A1 |
| ATOM | 589 | CA | GLU | 78 | 7.306 | 32.952 | 5.971 | 1.00 | 28.49 | A1 |
| ATOM | 590 | CB | GLU | 78 | 5.947 | 32.856 | 5.315 | 1.00 | 30.42 | A1 |
| ATOM | 591 | CG | GLU | 78 | 5.133 | 31.599 | 5.646 | 1.00 | 31.45 | A1 |
| ATOM | 592 | CD | GLU | 78 | 3.797 | 31.681 | 4.955 | 1.00 | 33.67 | A1 |
| ATOM | 593 | OE1 | GLU | 78 | 2.890 | 32.370 | 5.501 | 1.00 | 34.85 | A1 |
| ATOM | 594 | OE2 | GLU | 78 | 3.656 | 31.116 | 3.848 | 1.00 | 33.40 | A1 |
| ATOM | 595 | C | GLU | 78 | 8.161 | 31.740 | 5.648 | 1.00 | 27.82 | A1 |
| ATOM | 596 | O | GLU | 78 | 8.708 | 31.588 | 4.535 | 1.00 | 28.34 | A1 |
| ATOM | 597 | N | ILE | 79 | 8.322 | 30.880 | 6.639 | 1.00 | 26.70 | A1 |
| ATOM | 598 | CA | ILE | 79 | 9.097 | 29.671 | 6.433 | 1.00 | 25.67 | A1 |
| ATOM | 599 | CB | ILE | 79 | 9.902 | 29.208 | 7.739 | 1.00 | 25.60 | A1 |
| ATOM | 600 | CG2 | ILE | 79 | 10.224 | 27.693 | 7.636 | 1.00 | 23.34 | A1 |
| ATOM | 601 | CG1 | ILE | 79 | 11.187 | 30.053 | 7.937 | 1.00 | 23.66 | A1 |
| ATOM | 602 | CD1 | ILE | 79 | 10.943 | 31.531 | 8.226 | 1.00 | 22.51 | A1 |
| ATOM | 603 | C | ILE | 79 | 8.058 | 28.619 | 6.131 | 1.00 | 26.47 | A1 |
| ATOM | 604 | O | ILE | 79 | 7.055 | 28.501 | 6.836 | 1.00 | 26.91 | A1 |
| ATOM | 605 | N | ARG | 80 | 8.258 | 27.879 | 5.062 | 1.00 | 27.30 | A1 |
| ATOM | 606 | CA | ARG | 80 | 7.350 | 26.794 | 4.712 | 1.00 | 28.19 | A1 |
| ATOM | 607 | CB | ARG | 80 | 6.641 | 27.089 | 3.351 | 1.00 | 28.49 | A1 |
| ATOM | 608 | CG | ARG | 80 | 5.673 | 28.304 | 3.313 | 1.00 | 28.49 | A1 |
| ATOM | 609 | CD | ARG | 80 | 4.975 | 28.383 | 1.922 | 1.00 | 30.89 | A1 |
| ATOM | 610 | NE | ARG | 80 | 4.356 | 29.680 | 1.634 | 1.00 | 31.32 | A1 |
| ATOM | 611 | CZ | ARG | 80 | 3.847 | 30.049 | 0.460 | 1.00 | 31.60 | A1 |
| ATOM | 612 | NH1 | ARG | 80 | 3.865 | 29.226 | -0.584 | 1.00 | 31.89 | A1 |
| ATOM | 613 | NH2 | ARG | 80 | 3.354 | 31.272 | 0.320 | 1.00 | 31.19 | A1 |
| ATOM | 614 | C | ARG | 80 | 8.252 | 25.547 | 4.575 | 1.00 | 29.13 | A1 |
| ATOM | 615 | O | ARG | 80 | 9.503 | 25.666 | 4.493 | 1.00 | 27.83 | A1 |
| ATOM | 616 | N | LYS | 81 | 7.636 | 24.366 | 4.581 | 1.00 | 30.40 | A1 |
| ATOM | 617 | CA | LYS | 81 | 8.358 | 23.104 | 4.392 | 1.00 | 32.40 | A1 |
| ATOM | 618 | CB | LYS | 81 | 8.193 | 22.210 | 5.612 | 1.00 | 33.34 | A1 |
| ATOM | 619 | CG | LYS | 81 | 9.194 | 22.540 | 6.717 | 1.00 | 37.90 | A1 |

FIG. 3A-11

| | | | | | | | | | |
|---|---|---|---|---|---|---|---|---|---|
| ATOM | 620 | CD | LYS | 81 | 9.035 | 21.611 | 7.935 | 1.00 41.46 | A1 |
| ATOM | 621 | CE | LYS | 81 | 10.236 | 21.723 | 8.948 | 1.00 43.94 | A1 |
| ATOM | 622 | NZ | LYS | 81 | 9.836 | 21.172 | 10.319 | 1.00 44.22 | A1 |
| ATOM | 623 | C | LYS | 81 | 7.874 | 22.337 | 3.126 | 1.00 33.26 | A1 |
| ATOM | 624 | O | LYS | 81 | 6.669 | 22.225 | 2.875 | 1.00 32.50 | A1 |
| ATOM | 625 | N | ASP | 82 | 8.791 | 21.799 | 2.335 | 1.00 33.89 | A1 |
| ATOM | 626 | CA | ASP | 82 | 8.331 | 21.071 | 1.185 | 1.00 36.78 | A1 |
| ATOM | 627 | CB | ASP | 82 | 9.332 | 21.153 | 0.011 | 1.00 37.31 | A1 |
| ATOM | 628 | CG | ASP | 82 | 10.635 | 20.442 | 0.269 | 1.00 38.63 | A1 |
| ATOM | 629 | OD1 | ASP | 82 | 10.690 | 19.498 | 1.077 | 1.00 38.49 | A1 |
| ATOM | 630 | OD2 | ASP | 82 | 11.633 | 20.826 | -0.398 | 1.00 41.14 | A1 |
| ATOM | 631 | C | ASP | 82 | 7.962 | 19.627 | 1.512 | 1.00 37.29 | A1 |
| ATOM | 632 | O | ASP | 82 | 7.892 | 19.242 | 2.676 | 1.00 36.84 | A1 |
| ATOM | 633 | N | ALA | 83 | 7.688 | 18.840 | 0.481 | 1.00 38.27 | A1 |
| ATOM | 634 | CA | ALA | 83 | 7.281 | 17.446 | 0.677 | 1.00 40.15 | A1 |
| ATOM | 635 | CB | ALA | 83 | 7.085 | 16.751 | -0.707 | 1.00 41.30 | A1 |
| ATOM | 636 | C | ALA | 83 | 8.261 | 16.634 | 1.559 | 1.00 40.22 | A1 |
| ATOM | 637 | O | ALA | 83 | 7.842 | 15.798 | 2.359 | 1.00 40.09 | A1 |
| ATOM | 638 | N | ASN | 84 | 9.554 | 16.887 | 1.386 | 1.00 40.04 | A1 |
| ATOM | 639 | CA | ASN | 84 | 10.607 | 16.221 | 2.157 | 1.00 40.28 | A1 |
| ATOM | 640 | CB | ASN | 84 | 11.908 | 16.209 | 1.345 | 1.00 41.08 | A1 |
| ATOM | 641 | CG | ASN | 84 | 11.773 | 15.434 | 0.049 | 1.00 42.63 | A1 |
| ATOM | 642 | OD1 | ASN | 84 | 12.401 | 15.778 | -0.966 | 1.00 43.70 | A1 |
| ATOM | 643 | ND2 | ASN | 84 | 10.957 | 14.373 | 0.072 | 1.00 42.72 | A1 |
| ATOM | 644 | C | ASN | 84 | 10.897 | 16.895 | 3.513 | 1.00 39.63 | A1 |
| ATOM | 645 | O | ASN | 84 | 11.838 | 16.500 | 4.199 | 1.00 40.43 | A1 |
| ATOM | 646 | N | GLY | 85 | 10.114 | 17.899 | 3.903 | 1.00 38.52 | A1 |
| ATOM | 647 | CA | GLY | 85 | 10.365 | 18.584 | 5.172 | 1.00 37.04 | A1 |
| ATOM | 648 | C | GLY | 85 | 11.517 | 19.616 | 5.151 | 1.00 36.50 | A1 |
| ATOM | 649 | O | GLY | 85 | 11.921 | 20.112 | 6.201 | 1.00 37.45 | A1 |
| ATOM | 650 | N | LYS | 86 | 12.047 | 19.933 | 3.966 | 1.00 35.00 | A1 |
| ATOM | 651 | CA | LYS | 86 | 13.139 | 20.921 | 3.778 | 1.00 32.22 | A1 |
| ATOM | 652 | CB | LYS | 86 | 13.754 | 20.797 | 2.369 | 1.00 31.49 | A1 |
| ATOM | 653 | CG | LYS | 86 | 14.854 | 21.784 | 2.068 | 1.00 32.53 | A1 |
| ATOM | 654 | CD | LYS | 86 | 15.943 | 21.629 | 3.134 | 1.00 35.38 | A1 |
| ATOM | 655 | CE | LYS | 86 | 17.218 | 22.403 | 2.881 | 1.00 35.96 | A1 |
| ATOM | 656 | NZ | LYS | 86 | 16.966 | 23.771 | 3.262 | 1.00 37.11 | A1 |
| ATOM | 657 | C | LYS | 86 | 12.456 | 22.275 | 3.885 | 1.00 30.60 | A1 |
| ATOM | 658 | O | LYS | 86 | 11.489 | 22.523 | 3.193 | 1.00 29.77 | A1 |
| ATOM | 659 | N | PRO | 87 | 12.976 | 23.172 | 4.727 | 1.00 29.10 | A1 |
| ATOM | 660 | CD | PRO | 87 | 14.082 | 22.948 | 5.699 | 1.00 28.74 | A1 |
| ATOM | 661 | CA | PRO | 87 | 12.351 | 24.486 | 4.876 | 1.00 27.83 | A1 |
| ATOM | 662 | CB | PRO | 87 | 12.765 | 24.891 | 6.297 | 1.00 27.32 | A1 |
| ATOM | 663 | CG | PRO | 87 | 14.256 | 24.309 | 6.370 | 1.00 27.78 | A1 |
| ATOM | 664 | C | PRO | 87 | 12.783 | 25.517 | 3.801 | 1.00 27.06 | A1 |
| ATOM | 665 | O | PRO | 87 | 13.890 | 25.471 | 3.333 | 1.00 27.38 | A1 |
| ATOM | 666 | N | TYR | 88 | 11.883 | 26.395 | 3.374 | 1.00 25.32 | A1 |
| ATOM | 667 | CA | TYR | 88 | 12.248 | 27.448 | 2.411 | 1.00 25.06 | A1 |
| ATOM | 668 | CB | TYR | 88 | 11.917 | 27.069 | 0.947 | 1.00 24.22 | A1 |
| ATOM | 669 | CG | TYR | 88 | 10.463 | 26.735 | 0.656 | 1.00 23.29 | A1 |
| ATOM | 670 | CD1 | TYR | 88 | 9.599 | 27.704 | 0.100 | 1.00 22.42 | A1 |
| ATOM | 671 | CE1 | TYR | 88 | 8.247 | 27.406 | -0.174 | 1.00 23.37 | A1 |
| ATOM | 672 | CD2 | TYR | 88 | 9.952 | 25.460 | 0.937 | 1.00 23.26 | A1 |
| ATOM | 673 | CE2 | TYR | 88 | 8.615 | 25.141 | 0.686 | 1.00 23.66 | A1 |
| ATOM | 674 | CZ | TYR | 88 | 7.762 | 26.132 | 0.126 | 1.00 25.22 | A1 |
| ATOM | 675 | OH | TYR | 88 | 6.421 | 25.901 | -0.045 | 1.00 26.63 | A1 |
| ATOM | 676 | C | TYR | 88 | 11.520 | 28.712 | 2.850 | 1.00 24.33 | A1 |

FIG. 3A-12

| ATOM | 677 | O   | TYR | 88 | 10.546 | 28.651 | 3.582  | 1.00 | 23.08 | A1 |
|------|-----|-----|-----|----|--------|--------|--------|------|-------|----|
| ATOM | 678 | N   | ILE | 89 | 12.029 | 29.856 | 2.443  | 1.00 | 24.80 | A1 |
| ATOM | 679 | CA  | ILE | 89 | 11.453 | 31.120 | 2.833  | 1.00 | 24.53 | A1 |
| ATOM | 680 | CB  | ILE | 89 | 12.525 | 32.056 | 3.375  | 1.00 | 24.83 | A1 |
| ATOM | 681 | CG2 | ILE | 89 | 12.086 | 33.554 | 3.208  | 1.00 | 24.50 | A1 |
| ATOM | 682 | CG1 | ILE | 89 | 12.788 | 31.742 | 4.864  | 1.00 | 24.97 | A1 |
| ATOM | 683 | CD1 | ILE | 89 | 14.217 | 32.125 | 5.316  | 1.00 | 25.39 | A1 |
| ATOM | 684 | C   | ILE | 89 | 10.809 | 31.826 | 1.679  | 1.00 | 26.13 | A1 |
| ATOM | 685 | O   | ILE | 89 | 11.378 | 31.920 | 0.600  | 1.00 | 26.39 | A1 |
| ATOM | 686 | N   | ILE | 90 | 9.590  | 32.304 | 1.907  | 1.00 | 27.30 | A1 |
| ATOM | 687 | CA  | ILE | 90 | 8.905  | 33.116 | 0.911  | 1.00 | 27.73 | A1 |
| ATOM | 688 | CB  | ILE | 90 | 7.457  | 32.697 | 0.679  | 1.00 | 27.77 | A1 |
| ATOM | 689 | CG2 | ILE | 90 | 6.777  | 33.777 | -0.198 | 1.00 | 26.69 | A1 |
| ATOM | 690 | CG1 | ILE | 90 | 7.379  | 31.283 | 0.073  | 1.00 | 27.36 | A1 |
| ATOM | 691 | CD1 | ILE | 90 | 8.309  | 31.055 | -1.121 | 1.00 | 25.23 | A1 |
| ATOM | 692 | C   | ILE | 90 | 8.863  | 34.461 | 1.619  | 1.00 | 28.64 | A1 |
| ATOM | 693 | O   | ILE | 90 | 8.375  | 34.534 | 2.750  | 1.00 | 28.70 | A1 |
| ATOM | 694 | N   | CYS | 91 | 9.368  | 35.500 | 0.979  | 1.00 | 29.78 | A1 |
| ATOM | 695 | CA  | CYS | 91 | 9.394  | 36.846 | 1.529  | 1.00 | 31.18 | A1 |
| ATOM | 696 | CB  | CYS | 91 | 10.822 | 37.284 | 1.840  | 1.00 | 31.71 | A1 |
| ATOM | 697 | SG  | CYS | 91 | 10.958 | 39.042 | 2.467  | 1.00 | 33.30 | A1 |
| ATOM | 698 | C   | CYS | 91 | 8.795  | 37.798 | 0.492  | 1.00 | 32.78 | A1 |
| ATOM | 699 | O   | CYS | 91 | 9.160  | 37.750 | -0.701 | 1.00 | 32.93 | A1 |
| ATOM | 700 | N   | THR | 92 | 7.890  | 38.652 | 0.961  | 1.00 | 33.89 | A1 |
| ATOM | 701 | CA  | THR | 92 | 7.169  | 39.654 | 0.161  | 1.00 | 35.68 | A1 |
| ATOM | 702 | CB  | THR | 92 | 5.956  | 40.205 | 0.980  | 1.00 | 35.88 | A1 |
| ATOM | 703 | OG1 | THR | 92 | 6.424  | 40.914 | 2.147  | 1.00 | 35.36 | A1 |
| ATOM | 704 | CG2 | THR | 92 | 5.071  | 39.048 | 1.463  | 1.00 | 35.26 | A1 |
| ATOM | 705 | C   | THR | 92 | 8.007  | 40.867 | -0.298 | 1.00 | 37.04 | A1 |
| ATOM | 706 | O   | THR | 92 | 7.635  | 41.567 | -1.234 | 1.00 | 38.47 | A1 |
| ATOM | 707 | N   | LYS | 93 | 9.132  | 41.099 | 0.361  | 1.00 | 38.09 | A1 |
| ATOM | 708 | CA  | LYS | 93 | 10.018 | 42.238 | 0.091  | 1.00 | 39.21 | A1 |
| ATOM | 709 | CB  | LYS | 93 | 10.455 | 42.831 | 1.410  | 1.00 | 38.83 | A1 |
| ATOM | 710 | CG  | LYS | 93 | 9.355  | 43.459 | 2.165  | 1.00 | 41.82 | A1 |
| ATOM | 711 | CD  | LYS | 93 | 9.133  | 44.850 | 1.659  | 1.00 | 43.77 | A1 |
| ATOM | 712 | CE  | LYS | 93 | 8.287  | 45.660 | 2.603  | 1.00 | 45.90 | A1 |
| ATOM | 713 | NZ  | LYS | 93 | 6.866  | 45.285 | 2.448  | 1.00 | 48.15 | A1 |
| ATOM | 714 | C   | LYS | 93 | 11.277 | 41.938 | -0.700 | 1.00 | 39.21 | A1 |
| ATOM | 715 | O   | LYS | 93 | 12.037 | 42.843 | -1.033 | 1.00 | 38.83 | A1 |
| ATOM | 716 | N   | LEU | 94 | 11.495 | 40.663 | -0.980 | 1.00 | 40.77 | A1 |
| ATOM | 717 | CA  | LEU | 94 | 12.692 | 40.202 | -1.677 | 1.00 | 42.19 | A1 |
| ATOM | 718 | CB  | LEU | 94 | 13.065 | 38.808 | -1.152 | 1.00 | 41.91 | A1 |
| ATOM | 719 | CG  | LEU | 94 | 14.332 | 38.116 | -1.637 | 1.00 | 41.65 | A1 |
| ATOM | 720 | CD1 | LEU | 94 | 15.550 | 38.970 | -1.401 | 1.00 | 42.73 | A1 |
| ATOM | 721 | CD2 | LEU | 94 | 14.464 | 36.818 | -0.891 | 1.00 | 41.81 | A1 |
| ATOM | 722 | C   | LEU | 94 | 12.467 | 40.185 | -3.186 | 1.00 | 43.24 | A1 |
| ATOM | 723 | O   | LEU | 94 | 11.555 | 39.532 | -3.688 | 1.00 | 42.50 | A1 |
| ATOM | 724 | N   | SER | 95 | 13.329 | 40.899 | -3.897 | 1.00 | 45.02 | A1 |
| ATOM | 725 | CA  | SER | 95 | 13.229 | 41.029 | -5.343 | 1.00 | 47.26 | A1 |
| ATOM | 726 | CB  | SER | 95 | 13.094 | 42.524 | -5.673 | 1.00 | 47.88 | A1 |
| ATOM | 727 | OG  | SER | 95 | 13.153 | 42.763 | -7.070 | 1.00 | 50.21 | A1 |
| ATOM | 728 | C   | SER | 95 | 14.401 | 40.414 | -6.130 | 1.00 | 47.86 | A1 |
| ATOM | 729 | O   | SER | 95 | 15.558 | 40.660 | -5.815 | 1.00 | 47.15 | A1 |
| ATOM | 730 | N   | GLN | 96 | 14.079 | 39.602 | -7.138 | 1.00 | 48.90 | A1 |
| ATOM | 731 | CA  | GLN | 96 | 15.075 | 38.957 | -8.016 | 1.00 | 49.92 | A1 |
| ATOM | 732 | CB  | GLN | 96 | 15.506 | 39.944 | -9.123 | 1.00 | 52.77 | A1 |
| ATOM | 733 | CG  | GLN | 96 | 14.362 | 40.551 | -9.970 | 1.00 | 57.47 | A1 |

FIG. 3A-13

| ATOM | 734 | CD  | GLN | 96  | 13.996 | 39.744 | -11.255 | 1.00 | 60.94 | A1 |
| ATOM | 735 | OE1 | GLN | 96  | 12.988 | 40.062 | -11.934 | 1.00 | 63.96 | A1 |
| ATOM | 736 | NE2 | GLN | 96  | 14.802 | 38.727 | -11.597 | 1.00 | 60.89 | A1 |
| ATOM | 737 | C   | GLN | 96  | 16.335 | 38.405 | -7.322  | 1.00 | 48.68 | A1 |
| ATOM | 738 | O   | GLN | 96  | 17.465 | 38.849 | -7.592  | 1.00 | 48.55 | A1 |
| ATOM | 739 | N   | ALA | 97  | 16.150 | 37.427 | -6.443  | 1.00 | 46.14 | A1 |
| ATOM | 740 | CA  | ALA | 97  | 17.279 | 36.849 | -5.738  | 1.00 | 43.43 | A1 |
| ATOM | 741 | CB  | ALA | 97  | 17.720 | 37.792 | -4.625  | 1.00 | 42.90 | A1 |
| ATOM | 742 | C   | ALA | 97  | 16.834 | 35.512 | -5.174  | 1.00 | 41.43 | A1 |
| ATOM | 743 | O   | ALA | 97  | 15.649 | 35.275 | -5.016  | 1.00 | 42.26 | A1 |
| ATOM | 744 | N   | ALA | 98  | 17.781 | 34.633 | -4.888  | 1.00 | 38.63 | A1 |
| ATOM | 745 | CA  | ALA | 98  | 17.491 | 33.320 | -4.333  | 1.00 | 35.46 | A1 |
| ATOM | 746 | CB  | ALA | 98  | 18.340 | 32.283 | -5.027  | 1.00 | 34.45 | A1 |
| ATOM | 747 | C   | ALA | 98  | 17.829 | 33.355 | -2.843  | 1.00 | 33.41 | A1 |
| ATOM | 748 | O   | ALA | 98  | 18.818 | 33.969 | -2.447  | 1.00 | 32.79 | A1 |
| ATOM | 749 | N   | VAL | 99  | 17.005 | 32.711 | -2.034  | 1.00 | 31.25 | A1 |
| ATOM | 750 | CA  | VAL | 99  | 17.213 | 32.600 | -0.581  | 1.00 | 30.34 | A1 |
| ATOM | 751 | CB  | VAL | 99  | 15.994 | 32.977 | 0.278   | 1.00 | 32.21 | A1 |
| ATOM | 752 | CG1 | VAL | 99  | 16.452 | 33.374 | 1.688   | 1.00 | 30.41 | A1 |
| ATOM | 753 | CG2 | VAL | 99  | 15.153 | 33.979 | -0.393  | 1.00 | 32.69 | A1 |
| ATOM | 754 | C   | VAL | 99  | 17.339 | 31.136 | -0.206  | 1.00 | 29.01 | A1 |
| ATOM | 755 | O   | VAL | 99  | 16.558 | 30.319 | -0.680  | 1.00 | 27.15 | A1 |
| ATOM | 756 | N   | HIS | 100 | 18.299 | 30.810 | 0.651   | 1.00 | 28.69 | A1 |
| ATOM | 757 | CA  | HIS | 100 | 18.435 | 29.432 | 1.141   | 1.00 | 28.94 | A1 |
| ATOM | 758 | CB  | HIS | 100 | 19.735 | 28.813 | 0.699   | 1.00 | 31.55 | A1 |
| ATOM | 759 | CG  | HIS | 100 | 19.904 | 28.757 | -0.780  | 1.00 | 35.62 | A1 |
| ATOM | 760 | CD2 | HIS | 100 | 20.725 | 29.452 | -1.610  | 1.00 | 36.22 | A1 |
| ATOM | 761 | ND1 | HIS | 100 | 19.196 | 27.881 | -1.578  | 1.00 | 37.27 | A1 |
| ATOM | 762 | CE1 | HIS | 100 | 19.575 | 28.041 | -2.836  | 1.00 | 36.95 | A1 |
| ATOM | 763 | NE2 | HIS | 100 | 20.497 | 28.987 | -2.881  | 1.00 | 37.02 | A1 |
| ATOM | 764 | C   | HIS | 100 | 18.416 | 29.518 | 2.680   | 1.00 | 28.21 | A1 |
| ATOM | 765 | O   | HIS | 100 | 18.921 | 30.477 | 3.274   | 1.00 | 28.01 | A1 |
| ATOM | 766 | N   | VAL | 101 | 17.819 | 28.534 | 3.320   | 1.00 | 26.49 | A1 |
| ATOM | 767 | CA  | VAL | 101 | 17.731 | 28.521 | 4.755   | 1.00 | 25.36 | A1 |
| ATOM | 768 | CB  | VAL | 101 | 16.321 | 28.961 | 5.171   | 1.00 | 25.72 | A1 |
| ATOM | 769 | CG1 | VAL | 101 | 15.312 | 27.810 | 4.830   | 1.00 | 25.91 | A1 |
| ATOM | 770 | CG2 | VAL | 101 | 16.249 | 29.263 | 6.693   | 1.00 | 24.55 | A1 |
| ATOM | 771 | C   | VAL | 101 | 17.974 | 27.082 | 5.284   | 1.00 | 24.98 | A1 |
| ATOM | 772 | O   | VAL | 101 | 17.731 | 26.114 | 4.577   | 1.00 | 23.99 | A1 |
| ATOM | 773 | N   | SER | 102 | 18.460 | 26.968 | 6.525   | 1.00 | 25.05 | A1 |
| ATOM | 774 | CA  | SER | 102 | 18.654 | 25.705 | 7.218   | 1.00 | 25.32 | A1 |
| ATOM | 775 | CB  | SER | 102 | 20.016 | 25.077 | 6.943   | 1.00 | 25.69 | A1 |
| ATOM | 776 | OG  | SER | 102 | 20.078 | 23.796 | 7.570   | 1.00 | 26.81 | A1 |
| ATOM | 777 | C   | SER | 102 | 18.474 | 25.991 | 8.715   | 1.00 | 26.24 | A1 |
| ATOM | 778 | O   | SER | 102 | 18.990 | 26.948 | 9.279   | 1.00 | 26.44 | A1 |
| ATOM | 779 | N   | ILE | 103 | 17.727 | 25.118 | 9.347   | 1.00 | 27.73 | A1 |
| ATOM | 780 | CA  | ILE | 103 | 17.348 | 25.250 | 10.733  | 1.00 | 28.05 | A1 |
| ATOM | 781 | CB  | ILE | 103 | 15.823 | 25.429 | 10.771  | 1.00 | 28.38 | A1 |
| ATOM | 782 | CG2 | ILE | 103 | 15.257 | 25.564 | 12.273  | 1.00 | 26.15 | A1 |
| ATOM | 783 | CG1 | ILE | 103 | 15.482 | 26.676 | 9.967   | 1.00 | 27.93 | A1 |
| ATOM | 784 | CD1 | ILE | 103 | 13.976 | 26.855 | 9.714   | 1.00 | 27.56 | A1 |
| ATOM | 785 | C   | ILE | 103 | 17.743 | 23.982 | 11.474  | 1.00 | 29.39 | A1 |
| ATOM | 786 | O   | ILE | 103 | 17.594 | 22.882 | 10.953  | 1.00 | 28.59 | A1 |
| ATOM | 787 | N   | THR | 104 | 18.279 | 24.133 | 12.679  | 1.00 | 31.06 | A1 |
| ATOM | 788 | CA  | THR | 104 | 18.659 | 22.963 | 13.470  | 1.00 | 32.26 | A1 |
| ATOM | 789 | CB  | THR | 104 | 20.156 | 22.640 | 13.288  | 1.00 | 33.13 | A1 |
| ATOM | 790 | OG1 | THR | 104 | 20.417 | 21.334 | 13.796  | 1.00 | 36.05 | A1 |

FIG. 3A-14

| ATOM | 791 | CG2 | THR | 104 | 21.040 | 23.653 | 14.041 | 1.00 | 34.05 | A1 |
|------|-----|-----|-----|-----|--------|--------|--------|------|-------|-----|
| ATOM | 792 | C | THR | 104 | 18.337 | 23.236 | 14.945 | 1.00 | 32.20 | A1 |
| ATOM | 793 | O | THR | 104 | 18.251 | 24.383 | 15.375 | 1.00 | 32.07 | A1 |
| ATOM | 794 | N | HIS | 105 | 18.207 | 22.175 | 15.718 | 1.00 | 32.17 | A1 |
| ATOM | 795 | CA | HIS | 105 | 17.868 | 22.318 | 17.112 | 1.00 | 33.14 | A1 |
| ATOM | 796 | CB | HIS | 105 | 16.419 | 21.857 | 17.378 | 1.00 | 33.42 | A1 |
| ATOM | 797 | CG | HIS | 105 | 15.361 | 22.740 | 16.785 | 1.00 | 33.41 | A1 |
| ATOM | 798 | CD2 | HIS | 105 | 14.776 | 22.728 | 15.563 | 1.00 | 33.17 | A1 |
| ATOM | 799 | ND1 | HIS | 105 | 14.806 | 23.799 | 17.468 | 1.00 | 33.56 | A1 |
| ATOM | 800 | CE1 | HIS | 105 | 13.930 | 24.410 | 16.684 | 1.00 | 33.55 | A1 |
| ATOM | 801 | NE2 | HIS | 105 | 13.898 | 23.784 | 15.524 | 1.00 | 31.70 | A1 |
| ATOM | 802 | C | HIS | 105 | 18.732 | 21.440 | 17.955 | 1.00 | 33.28 | A1 |
| ATOM | 803 | O | HIS | 105 | 19.219 | 20.423 | 17.495 | 1.00 | 34.01 | A1 |
| ATOM | 804 | N | THR | 106 | 18.913 | 21.866 | 19.188 | 1.00 | 33.82 | A1 |
| ATOM | 805 | CA | THR | 106 | 19.571 | 21.079 | 20.231 | 1.00 | 35.50 | A1 |
| ATOM | 806 | CB | THR | 106 | 20.888 | 21.669 | 20.699 | 1.00 | 34.97 | A1 |
| ATOM | 807 | OG1 | THR | 106 | 20.649 | 23.006 | 21.184 | 1.00 | 35.76 | A1 |
| ATOM | 808 | CG2 | THR | 106 | 21.896 | 21.675 | 19.560 | 1.00 | 34.11 | A1 |
| ATOM | 809 | C | THR | 106 | 18.534 | 21.271 | 21.372 | 1.00 | 36.77 | A1 |
| ATOM | 810 | O | THR | 106 | 17.583 | 22.050 | 21.232 | 1.00 | 36.77 | A1 |
| ATOM | 811 | N | LYS | 107 | 18.705 | 20.579 | 22.488 | 1.00 | 38.69 | A1 |
| ATOM | 812 | CA | LYS | 107 | 17.766 | 20.700 | 23.606 | 1.00 | 39.45 | A1 |
| ATOM | 813 | CB | LYS | 107 | 18.217 | 19.791 | 24.744 | 1.00 | 41.81 | A1 |
| ATOM | 814 | CG | LYS | 107 | 18.548 | 18.426 | 24.200 | 1.00 | 45.50 | A1 |
| ATOM | 815 | CD | LYS | 107 | 17.376 | 17.906 | 23.316 | 1.00 | 48.48 | A1 |
| ATOM | 816 | CE | LYS | 107 | 17.726 | 16.573 | 22.670 | 1.00 | 49.87 | A1 |
| ATOM | 817 | NZ | LYS | 107 | 19.034 | 16.767 | 21.979 | 1.00 | 51.62 | A1 |
| ATOM | 818 | C | LYS | 107 | 17.629 | 22.131 | 24.102 | 1.00 | 38.70 | A1 |
| ATOM | 819 | O | LYS | 107 | 16.549 | 22.546 | 24.447 | 1.00 | 38.83 | A1 |
| ATOM | 820 | N | GLU | 108 | 18.717 | 22.890 | 24.129 | 1.00 | 38.25 | A1 |
| ATOM | 821 | CA | GLU | 108 | 18.634 | 24.266 | 24.600 | 1.00 | 38.46 | A1 |
| ATOM | 822 | CB | GLU | 108 | 19.784 | 24.546 | 25.551 | 1.00 | 41.56 | A1 |
| ATOM | 823 | CG | GLU | 108 | 19.689 | 23.806 | 26.905 | 1.00 | 46.25 | A1 |
| ATOM | 824 | CD | GLU | 108 | 21.046 | 23.723 | 27.532 | 1.00 | 49.16 | A1 |
| ATOM | 825 | OE1 | GLU | 108 | 21.297 | 22.804 | 28.359 | 1.00 | 51.02 | A1 |
| ATOM | 826 | OE2 | GLU | 108 | 21.875 | 24.583 | 27.165 | 1.00 | 50.23 | A1 |
| ATOM | 827 | C | GLU | 108 | 18.599 | 25.342 | 23.511 | 1.00 | 37.27 | A1 |
| ATOM | 828 | O | GLU | 108 | 18.241 | 26.490 | 23.775 | 1.00 | 37.57 | A1 |
| ATOM | 829 | N | TYR | 109 | 18.882 | 24.972 | 22.272 | 1.00 | 35.87 | A1 |
| ATOM | 830 | CA | TYR | 109 | 18.903 | 25.983 | 21.205 | 1.00 | 34.61 | A1 |
| ATOM | 831 | CB | TYR | 109 | 20.347 | 26.276 | 20.786 | 1.00 | 35.12 | A1 |
| ATOM | 832 | CG | TYR | 109 | 21.247 | 26.738 | 21.886 | 1.00 | 37.02 | A1 |
| ATOM | 833 | CD1 | TYR | 109 | 21.082 | 27.983 | 22.469 | 1.00 | 37.99 | A1 |
| ATOM | 834 | CE1 | TYR | 109 | 21.878 | 28.388 | 23.506 | 1.00 | 39.54 | A1 |
| ATOM | 835 | CD2 | TYR | 109 | 22.238 | 25.905 | 22.370 | 1.00 | 38.09 | A1 |
| ATOM | 836 | CE2 | TYR | 109 | 23.033 | 26.284 | 23.413 | 1.00 | 40.11 | A1 |
| ATOM | 837 | CZ | TYR | 109 | 22.848 | 27.524 | 23.983 | 1.00 | 40.67 | A1 |
| ATOM | 838 | OH | TYR | 109 | 23.585 | 27.851 | 25.080 | 1.00 | 42.84 | A1 |
| ATOM | 839 | C | TYR | 109 | 18.178 | 25.739 | 19.900 | 1.00 | 32.13 | A1 |
| ATOM | 840 | O | TYR | 109 | 17.993 | 24.593 | 19.476 | 1.00 | 31.90 | A1 |
| ATOM | 841 | N | ALA | 110 | 17.817 | 26.857 | 19.272 | 1.00 | 30.38 | A1 |
| ATOM | 842 | CA | ALA | 110 | 17.290 | 26.885 | 17.897 | 1.00 | 28.86 | A1 |
| ATOM | 843 | CB | ALA | 110 | 15.995 | 27.591 | 17.836 | 1.00 | 28.37 | A1 |
| ATOM | 844 | C | ALA | 110 | 18.370 | 27.712 | 17.127 | 1.00 | 29.23 | A1 |
| ATOM | 845 | O | ALA | 110 | 18.794 | 28.810 | 17.575 | 1.00 | 29.93 | A1 |
| ATOM | 846 | N | ALA | 111 | 18.882 | 27.187 | 16.022 | 1.00 | 27.52 | A1 |
| ATOM | 847 | CA | ALA | 111 | 19.837 | 27.950 | 15.237 | 1.00 | 25.45 | A1 |

FIG. 3A-15

| | | | | | | | | | |
|---|---|---|---|---|---|---|---|---|---|
| ATOM | 848 | CB | ALA | 111 | 21.158 | 27.349 | 15.323 | 1.00 24.00 | A1 |
| ATOM | 849 | C | ALA | 111 | 19.368 | 27.907 | 13.778 | 1.00 25.60 | A1 |
| ATOM | 850 | O | ALA | 111 | 18.808 | 26.889 | 13.333 | 1.00 25.88 | A1 |
| ATOM | 851 | N | ALA | 112 | 19.592 | 29.004 | 13.048 | 1.00 24.52 | A1 |
| ATOM | 852 | CA | ALA | 112 | 19.264 | 29.091 | 11.617 | 1.00 24.43 | A1 |
| ATOM | 853 | CB | ALA | 112 | 17.946 | 29.749 | 11.434 | 1.00 21.58 | A1 |
| ATOM | 854 | C | ALA | 112 | 20.339 | 29.907 | 10.848 | 1.00 25.57 | A1 |
| ATOM | 855 | O | ALA | 112 | 20.956 | 30.820 | 11.398 | 1.00 26.18 | A1 |
| ATOM | 856 | N | GLN | 113 | 20.556 | 29.564 | 9.586 | 1.00 25.23 | A1 |
| ATOM | 857 | CA | GLN | 113 | 21.470 | 30.320 | 8.770 | 1.00 26.13 | A1 |
| ATOM | 858 | CB | GLN | 113 | 22.760 | 29.543 | 8.517 | 1.00 26.47 | A1 |
| ATOM | 859 | CG | GLN | 113 | 22.662 | 28.453 | 7.592 | 1.00 29.75 | A1 |
| ATOM | 860 | CD | GLN | 113 | 23.958 | 27.673 | 7.572 | 1.00 32.50 | A1 |
| ATOM | 861 | OE1 | GLN | 113 | 24.926 | 28.054 | 8.255 | 1.00 36.57 | A1 |
| ATOM | 862 | NE2 | GLN | 113 | 23.992 | 26.573 | 6.829 | 1.00 31.90 | A1 |
| ATOM | 863 | C | GLN | 113 | 20.694 | 30.579 | 7.471 | 1.00 25.66 | A1 |
| ATOM | 864 | O | GLN | 113 | 19.859 | 29.755 | 7.045 | 1.00 24.97 | A1 |
| ATOM | 865 | N | VAL | 114 | 20.925 | 31.745 | 6.882 | 1.00 24.78 | A1 |
| ATOM | 866 | CA | VAL | 114 | 20.225 | 32.103 | 5.673 | 1.00 25.47 | A1 |
| ATOM | 867 | CB | VAL | 114 | 19.161 | 33.207 | 5.911 | 1.00 24.56 | A1 |
| ATOM | 868 | CG1 | VAL | 114 | 18.648 | 33.687 | 4.571 | 1.00 24.37 | A1 |
| ATOM | 869 | CG2 | VAL | 114 | 18.009 | 32.716 | 6.747 | 1.00 22.99 | A1 |
| ATOM | 870 | C | VAL | 114 | 21.192 | 32.670 | 4.638 | 1.00 26.69 | A1 |
| ATOM | 871 | O | VAL | 114 | 22.091 | 33.446 | 4.989 | 1.00 26.92 | A1 |
| ATOM | 872 | N | VAL | 115 | 21.018 | 32.286 | 3.371 | 1.00 27.22 | A1 |
| ATOM | 873 | CA | VAL | 115 | 21.834 | 32.879 | 2.303 | 1.00 28.03 | A1 |
| ATOM | 874 | CB | VAL | 115 | 22.795 | 31.856 | 1.613 | 1.00 27.69 | A1 |
| ATOM | 875 | CG1 | VAL | 115 | 23.605 | 32.534 | 0.410 | 1.00 25.99 | A1 |
| ATOM | 876 | CG2 | VAL | 115 | 23.795 | 31.316 | 2.637 | 1.00 27.55 | A1 |
| ATOM | 877 | C | VAL | 115 | 20.865 | 33.507 | 1.254 | 1.00 29.18 | A1 |
| ATOM | 878 | O | VAL | 115 | 19.864 | 32.900 | 0.824 | 1.00 27.88 | A1 |
| ATOM | 879 | N | ILE | 116 | 21.131 | 34.767 | 0.932 | 1.00 30.60 | A1 |
| ATOM | 880 | CA | ILE | 116 | 20.367 | 35.486 | -0.076 | 1.00 32.32 | A1 |
| ATOM | 881 | CB | ILE | 116 | 19.787 | 36.777 | 0.501 | 1.00 31.54 | A1 |
| ATOM | 882 | CG2 | ILE | 116 | 19.258 | 37.657 | -0.621 | 1.00 30.92 | A1 |
| ATOM | 883 | CG1 | ILE | 116 | 18.651 | 36.419 | 1.510 | 1.00 30.97 | A1 |
| ATOM | 884 | CD1 | ILE | 116 | 17.956 | 37.568 | 2.088 | 1.00 29.63 | A1 |
| ATOM | 885 | C | ILE | 116 | 21.423 | 35.756 | -1.170 | 1.00 36.07 | A1 |
| ATOM | 886 | O | ILE | 116 | 22.425 | 36.468 | -0.958 | 1.00 35.04 | A1 |
| ATOM | 887 | N | GLU | 117 | 21.201 | 35.130 | -2.316 | 1.00 39.41 | A1 |
| ATOM | 888 | CA | GLU | 117 | 22.104 | 35.182 | -3.479 | 1.00 44.07 | A1 |
| ATOM | 889 | CB | GLU | 117 | 22.420 | 33.781 | -4.007 | 1.00 44.80 | A1 |
| ATOM | 890 | CG | GLU | 117 | 23.090 | 32.856 | -3.087 | 1.00 47.54 | A1 |
| ATOM | 891 | CD | GLU | 117 | 23.439 | 31.583 | -3.800 | 1.00 49.39 | A1 |
| ATOM | 892 | OE1 | GLU | 117 | 22.506 | 30.829 | -4.213 | 1.00 49.67 | A1 |
| ATOM | 893 | OE2 | GLU | 117 | 24.661 | 31.354 | -3.953 | 1.00 50.54 | A1 |
| ATOM | 894 | C | GLU | 117 | 21.527 | 35.833 | -4.701 | 1.00 45.98 | A1 |
| ATOM | 895 | O | GLU | 117 | 20.347 | 36.079 | -4.779 | 1.00 46.28 | A1 |
| ATOM | 896 | N | ALA | 118 | 22.396 | 36.016 | -5.696 | 1.00 49.81 | A1 |
| ATOM | 897 | CA | ALA | 118 | 22.012 | 36.546 | -7.004 | 1.00 53.49 | A1 |
| ATOM | 898 | CB | ALA | 118 | 23.271 | 36.985 | -7.787 | 1.00 53.10 | A1 |
| ATOM | 899 | C | ALA | 118 | 21.344 | 35.312 | -7.683 | 1.00 56.40 | A1 |
| ATOM | 900 | O | ALA | 118 | 21.759 | 34.156 | -7.466 | 1.00 56.33 | A1 |
| ATOM | 901 | N | LEU | 119 | 20.314 | 35.556 | -8.485 | 1.00 58.93 | A1 |
| ATOM | 902 | CA | LEU | 119 | 19.614 | 34.475 | -9.176 | 1.00 62.13 | A1 |
| ATOM | 903 | CB | LEU | 119 | 18.385 | 35.046 | -9.902 | 1.00 62.98 | A1 |
| ATOM | 904 | CG | LEU | 119 | 17.128 | 35.145 | -9.029 | 1.00 64.50 | A1 |

FIG. 3A-16

| ATOM | 905 | CD1 | LEU | 119 | 15.976 | 35.783 | -9.797 | 1.00 | 64.92 | A1 |
| ATOM | 906 | CD2 | LEU | 119 | 16.746 | 33.722 | -8.584 | 1.00 | 65.21 | A1 |
| ATOM | 907 | C | LEU | 119 | 20.484 | 33.670 | -10.164 | 1.00 | 63.60 | A1 |
| ATOM | 908 | OT1 | LEU | 119 | 21.489 | 34.207 | -10.695 | 1.00 | 64.51 | A1 |
| ATOM | 909 | OT2 | LEU | 119 | 20.141 | 32.490 | -10.403 | 1.00 | 64.56 | A1 |
| ATOM | 910 | CB | ALA | 2 | 31.204 | 30.268 | -1.737 | 1.00 | 26.39 | B1 |
| ATOM | 911 | C | ALA | 2 | 33.074 | 29.689 | -3.244 | 1.00 | 25.91 | B1 |
| ATOM | 912 | O | ALA | 2 | 33.105 | 28.570 | -3.739 | 1.00 | 26.11 | B1 |
| ATOM | 913 | N | ALA | 2 | 30.781 | 29.877 | -4.115 | 1.00 | 25.73 | B1 |
| ATOM | 914 | CA | ALA | 2 | 31.761 | 30.434 | -3.139 | 1.00 | 25.92 | B1 |
| ATOM | 915 | N | TYR | 3 | 34.150 | 30.270 | -2.707 | 1.00 | 25.88 | B1 |
| ATOM | 916 | CA | TYR | 3 | 35.481 | 29.614 | -2.742 | 1.00 | 26.08 | B1 |
| ATOM | 917 | CB | TYR | 3 | 36.575 | 30.662 | -2.886 | 1.00 | 26.57 | B1 |
| ATOM | 918 | CG | TYR | 3 | 36.421 | 31.481 | -4.102 | 1.00 | 27.82 | B1 |
| ATOM | 919 | CD1 | TYR | 3 | 36.818 | 32.814 | -4.122 | 1.00 | 29.29 | B1 |
| ATOM | 920 | CE1 | TYR | 3 | 36.734 | 33.556 | -5.296 | 1.00 | 28.29 | B1 |
| ATOM | 921 | CD2 | TYR | 3 | 35.931 | 30.921 | -5.281 | 1.00 | 29.34 | B1 |
| ATOM | 922 | CE2 | TYR | 3 | 35.840 | 31.655 | -6.439 | 1.00 | 28.63 | B1 |
| ATOM | 923 | CZ | TYR | 3 | 36.243 | 32.960 | -6.437 | 1.00 | 28.80 | B1 |
| ATOM | 924 | OH | TYR | 3 | 36.164 | 33.677 | -7.609 | 1.00 | 30.80 | B1 |
| ATOM | 925 | C | TYR | 3 | 35.772 | 28.792 | -1.465 | 1.00 | 25.12 | B1 |
| ATOM | 926 | O | TYR | 3 | 36.490 | 27.795 | -1.518 | 1.00 | 23.25 | B1 |
| ATOM | 927 | N | GLY | 4 | 35.235 | 29.257 | -0.326 | 1.00 | 25.05 | B1 |
| ATOM | 928 | CA | GLY | 4 | 35.397 | 28.565 | 0.958 | 1.00 | 23.80 | B1 |
| ATOM | 929 | C | GLY | 4 | 34.387 | 29.073 | 1.990 | 1.00 | 24.49 | B1 |
| ATOM | 930 | O | GLY | 4 | 33.838 | 30.213 | 1.843 | 1.00 | 23.38 | B1 |
| ATOM | 931 | N | ILE | 5 | 34.096 | 28.253 | 3.014 | 1.00 | 24.35 | B1 |
| ATOM | 932 | CA | ILE | 5 | 33.215 | 28.684 | 4.077 | 1.00 | 24.74 | B1 |
| ATOM | 933 | CB | ILE | 5 | 31.806 | 28.117 | 3.996 | 1.00 | 25.07 | B1 |
| ATOM | 934 | CG2 | ILE | 5 | 31.156 | 28.471 | 2.641 | 1.00 | 24.89 | B1 |
| ATOM | 935 | CG1 | ILE | 5 | 31.819 | 26.585 | 4.228 | 1.00 | 26.94 | B1 |
| ATOM | 936 | CD1 | ILE | 5 | 30.415 | 25.916 | 4.024 | 1.00 | 25.53 | B1 |
| ATOM | 937 | C | ILE | 5 | 33.812 | 28.256 | 5.382 | 1.00 | 25.64 | B1 |
| ATOM | 938 | O | ILE | 5 | 34.669 | 27.397 | 5.431 | 1.00 | 26.38 | B1 |
| ATOM | 939 | N | GLY | 6 | 33.356 | 28.860 | 6.457 | 1.00 | 25.30 | B1 |
| ATOM | 940 | CA | GLY | 6 | 33.864 | 28.495 | 7.752 | 1.00 | 25.02 | B1 |
| ATOM | 941 | C | GLY | 6 | 32.887 | 28.860 | 8.862 | 1.00 | 25.03 | B1 |
| ATOM | 942 | O | GLY | 6 | 32.180 | 29.886 | 8.809 | 1.00 | 24.21 | B1 |
| ATOM | 943 | N | LEU | 7 | 32.882 | 28.022 | 9.892 | 1.00 | 25.45 | B1 |
| ATOM | 944 | CA | LEU | 7 | 32.023 | 28.217 | 11.036 | 1.00 | 26.13 | B1 |
| ATOM | 945 | CB | LEU | 7 | 30.893 | 27.176 | 11.031 | 1.00 | 27.37 | B1 |
| ATOM | 946 | CG | LEU | 7 | 29.911 | 27.230 | 12.202 | 1.00 | 27.44 | B1 |
| ATOM | 947 | CD1 | LEU | 7 | 29.025 | 28.487 | 12.083 | 1.00 | 28.47 | B1 |
| ATOM | 948 | CD2 | LEU | 7 | 29.047 | 26.014 | 12.156 | 1.00 | 27.61 | B1 |
| ATOM | 949 | C | LEU | 7 | 32.836 | 28.022 | 12.306 | 1.00 | 26.61 | B1 |
| ATOM | 950 | O | LEU | 7 | 33.773 | 27.217 | 12.350 | 1.00 | 26.23 | B1 |
| ATOM | 951 | N | ASP | 8 | 32.474 | 28.777 | 13.338 | 1.00 | 27.29 | B1 |
| ATOM | 952 | CA | ASP | 8 | 33.126 | 28.645 | 14.649 | 1.00 | 28.31 | B1 |
| ATOM | 953 | CB | ASP | 8 | 34.444 | 29.445 | 14.775 | 1.00 | 29.82 | B1 |
| ATOM | 954 | CG | ASP | 8 | 35.210 | 29.094 | 16.096 | 1.00 | 32.76 | B1 |
| ATOM | 955 | OD1 | ASP | 8 | 35.069 | 29.848 | 17.084 | 1.00 | 32.47 | B1 |
| ATOM | 956 | OD2 | ASP | 8 | 35.929 | 28.040 | 16.138 | 1.00 | 33.99 | B1 |
| ATOM | 957 | C | ASP | 8 | 32.194 | 29.076 | 15.750 | 1.00 | 26.75 | B1 |
| ATOM | 958 | O | ASP | 8 | 31.471 | 30.067 | 15.628 | 1.00 | 25.85 | B1 |
| ATOM | 959 | N | ILE | 9 | 32.193 | 28.280 | 16.805 | 1.00 | 26.88 | B1 |
| ATOM | 960 | CA | ILE | 9 | 31.379 | 28.564 | 17.999 | 1.00 | 27.43 | B1 |
| ATOM | 961 | CB | ILE | 9 | 30.312 | 27.446 | 18.244 | 1.00 | 27.59 | B1 |

FIG. 3A-17

| ATOM | 962 | CG2 | ILE | 9 | 29.559 | 27.658 | 19.599 | 1.00 | 27.04 | B1 |
| ATOM | 963 | CG1 | ILE | 9 | 29.318 | 27.430 | 17.044 | 1.00 | 28.13 | B1 |
| ATOM | 964 | CD1 | ILE | 9 | 28.148 | 26.387 | 17.150 | 1.00 | 27.19 | B1 |
| ATOM | 965 | C | ILE | 9 | 32.382 | 28.611 | 19.145 | 1.00 | 28.24 | B1 |
| ATOM | 966 | O | ILE | 9 | 33.151 | 27.690 | 19.321 | 1.00 | 28.60 | B1 |
| ATOM | 967 | N | THR | 10 | 32.353 | 29.685 | 19.926 | 1.00 | 29.28 | B1 |
| ATOM | 968 | CA | THR | 10 | 33.249 | 29.864 | 21.057 | 1.00 | 30.48 | B1 |
| ATOM | 969 | CB | THR | 10 | 34.188 | 31.052 | 20.742 | 1.00 | 31.33 | B1 |
| ATOM | 970 | OG1 | THR | 10 | 35.169 | 30.594 | 19.789 | 1.00 | 34.42 | B1 |
| ATOM | 971 | CG2 | THR | 10 | 34.917 | 31.538 | 21.956 | 1.00 | 32.00 | B1 |
| ATOM | 972 | C | THR | 10 | 32.526 | 30.036 | 22.419 | 1.00 | 29.95 | B1 |
| ATOM | 973 | O | THR | 10 | 31.531 | 30.720 | 22.529 | 1.00 | 28.39 | B1 |
| ATOM | 974 | N | GLU | 11 | 33.048 | 29.399 | 23.464 | 1.00 | 31.32 | B1 |
| ATOM | 975 | CA | GLU | 11 | 32.403 | 29.472 | 24.801 | 1.00 | 31.87 | B1 |
| ATOM | 976 | CB | GLU | 11 | 32.835 | 28.289 | 25.676 | 1.00 | 33.64 | B1 |
| ATOM | 977 | CG | GLU | 11 | 31.716 | 27.784 | 26.547 | 1.00 | 40.24 | B1 |
| ATOM | 978 | CD | GLU | 11 | 32.181 | 27.028 | 27.821 | 1.00 | 43.39 | B1 |
| ATOM | 979 | OE1 | GLU | 11 | 33.344 | 26.499 | 27.873 | 1.00 | 44.86 | B1 |
| ATOM | 980 | OE2 | GLU | 11 | 31.343 | 26.941 | 28.766 | 1.00 | 45.49 | B1 |
| ATOM | 981 | C | GLU | 11 | 32.804 | 30.770 | 25.481 | 1.00 | 30.40 | B1 |
| ATOM | 982 | O | GLU | 11 | 33.992 | 31.004 | 25.678 | 1.00 | 29.17 | B1 |
| ATOM | 983 | N | LEU | 12 | 31.823 | 31.610 | 25.801 | 1.00 | 29.04 | B1 |
| ATOM | 984 | CA | LEU | 12 | 32.089 | 32.876 | 26.454 | 1.00 | 31.07 | B1 |
| ATOM | 985 | CB | LEU | 12 | 30.801 | 33.681 | 26.662 | 1.00 | 32.99 | B1 |
| ATOM | 986 | CG | LEU | 12 | 30.053 | 34.021 | 25.359 | 1.00 | 35.90 | B1 |
| ATOM | 987 | CD1 | LEU | 12 | 28.665 | 34.596 | 25.624 | 1.00 | 35.82 | B1 |
| ATOM | 988 | CD2 | LEU | 12 | 30.901 | 35.004 | 24.552 | 1.00 | 36.85 | B1 |
| ATOM | 989 | C | LEU | 12 | 32.815 | 32.740 | 27.816 | 1.00 | 31.80 | B1 |
| ATOM | 990 | O | LEU | 12 | 33.708 | 33.553 | 28.106 | 1.00 | 31.13 | B1 |
| ATOM | 991 | N | ALA | 13 | 32.448 | 31.741 | 28.634 | 1.00 | 31.23 | B1 |
| ATOM | 992 | CA | ALA | 13 | 33.123 | 31.588 | 29.927 | 1.00 | 32.54 | B1 |
| ATOM | 993 | CB | ALA | 13 | 32.413 | 30.507 | 30.881 | 1.00 | 32.09 | B1 |
| ATOM | 994 | C | ALA | 13 | 34.588 | 31.260 | 29.733 | 1.00 | 31.41 | B1 |
| ATOM | 995 | O | ALA | 13 | 35.431 | 31.793 | 30.433 | 1.00 | 30.77 | B1 |
| ATOM | 996 | N | ARG | 14 | 34.891 | 30.414 | 28.754 | 1.00 | 31.73 | B1 |
| ATOM | 997 | CA | ARG | 14 | 36.286 | 30.039 | 28.459 | 1.00 | 30.99 | B1 |
| ATOM | 998 | CB | ARG | 14 | 36.259 | 29.020 | 27.327 | 1.00 | 30.57 | B1 |
| ATOM | 999 | CG | ARG | 14 | 37.526 | 28.328 | 27.173 | 1.00 | 31.14 | B1 |
| ATOM | 1000 | CD | ARG | 14 | 37.522 | 27.371 | 26.023 | 1.00 | 32.79 | B1 |
| ATOM | 1001 | NE | ARG | 14 | 38.887 | 26.847 | 25.848 | 1.00 | 32.33 | B1 |
| ATOM | 1002 | CZ | ARG | 14 | 39.262 | 25.977 | 24.925 | 1.00 | 31.66 | B1 |
| ATOM | 1003 | NH1 | ARG | 14 | 38.383 | 25.511 | 24.042 | 1.00 | 31.62 | B1 |
| ATOM | 1004 | NH2 | ARG | 14 | 40.513 | 25.543 | 24.926 | 1.00 | 31.83 | B1 |
| ATOM | 1005 | C | ARG | 14 | 37.125 | 31.325 | 28.076 | 1.00 | 30.35 | B1 |
| ATOM | 1006 | O | ARG | 14 | 38.204 | 31.580 | 28.588 | 1.00 | 29.54 | B1 |
| ATOM | 1007 | N | ILE | 15 | 36.585 | 32.141 | 27.185 | 1.00 | 30.11 | B1 |
| ATOM | 1008 | CA | ILE | 15 | 37.218 | 33.400 | 26.814 | 1.00 | 30.69 | B1 |
| ATOM | 1009 | CB | ILE | 15 | 36.361 | 34.204 | 25.754 | 1.00 | 30.02 | B1 |
| ATOM | 1010 | CG2 | ILE | 15 | 36.816 | 35.678 | 25.717 | 1.00 | 28.67 | B1 |
| ATOM | 1011 | CG1 | ILE | 15 | 36.417 | 33.502 | 24.393 | 1.00 | 28.37 | B1 |
| ATOM | 1012 | CD1 | ILE | 15 | 37.778 | 33.454 | 23.791 | 1.00 | 27.34 | B1 |
| ATOM | 1013 | C | ILE | 15 | 37.362 | 34.280 | 28.074 | 1.00 | 30.92 | B1 |
| ATOM | 1014 | O | ILE | 15 | 38.439 | 34.823 | 28.358 | 1.00 | 31.82 | B1 |
| ATOM | 1015 | N | ALA | 16 | 36.283 | 34.443 | 28.805 | 1.00 | 30.39 | B1 |
| ATOM | 1016 | CA | ALA | 16 | 36.326 | 35.247 | 30.020 | 1.00 | 31.94 | B1 |
| ATOM | 1017 | CB | ALA | 16 | 34.941 | 35.199 | 30.765 | 1.00 | 29.82 | B1 |
| ATOM | 1018 | C | ALA | 16 | 37.475 | 34.791 | 30.969 | 1.00 | 32.80 | B1 |

FIG. 3A-18

| ATOM | 1019 | O | ALA | 16 | 38.254 | 35.621 | 31.429 | 1.00 | 34.32 | B1 |
| ATOM | 1020 | N | SER | 17 | 37.568 | 33.501 | 31.267 | 1.00 | 32.89 | B1 |
| ATOM | 1021 | CA | SER | 17 | 38.629 | 32.978 | 32.125 | 1.00 | 34.00 | B1 |
| ATOM | 1022 | CB | SER | 17 | 38.517 | 31.476 | 32.260 | 1.00 | 32.84 | B1 |
| ATOM | 1023 | OG | SER | 17 | 37.194 | 31.136 | 32.461 | 1.00 | 35.05 | B1 |
| ATOM | 1024 | C | SER | 17 | 40.018 | 33.242 | 31.561 | 1.00 | 34.86 | B1 |
| ATOM | 1025 | O | SER | 17 | 40.946 | 33.597 | 32.273 | 1.00 | 33.03 | B1 |
| ATOM | 1026 | N | MET | 18 | 40.160 | 32.993 | 30.270 | 1.00 | 37.22 | B1 |
| ATOM | 1027 | CA | MET | 18 | 41.450 | 33.205 | 29.637 | 1.00 | 39.40 | B1 |
| ATOM | 1028 | CB | MET | 18 | 41.446 | 32.790 | 28.186 | 1.00 | 41.45 | B1 |
| ATOM | 1029 | CG | MET | 18 | 41.697 | 31.321 | 27.987 | 1.00 | 45.54 | B1 |
| ATOM | 1030 | SD | MET | 18 | 41.922 | 31.024 | 26.211 | 1.00 | 50.43 | B1 |
| ATOM | 1031 | CE | MET | 18 | 40.247 | 30.845 | 25.782 | 1.00 | 48.09 | B1 |
| ATOM | 1032 | C | MET | 18 | 41.878 | 34.643 | 29.726 | 1.00 | 39.53 | B1 |
| ATOM | 1033 | O | MET | 18 | 43.020 | 34.910 | 30.119 | 1.00 | 40.11 | B1 |
| ATOM | 1034 | N | ALA | 19 | 41.003 | 35.574 | 29.376 | 1.00 | 39.08 | B1 |
| ATOM | 1035 | CA | ALA | 19 | 41.412 | 36.973 | 29.473 | 1.00 | 39.54 | B1 |
| ATOM | 1036 | CB | ALA | 19 | 40.327 | 37.933 | 28.907 | 1.00 | 38.99 | B1 |
| ATOM | 1037 | C | ALA | 19 | 41.715 | 37.317 | 30.925 | 1.00 | 39.55 | B1 |
| ATOM | 1038 | O | ALA | 19 | 42.608 | 38.115 | 31.168 | 1.00 | 40.32 | B1 |
| ATOM | 1039 | N | GLY | 20 | 41.005 | 36.718 | 31.888 | 1.00 | 39.22 | B1 |
| ATOM | 1040 | CA | GLY | 20 | 41.269 | 37.037 | 33.277 | 1.00 | 39.09 | B1 |
| ATOM | 1041 | C | GLY | 20 | 42.655 | 36.569 | 33.713 | 1.00 | 39.90 | B1 |
| ATOM | 1042 | O | GLY | 20 | 43.421 | 37.278 | 34.382 | 1.00 | 39.40 | B1 |
| ATOM | 1043 | N | ARG | 21 | 42.957 | 35.353 | 33.288 | 1.00 | 39.88 | B1 |
| ATOM | 1044 | CA | ARG | 21 | 44.192 | 34.626 | 33.543 | 1.00 | 40.39 | B1 |
| ATOM | 1045 | CB | ARG | 21 | 43.920 | 33.149 | 33.162 | 1.00 | 39.16 | B1 |
| ATOM | 1046 | CG | ARG | 21 | 44.701 | 32.071 | 33.882 | 1.00 | 37.29 | B1 |
| ATOM | 1047 | CD | ARG | 21 | 44.013 | 30.718 | 33.776 | 1.00 | 35.14 | B1 |
| ATOM | 1048 | NE | ARG | 21 | 43.669 | 30.325 | 32.393 | 1.00 | 33.14 | B1 |
| ATOM | 1049 | CZ | ARG | 21 | 42.451 | 29.918 | 32.010 | 1.00 | 32.97 | B1 |
| ATOM | 1050 | NH1 | ARG | 21 | 41.444 | 29.861 | 32.898 | 1.00 | 32.98 | B1 |
| ATOM | 1051 | NH2 | ARG | 21 | 42.234 | 29.515 | 30.767 | 1.00 | 30.26 | B1 |
| ATOM | 1052 | C | ARG | 21 | 45.383 | 35.225 | 32.728 | 1.00 | 41.48 | B1 |
| ATOM | 1053 | O | ARG | 21 | 46.556 | 35.161 | 33.147 | 1.00 | 41.49 | B1 |
| ATOM | 1054 | N | GLN | 22 | 45.086 | 35.851 | 31.590 | 1.00 | 42.70 | B1 |
| ATOM | 1055 | CA | GLN | 22 | 46.149 | 36.426 | 30.758 | 1.00 | 43.56 | B1 |
| ATOM | 1056 | CB | GLN | 22 | 46.536 | 35.439 | 29.664 | 1.00 | 45.80 | B1 |
| ATOM | 1057 | CG | GLN | 22 | 47.813 | 35.827 | 28.972 | 1.00 | 49.05 | B1 |
| ATOM | 1058 | CD | GLN | 22 | 48.970 | 35.490 | 29.843 | 1.00 | 50.23 | B1 |
| ATOM | 1059 | OE1 | GLN | 22 | 49.851 | 36.326 | 30.101 | 1.00 | 50.93 | B1 |
| ATOM | 1060 | NE2 | GLN | 22 | 48.977 | 34.246 | 30.334 | 1.00 | 51.27 | B1 |
| ATOM | 1061 | C | GLN | 22 | 45.786 | 37.747 | 30.114 | 1.00 | 43.68 | B1 |
| ATOM | 1062 | O | GLN | 22 | 45.133 | 37.782 | 29.071 | 1.00 | 43.58 | B1 |
| ATOM | 1063 | N | LYS | 23 | 46.234 | 38.841 | 30.721 | 1.00 | 44.50 | B1 |
| ATOM | 1064 | CA | LYS | 23 | 45.932 | 40.197 | 30.213 | 1.00 | 45.41 | B1 |
| ATOM | 1065 | CB | LYS | 23 | 46.577 | 41.263 | 31.174 | 1.00 | 46.07 | B1 |
| ATOM | 1066 | C | LYS | 23 | 46.286 | 40.529 | 28.721 | 1.00 | 45.13 | B1 |
| ATOM | 1067 | O | LYS | 23 | 45.670 | 41.419 | 28.111 | 1.00 | 45.95 | B1 |
| ATOM | 1068 | N | ARG | 24 | 47.252 | 39.828 | 28.137 | 1.00 | 44.79 | B1 |
| ATOM | 1069 | CA | ARG | 24 | 47.647 | 40.066 | 26.734 | 1.00 | 44.30 | B1 |
| ATOM | 1070 | CB | ARG | 24 | 49.161 | 39.813 | 26.558 | 1.00 | 45.66 | B1 |
| ATOM | 1071 | CG | ARG | 24 | 50.091 | 40.916 | 27.138 | 1.00 | 48.65 | B1 |
| ATOM | 1072 | CD | ARG | 24 | 51.545 | 40.424 | 27.439 | 1.00 | 51.04 | B1 |
| ATOM | 1073 | NE | ARG | 24 | 52.170 | 39.768 | 26.281 | 1.00 | 53.16 | B1 |
| ATOM | 1074 | CZ | ARG | 24 | 52.409 | 38.460 | 26.181 | 1.00 | 52.98 | B1 |
| ATOM | 1075 | NH1 | ARG | 24 | 52.098 | 37.631 | 27.176 | 1.00 | 52.77 | B1 |

FIG. 3A-19

| ATOM | 1076 | NH2 | ARG | 24 | 52.911 | 37.976 | 25.050 | 1.00 | 53.75 | B1 |
|---|---|---|---|---|---|---|---|---|---|---|
| ATOM | 1077 | C | ARG | 24 | 46.862 | 39.224 | 25.682 | 1.00 | 43.41 | B1 |
| ATOM | 1078 | O | ARG | 24 | 47.117 | 39.342 | 24.476 | 1.00 | 41.77 | B1 |
| ATOM | 1079 | N | PHE | 25 | 45.904 | 38.396 | 26.122 | 1.00 | 41.98 | B1 |
| ATOM | 1080 | CA | PHE | 25 | 45.153 | 37.588 | 25.159 | 1.00 | 41.18 | B1 |
| ATOM | 1081 | CB | PHE | 25 | 44.145 | 36.674 | 25.866 | 1.00 | 40.68 | B1 |
| ATOM | 1082 | CG | PHE | 25 | 43.188 | 35.966 | 24.926 | 1.00 | 41.90 | B1 |
| ATOM | 1083 | CD1 | PHE | 25 | 43.657 | 35.222 | 23.852 | 1.00 | 40.31 | B1 |
| ATOM | 1084 | CD2 | PHE | 25 | 41.796 | 35.990 | 25.168 | 1.00 | 42.65 | B1 |
| ATOM | 1085 | CE1 | PHE | 25 | 42.793 | 34.515 | 23.047 | 1.00 | 40.58 | B1 |
| ATOM | 1086 | CE2 | PHE | 25 | 40.904 | 35.265 | 24.342 | 1.00 | 42.06 | B1 |
| ATOM | 1087 | CZ | PHE | 25 | 41.403 | 34.532 | 23.290 | 1.00 | 41.02 | B1 |
| ATOM | 1088 | C | PHE | 25 | 44.432 | 38.438 | 24.128 | 1.00 | 39.93 | B1 |
| ATOM | 1089 | O | PHE | 25 | 44.489 | 38.151 | 22.944 | 1.00 | 40.29 | B1 |
| ATOM | 1090 | N | ALA | 26 | 43.778 | 39.500 | 24.569 | 1.00 | 39.38 | B1 |
| ATOM | 1091 | CA | ALA | 26 | 43.052 | 40.358 | 23.659 | 1.00 | 39.11 | B1 |
| ATOM | 1092 | CB | ALA | 26 | 42.214 | 41.368 | 24.439 | 1.00 | 39.81 | B1 |
| ATOM | 1093 | C | ALA | 26 | 43.943 | 41.073 | 22.667 | 1.00 | 39.48 | B1 |
| ATOM | 1094 | O | ALA | 26 | 43.532 | 41.289 | 21.525 | 1.00 | 39.36 | B1 |
| ATOM | 1095 | N | GLU | 27 | 45.151 | 41.446 | 23.090 | 1.00 | 39.52 | B1 |
| ATOM | 1096 | CA | GLU | 27 | 46.105 | 42.137 | 22.214 | 1.00 | 39.44 | B1 |
| ATOM | 1097 | CB | GLU | 27 | 47.359 | 42.618 | 22.972 | 1.00 | 42.26 | B1 |
| ATOM | 1098 | CG | GLU | 27 | 47.153 | 43.846 | 23.880 | 1.00 | 46.62 | B1 |
| ATOM | 1099 | CD | GLU | 27 | 48.453 | 44.311 | 24.546 | 1.00 | 49.04 | B1 |
| ATOM | 1100 | OE1 | GLU | 27 | 48.791 | 43.779 | 25.635 | 1.00 | 49.32 | B1 |
| ATOM | 1101 | OE2 | GLU | 27 | 49.145 | 45.198 | 23.959 | 1.00 | 51.13 | B1 |
| ATOM | 1102 | C | GLU | 27 | 46.572 | 41.231 | 21.114 | 1.00 | 37.83 | B1 |
| ATOM | 1103 | O | GLU | 27 | 46.871 | 41.700 | 20.010 | 1.00 | 36.89 | B1 |
| ATOM | 1104 | N | ARG | 28 | 46.660 | 39.938 | 21.414 | 1.00 | 35.85 | B1 |
| ATOM | 1105 | CA | ARG | 28 | 47.092 | 38.981 | 20.403 | 1.00 | 35.38 | B1 |
| ATOM | 1106 | CB | ARG | 28 | 47.359 | 37.617 | 21.011 | 1.00 | 35.61 | B1 |
| ATOM | 1107 | CG | ARG | 28 | 48.442 | 36.892 | 20.272 | 1.00 | 37.83 | B1 |
| ATOM | 1108 | CD | ARG | 28 | 48.482 | 35.423 | 20.638 | 1.00 | 40.08 | B1 |
| ATOM | 1109 | NE | ARG | 28 | 49.440 | 34.762 | 19.763 | 1.00 | 41.90 | B1 |
| ATOM | 1110 | CZ | ARG | 28 | 50.761 | 34.831 | 19.905 | 1.00 | 43.04 | B1 |
| ATOM | 1111 | NH1 | ARG | 28 | 51.318 | 35.525 | 20.919 | 1.00 | 42.06 | B1 |
| ATOM | 1112 | NH2 | ARG | 28 | 51.532 | 34.225 | 18.999 | 1.00 | 43.51 | B1 |
| ATOM | 1113 | C | ARG | 28 | 46.041 | 38.782 | 19.314 | 1.00 | 34.81 | B1 |
| ATOM | 1114 | O | ARG | 28 | 46.384 | 38.692 | 18.146 | 1.00 | 34.82 | B1 |
| ATOM | 1115 | N | ILE | 29 | 44.770 | 38.705 | 19.727 | 1.00 | 34.29 | B1 |
| ATOM | 1116 | CA | ILE | 29 | 43.608 | 38.476 | 18.854 | 1.00 | 33.36 | B1 |
| ATOM | 1117 | CB | ILE | 29 | 42.388 | 38.009 | 19.716 | 1.00 | 32.64 | B1 |
| ATOM | 1118 | CG2 | ILE | 29 | 41.199 | 37.626 | 18.834 | 1.00 | 33.38 | B1 |
| ATOM | 1119 | CG1 | ILE | 29 | 42.790 | 36.826 | 20.581 | 1.00 | 32.81 | B1 |
| ATOM | 1120 | CD1 | ILE | 29 | 43.503 | 35.659 | 19.828 | 1.00 | 33.12 | B1 |
| ATOM | 1121 | C | ILE | 29 | 43.135 | 39.669 | 18.008 | 1.00 | 33.56 | B1 |
| ATOM | 1122 | O | ILE | 29 | 42.800 | 39.519 | 16.818 | 1.00 | 33.84 | B1 |
| ATOM | 1123 | N | LEU | 30 | 43.132 | 40.849 | 18.624 | 1.00 | 33.60 | B1 |
| ATOM | 1124 | CA | LEU | 30 | 42.591 | 42.069 | 18.017 | 1.00 | 34.10 | B1 |
| ATOM | 1125 | CB | LEU | 30 | 41.805 | 42.837 | 19.103 | 1.00 | 31.55 | B1 |
| ATOM | 1126 | CG | LEU | 30 | 40.805 | 41.980 | 19.917 | 1.00 | 30.29 | B1 |
| ATOM | 1127 | CD1 | LEU | 30 | 40.166 | 42.792 | 21.065 | 1.00 | 27.41 | B1 |
| ATOM | 1128 | CD2 | LEU | 30 | 39.717 | 41.460 | 18.934 | 1.00 | 28.50 | B1 |
| ATOM | 1129 | C | LEU | 30 | 43.577 | 43.006 | 17.365 | 1.00 | 35.65 | B1 |
| ATOM | 1130 | O | LEU | 30 | 44.731 | 43.105 | 17.773 | 1.00 | 37.79 | B1 |
| ATOM | 1131 | N | THR | 31 | 43.140 | 43.704 | 16.340 | 1.00 | 36.42 | B1 |
| ATOM | 1132 | CA | THR | 31 | 44.028 | 44.678 | 15.724 | 1.00 | 37.57 | B1 |

FIG. 3A-20

| ATOM | 1133 | CB | THR | 31 | 43.492 | 45.135 | 14.355 | 1.00 | 36.44 | B1 |
|---|---|---|---|---|---|---|---|---|---|---|
| ATOM | 1134 | OG1 | THR | 31 | 42.186 | 45.710 | 14.536 | 1.00 | 36.56 | B1 |
| ATOM | 1135 | CG2 | THR | 31 | 43.453 | 43.974 | 13.400 | 1.00 | 34.20 | B1 |
| ATOM | 1136 | C | THR | 31 | 43.988 | 45.866 | 16.684 | 1.00 | 38.90 | B1 |
| ATOM | 1137 | O | THR | 31 | 43.210 | 45.852 | 17.633 | 1.00 | 39.30 | B1 |
| ATOM | 1138 | N | ARG | 32 | 44.783 | 46.912 | 16.445 | 1.00 | 40.92 | B1 |
| ATOM | 1139 | CA | ARG | 32 | 44.761 | 48.057 | 17.370 | 1.00 | 42.16 | B1 |
| ATOM | 1140 | CB | ARG | 32 | 45.849 | 49.077 | 17.034 | 1.00 | 43.63 | B1 |
| ATOM | 1141 | CG | ARG | 32 | 46.249 | 49.896 | 18.307 | 1.00 | 45.88 | B1 |
| ATOM | 1142 | CD | ARG | 32 | 47.069 | 51.105 | 17.912 | 1.00 | 47.41 | B1 |
| ATOM | 1143 | NE | ARG | 32 | 47.817 | 50.791 | 16.700 | 1.00 | 49.09 | B1 |
| ATOM | 1144 | CZ | ARG | 32 | 49.068 | 50.357 | 16.675 | 1.00 | 49.50 | B1 |
| ATOM | 1145 | NH1 | ARG | 32 | 49.733 | 50.188 | 17.810 | 1.00 | 49.69 | B1 |
| ATOM | 1146 | NH2 | ARG | 32 | 49.650 | 50.097 | 15.506 | 1.00 | 50.68 | B1 |
| ATOM | 1147 | C | ARG | 32 | 43.402 | 48.763 | 17.353 | 1.00 | 42.65 | B1 |
| ATOM | 1148 | O | ARG | 32 | 42.878 | 49.222 | 18.391 | 1.00 | 41.41 | B1 |
| ATOM | 1149 | N | SER | 33 | 42.838 | 48.852 | 16.151 | 1.00 | 42.81 | B1 |
| ATOM | 1150 | CA | SER | 33 | 41.550 | 49.464 | 16.015 | 1.00 | 43.76 | B1 |
| ATOM | 1151 | CB | SER | 33 | 41.261 | 49.643 | 14.540 | 1.00 | 43.52 | B1 |
| ATOM | 1152 | OG | SER | 33 | 39.873 | 49.782 | 14.386 | 1.00 | 46.24 | B1 |
| ATOM | 1153 | C | SER | 33 | 40.438 | 48.629 | 16.733 | 1.00 | 43.65 | B1 |
| ATOM | 1154 | O | SER | 33 | 39.574 | 49.182 | 17.415 | 1.00 | 44.48 | B1 |
| ATOM | 1155 | N | GLU | 34 | 40.475 | 47.305 | 16.607 | 1.00 | 42.94 | B1 |
| ATOM | 1156 | CA | GLU | 34 | 39.470 | 46.465 | 17.259 | 1.00 | 41.95 | B1 |
| ATOM | 1157 | CB | GLU | 34 | 39.628 | 45.001 | 16.835 | 1.00 | 40.95 | B1 |
| ATOM | 1158 | CG | GLU | 34 | 39.348 | 44.750 | 15.393 | 1.00 | 40.15 | B1 |
| ATOM | 1159 | CD | GLU | 34 | 39.605 | 43.309 | 14.967 | 1.00 | 40.92 | B1 |
| ATOM | 1160 | OE1 | GLU | 34 | 40.597 | 42.695 | 15.431 | 1.00 | 40.90 | B1 |
| ATOM | 1161 | OE2 | GLU | 34 | 38.823 | 42.793 | 14.150 | 1.00 | 40.87 | B1 |
| ATOM | 1162 | C | GLU | 34 | 39.687 | 46.593 | 18.753 | 1.00 | 41.77 | B1 |
| ATOM | 1163 | O | GLU | 34 | 38.749 | 46.677 | 19.535 | 1.00 | 41.48 | B1 |
| ATOM | 1164 | N | LEU | 35 | 40.956 | 46.623 | 19.125 | 1.00 | 42.42 | B1 |
| ATOM | 1165 | CA | LEU | 35 | 41.393 | 46.745 | 20.504 | 1.00 | 43.24 | B1 |
| ATOM | 1166 | CB | LEU | 35 | 42.904 | 46.713 | 20.538 | 1.00 | 43.31 | B1 |
| ATOM | 1167 | CG | LEU | 35 | 43.622 | 45.884 | 21.580 | 1.00 | 43.75 | B1 |
| ATOM | 1168 | CD1 | LEU | 35 | 44.944 | 46.592 | 21.876 | 1.00 | 43.54 | B1 |
| ATOM | 1169 | CD2 | LEU | 35 | 42.805 | 45.720 | 22.833 | 1.00 | 43.33 | B1 |
| ATOM | 1170 | C | LEU | 35 | 40.897 | 48.053 | 21.130 | 1.00 | 43.93 | B1 |
| ATOM | 1171 | O | LEU | 35 | 40.421 | 48.060 | 22.280 | 1.00 | 43.01 | B1 |
| ATOM | 1172 | N | ASP | 36 | 41.005 | 49.157 | 20.387 | 1.00 | 44.72 | B1 |
| ATOM | 1173 | CA | ASP | 36 | 40.522 | 50.411 | 20.939 | 1.00 | 46.43 | B1 |
| ATOM | 1174 | CB | ASP | 36 | 40.834 | 51.625 | 20.047 | 1.00 | 46.32 | B1 |
| ATOM | 1175 | CG | ASP | 36 | 42.328 | 51.962 | 20.034 | 1.00 | 47.18 | B1 |
| ATOM | 1176 | OD1 | ASP | 36 | 43.011 | 51.676 | 21.042 | 1.00 | 47.46 | B1 |
| ATOM | 1177 | OD2 | ASP | 36 | 42.831 | 52.504 | 19.025 | 1.00 | 48.14 | B1 |
| ATOM | 1178 | C | ASP | 36 | 39.040 | 50.269 | 21.131 | 1.00 | 47.36 | B1 |
| ATOM | 1179 | O | ASP | 36 | 38.519 | 50.720 | 22.138 | 1.00 | 48.13 | B1 |
| ATOM | 1180 | N | GLN | 37 | 38.355 | 49.630 | 20.183 | 1.00 | 47.84 | B1 |
| ATOM | 1181 | CA | GLN | 37 | 36.918 | 49.445 | 20.333 | 1.00 | 48.02 | B1 |
| ATOM | 1182 | CB | GLN | 37 | 36.354 | 48.755 | 19.100 | 1.00 | 48.62 | B1 |
| ATOM | 1183 | CG | GLN | 37 | 36.416 | 49.589 | 17.849 | 1.00 | 50.60 | B1 |
| ATOM | 1184 | CD | GLN | 37 | 36.137 | 48.763 | 16.597 | 1.00 | 51.12 | B1 |
| ATOM | 1185 | OE1 | GLN | 37 | 35.145 | 48.050 | 16.531 | 1.00 | 51.75 | B1 |
| ATOM | 1186 | NE2 | GLN | 37 | 37.023 | 48.853 | 15.606 | 1.00 | 52.14 | B1 |
| ATOM | 1187 | C | GLN | 37 | 36.585 | 48.632 | 21.596 | 1.00 | 47.78 | B1 |
| ATOM | 1188 | O | GLN | 37 | 35.640 | 48.946 | 22.299 | 1.0Q | 48.37 | B1 |
| ATOM | 1189 | N | TYR | 38 | 37.374 | 47.603 | 21.885 | 1.00 | 47.54 | B1 |

FIG. 3A-21

```
ATOM   1190  CA   TYR  38    37.161  46.732  23.046  1.00  47.74    B1
ATOM   1191  CB   TYR  38    38.165  45.551  22.941  1.00  46.60    B1
ATOM   1192  CG   TYR  38    38.527  44.738  24.195  1.00  45.26    B1
ATOM   1193  CD1  TYR  38    39.691  45.014  24.905  1.00  44.68    B1
ATOM   1194  CE1  TYR  38    40.084  44.229  25.991  1.00  44.13    B1
ATOM   1195  CD2  TYR  38    37.749  43.647  24.616  1.00  44.67    B1
ATOM   1196  CE2  TYR  38    38.123  42.863  25.703  1.00  43.73    B1
ATOM   1197  CZ   TYR  38    39.298  43.160  26.382  1.00  44.36    B1
ATOM   1198  OH   TYR  38    39.717  42.401  27.450  1.00  44.63    B1
ATOM   1199  C    TYR  38    37.287  47.487  24.373  1.00  48.96    B1
ATOM   1200  O    TYR  38    36.502  47.282  25.296  1.00  48.92    B1
ATOM   1201  N    TYR  39    38.268  48.377  24.449  1.00  50.35    B1
ATOM   1202  CA   TYR  39    38.539  49.177  25.645  1.00  52.19    B1
ATOM   1203  CB   TYR  39    39.867  49.908  25.465  1.00  52.76    B1
ATOM   1204  CG   TYR  39    41.044  49.009  25.696  1.00  53.28    B1
ATOM   1205  CD1  TYR  39    42.182  49.086  24.901  1.00  52.99    B1
ATOM   1206  CE1  TYR  39    43.276  48.261  25.147  1.00  53.92    B1
ATOM   1207  CD2  TYR  39    41.023  48.084  26.742  1.00  53.93    B1
ATOM   1208  CE2  TYR  39    42.102  47.267  26.994  1.00  54.12    B1
ATOM   1209  CZ   TYR  39    43.222  47.355  26.204  1.00  54.32    B1
ATOM   1210  OH   TYR  39    44.295  46.532  26.502  1.00  56.15    B1
ATOM   1211  C    TYR  39    37.467  50.187  26.053  1.00  52.72    B1
ATOM   1212  O    TYR  39    37.457  50.646  27.185  1.00  53.04    B1
ATOM   1213  N    ALA  40    36.570  50.517  25.129  1.00  53.49    B1
ATOM   1214  CA   ALA  40    35.507  51.473  25.379  1.00  53.72    B1
ATOM   1215  CB   ALA  40    35.097  52.154  24.063  1.00  52.69    B1
ATOM   1216  C    ALA  40    34.293  50.818  26.013  1.00  54.49    B1
ATOM   1217  O    ALA  40    33.388  51.526  26.451  1.00  55.28    B1
ATOM   1218  N    LEU  41    34.268  49.483  26.073  1.00  54.98    B1
ATOM   1219  CA   LEU  41    33.107  48.746  26.622  1.00  55.00    B1
ATOM   1220  CB   LEU  41    32.825  47.481  25.789  1.00  53.64    B1
ATOM   1221  CG   LEU  41    33.130  47.485  24.293  1.00  53.38    B1
ATOM   1222  CD1  LEU  41    33.180  46.027  23.794  1.00  52.52    B1
ATOM   1223  CD2  LEU  41    32.103  48.303  23.537  1.00  52.98    B1
ATOM   1224  C    LEU  41    33.224  48.311  28.082  1.00  55.16    B1
ATOM   1225  O    LEU  41    34.318  48.191  28.616  1.00  55.63    B1
ATOM   1226  N    SER  42    32.076  48.041  28.695  1.00  55.74    B1
ATOM   1227  CA   SER  42    31.983  47.578  30.089  1.00  56.51    B1
ATOM   1228  CB   SER  42    30.520  47.412  30.508  1.00  57.31    B1
ATOM   1229  OG   SER  42    29.991  46.181  29.993  1.00  57.63    B1
ATOM   1230  C    SER  42    32.622  46.208  30.229  1.00  56.49    B1
ATOM   1231  O    SER  42    32.986  45.575  29.236  1.00  56.57    B1
ATOM   1232  N    ALA  43    32.715  45.734  31.466  1.00  56.33    B1
ATOM   1233  CA   ALA  43    33.291  44.420  31.713  1.00  56.63    B1
ATOM   1234  CB   ALA  43    33.418  44.151  33.257  1.00  56.01    B1
ATOM   1235  C    ALA  43    32.439  43.328  31.024  1.00  56.37    B1
ATOM   1236  O    ALA  43    32.973  42.344  30.504  1.00  56.24    B1
ATOM   1237  N    ALA  44    31.122  43.511  30.995  1.00  56.00    B1
ATOM   1238  CA   ALA  44    30.263  42.517  30.361  1.00  55.31    B1
ATOM   1239  CB   ALA  44    28.793  42.867  30.547  1.00  55.66    B1
ATOM   1240  C    ALA  44    30.583  42.505  28.887  1.00  55.23    B1
ATOM   1241  O    ALA  44    31.264  41.581  28.378  1.00  55.55    B1
ATOM   1242  N    ALA  45    30.083  43.546  28.222  1.00  52.94    B1
ATOM   1243  CA   ALA  45    30.242  43.735  26.799  1.00  51.15    B1
ATOM   1244  CB   ALA  45    29.909  45.174  26.441  1.00  51.88    B1
ATOM   1245  C    ALA  45    31.628  43.379  26.283  1.00  49.53    B1
ATOM   1246  O    ALA  45    31.789  43.067  25.112  1.00  49.20    B1
```

FIG. 3A-22

```
ATOM   1247  N    LYS   46      32.630  43.412  27.144  1.00 47.53           B1
ATOM   1248  CA   LYS   46      33.972  43.088  26.686  1.00 45.73           B1
ATOM   1249  CB   LYS   46      35.019  43.433  27.731  1.00 46.26           B1
ATOM   1250  CG   LYS   46      35.557  44.825  27.647  1.00 48.50           B1
ATOM   1251  CD   LYS   46      36.731  44.962  28.607  1.00 49.81           B1
ATOM   1252  CE   LYS   46      37.403  46.296  28.457  1.00 52.00           B1
ATOM   1253  NZ   LYS   46      38.669  46.353  29.255  1.00 53.15           B1
ATOM   1254  C    LYS   46      34.206  41.644  26.283  1.00 43.73           B1
ATOM   1255  O    LYS   46      34.819  41.413  25.245  1.00 43.15           B1
ATOM   1256  N    ASN   47      33.769  40.688  27.107  1.00 41.38           B1
ATOM   1257  CA   ASN   47      34.007  39.285  26.798  1.00 39.96           B1
ATOM   1258  CB   ASN   47      33.735  38.375  28.015  1.00 41.11           B1
ATOM   1259  CG   ASN   47      34.884  38.447  29.069  1.00 45.19           B1
ATOM   1260  OD1  ASN   47      34.648  38.357  30.307  1.00 46.49           B1
ATOM   1261  ND2  ASN   47      36.136  38.607  28.584  1.00 44.51           B1
ATOM   1262  C    ASN   47      33.248  38.821  25.561  1.00 37.98           B1
ATOM   1263  O    ASN   47      33.771  38.012  24.780  1.00 36.13           B1
ATOM   1264  N    GLU   48      32.048  39.353  25.351  1.00 36.77           B1
ATOM   1265  CA   GLU   48      31.310  38.951  24.177  1.00 37.17           B1
ATOM   1266  CB   GLU   48      29.812  39.230  24.325  1.00 40.44           B1
ATOM   1267  CG   GLU   48      29.446  40.643  24.622  1.00 44.46           B1
ATOM   1268  CD   GLU   48      28.807  40.796  26.024  1.00 47.35           B1
ATOM   1269  OE1  GLU   48      29.591  40.785  27.020  1.00 48.12           B1
ATOM   1270  OE2  GLU   48      27.546  40.917  26.113  1.00 46.80           B1
ATOM   1271  C    GLU   48      31.884  39.621  22.921  1.00 35.12           B1
ATOM   1272  O    GLU   48      31.886  39.015  21.866  1.00 34.22           B1
ATOM   1273  N    PHE   49      32.396  40.851  23.042  1.00 33.28           B1
ATOM   1274  CA   PHE   49      33.003  41.492  21.891  1.00 31.67           B1
ATOM   1275  CB   PHE   49      33.407  42.921  22.201  1.00 31.19           B1
ATOM   1276  CG   PHE   49      34.157  43.604  21.082  1.00 28.77           B1
ATOM   1277  CD1  PHE   49      33.480  44.281  20.078  1.00 28.58           B1
ATOM   1278  CD2  PHE   49      35.531  43.583  21.040  1.00 29.27           B1
ATOM   1279  CE1  PHE   49      34.173  44.935  19.041  1.00 26.85           B1
ATOM   1280  CE2  PHE   49      36.236  44.245  20.004  1.00 28.19           B1
ATOM   1281  CZ   PHE   49      35.545  44.913  19.017  1.00 26.97           B1
ATOM   1282  C    PHE   49      34.273  40.685  21.527  1.00 30.94           B1
ATOM   1283  O    PHE   49      34.521  40.391  20.353  1.00 29.62           B1
ATOM   1284  N    LEU   50      35.052  40.308  22.540  1.00 29.25           B1
ATOM   1285  CA   LEU   50      36.289  39.561  22.297  1.00 28.26           B1
ATOM   1286  CB   LEU   50      37.112  39.473  23.575  1.00 27.33           B1
ATOM   1287  CG   LEU   50      38.423  38.692  23.483  1.00 28.33           B1
ATOM   1288  CD1  LEU   50      39.317  39.237  22.326  1.00 26.30           B1
ATOM   1289  CD2  LEU   50      39.121  38.763  24.889  1.00 26.85           B1
ATOM   1290  C    LEU   50      35.956  38.170  21.746  1.00 27.90           B1
ATOM   1291  O    LEU   50      36.501  37.755  20.732  1.00 27.63           B1
ATOM   1292  N    ALA   51      35.024  37.466  22.388  1.00 26.98           B1
ATOM   1293  CA   ALA   51      34.645  36.140  21.915  1.00 25.11           B1
ATOM   1294  CB   ALA   51      33.603  35.538  22.857  1.00 23.27           B1
ATOM   1295  C    ALA   51      34.098  36.194  20.453  1.00 24.63           B1
ATOM   1296  O    ALA   51      34.356  35.291  19.621  1.00 23.74           B1
ATOM   1297  N    GLY   52      33.343  37.244  20.147  1.00 24.05           B1
ATOM   1298  CA   GLY   52      32.795  37.346  18.817  1.00 23.42           B1
ATOM   1299  C    GLY   52      33.874  37.557  17.775  1.00 24.52           B1
ATOM   1300  O    GLY   52      33.850  36.942  16.711  1.00 25.82           B1
ATOM   1301  N    ARG   53      34.833  38.430  18.052  1.00 25.23           B1
ATOM   1302  CA   ARG   53      35.856  38.701  17.061  1.00 26.47           B1
ATOM   1303  CB   ARG   53      36.676  39.970  17.419  1.00 27.84           B1
```

FIG. 3A-23

| ATOM | 1304 | CG  | ARG | 53 | 36.193 | 41.286 | 16.713 | 1.00 | 29.04 | B1 |
| --- | --- | --- | --- | --- | --- | --- | --- | --- | --- | --- |
| ATOM | 1305 | CD  | ARG | 53 | 34.753 | 41.748 | 17.040 | 1.00 | 32.70 | B1 |
| ATOM | 1306 | NE  | ARG | 53 | 34.323 | 42.926 | 16.256 | 1.00 | 33.45 | B1 |
| ATOM | 1307 | CZ  | ARG | 53 | 33.040 | 43.280 | 16.076 | 1.00 | 36.40 | B1 |
| ATOM | 1308 | NH1 | ARG | 53 | 32.065 | 42.555 | 16.620 | 1.00 | 37.75 | B1 |
| ATOM | 1309 | NH2 | ARG | 53 | 32.696 | 44.350 | 15.348 | 1.00 | 37.36 | B1 |
| ATOM | 1310 | C   | ARG | 53 | 36.727 | 37.503 | 16.895 | 1.00 | 25.54 | B1 |
| ATOM | 1311 | O   | ARG | 53 | 37.185 | 37.225 | 15.798 | 1.00 | 25.97 | B1 |
| ATOM | 1312 | N   | PHE | 54 | 36.971 | 36.790 | 17.989 | 1.00 | 25.78 | B1 |
| ATOM | 1313 | CA  | PHE | 54 | 37.782 | 35.573 | 17.916 | 1.00 | 24.70 | B1 |
| ATOM | 1314 | CB  | PHE | 54 | 37.986 | 34.967 | 19.304 | 1.00 | 23.11 | B1 |
| ATOM | 1315 | CG  | PHE | 54 | 38.758 | 33.676 | 19.275 | 1.00 | 23.50 | B1 |
| ATOM | 1316 | CD1 | PHE | 54 | 38.105 | 32.443 | 19.349 | 1.00 | 23.28 | B1 |
| ATOM | 1317 | CD2 | PHE | 54 | 40.143 | 33.685 | 19.117 | 1.00 | 24.40 | B1 |
| ATOM | 1318 | CE1 | PHE | 54 | 38.818 | 31.251 | 19.274 | 1.00 | 23.13 | B1 |
| ATOM | 1319 | CE2 | PHE | 54 | 40.874 | 32.486 | 19.037 | 1.00 | 23.88 | B1 |
| ATOM | 1320 | CZ  | PHE | 54 | 40.189 | 31.262 | 19.120 | 1.00 | 23.28 | B1 |
| ATOM | 1321 | C   | PHE | 54 | 37.030 | 34.564 | 17.021 | 1.00 | 24.85 | B1 |
| ATOM | 1322 | O   | PHE | 54 | 37.614 | 33.926 | 16.151 | 1.00 | 25.96 | B1 |
| ATOM | 1323 | N   | ALA | 55 | 35.723 | 34.433 | 17.238 | 1.00 | 23.60 | B1 |
| ATOM | 1324 | CA  | ALA | 55 | 34.921 | 33.500 | 16.443 | 1.00 | 22.67 | B1 |
| ATOM | 1325 | CB  | ALA | 55 | 33.412 | 33.474 | 16.986 | 1.00 | 19.81 | B1 |
| ATOM | 1326 | C   | ALA | 55 | 34.957 | 33.917 | 14.955 | 1.00 | 21.88 | B1 |
| ATOM | 1327 | O   | ALA | 55 | 35.168 | 33.087 | 14.064 | 1.00 | 22.44 | B1 |
| ATOM | 1328 | N   | ALA | 56 | 34.750 | 35.198 | 14.678 | 1.00 | 21.17 | B1 |
| ATOM | 1329 | CA  | ALA | 56 | 34.773 | 35.644 | 13.281 | 1.00 | 21.94 | B1 |
| ATOM | 1330 | CB  | ALA | 56 | 34.447 | 37.053 | 13.217 | 1.00 | 21.38 | B1 |
| ATOM | 1331 | C   | ALA | 56 | 36.141 | 35.385 | 12.634 | 1.00 | 23.12 | B1 |
| ATOM | 1332 | O   | ALA | 56 | 36.212 | 35.050 | 11.455 | 1.00 | 25.01 | B1 |
| ATOM | 1333 | N   | LYS | 57 | 37.225 | 35.473 | 13.411 | 1.00 | 22.35 | B1 |
| ATOM | 1334 | CA  | LYS | 57 | 38.527 | 35.253 | 12.814 | 1.00 | 23.06 | B1 |
| ATOM | 1335 | CB  | LYS | 57 | 39.679 | 35.933 | 13.598 | 1.00 | 21.11 | B1 |
| ATOM | 1336 | CG  | LYS | 57 | 39.543 | 37.437 | 13.622 | 1.00 | 19.67 | B1 |
| ATOM | 1337 | CD  | LYS | 57 | 40.779 | 38.119 | 14.201 | 1.00 | 19.94 | B1 |
| ATOM | 1338 | CE  | LYS | 57 | 40.524 | 39.636 | 14.269 | 1.00 | 21.28 | B1 |
| ATOM | 1339 | NZ  | LYS | 57 | 41.711 | 40.419 | 14.731 | 1.00 | 21.24 | B1 |
| ATOM | 1340 | C   | LYS | 57 | 38.794 | 33.786 | 12.657 | 1.00 | 23.67 | B1 |
| ATOM | 1341 | O   | LYS | 57 | 39.442 | 33.390 | 11.703 | 1.00 | 24.22 | B1 |
| ATOM | 1342 | N   | GLU | 58 | 38.314 | 32.966 | 13.581 | 1.00 | 23.83 | B1 |
| ATOM | 1343 | CA  | GLU | 58 | 38.519 | 31.539 | 13.370 | 1.00 | 24.27 | B1 |
| ATOM | 1344 | CB  | GLU | 58 | 38.056 | 30.755 | 14.590 | 1.00 | 26.87 | B1 |
| ATOM | 1345 | CG  | GLU | 58 | 39.034 | 30.808 | 15.772 | 1.00 | 32.81 | B1 |
| ATOM | 1346 | CD  | GLU | 58 | 40.209 | 29.836 | 15.554 | 1.00 | 36.83 | B1 |
| ATOM | 1347 | OE1 | GLU | 58 | 39.913 | 28.628 | 15.293 | 1.00 | 40.26 | B1 |
| ATOM | 1348 | OE2 | GLU | 58 | 41.398 | 30.262 | 15.628 | 1.00 | 36.84 | B1 |
| ATOM | 1349 | C   | GLU | 58 | 37.718 | 31.083 | 12.104 | 1.00 | 22.49 | B1 |
| ATOM | 1350 | O   | GLU | 58 | 38.230 | 30.372 | 11.253 | 1.00 | 21.87 | B1 |
| ATOM | 1351 | N   | ALA | 59 | 36.488 | 31.542 | 11.971 | 1.00 | 20.35 | B1 |
| ATOM | 1352 | CA  | ALA | 59 | 35.684 | 31.094 | 10.867 | 1.00 | 21.36 | B1 |
| ATOM | 1353 | CB  | ALA | 59 | 34.240 | 31.652 | 11.021 | 1.00 | 19.54 | B1 |
| ATOM | 1354 | C   | ALA | 59 | 36.326 | 31.557 | 9.513  | 1.00 | 22.84 | B1 |
| ATOM | 1355 | O   | ALA | 59 | 36.373 | 30.805 | 8.536  | 1.00 | 22.04 | B1 |
| ATOM | 1356 | N   | PHE | 60 | 36.795 | 32.801 | 9.490  | 1.00 | 22.02 | B1 |
| ATOM | 1357 | CA  | PHE | 60 | 37.420 | 33.345 | 8.316  | 1.00 | 22.50 | B1 |
| ATOM | 1358 | CB  | PHE | 60 | 37.822 | 34.807 | 8.572  | 1.00 | 23.42 | B1 |
| ATOM | 1359 | CG  | PHE | 60 | 38.562 | 35.379 | 7.442  | 1.00 | 23.85 | B1 |
| ATOM | 1360 | CD1 | PHE | 60 | 37.867 | 35.934 | 6.361  | 1.00 | 23.20 | B1 |

FIG. 3A-24

| ATOM | 1361 | CD2 | PHE | 60 | 39.942 | 35.274 | 7.402 | 1.00 | 23.36 | B1 |
|------|------|-----|-----|----|--------|--------|-------|------|-------|----|
| ATOM | 1362 | CE1 | PHE | 60 | 38.535 | 36.377 | 5.240 | 1.00 | 24.53 | B1 |
| ATOM | 1363 | CE2 | PHE | 60 | 40.662 | 35.710 | 6.283 | 1.00 | 26.01 | B1 |
| ATOM | 1364 | CZ  | PHE | 60 | 39.936 | 36.277 | 5.170 | 1.00 | 24.87 | B1 |
| ATOM | 1365 | C   | PHE | 60 | 38.659 | 32.529 | 7.946 | 1.00 | 22.51 | B1 |
| ATOM | 1366 | O   | PHE | 60 | 38.842 | 32.106 | 6.776 | 1.00 | 22.37 | B1 |
| ATOM | 1367 | N   | SER | 61 | 39.521 | 32.301 | 8.931 | 1.00 | 22.91 | B1 |
| ATOM | 1368 | CA  | SER | 61 | 40.732 | 31.509 | 8.660 | 1.00 | 23.52 | B1 |
| ATOM | 1369 | CB  | SER | 61 | 41.560 | 31.290 | 9.953 | 1.00 | 23.83 | B1 |
| ATOM | 1370 | OG  | SER | 61 | 40.958 | 30.284 | 10.809 | 1.00 | 25.53 | B1 |
| ATOM | 1371 | C   | SER | 61 | 40.343 | 30.136 | 8.063 | 1.00 | 23.43 | B1 |
| ATOM | 1372 | O   | SER | 61 | 41.105 | 29.571 | 7.304 | 1.00 | 24.15 | B1 |
| ATOM | 1373 | N   | LYS | 62 | 39.167 | 29.599 | 8.405 | 1.00 | 22.88 | B1 |
| ATOM | 1374 | CA  | LYS | 62 | 38.758 | 28.286 | 7.858 | 1.00 | 24.47 | B1 |
| ATOM | 1375 | CB  | LYS | 62 | 37.679 | 27.642 | 8.757 | 1.00 | 25.68 | B1 |
| ATOM | 1376 | CG  | LYS | 62 | 38.126 | 27.199 | 10.182 | 1.00 | 29.50 | B1 |
| ATOM | 1377 | CD  | LYS | 62 | 36.846 | 26.907 | 11.071 | 1.00 | 32.07 | B1 |
| ATOM | 1378 | CE  | LYS | 62 | 37.165 | 26.114 | 12.368 | 1.00 | 33.86 | B1 |
| ATOM | 1379 | NZ  | LYS | 62 | 36.250 | 26.459 | 13.585 | 1.00 | 36.00 | B1 |
| ATOM | 1380 | C   | LYS | 62 | 38.225 | 28.428 | 6.398 | 1.00 | 24.82 | B1 |
| ATOM | 1381 | O   | LYS | 62 | 38.453 | 27.602 | 5.552 | 1.00 | 23.97 | B1 |
| ATOM | 1382 | N   | ALA | 63 | 37.481 | 29.490 | 6.151 | 1.00 | 25.40 | B1 |
| ATOM | 1383 | CA  | ALA | 63 | 36.950 | 29.827 | 4.839 | 1.00 | 26.03 | B1 |
| ATOM | 1384 | CB  | ALA | 63 | 36.122 | 31.106 | 4.995 | 1.00 | 23.81 | B1 |
| ATOM | 1385 | C   | ALA | 63 | 38.193 | 30.109 | 3.936 | 1.00 | 26.63 | B1 |
| ATOM | 1386 | O   | ALA | 63 | 38.228 | 29.752 | 2.774 | 1.00 | 25.61 | B1 |
| ATOM | 1387 | N   | PHE | 64 | 39.186 | 30.795 | 4.498 | 1.00 | 27.51 | B1 |
| ATOM | 1388 | CA  | PHE | 64 | 40.422 | 31.136 | 3.772 | 1.00 | 29.24 | B1 |
| ATOM | 1389 | CB  | PHE | 64 | 41.315 | 32.016 | 4.664 | 1.00 | 29.05 | B1 |
| ATOM | 1390 | CG  | PHE | 64 | 42.531 | 32.577 | 3.977 | 1.00 | 30.71 | B1 |
| ATOM | 1391 | CD1 | PHE | 64 | 42.432 | 33.666 | 3.092 | 1.00 | 29.37 | B1 |
| ATOM | 1392 | CD2 | PHE | 64 | 43.808 | 32.082 | 4.293 | 1.00 | 30.61 | B1 |
| ATOM | 1393 | CE1 | PHE | 64 | 43.594 | 34.243 | 2.552 | 1.00 | 29.64 | B1 |
| ATOM | 1394 | CE2 | PHE | 64 | 44.978 | 32.657 | 3.761 | 1.00 | 30.30 | B1 |
| ATOM | 1395 | CZ  | PHE | 64 | 44.879 | 33.744 | 2.891 | 1.00 | 29.10 | B1 |
| ATOM | 1396 | C   | PHE | 64 | 41.147 | 29.851 | 3.386 | 1.00 | 30.09 | B1 |
| ATOM | 1397 | O   | PHE | 64 | 41.897 | 29.864 | 2.444 | 1.00 | 30.68 | B1 |
| ATOM | 1398 | N   | GLY | 65 | 40.926 | 28.756 | 4.139 | 1.00 | 30.98 | B1 |
| ATOM | 1399 | CA  | GLY | 65 | 41.527 | 27.472 | 3.815 | 1.00 | 31.37 | B1 |
| ATOM | 1400 | C   | GLY | 65 | 42.753 | 26.964 | 4.562 | 1.00 | 33.20 | B1 |
| ATOM | 1401 | O   | GLY | 65 | 43.211 | 25.837 | 4.342 | 1.00 | 33.31 | B1 |
| ATOM | 1402 | N   | THR | 66 | 43.274 | 27.738 | 5.498 | 1.00 | 32.35 | B1 |
| ATOM | 1403 | CA  | THR | 66 | 44.491 | 27.293 | 6.148 | 1.00 | 32.11 | B1 |
| ATOM | 1404 | CB  | THR | 66 | 45.613 | 28.232 | 5.794 | 1.00 | 30.57 | B1 |
| ATOM | 1405 | OG1 | THR | 66 | 45.290 | 29.511 | 6.364 | 1.00 | 28.59 | B1 |
| ATOM | 1406 | CG2 | THR | 66 | 45.747 | 28.354 | 4.300 | 1.00 | 30.33 | B1 |
| ATOM | 1407 | C   | THR | 66 | 44.470 | 27.332 | 7.652 | 1.00 | 33.04 | B1 |
| ATOM | 1408 | O   | THR | 66 | 45.398 | 26.826 | 8.260 | 1.00 | 33.53 | B1 |
| ATOM | 1409 | N   | GLY | 67 | 43.459 | 27.992 | 8.232 | 1.00 | 33.38 | B1 |
| ATOM | 1410 | CA  | GLY | 67 | 43.391 | 28.178 | 9.668 | 1.00 | 33.05 | B1 |
| ATOM | 1411 | C   | GLY | 67 | 44.432 | 29.247 | 9.963 | 1.00 | 33.13 | B1 |
| ATOM | 1412 | O   | GLY | 67 | 45.166 | 29.634 | 9.055 | 1.00 | 31.39 | B1 |
| ATOM | 1413 | N   | ILE | 68 | 44.479 | 29.728 | 11.207 | 1.00 | 33.97 | B1 |
| ATOM | 1414 | CA  | ILE | 68 | 45.444 | 30.751 | 11.657 | 1.00 | 33.80 | B1 |
| ATOM | 1415 | CB  | ILE | 68 | 45.022 | 31.343 | 13.056 | 1.00 | 32.72 | B1 |
| ATOM | 1416 | CG2 | ILE | 68 | 46.167 | 32.173 | 13.668 | 1.00 | 30.94 | B1 |
| ATOM | 1417 | CG1 | ILE | 68 | 43.746 | 32.163 | 12.916 | 1.00 | 32.01 | B1 |

FIG. 3A-25

| ATOM | 1418 | CD1 | ILE | 68 | 43.901 | 33.419 | 12.019 | 1.00 | 29.71 | B1 |
| --- | --- | --- | --- | --- | --- | --- | --- | --- | --- | --- |
| ATOM | 1419 | C | ILE | 68 | 46.855 | 30.146 | 11.788 | 1.00 | 35.01 | B1 |
| ATOM | 1420 | O | ILE | 68 | 47.015 | 29.005 | 12.185 | 1.00 | 34.63 | B1 |
| ATOM | 1421 | N | GLY | 69 | 47.874 | 30.926 | 11.429 | 1.00 | 36.79 | B1 |
| ATOM | 1422 | CA | GLY | 69 | 49.249 | 30.469 | 11.521 | 1.00 | 38.01 | B1 |
| ATOM | 1423 | C | GLY | 69 | 50.230 | 31.161 | 10.578 | 1.00 | 39.61 | B1 |
| ATOM | 1424 | O | GLY | 69 | 50.264 | 32.393 | 10.460 | 1.00 | 38.05 | B1 |
| ATOM | 1425 | N | ALA | 70 | 51.023 | 30.327 | 9.900 | 1.00 | 41.65 | B1 |
| ATOM | 1426 | CA | ALA | 70 | 52.024 | 30.765 | 8.944 | 1.00 | 43.14 | B1 |
| ATOM | 1427 | CB | ALA | 70 | 52.822 | 29.536 | 8.415 | 1.00 | 43.37 | B1 |
| ATOM | 1428 | C | ALA | 70 | 51.432 | 31.568 | 7.775 | 1.00 | 43.45 | B1 |
| ATOM | 1429 | O | ALA | 70 | 51.935 | 32.625 | 7.446 | 1.00 | 44.06 | B1 |
| ATOM | 1430 | N | GLN | 71 | 50.345 | 31.101 | 7.172 | 1.00 | 43.42 | B1 |
| ATOM | 1431 | CA | GLN | 71 | 49.782 | 31.872 | 6.033 | 1.00 | 43.43 | B1 |
| ATOM | 1432 | CB | GLN | 71 | 49.130 | 30.925 | 5.004 | 1.00 | 45.18 | B1 |
| ATOM | 1433 | CG | GLN | 71 | 50.095 | 29.867 | 4.411 | 1.00 | 48.80 | B1 |
| ATOM | 1434 | CD | GLN | 71 | 49.429 | 28.485 | 4.153 | 1.00 | 51.39 | B1 |
| ATOM | 1435 | OE1 | GLN | 71 | 49.030 | 28.175 | 3.023 | 1.00 | 54.02 | B1 |
| ATOM | 1436 | NE2 | GLN | 71 | 49.308 | 27.663 | 5.202 | 1.00 | 50.54 | B1 |
| ATOM | 1437 | C | GLN | 71 | 48.776 | 32.960 | 6.449 | 1.00 | 40.86 | B1 |
| ATOM | 1438 | O | GLN | 71 | 48.323 | 33.754 | 5.614 | 1.00 | 39.98 | B1 |
| ATOM | 1439 | N | LEU | 72 | 48.480 | 33.045 | 7.744 | 1.00 | 37.98 | B1 |
| ATOM | 1440 | CA | LEU | 72 | 47.478 | 34.009 | 8.190 | 1.00 | 36.26 | B1 |
| ATOM | 1441 | CB | LEU | 72 | 46.102 | 33.522 | 7.777 | 1.00 | 34.40 | B1 |
| ATOM | 1442 | CG | LEU | 72 | 44.902 | 34.399 | 8.050 | 1.00 | 32.85 | B1 |
| ATOM | 1443 | CD1 | LEU | 72 | 44.843 | 35.468 | 6.992 | 1.00 | 32.54 | B1 |
| ATOM | 1444 | CD2 | LEU | 72 | 43.629 | 33.535 | 8.011 | 1.00 | 31.85 | B1 |
| ATOM | 1445 | C | LEU | 72 | 47.472 | 34.216 | 9.682 | 1.00 | 36.26 | B1 |
| ATOM | 1446 | O | LEU | 72 | 47.304 | 33.262 | 10.467 | 1.00 | 35.99 | B1 |
| ATOM | 1447 | N | SER | 73 | 47.615 | 35.474 | 10.052 | 1.00 | 35.30 | B1 |
| ATOM | 1448 | CA | SER | 73 | 47.639 | 35.883 | 11.439 | 1.00 | 35.78 | B1 |
| ATOM | 1449 | CB | SER | 73 | 48.729 | 36.924 | 11.647 | 1.00 | 35.81 | B1 |
| ATOM | 1450 | OG | SER | 73 | 48.610 | 37.488 | 12.952 | 1.00 | 38.65 | B1 |
| ATOM | 1451 | C | SER | 73 | 46.321 | 36.512 | 11.889 | 1.00 | 35.17 | B1 |
| ATOM | 1452 | O | SER | 73 | 45.537 | 36.964 | 11.061 | 1.00 | 35.80 | B1 |
| ATOM | 1453 | N | PHE | 74 | 46.101 | 36.549 | 13.200 | 1.00 | 34.10 | B1 |
| ATOM | 1454 | CA | PHE | 74 | 44.908 | 37.177 | 13.750 | 1.00 | 33.89 | B1 |
| ATOM | 1455 | CB | PHE | 74 | 44.890 | 37.046 | 15.278 | 1.00 | 32.52 | B1 |
| ATOM | 1456 | CG | PHE | 74 | 44.502 | 35.675 | 15.764 | 1.00 | 32.11 | B1 |
| ATOM | 1457 | CD1 | PHE | 74 | 43.182 | 35.231 | 15.658 | 1.00 | 31.77 | B1 |
| ATOM | 1458 | CD2 | PHE | 74 | 45.460 | 34.806 | 16.306 | 1.00 | 31.78 | B1 |
| ATOM | 1459 | CE1 | PHE | 74 | 42.819 | 33.934 | 16.090 | 1.00 | 32.33 | B1 |
| ATOM | 1460 | CE2 | PHE | 74 | 45.108 | 33.502 | 16.745 | 1.00 | 31.95 | B1 |
| ATOM | 1461 | CZ | PHE | 74 | 43.780 | 33.066 | 16.631 | 1.00 | 30.79 | B1 |
| ATOM | 1462 | C | PHE | 74 | 44.986 | 38.685 | 13.364 | 1.00 | 34.20 | B1 |
| ATOM | 1463 | O | PHE | 74 | 43.953 | 39.338 | 13.079 | 1.00 | 31.60 | B1 |
| ATOM | 1464 | N | GLN | 75 | 46.228 | 39.201 | 13.334 | 1.00 | 34.11 | B1 |
| ATOM | 1465 | CA | GLN | 75 | 46.485 | 40.607 | 13.032 | 1.00 | 34.43 | B1 |
| ATOM | 1466 | CB | GLN | 75 | 47.942 | 40.950 | 13.352 | 1.00 | 36.57 | B1 |
| ATOM | 1467 | CG | GLN | 75 | 48.293 | 40.925 | 14.862 | 1.00 | 35.45 | B1 |
| ATOM | 1468 | CD | GLN | 75 | 47.372 | 41.779 | 15.674 | 1.00 | 36.29 | B1 |
| ATOM | 1469 | OE1 | GLN | 75 | 46.929 | 41.389 | 16.775 | 1.00 | 36.74 | B1 |
| ATOM | 1470 | NE2 | GLN | 75 | 47.069 | 42.966 | 15.154 | 1.00 | 37.01 | B1 |
| ATOM | 1471 | C | GLN | 75 | 46.165 | 41.006 | 11.608 | 1.00 | 33.88 | B1 |
| ATOM | 1472 | O | GLN | 75 | 45.993 | 42.171 | 11.339 | 1.00 | 34.13 | B1 |
| ATOM | 1473 | N | ASP | 76 | 46.080 | 40.050 | 10.698 | 1.00 | 33.62 | B1 |
| ATOM | 1474 | CA | ASP | 76 | 45.739 | 40.354 | 9.301 | 1.00 | 33.82 | B1 |

FIG. 3A-26

| ATOM | 1475 | CB  | ASP | 76 | 46.322 | 39.270 | 8.395  | 1.00 | 35.57 | B1 |
| ---- | ---- | --- | --- | -- | ------ | ------ | ------ | ---- | ----- | -- |
| ATOM | 1476 | CG  | ASP | 76 | 47.852 | 39.128 | 8.534  | 1.00 | 37.11 | B1 |
| ATOM | 1477 | OD1 | ASP | 76 | 48.552 | 40.144 | 8.846  | 1.00 | 36.68 | B1 |
| ATOM | 1478 | OD2 | ASP | 76 | 48.328 | 37.987 | 8.309  | 1.00 | 37.48 | B1 |
| ATOM | 1479 | C   | ASP | 76 | 44.210 | 40.422 | 9.012  | 1.00 | 34.06 | B1 |
| ATOM | 1480 | O   | ASP | 76 | 43.787 | 40.732 | 7.888  | 1.00 | 32.89 | B1 |
| ATOM | 1481 | N   | ILE | 77 | 43.398 | 40.089 | 10.018 | 1.00 | 33.00 | B1 |
| ATOM | 1482 | CA  | ILE | 77 | 41.955 | 40.077 | 9.870  | 1.00 | 33.14 | B1 |
| ATOM | 1483 | CB  | ILE | 77 | 41.341 | 38.684 | 10.249 | 1.00 | 31.81 | B1 |
| ATOM | 1484 | CG2 | ILE | 77 | 39.856 | 38.611 | 9.840  | 1.00 | 30.14 | B1 |
| ATOM | 1485 | CG1 | ILE | 77 | 42.099 | 37.549 | 9.512  | 1.00 | 31.15 | B1 |
| ATOM | 1486 | CD1 | ILE | 77 | 41.911 | 36.136 | 10.200 | 1.00 | 29.63 | B1 |
| ATOM | 1487 | C   | ILE | 77 | 41.355 | 41.143 | 10.764 | 1.00 | 34.04 | B1 |
| ATOM | 1488 | O   | ILE | 77 | 41.608 | 41.201 | 11.980 | 1.00 | 34.59 | B1 |
| ATOM | 1489 | N   | GLU | 78 | 40.571 | 42.014 | 10.160 | 1.00 | 34.50 | B1 |
| ATOM | 1490 | CA  | GLU | 78 | 39.948 | 43.026 | 10.950 | 1.00 | 35.99 | B1 |
| ATOM | 1491 | CB  | GLU | 78 | 40.631 | 44.366 | 10.676 | 1.00 | 38.42 | B1 |
| ATOM | 1492 | CG  | GLU | 78 | 40.066 | 45.544 | 11.396 | 1.00 | 41.11 | B1 |
| ATOM | 1493 | CD  | GLU | 78 | 41.027 | 46.714 | 11.296 | 1.00 | 43.67 | B1 |
| ATOM | 1494 | OE1 | GLU | 78 | 41.755 | 46.939 | 12.283 | 1.00 | 44.57 | B1 |
| ATOM | 1495 | OE2 | GLU | 78 | 41.081 | 47.377 | 10.223 | 1.00 | 44.87 | B1 |
| ATOM | 1496 | C   | GLU | 78 | 38.454 | 43.114 | 10.676 | 1.00 | 36.02 | B1 |
| ATOM | 1497 | O   | GLU | 78 | 37.994 | 43.186 | 9.522  | 1.00 | 36.20 | B1 |
| ATOM | 1498 | N   | ILE | 79 | 37.708 | 43.094 | 11.758 | 1.00 | 35.68 | B1 |
| ATOM | 1499 | CA  | ILE | 79 | 36.296 | 43.225 | 11.696 | 1.00 | 37.08 | B1 |
| ATOM | 1500 | CB  | ILE | 79 | 35.639 | 42.374 | 12.814 | 1.00 | 36.74 | B1 |
| ATOM | 1501 | CG2 | ILE | 79 | 34.146 | 42.704 | 12.920 | 1.00 | 36.28 | B1 |
| ATOM | 1502 | CG1 | ILE | 79 | 35.822 | 40.878 | 12.489 | 1.00 | 36.49 | B1 |
| ATOM | 1503 | CD1 | ILE | 79 | 37.253 | 40.448 | 12.415 | 1.00 | 37.09 | B1 |
| ATOM | 1504 | C   | ILE | 79 | 35.970 | 44.714 | 11.870 | 1.00 | 38.48 | B1 |
| ATOM | 1505 | O   | ILE | 79 | 36.470 | 45.350 | 12.795 | 1.00 | 37.73 | B1 |
| ATOM | 1506 | N   | ARG | 80 | 35.185 | 45.273 | 10.953 | 1.00 | 40.54 | B1 |
| ATOM | 1507 | CA  | ARG | 80 | 34.776 | 46.679 | 11.031 | 1.00 | 43.90 | B1 |
| ATOM | 1508 | CB  | ARG | 80 | 35.337 | 47.451 | 9.842  | 1.00 | 44.69 | B1 |
| ATOM | 1509 | CG  | ARG | 80 | 36.851 | 47.544 | 9.830  | 1.00 | 46.15 | B1 |
| ATOM | 1510 | CD  | ARG | 80 | 37.368 | 48.230 | 8.579  | 1.00 | 47.22 | B1 |
| ATOM | 1511 | NE  | ARG | 80 | 38.813 | 48.036 | 8.469  | 1.00 | 48.93 | B1 |
| ATOM | 1512 | CZ  | ARG | 80 | 39.512 | 48.260 | 7.365  | 1.00 | 49.88 | B1 |
| ATOM | 1513 | NH1 | ARG | 80 | 38.887 | 48.692 | 6.270  | 1.00 | 49.30 | B1 |
| ATOM | 1514 | NH2 | ARG | 80 | 40.828 | 48.046 | 7.351  | 1.00 | 49.32 | B1 |
| ATOM | 1515 | C   | ARG | 80 | 33.242 | 46.839 | 11.048 | 1.00 | 46.39 | B1 |
| ATOM | 1516 | O   | ARG | 80 | 32.493 | 45.980 | 10.556 | 1.00 | 46.33 | B1 |
| ATOM | 1517 | N   | ALA | 81 | 32.770 | 47.949 | 11.607 | 1.00 | 49.26 | B1 |
| ATOM | 1518 | CA  | ALA | 81 | 31.331 | 48.203 | 11.671 | 1.00 | 52.06 | B1 |
| ATOM | 1519 | CB  | ALA | 81 | 30.969 | 48.850 | 13.018 | 1.00 | 51.83 | B1 |
| ATOM | 1520 | C   | ALA | 81 | 31.018 | 49.136 | 10.509 | 1.00 | 53.95 | B1 |
| ATOM | 1521 | O   | ALA | 81 | 31.826 | 50.014 | 10.202 | 1.00 | 54.91 | B1 |
| ATOM | 1522 | N   | ASP | 82 | 29.882 | 48.956 | 9.846  | 1.00 | 55.55 | B1 |
| ATOM | 1523 | CA  | ASP | 82 | 29.580 | 49.823 | 8.720  | 1.00 | 58.10 | B1 |
| ATOM | 1524 | CB  | ASP | 82 | 28.899 | 49.023 | 7.606  | 1.00 | 57.68 | B1 |
| ATOM | 1525 | CG  | ASP | 82 | 27.483 | 48.625 | 7.966  | 1.00 | 57.85 | B1 |
| ATOM | 1526 | OD1 | ASP | 82 | 26.738 | 48.149 | 7.077  | 1.00 | 57.82 | B1 |
| ATOM | 1527 | OD2 | ASP | 82 | 27.119 | 48.789 | 9.151  | 1.00 | 57.88 | B1 |
| ATOM | 1528 | C   | ASP | 82 | 28.691 | 51.021 | 9.099  | 1.00 | 59.84 | B1 |
| ATOM | 1529 | O   | ASP | 82 | 28.675 | 51.469 | 10.244 | 1.00 | 60.02 | B1 |
| ATOM | 1530 | N   | GLN | 83 | 27.964 | 51.538 | 8.107  | 1.00 | 61.97 | B1 |
| ATOM | 1531 | CA  | GLN | 83 | 27.035 | 52.666 | 8.293  | 1.00 | 63.65 | B1 |

FIG. 3A-27

| ATOM | 1532 | CB | GLN | 83 | 26.184 | 52.848 | 7.031 | 1.00 | 64.43 | B1 |
|---|---|---|---|---|---|---|---|---|---|---|
| ATOM | 1533 | CG | GLN | 83 | 27.006 | 52.812 | 5.757 | 1.00 | 66.77 | B1 |
| ATOM | 1534 | CD | GLN | 83 | 26.149 | 52.707 | 4.501 | 1.00 | 68.23 | B1 |
| ATOM | 1535 | OE1 | GLN | 83 | 25.367 | 53.619 | 4.188 | 1.00 | 68.35 | B1 |
| ATOM | 1536 | NE2 | GLN | 83 | 26.296 | 51.587 | 3.766 | 1.00 | 68.89 | B1 |
| ATOM | 1537 | C | GLN | 83 | 26.101 | 52.378 | 9.479 | 1.00 | 63.85 | B1 |
| ATOM | 1538 | O | GLN | 83 | 26.173 | 53.032 | 10.534 | 1.00 | 63.94 | B1 |
| ATOM | 1539 | N | ASN | 84 | 25.233 | 51.387 | 9.301 | 1.00 | 63.70 | B1 |
| ATOM | 1540 | CA | ASN | 84 | 24.304 | 51.037 | 10.353 | 1.00 | 63.32 | B1 |
| ATOM | 1541 | CB | ASN | 84 | 23.000 | 50.557 | 9.737 | 1.00 | 64.23 | B1 |
| ATOM | 1542 | CG | ASN | 84 | 21.798 | 51.287 | 10.326 | 1.00 | 65.77 | B1 |
| ATOM | 1543 | OD1 | ASN | 84 | 21.424 | 52.388 | 9.867 | 1.00 | 65.94 | B1 |
| ATOM | 1544 | ND2 | ASN | 84 | 21.204 | 50.699 | 11.376 | 1.00 | 66.01 | B1 |
| ATOM | 1545 | C | ASN | 84 | 24.771 | 50.040 | 11.429 | 1.00 | 62.56 | B1 |
| ATOM | 1546 | O | ASN | 84 | 23.942 | 49.406 | 12.103 | 1.00 | 62.52 | B1 |
| ATOM | 1547 | N | GLY | 85 | 26.084 | 49.874 | 11.581 | 1.00 | 61.17 | B1 |
| ATOM | 1548 | CA | GLY | 85 | 26.580 | 48.986 | 12.626 | 1.00 | 59.18 | B1 |
| ATOM | 1549 | C | GLY | 85 | 26.957 | 47.538 | 12.336 | 1.00 | 57.65 | B1 |
| ATOM | 1550 | O | GLY | 85 | 27.729 | 46.943 | 13.108 | 1.00 | 57.89 | B1 |
| ATOM | 1551 | N | ALA | 86 | 26.420 | 46.952 | 11.269 | 1.00 | 55.17 | B1 |
| ATOM | 1552 | CA | ALA | 86 | 26.739 | 45.563 | 10.911 | 1.00 | 53.38 | B1 |
| ATOM | 1553 | CB | ALA | 86 | 25.931 | 45.151 | 9.650 | 1.00 | 52.68 | B1 |
| ATOM | 1554 | C | ALA | 86 | 28.278 | 45.347 | 10.687 | 1.00 | 51.50 | B1 |
| ATOM | 1555 | O | ALA | 86 | 29.000 | 46.268 | 10.262 | 1.00 | 51.32 | B1 |
| ATOM | 1556 | N | PRO | 87 | 28.784 | 44.130 | 10.998 | 1.00 | 49.44 | B1 |
| ATOM | 1557 | CD | PRO | 87 | 27.948 | 43.003 | 11.480 | 1.00 | 48.99 | B1 |
| ATOM | 1558 | CA | PRO | 87 | 30.201 | 43.717 | 10.868 | 1.00 | 46.89 | B1 |
| ATOM | 1559 | CB | PRO | 87 | 30.310 | 42.543 | 11.836 | 1.00 | 47.60 | B1 |
| ATOM | 1560 | CG | PRO | 87 | 28.943 | 41.819 | 11.567 | 1.00 | 48.65 | B1 |
| ATOM | 1561 | C | PRO | 87 | 30.560 | 43.267 | 9.464 | 1.00 | 44.00 | B1 |
| ATOM | 1562 | O | PRO | 87 | 29.740 | 42.683 | 8.758 | 1.00 | 43.26 | B1 |
| ATOM | 1563 | N | TYR | 88 | 31.773 | 43.575 | 9.043 | 1.00 | 41.45 | B1 |
| ATOM | 1564 | CA | TYR | 88 | 32.244 | 43.126 | 7.740 | 1.00 | 39.15 | B1 |
| ATOM | 1565 | CB | TYR | 88 | 31.843 | 44.102 | 6.590 | 1.00 | 39.61 | B1 |
| ATOM | 1566 | CG | TYR | 88 | 32.482 | 45.487 | 6.604 | 1.00 | 41.06 | B1 |
| ATOM | 1567 | CD1 | TYR | 88 | 33.675 | 45.743 | 5.894 | 1.00 | 41.16 | B1 |
| ATOM | 1568 | CE1 | TYR | 88 | 34.313 | 47.007 | 5.953 | 1.00 | 41.19 | B1 |
| ATOM | 1569 | CD2 | TYR | 88 | 31.934 | 46.533 | 7.368 | 1.00 | 41.56 | B1 |
| ATOM | 1570 | CE2 | TYR | 88 | 32.567 | 47.807 | 7.440 | 1.00 | 41.61 | B1 |
| ATOM | 1571 | CZ | TYR | 88 | 33.756 | 48.024 | 6.727 | 1.00 | 42.13 | B1 |
| ATOM | 1572 | OH | TYR | 88 | 34.396 | 49.247 | 6.800 | 1.00 | 43.16 | B1 |
| ATOM | 1573 | C | TYR | 88 | 33.744 | 42.976 | 7.937 | 1.00 | 36.73 | B1 |
| ATOM | 1574 | O | TYR | 88 | 34.324 | 43.493 | 8.883 | 1.00 | 34.70 | B1 |
| ATOM | 1575 | N | ILE | 89 | 34.360 | 42.263 | 7.029 | 1.00 | 35.89 | B1 |
| ATOM | 1576 | CA | ILE | 89 | 35.757 | 41.973 | 7.131 | 1.00 | 35.67 | B1 |
| ATOM | 1577 | CB | ILE | 89 | 35.961 | 40.450 | 7.207 | 1.00 | 35.14 | B1 |
| ATOM | 1578 | CG2 | ILE | 89 | 37.473 | 40.080 | 6.887 | 1.00 | 33.43 | B1 |
| ATOM | 1579 | CG1 | ILE | 89 | 35.493 | 39.959 | 8.569 | 1.00 | 33.89 | B1 |
| ATOM | 1580 | CD1 | ILE | 89 | 35.498 | 38.495 | 8.693 | 1.00 | 34.14 | B1 |
| ATOM | 1581 | C | ILE | 89 | 36.706 | 42.462 | 6.060 | 1.00 | 36.44 | B1 |
| ATOM | 1582 | O | ILE | 89 | 36.451 | 42.305 | 4.864 | 1.00 | 36.42 | B1 |
| ATOM | 1583 | N | ILE | 90 | 37.837 | 42.974 | 6.527 | 1.00 | 36.77 | B1 |
| ATOM | 1584 | CA | ILE | 90 | 38.917 | 43.418 | 5.652 | 1.00 | 37.18 | B1 |
| ATOM | 1585 | CB | ILE | 90 | 39.256 | 44.903 | 5.835 | 1.00 | 37.91 | B1 |
| ATOM | 1586 | CG2 | ILE | 90 | 40.363 | 45.286 | 4.829 | 1.00 | 39.62 | B1 |
| ATOM | 1587 | CG1 | ILE | 90 | 38.033 | 45.775 | 5.513 | 1.00 | 38.16 | B1 |
| ATOM | 1588 | CD1 | ILE | 90 | 37.522 | 45.595 | 4.070 | 1.00 | 35.21 | B1 |

FIG. 3A-28

| ATOM | 1589 | C | ILE | 90 | 40.132 | 42.593 | 6.034 | 1.00 | 36.19 | B1 |
|---|---|---|---|---|---|---|---|---|---|---|
| ATOM | 1590 | O | ILE | 90 | 40.564 | 42.623 | 7.166 | 1.00 | 36.53 | B1 |
| ATOM | 1591 | N | CYS | 91 | 40.621 | 41.804 | 5.092 | 1.00 | 35.99 | B1 |
| ATOM | 1592 | CA | CYS | 91 | 41.776 | 40.955 | 5.323 | 1.00 | 35.74 | B1 |
| ATOM | 1593 | CB | CYS | 91 | 41.455 | 39.490 | 5.037 | 1.00 | 35.10 | B1 |
| ATOM | 1594 | SG | CYS | 91 | 42.926 | 38.466 | 5.170 | 1.00 | 33.12 | B1 |
| ATOM | 1595 | C | CYS | 91 | 42.920 | 41.359 | 4.415 | 1.00 | 36.16 | B1 |
| ATOM | 1596 | O | CYS | 91 | 42.750 | 41.390 | 3.189 | 1.00 | 35.07 | B1 |
| ATOM | 1597 | N | THR | 92 | 44.085 | 41.591 | 5.024 | 1.00 | 36.82 | B1 |
| ATOM | 1598 | CA | THR | 92 | 45.287 | 42.019 | 4.300 | 1.00 | 38.35 | B1 |
| ATOM | 1599 | CB | THR | 92 | 46.507 | 42.197 | 5.248 | 1.00 | 38.75 | B1 |
| ATOM | 1600 | OG1 | THR | 92 | 46.761 | 40.963 | 5.936 | 1.00 | 37.76 | B1 |
| ATOM | 1601 | CG2 | THR | 92 | 46.263 | 43.298 | 6.272 | 1.00 | 39.01 | B1 |
| ATOM | 1602 | C | THR | 92 | 45.716 | 41.027 | 3.231 | 1.00 | 39.26 | B1 |
| ATOM | 1603 | O | THR | 92 | 46.323 | 41.413 | 2.264 | 1.00 | 39.63 | B1 |
| ATOM | 1604 | N | LYS | 93 | 45.407 | 39.745 | 3.421 | 1.00 | 39.79 | B1 |
| ATOM | 1605 | CA | LYS | 93 | 45.810 | 38.723 | 2.484 | 1.00 | 39.52 | B1 |
| ATOM | 1606 | CB | LYS | 93 | 46.010 | 37.393 | 3.198 | 1.00 | 40.17 | B1 |
| ATOM | 1607 | CG | LYS | 93 | 47.006 | 37.426 | 4.332 | 1.00 | 40.94 | B1 |
| ATOM | 1608 | CD | LYS | 93 | 48.307 | 38.081 | 3.926 | 1.00 | 41.78 | B1 |
| ATOM | 1609 | CE | LYS | 93 | 49.388 | 37.905 | 4.982 | 1.00 | 42.27 | B1 |
| ATOM | 1610 | NZ | LYS | 93 | 50.633 | 38.699 | 4.664 | 1.00 | 44.42 | B1 |
| ATOM | 1611 | C | LYS | 93 | 44.867 | 38.495 | 1.341 | 1.00 | 39.75 | B1 |
| ATOM | 1612 | O | LYS | 93 | 45.155 | 37.671 | 0.493 | 1.00 | 39.68 | B1 |
| ATOM | 1613 | N | LEU | 94 | 43.748 | 39.203 | 1.304 | 1.00 | 40.01 | B1 |
| ATOM | 1614 | CA | LEU | 94 | 42.774 | 39.014 | 0.217 | 1.00 | 41.18 | B1 |
| ATOM | 1615 | CB | LEU | 94 | 41.353 | 38.899 | 0.778 | 1.00 | 40.88 | B1 |
| ATOM | 1616 | CG | LEU | 94 | 40.856 | 37.581 | 1.350 | 1.00 | 40.77 | B1 |
| ATOM | 1617 | CD1 | LEU | 94 | 39.413 | 37.749 | 1.726 | 1.00 | 39.19 | B1 |
| ATOM | 1618 | CD2 | LEU | 94 | 41.054 | 36.453 | 0.312 | 1.00 | 39.78 | B1 |
| ATOM | 1619 | C | LEU | 94 | 42.718 | 40.145 | -0.806 | 1.00 | 41.93 | B1 |
| ATOM | 1620 | O | LEU | 94 | 42.764 | 41.313 | -0.438 | 1.00 | 42.74 | B1 |
| ATOM | 1621 | N | SER | 95 | 42.526 | 39.815 | -2.072 | 1.00 | 42.58 | B1 |
| ATOM | 1622 | CA | SER | 95 | 42.421 | 40.876 | -3.069 | 1.00 | 42.96 | B1 |
| ATOM | 1623 | CB | SER | 95 | 43.778 | 41.109 | -3.754 | 1.00 | 43.94 | B1 |
| ATOM | 1624 | OG | SER | 95 | 44.020 | 40.115 | -4.746 | 1.00 | 43.87 | B1 |
| ATOM | 1625 | C | SER | 95 | 41.379 | 40.672 | -4.150 | 1.00 | 42.89 | B1 |
| ATOM | 1626 | O | SER | 95 | 40.905 | 41.627 | -4.730 | 1.00 | 44.24 | B1 |
| ATOM | 1627 | N | GLN | 96 | 41.009 | 39.450 | -4.471 | 1.00 | 43.07 | B1 |
| ATOM | 1628 | CA | GLN | 96 | 40.033 | 39.325 | -5.561 | 1.00 | 42.39 | B1 |
| ATOM | 1629 | CB | GLN | 96 | 40.750 | 38.755 | -6.780 | 1.00 | 44.77 | B1 |
| ATOM | 1630 | CG | GLN | 96 | 41.943 | 39.613 | -7.243 | 1.00 | 47.44 | B1 |
| ATOM | 1631 | CD | GLN | 96 | 41.569 | 40.542 | -8.395 | 1.00 | 49.06 | B1 |
| ATOM | 1632 | OE1 | GLN | 96 | 42.357 | 41.411 | -8.776 | 1.00 | 49.80 | B1 |
| ATOM | 1633 | NE2 | GLN | 96 | 40.363 | 40.344 | -8.977 | 1.00 | 49.46 | B1 |
| ATOM | 1634 | C | GLN | 96 | 38.854 | 38.456 | -5.173 | 1.00 | 40.56 | B1 |
| ATOM | 1635 | O | GLN | 96 | 38.375 | 37.620 | -5.947 | 1.00 | 40.17 | B1 |
| ATOM | 1636 | N | ALA | 97 | 38.367 | 38.690 | -3.962 | 1.00 | 38.47 | B1 |
| ATOM | 1637 | CA | ALA | 97 | 37.270 | 37.906 | -3.429 | 1.00 | 36.12 | B1 |
| ATOM | 1638 | CB | ALA | 97 | 37.845 | 36.736 | -2.643 | 1.00 | 34.36 | B1 |
| ATOM | 1639 | C | ALA | 97 | 36.388 | 38.735 | -2.535 | 1.00 | 35.07 | B1 |
| ATOM | 1640 | O | ALA | 97 | 36.870 | 39.615 | -1.833 | 1.00 | 36.55 | B1 |
| ATOM | 1641 | N | ALA | 98 | 35.092 | 38.472 | -2.550 | 1.00 | 33.28 | B1 |
| ATOM | 1642 | CA | ALA | 98 | 34.201 | 39.183 | -1.629 | 1.00 | 31.74 | B1 |
| ATOM | 1643 | CB | ALA | 98 | 32.803 | 39.328 | -2.228 | 1.00 | 30.40 | B1 |
| ATOM | 1644 | C | ALA | 98 | 34.130 | 38.316 | -0.337 | 1.00 | 30.10 | B1 |
| ATOM | 1645 | O | ALA | 98 | 34.182 | 37.094 | -0.387 | 1.00 | 28.07 | B1 |

FIG. 3A-29

| ATOM | 1646 | N   | VAL | 99  | 33.978 | 38.966 | 0.799  | 1.00 | 30.22 | B1 |
| ATOM | 1647 | CA  | VAL | 99  | 33.900 | 38.260 | 2.058  | 1.00 | 30.56 | B1 |
| ATOM | 1648 | CB  | VAL | 99  | 35.113 | 38.595 | 2.968  | 1.00 | 30.62 | B1 |
| ATOM | 1649 | CG1 | VAL | 99  | 35.074 | 37.747 | 4.264  | 1.00 | 29.52 | B1 |
| ATOM | 1650 | CG2 | VAL | 99  | 36.397 | 38.287 | 2.246  | 1.00 | 31.07 | B1 |
| ATOM | 1651 | C   | VAL | 99  | 32.621 | 38.611 | 2.814  | 1.00 | 30.85 | B1 |
| ATOM | 1652 | O   | VAL | 99  | 32.270 | 39.801 | 2.952  | 1.00 | 30.29 | B1 |
| ATOM | 1653 | N   | HIS | 100 | 31.932 | 37.576 | 3.300  | 1.00 | 30.10 | B1 |
| ATOM | 1654 | CA  | HIS | 100 | 30.719 | 37.792 | 4.111  | 1.00 | 30.30 | B1 |
| ATOM | 1655 | CB  | HIS | 100 | 29.465 | 37.206 | 3.469  | 1.00 | 30.39 | B1 |
| ATOM | 1656 | CG  | HIS | 100 | 29.121 | 37.824 | 2.161  | 1.00 | 34.23 | B1 |
| ATOM | 1657 | CD2 | HIS | 100 | 29.355 | 37.408 | 0.894  | 1.00 | 34.42 | B1 |
| ATOM | 1658 | ND1 | HIS | 100 | 28.564 | 39.083 | 2.062  | 1.00 | 34.61 | B1 |
| ATOM | 1659 | CE1 | HIS | 100 | 28.476 | 39.420 | 0.787  | 1.00 | 36.03 | B1 |
| ATOM | 1660 | NE2 | HIS | 100 | 28.950 | 38.425 | 0.060  | 1.00 | 36.35 | B1 |
| ATOM | 1661 | C   | HIS | 100 | 30.869 | 37.141 | 5.477  | 1.00 | 29.01 | B1 |
| ATOM | 1662 | O   | HIS | 100 | 31.357 | 35.977 | 5.612  | 1.00 | 28.01 | B1 |
| ATOM | 1663 | N   | VAL | 101 | 30.390 | 37.880 | 6.466  | 1.00 | 27.15 | B1 |
| ATOM | 1664 | CA  | VAL | 101 | 30.432 | 37.420 | 7.803  | 1.00 | 27.02 | B1 |
| ATOM | 1665 | CB  | VAL | 101 | 31.533 | 38.118 | 8.577  | 1.00 | 26.29 | B1 |
| ATOM | 1666 | CG1 | VAL | 101 | 31.179 | 39.597 | 8.765  | 1.00 | 24.61 | B1 |
| ATOM | 1667 | CG2 | VAL | 101 | 31.724 | 37.451 | 9.899  | 1.00 | 24.54 | B1 |
| ATOM | 1668 | C   | VAL | 101 | 29.146 | 37.662 | 8.539  | 1.00 | 28.14 | B1 |
| ATOM | 1669 | O   | VAL | 101 | 28.482 | 38.698 | 8.356  | 1.00 | 29.45 | B1 |
| ATOM | 1670 | N   | SER | 102 | 28.766 | 36.707 | 9.379  | 1.00 | 28.04 | B1 |
| ATOM | 1671 | CA  | SER | 102 | 27.616 | 36.957 | 10.208 | 1.00 | 28.42 | B1 |
| ATOM | 1672 | CB  | SER | 102 | 26.399 | 36.166 | 9.718  | 1.00 | 27.56 | B1 |
| ATOM | 1673 | OG  | SER | 102 | 25.295 | 36.440 | 10.575 | 1.00 | 29.02 | B1 |
| ATOM | 1674 | C   | SER | 102 | 28.060 | 36.563 | 11.635 | 1.00 | 28.63 | B1 |
| ATOM | 1675 | O   | SER | 102 | 28.699 | 35.524 | 11.824 | 1.00 | 28.25 | B1 |
| ATOM | 1676 | N   | ILE | 103 | 27.749 | 37.392 | 12.630 | 1.00 | 28.89 | B1 |
| ATOM | 1677 | CA  | ILE | 103 | 28.156 | 37.096 | 13.994 | 1.00 | 29.90 | B1 |
| ATOM | 1678 | CB  | ILE | 103 | 29.152 | 38.131 | 14.536 | 1.00 | 30.84 | B1 |
| ATOM | 1679 | CG2 | ILE | 103 | 29.511 | 37.772 | 16.050 | 1.00 | 32.46 | B1 |
| ATOM | 1680 | CG1 | ILE | 103 | 30.430 | 38.125 | 13.682 | 1.00 | 30.85 | B1 |
| ATOM | 1681 | CD1 | ILE | 103 | 31.412 | 39.173 | 14.073 | 1.00 | 30.47 | B1 |
| ATOM | 1682 | C   | ILE | 103 | 26.972 | 37.048 | 14.933 | 1.00 | 30.17 | B1 |
| ATOM | 1683 | O   | ILE | 103 | 26.145 | 37.944 | 14.946 | 1.00 | 30.48 | B1 |
| ATOM | 1684 | N   | THR | 104 | 26.866 | 36.004 | 15.731 | 1.00 | 30.81 | B1 |
| ATOM | 1685 | CA  | THR | 104 | 25.712 | 35.941 | 16.635 | 1.00 | 31.45 | B1 |
| ATOM | 1686 | CB  | THR | 104 | 24.677 | 34.929 | 16.131 | 1.00 | 31.80 | B1 |
| ATOM | 1687 | OG1 | THR | 104 | 23.467 | 35.108 | 16.863 | 1.00 | 32.62 | B1 |
| ATOM | 1688 | CG2 | THR | 104 | 25.190 | 33.488 | 16.319 | 1.00 | 30.80 | B1 |
| ATOM | 1689 | C   | THR | 104 | 26.143 | 35.562 | 18.052 | 1.00 | 31.67 | B1 |
| ATOM | 1690 | O   | THR | 104 | 27.209 | 34.983 | 18.234 | 1.00 | 30.85 | B1 |
| ATOM | 1691 | N   | HIS | 105 | 25.285 | 35.878 | 19.028 | 1.00 | 32.96 | B1 |
| ATOM | 1692 | CA  | HIS | 105 | 25.557 | 35.637 | 20.466 | 1.00 | 34.13 | B1 |
| ATOM | 1693 | CB  | HIS | 105 | 25.928 | 36.950 | 21.166 | 1.00 | 34.78 | B1 |
| ATOM | 1694 | CG  | HIS | 105 | 27.158 | 37.587 | 20.644 | 1.00 | 37.03 | B1 |
| ATOM | 1695 | CD2 | HIS | 105 | 27.335 | 38.645 | 19.814 | 1.00 | 38.51 | B1 |
| ATOM | 1696 | ND1 | HIS | 105 | 28.423 | 37.129 | 20.961 | 1.00 | 38.91 | B1 |
| ATOM | 1697 | CE1 | HIS | 105 | 29.328 | 37.869 | 20.346 | 1.00 | 38.37 | B1 |
| ATOM | 1698 | NE2 | HIS | 105 | 28.696 | 38.799 | 19.644 | 1.00 | 40.30 | B1 |
| ATOM | 1699 | C   | HIS | 105 | 24.379 | 35.094 | 21.267 | 1.00 | 34.37 | B1 |
| ATOM | 1700 | O   | HIS | 105 | 23.261 | 35.499 | 21.025 | 1.00 | 33.67 | B1 |
| ATOM | 1701 | N   | THR | 106 | 24.659 | 34.189 | 22.209 | 1.00 | 34.82 | B1 |
| ATOM | 1702 | CA  | THR | 106 | 23.665 | 33.685 | 23.164 | 1.00 | 35.49 | B1 |

FIG. 3A-30

| ATOM | 1703 | CB | THR | 106 | 23.475 | 32.156 | 23.182 | 1.00 | 35.09 | B1 |
|------|------|-----|------|-----|--------|--------|--------|------|-------|-----|
| ATOM | 1704 | OG1 | THR | 106 | 24.707 | 31.544 | 23.546 | 1.00 | 34.36 | B1 |
| ATOM | 1705 | CG2 | THR | 106 | 22.953 | 31.632 | 21.823 | 1.00 | 35.91 | B1 |
| ATOM | 1706 | C | THR | 106 | 24.309 | 34.003 | 24.517 | 1.00 | 36.01 | B1 |
| ATOM | 1707 | O | THR | 106 | 25.409 | 34.565 | 24.562 | 1.00 | 35.69 | B1 |
| ATOM | 1708 | N | ALA | 107 | 23.663 | 33.602 | 25.613 | 1.00 | 36.11 | B1 |
| ATOM | 1709 | CA | ALA | 107 | 24.222 | 33.885 | 26.943 | 1.00 | 36.17 | B1 |
| ATOM | 1710 | CB | ALA | 107 | 23.182 | 33.498 | 28.093 | 1.00 | 36.40 | B1 |
| ATOM | 1711 | C | ALA | 107 | 25.560 | 33.172 | 27.162 | 1.00 | 35.49 | B1 |
| ATOM | 1712 | O | ALA | 107 | 26.469 | 33.727 | 27.769 | 1.00 | 35.34 | B1 |
| ATOM | 1713 | N | GLU | 108 | 25.706 | 31.971 | 26.625 | 1.00 | 35.10 | B1 |
| ATOM | 1714 | CA | GLU | 108 | 26.945 | 31.234 | 26.825 | 1.00 | 35.82 | B1 |
| ATOM | 1715 | CB | GLU | 108 | 26.639 | 29.789 | 27.251 | 1.00 | 38.90 | B1 |
| ATOM | 1716 | CG | GLU | 108 | 25.842 | 29.696 | 28.522 | 1.00 | 44.61 | B1 |
| ATOM | 1717 | CD | GLU | 108 | 25.599 | 28.262 | 28.937 | 1.00 | 48.58 | B1 |
| ATOM | 1718 | OE1 | GLU | 108 | 24.655 | 28.041 | 29.730 | 1.00 | 50.53 | B1 |
| ATOM | 1719 | OE2 | GLU | 108 | 26.362 | 27.357 | 28.489 | 1.00 | 51.47 | B1 |
| ATOM | 1720 | C | GLU | 108 | 27.922 | 31.137 | 25.666 | 1.00 | 34.54 | B1 |
| ATOM | 1721 | O | GLU | 108 | 29.067 | 30.773 | 25.877 | 1.00 | 33.82 | B1 |
| ATOM | 1722 | N | TYR | 109 | 27.475 | 31.424 | 24.445 | 1.00 | 33.83 | B1 |
| ATOM | 1723 | CA | TYR | 109 | 28.353 | 31.235 | 23.264 | 1.00 | 31.80 | B1 |
| ATOM | 1724 | CB | TYR | 109 | 27.875 | 30.013 | 22.503 | 1.00 | 31.67 | B1 |
| ATOM | 1725 | CG | TYR | 109 | 28.046 | 28.688 | 23.249 | 1.00 | 32.77 | B1 |
| ATOM | 1726 | CD1 | TYR | 109 | 29.273 | 28.051 | 23.250 | 1.00 | 33.33 | B1 |
| ATOM | 1727 | CE1 | TYR | 109 | 29.487 | 26.878 | 23.917 | 1.00 | 35.40 | B1 |
| ATOM | 1728 | CD2 | TYR | 109 | 27.005 | 28.103 | 23.962 | 1.00 | 33.45 | B1 |
| ATOM | 1729 | CE2 | TYR | 109 | 27.208 | 26.886 | 24.682 | 1.00 | 34.90 | B1 |
| ATOM | 1730 | CZ | TYR | 109 | 28.463 | 26.290 | 24.648 | 1.00 | 35.91 | B1 |
| ATOM | 1731 | OH | TYR | 109 | 28.808 | 25.152 | 25.354 | 1.00 | 37.81 | B1 |
| ATOM | 1732 | C | TYR | 109 | 28.417 | 32.380 | 22.310 | 1.00 | 30.50 | B1 |
| ATOM | 1733 | O | TYR | 109 | 27.554 | 33.228 | 22.303 | 1.00 | 30.99 | B1 |
| ATOM | 1734 | N | ALA | 110 | 29.461 | 32.420 | 21.505 | 1.00 | 29.56 | B1 |
| ATOM | 1735 | CA | ALA | 110 | 29.581 | 33.426 | 20.459 | 1.00 | 28.07 | B1 |
| ATOM | 1736 | CB | ALA | 110 | 30.834 | 34.276 | 20.657 | 1.00 | 28.86 | B1 |
| ATOM | 1737 | C | ALA | 110 | 29.738 | 32.524 | 19.210 | 1.00 | 27.13 | B1 |
| ATOM | 1738 | O | ALA | 110 | 30.402 | 31.493 | 19.291 | 1.00 | 26.29 | B1 |
| ATOM | 1739 | N | ALA | 111 | 29.118 | 32.894 | 18.081 | 1.00 | 25.13 | B1 |
| ATOM | 1740 | CA | ALA | 111 | 29.227 | 32.100 | 16.882 | 1.00 | 23.39 | B1 |
| ATOM | 1741 | CB | ALA | 111 | 28.013 | 31.175 | 16.746 | 1.00 | 22.39 | B1 |
| ATOM | 1742 | C | ALA | 111 | 29.356 | 33.008 | 15.679 | 1.00 | 22.70 | B1 |
| ATOM | 1743 | O | ALA | 111 | 28.867 | 34.126 | 15.682 | 1.00 | 22.85 | B1 |
| ATOM | 1744 | N | ALA | 112 | 30.089 | 32.558 | 14.686 | 1.00 | 21.46 | B1 |
| ATOM | 1745 | CA | ALA | 112 | 30.241 | 33.345 | 13.482 | 1.00 | 22.44 | B1 |
| ATOM | 1746 | CB | ALA | 112 | 31.486 | 34.252 | 13.589 | 1.00 | 21.22 | B1 |
| ATOM | 1747 | C | ALA | 112 | 30.398 | 32.430 | 12.266 | 1.00 | 23.59 | B1 |
| ATOM | 1748 | O | ALA | 112 | 30.879 | 31.293 | 12.375 | 1.00 | 24.32 | B1 |
| ATOM | 1749 | N | GLN | 113 | 29.993 | 32.935 | 11.115 | 1.00 | 23.66 | B1 |
| ATOM | 1750 | CA | GLN | 113 | 30.208 | 32.218 | 9.878 | 1.00 | 25.14 | B1 |
| ATOM | 1751 | CB | GLN | 113 | 28.908 | 31.534 | 9.383 | 1.00 | 25.14 | B1 |
| ATOM | 1752 | CG | GLN | 113 | 27.902 | 32.494 | 8.868 | 1.00 | 27.79 | B1 |
| ATOM | 1753 | CD | GLN | 113 | 26.589 | 31.847 | 8.350 | 1.00 | 28.98 | B1 |
| ATOM | 1754 | OE1 | GLN | 113 | 25.654 | 32.552 | 8.027 | 1.00 | 30.45 | B1 |
| ATOM | 1755 | NE2 | GLN | 113 | 26.531 | 30.530 | 8.284 | 1.00 | 30.54 | B1 |
| ATOM | 1756 | C | GLN | 113 | 30.776 | 33.195 | 8.822 | 1.00 | 24.53 | B1 |
| ATOM | 1757 | O | GLN | 113 | 30.519 | 34.401 | 8.807 | 1.00 | 23.39 | B1 |
| ATOM | 1758 | N | VAL | 114 | 31.571 | 32.644 | 7.944 | 1.00 | 24.96 | B1 |
| ATOM | 1759 | CA | VAL | 114 | 32.177 | 33.414 | 6.905 | 1.00 | 24.84 | B1 |

FIG. 3A-31

| ATOM | 1760 | CB | VAL | 114 | 33.652 | 33.625 | 7.242 | 1.00 | 24.26 | B1 |
|---|---|---|---|---|---|---|---|---|---|---|
| ATOM | 1761 | CG1 | VAL | 114 | 34.423 | 34.152 | 6.006 | 1.00 | 22.12 | B1 |
| ATOM | 1762 | CG2 | VAL | 114 | 33.757 | 34.606 | 8.465 | 1.00 | 21.27 | B1 |
| ATOM | 1763 | C | VAL | 114 | 32.030 | 32.714 | 5.545 | 1.00 | 26.84 | B1 |
| ATOM | 1764 | O | VAL | 114 | 32.043 | 31.466 | 5.430 | 1.00 | 28.29 | B1 |
| ATOM | 1765 | N | VAL | 115 | 31.806 | 33.504 | 4.513 | 1.00 | 27.25 | B1 |
| ATOM | 1766 | CA | VAL | 115 | 31.771 | 32.953 | 3.166 | 1.00 | 27.22 | B1 |
| ATOM | 1767 | CB | VAL | 115 | 30.349 | 33.016 | 2.574 | 1.00 | 28.50 | B1 |
| ATOM | 1768 | CG1 | VAL | 115 | 30.344 | 32.570 | 1.101 | 1.00 | 28.02 | B1 |
| ATOM | 1769 | CG2 | VAL | 115 | 29.410 | 32.124 | 3.431 | 1.00 | 28.89 | B1 |
| ATOM | 1770 | C | VAL | 115 | 32.738 | 33.848 | 2.383 | 1.00 | 27.02 | B1 |
| ATOM | 1771 | O | VAL | 115 | 32.711 | 35.075 | 2.508 | 1.00 | 26.76 | B1 |
| ATOM | 1772 | N | ILE | 116 | 33.677 | 33.218 | 1.686 | 1.00 | 27.52 | B1 |
| ATOM | 1773 | CA | ILE | 116 | 34.609 | 33.904 | 0.814 | 1.00 | 26.35 | B1 |
| ATOM | 1774 | CB | ILE | 116 | 36.075 | 33.488 | 1.072 | 1.00 | 26.60 | B1 |
| ATOM | 1775 | CG2 | ILE | 116 | 36.983 | 33.957 | -0.072 | 1.00 | 21.90 | B1 |
| ATOM | 1776 | CG1 | ILE | 116 | 36.563 | 34.055 | 2.443 | 1.00 | 25.67 | B1 |
| ATOM | 1777 | CD1 | ILE | 116 | 37.846 | 33.375 | 2.910 | 1.00 | 23.92 | B1 |
| ATOM | 1778 | C | ILE | 116 | 34.168 | 33.440 | -0.585 | 1.00 | 27.98 | B1 |
| ATOM | 1779 | O | ILE | 116 | 34.019 | 32.231 | -0.862 | 1.00 | 27.19 | B1 |
| ATOM | 1780 | N | GLU | 117 | 33.948 | 34.402 | -1.468 | 1.00 | 29.29 | B1 |
| ATOM | 1781 | CA | GLU | 117 | 33.483 | 34.060 | -2.793 | 1.00 | 32.80 | B1 |
| ATOM | 1782 | CB | GLU | 117 | 31.938 | 33.962 | -2.782 | 1.00 | 33.28 | B1 |
| ATOM | 1783 | CG | GLU | 117 | 31.267 | 35.318 | -2.609 | 1.00 | 35.65 | B1 |
| ATOM | 1784 | CD | GLU | 117 | 29.723 | 35.291 | -2.613 | 1.00 | 39.26 | B1 |
| ATOM | 1785 | OE1 | GLU | 117 | 29.134 | 36.419 | -2.643 | 1.00 | 39.69 | B1 |
| ATOM | 1786 | OE2 | GLU | 117 | 29.100 | 34.172 | -2.569 | 1.00 | 40.90 | B1 |
| ATOM | 1787 | C | GLU | 117 | 33.915 | 35.103 | -3.843 | 1.00 | 34.11 | B1 |
| ATOM | 1788 | O | GLU | 117 | 34.548 | 36.141 | -3.535 | 1.00 | 32.11 | B1 |
| ATOM | 1789 | N | ALA | 118 | 33.485 | 34.819 | -5.066 | 1.00 | 36.51 | B1 |
| ATOM | 1790 | CA | ALA | 118 | 33.783 | 35.630 | -6.233 | 1.00 | 40.20 | B1 |
| ATOM | 1791 | CB | ALA | 118 | 33.338 | 34.887 | -7.482 | 1.00 | 39.39 | B1 |
| ATOM | 1792 | C | ALA | 118 | 33.186 | 37.007 | -6.271 | 1.00 | 42.95 | B1 |
| ATOM | 1793 | O | ALA | 118 | 32.180 | 37.281 | -5.640 | 1.00 | 43.48 | B1 |
| ATOM | 1794 | N | LEU | 119 | 33.826 | 37.852 | -7.070 | 1.00 | 47.53 | B1 |
| ATOM | 1795 | CA | LEU | 119 | 33.378 | 39.215 | -7.384 | 1.00 | 49.83 | B1 |
| ATOM | 1796 | CB | LEU | 119 | 31.859 | 39.214 | -7.654 | 1.00 | 49.43 | B1 |
| ATOM | 1797 | CG | LEU | 119 | 30.968 | 40.454 | -7.784 | 1.00 | 50.65 | B1 |
| ATOM | 1798 | CD1 | LEU | 119 | 31.476 | 41.381 | -8.912 | 1.00 | 51.06 | B1 |
| ATOM | 1799 | CD2 | LEU | 119 | 29.527 | 39.980 | -8.097 | 1.00 | 50.28 | B1 |
| ATOM | 1800 | C | LEU | 119 | 33.756 | 40.162 | -6.277 | 1.00 | 51.63 | B1 |
| ATOM | 1801 | OT1 | LEU | 119 | 34.683 | 39.763 | -5.528 | 1.00 | 51.82 | B1 |
| ATOM | 1802 | OT2 | LEU | 119 | 33.142 | 41.276 | -6.215 | 1.00 | 53.62 | B1 |
| ATOM | 1803 | CB | TYR | 3 | 22.353 | 25.516 | -5.379 | 1.00 | 52.68 | C1 |
| ATOM | 1804 | CG | TYR | 3 | 23.167 | 26.530 | -4.597 | 1.00 | 55.12 | C1 |
| ATOM | 1805 | CD1 | TYR | 3 | 23.777 | 27.607 | -5.230 | 1.00 | 56.73 | C1 |
| ATOM | 1806 | CE1 | TYR | 3 | 24.534 | 28.530 | -4.502 | 1.00 | 57.50 | C1 |
| ATOM | 1807 | CD2 | TYR | 3 | 23.326 | 26.402 | -3.210 | 1.00 | 56.45 | C1 |
| ATOM | 1808 | CE2 | TYR | 3 | 24.059 | 27.308 | -2.471 | 1.00 | 56.85 | C1 |
| ATOM | 1809 | CZ | TYR | 3 | 24.663 | 28.372 | -3.111 | 1.00 | 57.87 | C1 |
| ATOM | 1810 | OH | TYR | 3 | 25.343 | 29.305 | -2.339 | 1.00 | 58.87 | C1 |
| ATOM | 1811 | C | TYR | 3 | 21.336 | 24.385 | -3.370 | 1.00 | 47.65 | C1 |
| ATOM | 1812 | O | TYR | 3 | 20.156 | 24.720 | -3.457 | 1.00 | 48.16 | C1 |
| ATOM | 1813 | N | TYR | 3 | 21.618 | 23.132 | -5.551 | 1.00 | 50.61 | C1 |
| ATOM | 1814 | CA | TYR | 3 | 22.181 | 24.174 | -4.640 | 1.00 | 50.00 | C1 |
| ATOM | 1815 | N | GLY | 4 | 21.970 | 24.178 | -2.205 | 1.00 | 43.78 | C1 |
| ATOM | 1816 | CA | GLY | 4 | 21.319 | 24.320 | -0.920 | 1.00 | 38.85 | C1 |

FIG. 3A-32

| ATOM | 1817 | C   | GLY | 4  | 22.345 | 24.450 | 0.208  | 1.00 | 36.34 | C1 |
|------|------|-----|-----|----|--------|--------|--------|------|-------|----|
| ATOM | 1818 | O   | GLY | 4  | 23.551 | 24.279 | -0.011 | 1.00 | 34.94 | C1 |
| ATOM | 1819 | N   | ILE | 5  | 21.879 | 24.771 | 1.417  | 1.00 | 32.79 | C1 |
| ATOM | 1820 | CA  | ILE | 5  | 22.812 | 24.856 | 2.499  | 1.00 | 30.68 | C1 |
| ATOM | 1821 | CB  | ILE | 5  | 23.048 | 26.321 | 2.948  | 1.00 | 30.63 | C1 |
| ATOM | 1822 | CG2 | ILE | 5  | 23.451 | 27.158 | 1.751  | 1.00 | 30.56 | C1 |
| ATOM | 1823 | CG1 | ILE | 5  | 21.785 | 26.866 | 3.658  | 1.00 | 28.48 | C1 |
| ATOM | 1824 | CD1 | ILE | 5  | 21.859 | 28.351 | 3.966  | 1.00 | 29.65 | C1 |
| ATOM | 1825 | C   | ILE | 5  | 22.278 | 24.030 | 3.675  | 1.00 | 30.17 | C1 |
| ATOM | 1826 | O   | ILE | 5  | 21.067 | 23.869 | 3.858  | 1.00 | 28.91 | C1 |
| ATOM | 1827 | N   | GLY | 6  | 23.204 | 23.501 | 4.470  | 1.00 | 28.77 | C1 |
| ATOM | 1828 | CA  | GLY | 6  | 22.815 | 22.720 | 5.628  | 1.00 | 27.45 | C1 |
| ATOM | 1829 | C   | GLY | 6  | 23.619 | 23.128 | 6.849  | 1.00 | 27.03 | C1 |
| ATOM | 1830 | O   | GLY | 6  | 24.801 | 23.444 | 6.791  | 1.00 | 26.98 | C1 |
| ATOM | 1831 | N   | LEU | 7  | 22.948 | 23.131 | 7.972  | 1.00 | 27.09 | C1 |
| ATOM | 1832 | CA  | LEU | 7  | 23.572 | 23.483 | 9.217  | 1.00 | 27.34 | C1 |
| ATOM | 1833 | CB  | LEU | 7  | 23.079 | 24.868 | 9.689  | 1.00 | 26.42 | C1 |
| ATOM | 1834 | CG  | LEU | 7  | 23.524 | 25.173 | 11.136 | 1.00 | 25.33 | C1 |
| ATOM | 1835 | CD1 | LEU | 7  | 25.069 | 25.163 | 11.156 | 1.00 | 24.79 | C1 |
| ATOM | 1836 | CD2 | LEU | 7  | 22.967 | 26.502 | 11.651 | 1.00 | 23.18 | C1 |
| ATOM | 1837 | C   | LEU | 7  | 23.155 | 22.464 | 10.256 | 1.00 | 28.20 | C1 |
| ATOM | 1838 | O   | LEU | 7  | 21.971 | 22.130 | 10.349 | 1.00 | 27.84 | C1 |
| ATOM | 1839 | N   | ASP | 8  | 24.102 | 21.939 | 11.023 | 1.00 | 29.28 | C1 |
| ATOM | 1840 | CA  | ASP | 8  | 23.706 | 21.056 | 12.115 | 1.00 | 30.50 | C1 |
| ATOM | 1841 | CB  | ASP | 8  | 23.763 | 19.571 | 11.768 | 1.00 | 31.66 | C1 |
| ATOM | 1842 | CG  | ASP | 8  | 23.427 | 18.685 | 13.011 | 1.00 | 35.63 | C1 |
| ATOM | 1843 | OD1 | ASP | 8  | 24.372 | 18.151 | 13.645 | 1.00 | 37.39 | C1 |
| ATOM | 1844 | OD2 | ASP | 8  | 22.219 | 18.555 | 13.405 | 1.00 | 36.31 | C1 |
| ATOM | 1845 | C   | ASP | 8  | 24.585 | 21.300 | 13.323 | 1.00 | 30.33 | C1 |
| ATOM | 1846 | O   | ASP | 8  | 25.762 | 21.585 | 13.166 | 1.00 | 30.47 | C1 |
| ATOM | 1847 | N   | ILE | 9  | 23.993 | 21.205 | 14.511 | 1.00 | 31.74 | C1 |
| ATOM | 1848 | CA  | ILE | 9  | 24.678 | 21.363 | 15.784 | 1.00 | 32.84 | C1 |
| ATOM | 1849 | CB  | ILE | 9  | 24.252 | 22.658 | 16.511 | 1.00 | 32.34 | C1 |
| ATOM | 1850 | CG2 | ILE | 9  | 25.067 | 22.797 | 17.803 | 1.00 | 30.24 | C1 |
| ATOM | 1851 | CG1 | ILE | 9  | 24.518 | 23.893 | 15.641 | 1.00 | 33.38 | C1 |
| ATOM | 1852 | CD1 | ILE | 9  | 24.043 | 25.227 | 16.283 | 1.00 | 33.77 | C1 |
| ATOM | 1853 | C   | ILE | 9  | 24.296 | 20.145 | 16.673 | 1.00 | 34.79 | C1 |
| ATOM | 1854 | O   | ILE | 9  | 23.122 | 19.971 | 17.004 | 1.00 | 35.36 | C1 |
| ATOM | 1855 | N   | THR | 10 | 25.269 | 19.328 | 17.073 | 1.00 | 35.74 | C1 |
| ATOM | 1856 | CA  | THR | 10 | 24.994 | 18.137 | 17.882 | 1.00 | 37.27 | C1 |
| ATOM | 1857 | CB  | THR | 10 | 25.472 | 16.876 | 17.144 | 1.00 | 37.49 | C1 |
| ATOM | 1858 | OG1 | THR | 10 | 24.647 | 16.636 | 15.995 | 1.00 | 38.81 | C1 |
| ATOM | 1859 | CG2 | THR | 10 | 25.451 | 15.678 | 18.065 | 1.00 | 38.55 | C1 |
| ATOM | 1860 | C   | THR | 10 | 25.681 | 18.138 | 19.248 | 1.00 | 38.47 | C1 |
| ATOM | 1861 | O   | THR | 10 | 26.890 | 18.376 | 19.350 | 1.00 | 38.09 | C1 |
| ATOM | 1862 | N   | GLU | 11 | 24.937 | 17.808 | 20.297 | 1.00 | 40.65 | C1 |
| ATOM | 1863 | CA  | GLU | 11 | 25.517 | 17.796 | 21.641 | 1.00 | 42.07 | C1 |
| ATOM | 1864 | CB  | GLU | 11 | 24.445 | 17.698 | 22.704 | 1.00 | 44.46 | C1 |
| ATOM | 1865 | CG  | GLU | 11 | 23.399 | 18.780 | 22.608 | 1.00 | 47.87 | C1 |
| ATOM | 1866 | CD  | GLU | 11 | 22.055 | 18.287 | 22.052 | 1.00 | 50.81 | C1 |
| ATOM | 1867 | OE1 | GLU | 11 | 21.992 | 17.793 | 20.875 | 1.00 | 52.69 | C1 |
| ATOM | 1868 | OE2 | GLU | 11 | 21.042 | 18.409 | 22.790 | 1.00 | 52.15 | C1 |
| ATOM | 1869 | C   | GLU | 11 | 26.487 | 16.655 | 21.798 | 1.00 | 42.23 | C1 |
| ATOM | 1870 | O   | GLU | 11 | 26.160 | 15.496 | 21.547 | 1.00 | 41.87 | C1 |
| ATOM | 1871 | N   | LEU | 12 | 27.703 | 16.998 | 22.197 | 1.00 | 43.04 | C1 |
| ATOM | 1872 | CA  | LEU | 12 | 28.755 | 16.015 | 22.402 | 1.00 | 44.92 | C1 |
| ATOM | 1873 | CB  | LEU | 12 | 30.050 | 16.762 | 22.759 | 1.00 | 45.32 | C1 |

FIG. 3A-33

```
ATOM   1874  CG   LEU  12    31.373  16.017  22.645  1.00  45.47     C1
ATOM   1875  CD1  LEU  12    31.521  15.493  21.223  1.00  45.90     C1
ATOM   1876  CD2  LEU  12    32.531  16.952  22.988  1.00  45.63     C1
ATOM   1877  C    LEU  12    28.445  14.905  23.462  1.00  45.67     C1
ATOM   1878  O    LEU  12    28.808  13.750  23.266  1.00  46.27     C1
ATOM   1879  N    LYS  13    27.804  15.257  24.570  1.00  46.36     C1
ATOM   1880  CA   LYS  13    27.478  14.283  25.614  1.00  48.63     C1
ATOM   1881  CB   LYS  13    26.628  14.935  26.733  1.00  48.16     C1
ATOM   1882  CG   LYS  13    25.200  15.282  26.310  1.00  50.76     C1
ATOM   1883  CD   LYS  13    24.417  16.187  27.292  1.00  52.14     C1
ATOM   1884  CE   LYS  13    23.891  15.429  28.541  1.00  53.30     C1
ATOM   1885  NZ   LYS  13    22.991  16.264  29.447  1.00  53.41     C1
ATOM   1886  C    LYS  13    26.732  13.083  25.015  1.00  49.49     C1
ATOM   1887  O    LYS  13    27.108  11.942  25.199  1.00  49.68     C1
ATOM   1888  N    ARG  14    25.686  13.359  24.265  1.00  50.80     C1
ATOM   1889  CA   ARG  14    24.892  12.318  23.663  1.00  52.14     C1
ATOM   1890  CB   ARG  14    23.783  12.965  22.866  1.00  51.84     C1
ATOM   1891  CG   ARG  14    23.042  13.982  23.692  1.00  51.93     C1
ATOM   1892  CD   ARG  14    22.047  14.703  22.828  1.00  53.26     C1
ATOM   1893  NE   ARG  14    21.053  13.803  22.252  1.00  53.51     C1
ATOM   1894  CZ   ARG  14    20.340  14.101  21.171  1.00  54.68     C1
ATOM   1895  NH1  ARG  14    20.523  15.261  20.563  1.00  54.94     C1
ATOM   1896  NH2  ARG  14    19.444  13.245  20.687  1.00  55.74     C1
ATOM   1897  C    ARG  14    25.680  11.361  22.795  1.00  53.45     C1
ATOM   1898  O    ARG  14    25.363  10.183  22.741  1.00  54.19     C1
ATOM   1899  N    ILE  15    26.717  11.843  22.128  1.00  54.83     C1
ATOM   1900  CA   ILE  15    27.474  10.964  21.267  1.00  57.01     C1
ATOM   1901  CB   ILE  15    28.057  11.749  20.059  1.00  56.55     C1
ATOM   1902  CG2  ILE  15    29.188  10.976  19.391  1.00  56.26     C1
ATOM   1903  CG1  ILE  15    26.929  11.991  19.053  1.00  56.70     C1
ATOM   1904  CD1  ILE  15    27.329  12.663  17.774  1.00  56.92     C1
ATOM   1905  C    ILE  15    28.547  10.195  22.020  1.00  58.74     C1
ATOM   1906  O    ILE  15    28.958   9.114  21.606  1.00  59.22     C1
ATOM   1907  N    ALA  16    28.994  10.740  23.138  1.00  60.96     C1
ATOM   1908  CA   ALA  16    30.002  10.064  23.939  1.00  63.12     C1
ATOM   1909  CB   ALA  16    30.797  11.077  24.740  1.00  63.01     C1
ATOM   1910  C    ALA  16    29.254   9.132  24.881  1.00  64.75     C1
ATOM   1911  O    ALA  16    29.784   8.098  25.285  1.00  65.27     C1
ATOM   1912  N    SER  17    28.017   9.519  25.208  1.00  66.19     C1
ATOM   1913  CA   SER  17    27.134   8.793  26.118  1.00  67.59     C1
ATOM   1914  CB   SER  17    25.826   9.574  26.347  1.00  67.92     C1
ATOM   1915  OG   SER  17    26.016  10.786  27.054  1.00  67.73     C1
ATOM   1916  C    SER  17    26.757   7.405  25.628  1.00  68.66     C1
ATOM   1917  O    SER  17    26.132   6.640  26.376  1.00  68.47     C1
ATOM   1918  N    MET  18    27.093   7.094  24.375  1.00  69.63     C1
ATOM   1919  CA   MET  18    26.786   5.777  23.798  1.00  70.99     C1
ATOM   1920  CB   MET  18    26.851   5.853  22.277  1.00  71.06     C1
ATOM   1921  CG   MET  18    25.973   6.933  21.711  1.00  71.97     C1
ATOM   1922  SD   MET  18    26.030   6.980  19.905  1.00  73.05     C1
ATOM   1923  CE   MET  18    24.315   6.428  19.528  1.00  73.21     C1
ATOM   1924  C    MET  18    27.749   4.697  24.321  1.00  71.40     C1
ATOM   1925  O    MET  18    28.673   4.264  23.633  1.00  71.07     C1
ATOM   1926  N    ALA  19    27.506   4.270  25.551  1.00  72.22     C1
ATOM   1927  CA   ALA  19    28.341   3.281  26.219  1.00  73.14     C1
ATOM   1928  CB   ALA  19    27.573   2.671  27.415  1.00  73.41     C1
ATOM   1929  C    ALA  19    28.821   2.189  25.267  1.00  73.29     C1
ATOM   1930  O    ALA  19    29.755   2.402  24.496  1.00  73.21     C1
```

FIG. 3A-34

```
ATOM   1931  N    GLY   20    28.187   1.022  25.339  1.00 73.39      C1
ATOM   1932  CA   GLY   20    28.550  -0.088  24.468  1.00 73.28      C1
ATOM   1933  C    GLY   20    27.835   0.042  23.133  1.00 72.78      C1
ATOM   1934  O    GLY   20    28.124  -0.687  22.172  1.00 73.18      C1
ATOM   1935  N    ALA   21    26.909   0.994  23.074  1.00 72.11      C1
ATOM   1936  CA   ALA   21    26.152  -1.257  21.864  1.00 71.43      C1
ATOM   1937  CB   ALA   21    24.775   1.796  22.230  1.00 71.48      C1
ATOM   1938  C    ALA   21    26.869   2.234  20.915  1.00 70.86      C1
ATOM   1939  O    ALA   21    26.378   2.496  19.814  1.00 71.29      C1
ATOM   1940  N    GLN   22    28.026   2.767  21.310  1.00 69.99      C1
ATOM   1941  CA   GLN   22    28.721   3.723  20.435  1.00 68.84      C1
ATOM   1942  CB   GLN   22    29.765   4.560  21.216  1.00 69.02      C1
ATOM   1943  CG   GLN   22    30.326   5.758  20.410  1.00 69.19      C1
ATOM   1944  CD   GLN   22    31.497   6.497  21.087  1.00 69.34      C1
ATOM   1945  OE1  GLN   22    31.310   7.185  22.095  1.00 69.45      C1
ATOM   1946  NE2  GLN   22    32.709   6.356  20.521  1.00 68.39      C1
ATOM   1947  C    GLN   22    29.391   3.081  19.218  1.00 67.50      C1
ATOM   1948  O    GLN   22    29.385   3.660  18.117  1.00 67.29      C1
ATOM   1949  N    LYS   23    29.960   1.887  19.405  1.00 66.01      C1
ATOM   1950  CA   LYS   23    30.647   1.197  18.306  1.00 63.66      C1
ATOM   1951  CB   LYS   23    31.376  -0.048  18.820  1.00 63.88      C1
ATOM   1952  C    LYS   23    29.697   0.828  17.178  1.00 61.94      C1
ATOM   1953  O    LYS   23    30.024   1.040  16.009  1.00 61.92      C1
ATOM   1954  N    ALA   24    28.531   0.276  17.501  1.00 59.42      C1
ATOM   1955  CA   ALA   24    27.608  -0.064  16.433  1.00 57.41      C1
ATOM   1956  CB   ALA   24    26.401  -0.809  16.978  1.00 58.14      C1
ATOM   1957  C    ALA   24    27.188   1.243  15.774  1.00 55.96      C1
ATOM   1958  O    ALA   24    26.959   1.309  14.560  1.00 55.56      C1
ATOM   1959  N    PHE   25    27.096   2.293  16.585  1.00 54.55      C1
ATOM   1960  CA   PHE   25    26.742   3.606  16.069  1.00 53.36      C1
ATOM   1961  CB   PHE   25    26.589   4.605  17.206  1.00 54.38      C1
ATOM   1962  CG   PHE   25    26.245   6.010  16.750  1.00 54.54      C1
ATOM   1963  CD1  PHE   25    25.001   6.302  16.224  1.00 53.95      C1
ATOM   1964  CD2  PHE   25    27.175   7.044  16.869  1.00 54.96      C1
ATOM   1965  CE1  PHE   25    24.690   7.594  15.826  1.00 54.26      C1
ATOM   1966  CE2  PHE   25    26.863   8.348  16.468  1.00 54.29      C1
ATOM   1967  CZ   PHE   25    25.622   8.616  15.950  1.00 54.55      C1
ATOM   1968  C    PHE   25    27.793   4.127  15.089  1.00 52.32      C1
ATOM   1969  O    PHE   25    27.439   4.764  14.115  1.00 51.87      C1
ATOM   1970  N    ALA   26    29.077   3.876  15.348  1.00 50.87      C1
ATOM   1971  CA   ALA   26    30.116   4.333  14.436  1.00 49.99      C1
ATOM   1972  CB   ALA   26    31.478   4.112  15.040  1.00 50.04      C1
ATOM   1973  C    ALA   26    29.997   3.573  13.123  1.00 49.93      C1
ATOM   1974  O    ALA   26    30.188   4.127  12.033  1.00 49.20      C1
ATOM   1975  N    GLU   27    29.649   2.295  13.234  1.00 50.16      C1
ATOM   1976  CA   GLU   27    29.496   1.448  12.070  1.00 50.47      C1
ATOM   1977  CB   GLU   27    29.173   0.024  12.510  1.00 52.03      C1
ATOM   1978  CG   GLU   27    30.367  -0.815  12.987  1.00 54.33      C1
ATOM   1979  CD   GLU   27    29.916  -2.070  13.746  1.00 55.34      C1
ATOM   1980  OE1  GLU   27    28.944  -2.729  13.292  1.00 56.02      C1
ATOM   1981  OE2  GLU   27    30.533  -2.398  14.787  1.00 55.46      C1
ATOM   1982  C    GLU   27    28.419   1.931  11.093  1.00 49.87      C1
ATOM   1983  O    GLU   27    28.528   1.710   9.895  1.00 49.63      C1
ATOM   1984  N    ARG   28    27.360   2.567  11.569  1.00 49.12      C1
ATOM   1985  CA   ARG   28    26.371   2.984  10.596  1.00 49.19      C1
ATOM   1986  CB   ARG   28    24.942   2.738  11.106  1.00 51.09      C1
ATOM   1987  CG   ARG   28    24.450   3.590  12.237  1.00 54.01      C1
```

FIG. 3A-35

| | | | | | | | | | |
|---|---|---|---|---|---|---|---|---|---|
| ATOM | 1988 | CD | ARG | 28 | 23.036 | 3.114 | 12.653 | 1.00 55.93 | C1 |
| ATOM | 1989 | NE | ARG | 28 | 22.209 | 2.863 | 11.476 | 1.00 57.95 | C1 |
| ATOM | 1990 | CZ | ARG | 28 | 20.924 | 2.507 | 11.517 | 1.00 58.79 | C1 |
| ATOM | 1991 | NH1 | ARG | 28 | 20.313 | 2.352 | 12.684 | 1.00 59.69 | C1 |
| ATOM | 1992 | NH2 | ARG | 28 | 20.243 | 2.340 | 10.389 | 1.00 58.73 | C1 |
| ATOM | 1993 | C | ARG | 28 | 26.553 | 4.409 | 10.124 | 1.00 48.21 | C1 |
| ATOM | 1994 | O | ARG | 28 | 26.098 | 4.762 | 9.053 | 1.00 47.43 | C1 |
| ATOM | 1995 | N | ILE | 29 | 27.272 | 5.201 | 10.912 | 1.00 47.42 | C1 |
| ATOM | 1996 | CA | ILE | 29 | 27.538 | 6.605 | 10.614 | 1.00 46.88 | C1 |
| ATOM | 1997 | CB | ILE | 29 | 27.707 | 7.408 | 11.976 | 1.00 47.32 | C1 |
| ATOM | 1998 | CG2 | ILE | 29 | 28.331 | 8.779 | 11.771 | 1.00 47.45 | C1 |
| ATOM | 1999 | CG1 | ILE | 29 | 26.334 | 7.637 | 12.586 | 1.00 48.41 | C1 |
| ATOM | 2000 | CD1 | ILE | 29 | 25.391 | 8.300 | 11.593 | 1.00 46.71 | C1 |
| ATOM | 2001 | C | ILE | 29 | 28.777 | 6.806 | 9.728 | 1.00 46.01 | C1 |
| ATOM | 2002 | O | ILE | 29 | 28.777 | 7.696 | 8.896 | 1.00 45.66 | C1 |
| ATOM | 2003 | N | LEU | 30 | 29.803 | 5.956 | 9.893 | 1.00 45.16 | C1 |
| ATOM | 2004 | CA | LEU | 30 | 31.074 | 6.085 | 9.173 | 1.00 44.13 | C1 |
| ATOM | 2005 | CB | LEU | 30 | 32.230 | 5.891 | 10.149 | 1.00 42.42 | C1 |
| ATOM | 2006 | CG | LEU | 30 | 32.220 | 6.792 | 11.380 | 1.00 40.57 | C1 |
| ATOM | 2007 | CD1 | LEU | 30 | 33.481 | 6.580 | 12.183 | 1.00 39.86 | C1 |
| ATOM | 2008 | CD2 | LEU | 30 | 32.155 | 8.253 | 10.937 | 1.00 40.97 | C1 |
| ATOM | 2009 | C | LEU | 30 | 31.314 | 5.199 | 7.983 | 1.00 44.93 | C1 |
| ATOM | 2010 | O | LEU | 30 | 30.702 | 4.163 | 7.832 | 1.00 46.00 | C1 |
| ATOM | 2011 | N | THR | 31 | 32.186 | 5.612 | 7.088 | 1.00 45.98 | C1 |
| ATOM | 2012 | CA | THR | 31 | 32.469 | 4.743 | 5.961 | 1.00 47.55 | C1 |
| ATOM | 2013 | CB | THR | 31 | 32.961 | 5.509 | 4.736 | 1.00 46.23 | C1 |
| ATOM | 2014 | OG1 | THR | 31 | 34.189 | 6.165 | 5.066 | 1.00 46.01 | C1 |
| ATOM | 2015 | CG2 | THR | 31 | 31.927 | 6.503 | 4.262 | 1.00 45.18 | C1 |
| ATOM | 2016 | C | THR | 31 | 33.632 | 3.869 | 6.463 | 1.00 49.42 | C1 |
| ATOM | 2017 | O | THR | 31 | 34.085 | 4.033 | 7.610 | 1.00 50.48 | C1 |
| ATOM | 2018 | N | ALA | 32 | 34.123 | 2.963 | 5.616 | 1.00 50.64 | C1 |
| ATOM | 2019 | CA | ALA | 32 | 35.253 | 2.106 | 5.991 | 1.00 51.68 | C1 |
| ATOM | 2020 | CB | ALA | 32 | 35.528 | 1.047 | 4.876 | 1.00 52.35 | C1 |
| ATOM | 2021 | C | ALA | 32 | 36.491 | 2.965 | 6.219 | 1.00 52.19 | C1 |
| ATOM | 2022 | O | ALA | 32 | 37.197 | 2.814 | 7.219 | 1.00 52.47 | C1 |
| ATOM | 2023 | N | SER | 33 | 36.759 | 3.875 | 5.290 | 1.00 52.78 | C1 |
| ATOM | 2024 | CA | SER | 33 | 37.923 | 4.754 | 5.443 | 1.00 53.37 | C1 |
| ATOM | 2025 | CB | SER | 33 | 38.091 | 5.616 | 4.192 | 1.00 54.79 | C1 |
| ATOM | 2026 | OG | SER | 33 | 39.472 | 5.820 | 3.917 | 1.00 57.32 | C1 |
| ATOM | 2027 | C | SER | 33 | 37.852 | 5.661 | 6.688 | 1.00 52.95 | C1 |
| ATOM | 2028 | O | SER | 33 | 38.883 | 6.095 | 7.211 | 1.00 53.00 | C1 |
| ATOM | 2029 | N | GLU | 34 | 36.635 | 5.958 | 7.152 | 1.00 52.41 | C1 |
| ATOM | 2030 | CA | GLU | 34 | 36.455 | 6.784 | 8.347 | 1.00 52.05 | .C1 |
| ATOM | 2031 | CB | GLU | 34 | 35.114 | 7.540 | 8.280 | 1.00 51.02 | C1 |
| ATOM | 2032 | CG | GLU | 34 | 35.061 | 8.615 | 7.156 | 1.00 49.60 | C1 |
| ATOM | 2033 | CD | GLU | 34 | 33.753 | 9.410 | 7.130 | 1.00 48.95 | C1 |
| ATOM | 2034 | OE1 | GLU | 34 | 32.684 | 8.769 | 7.085 | 1.00 47.99 | C1 |
| ATOM | 2035 | OE2 | GLU | 34 | 33.787 | 10.666 | 7.156 | 1.00 47.77 | C1 |
| ATOM | 2036 | C | GLU | 34 | 36.537 | 5.909 | 9.618 | 1.00 52.70 | C1 |
| ATOM | 2037 | O | GLU | 34 | 36.952 | 6.377 | 10.666 | 1.00 52.35 | C1 |
| ATOM | 2038 | N | LEU | 35 | 36.139 | 4.639 | 9.531 | 1.00 53.84 | C1 |
| ATOM | 2039 | CA | LEU | 35 | 36.242 | 3.754 | 10.695 | 1.00 54.78 | C1 |
| ATOM | 2040 | CB | LEU | 35 | 35.546 | 2.420 | 10.432 | 1.00 55.12 | C1 |
| ATOM | 2041 | CG | LEU | 35 | 34.076 | 2.277 | 10.820 | 1.00 55.35 | C1 |
| ATOM | 2042 | CD1 | LEU | 35 | 33.600 | 0.893 | 10.406 | 1.00 55.25 | C1 |
| ATOM | 2043 | CD2 | LEU | 35 | 33.898 | 2.501 | 12.333 | 1.00 54.93 | C1 |
| ATOM | 2044 | C | LEU | 35 | 37.705 | 3.480 | 11.030 | 1.00 55.08 | C1 |

FIG. 3A-36

| ATOM | 2045 | O   | LEU | 35 | 38.115 | 3.573  | 12.191 | 1.00 | 55.65 | C1 |
| ATOM | 2046 | N   | ASP | 36 | 38.485 | 3.130  | 10.009 | 1.00 | 55.26 | C1 |
| ATOM | 2047 | CA  | ASP | 36 | 39.904 | 2.848  | 10.203 | 1.00 | 55.75 | C1 |
| ATOM | 2048 | CB  | ASP | 36 | 40.635 | 2.737  | 8.850  | 1.00 | 56.59 | C1 |
| ATOM | 2049 | CG  | ASP | 36 | 40.120 | 1.578  | 7.996  | 1.00 | 57.54 | C1 |
| ATOM | 2050 | OD1 | ASP | 36 | 39.855 | 0.505  | 8.576  | 1.00 | 57.49 | C1 |
| ATOM | 2051 | OD2 | ASP | 36 | 39.985 | 1.732  | 6.753  | 1.00 | 58.09 | C1 |
| ATOM | 2052 | C   | ASP | 36 | 40.478 | 3.993  | 11.016 | 1.00 | 55.72 | C1 |
| ATOM | 2053 | O   | ASP | 36 | 41.169 | 3.788  | 11.997 | 1.00 | 56.02 | C1 |
| ATOM | 2054 | N   | GLN | 37 | 40.166 | 5.210  | 10.600 | 1.00 | 55.73 | C1 |
| ATOM | 2055 | CA  | GLN | 37 | 40.619 | 6.405  | 11.283 | 1.00 | 55.71 | C1 |
| ATOM | 2056 | CB  | GLN | 37 | 40.149 | 7.628  | 10.521 | 1.00 | 54.93 | C1 |
| ATOM | 2057 | CG  | GLN | 37 | 41.213 | 8.381  | 9.795  | 1.00 | 54.35 | C1 |
| ATOM | 2058 | CD  | GLN | 37 | 40.631 | 9.593  | 9.112  | 1.00 | 54.07 | C1 |
| ATOM | 2059 | OE1 | GLN | 37 | 39.960 | 9.478  | 8.075  | 1.00 | 52.71 | C1 |
| ATOM | 2060 | NE2 | GLN | 37 | 40.858 | 10.764 | 9.705  | 1.00 | 52.34 | C1 |
| ATOM | 2061 | C   | GLN | 37 | 40.101 | 6.530  | 12.708 | 1.00 | 56.36 | C1 |
| ATOM | 2062 | O   | GLN | 37 | 40.839 | 6.929  | 13.607 | 1.00 | 56.00 | C1 |
| ATOM | 2063 | N   | TYR | 38 | 38.821 | 6.219  | 12.909 | 1.00 | 57.07 | C1 |
| ATOM | 2064 | CA  | TYR | 38 | 38.219 | 6.361  | 14.237 | 1.00 | 58.12 | C1 |
| ATOM | 2065 | CB  | TYR | 38 | 36.686 | 6.298  | 14.132 | 1.00 | 56.44 | C1 |
| ATOM | 2066 | CG  | TYR | 38 | 35.946 | 5.851  | 15.376 | 1.00 | 55.07 | C1 |
| ATOM | 2067 | CD1 | TYR | 38 | 35.634 | 4.492  | 15.577 | 1.00 | 54.58 | C1 |
| ATOM | 2068 | CE1 | TYR | 38 | 34.888 | 4.081  | 16.665 | 1.00 | 54.40 | C1 |
| ATOM | 2069 | CD2 | TYR | 38 | 35.495 | 6.775  | 16.309 | 1.00 | 54.17 | C1 |
| ATOM | 2070 | CE2 | TYR | 38 | 34.743 | 6.383  | 17.403 | 1.00 | 54.20 | C1 |
| ATOM | 2071 | CZ  | TYR | 38 | 34.434 | 5.031  | 17.579 | 1.00 | 55.06 | C1 |
| ATOM | 2072 | OH  | TYR | 38 | 33.624 | 4.643  | 18.637 | 1.00 | 54.94 | C1 |
| ATOM | 2073 | C   | TYR | 38 | 38.746 | 5.362  | 15.259 | 1.00 | 59.63 | C1 |
| ATOM | 2074 | O   | TYR | 38 | 38.891 | 5.689  | 16.444 | 1.00 | 59.42 | C1 |
| ATOM | 2075 | N   | TYR | 39 | 39.033 | 4.147  | 14.814 | 1.00 | 61.46 | C1 |
| ATOM | 2076 | CA  | TYR | 39 | 39.556 | 3.170  | 15.746 | 1.00 | 63.73 | C1 |
| ATOM | 2077 | CB  | TYR | 39 | 39.643 | 1.793  | 15.071 | 1.00 | 64.25 | C1 |
| ATOM | 2078 | CG  | TYR | 39 | 38.272 | 1.181  | 14.835 | 1.00 | 64.53 | C1 |
| ATOM | 2079 | CD1 | TYR | 39 | 37.344 | 1.080  | 15.881 | 1.00 | 64.91 | C1 |
| ATOM | 2080 | CE1 | TYR | 39 | 36.072 | 0.506  | 15.680 | 1.00 | 65.28 | C1 |
| ATOM | 2081 | CD2 | TYR | 39 | 37.905 | 0.696  | 13.577 | 1.00 | 64.93 | C1 |
| ATOM | 2082 | CE2 | TYR | 39 | 36.642 | 0.121  | 13.361 | 1.00 | 65.37 | C1 |
| ATOM | 2083 | CZ  | TYR | 39 | 35.729 | 0.030  | 14.418 | 1.00 | 65.70 | C1 |
| ATOM | 2084 | OH  | TYR | 39 | 34.476 | -0.536 | 14.209 | 1.00 | 66.41 | C1 |
| ATOM | 2085 | C   | TYR | 39 | 40.921 | 3.650  | 16.250 | 1.00 | 64.86 | C1 |
| ATOM | 2086 | O   | TYR | 39 | 41.182 | 3.658  | 17.456 | 1.00 | 65.10 | C1 |
| ATOM | 2087 | N   | GLU | 40 | 41.762 | 4.121  | 15.335 | 1.00 | 65.88 | C1 |
| ATOM | 2088 | CA  | GLU | 40 | 43.089 | 4.588  | 15.700 | 1.00 | 66.96 | C1 |
| ATOM | 2089 | CB  | GLU | 40 | 43.841 | 5.007  | 14.437 | 1.00 | 68.15 | C1 |
| ATOM | 2090 | CG  | GLU | 40 | 43.834 | 3.971  | 13.306 | 1.00 | 70.60 | C1 |
| ATOM | 2091 | CD  | GLU | 40 | 44.773 | 2.804  | 13.551 | 1.00 | 71.61 | C1 |
| ATOM | 2092 | OE1 | GLU | 40 | 45.990 | 3.062  | 13.726 | 1.00 | 72.41 | C1 |
| ATOM | 2093 | OE2 | GLU | 40 | 44.300 | 1.640  | 13.560 | 1.00 | 72.06 | C1 |
| ATOM | 2094 | C   | GLU | 40 | 43.169 | 5.739  | 16.718 | 1.00 | 67.18 | C1 |
| ATOM | 2095 | O   | GLU | 40 | 44.278 | 6.191  | 17.025 | 1.00 | 67.28 | C1 |
| ATOM | 2096 | N   | LEU | 41 | 42.041 | 6.217  | 17.254 | 1.00 | 67.17 | C1 |
| ATOM | 2097 | CA  | LEU | 41 | 42.099 | 7.348  | 18.199 | 1.00 | 66.97 | C1 |
| ATOM | 2098 | CB  | LEU | 41 | 41.165 | 8.493  | 17.752 | 1.00 | 68.22 | C1 |
| ATOM | 2099 | CG  | LEU | 41 | 40.458 | 8.591  | 16.389 | 1.00 | 69.08 | C1 |
| ATOM | 2100 | CD1 | LEU | 41 | 39.582 | 9.844  | 16.385 | 1.00 | 69.66 | C1 |
| ATOM | 2101 | CD2 | LEU | 41 | 41.463 | 8.646  | 15.253 | 1.00 | 68.80 | C1 |

FIG. 3A-37

| ATOM | 2102 | C | LEU | 41 | 41.815 | 7.099 | 19.673 | 1.00 | 66.10 | C1 |
| ATOM | 2103 | O | LEU | 41 | 41.316 | 6.049 | 20.056 | 1.00 | 65.84 | C1 |
| ATOM | 2104 | N | SER | 42 | 42.121 | 8.118 | 20.481 | 1.00 | 65.38 | C1 |
| ATOM | 2105 | CA | SER | 42 | 41.900 | 8.119 | 21.927 | 1.00 | 64.65 | C1 |
| ATOM | 2106 | CB | SER | 42 | 42.509 | 9.379 | 22.550 | 1.00 | 65.06 | C1 |
| ATOM | 2107 | OG | SER | 42 | 41.588 | 10.451 | 22.500 | 1.00 | 65.28 | C1 |
| ATOM | 2108 | C | SER | 42 | 40.395 | 8.120 | 22.188 | 1.00 | 64.02 | C1 |
| ATOM | 2109 | O | SER | 42 | 39.614 | 8.129 | 21.247 | 1.00 | 64.03 | C1 |
| ATOM | 2110 | N | ALA | 43 | 39.982 | 8.135 | 23.453 | 1.00 | 63.26 | C1 |
| ATOM | 2111 | CA | ALA | 43 | 38.548 | 8.115 | 23.771 | 1.00 | 62.62 | C1 |
| ATOM | 2112 | CB | ALA | 43 | 38.320 | 7.715 | 25.241 | 1.00 | 63.05 | C1 |
| ATOM | 2113 | C | ALA | 43 | 37.864 | 9.443 | 23.490 | 1.00 | 62.12 | C1 |
| ATOM | 2114 | O | ALA | 43 | 36.805 | 9.473 | 22.853 | 1.00 | 61.61 | C1 |
| ATOM | 2115 | N | ALA | 44 | 38.465 | 10.530 | 23.986 | 1.00 | 61.56 | C1 |
| ATOM | 2116 | CA | ALA | 44 | 37.933 | 11.878 | 23.798 | 1.00 | 60.59 | C1 |
| ATOM | 2117 | CB | ALA | 44 | 38.706 | 12.916 | 24.672 | 1.00 | 60.16 | C1 |
| ATOM | 2118 | C | ALA | 44 | 37.978 | 12.284 | 22.326 | 1.00 | 59.80 | C1 |
| ATOM | 2119 | O | ALA | 44 | 37.012 | 12.828 | 21.824 | 1.00 | 59.42 | C1 |
| ATOM | 2120 | N | ARG | 45 | 39.098 | 12.030 | 21.649 | 1.00 | 59.45 | C1 |
| ATOM | 2121 | CA | ARG | 45 | 39.235 | 12.370 | 20.232 | 1.00 | 58.82 | C1 |
| ATOM | 2122 | CB | ARG | 45 | 40.678 | 12.131 | 19.761 | 1.00 | 59.70 | C1 |
| ATOM | 2123 | CG | ARG | 45 | 41.752 | 12.782 | 20.644 | 1.00 | 62.25 | C1 |
| ATOM | 2124 | CD | ARG | 45 | 41.628 | 14.315 | 20.713 | 1.00 | 64.07 | C1 |
| ATOM | 2125 | NE | ARG | 45 | 42.275 | 14.966 | 19.581 | 1.00 | 65.16 | C1 |
| ATOM | 2126 | CZ | ARG | 45 | 42.180 | 16.264 | 19.297 | 1.00 | 66.26 | C1 |
| ATOM | 2127 | NH1 | ARG | 45 | 41.458 | 17.081 | 20.062 | 1.00 | 66.17 | C1 |
| ATOM | 2128 | NH2 | ARG | 45 | 42.811 | 16.745 | 18.232 | 1.00 | 66.74 | C1 |
| ATOM | 2129 | C | ARG | 45 | 38.265 | 11.541 | 19.367 | 1.00 | 57.52 | C1 |
| ATOM | 2130 | O | ARG | 45 | 37.920 | 11.938 | 18.252 | 1.00 | 56.92 | C1 |
| ATOM | 2131 | N | LYS | 46 | 37.847 | 10.387 | 19.894 | 1.00 | 56.06 | C1 |
| ATOM | 2132 | CA | LYS | 46 | 36.907 | 9.486 | 19.224 | 1.00 | 54.03 | C1 |
| ATOM | 2133 | CB | LYS | 46 | 36.846 | 8.128 | 19.929 | 1.00 | 54.55 | C1 |
| ATOM | 2134 | CG | LYS | 46 | 37.435 | 6.971 | 19.164 | 1.00 | 54.57 | C1 |
| ATOM | 2135 | CD | LYS | 46 | 37.268 | 5.714 | 19.992 | 1.00 | 55.22 | C1 |
| ATOM | 2136 | CE | LYS | 46 | 38.104 | 4.549 | 19.478 | 1.00 | 55.72 | C1 |
| ATOM | 2137 | NZ | LYS | 46 | 38.363 | 3.564 | 20.603 | 1.00 | 56.26 | C1 |
| ATOM | 2138 | C | LYS | 46 | 35.520 | 10.089 | 19.273 | 1.00 | 52.55 | C1 |
| ATOM | 2139 | O | LYS | 46 | 34.821 | 10.106 | 18.258 | 1.00 | 52.04 | C1 |
| ATOM | 2140 | N | ASN | 47 | 35.121 | 10.569 | 20.454 | 1.00 | 51.04 | C1 |
| ATOM | 2141 | CA | ASN | 47 | 33.793 | 11.169 | 20.611 | 1.00 | 50.28 | C1 |
| ATOM | 2142 | CB | ASN | 47 | 33.479 | 11.536 | 22.077 | 1.00 | 50.72 | C1 |
| ATOM | 2143 | CG | ASN | 47 | 33.383 | 10.309 | 23.007 | 1.00 | 51.16 | C1 |
| ATOM | 2144 | OD1 | ASN | 47 | 33.148 | 9.176 | 22.575 | 1.00 | 50.76 | C1 |
| ATOM | 2145 | ND2 | ASN | 47 | 33.551 | 10.552 | 24.298 | 1.00 | 51.61 | C1 |
| ATOM | 2146 | C | ASN | 47 | 33.665 | 12.430 | 19.760 | 1.00 | 49.27 | C1 |
| ATOM | 2147 | O | ASN | 47 | 32.597 | 12.715 | 19.215 | 1.00 | 49.62 | C1 |
| ATOM | 2148 | N | GLU | 48 | 34.756 | 13.181 | 19.668 | 1.00 | 47.01 | C1 |
| ATOM | 2149 | CA | GLU | 48 | 34.787 | 14.405 | 18.890 | 1.00 | 45.47 | C1 |
| ATOM | 2150 | CB | GLU | 48 | 36.056 | 15.175 | 19.232 | 1.00 | 45.97 | C1 |
| ATOM | 2151 | CG | GLU | 48 | 36.313 | 16.414 | 18.420 | 1.00 | 48.61 | C1 |
| ATOM | 2152 | CD | GLU | 48 | 37.700 | 17.005 | 18.710 | 1.00 | 50.94 | C1 |
| ATOM | 2153 | OE1 | GLU | 48 | 37.954 | 17.311 | 19.905 | 1.00 | 51.25 | C1 |
| ATOM | 2154 | OE2 | GLU | 48 | 38.523 | 17.146 | 17.756 | 1.00 | 51.22 | C1 |
| ATOM | 2155 | C | GLU | 48 | 34.710 | 14.105 | 17.385 | 1.00 | 43.65 | C1 |
| ATOM | 2156 | O | GLU | 48 | 33.909 | 14.705 | 16.674 | 1.00 | 43.81 | C1 |
| ATOM | 2157 | N | PHE | 49 | 35.530 | 13.169 | 16.924 | 1.00 | 41.45 | C1 |
| ATOM | 2158 | CA | PHE | 49 | 35.583 | 12.746 | 15.520 | 1.00 | 40.40 | C1 |

FIG. 3A-38

| ATOM | 2159 | CB | PHE | 49 | 36.602 | 11.606 | 15.401 | 1.00 | 39.94 | C1 |
| ATOM | 2160 | CG | PHE | 49 | 36.716 | 11.001 | 14.030 | 1.00 | 39.65 | C1 |
| ATOM | 2161 | CD1 | PHE | 49 | 37.568 | 11.557 | 13.076 | 1.00 | 39.24 | C1 |
| ATOM | 2162 | CD2 | PHE | 49 | 35.956 | 9.872 | 13.683 | 1.00 | 39.25 | C1 |
| ATOM | 2163 | CE1 | PHE | 49 | 37.664 | 10.995 | 11.786 | 1.00 | 39.19 | C1 |
| ATOM | 2164 | CE2 | PHE | 49 | 36.045 | 9.309 | 12.416 | 1.00 | 39.13 | C1 |
| ATOM | 2165 | CZ | PHE | 49 | 36.898 | 9.870 | 11.465 | 1.00 | 39.13 | C1 |
| ATOM | 2166 | C | PHE | 49 | 34.223 | 12.285 | 14.969 | 1.00 | 39.44 | C1 |
| ATOM | 2167 | O | PHE | 49 | 33.853 | 12.569 | 13.837 | 1.00 | 38.77 | C1 |
| ATOM | 2168 | N | LEU | 50 | 33.493 | 11.585 | 15.822 | 1.00 | 39.24 | C1 |
| ATOM | 2169 | CA | LEU | 50 | 32.181 | 11.017 | 15.536 | 1.00 | 38.43 | C1 |
| ATOM | 2170 | CB | LEU | 50 | 31.894 | 9.933 | 16.563 | 1.00 | 40.17 | C1 |
| ATOM | 2171 | CG | LEU | 50 | 30.869 | 8.849 | 16.338 | 1.00 | 41.67 | C1 |
| ATOM | 2172 | CD1 | LEU | 50 | 31.036 | 8.226 | 14.967 | 1.00 | 41.34 | C1 |
| ATOM | 2173 | CD2 | LEU | 50 | 31.076 | 7.817 | 17.485 | 1.00 | 42.66 | C1 |
| ATOM | 2174 | C | LEU | 50 | 31.096 | 12.080 | 15.584 | 1.00 | 36.53 | C1 |
| ATOM | 2175 | O | LEU | 50 | 30.238 | 12.089 | 14.728 | 1.00 | 35.96 | C1 |
| ATOM | 2176 | N | ALA | 51 | 31.122 | 12.964 | 16.574 | 1.00 | 34.40 | C1 |
| ATOM | 2177 | CA | ALA | 51 | 30.119 | 14.037 | 16.624 | 1.00 | 33.68 | C1 |
| ATOM | 2178 | CB | ALA | 51 | 30.253 | 14.848 | 17.916 | 1.00 | 32.94 | C1 |
| ATOM | 2179 | C | ALA | 51 | 30.273 | 14.978 | 15.397 | 1.00 | 33.10 | C1 |
| ATOM | 2180 | O | ALA | 51 | 29.285 | 15.500 | 14.898 | 1.00 | 32.94 | C1 |
| ATOM | 2181 | N | GLY | 52 | 31.507 | 15.173 | 14.925 | 1.00 | 31.96 | C1 |
| ATOM | 2182 | CA | GLY | 52 | 31.733 | 16.031 | 13.780 | 1.00 | 31.80 | C1 |
| ATOM | 2183 | C | GLY | 52 | 31.252 | 15.353 | 12.494 | 1.00 | 31.78 | C1 |
| ATOM | 2184 | O | GLY | 52 | 30.628 | 15.983 | 11.644 | 1.00 | 31.70 | C1 |
| ATOM | 2185 | N | ARG | 53 | 31.541 | 14.069 | 12.343 | 1.00 | 30.89 | C1 |
| ATOM | 2186 | CA | ARG | 53 | 31.095 | 13.360 | 11.178 | 1.00 | 30.82 | C1 |
| ATOM | 2187 | CB | ARG | 53 | 31.696 | 11.955 | 11.140 | 1.00 | 31.36 | C1 |
| ATOM | 2188 | CG | ARG | 53 | 33.218 | 11.928 | 10.921 | 1.00 | 32.07 | C1 |
| ATOM | 2189 | CD | ARG | 53 | 33.616 | 12.890 | 9.806 | 1.00 | 32.32 | C1 |
| ATOM | 2190 | NE | ARG | 53 | 34.692 | 12.368 | 8.969 | 1.00 | 33.86 | C1 |
| ATOM | 2191 | CZ | ARG | 53 | 35.987 | 12.658 | 9.095 | 1.00 | 33.37 | C1 |
| ATOM | 2192 | NH1 | ARG | 53 | 36.428 | 13.486 | 10.054 | 1.00 | 33.63 | C1 |
| ATOM | 2193 | NH2 | ARG | 53 | 36.841 | 12.146 | 8.220 | 1.00 | 32.05 | C1 |
| ATOM | 2194 | C | ARG | 53 | 29.569 | 13.319 | 11.182 | 1.00 | 31.61 | C1 |
| ATOM | 2195 | O | ARG | 53 | 28.937 | 13.501 | 10.152 | 1.00 | 31.36 | C1 |
| ATOM | 2196 | N | PHE | 54 | 28.962 | 13.127 | 12.347 | 1.00 | 31.34 | C1 |
| ATOM | 2197 | CA | PHE | 54 | 27.525 | 13.108 | 12.372 | 1.00 | 31.44 | C1 |
| ATOM | 2198 | CB | PHE | 54 | 27.029 | 12.706 | 13.743 | 1.00 | 31.60 | C1 |
| ATOM | 2199 | CG | PHE | 54 | 25.526 | 12.607 | 13.832 | 1.00 | 31.67 | C1 |
| ATOM | 2200 | CD1 | PHE | 54 | 24.785 | 13.643 | 14.338 | 1.00 | 31.48 | C1 |
| ATOM | 2201 | CD2 | PHE | 54 | 24.872 | 11.431 | 13.469 | 1.00 | 33.28 | C1 |
| ATOM | 2202 | CE1 | PHE | 54 | 23.417 | 13.532 | 14.512 | 1.00 | 33.12 | C1 |
| ATOM | 2203 | CE2 | PHE | 54 | 23.498 | 11.304 | 13.636 | 1.00 | 33.43 | C1 |
| ATOM | 2204 | CZ | PHE | 54 | 22.768 | 12.356 | 14.159 | 1.00 | 32.71 | C1 |
| ATOM | 2205 | C | PHE | 54 | 26.956 | 14.500 | 12.004 | 1.00 | 31.59 | C1 |
| ATOM | 2206 | O | PHE | 54 | 25.979 | 14.607 | 11.221 | 1.00 | 31.51 | C1 |
| ATOM | 2207 | N | ALA | 55 | 27.557 | 15.561 | 12.556 | 1.00 | 30.03 | C1 |
| ATOM | 2208 | CA | ALA | 55 | 27.078 | 16.901 | 12.244 | 1.00 | 28.91 | C1 |
| ATOM | 2209 | CB | ALA | 55 | 27.818 | 17.954 | 13.085 | 1.00 | 27.86 | C1 |
| ATOM | 2210 | C | ALA | 55 | 27.269 | 17.201 | 10.759 | 1.00 | 27.31 | C1 |
| ATOM | 2211 | O | ALA | 55 | 26.382 | 17.727 | 10.093 | 1.00 | 27.19 | C1 |
| ATOM | 2212 | N | ALA | 56 | 28.422 | 16.827 | 10.237 | 1.00 | 26.94 | C1 |
| ATOM | 2213 | CA | ALA | 56 | 28.714 | 17.144 | 8.872 | 1.00 | 27.05 | C1 |
| ATOM | 2214 | CB | ALA | 56 | 30.187 | 16.884 | 8.580 | 1.00 | 24.76 | C1 |
| ATOM | 2215 | C | ALA | 56 | 27.795 | 16.412 | 7.896 | 1.00 | 27.88 | C1 |

FIG. 3A-39

| ATOM | 2216 | O   | ALA | 56  | 27.235 | 17.025 | 6.991  | 1.00 | 26.74 | C1 |
|------|------|-----|-----|-----|--------|--------|--------|------|-------|----|
| ATOM | 2217 | N   | LYS | 57  | 27.608 | 15.107 | 8.109  | 1.00 | 29.56 | C1 |
| ATOM | 2218 | CA  | LYS | 57  | 26.730 | 14.322 | 7.225  | 1.00 | 31.03 | C1 |
| ATOM | 2219 | CB  | LYS | 57  | 26.852 | 12.839 | 7.583  | 1.00 | 31.20 | C1 |
| ATOM | 2220 | CG  | LYS | 57  | 28.325 | 12.401 | 7.540  | 1.00 | 32.34 | C1 |
| ATOM | 2221 | CD  | LYS | 57  | 28.512 | 10.871 | 7.527  | 1.00 | 32.86 | C1 |
| ATOM | 2222 | CE  | LYS | 57  | 29.964 | 10.523 | 7.125  | 1.00 | 32.77 | C1 |
| ATOM | 2223 | NZ  | LYS | 57  | 30.182 | 9.068  | 6.836  | 1.00 | 34.27 | C1 |
| ATOM | 2224 | C   | LYS | 57  | 25.274 | 14.819 | 7.324  | 1.00 | 31.24 | C1 |
| ATOM | 2225 | O   | LYS | 57  | 24.590 | 14.833 | 6.318  | 1.00 | 31.30 | C1 |
| ATOM | 2226 | N   | GLU | 58  | 24.818 | 15.223 | 8.521  | 1.00 | 31.14 | C1 |
| ATOM | 2227 | CA  | GLU | 58  | 23.469 | 15.773 | 8.701  | 1.00 | 32.92 | C1 |
| ATOM | 2228 | CB  | GLU | 58  | 23.160 | 16.046 | 10.174 | 1.00 | 36.48 | C1 |
| ATOM | 2229 | CG  | GLU | 58  | 22.886 | 14.782 | 11.009 | 1.00 | 41.69 | C1 |
| ATOM | 2230 | CD  | GLU | 58  | 21.613 | 14.062 | 10.525 | 1.00 | 45.03 | C1 |
| ATOM | 2231 | OE1 | GLU | 58  | 20.590 | 14.119 | 11.249 | 1.00 | 46.29 | C1 |
| ATOM | 2232 | OE2 | GLU | 58  | 21.642 | 13.468 | 9.407  | 1.00 | 47.23 | C1 |
| ATOM | 2233 | C   | GLU | 58  | 23.369 | 17.113 | 7.960  | 1.00 | 33.31 | C1 |
| ATOM | 2234 | O   | GLU | 58  | 22.386 | 17.346 | 7.263  | 1.00 | 33.22 | C1 |
| ATOM | 2235 | N   | ALA | 59  | 24.380 | 17.986 | 8.106  | 1.00 | 32.66 | C1 |
| ATOM | 2236 | CA  | ALA | 59  | 24.364 | 19.285 | 7.436  | 1.00 | 32.45 | C1 |
| ATOM | 2237 | CB  | ALA | 59  | 25.613 | 20.073 | 7.756  | 1.00 | 30.78 | C1 |
| ATOM | 2238 | C   | ALA | 59  | 24.309 | 19.048 | 5.937  | 1.00 | 32.54 | C1 |
| ATOM | 2239 | O   | ALA | 59  | 23.592 | 19.712 | 5.207  | 1.00 | 30.95 | C1 |
| ATOM | 2240 | N   | PHE | 60  | 25.109 | 18.110 | 5.483  | 1.00 | 33.43 | C1 |
| ATOM | 2241 | CA  | PHE | 60  | 25.158 | 17.816 | 4.065  | 1.00 | 35.36 | C1 |
| ATOM | 2242 | CB  | PHE | 60  | 26.240 | 16.789 | 3.766  | 1.00 | 35.51 | C1 |
| ATOM | 2243 | CG  | PHE | 60  | 26.301 | 16.398 | 2.312  | 1.00 | 37.38 | C1 |
| ATOM | 2244 | CD1 | PHE | 60  | 27.001 | 17.173 | 1.391  | 1.00 | 38.64 | C1 |
| ATOM | 2245 | CD2 | PHE | 60  | 25.663 | 15.256 | 1.863  | 1.00 | 37.90 | C1 |
| ATOM | 2246 | CE1 | PHE | 60  | 27.061 | 16.786 | 0.032  | 1.00 | 38.44 | C1 |
| ATOM | 2247 | CE2 | PHE | 60  | 25.715 | 14.871 | 0.532  | 1.00 | 37.72 | C1 |
| ATOM | 2248 | CZ  | PHE | 60. | 26.411 | 15.626 | -0.379 | 1.00 | 38.22 | C1 |
| ATOM | 2249 | C   | PHE | 60  | 23.815 | 17.239 | 3.606  | 1.00 | 35.65 | C1 |
| ATOM | 2250 | O   | PHE | 60  | 23.355 | 17.504 | 2.497  | 1.00 | 35.06 | C1 |
| ATOM | 2251 | N   | SER | 61  | 23.196 | 16.441 | 4.470  | 1.00 | 36.40 | C1 |
| ATOM | 2252 | CA  | SER | 61  | 21.940 | 15.852 | 4.072  | 1.00 | 37.14 | C1 |
| ATOM | 2253 | CB  | SER | 61  | 21.545 | 14.691 | 5.006  | 1.00 | 36.12 | C1 |
| ATOM | 2254 | OG  | SER | 61  | 20.814 | 15.139 | 6.126  | 1.00 | 35.05 | C1 |
| ATOM | 2255 | C   | SER | 61  | 20.869 | 16.940 | 4.016  | 1.00 | 37.16 | C1 |
| ATOM | 2256 | O   | SER | 61  | 19.964 | 16.870 | 3.190  | 1.00 | 38.46 | C1 |
| ATOM | 2257 | N   | LYS | 62  | 20.970 | 17.955 | 4.857  | 1.00 | 37.48 | C1 |
| ATOM | 2258 | CA  | LYS | 62  | 19.954 | 19.006 | 4.813  | 1.00 | 37.83 | C1 |
| ATOM | 2259 | CB  | LYS | 62  | 20.021 | 19.903 | 6.021  | 1.00 | 38.42 | C1 |
| ATOM | 2260 | CG  | LYS | 62  | 19.610 | 19.236 | 7.327  | 1.00 | 40.35 | C1 |
| ATOM | 2261 | CD  | LYS | 62  | 19.854 | 20.259 | 8.406  | 1.00 | 41.61 | C1 |
| ATOM | 2262 | CE  | LYS | 62  | 19.418 | 19.814 | 9.748  | 1.00 | 43.22 | C1 |
| ATOM | 2263 | NZ  | LYS | 62  | 18.737 | 20.988 | 10.385 | 1.00 | 44.06 | C1 |
| ATOM | 2264 | C   | LYS | 62  | 20.178 | 19.805 | 3.557  | 1.00 | 37.95 | C1 |
| ATOM | 2265 | O   | LYS | 62  | 19.233 | 20.045 | 2.826  | 1.00 | 37.84 | C1 |
| ATOM | 2266 | N   | ALA | 63  | 21.425 | 20.183 | 3.293  | 1.00 | 38.21 | C1 |
| ATOM | 2267 | CA  | ALA | 63  | 21.790 | 20.925 | 2.090  | 1.00 | 39.70 | C1 |
| ATOM | 2268 | CB  | ALA | 63  | 23.306 | 21.094 | 1.994  | 1.00 | 38.23 | C1 |
| ATOM | 2269 | C   | ALA | 63  | 21.308 | 20.245 | 0.811  | 1.00 | 40.64 | C1 |
| ATOM | 2270 | O   | ALA | 63  | 20.823 | 20.897 | -0.098 | 1.00 | 40.84 | C1 |
| ATOM | 2271 | N   | PHE | 64  | 21.513 | 18.939 | 0.737  | 1.00 | 42.16 | C1 |
| ATOM | 2272 | CA  | PHE | 64  | 21.137 | 18.134 | -0.423 | 1.00 | 43.43 | C1 |

FIG. 3A-40

| | | | | | | | | | |
|---|---|---|---|---|---|---|---|---|---|
| ATOM | 2273 | CB | PHE | 64 | 21.748 | 16.747 | -0.186 | 1.00 44.71 | C1 |
| ATOM | 2274 | CG | PHE | 64 | 21.435 | 15.714 | -1.242 | 1.00 46.29 | C1 |
| ATOM | 2275 | CD1 | PHE | 64 | 22.246 | 15.577 | -2.371 | 1.00 47.02 | C1 |
| ATOM | 2276 | CD2 | PHE | 64 | 20.373 | 14.808 | -1.059 | 1.00 47.22 | C1 |
| ATOM | 2277 | CE1 | PHE | 64 | 22.019 | 14.543 | -3.300 | 1.00 47.15 | C1 |
| ATOM | 2278 | CE2 | PHE | 64 | 20.135 | 13.762 | -1.985 | 1.00 47.50 | C1 |
| ATOM | 2279 | CZ | PHE | 64 | 20.968 | 13.638 | -3.107 | 1.00 46.63 | C1 |
| ATOM | 2280 | C | PHE | 64 | 19.587 | 18.095 | -0.581 | 1.00 43.41 | C1 |
| ATOM | 2281 | O | PHE | 64 | 19.077 | 17.679 | -1.608 | 1.00 43.04 | C1 |
| ATOM | 2282 | N | GLY | 65 | 18.861 | 18.515 | 0.464 | 1.00 44.00 | C1 |
| ATOM | 2283 | CA | GLY | 65 | 17.401 | 18.551 | 0.442 | 1.00 44.61 | C1 |
| ATOM | 2284 | C | GLY | 65 | 16.547 | 17.360 | 0.900 | 1.00 45.23 | C1 |
| ATOM | 2285 | O | GLY | 65 | 15.319 | 17.481 | 1.024 | 1.00 44.77 | C1 |
| ATOM | 2286 | N | THR | 66 | 17.162 | 16.214 | 1.173 | 1.00 46.05 | C1 |
| ATOM | 2287 | CA | THR | 66 | 16.371 | 15.047 | 1.573 | 1.00 46.97 | C1 |
| ATOM | 2288 | CB | THR | 66 | 16.677 | 13.833 | 0.689 | 1.00 46.94 | C1 |
| ATOM | 2289 | OG1 | THR | 66 | 18.043 | 13.416 | 0.900 | 1.00 47.06 | C1 |
| ATOM | 2290 | CG2 | THR | 66 | 16.451 | 14.197 | -0.760 | 1.00 46.70 | C1 |
| ATOM | 2291 | C | THR | 66 | 16.499 | 14.540 | 2.986 | 1.00 47.71 | C1 |
| ATOM | 2292 | O | THR | 66 | 15.578 | 13.908 | 3.488 | 1.00 47.47 | C1 |
| ATOM | 2293 | N | GLY | 67 | 17.628 | 14.819 | 3.638 | 1.00 48.74 | C1 |
| ATOM | 2294 | CA | GLY | 67 | 17.816 | 14.259 | 4.966 | 1.00 49.20 | C1 |
| ATOM | 2295 | C | GLY | 67 | 18.312 | 12.825 | 4.726 | 1.00 49.52 | C1 |
| ATOM | 2296 | O | GLY | 67 | 18.463 | 12.380 | 3.569 | 1.00 49.17 | C1 |
| ATOM | 2297 | N | ILE | 68 | 18.599 | 12.106 | 5.802 | 1.00 50.08 | C1 |
| ATOM | 2298 | CA | ILE | 68 | 19.068 | 10.726 | 5.679 | 1.00 50.36 | C1 |
| ATOM | 2299 | CB | ILE | 68 | 19.859 | 10.258 | 6.956 | 1.00 49.26 | C1 |
| ATOM | 2300 | CG2 | ILE | 68 | 20.194 | 8.758 | 6.867 | 1.00 47.83 | C1 |
| ATOM | 2301 | CG1 | ILE | 68 | 21.154 | 11.072 | 7.095 | 1.00 48.45 | C1 |
| ATOM | 2302 | CD1 | ILE | 68 | 22.032 | 11.086 | 5.836 | 1.00 47.51 | C1 |
| ATOM | 2303 | C | ILE | 68 | 17.841 | 9.846 | 5.458 | 1.00 51.41 | C1 |
| ATOM | 2304 | O | ILE | 68 | 16.796 | 10.053 | 6.088 | 1.00 52.16 | C1 |
| ATOM | 2305 | N | GLY | 69 | 17.970 | 8.885 | 4.550 | 1.00 51.45 | C1 |
| ATOM | 2306 | CA | GLY | 69 | 16.876 | 7.988 | 4.246 | 1.00 51.52 | C1 |
| ATOM | 2307 | C | GLY | 69 | 17.034 | 7.313 | 2.887 | 1.00 51.85 | C1 |
| ATOM | 2308 | O | GLY | 69 | 18.136 | 6.957 | 2.487 | 1.00 51.77 | C1 |
| ATOM | 2309 | N | ALA | 70 | 15.921 | 7.156 | 2.174 | 1.00 52.21 | C1 |
| ATOM | 2310 | CA | ALA | 70 | 15.907 | 6.512 | 0.872 | 1.00 52.38 | C1 |
| ATOM | 2311 | CB | ALA | 70 | 14.459 | 6.445 | 0.355 | 1.00 52.35 | C1 |
| ATOM | 2312 | C | ALA | 70 | 16.806 | 7.202 | -0.156 | 1.00 52.84 | C1 |
| ATOM | 2313 | O | ALA | 70 | 17.647 | 6.563 | -0.801 | 1.00 53.61 | C1 |
| ATOM | 2314 | N | GLN | 71 | 16.641 | 8.512 | -0.300 | 1.00 52.78 | C1 |
| ATOM | 2315 | CA | GLN | 71 | 17.411 | 9.283 | -1.272 | 1.00 52.79 | C1 |
| ATOM | 2316 | CB | GLN | 71 | 16.740 | 10.668 | -1.450 | 1.00 53.71 | C1 |
| ATOM | 2317 | CG | GLN | 71 | 15.196 | 10.560 | -1.487 | 1.00 54.85 | C1. |
| ATOM | 2318 | CD | GLN | 71 | 14.471 | 11.904 | -1.600 | 1.00 56.44 | C1 |
| ATOM | 2319 | OE1 | GLN | 71 | 14.610 | 12.623 | -2.623 | 1.00 56.95 | C1 |
| ATOM | 2320 | NE2 | GLN | 71 | 13.689 | 12.262 | -0.548 | 1.00 55.97 | C1 |
| ATOM | 2321 | C | GLN | 71 | 18.910 | 9.433 | -0.974 | 1.00 51.80 | C1 |
| ATOM | 2322 | O | GLN | 71 | 19.691 | 9.693 | -1.900 | 1.00 52.03 | C1 |
| ATOM | 2323 | N | LEU | 72 | 19.316 | 9.270 | 0.293 | 1.00 50.94 | C1 |
| ATOM | 2324 | CA | LEU | 72 | 20.741 | 9.423 | 0.689 | 1.00 49.64 | C1 |
| ATOM | 2325 | CB | LEU | 72 | 21.143 | 10.909 | 0.726 | 1.00 48.92 | C1 |
| ATOM | 2326 | CG | LEU | 72 | 22.541 | 11.397 | 1.155 | 1.00 47.24 | C1 |
| ATOM | 2327 | CD1 | LEU | 72 | 23.540 | 11.368 | -0.012 | 1.00 45.52 | C1 |
| ATOM | 2328 | CD2 | LEU | 72 | 22.382 | 12.825 | 1.665 | 1.00 47.11 | C1 |
| ATOM | 2329 | C | LEU | 72 | 21.119 | 8.815 | 2.029 | 1.00 49.40 | C1 |

FIG. 3A-41

| ATOM | 2330 | O   | LEU | 72 | 20.426 | 9.008  | 3.057  | 1.00 | 48.89 | C1 |
| --- | --- | --- | --- | --- | --- | --- | --- | --- | --- | --- |
| ATOM | 2331 | N   | SER | 73 | 22.256 | 8.120  | 2.004  | 1.00 | 48.75 | C1 |
| ATOM | 2332 | CA  | SER | 73 | 22.801 | 7.450  | 3.173  | 1.00 | 48.80 | C1 |
| ATOM | 2333 | CB  | SER | 73 | 23.008 | 5.952  | 2.845  | 1.00 | 49.54 | C1 |
| ATOM | 2334 | OG  | SER | 73 | 23.967 | 5.331  | 3.711  | 1.00 | 50.91 | C1 |
| ATOM | 2335 | C   | SER | 73 | 24.136 | 8.027  | 3.677  | 1.00 | 48.34 | C1 |
| ATOM | 2336 | O   | SER | 73 | 24.914 | 8.609  | 2.915  | 1.00 | 48.05 | C1 |
| ATOM | 2337 | N   | PHE | 74 | 24.390 | 7.813  | 4.967  | 1.00 | 47.81 | C1 |
| ATOM | 2338 | CA  | PHE | 74 | 25.625 | 8.201  | 5.636  | 1.00 | 47.50 | C1 |
| ATOM | 2339 | CB  | PHE | 74 | 25.664 | 7.615  | 7.041  | 1.00 | 47.20 | C1 |
| ATOM | 2340 | CG  | PHE | 74 | 24.715 | 8.259  | 8.002  | 1.00 | 47.29 | C1 |
| ATOM | 2341 | CD1 | PHE | 74 | 24.850 | 9.620  | 8.337  | 1.00 | 46.98 | C1 |
| ATOM | 2342 | CD2 | PHE | 74 | 23.726 | 7.508  | 8.627  | 1.00 | 46.60 | C1 |
| ATOM | 2343 | CE1 | PHE | 74 | 24.026 | 10.216 | 9.278  | 1.00 | 45.88 | C1 |
| ATOM | 2344 | CE2 | PHE | 74 | 22.893 | 8.104  | 9.572  | 1.00 | 46.36 | C1 |
| ATOM | 2345 | CZ  | PHE | 74 | 23.051 | 9.465  | 9.895  | 1.00 | 45.98 | C1 |
| ATOM | 2346 | C   | PHE | 74 | 26.798 | 7.608  | 4.893  | 1.00 | 48.02 | C1 |
| ATOM | 2347 | O   | PHE | 74 | 27.849 | 8.235  | 4.714  | 1.00 | 47.41 | C1 |
| ATOM | 2348 | N   | GLN | 75 | 26.615 | 6.364  | 4.472  | 1.00 | 48.84 | C1 |
| ATOM | 2349 | CA  | GLN | 75 | 27.666 | 5.644  | 3.785  | 1.00 | 49.52 | C1 |
| ATOM | 2350 | CB  | GLN | 75 | 27.278 | 4.168  | 3.684  | 1.00 | 50.19 | C1 |
| ATOM | 2351 | CG  | GLN | 75 | 27.029 | 3.513  | 5.046  | 1.00 | 50.48 | C1 |
| ATOM | 2352 | CD  | GLN | 75 | 28.285 | 3.526  | 5.886  | 1.00 | 51.73 | C1 |
| ATOM | 2353 | OE1 | GLN | 75 | 29.353 | 3.130  | 5.412  | 1.00 | 52.49 | C1 |
| ATOM | 2354 | NE2 | GLN | 75 | 28.180 | 3.985  | 7.126  | 1.00 | 51.45 | C1 |
| ATOM | 2355 | C   | GLN | 75 | 27.988 | 6.235  | 2.421  | 1.00 | 49.96 | C1 |
| ATOM | 2356 | O   | GLN | 75 | 29.017 | 5.907  | 1.825  | 1.00 | 50.48 | C1 |
| ATOM | 2357 | N   | ASP | 76 | 27.130 | 7.122  | 1.927  | 1.00 | 50.43 | C1 |
| ATOM | 2358 | CA  | ASP | 76 | 27.365 | 7.761  | 0.619  | 1.00 | 50.67 | C1 |
| ATOM | 2359 | CB  | ASP | 76 | 26.054 | 8.166  | -0.046 | 1.00 | 51.37 | C1 |
| ATOM | 2360 | CG  | ASP | 76 | 25.287 | 6.997  | -0.560 | 1.00 | 52.52 | C1 |
| ATOM | 2361 | OD1 | ASP | 76 | 25.891 | 6.193  | -1.301 | 1.00 | 52.95 | C1 |
| ATOM | 2362 | OD2 | ASP | 76 | 24.086 | 6.888  | -0.224 | 1.00 | 53.95 | C1 |
| ATOM | 2363 | C   | ASP | 76 | 28.184 | 9.026  | 0.765  | 1.00 | 50.43 | C1 |
| ATOM | 2364 | O   | ASP | 76 | 28.669 | 9.579  | -0.223 | 1.00 | 51.13 | C1 |
| ATOM | 2365 | N   | ILE | 77 | 28.317 | 9.481  | 2.006  | 1.00 | 49.70 | C1 |
| ATOM | 2366 | CA  | ILE | 77 | 29.031 | 10.701 | 2.309  | 1.00 | 48.67 | C1 |
| ATOM | 2367 | CB  | ILE | 77 | 28.211 | 11.559 | 3.253  | 1.00 | 47.95 | C1 |
| ATOM | 2368 | CG2 | ILE | 77 | 28.817 | 12.936 | 3.353  | 1.00 | 47.84 | C1 |
| ATOM | 2369 | CG1 | ILE | 77 | 26.746 | 11.564 | 2.789  | 1.00 | 48.00 | C1 |
| ATOM | 2370 | CD1 | ILE | 77 | 25.808 | 12.444 | 3.603  | 1.00 | 47.22 | C1 |
| ATOM | 2371 | C   | ILE | 77 | 30.368 | 10.440 | 2.978  | 1.00 | 48.96 | C1 |
| ATOM | 2372 | O   | ILE | 77 | 30.434 | 9.757  | 3.997  | 1.00 | 48.72 | C1 |
| ATOM | 2373 | N   | GLU | 78 | 31.440 | 10.969 | 2.408  | 1.00 | 48.68 | C1 |
| ATOM | 2374 | CA  | GLU | 78 | 32.704 | 10.799 | 3.073  | 1.00 | 49.55 | C1 |
| ATOM | 2375 | CB  | GLU | 78 | 33.621 | 9.823  | 2.333  | 1.00 | 51.11 | C1 |
| ATOM | 2376 | CG  | GLU | 78 | 34.970 | 9.720  | 3.028  | 1.00 | 52.90 | C1 |
| ATOM | 2377 | CD  | GLU | 78 | 35.794 | 8.537  | 2.593  | 1.00 | 54.48 | C1 |
| ATOM | 2378 | OE1 | GLU | 78 | 37.012 | 8.540  | 2.910  | 1.00 | 55.00 | C1 |
| ATOM | 2379 | OE2 | GLU | 78 | 35.224 | 7.615  | 1.953  | 1.00 | 55.86 | C1 |
| ATOM | 2380 | C   | GLU | 78 | 33.438 | 12.115 | 3.287  | 1.00 | 48.60 | C1 |
| ATOM | 2381 | O   | GLU | 78 | 33.607 | 12.901 | 2.361  | 1.00 | 48.62 | C1 |
| ATOM | 2382 | N   | ILE | 79 | 33.877 | 12.325 | 4.526  | 1.00 | 47.38 | C1 |
| ATOM | 2383 | CA  | ILE | 79 | 34.619 | 13.513 | 4.920  | 1.00 | 45.83 | C1 |
| ATOM | 2384 | CB  | ILE | 79 | 34.182 | 14.038 | 6.320  | 1.00 | 44.21 | C1 |
| ATOM | 2385 | CG2 | ILE | 79 | 35.248 | 15.001 | 6.849  | 1.00 | 43.54 | C1 |
| ATOM | 2386 | CG1 | ILE | 79 | 32.840 | 14.777 | 6.243  | 1.00 | 43.11 | C1 |

FIG. 3A-42

| ATOM | 2387 | CD1 | ILE | 79 | 31.649 | 13.923 | 6.253 | 1.00 | 42.90 | C1 |
| ATOM | 2388 | C | ILE | 79 | 36.115 | 13.204 | 5.008 | 1.00 | 46.28 | C1 |
| ATOM | 2389 | O | ILE | 79 | 36.524 | 12.284 | 5.704 | 1.00 | 46.25 | C1 |
| ATOM | 2390 | N | ARG | 80 | 36.931 | 13.978 | 4.308 | 1.00 | 47.15 | C1 |
| ATOM | 2391 | CA | ARG | 80 | 38.381 | 13.810 | 4.363 | 1.00 | 47.86 | C1 |
| ATOM | 2392 | CB | ARG | 80 | 38.918 | 13.306 | 3.023 | 1.00 | 49.91 | C1 |
| ATOM | 2393 | CG | ARG | 80 | 38.470 | 11.879 | 2.682 | 1.00 | 53.47 | C1 |
| ATOM | 2394 | CD | ARG | 80 | 39.177 | 11.328 | 1.415 | 1.00 | 56.60 | C1 |
| ATOM | 2395 | NE | ARG | 80 | 38.299 | 10.415 | 0.673 | 1.00 | 59.57 | C1 |
| ATOM | 2396 | CZ | ARG | 80 | 38.580 | 9.892 | -0.520 | 1.00 | 61.29 | C1 |
| ATOM | 2397 | NH1 | ARG | 80 | 37.705 | 9.082 | -1.102 | 1.00 | 62.00 | C1 |
| ATOM | 2398 | NH2 | ARG | 80 | 39.732 | 10.170 | -1.133 | 1.00 | 61.67 | C1 |
| ATOM | 2399 | C | ARG | 80 | 38.998 | 15.154 | 4.702 | 1.00 | 47.04 | C1 |
| ATOM | 2400 | O | ARG | 80 | 38.302 | 16.172 | 4.696 | 1.00 | 46.98 | C1 |
| ATOM | 2401 | N | LYS | 81 | 40.285 | 15.164 | 5.021 | 1.00 | 46.29 | C1 |
| ATOM | 2402 | CA | LYS | 81 | 40.969 | 16.429 | 5.316 | 1.00 | 46.35 | C1 |
| ATOM | 2403 | CB | LYS | 81 | 41.221 | 16.598 | 6.822 | 1.00 | 46.29 | C1 |
| ATOM | 2404 | CG | LYS | 81 | 40.018 | 17.101 | 7.625 | 1.00 | 46.61 | C1 |
| ATOM | 2405 | CD | LYS | 81 | 40.403 | 17.303 | 9.096 | 1.00 | 46.26 | C1 |
| ATOM | 2406 | CE | LYS | 81 | 39.246 | 17.784 | 9.958 | 1.00 | 46.08 | C1 |
| ATOM | 2407 | NZ | LYS | 81 | 39.660 | 17.771 | 11.416 | 1.00 | 46.72 | C1 |
| ATOM | 2408 | C | LYS | 81 | 42.312 | 16.573 | 4.592 | 1.00 | 46.05 | C1 |
| ATOM | 2409 | O | LYS | 81 | 43.110 | 15.630 | 4.573 | 1.00 | 45.90 | C1 |
| ATOM | 2410 | N | ASP | 82 | 42.576 | 17.753 | 4.017 | 1.00 | 45.41 | C1 |
| ATOM | 2411 | CA | ASP | 82 | 43.872 | 17.963 | 3.356 | 1.00 | 45.00 | C1 |
| ATOM | 2412 | CB | ASP | 82 | 43.782 | 19.022 | 2.231 | 1.00 | 43.78 | C1 |
| ATOM | 2413 | CG | ASP | 82 | 43.524 | 20.455 | 2.742 | 1.00 | 43.90 | C1 |
| ATOM | 2414 | OD1 | ASP | 82 | 43.895 | 20.840 | 3.884 | 1.00 | 42.17 | C1 |
| ATOM | 2415 | OD2 | ASP | 82 | 42.962 | 21.224 | 1.935 | 1.00 | 43.52 | C1 |
| ATOM | 2416 | C | ASP | 82 | 44.983 | 18.330 | 4.374 | 1.00 | 44.67 | C1 |
| ATOM | 2417 | O | ASP | 82 | 44.750 | 18.333 | 5.598 | 1.00 | 43.85 | C1 |
| ATOM | 2418 | N | GLN | 83 | 46.172 | 18.643 | 3.855 | 1.00 | 44.78 | C1 |
| ATOM | 2419 | CA | GLN | 83 | 47.359 | 18.986 | 4.671 | 1.00 | 45.33 | C1 |
| ATOM | 2420 | CB | GLN | 83 | 48.573 | 19.193 | 3.759 | 1.00 | 45.91 | C1 |
| ATOM | 2421 | CG | GLN | 83 | 49.490 | 18.021 | 3.641 | 1.00 | 46.80 | C1 |
| ATOM | 2422 | CD | GLN | 83 | 48.747 | 16.733 | 3.714 | 1.00 | 48.38 | C1 |
| ATOM | 2423 | OE1 | GLN | 83 | 48.676 | 16.113 | 4.793 | 1.00 | 49.41 | C1 |
| ATOM | 2424 | NE2 | GLN | 83 | 48.152 | 16.315 | 2.584 | 1.00 | 47.83 | C1 |
| ATOM | 2425 | C | GLN | 83 | 47.240 | 20.217 | 5.550 | 1.00 | 44.80 | C1 |
| ATOM | 2426 | O | GLN | 83 | 48.041 | 20.408 | 6.448 | 1.00 | 44.50 | C1 |
| ATOM | 2427 | N | ASN | 84 | 46.254 | 21.060 | 5.250 | 1.00 | 44.80 | C1 |
| ATOM | 2428 | CA | ASN | 84 | 46.013 | 22.296 | 5.991 | 1.00 | 44.29 | C1 |
| ATOM | 2429 | CB | ASN | 84 | 45.585 | 23.412 | 5.032 | 1.00 | 44.06 | C1 |
| ATOM | 2430 | CG | ASN | 84 | 46.747 | 24.027 | 4.289 | 1.00 | 44.62 | C1 |
| ATOM | 2431 | OD1 | ASN | 84 | 46.624 | 24.390 | 3.111 | 1.00 | 44.59 | C1 |
| ATOM | 2432 | ND2 | ASN | 84 | 47.874 | 24.174 | 4.969 | 1.00 | 43.72 | C1 |
| ATOM | 2433 | C | ASN | 84 | 44.898 | 22.048 | 6.995 | 1.00 | 43.71 | C1 |
| ATOM | 2434 | O | ASN | 84 | 44.510 | 22.956 | 7.742 | 1.00 | 43.04 | C1 |
| ATOM | 2435 | N | GLY | 85 | 44.389 | 20.814 | 6.978 | 1.00 | 43.44 | C1 |
| ATOM | 2436 | CA | GLY | 85 | 43.311 | 20.406 | 7.867 | 1.00 | 42.84 | C1 |
| ATOM | 2437 | C | GLY | 85 | 41.948 | 20.869 | 7.404 | 1.00 | 42.40 | C1 |
| ATOM | 2438 | O | GLY | 85 | 41.025 | 20.958 | 8.209 | 1.00 | 43.31 | C1 |
| ATOM | 2439 | N | LYS | 86 | 41.808 | 21.182 | 6.123 | 1.00 | 41.80 | C1 |
| ATOM | 2440 | CA | LYS | 86 | 40.519 | 21.633 | 5.609 | 1.00 | 42.19 | C1 |
| ATOM | 2441 | CB | LYS | 86 | 40.674 | 22.537 | 4.380 | 1.00 | 41.23 | C1 |
| ATOM | 2442 | CG | LYS | 86 | 39.386 | 23.217 | 3.952 | 1.00 | 41.66 | C1 |
| ATOM | 2443 | CD | LYS | 86 | 39.513 | 23.859 | 2.566 | 1.00 | 42.36 | C1 |

FIG. 3A-43

| ATOM | 2444 | CE | LYS | 86 | 38.541 | 23.239 | 1.522 | 1.00 | 43.64 | C1 |
|---|---|---|---|---|---|---|---|---|---|---|
| ATOM | 2445 | NZ | LYS | 86 | 38.374 | 24.125 | 0.287 | 1.00 | 44.71 | C1 |
| ATOM | 2446 | C | LYS | 86 | 39.738 | 20.396 | 5.231 | 1.00 | 42.58 | C1 |
| ATOM | 2447 | O | LYS | 86 | 40.219 | 19.540 | 4.495 | 1.00 | 42.76 | C1 |
| ATOM | 2448 | N | PRO | 87 | 38.516 | 20.282 | 5.743 | 1.00 | 43.20 | C1 |
| ATOM | 2449 | CD | PRO | 87 | 37.872 | 21.103 | 6.786 | 1.00 | 43.03 | C1 |
| ATOM | 2450 | CA | PRO | 87 | 37.715 | 19.113 | 5.422 | 1.00 | 43.26 | C1 |
| ATOM | 2451 | CB | PRO | 87 | 36.722 | 19.061 | 6.555 | 1.00 | 43.23 | C1 |
| ATOM | 2452 | CG | PRO | 87 | 36.488 | 20.526 | 6.838 | 1.00 | 43.31 | C1 |
| ATOM | 2453 | C | PRO | 87 | 37.056 | 19.322 | 4.111 | 1.00 | 43.97 | C1 |
| ATOM | 2454 | O | PRO | 87 | 36.907 | 20.464 | 3.651 | 1.00 | 43.98 | C1 |
| ATOM | 2455 | N | TYR | 88 | 36.711 | 18.214 | 3.484 | 1.00 | 44.08 | C1 |
| ATOM | 2456 | CA | TYR | 88 | 36.033 | 18.278 | 2.230 | 1.00 | 45.68 | C1 |
| ATOM | 2457 | CB | TYR | 88 | 37.015 | 18.472 | 1.034 | 1.00 | 47.43 | C1 |
| ATOM | 2458 | CG | TYR | 88 | 38.189 | 17.526 | 0.886 | 1.00 | 49.08 | C1 |
| ATOM | 2459 | CD1 | TYR | 88 | 38.194 | 16.521 | -0.107 | 1.00 | 50.60 | C1 |
| ATOM | 2460 | CE1 | TYR | 88 | 39.336 | 15.701 | -0.334 | 1.00 | 50.63 | C1 |
| ATOM | 2461 | CD2 | TYR | 88 | 39.341 | 17.681 | 1.660 | 1.00 | 49.84 | C1 |
| ATOM | 2462 | CE2 | TYR | 88 | 40.476 | 16.862 | 1.450 | 1.00 | 50.93 | C1 |
| ATOM | 2463 | CZ | TYR | 88 | 40.464 | 15.885 | 0.451 | 1.00 | 51.22 | C1 |
| ATOM | 2464 | OH | TYR | 88 | 41.590 | 15.120 | 0.244 | 1.00 | 52.41 | C1 |
| ATOM | 2465 | C | TYR | 88 | 35.215 | 17.026 | 2.127 | 1.00 | 46.37 | C1 |
| ATOM | 2466 | O | TYR | 88 | 35.549 | 16.010 | 2.721 | 1.00 | 45.65 | C1 |
| ATOM | 2467 | N | ILE | 89 | 34.103 | 17.124 | 1.419 | 1.00 | 47.63 | C1 |
| ATOM | 2468 | CA | ILE | 89 | 33.221 | 15.998 | 1.275 | 1.00 | 50.50 | C1 |
| ATOM | 2469 | CB | ILE | 89 | 31.754 | 16.402 | 1.541 | 1.00 | 49.66 | C1 |
| ATOM | 2470 | CG2 | ILE | 89 | 30.825 | 15.216 | 1.273 | 1.00 | 48.82 | C1 |
| ATOM | 2471 | CG1 | ILE | 89 | 31.627 | 16.905 | 2.972 | 1.00 | 49.02 | C1 |
| ATOM | 2472 | CD1 | ILE | 89 | 30.227 | 17.264 | 3.369 | 1.00 | 48.76 | C1 |
| ATOM | 2473 | C | ILE | 89 | 33.276 | 15.340 | -0.095 | 1.00 | 52.86 | C1 |
| ATOM | 2474 | O | ILE | 89 | 33.365 | 16.004 | -1.123 | 1.00 | 53.08 | C1 |
| ATOM | 2475 | N | ILE | 90 | 33.229 | 14.021 | -0.093 | 1.00 | 55.54 | C1 |
| ATOM | 2476 | CA | ILE | 90 | 33.199 | 13.295 | -1.334 | 1.00 | 58.03 | C1 |
| ATOM | 2477 | CB | ILE | 90 | 34.292 | 12.261 | -1.404 | 1.00 | 57.72 | C1 |
| ATOM | 2478 | CG2 | ILE | 90 | 34.455 | 11.818 | -2.851 | 1.00 | 57.78 | C1 |
| ATOM | 2479 | CG1 | ILE | 90 | 35.618 | 12.870 | -0.947 | 1.00 | 58.26 | C1 |
| ATOM | 2480 | CD1 | ILE | 90 | 36.152 | 13.997 | -1.880 | 1.00 | 58.15 | C1 |
| ATOM | 2481 | C | ILE | 90 | 31.843 | 12.610 | -1.309 | 1.00 | 59.92 | C1 |
| ATOM | 2482 | O | ILE | 90 | 31.460 | 12.005 | -0.309 | 1.00 | 60.54 | C1 |
| ATOM | 2483 | N | CYS | 91 | 31.085 | 12.767 | -2.375 | 1.00 | 62.06 | C1 |
| ATOM | 2484 | CA | CYS | 91 | 29.789 | 12.135 | -2.442 | 1.00 | 65.02 | C1 |
| ATOM | 2485 | CB | CYS | 91 | 28.729 | 12.879 | -1.636 | 1.00 | 64.53 | C1 |
| ATOM | 2486 | SG | CYS | 91 | 27.007 | 12.228 | -1.893 | 1.00 | 65.15 | C1 |
| ATOM | 2487 | C | CYS | 91 | 29.339 | 12.047 | -3.872 | 1.00 | 67.19 | C1 |
| ATOM | 2488 | O | CYS | 91 | 28.809 | 13.012 | -4.450 | 1.00 | 67.57 | C1 |
| ATOM | 2489 | N | THR | 92 | 29.597 | 10.892 | -4.463 | 1.00 | 69.14 | C1 |
| ATOM | 2490 | CA | THR | 92 | 29.160 | 10.677 | -5.812 | 1.00 | 71.19 | C1 |
| ATOM | 2491 | CB | THR | 92 | 29.946 | 9.525 | -6.462 | 1.00 | 71.08 | C1 |
| ATOM | 2492 | OG1 | THR | 92 | 29.521 | 8.282 | -5.894 | 1.00 | 71.32 | C1 |
| ATOM | 2493 | CG2 | THR | 92 | 31.453 | 9.721 | -6.224 | 1.00 | 70.41 | C1 |
| ATOM | 2494 | C | THR | 92 | 27.722 | 10.304 | -5.485 | 1.00 | 72.70 | C1 |
| ATOM | 2495 | O | THR | 92 | 27.446 | 9.328 | -4.768 | 1.00 | 73.09 | C1 |
| ATOM | 2496 | N | LYS | 93 | 26.842 | 11.183 | -5.932 | 1.00 | 74.04 | C1 |
| ATOM | 2497 | CA | LYS | 93 | 25.406 | 11.099 | -5.769 | 1.00 | 75.40 | C1 |
| ATOM | 2498 | CB | LYS | 93 | 24.979 | 11.225 | -4.318 | 1.00 | 75.38 | C1 |
| ATOM | 2499 | CG | LYS | 93 | 24.537 | 9.897 | -3.689 | 1.00 | 75.40 | C1 |
| ATOM | 2500 | CD | LYS | 93 | 23.074 | 9.583 | -3.977 | 1.00 | 75.01 | C1 |

FIG. 3A-44

```
ATOM   2501  CE   LYS   93     22.649    8.273   -3.321  1.00 75.18      C1
ATOM   2502  NZ   LYS   93     21.168    8.059   -3.343  1.00 74.81      C1
ATOM   2503  C    LYS   93     25.077   12.351   -6.532  1.00 76.29      C1
ATOM   2504  O    LYS   93     24.070   13.017   -6.326  1.00 76.31      C1
ATOM   2505  N    LEU   94     26.036   12.641   -7.405  1.00 77.49      C1
ATOM   2506  CA   LEU   94     26.063   13.734   -8.361  1.00 78.53      C1
ATOM   2507  CB   LEU   94     24.692   14.417   -8.499  1.00 79.09      C1
ATOM   2508  CG   LEU   94     24.161   14.260   -9.936  1.00 79.46      C1
ATOM   2509  CD1  LEU   94     25.097   14.972  -10.908  1.00 79.49      C1
ATOM   2510  CD2  LEU   94     24.057   12.761  -10.301  1.00 79.47      C1
ATOM   2511  C    LEU   94     27.140   14.797   -8.236  1.00 78.47      C1
ATOM   2512  O    LEU   94     27.454   15.308   -7.149  1.00 79.19      C1
ATOM   2513  N    SER   95     27.732   15.068   -9.394  1.00 77.80      C1
ATOM   2514  CA   SER   95     28.721   16.095   -9.540  1.00 77.11      C1
ATOM   2515  CB   SER   95     29.745   15.726  -10.618  1.00 77.27      C1
ATOM   2516  OG   SER   95     31.066   15.770  -10.095  1.00 77.30      C1
ATOM   2517  C    SER   95     27.801   17.221  -10.024  1.00 76.59      C1
ATOM   2518  O    SER   95     26.679   17.383   -9.499  1.00 76.68      C1
ATOM   2519  N    ALA   96     28.234   17.954  -11.053  1.00 75.05      C1
ATOM   2520  CA   ALA   96     27.455   19.086  -11.550  1.00 73.08      C1
ATOM   2521  CB   ALA   96     26.078   18.610  -12.037  1.00 73.32      C1
ATOM   2522  C    ALA   96     27.318   20.027  -10.330  1.00 71.45      C1
ATOM   2523  O    ALA   96     26.471   20.959  -10.324  1.00 72.20      C1
ATOM   2524  N    ALA   97     28.182   19.779   -9.323  1.00 68.24      C1
ATOM   2525  CA   ALA   97     28.200   20.528   -8.066  1.00 64.53      C1
ATOM   2526  CB   ALA   97     26.974   20.148   -7.236  1.00 64.01      C1
ATOM   2527  C    ALA   97     29.461   20.384   -7.202  1.00 61.89      C1
ATOM   2528  O    ALA   97     29.994   19.301   -7.005  1.00 61.20      C1
ATOM   2529  N    ALA   98     29.925   21.507   -6.678  1.00 59.31      C1
ATOM   2530  CA   ALA   98     31.081   21.535   -5.794  1.00 56.05      C1
ATOM   2531  CB   ALA   98     31.933   22.771   -6.084  1.00 55.80      C1
ATOM   2532  C    ALA   98     30.465   21.618   -4.400  1.00 53.71      C1
ATOM   2533  O    ALA   98     29.341   22.108   -4.253  1.00 52.98      C1
ATOM   2534  N    VAL   99     31.195   21.146   -3.391  1.00 50.77      C1
ATOM   2535  CA   VAL   99     30.700   21.160   -2.017  1.00 47.45      C1
ATOM   2536  CB   VAL   99     30.513   19.706   -1.466  1.00 47.53      C1
ATOM   2537  CG1  VAL   99     29.641   19.692   -0.210  1.00 47.19      C1
ATOM   2538  CG2  VAL   99     29.933   18.819   -2.529  1.00 46.70      C1
ATOM   2539  C    VAL   99     31.693   21.864   -1.107  1.00 45.49      C1
ATOM   2540  O    VAL   99     32.904   21.743   -1.284  1.00 44.20      C1
ATOM   2541  N    HIS  100     31.168   22.613   -0.141  1.00 43.53      C1
ATOM   2542  CA   HIS  100     32.008   23.282    0.851  1.00 41.02      C1
ATOM   2543  CB   HIS  100     31.926   24.804    0.764  1.00 42.26      C1
ATOM   2544  CG   HIS  100     32.416   25.362   -0.526  1.00 43.68      C1
ATOM   2545  CD2  HIS  100     33.671   25.597   -0.971  1.00 44.46      C1
ATOM   2546  ND1  HIS  100     31.563   25.698   -1.559  1.00 44.71      C1
ATOM   2547  CE1  HIS  100     32.278   26.112   -2.593  1.00 45.41      C1
ATOM   2548  NE2  HIS  100     33.558   26.060   -2.263  1.00 46.23      C1
ATOM   2549  C    HIS  100     31.487   22.853    2.227  1.00 39.34      C1
ATOM   2550  O    HIS  100     30.277   22.772    2.477  1.00 37.89      C1
ATOM   2551  N    VAL  101     32.423   22.599    3.124  1.00 37.22      C1
ATOM   2552  CA   VAL  101     32.081   22.169    4.463  1.00 35.34      C1
ATOM   2553  CB   VAL  101     32.273   20.644    4.612  1.00 34.50      C1
ATOM   2554  CG1  VAL  101     33.691   20.325    4.422  1.00 34.09      C1
ATOM   2555  CG2  VAL  101     31.847   20.179    5.973  1.00 33.26      C1
ATOM   2556  C    VAL  101     32.994   22.813    5.450  1.00 33.51      C1
ATOM   2557  O    VAL  101     34.133   23.106    5.139  1.00 33.22      C1
```

FIG. 3A-45

| ATOM | 2558 | N | SER | 102 | 32.488 | 23.006 | 6.655 | 1.00 | 32.89 | C1 |
|---|---|---|---|---|---|---|---|---|---|---|
| ATOM | 2559 | CA | SER | 102 | 33.282 | 23.547 | 7.750 | 1.00 | 31.81 | C1 |
| ATOM | 2560 | CB | SER | 102 | 33.077 | 25.044 | 7.919 | 1.00 | 32.65 | C1 |
| ATOM | 2561 | OG | SER | 102 | 34.008 | 25.557 | 8.884 | 1.00 | 32.76 | C1 |
| ATOM | 2562 | C | SER | 102 | 32.786 | 22.837 | 8.993 | 1.00 | 32.14 | C1 |
| ATOM | 2563 | O | SER | 102 | 31.595 | 22.633 | 9.145 | 1.00 | 31.51 | C1 |
| ATOM | 2564 | N | ILE | 103 | 33.708 | 22.478 | 9.887 | 1.00 | 32.69 | C1 |
| ATOM | 2565 | CA | ILE | 103 | 33.383 | 21.774 | 11.127 | 1.00 | 32.36 | C1 |
| ATOM | 2566 | CB | ILE | 103 | 33.837 | 20.322 | 11.005 | 1.00 | 32.02 | C1 |
| ATOM | 2567 | CG2 | ILE | 103 | 33.518 | 19.539 | 12.311 | 1.00 | 30.43 | C1 |
| ATOM | 2568 | CG1 | ILE | 103 | 33.186 | 19.731 | 9.757 | 1.00 | 29.77 | C1 |
| ATOM | 2569 | CD1 | ILE | 103 | 33.800 | 18.433 | 9.328 | 1.00 | 31.21 | C1 |
| ATOM | 2570 | C | ILE | 103 | 34.097 | 22.437 | 12.308 | 1.00 | 33.22 | C1 |
| ATOM | 2571 | O | ILE | 103 | 35.255 | 22.798 | 12.203 | 1.00 | 33.37 | C1 |
| ATOM | 2572 | N | THR | 104 | 33.402 | 22.589 | 13.425 | 1.00 | 33.89 | C1 |
| ATOM | 2573 | CA | THR | 104 | 33.952 | 23.222 | 14.592 | 1.00 | 34.64 | C1 |
| ATOM | 2574 | CB | THR | 104 | 33.523 | 24.685 | 14.643 | 1.00 | 35.31 | C1 |
| ATOM | 2575 | OG1 | THR | 104 | 34.073 | 25.322 | 15.805 | 1.00 | 36.64 | C1 |
| ATOM | 2576 | CG2 | THR | 104 | 32.025 | 24.774 | 14.697 | 1.00 | 35.83 | C1 |
| ATOM | 2577 | C | THR | 104 | 33.484 | 22.531 | 15.865 | 1.00 | 34.82 | C1 |
| ATOM | 2578 | O | THR | 104 | 32.392 | 21.970 | 15.930 | 1.00 | 35.84 | C1 |
| ATOM | 2579 | N | HIS | 105 | 34.305 | 22.606 | 16.894 | 1.00 | 34.86 | C1 |
| ATOM | 2580 | CA | HIS | 105 | 33.998 | 21.958 | 18.158 | 1.00 | 35.82 | C1 |
| ATOM | 2581 | CB | HIS | 105 | 34.956 | 20.792 | 18.452 | 1.00 | 34.73 | C1 |
| ATOM | 2582 | CG | HIS | 105 | 34.945 | 19.743 | 17.398 | 1.00 | 34.83 | C1 |
| ATOM | 2583 | CD2 | HIS | 105 | 35.695 | 19.603 | 16.277 | 1.00 | 33.18 | C1 |
| ATOM | 2584 | ND1 | HIS | 105 | 34.027 | 18.711 | 17.391 | 1.00 | 34.52 | C1 |
| ATOM | 2585 | CE1 | HIS | 105 | 34.213 | 17.979 | 16.306 | 1.00 | 35.06 | C1 |
| ATOM | 2586 | NE2 | HIS | 105 | 35.217 | 18.497 | 15.615 | 1.00 | 34.71 | C1 |
| ATOM | 2587 | C | HIS | 105 | 34.158 | 22.908 | 19.280 | 1.00 | 35.73 | C1 |
| ATOM | 2588 | O | HIS | 105 | 34.987 | 23.794 | 19.246 | 1.00 | 33.92 | C1 |
| ATOM | 2589 | N | THR | 106 | 33.390 | 22.611 | 20.299 | 1.00 | 36.77 | C1 |
| ATOM | 2590 | CA | THR | 106 | 33.355 | 23.348 | 21.524 | 1.00 | 40.09 | C1 |
| ATOM | 2591 | CB | THR | 106 | 32.082 | 24.176 | 21.508 | 1.00 | 40.79 | C1 |
| ATOM | 2592 | OG1 | THR | 106 | 32.299 | 25.425 | 22.156 | 1.00 | 43.54 | C1 |
| ATOM | 2593 | CG2 | THR | 106 | 30.992 | 23.443 | 22.156 | 1.00 | 42.68 | C1 |
| ATOM | 2594 | C | THR | 106 | 33.358 | 22.224 | 22.608 | 1.00 | 41.25 | C1 |
| ATOM | 2595 | O | THR | 106 | 33.425 | 21.023 | 22.265 | 1.00 | 41.69 | C1 |
| ATOM | 2596 | N | ALA | 107 | 33.304 | 22.574 | 23.894 | 1.00 | 42.12 | C1 |
| ATOM | 2597 | CA | ALA | 107 | 33.328 | 21.526 | 24.912 | 1.00 | 42.01 | C1 |
| ATOM | 2598 | CB | ALA | 107 | 33.557 | 22.131 | 26.311 | 1.00 | 43.25 | C1 |
| ATOM | 2599 | C | ALA | 107 | 32.003 | 20.768 | 24.874 | 1.00 | 42.28 | C1 |
| ATOM | 2600 | O | ALA | 107 | 31.972 | 19.556 | 25.012 | 1.00 | 42.24 | C1 |
| ATOM | 2601 | N | GLU | 108 | 30.907 | 21.482 | 24.667 | 1.00 | 42.09 | C1 |
| ATOM | 2602 | CA | GLU | 108 | 29.604 | 20.842 | 24.612 | 1.00 | 41.95 | C1 |
| ATOM | 2603 | CB | GLU | 108 | 28.538 | 21.761 | 25.204 | 1.00 | 44.03 | C1 |
| ATOM | 2604 | CG | GLU | 108 | 28.709 | 22.065 | 26.689 | 1.00 | 48.57 | C1 |
| ATOM | 2605 | CD | GLU | 108 | 27.406 | 21.949 | 27.467 | 1.00 | 50.64 | C1 |
| ATOM | 2606 | OE1 | GLU | 108 | 27.493 | 21.903 | 28.720 | 1.00 | 52.40 | C1 |
| ATOM | 2607 | OE2 | GLU | 108 | 26.306 | 21.905 | 26.838 | 1.00 | 51.79 | C1 |
| ATOM | 2608 | C | GLU | 108 | 29.115 | 20.438 | 23.226 | 1.00 | 40.76 | C1 |
| ATOM | 2609 | O | GLU | 108 | 28.259 | 19.572 | 23.112 | 1.00 | 40.77 | C1 |
| ATOM | 2610 | N | TYR | 109 | 29.660 | 21.031 | 22.173 | 1.00 | 38.80 | C1 |
| ATOM | 2611 | CA | TYR | 109 | 29.118 | 20.760 | 20.851 | 1.00 | 36.61 | C1 |
| ATOM | 2612 | CB | TYR | 109 | 28.242 | 21.950 | 20.431 | 1.00 | 37.49 | C1 |
| ATOM | 2613 | CG | TYR | 109 | 27.115 | 22.270 | 21.350 | 1.00 | 39.09 | C1 |
| ATOM | 2614 | CD1 | TYR | 109 | 25.930 | 21.532 | 21.323 | 1.00 | 39.55 | C1 |

FIG. 3A-46

```
ATOM   2615  CE1 TYR   109     24.865  21.844  22.169  1.00 40.62      C1
ATOM   2616  CD2 TYR   109     27.215  23.324  22.242  1.00 40.44      C1
ATOM   2617  CE2 TYR   109     26.166  23.652  23.088  1.00 40.89      C1
ATOM   2618  CZ  TYR   109     24.997  22.913  23.050  1.00 41.89      C1
ATOM   2619  OH  TYR   109     23.958  23.262  23.905  1.00 44.16      C1
ATOM   2620  C   TYR   109     30.033 -20.503  19.682  1.00 34.46      C1
ATOM   2621  O   TYR   109     31.192  20.822  19.708  1.00 33.77      C1
ATOM   2622  N   ALA   110     29.456  19.905  18.642  1.00 32.46      C1
ATOM   2623  CA  ALA   110     30.128  19.719  17.376  1.00 30.31      C1
ATOM   2624  CB  ALA   110     30.296  18.263  17.029  1.00 30.67      C1
ATOM   2625  C   ALA   110     29.083  20.384  16.474  1.00 29.65      C1
ATOM   2626  O   ALA   110     27.879  20.217  16.667  1.00 29.10      C1
ATOM   2627  N   ALA   111     29.540  21.163  15.512  1.00 28.10      C1
ATOM   2628  CA  ALA   111     28.639  21.853  14.609  1.00 26.34      C1
ATOM   2629  CB  ALA   111     28.478  23.284  15.055  1.00 26.00      C1
ATOM   2630  C   ALA   111     29.257  21.788  13.211  1.00 25.08      C1
ATOM   2631  O   ALA   111     30.464  21.589  13.065  1.00 24.72      C1
ATOM   2632  N   ALA   112     28.441  21.946  12.185  1.00 24.25      C1
ATOM   2633  CA  ALA   112     28.974  21.875  10.820  1.00 24.68      C1
ATOM   2634  CB  ALA   112     29.189  20.419  10.395  1.00 21.72      C1
ATOM   2635  C   ALA   112     28.044  22.566   9.838  1.00 25.11      C1
ATOM   2636  O   ALA   112     26.848  22.689  10.058  1.00 25.98      C1
ATOM   2637  N   GLN   113     28.597  23.045   8.753  1.00 26.72      C1
ATOM   2638  CA  GLN   113     27.749  23.684   7.781  1.00 28.89      C1
ATOM   2639  CB  GLN   113     27.860  25.200   7.850  1.00 29.76      C1
ATOM   2640  CG  GLN   113     29.227  25.758   7.596  1.00 32.46      C1
ATOM   2641  CD  GLN   113     29.173  27.298   7.531  1.00 33.88      C1
ATOM   2642  OE1 GLN   113     28.130  27.865   7.233  1.00 36.87      C1
ATOM   2643  NE2 GLN   113     30.276  27.955   7.797  1.00 34.55      C1
ATOM   2644  C   GLN   113     28.204  23.199   6.447  1.00 28.78      C1
ATOM   2645  O   GLN   113     29.369  22.848   6.248  1.00 27.81      C1
ATOM   2646  N   VAL   114     27.259  23.153   5.535  1.00 29.54      C1
ATOM   2647  CA  VAL   114     27.572  22.712   4.204  1.00 29.98      C1
ATOM   2648  CB  VAL   114     27.078  21.237   3.967  1.00 30.15      C1
ATOM   2649  CG1 VAL   114     27.057  20.936   2.442  1.00 29.05      C1
ATOM   2650  CG2 VAL   114     27.992  20.250   4.686  1.00 28.96      C1
ATOM   2651  C   VAL   114     26.876  23.603   3.177  1.00 29.81      C1
ATOM   2652  O   VAL   114     25.766  24.049   3.378  1.00 29.57      C1
ATOM   2653  N   VAL   115     27.560  23.858   2.086  1.00 30.84      C1
ATOM   2654  CA  VAL   115     26.971  24.574   0.986  1.00 32.60      C1
ATOM   2655  CB  VAL   115     27.618  25.931   0.695  1.00 32.10      C1
ATOM   2656  CG1 VAL   115     27.048  26.474  -0.664  1.00 32.24      C1
ATOM   2657  CG2 VAL   115     27.301  26.925   1.848  1.00 32.42      C1
ATOM   2658  C   VAL   115     27.195  23.691  -0.241  1.00 34.20      C1
ATOM   2659  O   VAL   115     28.337  23.287  -0.547  1.00 34.19      C1
ATOM   2660  N   ILE   116     26.108  23.355  -0.916  1.00 35.87      C1
ATOM   2661  CA  ILE   116     26.244  22.600  -2.154  1.00 38.89      C1
ATOM   2662  CB  ILE   116     25.349  21.370  -2.186  1.00 38.31      C1
ATOM   2663  CG2 ILE   116     25.267  20.863  -3.656  1.00 38.34      C1
ATOM   2664  CG1 ILE   116     25.881  20.292  -1.237  1.00 36.78      C1
ATOM   2665  CD1 ILE   116     24.830  19.301  -0.953  1.00 36.94      C1
ATOM   2666  C   ILE   116     25.753  23.555  -3.263  1.00 40.86      C1
ATOM   2667  O   ILE   116     24.616  24.034  -3.217  1.00 40.74      C1
ATOM   2668  N   GLU   117     26.584  23.844  -4.243  1.00 43.03      C1
ATOM   2669  CA  GLU   117     26.142  24.728  -5.316  1.00 45.86      C1
ATOM   2670  CB  GLU   117     26.865  26.075  -5.184  1.00 47.20      C1
ATOM   2671  CG  GLU   117     28.404  25.981  -5.155  1.00 48.86      C1
```

FIG. 3A-47

```
ATOM   2672  CD   GLU  117     29.015  27.249  -4.545  1.00 49.86      C1
ATOM   2673  OE1  GLU  117     28.231  28.110  -4.057  1.00 51.10      C1
ATOM   2674  OE2  GLU  117     30.261  27.380  -4.527  1.00 50.18      C1
ATOM   2675  C    GLU  117     26.395  24.073  -6.677  1.00 46.30      C1
ATOM   2676  O    GLU  117     27.005  23.029  -6.745  1.00 45.75      C1
ATOM   2677  N    ALA  118     25.930  24.667  -7.772  1.00 48.77      C1
ATOM   2678  CA   ALA  118     26.148  24.030  -9.086  1.00 50.57      C1
ATOM   2679  CB   ALA  118     24.913  24.136  -9.897  1.00 50.60      C1
ATOM   2680  C    ALA  118     27.371  24.456  -9.924  1.00 52.10      C1
ATOM   2681  OT1  ALA  118     28.273  25.169  -9.411  1.00 53.16      C1
ATOM   2682  OT2  ALA  118     27.454  24.034 -11.108  1.00 54.02      C1
ATOM   2683  N    SER    0     68.967  23.776  26.894  1.00 20.00      AP1
ATOM   2684  CA   SER    0     68.672  23.405  28.273  1.00 20.00      AP1
ATOM   2685  C    SER    0     68.067  22.002  28.361  1.00 20.00      AP1
ATOM   2686  O    SER    0     68.040  21.159  27.474  1.00 20.00      AP1
ATOM   2687  CB   SER    0     68.207  24.675  28.953  1.00 20.00      AP1
ATOM   2688  OG   SER    0     69.266  25.630  29.017  1.00 20.00      AP1
ATOM   2689  CB   ALA    1     68.176  19.343  30.518  1.00 84.05      AP1
ATOM   2690  C    ALA    1     66.353  20.967  31.144  1.00 83.83      AP1
ATOM   2691  O    ALA    1     65.915  20.207  32.017  1.00 83.53      AP1
ATOM   2692  N    ALA    1     68.040  21.577  29.427  1.00 84.15      AP1
ATOM   2693  CA   ALA    1     67.243  20.455  30.009  1.00 84.11      AP1
ATOM   2694  N    ASP    2     66.766  22.112  31.200  1.00 83.55      AP1
ATOM   2695  CA   ASP    2     66.164  23.057  32.134  1.00 83.11      AP1
ATOM   2696  CB   ASP    2     67.112  24.243  32.351  1.00 83.20      AP1
ATOM   2697  CG   ASP    2     66.448  25.416  33.064  1.00 83.58      AP1
ATOM   2698  OD1  ASP    2     65.906  25.229  34.181  1.00 83.39      AP1
ATOM   2699  OD2  ASP    2     66.481  26.536  32.505  1.00 83.39      AP1
ATOM   2700  C    ASP    2     64.857  23.534  31.486  1.00 82.74      AP1
ATOM   2701  O    ASP    2     63.759  23.407  32.062  1.00 82.60      AP1
ATOM   2702  N    THR    3     64.988  24.067  30.273  1.00 81.72      AP1
ATOM   2703  CA   THR    3     63.836  24.561  29.539  1.00 80.65      AP1
ATOM   2704  CB   THR    3     64.230  25.062  28.148  1.00 80.87      AP1
ATOM   2705  OG1  THR    3     64.460  23.941  27.283  1.00 81.31      AP1
ATOM   2706  CG2  THR    3     65.495  25.900  28.237  1.00 80.59      AP1
ATOM   2707  C    THR    3     62.793  23.467  29.379  1.00 79.71      AP1
ATOM   2708  O    THR    3     61.605  23.759  29.317  1.00 79.30      AP1
ATOM   2709  N    LEU    4     63.222  22.208  29.321  1.00 78.77      AP1
ATOM   2710  CA   LEU    4     62.251  21.132  29.156  1.00 78.22      AP1
ATOM   2711  CB   LEU    4     62.923  19.801  28.851  1.00 77.88      AP1
ATOM   2712  CG   LEU    4     61.828  18.727  28.731  1.00 77.68      AP1
ATOM   2713  CD1  LEU    4     60.998  19.049  27.513  1.00 77.33      AP1
ATOM   2714  CD2  LEU    4     62.403  17.321  28.629  1.00 77.20      AP1
ATOM   2715  C    LEU    4     61.331  20.916  30.346  1.00 78.03      AP1
ATOM   2716  O    LEU    4     60.136  20.639  30.178  1.00 77.68      AP1
ATOM   2717  N    ALA    5     61.886  21.017  31.549  1.00 77.86      AP1
ATOM   2718  CA   ALA    5     61.085  20.810  32.747  1.00 77.70      AP1
ATOM   2719  CB   ALA    5     62.017  20.587  33.932  1.00 78.40      AP1
ATOM   2720  C    ALA    5     60.210  22.036  33.016  1.00 76.70      AP1
ATOM   2721  O    ALA    5     59.170  21.935  33.663  1.00 76.78      AP1
ATOM   2722  N    ARG    6     60.632  23.190  32.514  1.00 75.48      AP1
ATOM   2723  CA   ARG    6     59.832  24.397  32.661  1.00 74.44      AP1
ATOM   2724  CB   ARG    6     60.684  25.657  32.435  1.00 73.87      AP1
ATOM   2725  CG   ARG    6     61.473  26.120  33.670  1.00 73.31      AP1
ATOM   2726  CD   ARG    6     61.862  27.604  33.562  1.00 72.64      AP1
ATOM   2727  NE   ARG    6     63.062  27.818  32.760  1.00 71.95      AP1
ATOM   2728  CZ   ARG    6     63.467  28.995  32.277  1.00 71.96      AP1
```

FIG. 3A-48

| ATOM | 2729 | NH1 | ARG | 6 | 62.761 | 30.091 | 32.501 | 1.00 | 71.89 | AP1 |
|------|------|-----|-----|---|--------|--------|--------|------|-------|-----|
| ATOM | 2730 | NH2 | ARG | 6 | 64.600 | 29.082 | 31.580 | 1.00 | 71.79 | AP1 |
| ATOM | 2731 | C | ARG | 6 | 58.668 | 24.341 | 31.640 | 1.00 | 74.00 | AP1 |
| ATOM | 2732 | O | ARG | 6 | 57.600 | 24.921 | 31.880 | 1.00 | 74.10 | AP1 |
| ATOM | 2733 | N | VAL | 7 | 58.882 | 23.635 | 30.519 | 1.00 | 72.52 | AP1 |
| ATOM | 2734 | CA | VAL | 7 | 57.875 | 23.476 | 29.474 | 1.00 | 71.13 | AP1 |
| ATOM | 2735 | CB | VAL | 7 | 58.528 | 23.150 | 28.081 | 1.00 | 70.76 | AP1 |
| ATOM | 2736 | CG1 | VAL | 7 | 57.473 | 22.682 | 27.082 | 1.00 | 69.94 | AP1 |
| ATOM | 2737 | CG2 | VAL | 7 | 59.224 | 24.379 | 27.531 | 1.00 | 70.02 | AP1 |
| ATOM | 2738 | C | VAL | 7 | 56.880 | 22.362 | 29.842 | 1.00 | 70.99 | AP1 |
| ATOM | 2739 | O | VAL | 7 | 55.696 | 22.448 | 29.487 | 1.00 | 70.50 | AP1 |
| ATOM | 2740 | N | THR | 8 | 57.343 | 21.315 | 30.532 | 1.00 | 70.31 | AP1 |
| ATOM | 2741 | CA | THR | 8 | 56.437 | 20.228 | 30.924 | 1.00 | 69.89 | AP1 |
| ATOM | 2742 | CB | THR | 8 | 57.207 | 19.000 | 31.436 | 1.00 | 70.39 | AP1 |
| ATOM | 2743 | OG1 | THR | 8 | 58.176 | 18.604 | 30.455 | 1.00 | 71.27 | AP1 |
| ATOM | 2744 | CG2 | THR | 8 | 56.258 | 17.844 | 31.677 | 1.00 | 69.84 | AP1 |
| ATOM | 2745 | C | THR | 8 | 55.496 | 20.740 | 32.028 | 1.00 | 69.21 | AP1 |
| ATOM | 2746 | O | THR | 8 | 54.310 | 20.395 | 32.074 | 1.00 | 68.80 | AP1 |
| ATOM | 2747 | N | LYS | 9 | 56.033 | 21.588 | 32.902 | 1.00 | 68.48 | AP1 |
| ATOM | 2748 | CA | LYS | 9 | 55.243 | 22.183 | 33.976 | 1.00 | 67.55 | AP1 |
| ATOM | 2749 | CB | LYS | 9 | 56.112 | 23.128 | 34.830 | 1.00 | 67.47 | AP1 |
| ATOM | 2750 | CG | LYS | 9 | 55.319 | 23.931 | 35.878 | 1.00 | 68.25 | AP1 |
| ATOM | 2751 | CD | LYS | 9 | 56.210 | 24.545 | 36.983 | 1.00 | 68.59 | AP1 |
| ATOM | 2752 | CE | LYS | 9 | 55.418 | 25.517 | 37.861 | 1.00 | 68.36 | AP1 |
| ATOM | 2753 | NZ | LYS | 9 | 54.123 | 24.921 | 38.323 | 1.00 | 68.66 | AP1 |
| ATOM | 2754 | C | LYS | 9 | 54.103 | 22.966 | 33.329 | 1.00 | 66.72 | AP1 |
| ATOM | 2755 | O | LYS | 9 | 52.939 | 22.773 | 33.659 | 1.00 | 66.23 | AP1 |
| ATOM | 2756 | N | ILE | 10 | 54.468 | 23.841 | 32.395 | 1.00 | 66.18 | AP1 |
| ATOM | 2757 | CA | ILE | 10 | 53.531 | 24.685 | 31.660 | 1.00 | 65.16 | AP1 |
| ATOM | 2758 | CB | ILE | 10 | 54.291 | 25.543 | 30.628 | 1.00 | 65.28 | AP1 |
| ATOM | 2759 | CG2 | ILE | 10 | 53.314 | 26.400 | 29.843 | 1.00 | 64.89 | AP1 |
| ATOM | 2760 | CG1 | ILE | 10 | 55.385 | 26.357 | 31.319 | 1.00 | 64.70 | AP1 |
| ATOM | 2761 | CD1 | ILE | 10 | 55.044 | 27.783 | 31.590 | 1.00 | 65.19 | AP1 |
| ATOM | 2762 | C | ILE | 10 | 52.441 | 23.904 | 30.912 | 1.00 | 64.66 | AP1 |
| ATOM | 2763 | O | ILE | 10 | 51.287 | 24.308 | 30.896 | 1.00 | 64.47 | AP1 |
| ATOM | 2764 | N | ILE | 11 | 52.815 | 22.789 | 30.298 | 1.00 | 64.80 | AP1 |
| ATOM | 2765 | CA | ILE | 11 | 51.889 | 21.963 | 29.521 | 1.00 | 65.01 | AP1 |
| ATOM | 2766 | CB | ILE | 11 | 52.663 | 20.931 | 28.676 | 1.00 | 64.05 | AP1 |
| ATOM | 2767 | CG2 | ILE | 11 | 51.740 | 19.861 | 28.151 | 1.00 | 63.58 | AP1 |
| ATOM | 2768 | CG1 | ILE | 11 | 53.380 | 21.657 | 27.546 | 1.00 | 63.60 | AP1 |
| ATOM | 2769 | CD1 | ILE | 11 | 54.255 | 20.768 | 26.702 | 1.00 | 63.69 | AP1 |
| ATOM | 2770 | C | ILE | 11 | 50.898 | 21.251 | 30.405 | 1.00 | 66.13 | AP1 |
| ATOM | 2771 | O | ILE | 11 | 49.685 | 21.345 | 30.202 | 1.00 | 65.72 | AP1 |
| ATOM | 2772 | N | VAL | 12 | 51.428 | 20.538 | 31.395 | 1.00 | 67.85 | AP1 |
| ATOM | 2773 | CA | VAL | 12 | 50.607 | 19.799 | 32.342 | 1.00 | 69.32 | AP1 |
| ATOM | 2774 | CB | VAL | 12 | 51.492 | 19.164 | 33.428 | 1.00 | 70.03 | AP1 |
| ATOM | 2775 | CG1 | VAL | 12 | 50.641 | 18.275 | 34.359 | 1.00 | 70.41 | AP1 |
| ATOM | 2776 | CG2 | VAL | 12 | 52.600 | 18.352 | 32.763 | 1.00 | 70.07 | AP1 |
| ATOM | 2777 | C | VAL | 12 | 49.586 | 20.734 | 32.992 | 1.00 | 70.16 | AP1 |
| ATOM | 2778 | O | VAL | 12 | 48.399 | 20.418 | 33.059 | 1.00 | 69.91 | AP1 |
| ATOM | 2779 | N | ASP | 13 | 50.056 | 21.890 | 33.455 | 1.00 | 71.30 | AP1 |
| ATOM | 2780 | CA | ASP | 13 | 49.181 | 22.866 | 34.085 | 1.00 | 72.67 | AP1 |
| ATOM | 2781 | CB | ASP | 13 | 49.946 | 24.159 | 34.443 | 1.00 | 73.98 | AP1 |
| ATOM | 2782 | CG | ASP | 13 | 50.819 | 24.015 | 35.704 | 1.00 | 75.23 | AP1 |
| ATOM | 2783 | OD1 | ASP | 13 | 50.890 | 22.888 | 36.255 | 1.00 | 76.30 | AP1 |
| ATOM | 2784 | OD2 | ASP | 13 | 51.440 | 25.026 | 36.144 | 1.00 | 75.56 | AP1 |
| ATOM | 2785 | C | ASP | 13 | 48.043 | 23.214 | 33.148 | 1.00 | 72.95 | AP1 |

FIG. 3A-49

| ATOM | 2786 | O | ASP | 13 | 46.876 | 23.099 | 33.513 | 1.00 | 73.09 | AP1 |
|---|---|---|---|---|---|---|---|---|---|---|
| ATOM | 2787 | N | ARG | 14 | 48.398 | 23.620 | 31.931 | 1.00 | 73.49 | AP1 |
| ATOM | 2788 | CA | ARG | 14 | 47.429 | 24.028 | 30.931 | 1.00 | 73.84 | AP1 |
| ATOM | 2789 | CB | ARG | 14 | 48.141 | 24.758 | 29.814 | 1.00 | 73.31 | AP1 |
| ATOM | 2790 | CG | ARG | 14 | 48.317 | 26.230 | 30.103 | 1.00 | 72.15 | AP1 |
| ATOM | 2791 | CD | ARG | 14 | 47.264 | 27.078 | 29.385 | 1.00 | 70.90 | AP1 |
| ATOM | 2792 | NE | ARG | 14 | 45.891 | 26.836 | 29.822 | 1.00 | 69.36 | AP1 |
| ATOM | 2793 | CZ | ARG | 14 | 45.389 | 27.215 | 30.997 | 1.00 | 68.61 | AP1 |
| ATOM | 2794 | NH1 | ARG | 14 | 46.138 | 27.869 | 31.883 | 1.00 | 66.65 | AP1 |
| ATOM | 2795 | NH2 | ARG | 14 | 44.123 | 26.925 | 31.282 | 1.00 | 67.78 | AP1 |
| ATOM | 2796 | C | ARG | 14 | 46.515 | 22.990 | 30.332 | 1.00 | 74.92 | AP1 |
| ATOM | 2797 | O | ARG | 14 | 45.306 | 23.073 | 30.506 | 1.00 | 75.02 | AP1 |
| ATOM | 2798 | N | LEU | 15 | 47.073 | 22.020 | 29.621 | 1.00 | 76.33 | AP1 |
| ATOM | 2799 | CA | LEU | 15 | 46.254 | 20.988 | 28.980 | 1.00 | 77.82 | AP1 |
| ATOM | 2800 | CB | LEU | 15 | 47.016 | 20.345 | 27.824 | 1.00 | 77.66 | AP1 |
| ATOM | 2801 | CG | LEU | 15 | 47.558 | 21.237 | 26.711 | 1.00 | 77.79 | AP1 |
| ATOM | 2802 | CD1 | LEU | 15 | 48.132 | 20.348 | 25.613 | 1.00 | 77.88 | AP1 |
| ATOM | 2803 | CD2 | LEU | 15 | 46.455 | 22.123 | 26.158 | 1.00 | 77.57 | AP1 |
| ATOM | 2804 | C | LEU | 15 | 45.773 | 19.869 | 29.899 | 1.00 | 79.19 | AP1 |
| ATOM | 2805 | O | LEU | 15 | 46.049 | 19.859 | 31.110 | 1.00 | 79.28 | AP1 |
| ATOM | 2806 | N | GLY | 16 | 45.048 | 18.922 | 29.306 | 1.00 | 80.67 | AP1 |
| ATOM | 2807 | CA | GLY | 16 | 44.559 | 17.789 | 30.071 | 1.00 | 82.85 | AP1 |
| ATOM | 2808 | C | GLY | 16 | 45.767 | 17.061 | 30.637 | 1.00 | 84.35 | AP1 |
| ATOM | 2809 | O | GLY | 16 | 45.945 | 16.974 | 31.855 | 1.00 | 84.11 | AP1 |
| ATOM | 2810 | N | VAL | 17 | 46.607 | 16.578 | 29.721 | 1.00 | 85.77 | AP1 |
| ATOM | 2811 | CA | VAL | 17 | 47.844 | 15.839 | 30.001 | 1.00 | 87.22 | AP1 |
| ATOM | 2812 | CB | VAL | 17 | 49.070 | 16.474 | 29.301 | 1.00 | 87.11 | AP1 |
| ATOM | 2813 | CG1 | VAL | 17 | 48.710 | 16.869 | 27.893 | 1.00 | 87.54 | AP1 |
| ATOM | 2814 | CG2 | VAL | 17 | 49.584 | 17.663 | 30.103 | 1.00 | 87.15 | AP1 |
| ATOM | 2815 | C | VAL | 17 | 48.289 | 15.579 | 31.429 | 1.00 | 88.17 | AP1 |
| ATOM | 2816 | O | VAL | 17 | 48.000 | 16.321 | 32.373 | 1.00 | 88.26 | AP1 |
| ATOM | 2817 | N | ASP | 18 | 49.056 | 14.505 | 31.537 | 1.00 | 89.54 | AP1 |
| ATOM | 2818 | CA | ASP | 18 | 49.619 | 14.041 | 32.787 | 1.00 | 90.63 | AP1 |
| ATOM | 2819 | CB | ASP | 18 | 49.655 | 12.509 | 32.759 | 1.00 | 91.40 | AP1 |
| ATOM | 2820 | CG | ASP | 18 | 48.388 | 11.910 | 32.118 | 1.00 | 92.34 | AP1 |
| ATOM | 2821 | OD1 | ASP | 18 | 47.900 | 10.854 | 32.597 | 1.00 | 92.79 | AP1 |
| ATOM | 2822 | OD2 | ASP | 18 | 47.881 | 12.497 | 31.128 | 1.00 | 92.45 | AP1 |
| ATOM | 2823 | C | ASP | 18 | 51.017 | 14.660 | 32.913 | 1.00 | 90.91 | AP1 |
| ATOM | 2824 | O | ASP | 18 | 51.150 | 15.889 | 32.892 | 1.00 | 91.13 | AP1 |
| ATOM | 2825 | N | GLU | 19 | 52.053 | 13.839 | 33.037 | 1.00 | 90.94 | AP1 |
| ATOM | 2826 | CA | GLU | 19 | 53.415 | 14.359 | 33.152 | 1.00 | 91.05 | AP1 |
| ATOM | 2827 | CB | GLU | 19 | 53.824 | 14.457 | 34.628 | 1.00 | 91.09 | AP1 |
| ATOM | 2828 | CG | GLU | 19 | 54.855 | 15.536 | 34.961 | 1.00 | 91.09 | AP1 |
| ATOM | 2829 | CD | GLU | 19 | 56.226 | 15.279 | 34.357 | 1.00 | 91.30 | AP1 |
| ATOM | 2830 | OE1 | GLU | 19 | 56.573 | 14.093 | 34.145 | 1.00 | 91.36 | AP1 |
| ATOM | 2831 | OE2 | GLU | 19 | 56.966 | 16.263 | 34.117 | 1.00 | 91.19 | AP1 |
| ATOM | 2832 | C | GLU | 19 | 54.284 | 13.352 | 32.409 | 1.00 | 91.17 | AP1 |
| ATOM | 2833 | O | GLU | 19 | 55.365 | 13.670 | 31.906 | 1.00 | 91.03 | AP1 |
| ATOM | 2834 | N | ALA | 20 | 53.787 | 12.122 | 32.352 | 1.00 | 91.10 | AP1 |
| ATOM | 2835 | CA | ALA | 20 | 54.470 | 11.056 | 31.650 | 1.00 | 90.83 | AP1 |
| ATOM | 2836 | CB | ALA | 20 | 54.346 | 9.742 | 32.422 | 1.00 | 90.97 | AP1 |
| ATOM | 2837 | C | ALA | 20 | 53.745 | 10.975 | 30.319 | 1.00 | 90.53 | AP1 |
| ATOM | 2838 | O | ALA | 20 | 53.250 | 9.921 | 29.921 | 1.00 | 90.54 | AP1 |
| ATOM | 2839 | N | ASP | 21 | 53.673 | 12.120 | 29.649 | 1.00 | 90.01 | AP1 |
| ATOM | 2840 | CA | ASP | 21 | 53.011 | 12.240 | 28.356 | 1.00 | 89.51 | AP1 |
| ATOM | 2841 | CB | ASP | 21 | 51.573 | 12.703 | 28.540 | 1.00 | 90.00 | AP1 |
| ATOM | 2842 | CG | ASP | 21 | 50.671 | 11.607 | 29.018 | 1.00 | 90.37 | AP1 |

FIG. 3A-50

| ATOM | 2843 | OD1 | ASP | 21 | 51.172 | 10.479 | 29.200 | 1.00 | 90.49 | AP1 |
| ATOM | 2844 | OD2 | ASP | 21 | 49.463 | 11.878 | 29.201 | 1.00 | 90.73 | AP1 |
| ATOM | 2845 | C | ASP | 21 | 53.742 | 13.265 | 27.512 | 1.00 | 88.90 | AP1 |
| ATOM | 2846 | O | ASP | 21 | 53.788 | 13.161 | 26.288 | 1.00 | 88.82 | AP1 |
| ATOM | 2847 | N | VAL | 22 | 54.287 | 14.273 | 28.186 | 1.00 | 88.02 | AP1 |
| ATOM | 2848 | CA | VAL | 22 | 55.034 | 15.336 | 27.534 | 1.00 | 86.78 | AP1 |
| ATOM | 2849 | CB | VAL | 22 | 55.323 | 16.508 | 28.529 | 1.00 | 87.06 | AP1 |
| ATOM | 2850 | CG1 | VAL | 22 | 56.038 | 17.662 | 27.822 | 1.00 | 86.97 | AP1 |
| ATOM | 2851 | CG2 | VAL | 22 | 54.014 | 16.997 | 29.147 | 1.00 | 87.18 | AP1 |
| ATOM | 2852 | C | VAL | 22 | 56.348 | 14.744 | 27.032 | 1.00 | 85.76 | AP1 |
| ATOM | 2853 | O | VAL | 22 | 57.414 | 14.993 | 27.596 | 1.00 | 85.65 | AP1 |
| ATOM | 2854 | N | LYS | 23 | 56.253 | 13.930 | 25.985 | 1.00 | 84.59 | AP1 |
| ATOM | 2855 | CA | LYS | 23 | 57.427 | 13.314 | 25.382 | 1.00 | 83.57 | AP1 |
| ATOM | 2856 | CB | LYS | 23 | 57.121 | 11.861 | 24.978 | 1.00 | 83.52 | AP1 |
| ATOM | 2857 | C | LYS | 23 | 57.719 | 14.171 | 24.154 | 1.00 | 82.69 | AP1 |
| ATOM | 2858 | O | LYS | 23 | 56.838 | 14.353 | 23.317 | 1.00 | 82.89 | AP1 |
| ATOM | 2859 | N | LEU | 24 | 58.943 | 14.691 | 24.056 | 1.00 | 81.40 | AP1 |
| ATOM | 2860 | CA | LEU | 24 | 59.356 | 15.573 | 22.955 | 1.00 | 80.08 | AP1 |
| ATOM | 2861 | CB | LEU | 24 | 60.872 | 15.489 | 22.737 | 1.00 | 79.75 | AP1 |
| ATOM | 2862 | CG | LEU | 24 | 61.731 | 16.258 | 23.739 | 1.00 | 79.50 | AP1 |
| ATOM | 2863 | CD1 | LEU | 24 | 61.624 | 15.608 | 25.106 | 1.00 | 79.62 | AP1 |
| ATOM | 2864 | CD2 | LEU | 24 | 63.163 | 16.267 | 23.275 | 1.00 | 79.59 | AP1 |
| ATOM | 2865 | C | LEU | 24 | 58.655 | 15.423 | 21.610 | 1.00 | 79.43 | AP1 |
| ATOM | 2866 | O | LEU | 24 | 58.428 | 16.416 | 20.920 | 1.00 | 79.17 | AP1 |
| ATOM | 2867 | N | GLU | 25 | 58.306 | 14.198 | 21.235 | 1.00 | 78.68 | AP1 |
| ATOM | 2868 | CA | GLU | 25 | 57.650 | 13.981 | 19.952 | 1.00 | 78.37 | AP1 |
| ATOM | 2869 | CB | GLU | 25 | 57.965 | 12.579 | 19.408 | 1.00 | 78.68 | AP1 |
| ATOM | 2870 | CG | GLU | 25 | 59.443 | 12.271 | 19.291 | 1.00 | 79.23 | AP1 |
| ATOM | 2871 | CD | GLU | 25 | 59.891 | 11.221 | 20.293 | 1.00 | 79.42 | AP1 |
| ATOM | 2872 | OE1 | GLU | 25 | 59.178 | 11.021 | 21.303 | 1.00 | 79.38 | AP1 |
| ATOM | 2873 | OE2 | GLU | 25 | 60.956 | 10.606 | 20.072 | 1.00 | 79.41 | AP1 |
| ATOM | 2874 | C | GLU | 25 | 56.138 | 14.163 | 19.977 | 1.00 | 77.58 | AP1 |
| ATOM | 2875 | O | GLU | 25 | 55.499 | 14.132 | 18.931 | 1.00 | 77.72 | AP1 |
| ATOM | 2876 | N | ALA | 26 | 55.566 | 14.345 | 21.161 | 1.00 | 76.67 | AP1 |
| ATOM | 2877 | CA | ALA | 26 | 54.123 | 14.513 | 21.286 | 1.00 | 75.78 | AP1 |
| ATOM | 2878 | CB | ALA | 26 | 53.695 | 14.309 | 22.740 | 1.00 | 75.80 | AP1 |
| ATOM | 2879 | C | ALA | 26 | 53.625 | 15.869 | 20.790 | 1.00 | 75.27 | AP1 |
| ATOM | 2880 | O | ALA | 26 | 54.006 | 16.920 | 21.328 | 1.00 | 75.04 | AP1 |
| ATOM | 2881 | N | SER | 27 | 52.783 | 15.839 | 19.755 | 1.00 | 74.60 | AP1 |
| ATOM | 2882 | CA | SER | 27 | 52.188 | 17.064 | 19.214 | 1.00 | 73.92 | AP1 |
| ATOM | 2883 | CB | SER | 27 | 51.502 | 16.804 | 17.874 | 1.00 | 73.95 | AP1 |
| ATOM | 2884 | OG | SER | 27 | 50.754 | 17.940 | 17.470 | 1.00 | 73.19 | AP1 |
| ATOM | 2885 | C | SER | 27 | 51.141 | 17.561 | 20.205 | 1.00 | 73.32 | AP1 |
| ATOM | 2886 | O | SER | 27 | 50.448 | 16.765 | 20.839 | 1.00 | 73.44 | AP1 |
| ATOM | 2887 | N | PHE | 28 | 51.020 | 18.874 | 20.333 | 1.00 | 72.76 | AP1 |
| ATOM | 2888 | CA | PHE | 28 | 50.057 | 19.439 | 21.264 | 1.00 | 72.39 | AP1 |
| ATOM | 2889 | CB | PHE | 28 | 50.196 | 20.969 | 21.345 | 1.00 | 71.67 | AP1 |
| ATOM | 2890 | CG | PHE | 28 | 51.538 | 21.431 | 21.825 | 1.00 | 70.96 | AP1 |
| ATOM | 2891 | CD1 | PHE | 28 | 51.948 | 21.175 | 23.131 | 1.00 | 70.16 | AP1 |
| ATOM | 2892 | CD2 | PHE | 28 | 52.407 | 22.105 | 20.962 | 1.00 | 70.39 | AP1 |
| ATOM | 2893 | CE1 | PHE | 28 | 53.207 | 21.579 | 23.571 | 1.00 | 69.79 | AP1 |
| ATOM | 2894 | CE2 | PHE | 28 | 53.668 | 22.515 | 21.393 | 1.00 | 69.61 | AP1 |
| ATOM | 2895 | CZ | PHE | 28 | 54.068 | 22.251 | 22.697 | 1.00 | 69.78 | AP1 |
| ATOM | 2896 | C | PHE | 28 | 48.635 | 19.090 | 20.870 | 1.00 | 72.17 | AP1 |
| ATOM | 2897 | O | PHE | 28 | 47.913 | 18.445 | 21.628 | 1.00 | 71.91 | AP1 |
| ATOM | 2898 | N | LYS | 29 | 48.239 | 19.499 | 19.675 | 1.00 | 72.50 | AP1 |
| ATOM | 2899 | CA | LYS | 29 | 46.877 | 19.262 | 19.244 | 1.00 | 73.27 | AP1 |

FIG. 3A-51

| | | | | | | | | | |
|---|---|---|---|---|---|---|---|---|---|
| ATOM | 2900 | CB | LYS | 29 | 46.622 | 19.945 | 17.898 | 1.00 73.40 | AP1 |
| ATOM | 2901 | CG | LYS | 29 | 47.348 | 21.272 | 17.766 | 1.00 73.52 | AP1 |
| ATOM | 2902 | CD | LYS | 29 | 46.788 | 22.164 | 16.669 | 1.00 73.98 | AP1 |
| ATOM | 2903 | CE | LYS | 29 | 45.573 | 22.953 | 17.146 | 1.00 74.17 | AP1 |
| ATOM | 2904 | NZ | LYS | 29 | 45.197 | 24.052 | 16.207 | 1.00 73.83 | AP1 |
| ATOM | 2905 | C | LYS | 29 | 46.551 | 17.782 | 19.170 | 1.00 73.71 | AP1 |
| ATOM | 2906 | O | LYS | 29 | 45.597 | 17.329 | 19.805 | 1.00 73.88 | AP1 |
| ATOM | 2907 | N | GLU | 30 | 47.368 | 17.023 | 18.446 | 1.00 74.16 | AP1 |
| ATOM | 2908 | CA | GLU | 30 | 47.126 | 15.590 | 18.271 | 1.00 74.65 | AP1 |
| ATOM | 2909 | CB | GLU | 30 | 48.023 | 15.049 | 17.170 | 1.00 75.07 | AP1 |
| ATOM | 2910 | CG | GLU | 30 | 47.947 | 15.852 | 15.929 | 1.00 76.86 | AP1 |
| ATOM | 2911 | CD | GLU | 30 | 48.057 | 14.977 | 14.718 | 1.00 78.78 | AP1 |
| ATOM | 2912 | OE1 | GLU | 30 | 49.056 | 14.212 | 14.642 | 1.00 79.54 | AP1 |
| ATOM | 2913 | OE2 | GLU | 30 | 47.147 | 15.046 | 13.847 | 1.00 79.33 | AP1 |
| ATOM | 2914 | C | GLU | 30 | 47.257 | 14.667 | 19.484 | 1.00 74.38 | AP1 |
| ATOM | 2915 | O | GLU | 30 | 46.340 | 13.875 | 19.775 | 1.00 74.75 | AP1 |
| ATOM | 2916 | N | ASP | 31 | 48.381 | 14.769 | 20.192 | 1.00 73.09 | AP1 |
| ATOM | 2917 | CA | ASP | 31 | 48.636 | 13.897 | 21.328 | 1.00 71.86 | AP1 |
| ATOM | 2918 | CB | ASP | 31 | 50.132 | 13.566 | 21.384 | 1.00 72.88 | AP1 |
| ATOM | 2919 | CG | ASP | 31 | 50.652 | 13.051 | 20.069 | 1.00 73.78 | AP1 |
| ATOM | 2920 | OD1 | ASP | 31 | 50.012 | 12.137 | 19.501 | 1.00 74.25 | AP1 |
| ATOM | 2921 | OD2 | ASP | 31 | 51.695 | 13.561 | 19.601 | 1.00 75.05 | AP1 |
| ATOM | 2922 | C | ASP | 31 | 48.184 | 14.360 | 22.706 | 1.00 70.61 | AP1 |
| ATOM | 2923 | O | ASP | 31 | 47.738 | 13.543 | 23.527 | 1.00 70.48 | AP1 |
| ATOM | 2924 | N | LEU | 32 | 48.286 | 15.659 | 22.970 | 1.00 68.61 | AP1 |
| ATOM | 2925 | CA | LEU | 32 | 47.934 | 16.158 | 24.296 | 1.00 66.10 | AP1 |
| ATOM | 2926 | CB | LEU | 32 | 48.990 | 17.177 | 24.745 | 1.00 65.45 | AP1 |
| ATOM | 2927 | CG | LEU | 32 | 50.426 | 16.633 | 24.584 | 1.00 64.39 | AP1 |
| ATOM | 2928 | CD1 | LEU | 32 | 51.434 | 17.693 | 24.928 | 1.00 64.02 | AP1 |
| ATOM | 2929 | CD2 | LEU | 32 | 50.618 | 15.417 | 25.477 | 1.00 63.67 | AP1 |
| ATOM | 2930 | C | LEU | 32 | 46.542 | 16.731 | 24.419 | 1.00 64.48 | AP1 |
| ATOM | 2931 | O | LEU | 32 | 46.238 | 17.395 | 25.403 | 1.00 65.05 | AP1 |
| ATOM | 2932 | N | GLY | 33 | 45.704 | 16.464 | 23.422 | 1.00 62.24 | AP1 |
| ATOM | 2933 | CA | GLY | 33 | 44.326 | 16.944 | 23.434 | 1.00 59.99 | AP1 |
| ATOM | 2934 | C | GLY | 33 | 44.083 | 18.452 | 23.397 | 1.00 58.02 | AP1 |
| ATOM | 2935 | O | GLY | 33 | 43.140 | 18.960 | 24.018 | 1.00 57.75 | AP1 |
| ATOM | 2936 | N | ALA | 34 | 44.904 | 19.172 | 22.639 | 1.00 55.70 | AP1 |
| ATOM | 2937 | CA | ALA | 34 | 44.774 | 20.612 | 22.568 | 1.00 53.12 | AP1 |
| ATOM | 2938 | CB | ALA | 34 | 46.160 | 21.243 | 22.618 | 1.00 51.50 | AP1 |
| ATOM | 2939 | C | ALA | 34 | 43.996 | 21.131 | 21.357 | 1.00 51.67 | AP1 |
| ATOM | 2940 | O | ALA | 34 | 44.030 | 20.555 | 20.265 | 1.00 52.46 | AP1 |
| ATOM | 2941 | N | ASP | 35 | 43.254 | 22.203 | 21.577 | 1.00 49.18 | AP1 |
| ATOM | 2942 | CA | ASP | 35 | 42.542 | 22.835 | 20.495 | 1.00 47.71 | AP1 |
| ATOM | 2943 | CB | ASP | 35 | 41.047 | 23.038 | 20.817 | 1.00 47.47 | AP1 |
| ATOM | 2944 | CG | ASP | 35 | 40.800 | 23.937 | 22.053 | 1.00 48.06 | AP1 |
| ATOM | 2945 | OD1 | ASP | 35 | 41.772 | 24.521 | 22.632 | 1.00 47.16 | AP1 |
| ATOM | 2946 | OD2 | ASP | 35 | 39.605 | 24.042 | 22.435 | 1.00 47.60 | AP1 |
| ATOM | 2947 | C | ASP | 35 | 43.241 | 24.178 | 20.327 | 1.00 46.40 | AP1 |
| ATOM | 2948 | O | ASP | 35 | 44.248 | 24.448 | 21.002 | 1.00 45.96 | AP1 |
| ATOM | 2949 | CA | PAN | 36 | 43.266 | 26.327 | 19.165 | 1.00 43.36 | AP1 |
| ATOM | 2950 | N | PAN | 36 | 42.705 | 25.005 | 19.437 | 1.00 44.57 | AP1 |
| ATOM | 2951 | C | PAN | 36 | 43.389 | 27.308 | 20.387 | 1.00 41.47 | AP1 |
| ATOM | 2952 | O | PAN | 36 | 44.435 | 27.948 | 20.563 | 1.00 39.31 | AP1 |
| ATOM | 2953 | O5 | PAN | 36 | 43.295 | 28.035 | 17.578 | 1.00 47.40 | AP1 |
| ATOM | 2954 | P6 | PAN | 36 | 44.014 | 27.865 | 16.147 | 1.00 49.84 | AP1 |
| ATOM | 2955 | O7 | PAN | 36 | 43.369 | 29.013 | 15.282 | 1.00 47.80 | AP1 |
| ATOM | 2956 | O8 | PAN | 36 | 43.594 | 26.426 | 15.540 | 1.00 47.32 | AP1 |

FIG. 3A-52

| ATOM | 2957 | O9 | PAN | 36 | 45.529 | 28.004 | 16.288 | 1.00 | 48.61 | AP1 |
| ATOM | 2958 | CB | PAN | 36 | 42.468 | 26.996 | 18.055 | 1.00 | 43.60 | AP1 |
| ATOM | 2959 | N | LEU | 37 | 42.317 | 27.456 | 21.167 | 1.00 | 38.73 | AP1 |
| ATOM | 2960 | CA | LEU | 37 | 42.342 | 28.307 | 22.361 | 1.00 | 38.63 | AP1 |
| ATOM | 2961 | CB | LEU | 37 | 40.970 | 28.384 | 23.033 | 1.00 | 38.45 | AP1 |
| ATOM | 2962 | CG | LEU | 37 | 40.084 | 29.491 | 22.490 | 1.00 | 39.46 | AP1 |
| ATOM | 2963 | CD1 | LEU | 37 | 38.726 | 29.397 | 23.139 | 1.00 | 40.89 | AP1 |
| ATOM | 2964 | CD2 | LEU | 37 | 40.730 | 30.853 | 22.756 | 1.00 | 39.88 | AP1 |
| ATOM | 2965 | C | LEU | 37 | 43.362 | 27.750 | 23.371 | 1.00 | 38.10 | AP1 |
| ATOM | 2966 | O | LEU | 37 | 44.001 | 28.511 | 24.055 | 1.00 | 37.69 | AP1 |
| ATOM | 2967 | N | ASP | 38 | 43.508 | 26.424 | 23.440 | 1.00 | 37.30 | AP1 |
| ATOM | 2968 | CA | ASP | 38 | 44.480 | 25.846 | 24.318 | 1.00 | 37.41 | AP1 |
| ATOM | 2969 | CB | ASP | 38 | 44.312 | 24.319 | 24.400 | 1.00 | 39.77 | AP1 |
| ATOM | 2970 | CG | ASP | 38 | 43.138 | 23.905 | 25.321 | 1.00 | 43.20 | AP1 |
| ATOM | 2971 | OD1 | ASP | 38 | 42.294 | 23.072 | 24.867 | 1.00 | 44.70 | AP1 |
| ATOM | 2972 | OD2 | ASP | 38 | 43.061 | 24.418 | 26.492 | 1.00 | 44.13 | AP1 |
| ATOM | 2973 | C | ASP | 38 | 45.895 | 26.193 | 23.881 | 1.00 | 36.29 | AP1 |
| ATOM | 2974 | O | ASP | 38 | 46.726 | 26.520 | 24.719 | 1.00 | 35.72 | AP1 |
| ATOM | 2975 | N | VAL | 39 | 46.185 | 26.160 | 22.578 | 1.00 | 34.94 | AP1 |
| ATOM | 2976 | CA | VAL | 39 | 47.551 | 26.435 | 22.162 | 1.00 | 33.47 | AP1 |
| ATOM | 2977 | CB | VAL | 39 | 47.891 | 25.854 | 20.691 | 1.00 | 33.86 | AP1 |
| ATOM | 2978 | CG1 | VAL | 39 | 46.700 | 25.967 | 19.759 | 1.00 | 33.20 | AP1 |
| ATOM | 2979 | CG2 | VAL | 39 | 49.064 | 26.630 | 20.071 | 1.00 | 34.16 | AP1 |
| ATOM | 2980 | C | VAL | 39 | 47.880 | 27.918 | 22.250 | 1.00 | 33.32 | AP1 |
| ATOM | 2981 | O | VAL | 39 | 49.011 | 28.262 | 22.562 | 1.00 | 32.10 | AP1 |
| ATOM | 2982 | N | VAL | 40 | 46.934 | 28.826 | 22.015 | 1.00 | 33.82 | AP1 |
| ATOM | 2983 | CA | VAL | 40 | 47.407 | 30.174 | 22.138 | 1.00 | 36.01 | AP1 |
| ATOM | 2984 | CB | VAL | 40 | 46.499 | 31.306 | 21.493 | 1.00 | 36.85 | AP1 |
| ATOM | 2985 | CG1 | VAL | 40 | 45.532 | 30.732 | 20.402 | 1.00 | 37.16 | AP1 |
| ATOM | 2986 | CG2 | VAL | 40 | 45.841 | 32.142 | 22.569 | 1.00 | 37.08 | AP1 |
| ATOM | 2987 | C | VAL | 40 | 47.660 | 30.465 | 23.597 | 1.00 | 36.87 | AP1 |
| ATOM | 2988 | O | VAL | 40 | 48.564 | 31.235 | 23.899 | 1.00 | 36.77 | AP1 |
| ATOM | 2989 | N | GLU | 41 | 46.904 | 29.854 | 24.505 | 1.00 | 36.94 | AP1 |
| ATOM | 2990 | CA | GLU | 41 | 47.171 | 30.150 | 25.886 | 1.00 | 38.60 | AP1 |
| ATOM | 2991 | CB | GLU | 41 | 46.139 | 29.525 | 26.818 | 1.00 | 39.00 | AP1 |
| ATOM | 2992 | CG | GLU | 41 | 46.536 | 29.747 | 28.282 | 1.00 | 40.88 | AP1 |
| ATOM | 2993 | CD | GLU | 41 | 45.374 | 30.037 | 29.249 | 1.00 | 41.76 | AP1 |
| ATOM | 2994 | OE1 | GLU | 41 | 44.188 | 29.696 | 28.971 | 1.00 | 40.79 | AP1 |
| ATOM | 2995 | OE2 | GLU | 41 | 45.683 | 30.631 | 30.315 | 1.00 | 42.76 | AP1 |
| ATOM | 2996 | C | GLU | 41 | 48.580 | 29.659 | 26.229 | 1.00 | 38.97 | AP1 |
| ATOM | 2997 | O | GLU | 41 | 49.363 | 30.383 | 26.838 | 1.00 | 38.23 | AP1 |
| ATOM | 2998 | N | LEU | 42 | 48.861 | 28.430 | 25.796 | 1.00 | 39.97 | AP1 |
| ATOM | 2999 | CA | LEU | 42 | 50.133 | 27.723 | 25.954 | 1.00 | 40.75 | AP1 |
| ATOM | 3000 | CB | LEU | 42 | 50.101 | 26.447 | 25.109 | 1.00 | 41.63 | AP1 |
| ATOM | 3001 | CG | LEU | 42 | 50.783 | 25.184 | 25.623 | 1.00 | 43.50 | AP1 |
| ATOM | 3002 | CD1 | LEU | 42 | 50.961 | 25.237 | 27.132 | 1.00 | 44.32 | AP1 |
| ATOM | 3003 | CD2 | LEU | 42 | 49.923 | 23.986 | 25.254 | 1.00 | 44.23 | AP1 |
| ATOM | 3004 | C | LEU | 42 | 51.248 | 28.618 | 25.448 | 1.00 | 41.88 | AP1 |
| ATOM | 3005 | O | LEU | 42 | 52.310 | 28.774 | 26.107 | 1.00 | 41.87 | AP1 |
| ATOM | 3006 | N | VAL | 43 | 51.019 | 29.192 | 24.271 | 1.00 | 41.61 | AP1 |
| ATOM | 3007 | CA | VAL | 43 | 52.002 | 30.099 | 23.698 | 1.00 | 43.10 | AP1 |
| ATOM | 3008 | CB | VAL | 43 | 51.573 | 30.626 | 22.280 | 1.00 | 41.95 | AP1 |
| ATOM | 3009 | CG1 | VAL | 43 | 52.461 | 31.773 | 21.849 | 1.00 | 42.05 | AP1 |
| ATOM | 3010 | CG2 | VAL | 43 | 51.683 | 29.525 | 21.272 | 1.00 | 41.68 | AP1 |
| ATOM | 3011 | C | VAL | 43 | 52.205 | 31.299 | 24.642 | 1.00 | 44.58 | AP1 |
| ATOM | 3012 | O | VAL | 43 | 53.334 | 31.710 | 24.885 | 1.00 | 44.40 | AP1 |
| ATOM | 3013 | N | MET | 44 | 51.129 | 31.846 | 25.198 | 1.00 | 46.55 | AP1 |

FIG. 3A-53

| ATOM | 3014 | CA | MET | 44 | 51.271 | 33.002 | 26.081 | 1.00 | 48.50 | AP1 |
|---|---|---|---|---|---|---|---|---|---|---|
| ATOM | 3015 | CB | MET | 44 | 49.903 | 33.596 | 26.411 | 1.00 | 50.62 | AP1 |
| ATOM | 3016 | CG | MET | 44 | 49.036 | 33.830 | 25.191 | 1.00 | 53.31 | AP1 |
| ATOM | 3017 | SD | MET | 44 | 48.010 | 35.308 | 25.274 | 1.00 | 56.48 | AP1 |
| ATOM | 3018 | CE | MET | 44 | 49.023 | 36.381 | 24.091 | 1.00 | 56.10 | AP1 |
| ATOM | 3019 | C | MET | 44 | 52.030 | 32.673 | 27.367 | 1.00 | 48.61 | AP1 |
| ATOM | 3020 | O | MET | 44 | 52.746 | 33.505 | 27.895 | 1.00 | 47.98 | AP1 |
| ATOM | 3021 | N | GLU | 45 | 51.862 | 31.456 | 27.850 | 1.00 | 49.57 | AP1 |
| ATOM | 3022 | CA | GLU | 45 | 52.537 | 30.979 | 29.047 | 1.00 | 51.80 | AP1 |
| ATOM | 3023 | CB | GLU | 45 | 52.109 | 29.544 | 29.311 | 1.00 | 53.29 | AP1 |
| ATOM | 3024 | CG | GLU | 45 | 51.852 | 29.175 | 30.731 | 1.00 | 56.51 | AP1 |
| ATOM | 3025 | CD | GLU | 45 | 50.397 | 29.315 | 31.099 | 1.00 | 58.24 | AP1 |
| ATOM | 3026 | OE1 | GLU | 45 | 50.000 | 30.403 | 31.586 | 1.00 | 60.07 | AP1 |
| ATOM | 3027 | OE2 | GLU | 45 | 49.646 | 28.331 | 30.896 | 1.00 | 59.11 | AP1 |
| ATOM | 3028 | C | GLU | 45 | 54.058 | 31.013 | 28.761 | 1.00 | 52.25 | AP1 |
| ATOM | 3029 | O | GLU | 45 | 54.836 | 31.596 | 29.526 | 1.00 | 52.28 | AP1 |
| ATOM | 3030 | N | LEU | 46 | 54.456 | 30.385 | 27.647 | 1.00 | 52.33 | AP1 |
| ATOM | 3031 | CA | LEU | 46 | 55.846 | 30.334 | 27.202 | 1.00 | 52.07 | AP1 |
| ATOM | 3032 | CB | LEU | 46 | 55.940 | 29.537 | 25.901 | 1.00 | 50.17 | AP1 |
| ATOM | 3033 | CG | LEU | 46 | 55.566 | 28.059 | 26.106 | 1.00 | 49.48 | AP1 |
| ATOM | 3034 | CD1 | LEU | 46 | 55.363 | 27.370 | 24.784 | 1.00 | 47.80 | AP1 |
| ATOM | 3035 | CD2 | LEU | 46 | 56.621 | 27.370 | 26.902 | 1.00 | 47.59 | AP1 |
| ATOM | 3036 | C | LEU | 46 | 56.453 | 31.735 | 27.029 | 1.00 | 53.27 | AP1 |
| ATOM | 3037 | O | LEU | 46 | 57.541 | 31.975 | 27.531 | 1.00 | 53.30 | AP1 |
| ATOM | 3038 | N | GLU | 47 | 55.760 | 32.656 | 26.344 | 1.00 | 54.28 | AP1 |
| ATOM | 3039 | CA | GLU | 47 | 56.254 | 34.042 | 26.152 | 1.00 | 55.41 | AP1 |
| ATOM | 3040 | CB | GLU | 47 | 55.254 | 34.859 | 25.313 | 1.00 | 55.37 | AP1 |
| ATOM | 3041 | CG | GLU | 47 | 54.558 | 34.403 | 24.030 | 1.00 | 20.00 | AP1 |
| ATOM | 3042 | CD | GLU | 47 | 53.941 | 35.658 | 23.455 | 1.00 | 20.00 | AP1 |
| ATOM | 3043 | OE1 | GLU | 47 | 53.223 | 36.026 | 24.374 | 1.00 | 20.00 | AP1 |
| ATOM | 3044 | OE2 | GLU | 47 | 53.948 | 36.198 | 22.351 | 1.00 | 20.00 | AP1 |
| ATOM | 3045 | C | GLU | 47 | 56.579 | 34.717 | 27.501 | 1.00 | 56.17 | AP1 |
| ATOM | 3046 | O | GLU | 47 | 57.556 | 35.469 | 27.650 | 1.00 | 55.04 | AP1 |
| ATOM | 3047 | N | ASP | 48 | 55.699 | 34.470 | 28.460 | 1.00 | 57.41 | AP1 |
| ATOM | 3048 | CA | ASP | 48 | 55.841 | 35.008 | 29.798 | 1.00 | 58.55 | AP1 |
| ATOM | 3049 | CB | ASP | 48 | 54.522 | 34.865 | 30.572 | 1.00 | 59.09 | AP1 |
| ATOM | 3050 | CG | ASP | 48 | 53.486 | 35.890 | 30.153 | 1.00 | 60.41 | AP1 |
| ATOM | 3051 | OD1 | ASP | 48 | 53.856 | 36.825 | 29.408 | 1.00 | 60.98 | AP1 |
| ATOM | 3052 | OD2 | ASP | 48 | 52.308 | 35.775 | 30.581 | 1.00 | 61.28 | AP1 |
| ATOM | 3053 | C | ASP | 48 | 56.959 | 34.278 | 30.523 | 1.00 | 58.58 | AP1 |
| ATOM | 3054 | O | ASP | 48 | 57.880 | 34.911 | 31.005 | 1.00 | 58.57 | AP1 |
| ATOM | 3055 | N | GLU | 49 | 56.888 | 32.952 | 30.565 | 1.00 | 59.20 | AP1 |
| ATOM | 3056 | CA | GLU | 49 | 57.884 | 32.133 | 31.251 | 1.00 | 60.01 | AP1 |
| ATOM | 3057 | CB | GLU | 49 | 57.414 | 30.677 | 31.237 | 1.00 | 60.67 | AP1 |
| ATOM | 3058 | CG | GLU | 49 | 58.437 | 29.655 | 31.732 | 1.00 | 61.95 | AP1 |
| ATOM | 3059 | CD | GLU | 49 | 58.960 | 30.013 | 33.107 | 1.00 | 62.06 | AP1 |
| ATOM | 3060 | OE1 | GLU | 49 | 58.130 | 30.354 | 33.981 | 1.00 | 62.53 | AP1 |
| ATOM | 3061 | OE2 | GLU | 49 | 60.188 | 29.960 | 33.313 | 1.00 | 61.75 | AP1 |
| ATOM | 3062 | C | GLU | 49 | 59.333 | 32.194 | 30.737 | 1.00 | 60.39 | AP1 |
| ATOM | 3063 | O | GLU | 49 | 60.240 | 31.675 | 31.382 | 1.00 | 60.33 | AP1 |
| ATOM | 3064 | N | PHE | 50 | 59.566 | 32.832 | 29.597 | 1.00 | 60.48 | AP1 |
| ATOM | 3065 | CA | PHE | 50 | 60.908 | 32.856 | 29.019 | 1.00 | 61.05 | AP1 |
| ATOM | 3066 | CB | PHE | 50 | 61.071 | 31.784 | 27.935 | 1.00 | 59.10 | AP1 |
| ATOM | 3067 | CG | PHE | 50 | 61.038 | 30.362 | 28.437 | 1.00 | 57.27 | AP1 |
| ATOM | 3068 | CD1 | PHE | 50 | 62.133 | 29.808 | 29.079 | 1.00 | 56.58 | AP1 |
| ATOM | 3069 | CD2 | PHE | 50 | 59.922 | 29.563 | 28.224 | 1.00 | 56.22 | AP1 |
| ATOM | 3070 | CE1 | PHE | 50 | 62.110 | 28.478 | 29.496 | 1.00 | 56.30 | AP1 |

FIG. 3A-54

| ATOM | 3071 | CE2 | PHE | 50 | 59.897 | 28.235 | 28.642 | 1.00 | 55.50 | AP1 |
| --- | --- | --- | --- | --- | --- | --- | --- | --- | --- | --- |
| ATOM | 3072 | CZ | PHE | 50 | 60.992 | 27.693 | 29.276 | 1.00 | 55.77 | AP1 |
| ATOM | 3073 | C | PHE | 50 | 61.159 | 34.167 | 28.353 | 1.00 | 62.82 | AP1 |
| ATOM | 3074 | O | PHE | 50 | 62.021 | 34.265 | 27.484 | 1.00 | 63.54 | AP1 |
| ATOM | 3075 | N | ASP | 51 | 60.379 | 35.173 | 28.711 | 1.00 | 64.37 | AP1 |
| ATOM | 3076 | CA | ASP | 51 | 60.579 | 36.477 | 28.118 | 1.00 | 66.05 | AP1 |
| ATOM | 3077 | CB | ASP | 51 | 61.683 | 37.213 | 28.893 | 1.00 | 66.72 | AP1 |
| ATOM | 3078 | CG | ASP | 51 | 62.056 | 38.540 | 28.265 | 1.00 | 67.40 | AP1 |
| ATOM | 3079 | OD1 | ASP | 51 | 61.179 | 39.425 | 28.226 | 1.00 | 68.03 | AP1 |
| ATOM | 3080 | OD2 | ASP | 51 | 63.215 | 38.699 | 27.808 | 1.00 | 67.55 | AP1 |
| ATOM | 3081 | C | ASP | 51 | 60.932 | 36.430 | 26.618 | 1.00 | 66.81 | AP1 |
| ATOM | 3082 | O | ASP | 51 | 62.073 | 36.731 | 26.236 | 1.00 | 67.47 | AP1 |
| ATOM | 3083 | N | MET | 52 | 59.968 | 36.028 | 25.780 | 1.00 | 67.15 | AP1 |
| ATOM | 3084 | CA | MET | 52 | 60.145 | 36.013 | 24.317 | 1.00 | 66.82 | AP1 |
| ATOM | 3085 | CB | MET | 52 | 60.497 | 34.615 | 23.776 | 1.00 | 68.05 | AP1 |
| ATOM | 3086 | CG | MET | 52 | 60.181 | 33.433 | 24.675 | 1.00 | 69.70 | AP1 |
| ATOM | 3087 | SD | MET | 52 | 60.796 | 31.866 | 23.923 | 1.00 | 72.25 | AP1 |
| ATOM | 3088 | CE | MET | 52 | 62.181 | 31.386 | 25.057 | 1.00 | 71.72 | AP1 |
| ATOM | 3089 | C | MET | 52 | 58.877 | 36.557 | 23.637 | 1.00 | 65.95 | AP1 |
| ATOM | 3090 | O | MET | 52 | 57.921 | 36.956 | 24.315 | 1.00 | 65.80 | AP1 |
| ATOM | 3091 | N | GLU | 53 | 58.861 | 36.580 | 22.310 | 1.00 | 64.45 | AP1 |
| ATOM | 3092 | CA | GLU | 53 | 57.714 | 37.128 | 21.607 | 1.00 | 63.42 | AP1 |
| ATOM | 3093 | CB | GLU | 53 | 58.201 | 38.195 | 20.621 | 1.00 | 64.63 | AP1 |
| ATOM | 3094 | CG | GLU | 53 | 57.177 | 39.291 | 20.326 | 1.00 | 66.71 | AP1 |
| ATOM | 3095 | CD | GLU | 53 | 57.823 | 40.623 | 19.911 | 1.00 | 67.92 | AP1 |
| ATOM | 3096 | OE1 | GLU | 53 | 58.632 | 40.625 | 18.944 | 1.00 | 68.49 | AP1 |
| ATOM | 3097 | OE2 | GLU | 53 | 57.517 | 41.663 | 20.559 | 1.00 | 68.15 | AP1 |
| ATOM | 3098 | C | GLU | 53 | 57.754 | 35.920 | 20.646 | 1.00 | 61.78 | AP1 |
| ATOM | 3099 | O | GLU | 53 | 58.839 | 35.510 | 20.228 | 1.00 | 62.18 | AP1 |
| ATOM | 3100 | N | ILE | 54 | 56.598 | 35.363 | 20.297 | 1.00 | 59.09 | AP1 |
| ATOM | 3101 | CA | ILE | 54 | 56.484 | 34.192 | 19.385 | 1.00 | 56.93 | AP1 |
| ATOM | 3102 | CB | ILE | 54 | 56.061 | 32.975 | 20.277 | 1.00 | 55.84 | AP1 |
| ATOM | 3103 | CG2 | ILE | 54 | 55.752 | 31.773 | 19.377 | 1.00 | 55.47 | AP1 |
| ATOM | 3104 | CG1 | ILE | 54 | 57.196 | 32.570 | 21.220 | 1.00 | 56.28 | AP1 |
| ATOM | 3105 | CD1 | ILE | 54 | 56.839 | 31.459 | 22.208 | 1.00 | 56.74 | AP1 |
| ATOM | 3106 | C | ILE | 54 | 55.225 | 34.629 | 18.600 | 1.00 | 55.56 | AP1 |
| ATOM | 3107 | O | ILE | 54 | 54.095 | 34.632 | 19.122 | 1.00 | 55.94 | AP1 |
| ATOM | 3108 | N | SER | 55 | 55.424 | 34.947 | 17.328 | 1.00 | 53.24 | AP1 |
| ATOM | 3109 | CA | SER | 55 | 54.345 | 35.363 | 16.445 | 1.00 | 51.67 | AP1 |
| ATOM | 3110 | CB | SER | 55 | 54.957 | 35.881 | 15.149 | 1.00 | 51.59 | AP1 |
| ATOM | 3111 | OG | SER | 55 | 55.754 | 34.843 | 14.601 | 1.00 | 50.98 | AP1 |
| ATOM | 3112 | C | SER | 55 | 53.396 | 34.188 | 16.111 | 1.00 | 50.89 | AP1 |
| ATOM | 3113 | O | SER | 55 | 53.686 | 33.025 | 16.427 | 1.00 | 50.20 | AP1 |
| ATOM | 3114 | N | ASP | 56 | 52.263 | 34.505 | 15.477 | 1.00 | 50.52 | AP1 |
| ATOM | 3115 | CA | ASP | 56 | 51.301 | 33.486 | 15.055 | 1.00 | 50.73 | AP1 |
| ATOM | 3116 | CB | ASP | 56 | 50.115 | 34.112 | 14.282 | 1.00 | 51.39 | AP1 |
| ATOM | 3117 | CG | ASP | 56 | 49.076 | 34.796 | 15.193 | 1.00 | 52.27 | AP1 |
| ATOM | 3118 | OD1 | ASP | 56 | 48.939 | 34.396 | 16.388 | 1.00 | 53.22 | AP1 |
| ATOM | 3119 | OD2 | ASP | 56 | 48.379 | 35.718 | 14.699 | 1.00 | 50.84 | AP1 |
| ATOM | 3120 | C | ASP | 56 | 52.062 | 32.536 | 14.109 | 1.00 | 50.93 | AP1 |
| ATOM | 3121 | O | ASP | 56 | 51.741 | 31.347 | 13.989 | 1.00 | 49.65 | AP1 |
| ATOM | 3122 | N | GLU | 57 | 53.073 | 33.080 | 13.430 | 1.00 | 51.57 | AP1 |
| ATOM | 3123 | CA | GLU | 57 | 53.881 | 32.285 | 12.510 | 1.00 | 52.66 | AP1 |
| ATOM | 3124 | CB | GLU | 57 | 54.800 | 33.183 | 11.681 | 1.00 | 53.96 | AP1 |
| ATOM | 3125 | CG | GLU | 57 | 55.384 | 32.498 | 10.470 | 1.00 | 56.75 | AP1 |
| ATOM | 3126 | CD | GLU | 57 | 56.048 | 33.482 | 9.499 | 1.00 | 58.76 | AP1 |
| ATOM | 3127 | OE1 | GLU | 57 | 57.233 | 33.860 | 9.730 | 1.00 | 59.00 | AP1 |

FIG. 3A-55

```
ATOM   3128  OE2  GLU  57    55.365   33.881    8.511  1.00 59.50      AP1
ATOM   3129  C    GLU  57    54.702   31.276   13.309  1.00 52.17      AP1
ATOM   3130  O    GLU  57    54.669   30.082   13.030  1.00 50.84      AP1
ATOM   3131  N    ASP  58    55.404   31.757   14.325  1.00 52.81      AP1
ATOM   3132  CA   ASP  58    56.208   30.863   15.154  1.00 54.03      AP1
ATOM   3133  CB   ASP  58    57.101   31.661   16.094  1.00 53.98      AP1
ATOM   3134  CG   ASP  58    58.039   32.606   15.349  1.00 55.50      AP1
ATOM   3135  OD1  ASP  58    58.353   32.363   14.146  1.00 54.46      AP1
ATOM   3136  OD2  ASP  58    58.468   33.599   15.993  1.00 57.16      AP1
ATOM   3137  C    ASP  58    55.328   29.901   15.960  1.00 54.50      AP1
ATOM   3138  O    ASP  58    55.769   28.803   16.345  1.00 54.65      AP1
ATOM   3139  N    ALA  59    54.083   30.294   16.215  1.00 54.12      AP1
ATOM   3140  CA   ALA  59    53.206   29.405   16.957  1.00 54.32      AP1
ATOM   3141  CB   ALA  59    51.865   30.091   17.249  1.00 54.13      AP1
ATOM   3142  C    ALA  59    52.997   28.171   16.096  1.00 54.49      AP1
ATOM   3143  O    ALA  59    53.039   27.045   16.571  1.00 53.95      AP1
ATOM   3144  N    GLU  60    52.803   28.376   14.805  1.00 55.25      AP1
ATOM   3145  CA   GLU  60    52.573   27.223   13.962  1.00 56.49      AP1
ATOM   3146  CB   GLU  60    52.040   27.639   12.596  1.00 56.75      AP1
ATOM   3147  CG   GLU  60    51.899   26.484   11.628  1.00 58.07      AP1
ATOM   3148  CD   GLU  60    51.013   26.849   10.463  1.00 59.05      AP1
ATOM   3149  OE1  GLU  60    49.784   26.570   10.543  1.00 60.39      AP1
ATOM   3150  OE2  GLU  60    51.540   27.436    9.490  1.00 58.55      AP1
ATOM   3151  C    GLU  60    53.820   26.367   13.820  1.00 56.93      AP1
ATOM   3152  O    GLU  60    53.703   25.155   13.593  1.00 57.48      AP1
ATOM   3153  N    LYS  61    55.014   26.947   13.965  1.00 56.79      AP1
ATOM   3154  CA   LYS  61    56.174   26.073   13.861  1.00 57.27      AP1
ATOM   3155  CB   LYS  61    57.519   26.797   13.840  1.00 57.94      AP1
ATOM   3156  CG   LYS  61    58.612   25.719   13.702  1.00 59.35      AP1
ATOM   3157  CD   LYS  61    60.038   26.222   13.793  1.00 61.65      AP1
ATOM   3158  CE   LYS  61    61.023   25.049   13.679  1.00 61.95      AP1
ATOM   3159  NZ   LYS  61    62.451   25.504   13.695  1.00 62.10      AP1
ATOM   3160  C    LYS  61    56.246   25.084   15.005  1.00 56.70      AP1
ATOM   3161  O    LYS  61    56.534   23.906   14.792  1.00 56.75      AP1
ATOM   3162  N    ILE  62    55.985   25.552   16.224  1.00 56.23      AP1
ATOM   3163  CA   ILE  62    56.084   24.651   17.355  1.00 55.58      AP1
ATOM   3164  CB   ILE  62    56.520   25.434   18.608  1.00 55.21      AP1
ATOM   3165  CG2  ILE  62    57.819   26.184   18.284  1.00 54.70      AP1
ATOM   3166  CG1  ILE  62    55.491   26.474   19.002  1.00 54.99      AP1
ATOM   3167  CD1  ILE  62    55.913   27.242   20.214  1.00 54.20      AP1
ATOM   3168  C    ILE  62    54.887   23.723   17.593  1.00 55.31      AP1
ATOM   3169  O    ILE  62    54.109   23.854   18.542  1.00 55.02      AP1
ATOM   3170  N    ALA  63    54.799   22.741   16.704  1.00 55.03      AP1
ATOM   3171  CA   ALA  63    53.758   21.722   16.726  1.00 54.72      AP1
ATOM   3172  CB   ALA  63    53.658   21.063   15.349  1.00 54.68      AP1
ATOM   3173  C    ALA  63    53.950   20.640   17.790  1.00 54.19      AP1
ATOM   3174  O    ALA  63    52.979   20.028   18.223  1.00 54.15      AP1
ATOM   3175  N    THR  64    55.192   20.381   18.195  1.00 53.96      AP1
ATOM   3176  CA   THR  64    55.457   19.358   19.222  1.00 53.49      AP1
ATOM   3177  CB   THR  64    56.341   18.195   18.695  1.00 52.92      AP1
ATOM   3178  OG1  THR  64    57.656   18.696   18.412  1.00 51.65      AP1
ATOM   3179  CG2  THR  64    55.731   17.563   17.439  1.00 53.03      AP1
ATOM   3180  C    THR  64    56.194   19.899   20.439  1.00 53.33      AP1
ATOM   3181  O    THR  64    56.707   21.012   20.438  1.00 52.73      AP1
ATOM   3182  N    VAL  65    56.262   19.067   21.472  1.00 53.66      AP1
ATOM   3183  CA   VAL  65    56.961   19.426   22.696  1.00 54.06      AP1
ATOM   3184  CB   VAL  65    56.907   18.244   23.702  1.00 54.27      AP1
```

FIG. 3A-56

| ATOM | 3185 | CG1 | VAL | 65 | 57.520 | 18.646 | 25.030 | 1.00 | 54.06 | AP1 |
|---|---|---|---|---|---|---|---|---|---|---|
| ATOM | 3186 | CG2 | VAL | 65 | 55.465 | 17.803 | 23.892 | 1.00 | 54.41 | AP1 |
| ATOM | 3187 | C | VAL | 65 | 58.439 | 19.770 | 22.380 | 1.00 | 53.79 | AP1 |
| ATOM | 3188 | O | VAL | 65 | 58.992 | 20.727 | 22.922 | 1.00 | 53.70 | AP1 |
| ATOM | 3189 | N | GLY | 66 | 59.058 | 18.982 | 21.497 | 1.00 | 53.49 | AP1 |
| ATOM | 3190 | CA | GLY | 66 | 60.448 | 19.199 | 21.126 | 1.00 | 52.65 | AP1 |
| ATOM | 3191 | C | GLY | 66 | 60.633 | 20.472 | 20.339 | 1.00 | 52.63 | AP1 |
| ATOM | 3192 | O | GLY | 66 | 61.672 | 21.145 | 20.420 | 1.00 | 51.80 | AP1 |
| ATOM | 3193 | N | ASP | 67 | 59.607 | 20.815 | 19.575 | 1.00 | 53.18 | AP1 |
| ATOM | 3194 | CA | ASP | 67 | 59.631 | 22.031 | 18.778 | 1.00 | 53.33 | AP1 |
| ATOM | 3195 | CB | ASP | 67 | 58.347 | 22.085 | 17.939 | 1.00 | 54.43 | AP1 |
| ATOM | 3196 | CG | ASP | 67 | 58.291 | 20.970 | 16.900 | 1.00 | 55.53 | AP1 |
| ATOM | 3197 | OD1 | ASP | 67 | 57.211 | 20.358 | 16.671 | 1.00 | 55.75 | AP1 |
| ATOM | 3198 | OD2 | ASP | 67 | 59.353 | 20.719 | 16.294 | 1.00 | 56.16 | AP1 |
| ATOM | 3199 | C | ASP | 67 | 59.745 | 23.248 | 19.715 | 1.00 | 53.22 | AP1 |
| ATOM | 3200 | O | ASP | 67 | 60.588 | 24.156 | 19.528 | 1.00 | 52.14 | AP1 |
| ATOM | 3201 | N | ALA | 68 | 58.905 | 23.270 | 20.741 | 1.00 | 53.13 | AP1 |
| ATOM | 3202 | CA | ALA | 68 | 58.971 | 24.384 | 21.666 | 1.00 | 53.88 | AP1 |
| ATOM | 3203 | CB | ALA | 68 | 57.936 | 24.246 | 22.742 | 1.00 | 52.72 | AP1 |
| ATOM | 3204 | C | ALA | 68 | 60.367 | 24.425 | 22.280 | 1.00 | 53.95 | AP1 |
| ATOM | 3205 | O | ALA | 68 | 61.017 | 25.454 | 22.264 | 1.00 | 54.56 | AP1 |
| ATOM | 3206 | N | VAL | 69 | 60.833 | 23.309 | 22.807 | 1.00 | 54.46 | AP1 |
| ATOM | 3207 | CA | VAL | 69 | 62.161 | 23.283 | 23.417 | 1.00 | 55.62 | AP1 |
| ATOM | 3208 | CB | VAL | 69 | 62.548 | 21.836 | 23.806 | 1.00 | 55.19 | AP1 |
| ATOM | 3209 | CG1 | VAL | 69 | 63.998 | 21.787 | 24.255 | 1.00 | 56.16 | AP1 |
| ATOM | 3210 | CG2 | VAL | 69 | 61.638 | 21.338 | 24.923 | 1.00 | 54.08 | AP1 |
| ATOM | 3211 | C | VAL | 69 | 63.223 | 23.905 | 22.491 | 1.00 | 56.45 | AP1 |
| ATOM | 3212 | O | VAL | 69 | 63.865 | 24.895 | 22.849 | 1.00 | 55.15 | AP1 |
| ATOM | 3213 | N | ASN | 70 | 63.387 | 23.335 | 21.298 | 1.00 | 58.25 | AP1 |
| ATOM | 3214 | CA | ASN | 70 | 64.356 | 23.856 | 20.326 | 1.00 | 60.36 | AP1 |
| ATOM | 3215 | CB | ASN | 70 | 64.185 | 23.230 | 18.930 | 1.00 | 60.51 | AP1 |
| ATOM | 3216 | CG | ASN | 70 | 64.407 | 21.739 | 18.914 | 1.00 | 60.64 | AP1 |
| ATOM | 3217 | OD1 | ASN | 70 | 65.442 | 21.254 | 19.343 | 1.00 | 61.77 | AP1 |
| ATOM | 3218 | ND2 | ASN | 70 | 63.432 | 21.003 | 18.404 | 1.00 | 60.71 | AP1 |
| ATOM | 3219 | C | ASN | 70 | 64.174 | 25.345 | 20.137 | 1.00 | 61.62 | AP1 |
| ATOM | 3220 | O | ASN | 70 | 65.157 | 26.080 | 20.052 | 1.00 | 61.81 | AP1 |
| ATOM | 3221 | N | TYR | 71 | 62.915 | 25.776 | 20.037 | 1.00 | 63.25 | AP1 |
| ATOM | 3222 | CA | TYR | 71 | 62.599 | 27.181 | 19.821 | 1.00 | 65.19 | AP1 |
| ATOM | 3223 | CB | TYR | 71 | 61.097 | 27.371 | 19.585 | 1.00 | 65.08 | AP1 |
| ATOM | 3224 | CG | TYR | 71 | 60.728 | 28.814 | 19.325 | 1.00 | 64.90 | AP1 |
| ATOM | 3225 | CD1 | TYR | 71 | 60.413 | 29.668 | 20.377 | 1.00 | 64.71 | AP1 |
| ATOM | 3226 | CE1 | TYR | 71 | 60.151 | 31.008 | 20.160 | 1.00 | 65.27 | AP1 |
| ATOM | 3227 | CD2 | TYR | 71 | 60.769 | 29.342 | 18.034 | 1.00 | 64.62 | AP1 |
| ATOM | 3228 | CE2 | TYR | 71 | 60.508 | 30.683 | 17.800 | 1.00 | 64.75 | AP1 |
| ATOM | 3229 | CZ | TYR | 71 | 60.197 | 31.517 | 18.866 | 1.00 | 65.04 | AP1 |
| ATOM | 3230 | OH | TYR | 71 | 59.928 | 32.854 | 18.650 | 1.00 | 64.43 | AP1 |
| ATOM | 3231 | C | TYR | 71 | 63.069 | 28.048 | 20.980 | 1.00 | 66.81 | AP1 |
| ATOM | 3232 | O | TYR | 71 | 63.375 | 29.238 | 20.803 | 1.00 | 66.70 | AP1 |
| ATOM | 3233 | N | ILE | 72 | 63.138 | 27.440 | 22.161 | 1.00 | 68.59 | AP1 |
| ATOM | 3234 | CA | ILE | 72 | 63.609 | 28.126 | 23.354 | 1.00 | 70.76 | AP1 |
| ATOM | 3235 | CB | ILE | 72 | 62.898 | 27.583 | 24.594 | 1.00 | 70.58 | AP1 |
| ATOM | 3236 | CG2 | ILE | 72 | 63.445 | 28.260 | 25.878 | 1.00 | 70.73 | AP1 |
| ATOM | 3237 | CG1 | ILE | 72 | 61.394 | 27.804 | 24.416 | 1.00 | 70.49 | AP1 |
| ATOM | 3238 | CD1 | ILE | 72 | 60.562 | 27.205 | 25.496 | 1.00 | 69.78 | AP1 |
| ATOM | 3239 | C | ILE | 72 | 65.130 | 27.925 | 23.466 | 1.00 | 72.57 | AP1 |
| ATOM | 3240 | O | ILE | 72 | 65.684 | 27.630 | 24.533 | 1.00 | 73.27 | AP1 |
| ATOM | 3241 | N | GLN | 73 | 65.791 | 28.072 | 22.325 | 1.00 | 74.34 | AP1 |

FIG. 3A-57

| ATOM | 3242 | CA | GLN | 73 | 67.235 | 27.953 | 22.214 | 1.00 | 75.70 | AP1 |
|---|---|---|---|---|---|---|---|---|---|---|
| ATOM | 3243 | CB | GLN | 73 | 67.636 | 26.483 | 22.085 | 1.00 | 76.75 | AP1 |
| ATOM | 3244 | CG | GLN | 73 | 67.369 | 25.611 | 23.306 | 1.00 | 79.08 | AP1 |
| ATOM | 3245 | CD | GLN | 73 | 67.842 | 24.174 | 23.089 | 1.00 | 80.59 | AP1 |
| ATOM | 3246 | OE1 | GLN | 73 | 68.958 | 23.944 | 22.606 | 1.00 | 81.29 | AP1 |
| ATOM | 3247 | NE2 | GLN | 73 | 67.006 | 23.201 | 23.449 | 1.00 | 80.77 | AP1 |
| ATOM | 3248 | C | GLN | 73 | 67.593 | 28.719 | 20.931 | 1.00 | 76.07 | AP1 |
| ATOM | 3249 | OT1 | GLN | 73 | 67.901 | 29.933 | 21.027 | 1.00 | 76.06 | AP1 |
| ATOM | 3250 | OT2 | GLN | 73 | 67.520 | 28.109 | 19.835 | 1.00 | 76.30 | AP1 |
| ATOM | 3251 | CB | ALA | 1 | 6.645 | 63.605 | 34.695 | 1.00 | 86.31 | AP2 |
| ATOM | 3252 | C | ALA | 1 | 6.820 | 61.130 | 34.410 | 1.00 | 86.49 | AP2 |
| ATOM | 3253 | O | ALA | 1 | 7.722 | 60.410 | 34.845 | 1.00 | 86.43 | AP2 |
| ATOM | 3254 | N | ALA | 1 | 6.500 | 62.631 | 32.424 | 1.00 | 86.34 | AP2 |
| ATOM | 3255 | CA | ALA | 1 | 7.130 | 62.486 | 33.774 | 1.00 | 86.44 | AP2 |
| ATOM | 3256 | N | ASP | 2 | 5.531 | 60.806 | 34.476 | 1.00 | 86.48 | AP2 |
| ATOM | 3257 | CA | ASP | 2 | 5.054 | 59.549 | 35.054 | 1.00 | 86.12 | AP2 |
| ATOM | 3258 | CB | ASP | 2 | 3.540 | 59.631 | 35.306 | 1.00 | 86.68 | AP2 |
| ATOM | 3259 | CG | ASP | 2 | 2.875 | 58.258 | 35.366 | 1.00 | 87.31 | AP2 |
| ATOM | 3260 | OD1 | ASP | 2 | 3.170 | 57.480 | 36.303 | 1.00 | 87.86 | AP2 |
| ATOM | 3261 | OD2 | ASP | 2 | 2.057 | 57.953 | 34.466 | 1.00 | 87.63 | AP2 |
| ATOM | 3262 | C | ASP | 2 | 5.355 | 58.396 | 34.108 | 1.00 | 85.41 | AP2 |
| ATOM | 3263 | O | ASP | 2 | 5.719 | 57.291 | 34.538 | 1.00 | 85.00 | AP2 |
| ATOM | 3264 | N | THR | 3 | 5.199 | 58.662 | 32.815 | 1.00 | 84.56 | AP2 |
| ATOM | 3265 | CA | THR | 3 | 5.455 | 57.639 | 31.824 | 1.00 | 83.93 | AP2 |
| ATOM | 3266 | CB | THR | 3 | 5.146 | 58.144 | 30.366 | 1.00 | 84.30 | AP2 |
| ATOM | 3267 | OG1 | THR | 3 | 6.165 | 59.047 | 29.927 | 1.00 | 84.66 | AP2 |
| ATOM | 3268 | CG2 | THR | 3 | 3.779 | 58.857 | 30.315 | 1.00 | 83.94 | AP2 |
| ATOM | 3269 | C | THR | 3 | 6.905 | 57.162 | 31.967 | 1.00 | 83.08 | AP2 |
| ATOM | 3270 | O | THR | 3 | 7.174 | 55.971 | 31.831 | 1.00 | 83.08 | AP2 |
| ATOM | 3271 | N | LEU | 4 | 7.827 | 58.073 | 32.275 | 1.00 | 82.05 | AP2 |
| ATOM | 3272 | CA | LEU | 4 | 9.230 | 57.688 | 32.450 | 1.00 | 81.45 | AP2 |
| ATOM | 3273 | CB | LEU | 4 | 10.132 | 58.918 | 32.629 | 1.00 | 81.43 | AP2 |
| ATOM | 3274 | CG | LEU | 4 | 11.604 | 58.706 | 33.043 | 1.00 | 81.05 | AP2 |
| ATOM | 3275 | CD1 | LEU | 4 | 12.368 | 57.866 | 32.045 | 1.00 | 80.62 | AP2 |
| ATOM | 3276 | CD2 | LEU | 4 | 12.262 | 60.051 | 33.161 | 1.00 | 80.98 | AP2 |
| ATOM | 3277 | C | LEU | 4 | 9.405 | 56.766 | 33.649 | 1.00 | 80.96 | AP2 |
| ATOM | 3278 | O | LEU | 4 | 10.243 | 55.866 | 33.634 | 1.00 | 80.86 | AP2 |
| ATOM | 3279 | N | GLU | 5 | 8.621 | 56.992 | 34.695 | 1.00 | 80.52 | AP2 |
| ATOM | 3280 | CA | GLU | 5 | 8.711 | 56.149 | 35.875 | 1.00 | 80.14 | AP2 |
| ATOM | 3281 | CB | GLU | 5 | 7.842 | 56.718 | 37.013 | 1.00 | 81.37 | AP2 |
| ATOM | 3282 | CG | GLU | 5 | 8.638 | 57.408 | 38.133 | 1.00 | 83.32 | AP2 |
| ATOM | 3283 | CD | GLU | 5 | 9.550 | 58.535 | 37.610 | 1.00 | 84.89 | AP2 |
| ATOM | 3284 | OE1 | GLU | 5 | 9.007 | 59.558 | 37.117 | 1.00 | 85.35 | AP2 |
| ATOM | 3285 | OE2 | GLU | 5 | 10.805 | 58.395 | 37.682 | 1.00 | 85.07 | AP2 |
| ATOM | 3286 | C | GLU | 5 | 8.264 | 54.733 | 35.502 | 1.00 | 79.23 | AP2 |
| ATOM | 3287 | O | GLU | 5 | 8.918 | 53.746 | 35.863 | 1.00 | 78.62 | AP2 |
| ATOM | 3288 | N | ARG | 6 | 7.155 | 54.635 | 34.769 | 1.00 | 78.13 | AP2 |
| ATOM | 3289 | CA | ARG | 6 | 6.658 | 53.331 | 34.355 | 1.00 | 77.16 | AP2 |
| ATOM | 3290 | CB | ARG | 6 | 5.225 | 53.430 | 33.827 | 1.00 | 77.18 | AP2 |
| ATOM | 3291 | CG | ARG | 6 | 4.171 | 53.413 | 34.942 | 1.00 | 77.34 | AP2 |
| ATOM | 3292 | CD | ARG | 6 | 2.764 | 53.134 | 34.408 | 1.00 | 76.80 | AP2 |
| ATOM | 3293 | NE | ARG | 6 | 2.136 | 54.303 | 33.801 | 1.00 | 75.86 | AP2 |
| ATOM | 3294 | CZ | ARG | 6 | 1.053 | 54.245 | 33.030 | 1.00 | 75.80 | AP2 |
| ATOM | 3295 | NH1 | ARG | 6 | 0.482 | 53.071 | 32.771 | 1.00 | 75.17 | AP2 |
| ATOM | 3296 | NH2 | ARG | 6 | 0.532 | 55.361 | 32.523 | 1.00 | 75.41 | AP2 |
| ATOM | 3297 | C | ARG | 6 | 7.571 | 52.706 | 33.310 | 1.00 | 76.44 | AP2 |
| ATOM | 3298 | O | ARG | 6 | 7.896 | 51.521 | 33.405 | 1.00 | 76.54 | AP2 |

FIG. 3A-58

| ATOM | 3299 | N | VAL | 7 | 7.995 | 53.493 | 32.324 | 1.00 | 75.18 | AP2 |
|---|---|---|---|---|---|---|---|---|---|---|
| ATOM | 3300 | CA | VAL | 7 | 8.894 | 52.981 | 31.306 | 1.00 | 74.11 | AP2 |
| ATOM | 3301 | CB | VAL | 7 | 9.345 | 54.067 | 30.323 | 1.00 | 73.72 | AP2 |
| ATOM | 3302 | CG1 | VAL | 7 | 10.514 | 53.549 | 29.513 | 1.00 | 73.33 | AP2 |
| ATOM | 3303 | CG2 | VAL | 7 | 8.216 | 54.462 | 29.404 | 1.00 | 72.85 | AP2 |
| ATOM | 3304 | C | VAL | 7 | 10.149 | 52.453 | 31.966 | 1.00 | 74.07 | AP2 |
| ATOM | 3305 | O | VAL | 7 | 10.634 | 51.386 | 31.626 | 1.00 | 74.04 | AP2 |
| ATOM | 3306 | N | THR | 8 | 10.680 | 53.209 | 32.916 | 1.00 | 74.19 | AP2 |
| ATOM | 3307 | CA | THR | 8 | 11.906 | 52.802 | 33.583 | 1.00 | 74.59 | AP2 |
| ATOM | 3308 | CB | THR | 8 | 12.395 | 53.893 | 34.580 | 1.00 | 74.78 | AP2 |
| ATOM | 3309 | OG1 | THR | 8 | 12.916 | 55.016 | 33.852 | 1.00 | 74.74 | AP2 |
| ATOM | 3310 | CG2 | THR | 8 | 13.493 | 53.348 | 35.489 | 1.00 | 74.82 | AP2 |
| ATOM | 3311 | C | THR | 8 | 11.721 | 51.488 | 34.315 | 1.00 | 74.86 | AP2 |
| ATOM | 3312 | O | THR | 8 | 12.585 | 50.603 | 34.259 | 1.00 | 74.74 | AP2 |
| ATOM | 3313 | N | LYS | 9 | 10.590 | 51.368 | 35.001 | 1.00 | 75.13 | AP2 |
| ATOM | 3314 | CA | LYS | 9 | 10.279 | 50.166 | 35.758 | 1.00 | 75.62 | AP2 |
| ATOM | 3315 | CB | LYS | 9 | 8.920 | 50.345 | 36.462 | 1.00 | 76.59 | AP2 |
| ATOM | 3316 | CG | LYS | 9 | 8.406 | 49.178 | 37.316 | 1.00 | 77.37 | AP2 |
| ATOM | 3317 | CD | LYS | 9 | 6.994 | 49.508 | 37.828 | 1.00 | 78.26 | AP2 |
| ATOM | 3318 | CE | LYS | 9 | 6.274 | 48.308 | 38.446 | 1.00 | 78.59 | AP2 |
| ATOM | 3319 | NZ | LYS | 9 | 6.887 | 47.838 | 39.724 | 1.00 | 79.09 | AP2 |
| ATOM | 3320 | C | LYS | 9 | 10.263 | 48.983 | 34.790 | 1.00 | 75.49 | AP2 |
| ATOM | 3321 | O | LYS | 9 | 10.794 | 47.921 | 35.094 | 1.00 | 75.37 | AP2 |
| ATOM | 3322 | N | ILE | 10 | 9.673 | 49.176 | 33.613 | 1.00 | 75.59 | AP2 |
| ATOM | 3323 | CA | ILE | 10 | 9.609 | 48.111 | 32.607 | 1.00 | 75.37 | AP2 |
| ATOM | 3324 | CB | ILE | 10 | 8.897 | 48.569 | 31.322 | 1.00 | 74.85 | AP2 |
| ATOM | 3325 | CG2 | ILE | 10 | 8.826 | 47.408 | 30.363 | 1.00 | 75.13 | AP2 |
| ATOM | 3326 | CG1 | ILE | 10 | 7.499 | 49.103 | 31.621 | 1.00 | 74.65 | AP2 |
| ATOM | 3327 | CD1 | ILE | 10 | 6.486 | 48.042 | 31.950 | 1.00 | 74.86 | AP2 |
| ATOM | 3328 | C | ILE | 10 | 11.024 | 47.697 | 32.203 | 1.00 | 75.44 | AP2 |
| ATOM | 3329 | O | ILE | 10 | 11.367 | 46.515 | 32.216 | 1.00 | 74.81 | AP2 |
| ATOM | 3330 | N | ILE | 11 | 11.831 | 48.689 | 31.836 | 1.00 | 76.08 | AP2 |
| ATOM | 3331 | CA | ILE | 11 | 13.208 | 48.459 | 31.408 | 1.00 | 77.08 | AP2 |
| ATOM | 3332 | CB | ILE | 11 | 13.918 | 49.787 | 31.105 | 1.00 | 76.69 | AP2 |
| ATOM | 3333 | CG2 | ILE | 11 | 15.360 | 49.522 | 30.722 | 1.00 | 76.30 | AP2 |
| ATOM | 3334 | CG1 | ILE | 11 | 13.187 | 50.514 | 29.974 | 1.00 | 76.78 | AP2 |
| ATOM | 3335 | CD1 | ILE | 11 | 13.840 | 51.819 | 29.527 | 1.00 | 76.66 | AP2 |
| ATOM | 3336 | C | ILE | 11 | 14.039 | 47.696 | 32.431 | 1.00 | 78.04 | AP2 |
| ATOM | 3337 | O | ILE | 11 | 14.696 | 46.706 | 32.102 | 1.00 | 77.63 | AP2 |
| ATOM | 3338 | N | VAL | 12 | 14.009 | 48.172 | 33.672 | 1.00 | 79.25 | AP2 |
| ATOM | 3339 | CA | VAL | 12 | 14.761 | 47.547 | 34.755 | 1.00 | 80.48 | AP2 |
| ATOM | 3340 | CB | VAL | 12 | 14.604 | 48.343 | 36.088 | 1.00 | 80.56 | AP2 |
| ATOM | 3341 | CG1 | VAL | 12 | 15.410 | 47.676 | 37.191 | 1.00 | 80.75 | AP2 |
| ATOM | 3342 | CG2 | VAL | 12 | 15.063 | 49.779 | 35.899 | 1.00 | 80.30 | AP2 |
| ATOM | 3343 | C | VAL | 12 | 14.298 | 46.116 | 34.989 | 1.00 | 81.20 | AP2 |
| ATOM | 3344 | O | VAL | 12 | 15.101 | 45.194 | 35.041 | 1.00 | 81.20 | AP2 |
| ATOM | 3345 | N | ASP | 13 | 12.992 | 45.942 | 35.121 | 1.00 | 82.40 | AP2 |
| ATOM | 3346 | CA | ASP | 13 | 12.402 | 44.634 | 35.375 | 1.00 | 83.84 | AP2 |
| ATOM | 3347 | CB | ASP | 13 | 10.901 | 44.804 | 35.657 | 1.00 | 84.55 | AP2 |
| ATOM | 3348 | CG | ASP | 13 | 10.618 | 45.767 | 36.829 | 1.00 | 85.50 | AP2 |
| ATOM | 3349 | OD1 | ASP | 13 | 11.513 | 46.577 | 37.182 | 1.00 | 85.54 | AP2 |
| ATOM | 3350 | OD2 | ASP | 13 | 9.491 | 45.726 | 37.386 | 1.00 | 85.79 | AP2 |
| ATOM | 3351 | C | ASP | 13 | 12.627 | 43.600 | 34.256 | 1.00 | 84.60 | AP2 |
| ATOM | 3352 | O | ASP | 13 | 12.466 | 42.395 | 34.485 | 1.00 | 84.91 | AP2 |
| ATOM | 3353 | N | ARG | 14 | 12.993 | 44.060 | 33.056 | 1.00 | 85.13 | AP2 |
| ATOM | 3354 | CA | ARG | 14 | 13.252 | 43.158 | 31.915 | 1.00 | 85.53 | AP2 |
| ATOM | 3355 | CB | ARG | 14 | 12.667 | 43.725 | 30.602 | 1.00 | 85.39 | AP2 |

FIG. 3A-59

| ATOM | 3356 | CG | ARG | 14 | 11.133 | 43.788 | 30.506 | 1.00 | 85.43 | AP2 |
|---|---|---|---|---|---|---|---|---|---|---|
| ATOM | 3357 | CD | ARG | 14 | 10.493 | 42.407 | 30.616 | 1.00 | 85.43 | AP2 |
| ATOM | 3358 | NE | ARG | 14 | 11.253 | 41.397 | 29.883 | 1.00 | 85.32 | AP2 |
| ATOM | 3359 | CZ | ARG | 14 | 10.950 | 40.102 | 29.862 | 1.00 | 85.25 | AP2 |
| ATOM | 3360 | NH1 | ARG | 14 | 9.894 | 39.663 | 30.536 | 1.00 | 85.24 | AP2 |
| ATOM | 3361 | NH2 | ARG | 14 | 11.707 | 39.246 | 29.182 | 1.00 | 84.65 | AP2 |
| ATOM | 3362 | C | ARG | 14 | 14.760 | 42.939 | 31.717 | 1.00 | 85.76 | AP2 |
| ATOM | 3363 | O | ARG | 14 | 15.315 | 41.907 | 32.112 | 1.00 | 85.85 | AP2 |
| ATOM | 3364 | N | LEU | 15 | 15.405 | 43.929 | 31.106 | 1.00 | 85.73 | AP2 |
| ATOM | 3365 | CA | LEU | 15 | 16.828 | 43.896 | 30.831 | 1.00 | 86.03 | AP2 |
| ATOM | 3366 | CB | LEU | 15 | 17.192 | 45.082 | 29.947 | 1.00 | 85.82 | AP2 |
| ATOM | 3367 | CG | LEU | 15 | 16.136 | 45.523 | 28.925 | 1.00 | 85.68 | AP2 |
| ATOM | 3368 | CD1 | LEU | 15 | 16.630 | 46.758 | 28.206 | 1.00 | 85.55 | AP2 |
| ATOM | 3369 | CD2 | LEU | 15 | 15.843 | 44.414 | 27.933 | 1.00 | 85.29 | AP2 |
| ATOM | 3370 | C | LEU | 15 | 17.686 | 43.935 | 32.096 | 1.00 | 86.63 | AP2 |
| ATOM | 3371 | O | LEU | 15 | 18.914 | 43.909 | 32.005 | 1.00 | 86.53 | AP2 |
| ATOM | 3372 | N | GLY | 16 | 17.045 | 44.012 | 33.264 | 1.00 | 87.36 | AP2 |
| ATOM | 3373 | CA | GLY | 16 | 17.775 | 44.064 | 34.527 | 1.00 | 88.66 | AP2 |
| ATOM | 3374 | C | GLY | 16 | 19.053 | 44.883 | 34.456 | 1.00 | 89.59 | AP2 |
| ATOM | 3375 | O | GLY | 16 | 20.143 | 44.321 | 34.326 | 1.00 | 89.42 | AP2 |
| ATOM | 3376 | N | VAL | 17 | 18.928 | 46.207 | 34.553 | 1.00 | 90.59 | AP2 |
| ATOM | 3377 | CA | VAL | 17 | 20.092 | 47.092 | 34.452 | 1.00 | 91.73 | AP2 |
| ATOM | 3378 | CB | VAL | 17 | 20.148 | 47.718 | 33.034 | 1.00 | 91.33 | AP2 |
| ATOM | 3379 | CG1 | VAL | 17 | 20.461 | 46.641 | 32.006 | 1.00 | 91.06 | AP2 |
| ATOM | 3380 | CG2 | VAL | 17 | 18.816 | 48.361 | 32.700 | 1.00 | 91.16 | AP2 |
| ATOM | 3381 | C | VAL | 17 | 20.228 | 48.205 | 35.521 | 1.00 | 92.74 | AP2 |
| ATOM | 3382 | O | VAL | 17 | 20.108 | 49.412 | 35.233 | 1.00 | 92.96 | AP2 |
| ATOM | 3383 | N | ASP | 18 | 20.496 | 47.780 | 36.755 | 1.00 | 93.61 | AP2 |
| ATOM | 3384 | CA | ASP | 18 | 20.682 | 48.690 | 37.887 | 1.00 | 94.45 | AP2 |
| ATOM | 3385 | CB | ASP | 18 | 21.912 | 49.587 | 37.648 | 1.00 | 94.58 | AP2 |
| ATOM | 3386 | CG | ASP | 18 | 23.091 | 49.238 | 38.562 | 1.00 | 94.83 | AP2 |
| ATOM | 3387 | OD1 | ASP | 18 | 23.038 | 48.187 | 39.248 | 1.00 | 94.73 | AP2 |
| ATOM | 3388 | OD2 | ASP | 18 | 24.074 | 50.017 | 38.586 | 1.00 | 94.69 | AP2 |
| ATOM | 3389 | C | ASP | 18 | 19.486 | 49.575 | 38.233 | 1.00 | 94.87 | AP2 |
| ATOM | 3390 | O | ASP | 18 | 18.648 | 49.220 | 39.072 | 1.00 | 95.08 | AP2 |
| ATOM | 3391 | N | GLU | 19 | 19.428 | 50.725 | 37.569 | 1.00 | 95.17 | AP2 |
| ATOM | 3392 | CA | GLU | 19 | 18.406 | 51.745 | 37.786 | 1.00 | 95.47 | AP2 |
| ATOM | 3393 | CB | GLU | 19 | 17.856 | 51.675 | 39.219 | 1.00 | 95.60 | AP2 |
| ATOM | 3394 | CG | GLU | 19 | 16.350 | 51.546 | 39.320 | 1.00 | 96.31 | AP2 |
| ATOM | 3395 | CD | GLU | 19 | 15.637 | 52.864 | 39.091 | 1.00 | 96.93 | AP2 |
| ATOM | 3396 | OE1 | GLU | 19 | 16.190 | 53.720 | 38.362 | 1.00 | 97.29 | AP2 |
| ATOM | 3397 | OE2 | GLU | 19 | 14.518 | 53.040 | 39.629 | 1.00 | 97.32 | AP2 |
| ATOM | 3398 | C | GLU | 19 | 19.290 | 52.971 | 37.638 | 1.00 | 95.49 | AP2 |
| ATOM | 3399 | O | GLU | 19 | 20.496 | 52.819 | 37.420 | 1.00 | 95.65 | AP2 |
| ATOM | 3400 | N | ALA | 20 | 18.725 | 54.168 | 37.753 | 1.00 | 95.26 | AP2 |
| ATOM | 3401 | CA | ALA | 20 | 19.529 | 55.383 | 37.627 | 1.00 | 95.13 | AP2 |
| ATOM | 3402 | CB | ALA | 20 | 20.298 | 55.638 | 38.919 | 1.00 | 94.92 | AP2 |
| ATOM | 3403 | C | ALA | 20 | 20.503 | 55.217 | 36.464 | 1.00 | 94.92 | AP2 |
| ATOM | 3404 | O | ALA | 20 | 21.551 | 55.865 | 36.407 | 1.00 | 94.78 | AP2 |
| ATOM | 3405 | N | ASP | 21 | 20.133 | 54.333 | 35.542 | 1.00 | 94.78 | AP2 |
| ATOM | 3406 | CA | ASP | 21 | 20.946 | 54.030 | 34.376 | 1.00 | 94.36 | AP2 |
| ATOM | 3407 | CB | ASP | 21 | 21.514 | 52.619 | 34.503 | 1.00 | 94.73 | AP2 |
| ATOM | 3408 | CG | ASP | 21 | 22.692 | 52.402 | 33.603 | 1.00 | 95.30 | AP2 |
| ATOM | 3409 | OD1 | ASP | 21 | 23.821 | 52.771 | 34.000 | 1.00 | 95.81 | AP2 |
| ATOM | 3410 | OD2 | ASP | 21 | 22.486 | 51.887 | 32.487 | 1.00 | 95.82 | AP2 |
| ATOM | 3411 | C | ASP | 21 | 20.055 | 54.120 | 33.141 | 1.00 | 93.80 | AP2 |
| ATOM | 3412 | O | ASP | 21 | 20.425 | 53.706 | 32.037 | 1.00 | 93.62 | AP2 |

FIG. 3A-60

```
ATOM   3413  N    VAL   22      18.877   54.690   33.354  1.00  92.94      AP2
ATOM   3414  CA   VAL   22      17.878   54.846   32.315  1.00  92.17      AP2
ATOM   3415  CB   VAL   22      16.523   54.320   32.855  1.00  92.24      AP2
ATOM   3416  CG1  VAL   22      15.484   54.285   31.758  1.00  92.28      AP2
ATOM   3417  CG2  VAL   22      16.722   52.933   33.472  1.00  91.98      AP2
ATOM   3418  C    VAL   22      17.741   56.308   31.843  1.00  91.45      AP2
ATOM   3419  O    VAL   22      16.783   56.992   32.194  1.00  91.67      AP2
ATOM   3420  N    LYS   23      18.693   56.787   31.044  1.00  90.56      AP2
ATOM   3421  CA   LYS   23      18.653   58.168   30.540  1.00  89.58      AP2
ATOM   3422  CB   LYS   23      20.078   58.706   30.378  1.00  89.69      AP2
ATOM   3423  C    LYS   23      17.899   58.274   29.211  1.00  88.74      AP2
ATOM   3424  O    LYS   23      17.965   57.369   28.388  1.00  88.66      AP2
ATOM   3425  N    LEU   24      17.193   59.381   28.996  1.00  87.78      AP2
ATOM   3426  CA   LEU   24      16.423   59.565   27.760  1.00  86.87      AP2
ATOM   3427  CB   LEU   24      15.801   60.976   27.689  1.00  86.41      AP2
ATOM   3428  CG   LEU   24      14.684   61.499   28.603  1.00  86.03      AP2
ATOM   3429  CD1  LEU   24      13.613   60.437   28.744  1.00  86.18      AP2
ATOM   3430  CD2  LEU   24      15.231   61.899   29.956  1.00  85.71      AP2
ATOM   3431  C    LEU   24      17.255   59.347   26.497  1.00  86.36      AP2
ATOM   3432  O    LEU   24      16.716   59.246   25.396  1.00  86.46      AP2
ATOM   3433  N    GLU   25      18.570   59.285   26.663  1.00  85.76      AP2
ATOM   3434  CA   GLU   25      19.500   59.103   25.545  1.00  85.09      AP2
ATOM   3435  CB   GLU   25      20.607   60.138   25.649  1.00  85.64      AP2
ATOM   3436  CG   GLU   25      21.204   60.175   27.047  1.00  86.77      AP2
ATOM   3437  CD   GLU   25      21.379   61.586   27.571  1.00  87.43      AP2
ATOM   3438  OE1  GLU   25      22.292   62.287   27.075  1.00  87.74      AP2
ATOM   3439  OE2  GLU   25      20.601   61.989   28.470  1.00  87.25      AP2
ATOM   3440  C    GLU   25      20.117   57.713   25.561  1.00  84.14      AP2
ATOM   3441  O    GLU   25      20.876   57.349   24.662  1.00  84.00      AP2
ATOM   3442  N    ALA   26      19.798   56.957   26.607  1.00  83.18      AP2
ATOM   3443  CA   ALA   26      20.289   55.591   26.776  1.00  82.20      AP2
ATOM   3444  CB   ALA   26      19.927   55.065   28.174  1.00  81.62      AP2
ATOM   3445  C    ALA   26      19.676   54.684   25.708  1.00  81.46      AP2
ATOM   3446  O    ALA   26      18.469   54.418   25.724  1.00  81.38      AP2
ATOM   3447  N    SER   27      20.508   54.236   24.771  1.00  80.43      AP2
ATOM   3448  CA   SER   27      20.066   53.338   23.709  1.00  79.24      AP2
ATOM   3449  CB   SER   27      21.121   53.254   22.598  1.00  78.96      AP2
ATOM   3450  OG   SER   27      20.722   52.381   21.556  1.00  78.46      AP2
ATOM   3451  C    SER   27      19.856   51.956   24.321  1.00  78.58      AP2
ATOM   3452  O    SER   27      20.722   51.452   25.052  1.00  78.03      AP2
ATOM   3453  N    PHE   28      18.697   51.365   24.033  1.00  77.69      AP2
ATOM   3454  CA   PHE   28      18.364   50.046   24.537  1.00  77.23      AP2
ATOM   3455  CB   PHE   28      17.005   49.606   24.002  1.00  77.11      AP2
ATOM   3456  CG   PHE   28      15.874   50.490   24.413  1.00  76.99      AP2
ATOM   3457  CD1  PHE   28      15.477   50.556   25.750  1.00  76.84      AP2
ATOM   3458  CD2  PHE   28      15.194   51.248   23.466  1.00  76.77      AP2
ATOM   3459  CE1  PHE   28      14.422   51.357   26.137  1.00  76.38      AP2
ATOM   3460  CE2  PHE   28      14.136   52.056   23.835  1.00  76.78      AP2
ATOM   3461  CZ   PHE   28      13.747   52.112   25.177  1.00  77.00      AP2
ATOM   3462  C    PHE   28      19.412   49.034   24.082  1.00  77.03      AP2
ATOM   3463  O    PHE   28      19.960   48.275   24.880  1.00  76.80      AP2
ATOM   3464  N    LYS   29      19.683   49.039   22.785  1.00  76.69      AP2
ATOM   3465  CA   LYS   29      20.625   48.109   22.197  1.00  76.65      AP2
ATOM   3466  CB   LYS   29      20.549   48.208   20.671  1.00  77.14      AP2
ATOM   3467  CG   LYS   29      19.127   48.454   20.149  1.00  77.87      AP2
ATOM   3468  CD   LYS   29      18.817   47.607   18.923  1.00  78.22      AP2
ATOM   3469  CE   LYS   29      19.009   46.118   19.223  1.00  77.99      AP2
```

FIG. 3A-61

| ATOM | 3470 | NZ | LYS | 29 | 18.729 | 45.262 | 18.028 | 1.00 | 77.84 | AP2 |
|---|---|---|---|---|---|---|---|---|---|---|
| ATOM | 3471 | C | LYS | 29 | 22.055 | 48.331 | 22.661 | 1.00 | 76.29 | AP2 |
| ATOM | 3472 | O | LYS | 29 | 22.691 | 47.426 | 23.204 | 1.00 | 76.44 | AP2 |
| ATOM | 3473 | N | GLU | 30 | 22.555 | 49.544 | 22.465 | 1.00 | 75.77 | AP2 |
| ATOM | 3474 | CA | GLU | 30 | 23.925 | 49.864 | 22.831 | 1.00 | 74.94 | AP2 |
| ATOM | 3475 | CB | GLU | 30 | 24.388 | 51.081 | 22.042 | 1.00 | 75.30 | AP2 |
| ATOM | 3476 | CG | GLU | 30 | 24.388 | 50.883 | 20.545 | 1.00 | 76.33 | AP2 |
| ATOM | 3477 | CD | GLU | 30 | 24.656 | 52.184 | 19.800 | 1.00 | 77.36 | AP2 |
| ATOM | 3478 | OE1 | GLU | 30 | 23.737 | 53.042 | 19.722 | 1.00 | 77.95 | AP2 |
| ATOM | 3479 | OE2 | GLU | 30 | 25.796 | 52.355 | 19.305 | 1.00 | 77.61 | AP2 |
| ATOM | 3480 | C | GLU | 30 | 24.256 | 50.089 | 24.301 | 1.00 | 73.99 | AP2 |
| ATOM | 3481 | O | GLU | 30 | 25.149 | 49.438 | 24.847 | 1.00 | 74.25 | AP2 |
| ATOM | 3482 | N | ASP | 31 | 23.549 | 50.996 | 24.953 | 1.00 | 72.54 | AP2 |
| ATOM | 3483 | CA | ASP | 31 | 23.873 | 51.311 | 26.335 | 1.00 | 71.31 | AP2 |
| ATOM | 3484 | CB | ASP | 31 | 23.524 | 52.781 | 26.580 | 1.00 | 72.36 | AP2 |
| ATOM | 3485 | CG | ASP | 31 | 24.270 | 53.725 | 25.619 | 1.00 | 73.52 | AP2 |
| ATOM | 3486 | OD1 | ASP | 31 | 25.514 | 53.605 | 25.518 | 1.00 | 74.32 | AP2 |
| ATOM | 3487 | OD2 | ASP | 31 | 23.632 | 54.585 | 24.965 | 1.00 | 73.71 | AP2 |
| ATOM | 3488 | C | ASP | 31 | 23.284 | 50.417 | 27.429 | 1.00 | 70.06 | AP2 |
| ATOM | 3489 | O | ASP | 31 | 23.823 | 50.337 | 28.536 | 1.00 | 69.24 | AP2 |
| ATOM | 3490 | N | LEU | 32 | 22.205 | 49.711 | 27.110 | 1.00 | 68.91 | AP2 |
| ATOM | 3491 | CA | LEU | 32 | 21.541 | 48.861 | 28.089 | 1.00 | 67.85 | AP2 |
| ATOM | 3492 | CB | LEU | 32 | 20.073 | 49.255 | 28.110 | 1.00 | 68.54 | AP2 |
| ATOM | 3493 | CG | LEU | 32 | 19.920 | 50.701 | 28.569 | 1.00 | 68.87 | AP2 |
| ATOM | 3494 | CD1 | LEU | 32 | 18.472 | 51.131 | 28.462 | 1.00 | 69.10 | AP2 |
| ATOM | 3495 | CD2 | LEU | 32 | 20.422 | 50.809 | 30.012 | 1.00 | 69.20 | AP2 |
| ATOM | 3496 | C | LEU | 32 | 21.686 | 47.323 | 28.021 | 1.00 | 66.73 | AP2 |
| ATOM | 3497 | O | LEU | 32 | 21.176 | 46.610 | 28.894 | 1.00 | 66.96 | AP2 |
| ATOM | 3498 | N | GLY | 33 | 22.373 | 46.811 | 27.003 | 1.00 | 65.33 | AP2 |
| ATOM | 3499 | CA | GLY | 33 | 22.581 | 45.370 | 26.884 | 1.00 | 63.55 | AP2 |
| ATOM | 3500 | C | GLY | 33 | 21.416 | 44.529 | 26.372 | 1.00 | 62.11 | AP2 |
| ATOM | 3501 | O | GLY | 33 | 21.169 | 43.428 | 26.874 | 1.00 | 62.07 | AP2 |
| ATOM | 3502 | N | ALA | 34 | 20.704 | 45.039 | 25.370 | 1.00 | 60.47 | AP2 |
| ATOM | 3503 | CA | ALA | 34 | 19.556 | 44.331 | 24.810 | 1.00 | 58.47 | AP2 |
| ATOM | 3504 | CB | ALA | 34 | 18.316 | 45.248 | 24.802 | 1.00 | 58.39 | AP2 |
| ATOM | 3505 | C | ALA | 34 | 19.805 | 43.797 | 23.407 | 1.00 | 56.71 | AP2 |
| ATOM | 3506 | O | ALA | 34 | 20.259 | 44.534 | 22.516 | 1.00 | 56.50 | AP2 |
| ATOM | 3507 | N | ASP | 35 | 19.526 | 42.507 | 23.225 | 1.00 | 54.43 | AP2 |
| ATOM | 3508 | CA | ASP | 35 | 19.663 | 41.882 | 21.910 | 1.00 | 52.45 | AP2 |
| ATOM | 3509 | CB | ASP | 35 | 19.991 | 40.383 | 22.019 | 1.00 | 51.39 | AP2 |
| ATOM | 3510 | CG | ASP | 35 | 18.982 | 39.589 | 22.864 | 1.00 | 50.25 | AP2 |
| ATOM | 3511 | OD1 | ASP | 35 | 17.860 | 40.067 | 23.129 | 1.00 | 48.54 | AP2 |
| ATOM | 3512 | OD2 | ASP | 35 | 19.338 | 38.455 | 23.241 | 1.00 | 48.62 | AP2 |
| ATOM | 3513 | C | ASP | 35 | 18.324 | 42.080 | 21.226 | 1.00 | 52.01 | AP2 |
| ATOM | 3514 | O | ASP | 35 | 17.462 | 42.783 | 21.770 | 1.00 | 52.08 | AP2 |
| ATOM | 3515 | CA | PAN | 36 | 16.850 | 41.659 | 19.373 | 1.00 | 50.23 | AP2 |
| ATOM | 3516 | N | PAN | 36 | 18.121 | 41.475 | 20.056 | 1.00 | 51.20 | AP2 |
| ATOM | 3517 | C | PAN | 36 | 15.682 | 41.035 | 20.163 | 1.00 | 49.09 | AP2 |
| ATOM | 3518 | O | PAN | 36 | 14.624 | 41.642 | 20.258 | 1.00 | 47.77 | AP2 |
| ATOM | 3519 | O5 | PAN | 36 | 15.669 | 41.227 | 17.265 | 1.00 | 54.25 | AP2 |
| ATOM | 3520 | P6 | PAN | 36 | 15.526 | 42.266 | 16.074 | 1.00 | 55.70 | AP2 |
| ATOM | 3521 | O7 | PAN | 36 | 15.304 | 41.457 | 14.765 | 1.00 | 55.98 | AP2 |
| ATOM | 3522 | O8 | PAN | 36 | 16.936 | 43.007 | 15.954 | 1.00 | 55.85 | AP2 |
| ATOM | 3523 | O9 | PAN | 36 | 14.356 | 43.189 | 16.312 | 1.00 | 55.46 | AP2 |
| ATOM | 3524 | CB | PAN | 36 | 16.941 | 41.113 | 17.950 | 1.00 | 51.54 | AP2 |
| ATOM | 3525 | N | LEU | 37 | 15.865 | 39.849 | 20.737 | 1.00 | 48.10 | AP2 |
| ATOM | 3526 | CA | LEU | 37 | 14.782 | 39.240 | 21.505 | 1.00 | 47.87 | AP2 |

FIG. 3A-62

| ATOM | 3527 | CB  | LEU | 37 | 15.158 | 37.825 | 21.961 | 1.00 | 47.41 | AP2 |
| ATOM | 3528 | CG  | LEU | 37 | 14.000 | 37.054 | 22.630 | 1.00 | 49.24 | AP2 |
| ATOM | 3529 | CD1 | LEU | 37 | 12.869 | 36.789 | 21.613 | 1.00 | 48.71 | AP2 |
| ATOM | 3530 | CD2 | LEU | 37 | 14.491 | 35.718 | 23.189 | 1.00 | 49.58 | AP2 |
| ATOM | 3531 | C   | LEU | 37 | 14.382 | 40.114 | 22.731 | 1.00 | 47.82 | AP2 |
| ATOM | 3532 | O   | LEU | 37 | 13.201 | 40.221 | 23.046 | 1.00 | 46.87 | AP2 |
| ATOM | 3533 | N   | ASP | 38 | 15.349 | 40.772 | 23.388 | 1.00 | 47.86 | AP2 |
| ATOM | 3534 | CA  | ASP | 38 | 15.015 | 41.602 | 24.551 | 1.00 | 47.84 | AP2 |
| ATOM | 3535 | CB  | ASP | 38 | 16.264 | 42.164 | 25.278 | 1.00 | 47.82 | AP2 |
| ATOM | 3536 | CG  | ASP | 38 | 17.157 | 41.078 | 25.909 | 1.00 | 47.77 | AP2 |
| ATOM | 3537 | OD1 | ASP | 38 | 18.384 | 41.221 | 25.817 | 1.00 | 47.55 | AP2 |
| ATOM | 3538 | OD2 | ASP | 38 | 16.663 | 40.095 | 26.506 | 1.00 | 48.56 | AP2 |
| ATOM | 3539 | C   | ASP | 38 | 14.176 | 42.767 | 24.072 | 1.00 | 47.53 | AP2 |
| ATOM | 3540 | O   | ASP | 38 | 13.221 | 43.171 | 24.728 | 1.00 | 47.07 | AP2 |
| ATOM | 3541 | N   | VAL | 39 | 14.505 | 43.295 | 22.905 | 1.00 | 47.99 | AP2 |
| ATOM | 3542 | CA  | VAL | 39 | 13.747 | 44.441 | 22.426 | 1.00 | 47.95 | AP2 |
| ATOM | 3543 | CB  | VAL | 39 | 14.466 | 45.138 | 21.301 | 1.00 | 47.96 | AP2 |
| ATOM | 3544 | CG1 | VAL | 39 | 14.203 | 44.460 | 19.969 | 1.00 | 49.07 | AP2 |
| ATOM | 3545 | CG2 | VAL | 39 | 14.002 | 46.543 | 21.270 | 1.00 | 49.98 | AP2 |
| ATOM | 3546 | C   | VAL | 39 | 12.291 | 44.172 | 22.034 | 1.00 | 47.86 | AP2 |
| ATOM | 3547 | O   | VAL | 39 | 11.438 | 45.056 | 22.217 | 1.00 | 47.51 | AP2 |
| ATOM | 3548 | N   | VAL | 40 | 11.976 | 42.981 | 21.505 | 1.00 | 47.55 | AP2 |
| ATOM | 3549 | CA  | VAL | 40 | 10.564 | 42.723 | 21.185 | 1.00 | 48.42 | AP2 |
| ATOM | 3550 | CB  | VAL | 40 | 10.296 | 41.526 | 20.144 | 1.00 | 47.99 | AP2 |
| ATOM | 3551 | CG1 | VAL | 40 | 11.559 | 40.997 | 19.585 | 1.00 | 48.02 | AP2 |
| ATOM | 3552 | CG2 | VAL | 40 | 9.484  | 40.438 | 20.758 | 1.00 | 48.83 | AP2 |
| ATOM | 3553 | C   | VAL | 40 | 9.766  | 42.494 | 22.480 | 1.00 | 48.47 | AP2 |
| ATOM | 3554 | O   | VAL | 40 | 8.618  | 42.879 | 22.549 | 1.00 | 47.57 | AP2 |
| ATOM | 3555 | N   | GLU | 41 | 10.370 | 41.886 | 23.502 | 1.00 | 49.18 | AP2 |
| ATOM | 3556 | CA  | GLU | 41 | 9.643  | 41.685 | 24.753 | 1.00 | 50.93 | AP2 |
| ATOM | 3557 | CB  | GLU | 41 | 10.387 | 40.718 | 25.673 | 1.00 | 53.01 | AP2 |
| ATOM | 3558 | CG  | GLU | 41 | 10.074 | 39.232 | 25.400 | 1.00 | 56.63 | AP2 |
| ATOM | 3559 | CD  | GLU | 41 | 10.552 | 38.329 | 26.536 | 1.00 | 58.01 | AP2 |
| ATOM | 3560 | OE1 | GLU | 41 | 11.776 | 38.066 | 26.609 | 1.00 | 59.21 | AP2 |
| ATOM | 3561 | OE2 | GLU | 41 | 9.704  | 37.902 | 27.366 | 1.00 | 59.16 | AP2 |
| ATOM | 3562 | C   | GLU | 41 | 9.440  | 43.020 | 25.451 | 1.00 | 50.42 | AP2 |
| ATOM | 3563 | O   | GLU | 41 | 8.452  | 43.233 | 26.134 | 1.00 | 49.86 | AP2 |
| ATOM | 3564 | N   | LEU | 42 | 10.393 | 43.923 | 25.248 | 1.00 | 50.66 | AP2 |
| ATOM | 3565 | CA  | LEU | 42 | 10.331 | 45.247 | 25.822 | 1.00 | 50.65 | AP2 |
| ATOM | 3566 | CB  | LEU | 42 | 11.630 | 45.984 | 25.529 | 1.00 | 51.48 | AP2 |
| ATOM | 3567 | CG  | LEU | 42 | 11.958 | 47.238 | 26.337 | 1.00 | 52.85 | AP2 |
| ATOM | 3568 | CD1 | LEU | 42 | 11.999 | 46.858 | 27.818 | 1.00 | 53.64 | AP2 |
| ATOM | 3569 | CD2 | LEU | 42 | 13.327 | 47.821 | 25.899 | 1.00 | 52.34 | AP2 |
| ATOM | 3570 | C   | LEU | 42 | 9.143  | 45.946 | 25.167 | 1.00 | 50.78 | AP2 |
| ATOM | 3571 | O   | LEU | 42 | 8.256  | 46.454 | 25.860 | 1.00 | 50.87 | AP2 |
| ATOM | 3572 | N   | VAL | 43 | 9.109  | 45.933 | 23.839 | 1.00 | 50.50 | AP2 |
| ATOM | 3573 | CA  | VAL | 43 | 8.026  | 46.554 | 23.081 | 1.00 | 51.44 | AP2 |
| ATOM | 3574 | CB  | VAL | 43 | 8.222  | 46.359 | 21.529 | 1.00 | 50.86 | AP2 |
| ATOM | 3575 | CG1 | VAL | 43 | 6.963  | 46.746 | 20.762 | 1.00 | 50.60 | AP2 |
| ATOM | 3576 | CG2 | VAL | 43 | 9.376  | 47.197 | 21.041 | 1.00 | 50.67 | AP2 |
| ATOM | 3577 | C   | VAL | 43 | 6.679  | 45.964 | 23.480 | 1.00 | 52.40 | AP2 |
| ATOM | 3578 | O   | VAL | 43 | 5.695  | 46.665 | 23.618 | 1.00 | 51.57 | AP2 |
| ATOM | 3579 | N   | MET | 44 | 6.633  | 44.656 | 23.658 | 1.00 | 54.33 | AP2 |
| ATOM | 3580 | CA  | MET | 44 | 5.383  | 44.020 | 24.030 | 1.00 | 56.33 | AP2 |
| ATOM | 3581 | CB  | MET | 44 | 5.557  | 42.509 | 24.002 | 1.00 | 56.08 | AP2 |
| ATOM | 3582 | CG  | MET | 44 | 6.120  | 42.014 | 22.700 | 1.00 | 57.30 | AP2 |
| ATOM | 3583 | SD  | MET | 44 | 5.978  | 40.248 | 22.480 | 1.00 | 57.38 | AP2 |

FIG. 3A-63

| ATOM | 3584 | CE  | MET | 44 | 4.348  | 40.338 | 21.654 | 1.00 | 57.15 | AP2 |
| ---- | ---- | --- | --- | -- | ------ | ------ | ------ | ---- | ----- | --- |
| ATOM | 3585 | C   | MET | 44 | 4.916  | 44.501 | 25.414 | 1.00 | 57.88 | AP2 |
| ATOM | 3586 | O   | MET | 44 | 3.734  | 44.764 | 25.619 | 1.00 | 57.09 | AP2 |
| ATOM | 3587 | N   | GLU | 45 | 5.863  | 44.646 | 26.341 | 1.00 | 59.93 | AP2 |
| ATOM | 3588 | CA  | GLU | 45 | 5.554  | 45.105 | 27.691 | 1.00 | 62.06 | AP2 |
| ATOM | 3589 | CB  | GLU | 45 | 6.834  | 45.156 | 28.544 | 1.00 | 63.72 | AP2 |
| ATOM | 3590 | CG  | GLU | 45 | 6.613  | 44.808 | 30.038 | 1.00 | 67.19 | AP2 |
| ATOM | 3591 | CD  | GLU | 45 | 6.406  | 43.296 | 30.299 | 1.00 | 69.02 | AP2 |
| ATOM | 3592 | OE1 | GLU | 45 | 5.445  | 42.704 | 29.729 | 1.00 | 69.48 | AP2 |
| ATOM | 3593 | OE2 | GLU | 45 | 7.212  | 42.701 | 31.074 | 1.00 | 69.81 | AP2 |
| ATOM | 3594 | C   | GLU | 45 | 4.927  | 46.491 | 27.580 | 1.00 | 62.29 | AP2 |
| ATOM | 3595 | O   | GLU | 45 | 3.927  | 46.777 | 28.232 | 1.00 | 62.46 | AP2 |
| ATOM | 3596 | N   | LEU | 46 | 5.508  | 47.338 | 26.730 | 1.00 | 62.52 | AP2 |
| ATOM | 3597 | CA  | LEU | 46 | 4.998  | 48.686 | 26.514 | 1.00 | 62.72 | AP2 |
| ATOM | 3598 | CB  | LEU | 46 | 5.938  | 49.485 | 25.595 | 1.00 | 62.51 | AP2 |
| ATOM | 3599 | CG  | LEU | 46 | 7.442  | 49.583 | 25.906 | 1.00 | 62.73 | AP2 |
| ATOM | 3600 | CD1 | LEU | 46 | 8.093  | 50.528 | 24.900 | 1.00 | 61.98 | AP2 |
| ATOM | 3601 | CD2 | LEU | 46 | 7.673  | 50.082 | 27.318 | 1.00 | 62.24 | AP2 |
| ATOM | 3602 | C   | LEU | 46 | 3.604  | 48.629 | 25.884 | 1.00 | 63.09 | AP2 |
| ATOM | 3603 | O   | LEU | 46 | 2.758  | 49.481 | 26.150 | 1.00 | 62.76 | AP2 |
| ATOM | 3604 | N   | GLU | 47 | 3.373  | 47.617 | 25.050 | 1.00 | 63.87 | AP2 |
| ATOM | 3605 | CA  | GLU | 47 | 2.090  | 47.440 | 24.372 | 1.00 | 64.51 | AP2 |
| ATOM | 3606 | CB  | GLU | 47 | 2.157  | 46.295 | 23.344 | 1.00 | 64.64 | AP2 |
| ATOM | 3607 | CG  | GLU | 47 | 2.460  | 46.416 | 21.850 | 1.00 | 20.00 | AP2 |
| ATOM | 3608 | CD  | GLU | 47 | 2.451  | 45.221 | 20.924 | 1.00 | 20.00 | AP2 |
| ATOM | 3609 | OE1 | GLU | 47 | 2.262  | 44.023 | 21.080 | 1.00 | 20.00 | AP2 |
| ATOM | 3610 | OE2 | GLU | 47 | 2.447  | 45.762 | 19.820 | 1.00 | 20.00 | AP2 |
| ATOM | 3611 | C   | GLU | 47 | 0.990  | 47.250 | 25.411 | 1.00 | 64.90 | AP2 |
| ATOM | 3612 | O   | GLU | 47 | -0.092 | 47.818 | 25.292 | 1.00 | 64.70 | AP2 |
| ATOM | 3613 | N   | ASP | 48 | 1.282  | 46.458 | 26.431 | 1.00 | 65.21 | AP2 |
| ATOM | 3614 | CA  | ASP | 48 | 0.311  | 46.171 | 27.460 | 1.00 | 66.10 | AP2 |
| ATOM | 3615 | CB  | ASP | 48 | 0.675  | 44.868 | 28.155 | 1.00 | 66.99 | AP2 |
| ATOM | 3616 | CG  | ASP | 48 | 0.739  | 43.704 | 27.175 | 1.00 | 68.14 | AP2 |
| ATOM | 3617 | OD1 | ASP | 48 | -0.039 | 43.720 | 26.181 | 1.00 | 68.23 | AP2 |
| ATOM | 3618 | OD2 | ASP | 48 | 1.561  | 42.782 | 27.394 | 1.00 | 68.71 | AP2 |
| ATOM | 3619 | C   | ASP | 48 | 0.198  | 47.284 | 28.451 | 1.00 | 66.30 | AP2 |
| ATOM | 3620 | O   | ASP | 48 | -0.862 | 47.863 | 28.609 | 1.00 | 66.33 | AP2 |
| ATOM | 3621 | N   | GLU | 49 | 1.310  | 47.593 | 29.094 | 1.00 | 66.84 | AP2 |
| ATOM | 3622 | CA  | GLU | 49 | 1.390  | 48.652 | 30.085 | 1.00 | 67.24 | AP2 |
| ATOM | 3623 | CB  | GLU | 49 | 2.852  | 48.913 | 30.425 | 1.00 | 68.55 | AP2 |
| ATOM | 3624 | CG  | GLU | 49 | 3.081  | 49.967 | 31.498 | 1.00 | 70.53 | AP2 |
| ATOM | 3625 | CD  | GLU | 49 | 2.745  | 49.446 | 32.885 | 1.00 | 71.90 | AP2 |
| ATOM | 3626 | OE1 | GLU | 49 | 3.012  | 48.237 | 33.122 | 1.00 | 72.29 | AP2 |
| ATOM | 3627 | OE2 | GLU | 49 | 2.234  | 50.237 | 33.725 | 1.00 | 72.12 | AP2 |
| ATOM | 3628 | C   | GLU | 49 | 0.769  | 49.977 | 29.678 | 1.00 | 67.07 | AP2 |
| ATOM | 3629 | O   | GLU | 49 | 0.421  | 50.778 | 30.542 | 1.00 | 67.58 | AP2 |
| ATOM | 3630 | N   | PHE | 50 | 0.636  | 50.235 | 28.381 | 1.00 | 66.27 | AP2 |
| ATOM | 3631 | CA  | PHE | 50 | 0.084  | 51.515 | 27.953 | 1.00 | 65.90 | AP2 |
| ATOM | 3632 | CB  | PHE | 50 | 1.183  | 52.350 | 27.295 | 1.00 | 65.47 | AP2 |
| ATOM | 3633 | CG  | PHE | 50 | 2.157  | 52.959 | 28.271 | 1.00 | 65.11 | AP2 |
| ATOM | 3634 | CD1 | PHE | 50 | 1.881  | 54.185 | 28.882 | 1.00 | 64.59 | AP2 |
| ATOM | 3635 | CD2 | PHE | 50 | 3.343  | 52.306 | 28.595 | 1.00 | 64.67 | AP2 |
| ATOM | 3636 | CE1 | PHE | 50 | 2.767  | 54.745 | 29.791 | 1.00 | 64.20 | AP2 |
| ATOM | 3637 | CE2 | PHE | 50 | 4.237  | 52.870 | 29.512 | 1.00 | 64.53 | AP2 |
| ATOM | 3638 | CZ  | PHE | 50 | 3.947  | 54.086 | 30.105 | 1.00 | 64.19 | AP2 |
| ATOM | 3639 | C   | PHE | 50 | -1.081 | 51.349 | 27.001 | 1.00 | 66.10 | AP2 |
| ATOM | 3640 | O   | PHE | 50 | -1.685 | 52.316 | 26.534 | 1.00 | 66.26 | AP2 |

FIG. 3A-64

| ATOM | 3641 | N | ASP | 51 | -1.402 | 50.103 | 26.713 | 1.00 | 66.29 | AP2 |
|---|---|---|---|---|---|---|---|---|---|---|
| ATOM | 3642 | CA | ASP | 51 | -2.487 | 49.794 | 25.809 | 1.00 | 66.30 | AP2 |
| ATOM | 3643 | CB | ASP | 51 | -3.818 | 50.201 | 26.427 | 1.00 | 67.89 | AP2 |
| ATOM | 3644 | CG | ASP | 51 | -4.959 | 49.359 | 25.908 | 1.00 | 68.99 | AP2 |
| ATOM | 3645 | OD1 | ASP | 51 | -4.916 | 48.131 | 26.144 | 1.00 | 69.70 | AP2 |
| ATOM | 3646 | OD2 | ASP | 51 | -5.881 | 49.909 | 25.252 | 1.00 | 70.00 | AP2 |
| ATOM | 3647 | C | ASP | 51 | -2.360 | 50.406 | 24.412 | 1.00 | 65.79 | AP2 |
| ATOM | 3648 | O | ASP | 51 | -3.275 | 51.088 | 23.938 | 1.00 | 65.17 | AP2 |
| ATOM | 3649 | N | MET | 52 | -1.215 | 50.155 | 23.766 | 1.00 | 65.48 | AP2 |
| ATOM | 3650 | CA | MET | 52 | -0.951 | 50.606 | 22.400 | 1.00 | 65.07 | AP2 |
| ATOM | 3651 | CB | MET | 52 | 0.032 | 51.782 | 22.387 | 1.00 | 65.16 | AP2 |
| ATOM | 3652 | CG | MET | 52 | 1.226 | 51.618 | 23.307 | 1.00 | 65.99 | AP2 |
| ATOM | 3653 | SD | MET | 52 | 2.324 | 53.078 | 23.241 | 1.00 | 66.46 | AP2 |
| ATOM | 3654 | CE | MET | 52 | 1.109 | 54.407 | 23.535 | 1.00 | 66.61 | AP2 |
| ATOM | 3655 | C | MET | 52 | -0.413 | 49.420 | 21.577 | 1.00 | 64.74 | AP2 |
| ATOM | 3656 | O | MET | 52 | -0.176 | 48.338 | 22.124 | 1.00 | 64.50 | AP2 |
| ATOM | 3657 | N | GLU | 53 | -0.233 | 49.621 | 20.270 | 1.00 | 64.21 | AP2 |
| ATOM | 3658 | CA | GLU | 53 | 0.240 | 48.561 | 19.383 | 1.00 | 63.66 | AP2 |
| ATOM | 3659 | CB | GLU | 53 | -0.438 | 48.681 | 18.021 | 1.00 | 65.03 | AP2 |
| ATOM | 3660 | CG | GLU | 53 | -1.947 | 48.589 | 18.025 | 1.00 | 67.15 | AP2 |
| ATOM | 3661 | CD | GLU | 53 | -2.502 | 48.558 | 16.606 | 1.00 | 68.94 | AP2 |
| ATOM | 3662 | OE1 | GLU | 53 | -1.772 | 49.026 | 15.698 | 1.00 | 69.75 | AP2 |
| ATOM | 3663 | OE2 | GLU | 53 | -3.651 | 48.077 | 16.391 | 1.00 | 69.40 | AP2 |
| ATOM | 3664 | C | GLU | 53 | 1.370 | 49.384 | 18.714 | 1.00 | 62.69 | AP2 |
| ATOM | 3665 | O | GLU | 53 | 1.138 | 50.531 | 18.242 | 1.00 | 62.84 | AP2 |
| ATOM | 3666 | N | ILE | 54 | 2.577 | 48.811 | 18.703 | 1.00 | 60.28 | AP2 |
| ATOM | 3667 | CA | ILE | 54 | 3.777 | 49.462 | 18.159 | 1.00 | 58.22 | AP2 |
| ATOM | 3668 | CB | ILE | 54 | 4.722 | 49.262 | 19.364 | 1.00 | 58.17 | AP2 |
| ATOM | 3669 | CG2 | ILE | 54 | 6.177 | 49.590 | 18.924 | 1.00 | 58.30 | AP2 |
| ATOM | 3670 | CG1 | ILE | 54 | 4.302 | 50.170 | 20.534 | 1.00 | 58.24 | AP2 |
| ATOM | 3671 | CD1 | ILE | 54 | 5.286 | 50.195 | 21.696 | 1.00 | 57.29 | AP2 |
| ATOM | 3672 | C | ILE | 54 | 4.147 | 48.405 | 17.101 | 1.00 | 56.70 | AP2 |
| ATOM | 3673 | O | ILE | 54 | 4.502 | 47.272 | 17.413 | 1.00 | 56.48 | AP2 |
| ATOM | 3674 | N | SER | 55 | 4.053 | 48.804 | 15.842 | 1.00 | 54.79 | AP2 |
| ATOM | 3675 | CA | SER | 55 | 4.389 | 47.968 | 14.704 | 1.00 | 52.52 | AP2 |
| ATOM | 3676 | CB | SER | 55 | 4.019 | 48.705 | 13.434 | 1.00 | 52.24 | AP2 |
| ATOM | 3677 | OG | SER | 55 | 4.831 | 49.876 | 13.340 | 1.00 | 50.08 | AP2 |
| ATOM | 3678 | C | SER | 55 | 5.896 | 47.742 | 14.651 | 1.00 | 52.02 | AP2 |
| ATOM | 3679 | O | SER | 55 | 6.653 | 48.361 | 15.400 | 1.00 | 50.47 | AP2 |
| ATOM | 3680 | N | ASP | 56 | 6.316 | 46.870 | 13.734 | 1.00 | 51.52 | AP2 |
| ATOM | 3681 | CA | ASP | 56 | 7.734 | 46.611 | 13.526 | 1.00 | 51.65 | AP2 |
| ATOM | 3682 | CB | ASP | 56 | 7.955 | 45.432 | 12.561 | 1.00 | 51.39 | AP2 |
| ATOM | 3683 | CG | ASP | 56 | 7.585 | 44.072 | 13.173 | 1.00 | 51.27 | AP2 |
| ATOM | 3684 | OD1 | ASP | 56 | 7.718 | 43.888 | 14.397 | 1.00 | 50.03 | AP2 |
| ATOM | 3685 | OD2 | ASP | 56 | 7.180 | 43.173 | 12.405 | 1.00 | 51.66 | AP2 |
| ATOM | 3686 | C | ASP | 56 | 8.335 | 47.897 | 12.926 | 1.00 | 51.59 | AP2 |
| ATOM | 3687 | O | ASP | 56 | 9.470 | 48.254 | 13.208 | 1.00 | 50.53 | AP2 |
| ATOM | 3688 | N | GLU | 57 | 7.549 | 48.608 | 12.127 | 1.00 | 52.32 | AP2 |
| ATOM | 3689 | CA | GLU | 57 | 8.036 | 49.834 | 11.523 | 1.00 | 54.22 | AP2 |
| ATOM | 3690 | CB | GLU | 57 | 6.990 | 50.414 | 10.550 | 1.00 | 55.66 | AP2 |
| ATOM | 3691 | CG | GLU | 57 | 7.397 | 51.743 | 9.901 | 1.00 | 57.60 | AP2 |
| ATOM | 3692 | CD | GLU | 57 | 6.659 | 52.010 | 8.598 | 1.00 | 59.28 | AP2 |
| ATOM | 3693 | OE1 | GLU | 57 | 5.490 | 52.440 | 8.637 | 1.00 | 59.81 | AP2 |
| ATOM | 3694 | OE2 | GLU | 57 | 7.244 | 51.779 | 7.516 | 1.00 | 60.85 | AP2 |
| ATOM | 3695 | C | GLU | 57 | 8.353 | 50.849 | 12.606 | 1.00 | 54.45 | AP2 |
| ATOM | 3696 | O | GLU | 57 | 9.366 | 51.522 | 12.541 | 1.00 | 54.39 | AP2 |
| ATOM | 3697 | N | ASP | 58 | 7.465 | 50.933 | 13.596 | 1.00 | 55.48 | AP2 |

FIG. 3A-65

| ATOM | 3698 | CA | ASP | 58 | 7.567 | 51.848 | 14.737 | 1.00 | 55.90 | AP2 |
|---|---|---|---|---|---|---|---|---|---|---|
| ATOM | 3699 | CB | ASP | 58 | 6.199 | 51.991 | 15.409 | 1.00 | 56.10 | AP2 |
| ATOM | 3700 | CG | ASP | 58 | 5.191 | 52.738 | 14.539 | 1.00 | 56.92 | AP2 |
| ATOM | 3701 | OD1 | ASP | 58 | 5.622 | 53.558 | 13.695 | 1.00 | 57.78 | AP2 |
| ATOM | 3702 | OD2 | ASP | 58 | 3.968 | 52.527 | 14.712 | 1.00 | 57.12 | AP2 |
| ATOM | 3703 | C | ASP | 58 | 8.597 | 51.449 | 15.790 | 1.00 | 56.08 | AP2 |
| ATOM | 3704 | O | ASP | 58 | 9.222 | 52.309 | 16.422 | 1.00 | 56.33 | AP2 |
| ATOM | 3705 | N | ALA | 59 | 8.762 | 50.154 | 15.999 | 1.00 | 56.24 | AP2 |
| ATOM | 3706 | CA | ALA | 59 | 9.727 | 49.677 | 16.970 | 1.00 | 57.11 | AP2 |
| ATOM | 3707 | CB | ALA | 59 | 9.596 | 48.172 | 17.133 | 1.00 | 56.29 | AP2 |
| ATOM | 3708 | C | ALA | 59 | 11.151 | 50.041 | 16.537 | 1.00 | 58.31 | AP2 |
| ATOM | 3709 | O | ALA | 59 | 12.033 | 50.211 | 17.370 | 1.00 | 58.41 | AP2 |
| ATOM | 3710 | N | GLU | 60 | 11.385 | 50.149 | 15.235 | 1.00 | 59.58 | AP2 |
| ATOM | 3711 | CA | GLU | 60 | 12.716 | 50.510 | 14.759 | 1.00 | 61.45 | AP2 |
| ATOM | 3712 | CB | GLU | 60 | 12.863 | 50.206 | 13.261 | 1.00 | 62.21 | AP2 |
| ATOM | 3713 | CG | GLU | 60 | 14.185 | 50.674 | 12.636 | 1.00 | 62.75 | AP2 |
| ATOM | 3714 | CD | GLU | 60 | 14.216 | 50.448 | 11.142 | 1.00 | 63.75 | AP2 |
| ATOM | 3715 | OE1 | GLU | 60 | 14.397 | 49.285 | 10.719 | 1.00 | 65.16 | AP2 |
| ATOM | 3716 | OE2 | GLU | 60 | 14.045 | 51.419 | 10.380 | 1.00 | 64.13 | AP2 |
| ATOM | 3717 | C | GLU | 60 | 12.928 | 52.000 | 15.006 | 1.00 | 62.56 | AP2 |
| ATOM | 3718 | O | GLU | 60 | 14.036 | 52.442 | 15.314 | 1.00 | 62.46 | AP2 |
| ATOM | 3719 | N | LYS | 61 | 11.845 | 52.762 | 14.886 | 1.00 | 63.87 | AP2 |
| ATOM | 3720 | CA | LYS | 61 | 11.887 | 54.200 | 15.086 | 1.00 | 65.19 | AP2 |
| ATOM | 3721 | CB | LYS | 61 | 10.522 | 54.809 | 14.761 | 1.00 | 66.28 | AP2 |
| ATOM | 3722 | CG | LYS | 61 | 10.507 | 56.330 | 14.791 | 1.00 | 67.81 | AP2 |
| ATOM | 3723 | CD | LYS | 61 | 9.102 | 56.930 | 15.010 | 1.00 | 68.60 | AP2 |
| ATOM | 3724 | CE | LYS | 61 | 9.225 | 58.430 | 15.426 | 1.00 | 69.32 | AP2 |
| ATOM | 3725 | NZ | LYS | 61 | 7.943 | 59.126 | 15.786 | 1.00 | 68.93 | AP2 |
| ATOM | 3726 | C | LYS | 61 | 12.289 | 54.577 | 16.510 | 1.00 | 65.76 | AP2 |
| ATOM | 3727 | O | LYS | 61 | 12.885 | 55.619 | 16.719 | 1.00 | 66.25 | AP2 |
| ATOM | 3728 | N | ILE | 62 | 11.979 | 53.744 | 17.499 | 1.00 | 66.49 | AP2 |
| ATOM | 3729 | CA | ILE | 62 | 12.341 | 54.089 | 18.872 | 1.00 | 66.91 | AP2 |
| ATOM | 3730 | CB | ILE | 62 | 11.135 | 53.957 | 19.833 | 1.00 | 66.83 | AP2 |
| ATOM | 3731 | CG2 | ILE | 62 | 10.425 | 55.289 | 19.929 | 1.00 | 67.42 | AP2 |
| ATOM | 3732 | CG1 | ILE | 62 | 10.154 | 52.896 | 19.349 | 1.00 | 66.56 | AP2 |
| ATOM | 3733 | CD1 | ILE | 62 | 8.929 | 52.796 | 20.241 | 1.00 | 65.95 | AP2 |
| ATOM | 3734 | C | ILE | 62 | 13.535 | 53.360 | 19.467 | 1.00 | 67.38 | AP2 |
| ATOM | 3735 | O | ILE | 62 | 13.415 | 52.271 | 20.038 | 1.00 | 67.69 | AP2 |
| ATOM | 3736 | N | ALA | 63 | 14.691 | 54.010 | 19.360 | 1.00 | 68.00 | AP2 |
| ATOM | 3737 | CA | ALA | 63 | 15.958 | 53.465 | 19.847 | 1.00 | 68.34 | AP2 |
| ATOM | 3738 | CB | ALA | 63 | 17.099 | 53.977 | 18.965 | 1.00 | 68.67 | AP2 |
| ATOM | 3739 | C | ALA | 63 | 16.286 | 53.741 | 21.322 | 1.00 | 68.26 | AP2 |
| ATOM | 3740 | O | ALA | 63 | 16.791 | 52.851 | 22.025 | 1.00 | 68.25 | AP2 |
| ATOM | 3741 | N | THR | 64 | 16.016 | 54.966 | 21.780 | 1.00 | 67.85 | AP2 |
| ATOM | 3742 | CA | THR | 64 | 16.312 | 55.352 | 23.164 | 1.00 | 67.48 | AP2 |
| ATOM | 3743 | CB | THR | 64 | 16.968 | 56.751 | 23.239 | 1.00 | 67.62 | AP2 |
| ATOM | 3744 | OG1 | THR | 64 | 16.115 | 57.709 | 22.594 | 1.00 | 68.15 | AP2 |
| ATOM | 3745 | CG2 | THR | 64 | 18.340 | 56.749 | 22.572 | 1.00 | 67.72 | AP2 |
| ATOM | 3746 | C | THR | 64 | 15.098 | 55.379 | 24.092 | 1.00 | 67.10 | AP2 |
| ATOM | 3747 | O | THR | 64 | 13.941 | 55.343 | 23.651 | 1.00 | 67.12 | AP2 |
| ATOM | 3748 | N | VAL | 65 | 15.392 | 55.448 | 25.386 | 1.00 | 66.32 | AP2 |
| ATOM | 3749 | CA | VAL | 65 | 14.378 | 55.500 | 26.414 | 1.00 | 65.55 | AP2 |
| ATOM | 3750 | CB | VAL | 65 | 15.018 | 55.579 | 27.777 | 1.00 | 65.53 | AP2 |
| ATOM | 3751 | CG1 | VAL | 65 | 13.940 | 55.593 | 28.848 | 1.00 | 65.46 | AP2 |
| ATOM | 3752 | CG2 | VAL | 65 | 15.967 | 54.392 | 27.959 | 1.00 | 65.23 | AP2 |
| ATOM | 3753 | C | VAL | 65 | 13.534 | 56.731 | 26.180 | 1.00 | 65.33 | AP2 |
| ATOM | 3754 | O | VAL | 65 | 12.315 | 56.705 | 26.308 | 1.00 | 64.73 | AP2 |

FIG. 3A-66

| ATOM | 3755 | N   | GLY | 66 | 14.198 | 57.814 | 25.813 | 1.00 | 65.45 | AP2 |
|------|------|-----|-----|----|--------|--------|--------|------|-------|-----|
| ATOM | 3756 | CA  | GLY | 66 | 13.488 | 59.043 | 25.533 | 1.00 | 65.51 | AP2 |
| ATOM | 3757 | C   | GLY | 66 | 12.603 | 58.856 | 24.320 | 1.00 | 65.64 | AP2 |
| ATOM | 3758 | O   | GLY | 66 | 11.508 | 59.419 | 24.261 | 1.00 | 65.65 | AP2 |
| ATOM | 3759 | N   | ASP | 67 | 13.085 | 58.078 | 23.347 | 1.00 | 65.58 | AP2 |
| ATOM | 3760 | CA  | ASP | 67 | 12.322 | 57.797 | 22.139 | 1.00 | 65.56 | AP2 |
| ATOM | 3761 | CB  | ASP | 67 | 13.137 | 56.932 | 21.176 | 1.00 | 66.26 | AP2 |
| ATOM | 3762 | CG  | ASP | 67 | 14.045 | 57.744 | 20.277 | 1.00 | 66.73 | AP2 |
| ATOM | 3763 | OD1 | ASP | 67 | 14.975 | 57.140 | 19.697 | 1.00 | 66.67 | AP2 |
| ATOM | 3764 | OD2 | ASP | 67 | 13.822 | 58.972 | 20.141 | 1.00 | 67.11 | AP2 |
| ATOM | 3765 | C   | ASP | 67 | 11.076 | 57.037 | 22.548 | 1.00 | 65.28 | AP2 |
| ATOM | 3766 | O   | ASP | 67 | 9.992  | 57.248 | 22.002 | 1.00 | 65.07 | AP2 |
| ATOM | 3767 | N   | ALA | 68 | 11.246 | 56.136 | 23.511 | 1.00 | 65.21 | AP2 |
| ATOM | 3768 | CA  | ALA | 68 | 10.136 | 55.333 | 24.014 | 1.00 | 65.16 | AP2 |
| ATOM | 3769 | CB  | ALA | 68 | 10.649 | 54.312 | 25.014 | 1.00 | 64.87 | AP2 |
| ATOM | 3770 | C   | ALA | 68 | 9.122  | 56.259 | 24.670 | 1.00 | 65.09 | AP2 |
| ATOM | 3771 | O   | ALA | 68 | 7.935  | 56.235 | 24.355 | 1.00 | 64.84 | AP2 |
| ATOM | 3772 | N   | VAL | 69 | 9.611  | 57.096 | 25.570 | 1.00 | 65.44 | AP2 |
| ATOM | 3773 | CA  | VAL | 69 | 8.762  | 58.038 | 26.271 | 1.00 | 65.98 | AP2 |
| ATOM | 3774 | CB  | VAL | 69 | 9.615  | 58.912 | 27.239 | 1.00 | 66.24 | AP2 |
| ATOM | 3775 | CG1 | VAL | 69 | 8.723  | 59.905 | 27.975 | 1.00 | 66.37 | AP2 |
| ATOM | 3776 | CG2 | VAL | 69 | 10.340 | 58.011 | 28.258 | 1.00 | 66.23 | AP2 |
| ATOM | 3777 | C   | VAL | 69 | 8.010  | 58.911 | 25.261 | 1.00 | 66.16 | AP2 |
| ATOM | 3778 | O   | VAL | 69 | 6.786  | 59.030 | 25.314 | 1.00 | 66.01 | AP2 |
| ATOM | 3779 | N   | ASN | 70 | 8.738  | 59.491 | 24.318 | 1.00 | 66.66 | AP2 |
| ATOM | 3780 | CA  | ASN | 70 | 8.119  | 60.343 | 23.304 | 1.00 | 67.53 | AP2 |
| ATOM | 3781 | CB  | ASN | 70 | 9.173  | 60.910 | 22.360 | 1.00 | 67.86 | AP2 |
| ATOM | 3782 | CG  | ASN | 70 | 9.775  | 62.168 | 22.887 | 1.00 | 68.32 | AP2 |
| ATOM | 3783 | OD1 | ASN | 70 | 9.102  | 62.932 | 23.581 | 1.00 | 68.33 | AP2 |
| ATOM | 3784 | ND2 | ASN | 70 | 11.040 | 62.412 | 22.561 | 1.00 | 68.72 | AP2 |
| ATOM | 3785 | C   | ASN | 70 | 7.041  | 59.667 | 22.472 | 1.00 | 67.96 | AP2 |
| ATOM | 3786 | O   | ASN | 70 | 6.031  | 60.300 | 22.118 | 1.00 | 67.43 | AP2 |
| ATOM | 3787 | N   | TYR | 71 | 7.275  | 58.395 | 22.141 | 1.00 | 68.35 | AP2 |
| ATOM | 3788 | CA  | TYR | 71 | 6.321  | 57.643 | 21.357 | 1.00 | 68.79 | AP2 |
| ATOM | 3789 | CB  | TYR | 71 | 6.846  | 56.259 | 21.032 | 1.00 | 68.30 | AP2 |
| ATOM | 3790 | CG  | TYR | 71 | 5.923  | 55.514 | 20.104 | 1.00 | 68.05 | AP2 |
| ATOM | 3791 | CD1 | TYR | 71 | 4.870  | 54.753 | 20.601 | 1.00 | 67.75 | AP2 |
| ATOM | 3792 | CE1 | TYR | 71 | 4.015  | 54.060 | 19.743 | 1.00 | 67.76 | AP2 |
| ATOM | 3793 | CD2 | TYR | 71 | 6.095  | 55.574 | 18.724 | 1.00 | 67.68 | AP2 |
| ATOM | 3794 | CE2 | TYR | 71 | 5.244  | 54.891 | 17.862 | 1.00 | 67.56 | AP2 |
| ATOM | 3795 | CZ  | TYR | 71 | 4.209  | 54.130 | 18.375 | 1.00 | 67.54 | AP2 |
| ATOM | 3796 | OH  | TYR | 71 | 3.398  | 53.405 | 17.526 | 1.00 | 67.12 | AP2 |
| ATOM | 3797 | C   | TYR | 71 | 5.050  | 57.547 | 22.167 | 1.00 | 69.54 | AP2 |
| ATOM | 3798 | O   | TYR | 71 | 3.972  | 57.833 | 21.665 | 1.00 | 69.15 | AP2 |
| ATOM | 3799 | N   | ILE | 72 | 5.178  | 57.137 | 23.421 | 1.00 | 70.67 | AP2 |
| ATOM | 3800 | CA  | ILE | 72 | 4.019  | 57.064 | 24.291 | 1.00 | 72.16 | AP2 |
| ATOM | 3801 | CB  | ILE | 72 | 4.409  | 56.482 | 25.638 | 1.00 | 71.69 | AP2 |
| ATOM | 3802 | CG2 | ILE | 72 | 3.192  | 56.337 | 26.507 | 1.00 | 71.53 | AP2 |
| ATOM | 3803 | CG1 | ILE | 72 | 5.075  | 55.120 | 25.433 | 1.00 | 71.64 | AP2 |
| ATOM | 3804 | CD1 | ILE | 72 | 5.828  | 54.632 | 26.651 | 1.00 | 70.95 | AP2 |
| ATOM | 3805 | C   | ILE | 72 | 3.613  | 58.528 | 24.461 | 1.00 | 73.58 | AP2 |
| ATOM | 3806 | O   | ILE | 72 | 4.055  | 59.183 | 25.401 | 1.00 | 73.89 | AP2 |
| ATOM | 3807 | N   | GLN | 73 | 2.811  | 59.025 | 23.510 | 1.00 | 74.98 | AP2 |
| ATOM | 3808 | CA  | GLN | 73 | 2.308  | 60.418 | 23.421 | 1.00 | 75.56 | AP2 |
| ATOM | 3809 | CB  | GLN | 73 | 3.282  | 61.415 | 24.068 | 1.00 | 76.72 | AP2 |
| ATOM | 3810 | CG  | GLN | 73 | 3.248  | 61.493 | 25.597 | 1.00 | 78.78 | AP2 |
| ATOM | 3811 | CD  | GLN | 73 | 4.435  | 62.272 | 26.189 | 1.00 | 79.69 | AP2 |

FIG. 3A-67

| ATOM | 3812 | OE1 | GLN | 73 | 4.730 | 63.398 | 25.764 | 1.00 | 80.13 | AP2 |
| --- | --- | --- | --- | --- | --- | --- | --- | --- | --- | --- |
| ATOM | 3813 | NE2 | GLN | 73 | 5.100 | 61.685 | 27.188 | 1.00 | 79.77 | AP2 |
| ATOM | 3814 | C | GLN | 73 | 2.171 | 60.766 | 21.921 | 1.00 | 75.34 | AP2 |
| ATOM | 3815 | OT1 | GLN | 73 | 1.145 | 60.381 | 21.304 | 1.00 | 74.80 | AP2 |
| ATOM | 3816 | OT2 | GLN | 73 | 3.114 | 61.391 | 21.370 | 1.00 | 75.08 | AP2 |
| ATOM | 3817 | CB | ALA | 1 | 1.800 | -6.041 | 21.213 | 1.00 | 80.30 | AP3 |
| ATOM | 3818 | C | ALA | 1 | 2.577 | -6.903 | 23.453 | 1.00 | 80.06 | AP3 |
| ATOM | 3819 | O | ALA | 1 | 2.622 | -5.935 | 24.217 | 1.00 | 80.11 | AP3 |
| ATOM | 3820 | N | ALA | 1 | 0.099 | -6.809 | 22.864 | 1.00 | 80.88 | AP3 |
| ATOM | 3821 | CA | ALA | 1 | 1.493 | -7.021 | 22.374 | 1.00 | 80.41 | AP3 |
| ATOM | 3822 | N | ASP | 2 | 3.439 | -7.912 | 23.516 | 1.00 | 79.63 | AP3 |
| ATOM | 3823 | CA | ASP | 2 | 4.556 | -7.909 | 24.444 | 1.00 | 79.28 | AP3 |
| ATOM | 3824 | CB | ASP | 2 | 4.998 | -9.318 | 24.788 | 1.00 | 78.93 | AP3 |
| ATOM | 3825 | CG | ASP | 2 | 6.087 | -9.342 | 25.821 | 1.00 | 78.75 | AP3 |
| ATOM | 3826 | OD1 | ASP | 2 | 5.841 | -8.839 | 26.940 | 1.00 | 78.53 | AP3 |
| ATOM | 3827 | OD2 | ASP | 2 | 7.181 | -9.868 | 25.520 | 1.00 | 78.56 | AP3 |
| ATOM | 3828 | C | ASP | 2 | 5.634 | -7.256 | 23.609 | 1.00 | 79.40 | AP3 |
| ATOM | 3829 | O | ASP | 2 | 6.715 | -6.942 | 24.100 | 1.00 | 79.66 | AP3 |
| ATOM | 3830 | N | THR | 3 | 5.337 | -7.089 | 22.322 | 1.00 | 78.88 | AP3 |
| ATOM | 3831 | CA | THR | 3 | 6.260 | -6.440 | 21.413 | 1.00 | 78.63 | AP3 |
| ATOM | 3832 | CB | THR | 3 | 5.832 | -6.637 | 19.947 | 1.00 | 77.90 | AP3 |
| ATOM | 3833 | OG1 | THR | 3 | 6.193 | -7.955 | 19.528 | 1.00 | 77.32 | AP3 |
| ATOM | 3834 | CG2 | THR | 3 | 6.513 | -5.630 | 19.039 | 1.00 | 77.44 | AP3 |
| ATOM | 3835 | C | THR | 3 | 6.239 | -4.957 | 21.783 | 1.00 | 79.14 | AP3 |
| ATOM | 3836 | O | THR | 3 | 7.285 | -4.310 | 21.858 | 1.00 | 79.19 | AP3 |
| ATOM | 3837 | N | LEU | 4 | 5.040 | -4.435 | 22.035 | 1.00 | 79.46 | AP3 |
| ATOM | 3838 | CA | LEU | 4 | 4.856 | -3.039 | 22.419 | 1.00 | 79.70 | AP3 |
| ATOM | 3839 | CB | LEU | 4 | 3.379 | -2.702 | 22.486 | 1.00 | 79.44 | AP3 |
| ATOM | 3840 | CG | LEU | 4 | 3.055 | -1.299 | 22.973 | 1.00 | 79.41 | AP3 |
| ATOM | 3841 | CD1 | LEU | 4 | 3.240 | -0.335 | 21.815 | 1.00 | 78.99 | AP3 |
| ATOM | 3842 | CD2 | LEU | 4 | 1.611 | -1.253 | 23.493 | 1.00 | 79.05 | AP3 |
| ATOM | 3843 | C | LEU | 4 | 5.458 | -2.832 | 23.792 | 1.00 | 79.95 | AP3 |
| ATOM | 3844 | O | LEU | 4 | 6.116 | -1.832 | 24.040 | 1.00 | 79.62 | AP3 |
| ATOM | 3845 | N | GLU | 5 | 5.220 | -3.789 | 24.682 | 1.00 | 80.50 | AP3 |
| ATOM | 3846 | CA | GLU | 5 | 5.744 | -3.725 | 26.043 | 1.00 | 81.25 | AP3 |
| ATOM | 3847 | CB | GLU | 5 | 5.352 | -4.988 | 26.828 | 1.00 | 82.17 | AP3 |
| ATOM | 3848 | CG | GLU | 5 | 4.862 | -4.727 | 28.256 | 1.00 | 83.74 | AP3 |
| ATOM | 3849 | CD | GLU | 5 | 3.754 | -3.667 | 28.302 | 1.00 | 84.88 | AP3 |
| ATOM | 3850 | OE1 | GLU | 5 | 2.717 | -3.846 | 27.619 | 1.00 | 85.02 | AP3 |
| ATOM | 3851 | OE2 | GLU | 5 | 3.921 | -2.649 | 29.016 | 1.00 | 85.43 | AP3 |
| ATOM | 3852 | C | GLU | 5 | 7.267 | -3.595 | 25.998 | 1.00 | 81.11 | AP3 |
| ATOM | 3853 | O | GLU | 5 | 7.869 | -2.915 | 26.835 | 1.00 | 81.30 | AP3 |
| ATOM | 3854 | N | ARG | 6 | 7.881 | -4.248 | 25.011 | 1.00 | 80.60 | AP3 |
| ATOM | 3855 | CA | ARG | 6 | 9.325 | -4.221 | 24.843 | 1.00 | 79.96 | AP3 |
| ATOM | 3856 | CB | ARG | 6 | 9.816 | -5.499 | 24.149 | 1.00 | 79.81 | AP3 |
| ATOM | 3857 | CG | ARG | 6 | 9.847 | -6.716 | 25.055 | 1.00 | 79.18 | AP3 |
| ATOM | 3858 | CD | ARG | 6 | 10.927 | -7.684 | 24.616 | 1.00 | 79.45 | AP3 |
| ATOM | 3859 | NE | ARG | 6 | 10.589 | -8.357 | 23.372 | 1.00 | 78.96 | AP3 |
| ATOM | 3860 | CZ | ARG | 6 | 11.448 | -9.047 | 22.629 | 1.00 | 78.97 | AP3 |
| ATOM | 3861 | NH1 | ARG | 6 | 12.713 | -9.163 | 22.991 | 1.00 | 79.03 | AP3 |
| ATOM | 3862 | NH2 | ARG | 6 | 11.038 | -9.629 | 21.514 | 1.00 | 79.17 | AP3 |
| ATOM | 3863 | C | ARG | 6 | 9.762 | -2.999 | 24.058 | 1.00 | 79.85 | AP3 |
| ATOM | 3864 | O | ARG | 6 | 10.894 | -2.527 | 24.204 | 1.00 | 79.66 | AP3 |
| ATOM | 3865 | N | VAL | 7 | 8.862 | -2.491 | 23.225 | 1.00 | 79.59 | AP3 |
| ATOM | 3866 | CA | VAL | 7 | 9.152 | -1.308 | 22.439 | 1.00 | 79.61 | AP3 |
| ATOM | 3867 | CB | VAL | 7 | 8.142 | -1.136 | 21.275 | 1.00 | 79.79 | AP3 |
| ATOM | 3868 | CG1 | VAL | 7 | 7.714 | 0.317 | 21.147 | 1.00 | 79.88 | AP3 |

FIG. 3A-68

| ATOM | 3869 | CG2 | VAL | 7 | 8.779 | -1.601 | 19.960 | 1.00 | 79.63 | AP3 |
| --- | --- | --- | --- | --- | --- | --- | --- | --- | --- | --- |
| ATOM | 3870 | C | VAL | 7 | 9.084 | -0.107 | 23.359 | 1.00 | 79.59 | AP3 |
| ATOM | 3871 | O | VAL | 7 | 9.918 | 0.788 | 23.282 | 1.00 | 79.69 | AP3 |
| ATOM | 3872 | N | THR | 8 | 8.099 | -0.104 | 24.246 | 1.00 | 79.81 | AP3 |
| ATOM | 3873 | CA | THR | 8 | 7.924 | 1.002 | 25.177 | 1.00 | 80.35 | AP3 |
| ATOM | 3874 | CB | THR | 8 | 6.535 | 0.924 | 25.869 | 1.00 | 80.28 | AP3 |
| ATOM | 3875 | OG1 | THR | 8 | 5.510 | 1.227 | 24.908 | 1.00 | 80.23 | AP3 |
| ATOM | 3876 | CG2 | THR | 8 | 6.440 | 1.913 | 27.020 | 1.00 | 80.18 | AP3 |
| ATOM | 3877 | C | THR | 8 | 9.048 | 1.087 | 26.214 | 1.00 | 80.61 | AP3 |
| ATOM | 3878 | O | THR | 8 | 9.490 | 2.180 | 26.567 | 1.00 | 80.23 | AP3 |
| ATOM | 3879 | N | LYS | 9 | 9.527 | -0.061 | 26.683 | 1.00 | 80.99 | AP3 |
| ATOM | 3880 | CA | LYS | 9 | 10.610 | -0.062 | 27.656 | 1.00 | 81.53 | AP3 |
| ATOM | 3881 | CB | LYS | 9 | 10.917 | -1.493 | 28.130 | 1.00 | 81.32 | AP3 |
| ATOM | 3882 | CG | LYS | 9 | 12.160 | -1.594 | 29.023 | 1.00 | 81.21 | AP3 |
| ATOM | 3883 | CD | LYS | 9 | 12.144 | -2.839 | 29.918 | 1.00 | 81.53 | AP3 |
| ATOM | 3884 | CE | LYS | 9 | 13.543 | -3.165 | 30.484 | 1.00 | 81.08 | AP3 |
| ATOM | 3885 | NZ | LYS | 9 | 14.162 | -2.051 | 31.270 | 1.00 | 80.56 | AP3 |
| ATOM | 3886 | C | LYS | 9 | 11.860 | 0.579 | 27.041 | 1.00 | 81.86 | AP3 |
| ATOM | 3887 | O | LYS | 9 | 12.609 | 1.287 | 27.715 | 1.00 | 82.11 | AP3 |
| ATOM | 3888 | N | ILE | 10 | 12.075 | 0.334 | 25.753 | 1.00 | 81.96 | AP3 |
| ATOM | 3889 | CA | ILE | 10 | 13.225 | 0.885 | 25.048 | 1.00 | 81.82 | AP3 |
| ATOM | 3890 | CB | ILE | 10 | 13.390 | 0.203 | 23.654 | 1.00 | 81.28 | AP3 |
| ATOM | 3891 | CG2 | ILE | 10 | 14.375 | 0.966 | 22.795 | 1.00 | 81.09 | AP3 |
| ATOM | 3892 | CG1 | ILE | 10 | 13.783 | -1.272 | 23.838 | 1.00 | 81.30 | AP3 |
| ATOM | 3893 | CD1 | ILE | 10 | 14.806 | -1.554 | 24.964 | 1.00 | 81.09 | AP3 |
| ATOM | 3894 | C | ILE | 10 | 13.093 | 2.401 | 24.871 | 1.00 | 82.11 | AP3 |
| ATOM | 3895 | O | ILE | 10 | 14.082 | 3.136 | 24.999 | 1.00 | 81.77 | AP3 |
| ATOM | 3896 | N | ILE | 11 | 11.867 | 2.849 | 24.589 | 1.00 | 82.41 | AP3 |
| ATOM | 3897 | CA | ILE | 11 | 11.562 | 4.262 | 24.368 | 1.00 | 82.78 | AP3 |
| ATOM | 3898 | CB | ILE | 11 | 10.186 | 4.426 | 23.670 | 1.00 | 82.33 | AP3 |
| ATOM | 3899 | CG2 | ILE | 11 | 9.797 | 5.896 | 23.575 | 1.00 | 82.07 | AP3 |
| ATOM | 3900 | CG1 | ILE | 11 | 10.255 | 3.827 | 22.270 | 1.00 | 82.32 | AP3 |
| ATOM | 3901 | CD1 | ILE | 11 | 8.945 | 3.876 | 21.506 | 1.00 | 82.44 | AP3 |
| ATOM | 3902 | C | ILE | 11 | 11.568 | 5.098 | 25.644 | 1.00 | 83.30 | AP3 |
| ATOM | 3903 | O | ILE | 11 | 11.935 | 6.269 | 25.620 | 1.00 | 83.45 | AP3 |
| ATOM | 3904 | N | VAL | 12 | 11.164 | 4.501 | 26.760 | 1.00 | 83.91 | AP3 |
| ATOM | 3905 | CA | VAL | 12 | 11.127 | 5.227 | 28.019 | 1.00 | 84.43 | AP3 |
| ATOM | 3906 | CB | VAL | 12 | 10.158 | 4.540 | 29.031 | 1.00 | 84.31 | AP3 |
| ATOM | 3907 | CG1 | VAL | 12 | 10.373 | 5.070 | 30.435 | 1.00 | 84.17 | AP3 |
| ATOM | 3908 | CG2 | VAL | 12 | 8.724 | 4.811 | 28.623 | 1.00 | 84.03 | AP3 |
| ATOM | 3909 | C | VAL | 12 | 12.520 | 5.340 | 28.619 | 1.00 | 84.94 | AP3 |
| ATOM | 3910 | O | VAL | 12 | 12.701 | 5.944 | 29.678 | 1.00 | 85.35 | AP3 |
| ATOM | 3911 | N | ASP | 13 | 13.513 | 4.783 | 27.936 | 1.00 | 85.34 | AP3 |
| ATOM | 3912 | CA | ASP | 13 | 14.878 | 4.833 | 28.454 | 1.00 | 86.04 | AP3 |
| ATOM | 3913 | CB | ASP | 13 | 15.334 | 3.420 | 28.853 | 1.00 | 86.48 | AP3 |
| ATOM | 3914 | CG | ASP | 13 | 14.386 | 2.767 | 29.869 | 1.00 | 87.14 | AP3 |
| ATOM | 3915 | OD1 | ASP | 13 | 13.717 | 3.520 | 30.620 | 1.00 | 87.08 | AP3 |
| ATOM | 3916 | OD2 | ASP | 13 | 14.317 | 1.511 | 29.929 | 1.00 | 87.02 | AP3 |
| ATOM | 3917 | C | ASP | 13 | 15.878 | 5.476 | 27.490 | 1.00 | 86.16 | AP3 |
| ATOM | 3918 | O | ASP | 13 | 17.056 | 5.644 | 27.812 | 1.00 | 86.06 | AP3 |
| ATOM | 3919 | N | ARG | 14 | 15.395 | 5.850 | 26.313 | 1.00 | 86.23 | AP3 |
| ATOM | 3920 | CA | ARG | 14 | 16.233 | 6.481 | 25.310 | 1.00 | 86.55 | AP3 |
| ATOM | 3921 | CB | ARG | 14 | 16.109 | 5.733 | 23.987 | 1.00 | 86.57 | AP3 |
| ATOM | 3922 | CG | ARG | 14 | 16.725 | 4.339 | 23.997 | 1.00 | 86.67 | AP3 |
| ATOM | 3923 | CD | ARG | 14 | 18.206 | 4.391 | 23.645 | 1.00 | 86.53 | AP3 |
| ATOM | 3924 | NE | ARG | 14 | 19.027 | 5.031 | 24.669 | 1.00 | 86.50 | AP3 |
| ATOM | 3925 | CZ | ARG | 14 | 19.365 | 4.472 | 25.828 | 1.00 | 86.59 | AP3 |

FIG. 3A-69

| ATOM | 3926 | NH1 | ARG | 14 | 18.960 | 3.245 | 26.142 | 1.00 | 86.74 | AP3 |
| ATOM | 3927 | NH2 | ARG | 14 | 20.117 | 5.145 | 26.682 | 1.00 | 86.67 | AP3 |
| ATOM | 3928 | C | ARG | 14 | 15.761 | 7.914 | 25.143 | 1.00 | 86.71 | AP3 |
| ATOM | 3929 | O | ARG | 14 | 16.544 | 8.812 | 24.823 | 1.00 | 86.83 | AP3 |
| ATOM | 3930 | N | LEU | 15 | 14.468 | 8.111 | 25.371 | 1.00 | 86.78 | AP3 |
| ATOM | 3931 | CA | LEU | 15 | 13.847 | 9.419 | 25.263 | 1.00 | 87.14 | AP3 |
| ATOM | 3932 | CB | LEU | 15 | 12.632 | 9.351 | 24.343 | 1.00 | 86.46 | AP3 |
| ATOM | 3933 | CG | LEU | 15 | 12.945 | 9.019 | 22.895 | 1.00 | 85.94 | AP3 |
| ATOM | 3934 | CD1 | LEU | 15 | 11.689 | 9.228 | 22.079 | 1.00 | 86.10 | AP3 |
| ATOM | 3935 | CD2 | LEU | 15 | 14.064 | 9.913 | 22.386 | 1.00 | 85.45 | AP3 |
| ATOM | 3936 | C | LEU | 15 | 13.421 | 9.930 | 26.634 | 1.00 | 87.71 | AP3 |
| ATOM | 3937 | O | LEU | 15 | 13.111 | 11.111 | 26.798 | 1.00 | 87.66 | AP3 |
| ATOM | 3938 | N | GLY | 16 | 13.401 | 9.028 | 27.609 | 1.00 | 88.38 | AP3 |
| ATOM | 3939 | CA | GLY | 16 | 13.024 | 9.387 | 28.962 | 1.00 | 89.57 | AP3 |
| ATOM | 3940 | C | GLY | 16 | 11.685 | 10.083 | 29.141 | 1.00 | 90.52 | AP3 |
| ATOM | 3941 | O | GLY | 16 | 11.634 | 11.185 | 29.686 | 1.00 | 90.64 | AP3 |
| ATOM | 3942 | N | VAL | 17 | 10.606 | 9.456 | 28.680 | 1.00 | 91.37 | AP3 |
| ATOM | 3943 | CA | VAL | 17 | 9.260 | 10.011 | 28.830 | 1.00 | 92.27 | AP3 |
| ATOM | 3944 | CB | VAL | 17 | 8.411 | 9.821 | 27.510 | 1.00 | 92.11 | AP3 |
| ATOM | 3945 | CG1 | VAL | 17 | 8.673 | 10.969 | 26.535 | 1.00 | 91.59 | AP3 |
| ATOM | 3946 | CG2 | VAL | 17 | 8.763 | 8.495 | 26.833 | 1.00 | 91.92 | AP3 |
| ATOM | 3947 | C | VAL | 17 | 8.617 | 9.272 | 30.025 | 1.00 | 93.10 | AP3 |
| ATOM | 3948 | O | VAL | 17 | 9.327 | 8.596 | 30.778 | 1.00 | 93.19 | AP3 |
| ATOM | 3949 | N | ASP | 18 | 7.302 | 9.407 | 30.219 | 1.00 | 94.20 | AP3 |
| ATOM | 3950 | CA | ASP | 18 | 6.603 | 8.720 | 31.325 | 1.00 | 95.26 | AP3 |
| ATOM | 3951 | CB | ASP | 18 | 5.262 | 9.404 | 31.641 | 1.00 | 95.83 | AP3 |
| ATOM | 3952 | CG | ASP | 18 | 5.430 | 10.780 | 32.271 | 1.00 | 96.39 | AP3 |
| ATOM | 3953 | OD1 | ASP | 18 | 6.051 | 10.865 | 33.360 | 1.00 | 96.57 | AP3 |
| ATOM | 3954 | OD2 | ASP | 18 | 4.936 | 11.774 | 31.679 | 1.00 | 96.48 | AP3 |
| ATOM | 3955 | C | ASP | 18 | 6.331 | 7.258 | 30.951 | 1.00 | 95.69 | AP3 |
| ATOM | 3956 | O | ASP | 18 | 7.187 | 6.389 | 31.122 | 1.00 | 96.20 | AP3 |
| ATOM | 3957 | N | GLU | 19 | 5.122 | 6.990 | 30.469 | 1.00 | 95.81 | AP3 |
| ATOM | 3958 | CA | GLU | 19 | 4.741 | 5.654 | 30.025 | 1.00 | 95.73 | AP3 |
| ATOM | 3959 | CB | GLU | 19 | 4.592 | 4.669 | 31.179 | 1.00 | 95.35 | AP3 |
| ATOM | 3960 | CG | GLU | 19 | 4.271 | 3.268 | 30.674 | 1.00 | 94.53 | AP3 |
| ATOM | 3961 | CD | GLU | 19 | 4.963 | 2.186 | 31.467 | 1.00 | 94.17 | AP3 |
| ATOM | 3962 | OE1 | GLU | 19 | 6.103 | 2.413 | 31.924 | 1.00 | 93.98 | AP3 |
| ATOM | 3963 | OE2 | GLU | 19 | 4.374 | 1.100 | 31.617 | 1.00 | 93.93 | AP3 |
| ATOM | 3964 | C | GLU | 19 | 3.432 | 5.744 | 29.279 | 1.00 | 95.95 | AP3 |
| ATOM | 3965 | O | GLU | 19 | 3.344 | 5.344 | 28.120 | 1.00 | 96.20 | AP3 |
| ATOM | 3966 | N | ALA | 20 | 2.405 | 6.265 | 29.938 | 1.00 | 96.02 | AP3 |
| ATOM | 3967 | CA | ALA | 20 | 1.123 | 6.407 | 29.269 | 1.00 | 96.23 | AP3 |
| ATOM | 3968 | CB | ALA | 20 | 0.082 | 6.948 | 30.227 | 1.00 | 96.45 | AP3 |
| ATOM | 3969 | C | ALA | 20 | 1.361 | 7.383 | 28.123 | 1.00 | 96.14 | AP3 |
| ATOM | 3970 | O | ALA | 20 | 0.504 | 7.580 | 27.255 | 1.00 | 96.23 | AP3 |
| ATOM | 3971 | N | ASP | 21 | 2.548 | 7.987 | 28.142 | 1.00 | 95.88 | AP3 |
| ATOM | 3972 | CA | ASP | 21 | 2.972 | 8.934 | 27.120 | 1.00 | 95.67 | AP3 |
| ATOM | 3973 | CB | ASP | 21 | 4.335 | 9.526 | 27.494 | 1.00 | 95.98 | AP3 |
| ATOM | 3974 | CG | ASP | 21 | 4.226 | 10.896 | 28.144 | 1.00 | 96.43 | AP3 |
| ATOM | 3975 | OD1 | ASP | 21 | 3.313 | 11.079 | 28.979 | 1.00 | 96.41 | AP3 |
| ATOM | 3976 | OD2 | ASP | 21 | 5.064 | 11.783 | 27.831 | 1.00 | 96.37 | AP3 |
| ATOM | 3977 | C | ASP | 21 | 3.093 | 8.192 | 25.798 | 1.00 | 95.36 | AP3 |
| ATOM | 3978 | O | ASP | 21 | 2.740 | 8.720 | 24.740 | 1.00 | 95.36 | AP3 |
| ATOM | 3979 | N | VAL | 22 | 3.593 | 6.959 | 25.877 | 1.00 | 95.01 | AP3 |
| ATOM | 3980 | CA | VAL | 22 | 3.802 | 6.107 | 24.706 | 1.00 | 94.72 | AP3 |
| ATOM | 3981 | CB | VAL | 22 | 4.975 | 5.105 | 24.935 | 1.00 | 94.84 | AP3 |
| ATOM | 3982 | CG1 | VAL | 22 | 5.062 | 4.115 | 23.777 | 1.00 | 94.84 | AP3 |

FIG. 3A-70

| ATOM | 3983 | CG2 | VAL | 22 | 6.294 | 5.861 | 25.076 | 1.00 | 95.01 | AP3 |
| ATOM | 3984 | C | VAL | 22 | 2.580 | 5.297 | 24.301 | 1.00 | 94.29 | AP3 |
| ATOM | 3985 | O | VAL | 22 | 2.334 | 4.225 | 24.843 | 1.00 | 94.13 | AP3 |
| ATOM | 3986 | N | LYS | 23 | 1.822 | 5.815 | 23.343 | 1.00 | 94.07 | AP3 |
| ATOM | 3987 | CA | LYS | 23 | 0.642 | 5.120 | 22.847 | 1.00 | 93.68 | AP3 |
| ATOM | 3988 | CB | LYS | 23 | -0.524 | 6.087 | 22.694 | 1.00 | 93.74 | AP3 |
| ATOM | 3989 | C | LYS | 23 | 1.046 | 4.550 | 21.498 | 1.00 | 93.39 | AP3 |
| ATOM | 3990 | O | LYS | 23 | 2.170 | 4.759 | 21.050 | 1.00 | 93.48 | AP3 |
| ATOM | 3991 | N | LEU | 24 | 0.134 | 3.842 | 20.846 | 1.00 | 93.12 | AP3 |
| ATOM | 3992 | CA | LEU | 24 | 0.438 | 3.233 | 19.557 | 1.00 | 92.79 | AP3 |
| ATOM | 3993 | CB | LEU | 24 | -0.584 | 2.123 | 19.247 | 1.00 | 92.55 | AP3 |
| ATOM | 3994 | CG | LEU | 24 | -0.066 | 0.793 | 18.668 | 1.00 | 92.42 | AP3 |
| ATOM | 3995 | CD1 | LEU | 24 | 0.765 | 0.040 | 19.714 | 1.00 | 91.85 | AP3 |
| ATOM | 3996 | CD2 | LEU | 24 | -1.248 | -0.060 | 18.216 | 1.00 | 92.20 | AP3 |
| ATOM | 3997 | C | LEU | 24 | 0.489 | 4.239 | 18.405 | 1.00 | 92.49 | AP3 |
| ATOM | 3998 | O | LEU | 24 | 1.330 | 4.135 | 17.522 | 1.00 | 92.33 | AP3 |
| ATOM | 3999 | N | GLU | 25 | -0.400 | 5.219 | 18.407 | 1.00 | 92.48 | AP3 |
| ATOM | 4000 | CA | GLU | 25 | -0.389 | 6.189 | 17.325 | 1.00 | 92.80 | AP3 |
| ATOM | 4001 | CB | GLU | 25 | -1.810 | 6.654 | 17.015 | 1.00 | 93.44 | AP3 |
| ATOM | 4002 | CG | GLU | 25 | -2.765 | 5.516 | 16.729 | 1.00 | 94.57 | AP3 |
| ATOM | 4003 | CD | GLU | 25 | -4.153 | 6.007 | 16.407 | 1.00 | 95.36 | AP3 |
| ATOM | 4004 | OE1 | GLU | 25 | -4.514 | 7.089 | 16.930 | 1.00 | 95.95 | AP3 |
| ATOM | 4005 | OE2 | GLU | 25 | -4.879 | 5.311 | 15.650 | 1.00 | 95.66 | AP3 |
| ATOM | 4006 | C | GLU | 25 | 0.493 | 7.391 | 17.655 | 1.00 | 92.51 | AP3 |
| ATOM | 4007 | O | GLU | 25 | 0.436 | 8.419 | 16.973 | 1.00 | 92.63 | AP3 |
| ATOM | 4008 | N | ALA | 26 | 1.311 | 7.262 | 18.697 | 1.00 | 91.90 | AP3 |
| ATOM | 4009 | CA | ALA | 26 | 2.200 | 8.346 | 19.093 | 1.00 | 91.28 | AP3 |
| ATOM | 4010 | CB | ALA | 26 | 2.729 | 8.101 | 20.505 | 1.00 | 90.92 | AP3 |
| ATOM | 4011 | C | ALA | 26 | 3.360 | 8.459 | 18.100 | 1.00 | 91.07 | AP3 |
| ATOM | 4012 | O | ALA | 26 | 4.005 | 7.459 | 17.769 | 1.00 | 91.02 | AP3 |
| ATOM | 4013 | N | SER | 27 | 3.602 | 9.674 | 17.605 | 1.00 | 90.75 | AP3 |
| ATOM | 4014 | CA | SER | 27 | 4.702 | 9.924 | 16.666 | 1.00 | 90.16 | AP3 |
| ATOM | 4015 | CB | SER | 27 | 4.460 | 11.190 | 15.826 | 1.00 | 90.40 | AP3 |
| ATOM | 4016 | OG | SER | 27 | 5.623 | 11.544 | 15.080 | 1.00 | 90.09 | AP3 |
| ATOM | 4017 | C | SER | 27 | 6.001 | 10.095 | 17.427 | 1.00 | 89.59 | AP3 |
| ATOM | 4018 | O | SER | 27 | 6.040 | 10.694 | 18.501 | 1.00 | 89.05 | AP3 |
| ATOM | 4019 | N | PHE | 28 | 7.069 | 9.566 | 16.857 | 1.00 | 89.40 | AP3 |
| ATOM | 4020 | CA | PHE | 28 | 8.364 | 9.671 | 17.488 | 1.00 | 89.33 | AP3 |
| ATOM | 4021 | CB | PHE | 28 | 9.377 | 8.800 | 16.740 | 1.00 | 88.83 | AP3 |
| ATOM | 4022 | CG | PHE | 28 | 9.274 | 7.333 | 17.065 | 1.00 | 87.80 | AP3 |
| ATOM | 4023 | CD1 | PHE | 28 | 9.394 | 6.891 | 18.382 | 1.00 | 87.34 | AP3 |
| ATOM | 4024 | CD2 | PHE | 28 | 9.061 | 6.399 | 16.061 | 1.00 | 87.22 | AP3 |
| ATOM | 4025 | CE1 | PHE | 28 | 9.306 | 5.545 | 18.697 | 1.00 | 86.85 | AP3 |
| ATOM | 4026 | CE2 | PHE | 28 | 8.971 | 5.049 | 16.368 | 1.00 | 87.12 | AP3 |
| ATOM | 4027 | CZ | PHE | 28 | 9.095 | 4.624 | 17.693 | 1.00 | 86.87 | AP3 |
| ATOM | 4028 | C | PHE | 28 | 8.835 | 11.121 | 17.543 | 1.00 | 89.67 | AP3 |
| ATOM | 4029 | O | PHE | 28 | 9.341 | 11.566 | 18.573 | 1.00 | 89.45 | AP3 |
| ATOM | 4030 | N | LYS | 29 | 8.652 | 11.865 | 16.451 | 1.00 | 90.18 | AP3 |
| ATOM | 4031 | CA | LYS | 29 | 9.095 | 13.263 | 16.417 | 1.00 | 90.72 | AP3 |
| ATOM | 4032 | CB | LYS | 29 | 9.453 | 13.681 | 14.986 | 1.00 | 90.81 | AP3 |
| ATOM | 4033 | CG | LYS | 29 | 10.959 | 13.633 | 14.692 | 1.00 | 90.99 | AP3 |
| ATOM | 4034 | CD | LYS | 29 | 11.237 | 13.776 | 13.195 | 1.00 | 91.39 | AP3 |
| ATOM | 4035 | CE | LYS | 29 | 12.690 | 13.466 | 12.840 | 1.00 | 91.39 | AP3 |
| ATOM | 4036 | NZ | LYS | 29 | 12.835 | 13.201 | 11.371 | 1.00 | 91.17 | AP3 |
| ATOM | 4037 | C | LYS | 29 | 8.115 | 14.268 | 17.001 | 1.00 | 90.70 | AP3 |
| ATOM | 4038 | O | LYS | 29 | 8.477 | 15.063 | 17.869 | 1.00 | 90.68 | AP3 |
| ATOM | 4039 | N | GLU | 30 | 6.875 | 14.214 | 16.528 | 1.00 | 90.93 | AP3 |

FIG. 3A-71

| | | | | | | | | | |
|---|---|---|---|---|---|---|---|---|---|
| ATOM | 4040 | CA | GLU | 30 | 5.820 | 15.131 | 16.961 | 1.00 90.95 | AP3 |
| ATOM | 4041 | CB | GLU | 30 | 4.680 | 15.046 | 15.936 | 1.00 91.42 | AP3 |
| ATOM | 4042 | CG | GLU | 30 | 5.175 | 15.444 | 14.528 | 1.00 93.07 | AP3 |
| ATOM | 4043 | CD | GLU | 30 | 6.132 | 16.654 | 14.488 | 1.00 93.86 | AP3 |
| ATOM | 4044 | OE1 | GLU | 30 | 6.077 | 17.504 | 15.408 | 1.00 94.24 | AP3 |
| ATOM | 4045 | OE2 | GLU | 30 | 6.921 | 16.768 | 13.512 | 1.00 94.24 | AP3 |
| ATOM | 4046 | C | GLU | 30 | 5.295 | 15.001 | 18.406 | 1.00 90.36 | AP3 |
| ATOM | 4047 | O | GLU | 30 | 5.120 | 16.014 | 19.091 | 1.00 90.24 | AP3 |
| ATOM | 4048 | N | ASP | 31 | 5.073 | 13.771 | 18.875 | 1.00 89.92 | AP3 |
| ATOM | 4049 | CA | ASP | 31 | 4.547 | 13.519 | 20.232 | 1.00 89.32 | AP3 |
| ATOM | 4050 | CB | ASP | 31 | 3.481 | 12.396 | 20.207 | 1.00 89.62 | AP3 |
| ATOM | 4051 | CG | ASP | 31 | 2.159 | 12.822 | 19.558 | 1.00 89.86 | AP3 |
| ATOM | 4052 | OD1 | ASP | 31 | 1.483 | 13.725 | 20.107 | 1.00 90.00 | AP3 |
| ATOM | 4053 | OD2 | ASP | 31 | 1.790 | 12.243 | 18.504 | 1.00 89.74 | AP3 |
| ATOM | 4054 | C | ASP | 31 | 5.598 | 13.141 | 21.286 | 1.00 88.79 | AP3 |
| ATOM | 4055 | O | ASP | 31 | 5.439 | 13.436 | 22.471 | 1.00 88.28 | AP3 |
| ATOM | 4056 | N | LEU | 32 | 6.662 | 12.467 | 20.864 | 1.00 88.48 | AP3 |
| ATOM | 4057 | CA | LEU | 32 | 7.696 | 12.039 | 21.808 | 1.00 88.08 | AP3 |
| ATOM | 4058 | CB | LEU | 32 | 8.178 | 10.628 | 21.443 | 1.00 88.20 | AP3 |
| ATOM | 4059 | CG | LEU | 32 | 7.092 | 9.545 | 21.393 | 1.00 88.29 | AP3 |
| ATOM | 4060 | CD1 | LEU | 32 | 7.714 | 8.208 | 21.024 | 1.00 88.43 | AP3 |
| ATOM | 4061 | CD2 | LEU | 32 | 6.399 | 9.453 | 22.747 | 1.00 88.22 | AP3 |
| ATOM | 4062 | C | LEU | 32 | 8.886 | 13.002 | 21.878 | 1.00 87.67 | AP3 |
| ATOM | 4063 | O | LEU | 32 | 9.632 | 13.015 | 22.877 | 1.00 87.89 | AP3 |
| ATOM | 4064 | N | GLY | 33 | 9.059 | 13.793 | 20.816 | 1.00 86.61 | AP3 |
| ATOM | 4065 | CA | GLY | 33 | 10.138 | 14.763 | 20.766 | 1.00 85.37 | AP3 |
| ATOM | 4066 | C | GLY | 33 | 11.502 | 14.142 | 20.557 | 1.00 84.27 | AP3 |
| ATOM | 4067 | O | GLY | 33 | 12.447 | 14.401 | 21.311 | 1.00 84.12 | AP3 |
| ATOM | 4068 | N | ALA | 34 | 11.595 | 13.307 | 19.532 | 1.00 83.28 | AP3 |
| ATOM | 4069 | CA | ALA | 34 | 12.843 | 12.649 | 19.198 | 1.00 82.21 | AP3 |
| ATOM | 4070 | CB | ALA | 34 | 12.614 | 11.151 | 18.992 | 1.00 81.82 | AP3 |
| ATOM | 4071 | C | ALA | 34 | 13.410 | 13.279 | 17.933 | 1.00 81.35 | AP3 |
| ATOM | 4072 | O | ALA | 34 | 12.691 | 13.478 | 16.953 | 1.00 81.03 | AP3 |
| ATOM | 4073 | N | ASP | 35 | 14.698 | 13.606 | 17.971 | 1.00 80.45 | AP3 |
| ATOM | 4074 | CA | ASP | 35 | 15.348 | 14.198 | 16.818 | 1.00 79.95 | AP3 |
| ATOM | 4075 | CB | ASP | 35 | 16.295 | 15.343 | 17.224 | 1.00 79.22 | AP3 |
| ATOM | 4076 | CG | ASP | 35 | 17.324 | 14.928 | 18.258 | 1.00 79.03 | AP3 |
| ATOM | 4077 | OD1 | ASP | 35 | 17.556 | 13.710 | 18.421 | 1.00 78.87 | AP3 |
| ATOM | 4078 | OD2 | ASP | 35 | 17.914 | 15.829 | 18.902 | 1.00 78.65 | AP3 |
| ATOM | 4079 | C | ASP | 35 | 16.117 | 13.146 | 16.049 | 1.00 79.63 | AP3 |
| ATOM | 4080 | O | ASP | 35 | 16.163 | 11.983 | 16.446 | 1.00 79.61 | AP3 |
| ATOM | 4081 | CA | PAN | 36 | 17.510 | 12.743 | 14.053 | 1.00 79.08 | AP3 |
| ATOM | 4082 | N | PAN | 36 | 16.721 | 13.582 | 14.947 | 1.00 79.50 | AP3 |
| ATOM | 4083 | C | PAN | 36 | 18.515 | 11.845 | 14.766 | 1.00 77.61 | AP3 |
| ATOM | 4084 | O | PAN | 36 | 18.825 | 10.763 | 14.288 | 1.00 77.16 | AP3 |
| ATOM | 4085 | O5 | PAN | 36 | 17.274 | 14.569 | 12.565 | 1.00 85.24 | AP3 |
| ATOM | 4086 | P6 | PAN | 36 | 16.757 | 14.374 | 11.104 | 1.00 88.14 | AP3 |
| ATOM | 4087 | O7 | PAN | 36 | 15.217 | 14.054 | 11.218 | 1.00 88.33 | AP3 |
| ATOM | 4088 | O8 | PAN | 36 | 17.499 | 13.109 | 10.488 | 1.00 87.44 | AP3 |
| ATOM | 4089 | O9 | PAN | 36 | 17.008 | 15.600 | 10.291 | 1.00 88.61 | AP3 |
| ATOM | 4090 | CB | PAN | 36 | 18.231 | 13.636 | 13.050 | 1.00 81.25 | AP3 |
| ATOM | 4091 | N | LEU | 37 | 19.032 | 12.297 | 15.902 | 1.00 76.08 | AP3 |
| ATOM | 4092 | CA | LEU | 37 | 19.979 | 11.494 | 16.647 | 1.00 74.58 | AP3 |
| ATOM | 4093 | CB | LEU | 37 | 20.902 | 12.393 | 17.496 | 1.00 73.85 | AP3 |
| ATOM | 4094 | CG | LEU | 37 | 22.259 | 11.862 | 18.031 | 1.00 72.85 | AP3 |
| ATOM | 4095 | CD1 | LEU | 37 | 22.125 | 11.234 | 19.393 | 1.09 72.07 | AP3 |
| ATOM | 4096 | CD2 | LEU | 37 | 22.841 | 10.874 | 17.044 | 1.00 72.39 | AP3 |

FIG. 3A-72

| ATOM | 4097 | C | LEU | 37 | 19.179 | 10.522 | 17.521 | 1.00 | 73.97 | AP3 |
|------|------|---|-----|----|--------|--------|--------|------|-------|-----|
| ATOM | 4098 | O | LEU | 37 | 19.524 | 9.352 | 17.628 | 1.00 | 73.50 | AP3 |
| ATOM | 4099 | N | ASP | 38 | 18.101 | 10.993 | 18.138 | 1.00 | 73.53 | AP3 |
| ATOM | 4100 | CA | ASP | 38 | 17.301 | 10.098 | 18.970 | 1.00 | 72.79 | AP3 |
| ATOM | 4101 | CB | ASP | 38 | 16.124 | 10.842 | 19.607 | 1.00 | 73.04 | AP3 |
| ATOM | 4102 | CG | ASP | 38 | 16.481 | 11.464 | 20.962 | 1.00 | 73.81 | AP3 |
| ATOM | 4103 | OD1 | ASP | 38 | 15.731 | 12.358 | 21.431 | 1.00 | 73.99 | AP3 |
| ATOM | 4104 | OD2 | ASP | 38 | 17.504 | 11.055 | 21.572 | 1.00 | 74.36 | AP3 |
| ATOM | 4105 | C | ASP | 38 | 16.799 | 8.959 | 18.094 | 1.00 | 72.08 | AP3 |
| ATOM | 4106 | O | ASP | 38 | 16.909 | 7.787 | 18.460 | 1.00 | 71.86 | AP3 |
| ATOM | 4107 | N | VAL | 39 | 16.287 | 9.300 | 16.919 | 1.00 | 71.14 | AP3 |
| ATOM | 4108 | CA | VAL | 39 | 15.779 | 8.277 | 16.025 | 1.00 | 71.01 | AP3 |
| ATOM | 4109 | CB | VAL | 39 | 15.220 | 8.869 | 14.664 | 1.00 | 71.24 | AP3 |
| ATOM | 4110 | CG1 | VAL | 39 | 16.325 | 9.539 | 13.844 | 1.00 | 71.90 | AP3 |
| ATOM | 4111 | CG2 | VAL | 39 | 14.602 | 7.764 | 13.839 | 1.00 | 71.08 | AP3 |
| ATOM | 4112 | C | VAL | 39 | 16.793 | 7.170 | 15.739 | 1.00 | 70.58 | AP3 |
| ATOM | 4113 | O | VAL | 39 | 16.450 | 5.996 | 15.879 | 1.00 | 70.63 | AP3 |
| ATOM | 4114 | N | VAL | 40 | 18.034 | 7.491 | 15.369 | 1.00 | 70.04 | AP3 |
| ATOM | 4115 | CA | VAL | 40 | 18.956 | 6.386 | 15.087 | 1.00 | 69.56 | AP3 |
| ATOM | 4116 | CB | VAL | 40 | 20.255 | 6.798 | 14.328 | 1.00 | 69.09 | AP3 |
| ATOM | 4117 | CG1 | VAL | 40 | 20.024 | 8.040 | 13.501 | 1.00 | 68.25 | AP3 |
| ATOM | 4118 | CG2 | VAL | 40 | 21.398 | 6.934 | 15.286 | 1.00 | 68.70 | AP3 |
| ATOM | 4119 | C | VAL | 40 | 19.355 | 5.609 | 16.330 | 1.00 | 69.75 | AP3 |
| ATOM | 4120 | O | VAL | 40 | 19.632 | 4.419 | 16.236 | 1.00 | 69.52 | AP3 |
| ATOM | 4121 | N | GLU | 41 | 19.394 | 6.251 | 17.494 | 1.00 | 70.53 | AP3 |
| ATOM | 4122 | CA | GLU | 41 | 19.750 | 5.501 | 18.691 | 1.00 | 71.26 | AP3 |
| ATOM | 4123 | CB | GLU | 41 | 20.063 | 6.413 | 19.881 | 1.00 | 71.93 | AP3 |
| ATOM | 4124 | CG | GLU | 41 | 20.212 | 5.583 | 21.164 | 1.00 | 74.01 | AP3 |
| ATOM | 4125 | CD | GLU | 41 | 20.933 | 6.295 | 22.307 | 1.00 | 75.35 | AP3 |
| ATOM | 4126 | OE1 | GLU | 41 | 20.488 | 7.410 | 22.704 | 1.00 | 76.32 | AP3 |
| ATOM | 4127 | OE2 | GLU | 41 | 21.938 | 5.723 | 22.815 | 1.00 | 74.88 | AP3 |
| ATOM | 4128 | C | GLU | 41 | 18.569 | 4.574 | 19.029 | 1.00 | 71.15 | AP3 |
| ATOM | 4129 | O | GLU | 41 | 18.753 | 3.453 | 19.535 | 1.00 | 71.23 | AP3 |
| ATOM | 4130 | N | LEU | 42 | 17.366 | 5.053 | 18.718 | 1.00 | 70.41 | AP3 |
| ATOM | 4131 | CA | LEU | 42 | 16.132 | 4.309 | 18.947 | 1.00 | 69.86 | AP3 |
| ATOM | 4132 | CB | LEU | 42 | 14.937 | 5.219 | 18.664 | 1.00 | 69.83 | AP3 |
| ATOM | 4133 | CG | LEU | 42 | 13.790 | 5.127 | 19.661 | 1.00 | 70.14 | AP3 |
| ATOM | 4134 | CD1 | LEU | 42 | 14.294 | 5.398 | 21.072 | 1.00 | 70.26 | AP3 |
| ATOM | 4135 | CD2 | LEU | 42 | 12.735 | 6.126 | 19.280 | 1.00 | 70.54 | AP3 |
| ATOM | 4136 | C | LEU | 42 | 16.081 | 3.076 | 18.033 | 1.00 | 69.20 | AP3 |
| ATOM | 4137 | O | LEU | 42 | 15.799 | 1.969 | 18.480 | 1.00 | 68.64 | AP3 |
| ATOM | 4138 | N | VAL | 43 | 16.352 | 3.287 | 16.751 | 1.00 | 68.63 | AP3 |
| ATOM | 4139 | CA | VAL | 43 | 16.371 | 2.211 | 15.783 | 1.00 | 68.57 | AP3 |
| ATOM | 4140 | CB | VAL | 43 | 16.651 | 2.761 | 14.361 | 1.00 | 68.12 | AP3 |
| ATOM | 4141 | CG1 | VAL | 43 | 17.349 | 1.716 | 13.520 | 1.00 | 68.00 | AP3 |
| ATOM | 4142 | CG2 | VAL | 43 | 15.357 | 3.167 | 13.691 | 1.00 | 67.66 | AP3 |
| ATOM | 4143 | C | VAL | 43 | 17.434 | 1.161 | 16.136 | 1.00 | 68.96 | AP3 |
| ATOM | 4144 | O | VAL | 43 | 17.221 | -0.025 | 15.965 | 1.00 | 69.09 | AP3 |
| ATOM | 4145 | N | MET | 44 | 18.584 | 1.584 | 16.634 | 1.00 | 69.75 | AP3 |
| ATOM | 4146 | CA | MET | 44 | 19.624 | 0.616 | 16.954 | 1.00 | 70.62 | AP3 |
| ATOM | 4147 | CB | MET | 44 | 20.955 | 1.333 | 17.165 | 1.00 | 70.97 | AP3 |
| ATOM | 4148 | CG | MET | 44 | 21.520 | 1.984 | 15.900 | 1.00 | 70.88 | AP3 |
| ATOM | 4149 | SD | MET | 44 | 23.026 | 2.871 | 16.329 | 1.00 | 71.36 | AP3 |
| ATOM | 4150 | CE | MET | 44 | 24.138 | 1.540 | 16.501 | 1.00 | 71.46 | AP3 |
| ATOM | 4151 | C | MET | 44 | 19.267 | -0.219 | 18.171 | 1.00 | 70.87 | AP3 |
| ATOM | 4152 | O | MET | 44 | 19.633 | -1.377 | 18.281 | 1.00 | 70.84 | AP3 |
| ATOM | 4153 | N | GLU | 45 | 18.550 | 0.374 | 19.098 | 1.00 | 71.61 | AP3 |

FIG. 3A-73

```
ATOM   4154  CA   GLU  45    18.148   -0.364  20.265  1.00  72.72    AP3
ATOM   4155  CB   GLU  45    17.465    0.574  21.241  1.00  74.12    AP3
ATOM   4156  CG   GLU  45    17.616    0.132  22.660  1.00  76.86    AP3
ATOM   4157  CD   GLU  45    18.162    1.241  23.512  1.00  78.21    AP3
ATOM   4158  OE1  GLU  45    19.158    1.860  23.070  1.00  79.78    AP3
ATOM   4159  OE2  GLU  45    17.607    1.494  24.609  1.00  78.92    AP3
ATOM   4160  C    GLU  45    17.176   -1.470  19.830  1.00  72.48    AP3
ATOM   4161  O    GLU  45    17.188   -2.579  20.368  1.00  71.93    AP3
ATOM   4162  N    LEU  46    16.332   -1.148  18.856  1.00  72.22    AP3
ATOM   4163  CA   LEU  46    15.369   -2.101  18.338  1.00  72.56    AP3
ATOM   4164  CB   LEU  46    14.345   -1.402  17.434  1.00  71.96    AP3
ATOM   4165  CG   LEU  46    13.399   -0.406  18.112  1.00  71.81    AP3
ATOM   4166  CD1  LEU  46    12.653    0.403  17.061  1.00  71.44    AP3
ATOM   4167  CD2  LEU  46    12.434   -1.141  19.030  1.00  71.22    AP3
ATOM   4168  C    LEU  46    16.145   -3.137  17.538  1.00  73.07    AP3
ATOM   4169  O    LEU  46    15.716   -4.281  17.407  1.00  73.17    AP3
ATOM   4170  N    GLU  47    17.288   -2.726  16.996  1.00  73.44    AP3
ATOM   4171  CA   GLU  47    18.127   -3.638  16.233  1.00  74.04    AP3
ATOM   4172  CB   GLU  47    19.261   -2.932  15.466  1.00  73.93    AP3
ATOM   4173  CG   GLU  47    18.998   -2.437  14.043  1.00  20.00    AP3
ATOM   4174  CD   GLU  47    20.090   -1.830  13.191  1.00  20.00    AP3
ATOM   4175  OE1  GLU  47    21.243   -1.687  13.573  1.00  20.00    AP3
ATOM   4176  OE2  GLU  47    19.767   -1.801  12.004  1.00  20.00    AP3
ATOM   4177  C    GLU  47    18.578   -4.672  17.245  1.00  74.60    AP3
ATOM   4178  O    GLU  47    18.464   -5.862  17.025  1.00  74.69    AP3
ATOM   4179  N    ASP  48    19.077   -4.191  18.373  1.00  75.61    AP3
ATOM   4180  CA   ASP  48    19.559   -5.051  19.446  1.00  76.66    AP3
ATOM   4181  CB   ASP  48    20.135   -4.162  20.574  1.00  76.52    AP3
ATOM   4182  CG   ASP  48    21.552   -4.573  21.002  1.00  76.90    AP3
ATOM   4183  OD1  ASP  48    22.385   -4.922  20.131  1.00  76.48    AP3
ATOM   4184  OD2  ASP  48    21.840   -4.527  22.221  1.00  76.87    AP3
ATOM   4185  C    ASP  48    18.431   -5.969  19.981  1.00  77.22    AP3
ATOM   4186  O    ASP  48    18.467   -7.186  19.792  1.00  77.42    AP3
ATOM   4187  N    GLU  49    17.427   -5.373  20.623  1.00  77.74    AP3
ATOM   4188  CA   GLU  49    16.305   -6.110  21.216  1.00  78.13    AP3
ATOM   4189  CB   GLU  49    15.181   -5.135  21.601  1.00  78.45    AP3
ATOM   4190  CG   GLU  49    14.040   -5.768  22.413  1.00  78.97    AP3
ATOM   4191  CD   GLU  49    14.522   -6.426  23.708  1.00  79.44    AP3
ATOM   4192  OE1  GLU  49    15.314   -5.805  24.456  1.00  79.86    AP3
ATOM   4193  OE2  GLU  49    14.103   -7.565  23.986  1.00  79.37    AP3
ATOM   4194  C    GLU  49    15.702   -7.248  20.394  1.00  78.17    AP3
ATOM   4195  O    GLU  49    15.764   -8.406  20.794  1.00  78.04    AP3
ATOM   4196  N    PHE  50    15.112   -6.899  19.258  1.00  78.28    AP3
ATOM   4197  CA   PHE  50    14.457   -7.854  18.378  1.00  78.51    AP3
ATOM   4198  CB   PHE  50    13.297   -7.153  17.675  1.00  78.05    AP3
ATOM   4199  CG   PHE  50    12.305   -6.526  18.616  1.00  77.86    AP3
ATOM   4200  CD1  PHE  50    11.336   -7.298  19.249  1.00  77.75    AP3
ATOM   4201  CD2  PHE  50    12.349   -5.166  18.884  1.00  77.65    AP3
ATOM   4202  CE1  PHE  50    10.429   -6.727  20.134  1.00  77.49    AP3
ATOM   4203  CE2  PHE  50    11.446   -4.588  19.767  1.00  77.81    AP3
ATOM   4204  CZ   PHE  50    10.483   -5.374  20.393  1.00  77.71    AP3
ATOM   4205  C    PHE  50    15.390   -8.485  17.338  1.00  79.21    AP3
ATOM   4206  O    PHE  50    14.962   -9.268  16.482  1.00  79.08    AP3
ATOM   4207  N    ASP  51    16.666   -8.141  17.406  1.00  79.94    AP3
ATOM   4208  CA   ASP  51    17.650   -8.677  16.469  1.00  80.87    AP3
ATOM   4209  CB   ASP  51    17.937  -10.141  16.782  1.00  81.48    AP3
ATOM   4210  CG   ASP  51    19.097  -10.683  15.970  1.00  82.44    AP3
```

FIG. 3A-74

| ATOM | 4211 | OD1 | ASP | 51 | 20.252 | -10.277 | 16.260 | 1.00 | 82.50 | AP3 |
|------|------|-----|-----|----|--------|---------|--------|------|-------|-----|
| ATOM | 4212 | OD2 | ASP | 51 | 18.856 | -11.499 | 15.041 | 1.00 | 82.89 | AP3 |
| ATOM | 4213 | C | ASP | 51 | 17.319 | -8.568 | 14.978 | 1.00 | 81.25 | AP3 |
| ATOM | 4214 | O | ASP | 51 | 17.156 | -9.580 | 14.299 | 1.00 | 81.47 | AP3 |
| ATOM | 4215 | N | MET | 52 | 17.212 | -7.350 | 14.462 | 1.00 | 81.48 | AP3 |
| ATOM | 4216 | CA | MET | 52 | 16.957 | -7.173 | 13.040 | 1.00 | 82.01 | AP3 |
| ATOM | 4217 | CB | MET | 52 | 15.510 | -6.750 | 12.775 | 1.00 | 82.14 | AP3 |
| ATOM | 4218 | CG | MET | 52 | 14.696 | -6.381 | 14.007 | 1.00 | 82.31 | AP3 |
| ATOM | 4219 | SD | MET | 52 | 13.071 | -5.722 | 13.542 | 1.00 | 82.25 | AP3 |
| ATOM | 4220 | CE | MET | 52 | 12.014 | -7.194 | 13.718 | 1.00 | 82.26 | AP3 |
| ATOM | 4221 | C | MET | 52 | 17.926 | -6.121 | 12.519 | 1.00 | 82.34 | AP3 |
| ATOM | 4222 | O | MET | 52 | 18.885 | -5.763 | 13.209 | 1.00 | 82.16 | AP3 |
| ATOM | 4223 | N | GLU | 53 | 17.702 | -5.627 | 11.308 | 1.00 | 82.90 | AP3 |
| ATOM | 4224 | CA | GLU | 53 | 18.610 | -4.614 | 10.779 | 1.00 | 83.60 | AP3 |
| ATOM | 4225 | CB | GLU | 53 | 19.123 | -5.031 | 9.393 | 1.00 | 84.21 | AP3 |
| ATOM | 4226 | CG | GLU | 53 | 20.382 | -5.919 | 9.461 | 1.00 | 85.24 | AP3 |
| ATOM | 4227 | CD | GLU | 53 | 20.835 | -6.458 | 8.097 | 1.00 | 85.76 | AP3 |
| ATOM | 4228 | OE1 | GLU | 53 | 21.136 | -5.656 | 7.182 | 1.00 | 85.78 | AP3 |
| ATOM | 4229 | OE2 | GLU | 53 | 20.899 | -7.696 | 7.942 | 1.00 | 86.03 | AP3 |
| ATOM | 4230 | C | GLU | 53 | 17.612 | -3.738 | 10.000 | 1.00 | 83.76 | AP3 |
| ATOM | 4231 | O | GLU | 53 | 16.959 | -4.220 | 9.060 | 1.00 | 84.12 | AP3 |
| ATOM | 4232 | N | ILE | 54 | 17.503 | -2.461 | 10.362 | 1.00 | 83.35 | AP3 |
| ATOM | 4233 | CA | ILE | 54 | 16.552 | -1.545 | 9.704 | 1.00 | 82.72 | AP3 |
| ATOM | 4234 | CB | ILE | 54 | 16.164 | -0.927 | 11.074 | 1.00 | 82.40 | AP3 |
| ATOM | 4235 | CG2 | ILE | 54 | 15.129 | 0.174 | 10.882 | 1.00 | 82.02 | AP3 |
| ATOM | 4236 | CG1 | ILE | 54 | 15.556 | -1.994 | 11.975 | 1.00 | 82.36 | AP3 |
| ATOM | 4237 | CD1 | ILE | 54 | 15.194 | -1.481 | 13.334 | 1.00 | 82.18 | AP3 |
| ATOM | 4238 | C | ILE | 54 | 17.561 | -0.609 | 9.007 | 1.00 | 82.25 | AP3 |
| ATOM | 4239 | O | ILE | 54 | 18.456 | -0.037 | 9.633 | 1.00 | 81.65 | AP3 |
| ATOM | 4240 | N | SER | 55 | 17.408 | -0.482 | 7.693 | 1.00 | 81.94 | AP3 |
| ATOM | 4241 | CA | SER | 55 | 18.277 | 0.359 | 6.884 | 1.00 | 81.54 | AP3 |
| ATOM | 4242 | CB | SER | 55 | 18.019 | 0.082 | 5.399 | 1.00 | 80.92 | AP3 |
| ATOM | 4243 | OG | SER | 55 | 16.645 | 0.198 | 5.090 | 1.00 | 79.92 | AP3 |
| ATOM | 4244 | C | SER | 55 | 18.010 | 1.824 | 7.202 | 1.00 | 81.54 | AP3 |
| ATOM | 4245 | O | SER | 55 | 17.098 | 2.137 | 7.970 | 1.00 | 81.30 | AP3 |
| ATOM | 4246 | N | ASP | 56 | 18.798 | 2.724 | 6.618 | 1.00 | 81.47 | AP3 |
| ATOM | 4247 | CA | ASP | 56 | 18.590 | 4.145 | 6.872 | 1.00 | 81.81 | AP3 |
| ATOM | 4248 | CB | ASP | 56 | 19.683 | 5.001 | 6.193 | 1.00 | 81.44 | AP3 |
| ATOM | 4249 | CG | ASP | 56 | 21.040 | 4.968 | 6.948 | 1.00 | 81.79 | AP3 |
| ATOM | 4250 | OD1 | ASP | 56 | 21.046 | 4.792 | 8.192 | 1.00 | 81.20 | AP3 |
| ATOM | 4251 | OD2 | ASP | 56 | 22.105 | 5.147 | 6.298 | 1.00 | 81.38 | AP3 |
| ATOM | 4252 | C | ASP | 56 | 17.193 | 4.522 | 6.353 | 1.00 | 82.06 | AP3 |
| ATOM | 4253 | O | ASP | 56 | 16.468 | 5.310 | 6.971 | 1.00 | 81.65 | AP3 |
| ATOM | 4254 | N | GLU | 57 | 16.812 | 3.922 | 5.231 | 1.00 | 82.50 | AP3 |
| ATOM | 4255 | CA | GLU | 57 | 15.519 | 4.181 | 4.617 | 1.00 | 83.23 | AP3 |
| ATOM | 4256 | CB | GLU | 57 | 15.489 | 3.600 | 3.212 | 1.00 | 83.97 | AP3 |
| ATOM | 4257 | CG | GLU | 57 | 14.093 | 3.344 | 2.663 | 1.00 | 85.29 | AP3 |
| ATOM | 4258 | CD | GLU | 57 | 14.151 | 2.565 | 1.360 | 1.00 | 86.35 | AP3 |
| ATOM | 4259 | OE1 | GLU | 57 | 14.973 | 1.619 | 1.297 | 1.00 | 86.59 | AP3 |
| ATOM | 4260 | OE2 | GLU | 57 | 13.388 | 2.891 | 0.414 | 1.00 | 86.49 | AP3 |
| ATOM | 4261 | C | GLU | 57 | 14.389 | 3.582 | 5.410 | 1.00 | 83.25 | AP3 |
| ATOM | 4262 | O | GLU | 57 | 13.307 | 4.140 | 5.485 | 1.00 | 83.37 | AP3 |
| ATOM | 4263 | N | ASP | 58 | 14.645 | 2.419 | 5.977 | 1.00 | 83.61 | AP3 |
| ATOM | 4264 | CA | ASP | 58 | 13.643 | 1.733 | 6.762 | 1.00 | 84.08 | AP3 |
| ATOM | 4265 | CB | ASP | 58 | 14.221 | 0.420 | 7.298 | 1.00 | 84.48 | AP3 |
| ATOM | 4266 | CG | ASP | 58 | 13.920 | -0.757 | 6.399 | 1.00 | 84.79 | AP3 |
| ATOM | 4267 | OD1 | ASP | 58 | 13.894 | -0.578 | 5.161 | 1.00 | 84.94 | AP3 |

FIG. 3A-75

| | | | | | | | | | |
|---|---|---|---|---|---|---|---|---|---|
| ATOM | 4268 | OD2 | ASP | 58 | 13.718 | -1.866 | 6.937 | 1.00 85.28 | AP3 |
| ATOM | 4269 | C | ASP | 58 | 13.161 | 2.594 | 7.916 | 1.00 84.20 | AP3 |
| ATOM | 4270 | O | ASP | 58 | 11.956 | 2.768 | 8.106 | 1.00 84.18 | AP3 |
| ATOM | 4271 | N | ALA | 59 | 14.110 | 3.127 | 8.682 | 1.00 84.44 | AP3 |
| ATOM | 4272 | CA | ALA | 59 | 13.800 | 3.947 | 9.847 | 1.00 84.80 | AP3 |
| ATOM | 4273 | CB | ALA | 59 | 15.090 | 4.324 | 10.576 | 1.00 84.94 | AP3 |
| ATOM | 4274 | C | ALA | 59 | 13.012 | 5.196 | 9.490 | 1.00 85.16 | AP3 |
| ATOM | 4275 | O | ALA | 59 | 12.270 | 5.733 | 10.320 | 1.00 84.92 | AP3 |
| ATOM | 4276 | N | GLU | 60 | 13.179 | 5.649 | 8.251 | 1.00 85.66 | AP3 |
| ATOM | 4277 | CA | GLU | 60 | 12.491 | 6.829 | 7.756 | 1.00 86.22 | AP3 |
| ATOM | 4278 | CB | GLU | 60 | 13.172 | 7.307 | 6.472 | 1.00 86.31 | AP3 |
| ATOM | 4279 | CG | GLU | 60 | 12.273 | 7.576 | 5.288 | 1.00 86.31 | AP3 |
| ATOM | 4280 | CD | GLU | 60 | 13.066 | 8.014 | 4.068 | 1.00 86.35 | AP3 |
| ATOM | 4281 | OE1 | GLU | 60 | 13.683 | 9.096 | 4.127 | 1.00 86.38 | AP3 |
| ATOM | 4282 | OE2 | GLU | 60 | 13.086 | 7.277 | 3.056 | 1.00 86.60 | AP3 |
| ATOM | 4283 | C | GLU | 60 | 11.011 | 6.543 | 7.528 | 1.00 86.77 | AP3 |
| ATOM | 4284 | O | GLU | 60 | 10.228 | 7.453 | 7.250 | 1.00 87.01 | AP3 |
| ATOM | 4285 | N | LYS | 61 | 10.623 | 5.277 | 7.653 | 1.00 87.25 | AP3 |
| ATOM | 4286 | CA | LYS | 61 | 9.220 | 4.909 | 7.488 | 1.00 87.61 | AP3 |
| ATOM | 4287 | CB | LYS | 61 | 9.074 | 3.593 | 6.731 | 1.00 88.37 | AP3 |
| ATOM | 4288 | CG | LYS | 61 | 7.624 | 3.104 | 6.665 | 1.00 89.43 | AP3 |
| ATOM | 4289 | CD | LYS | 61 | 7.551 | 1.686 | 6.112 | 1.00 90.13 | AP3 |
| ATOM | 4290 | CE | LYS | 61 | 6.127 | 1.165 | 6.055 | 1.00 90.43 | AP3 |
| ATOM | 4291 | NZ | LYS | 61 | 6.108 | -0.219 | 5.489 | 1.00 90.66 | AP3 |
| ATOM | 4292 | C | LYS | 61 | 8.503 | 4.778 | 8.830 | 1.00 87.34 | AP3 |
| ATOM | 4293 | O | LYS | 61 | 7.396 | 5.299 | 8.987 | 1.00 87.16 | AP3 |
| ATOM | 4294 | N | ILE | 62 | 9.122 | 4.090 | 9.791 | 1.00 87.02 | AP3 |
| ATOM | 4295 | CA | ILE | 62 | 8.488 | 3.909 | 11.094 | 1.00 86.92 | AP3 |
| ATOM | 4296 | CB | ILE | 62 | 9.281 | 2.898 | 11.997 | 1.00 86.84 | AP3 |
| ATOM | 4297 | CG2 | ILE | 62 | 9.711 | 1.698 | 11.164 | 1.00 86.77 | AP3 |
| ATOM | 4298 | CG1 | ILE | 62 | 10.516 | 3.547 | 12.621 | 1.00 86.82 | AP3 |
| ATOM | 4299 | CD1 | ILE | 62 | 11.170 | 2.683 | 13.670 | 1.00 86.27 | AP3 |
| ATOM | 4300 | C | ILE | 62 | 8.285 | 5.258 | 11.802 | 1.00 86.84 | AP3 |
| ATOM | 4301 | O | ILE | 62 | 9.041 | 5.659 | 12.698 | 1.00 86.83 | AP3 |
| ATOM | 4302 | N | ALA | 63 | 7.228 | 5.941 | 11.373 | 1.00 86.40 | AP3 |
| ATOM | 4303 | CA | ALA | 63 | 6.847 | 7.255 | 11.876 | 1.00 85.95 | AP3 |
| ATOM | 4304 | CB | ALA | 63 | 5.758 | 7.850 | 10.975 | 1.00 86.18 | AP3 |
| ATOM | 4305 | C | ALA | 63 | 6.376 | 7.268 | 13.323 | 1.00 85.54 | AP3 |
| ATOM | 4306 | O | ALA | 63 | 6.790 | 8.124 | 14.109 | 1.00 85.58 | AP3 |
| ATOM | 4307 | N | THR | 64 | 5.494 | 6.335 | 13.670 | 1.00 84.92 | AP3 |
| ATOM | 4308 | CA | THR | 64 | 4.977 | 6.272 | 15.033 | 1.00 84.10 | AP3 |
| ATOM | 4309 | CB | THR | 64 | 3.462 | 6.508 | 15.069 | 1.00 84.08 | AP3 |
| ATOM | 4310 | OG1 | THR | 64 | 2.779 | 5.266 | 14.876 | 1.00 84.50 | AP3 |
| ATOM | 4311 | CG2 | THR | 64 | 3.052 | 7.468 | 13.959 | 1.00 84.49 | AP3 |
| ATOM | 4312 | C | THR | 64 | 5.279 | 4.911 | 15.638 | 1.00 83.31 | AP3 |
| ATOM | 4313 | O | THR | 64 | 5.930 | 4.074 | 15.008 | 1.00 83.15 | AP3 |
| ATOM | 4314 | N | VAL | 65 | 4.797 | 4.697 | 16.858 | 1.00 82.39 | AP3 |
| ATOM | 4315 | CA | VAL | 65 | 5.026 | 3.441 | 17.567 | 1.00 81.57 | AP3 |
| ATOM | 4316 | CB | VAL | 65 | 4.426 | 3.504 | 18.998 | 1.00 81.36 | AP3 |
| ATOM | 4317 | CG1 | VAL | 65 | 4.872 | 2.300 | 19.806 | 1.00 81.23 | AP3 |
| ATOM | 4318 | CG2 | VAL | 65 | 4.856 | 4.790 | 19.687 | 1.00 81.01 | AP3 |
| ATOM | 4319 | C | VAL | 65 | 4.435 | 2.246 | 16.807 | 1.00 81.21 | AP3 |
| ATOM | 4320 | O | VAL | 65 | 5.159 | 1.333 | 16.406 | 1.00 80.81 | AP3 |
| ATOM | 4321 | N | GLY | 66 | 3.118 | 2.270 | 16.603 | 1.00 80.94 | AP3 |
| ATOM | 4322 | CA | GLY | 66 | 2.440 | 1.198 | 15.887 | 1.00 80.21 | AP3 |
| ATOM | 4323 | C | GLY | 66 | 3.238 | 0.690 | 14.702 | 1.00 79.61 | AP3 |
| ATOM | 4324 | O | GLY | 66 | 3.559 | -0.492 | 14.644 | 1.00 80.05 | AP3 |

FIG. 3A-76

| ATOM | 4325 | N   | ASP | 67 | 3.560  | 1.586  | 13.768 | 1.00 | 78.67 | AP3 |
| ATOM | 4326 | CA  | ASP | 67 | 4.334  | 1.250  | 12.577 | 1.00 | 77.46 | AP3 |
| ATOM | 4327 | CB  | ASP | 67 | 4.810  | 2.527  | 11.866 | 1.00 | 78.12 | AP3 |
| ATOM | 4328 | CG  | ASP | 67 | 3.663  | 3.435  | 11.426 | 1.00 | 78.60 | AP3 |
| ATOM | 4329 | OD1 | ASP | 67 | 3.948  | 4.595  | 11.038 | 1.00 | 78.50 | AP3 |
| ATOM | 4330 | OD2 | ASP | 67 | 2.484  | 2.998  | 11.460 | 1.00 | 79.03 | AP3 |
| ATOM | 4331 | C   | ASP | 67 | 5.553  | 0.427  | 12.966 | 1.00 | 76.39 | AP3 |
| ATOM | 4332 | O   | ASP | 67 | 5.847  | -0.586 | 12.349 | 1.00 | 76.25 | AP3 |
| ATOM | 4333 | N   | ALA | 68 | 6.265  | 0.875  | 13.992 | 1.00 | 75.14 | AP3 |
| ATOM | 4334 | CA  | ALA | 68 | 7.461  | 0.177  | 14.443 | 1.00 | 74.09 | AP3 |
| ATOM | 4335 | CB  | ALA | 68 | 8.127  | 0.958  | 15.557 | 1.00 | 73.75 | AP3 |
| ATOM | 4336 | C   | ALA | 68 | 7.126  | -1.231 | 14.923 | 1.00 | 73.41 | AP3 |
| ATOM | 4337 | O   | ALA | 68 | 7.901  | -2.178 | 14.722 | 1.00 | 72.94 | AP3 |
| ATOM | 4338 | N   | VAL | 69 | 5.977  | -1.353 | 15.583 | 1.00 | 72.59 | AP3 |
| ATOM | 4339 | CA  | VAL | 69 | 5.516  | -2.640 | 16.078 | 1.00 | 71.94 | AP3 |
| ATOM | 4340 | CB  | VAL | 69 | 4.233  | -2.496 | 16.913 | 1.00 | 71.70 | AP3 |
| ATOM | 4341 | CG1 | VAL | 69 | 3.613  | -3.860 | 17.128 | 1.00 | 72.09 | AP3 |
| ATOM | 4342 | CG2 | VAL | 69 | 4.550  | -1.867 | 18.264 | 1.00 | 71.85 | AP3 |
| ATOM | 4343 | C   | VAL | 69 | 5.235  | -3.533 | 14.874 | 1.00 | 71.56 | AP3 |
| ATOM | 4344 | O   | VAL | 69 | 5.670  | -4.677 | 14.834 | 1.00 | 71.28 | AP3 |
| ATOM | 4345 | N   | ASN | 70 | 4.536  | -2.977 | 13.888 | 1.00 | 71.51 | AP3 |
| ATOM | 4346 | CA  | ASN | 70 | 4.173  | -3.684 | 12.670 | 1.00 | 71.50 | AP3 |
| ATOM | 4347 | CB  | ASN | 70 | 3.286  | -2.806 | 11.784 | 1.00 | 72.56 | AP3 |
| ATOM | 4348 | CG  | ASN | 70 | 1.985  | -2.388 | 12.481 | 1.00 | 74.31 | AP3 |
| ATOM | 4349 | OD1 | ASN | 70 | 1.333  | -3.194 | 13.183 | 1.00 | 74.53 | AP3 |
| ATOM | 4350 | ND2 | ASN | 70 | 1.591  | -1.124 | 12.279 | 1.00 | 74.65 | AP3 |
| ATOM | 4351 | C   | ASN | 70 | 5.365  | -4.164 | 11.864 | 1.00 | 70.88 | AP3 |
| ATOM | 4352 | O   | ASN | 70 | 5.292  | -5.213 | 11.226 | 1.00 | 71.14 | AP3 |
| ATOM | 4353 | N   | TYR | 71 | 6.457  | -3.405 | 11.887 | 1.00 | 69.74 | AP3 |
| ATOM | 4354 | CA  | TYR | 71 | 7.656  | -3.775 | 11.148 | 1.00 | 68.50 | AP3 |
| ATOM | 4355 | CB  | TYR | 71 | 8.579  | -2.564 | 10.985 | 1.00 | 68.49 | AP3 |
| ATOM | 4356 | CG  | TYR | 71 | 9.941  | -2.875 | 10.408 | 1.00 | 68.25 | AP3 |
| ATOM | 4357 | CD1 | TYR | 71 | 10.983 | -3.316 | 11.223 | 1.00 | 68.37 | AP3 |
| ATOM | 4358 | CE1 | TYR | 71 | 12.246 | -3.579 | 10.700 | 1.00 | 68.50 | AP3 |
| ATOM | 4359 | CD2 | TYR | 71 | 10.195 | -2.709 | 9.048  | 1.00 | 68.69 | AP3 |
| ATOM | 4360 | CE2 | TYR | 71 | 11.452 | -2.968 | 8.512  | 1.00 | 68.85 | AP3 |
| ATOM | 4361 | CZ  | TYR | 71 | 12.476 | -3.397 | 9.342  | 1.00 | 68.83 | AP3 |
| ATOM | 4362 | OH  | TYR | 71 | 13.740 | -3.604 | 8.823  | 1.00 | 68.91 | AP3 |
| ATOM | 4363 | C   | TYR | 71 | 8.381  | -4.890 | 11.876 | 1.00 | 67.81 | AP3 |
| ATOM | 4364 | O   | TYR | 71 | 9.000  | -5.753 | 11.250 | 1.00 | 67.59 | AP3 |
| ATOM | 4365 | N   | ILE | 72 | 8.307  | -4.867 | 13.201 | 1.00 | 66.78 | AP3 |
| ATOM | 4366 | CA  | ILE | 72 | 8.952  | -5.895 | 14.004 | 1.00 | 66.16 | AP3 |
| ATOM | 4367 | CB  | ILE | 72 | 8.971  | -5.479 | 15.475 | 1.00 | 65.95 | AP3 |
| ATOM | 4368 | CG2 | ILE | 72 | 9.601  | -6.577 | 16.323 | 1.00 | 65.37 | AP3 |
| ATOM | 4369 | CG1 | ILE | 72 | 9.738  | -4.161 | 15.605 | 1.00 | 65.65 | AP3 |
| ATOM | 4370 | CD1 | ILE | 72 | 9.745  | -3.580 | 16.986 | 1.00 | 65.29 | AP3 |
| ATOM | 4371 | C   | ILE | 72 | 8.254  | -7.259 | 13.831 | 1.00 | 65.87 | AP3 |
| ATOM | 4372 | O   | ILE | 72 | 8.826  | -8.301 | 14.112 | 1.00 | 65.61 | AP3 |
| ATOM | 4373 | N   | GLN | 73 | 7.015  | -7.235 | 13.361 | 1.00 | 65.77 | AP3 |
| ATOM | 4374 | CA  | GLN | 73 | 6.263  | -8.454 | 13.096 | 1.00 | 66.13 | AP3 |
| ATOM | 4375 | CB  | GLN | 73 | 4.798  | -8.278 | 13.581 | 1.00 | 65.55 | AP3 |
| ATOM | 4376 | CG  | GLN | 73 | 4.647  | -7.843 | 15.063 | 1.00 | 64.13 | AP3 |
| ATOM | 4377 | CD  | GLN | 73 | 3.220  | -7.421 | 15.452 | 1.00 | 64.08 | AP3 |
| ATOM | 4378 | OE1 | GLN | 73 | 2.478  | -6.865 | 14.644 | 1.00 | 63.85 | AP3 |
| ATOM | 4379 | NE2 | GLN | 73 | 2.847  | -7.663 | 16.704 | 1.00 | 63.21 | AP3 |
| ATOM | 4380 | C   | GLN | 73 | 6.332  | -8.670 | 11.555 | 1.00 | 66.46 | AP3 |
| ATOM | 4381 | OT1 | GLN | 73 | 7.311  | -9.301 | 11.073 | 1.00 | 66.98 | AP3 |

FIG. 3A-77

| ATOM | 4382 | OT2 | GLN | 73 | 5.443 | -8.169 | 10.822 | 1.00 | 66.91 | AP3 |
|---|---|---|---|---|---|---|---|---|---|---|
| ATOM | 4383 | Na | Na | 74 | 20.764 | 19.142 | 15.649 | 1.00 | 20.00 | AP3 |
| ATOM | 4384 | Cl | Cl | 75 | 48.270 | 38.501 | 33.120 | 1.00 | 20.00 | AP3 |
| ATOM | 4385 | O | HOH | 1 | 20.971 | 35.418 | 19.446 | 1.00 | 28.08 | W |
| ATOM | 4386 | O | HOH | 3 | 17.476 | 26.774 | 26.314 | 1.00 | 30.37 | W |
| ATOM | 4387 | O | HOH | 4 | 12.070 | 27.791 | 30.387 | 1.00 | 43.18 | W |
| ATOM | 4388 | O | HOH | 6 | -0.243 | 36.108 | 7.284 | 1.00 | 29.98 | W |
| ATOM | 4389 | O | HOH | 7 | 0.953 | 30.812 | 3.352 | 1.00 | 25.95 | W |
| ATOM | 4390 | O | HOH | 8 | 4.210 | 27.477 | 6.553 | 1.00 | 39.30 | W |
| ATOM | 4391 | O | HOH | 9 | 0.717 | 18.079 | 16.564 | 1.00 | 67.04 | W |
| ATOM | 4392 | O | HOH | 11 | 15.048 | 43.095 | -2.130 | 1.00 | 39.40 | W |
| ATOM | 4393 | O | HOH | 12 | 17.559 | 22.506 | 6.739 | 1.00 | 26.96 | W |
| ATOM | 4394 | O | HOH | 13 | 12.217 | 24.755 | 13.778 | 1.00 | 46.52 | W |
| ATOM | 4395 | O | HOH | 15 | 35.287 | 26.338 | 18.440 | 1.00 | 20.30 | W |
| ATOM | 4396 | O | HOH | 17 | 18.594 | 25.738 | 2.095 | 1.00 | 35.11 | W |
| ATOM | 4397 | O | HOH | 18 | 15.737 | 27.004 | 1.792 | 1.00 | 44.57 | W |
| ATOM | 4398 | O | HOH | 19 | 17.787 | 25.982 | -0.493 | 1.00 | 47.08 | W |
| ATOM | 4399 | O | HOH | 20 | 14.655 | 29.401 | 1.057 | 1.00 | 29.13 | W |
| ATOM | 4400 | O | HOH | 22 | 10.016 | 35.007 | -1.744 | 1.00 | 28.29 | W |
| ATOM | 4401 | O | HOH | 23 | 36.914 | 24.143 | 16.155 | 1.00 | 45.82 | W |
| ATOM | 4402 | O | HOH | 25 | 50.466 | 41.898 | 3.162 | 1.00 | 51.46 | W |
| ATOM | 4403 | O | HOH | 30 | 37.884 | 38.482 | 31.771 | 1.00 | 44.83 | W |
| ATOM | 4404 | O | HOH | 33 | 2.929 | 18.357 | 18.770 | 1.00 | 39.37 | W |
| ATOM | 4405 | O | HOH | 35 | 36.000 | 25.296 | 5.752 | 1.00 | 51.16 | W |
| ATOM | 4406 | O | HOH | 36 | 36.246 | 24.282 | 8.528 | 1.00 | 26.38 | W |
| ATOM | 4407 | O | HOH | 37 | 28.425 | 33.179 | 30.115 | 1.00 | 38.91 | W |
| ATOM | 4408 | O | HOH | 41 | 21.454 | 21.279 | 24.073 | 1.00 | 42.35 | W |
| ATOM | 4409 | O | HOH | 43 | 32.713 | 18.758 | 19.974 | 1.00 | 39.89 | W |
| ATOM | 4410 | O | HOH | 45 | 27.158 | 17.997 | 25.229 | 1.00 | 42.25 | W |
| ATOM | 4411 | O | HOH | 47 | 15.063 | 24.776 | 27.152 | 1.00 | 51.90 | W |
| ATOM | 4412 | O | HOH | 48 | 3.825 | 36.800 | 4.340 | 1.00 | 34.80 | W |
| ATOM | 4413 | O | HOH | 50 | 20.567 | 27.887 | 27.820 | 1.00 | 55.40 | W |
| ATOM | 4414 | O | HOH | 51 | 4.233 | 27.038 | 25.001 | 1.00 | 46.58 | W |
| ATOM | 4415 | O | HOH | 52 | 29.473 | 30.435 | 6.152 | 1.00 | 30.54 | W |
| ATOM | 4416 | O | HOH | 53 | 35.273 | 26.999 | 22.829 | 1.00 | 20.05 | W |
| ATOM | 4417 | O | HOH | 55 | 42.995 | 43.869 | 7.601 | 1.00 | 34.30 | W |
| ATOM | 4418 | O | HOH | 56 | 44.770 | 43.791 | 9.728 | 1.00 | 38.02 | W |
| ATOM | 4419 | O | HOH | 57 | 16.116 | 25.445 | 30.290 | 1.00 | 58.80 | W |
| ATOM | 4420 | O | HOH | 58 | 0.147 | 32.556 | 5.561 | 1.00 | 35.33 | W |
| ATOM | 4421 | O | HOH | 59 | -0.841 | 26.194 | 8.298 | 1.00 | 52.99 | W |
| ATOM | 4422 | O | HOH | 60 | 10.370 | 26.637 | 13.493 | 1.00 | 36.98 | W |
| ATOM | 4423 | O | HOH | 61 | 8.214 | 23.987 | 10.644 | 1.00 | 40.29 | W |
| ATOM | 4424 | O | HOH | 62 | 7.673 | 46.913 | 8.463 | 1.00 | 47.90 | W |
| ATOM | 4425 | O | HOH | 63 | 4.946 | 41.758 | 13.539 | 1.00 | 40.09 | W |
| ATOM | 4426 | O | HOH | 64 | 2.008 | 26.400 | 4.288 | 1.00 | 44.86 | W |
| ATOM | 4427 | O | HOH | 65 | 32.337 | 32.228 | -5.705 | 1.00 | 32.42 | W |
| ATOM | 4428 | O | HOH | 66 | 27.158 | 29.103 | 4.575 | 1.00 | 46.49 | W |
| ATOM | 4429 | O | HOH | 67 | 51.087 | 34.911 | 10.070 | 1.00 | 39.28 | W |
| ATOM | 4430 | O | HOH | 68 | 32.466 | 40.888 | 5.401 | 1.00 | 33.93 | W |
| ATOM | 4431 | O | HOH | 69 | 39.494 | 41.762 | 2.408 | 1.00 | 58.71 | W |
| ATOM | 4432 | O | HOH | 70 | 38.446 | 9.804 | 5.548 | 1.00 | 44.19 | W |
| ATOM | 4433 | O | HOH | 71 | 37.802 | 15.483 | 14.333 | 1.00 | 53.16 | W |
| ATOM | 4434 | O | HOH | 72 | 36.104 | 17.125 | 13.465 | 1.00 | 49.31 | W |
| ATOM | 4435 | O | HOH | 73 | 35.093 | 14.562 | 11.995 | 1.00 | 37.15 | W |
| ATOM | 4436 | O | HOH | 74 | 39.249 | 13.856 | 9.700 | 1.00 | 43.73 | W |
| ATOM | 4437 | O | HOH | 75 | 40.786 | 20.731 | -0.083 | 1.00 | 41.60 | W |
| ATOM | 4438 | O | HOH | 76 | 42.538 | 13.280 | 2.142 | 1.00 | 53.85 | W |

FIG. 3A-78

| ATOM | 4439 | O | HOH | 77  | 43.889 | 24.163 | 2.388   | 1.00 | 37.18 | W |
| ---- | ---- | - | --- | --- | ------ | ------ | ------- | ---- | ----- | - |
| ATOM | 4440 | O | HOH | 79  | 2.540  | 34.722 | 4.575   | 1.00 | 52.66 | W |
| ATOM | 4441 | O | HOH | 80  | 43.300 | 39.495 | 27.764  | 1.00 | 44.05 | W |
| ATOM | 4442 | O | HOH | 81  | 30.076 | 30.368 | 28.457  | 1.00 | 41.35 | W |
| ATOM | 4443 | O | HOH | 82  | 0.554  | 36.258 | 25.377  | 1.00 | 53.47 | W |
| ATOM | 4444 | O | HOH | 83  | 42.781 | 28.492 | 12.843  | 1.00 | 51.06 | W |
| ATOM | 4445 | O | HOH | 84  | 17.785 | 20.002 | 14.425  | 1.00 | 47.01 | W |
| ATOM | 4446 | O | HOH | 85  | 57.006 | 35.947 | 12.705  | 1.00 | 61.42 | W |
| ATOM | 4447 | O | HOH | 86  | 35.408 | 25.621 | 2.707   | 1.00 | 51.93 | W |
| ATOM | 4448 | O | HOH | 87  | 26.037 | 26.711 | 5.073   | 1.00 | 55.68 | W |
| ATOM | 4449 | O | HOH | 88  | -0.037 | 36.618 | 11.554  | 1.00 | 62.51 | W |
| ATOM | 4450 | O | HOH | 89  | 18.549 | 21.897 | -0.102  | 1.00 | 57.85 | W |
| ATOM | 4451 | O | HOH | 90  | 35.373 | 45.010 | 15.224  | 1.00 | 44.09 | W |
| ATOM | 4452 | O | HOH | 91  | 43.922 | 17.170 | -0.889  | 1.00 | 54.42 | W |
| ATOM | 4453 | O | HOH | 92  | 7.281  | 53.078 | 4.234   | 1.00 | 54.35 | W |
| ATOM | 4454 | O | HOH | 93  | 36.648 | -0.702 | 8.498   | 1.00 | 47.55 | W |
| ATOM | 4455 | O | HOH | 94  | 24.724 | 39.269 | 9.469   | 1.00 | 53.05 | W |
| ATOM | 4456 | O | HOH | 95  | 19.529 | 33.965 | 22.828  | 1.00 | 58.72 | W |
| ATOM | 4457 | O | HOH | 96  | 25.749 | 39.500 | 11.779  | 1.00 | 57.45 | W |
| ATOM | 4458 | O | HOH | 98  | 2.556  | 39.351 | 3.903   | 1.00 | 60.67 | W |
| ATOM | 4459 | O | HOH | 99  | 4.962  | 24.357 | 5.423   | 1.00 | 50.93 | W |
| ATOM | 4460 | O | HOH | 100 | 52.895 | 36.138 | 12.412  | 1.00 | 58.46 | W |
| ATOM | 4461 | O | HOH | 101 | 29.825 | 40.539 | 5.862   | 1.00 | 49.27 | W |
| ATOM | 4462 | O | HOH | 102 | 21.479 | 17.255 | 17.560  | 1.00 | 57.74 | W |
| ATOM | 4463 | O | HOH | 103 | 17.766 | 38.296 | 19.527  | 1.00 | 57.08 | W |
| ATOM | 4464 | O | HOH | 104 | 1.919  | 40.589 | 25.467  | 1.00 | 69.59 | W |
| ATOM | 4465 | O | HOH | 105 | 45.650 | 16.023 | 1.737   | 1.00 | 68.18 | W |
| ATOM | 4466 | O | HOH | 106 | 39.326 | 28.368 | 32.930  | 1.00 | 53.77 | W |
| ATOM | 4467 | O | HOH | 107 | 3.591  | 33.811 | 2.107   | 1.00 | 46.49 | W |
| ATOM | 4468 | O | HOH | 108 | 33.929 | 42.844 | 3.314   | 1.00 | 55.14 | W |
| ATOM | 4469 | O | HOH | 109 | 46.647 | 46.329 | 14.321  | 1.00 | 59.44 | W |
| ATOM | 4470 | O | HOH | 110 | 39.222 | 24.809 | 6.979   | 1.00 | 50.22 | W |
| ATOM | 4471 | O | HOH | 111 | 49.804 | 23.224 | 6.539   | 1.00 | 58.63 | W |
| ATOM | 4472 | O | HOH | 112 | -3.058 | 18.507 | 16.487  | 1.00 | 53.33 | W |
| ATOM | 4473 | O | HOH | 113 | 27.700 | 31.120 | -5.231  | 1.00 | 69.60 | W |
| ATOM | 4474 | O | HOH | 114 | 29.929 | 38.507 | -4.418  | 1.00 | 52.20 | W |
| ATOM | 4475 | O | HOH | 115 | 34.570 | 42.009 | 0.898   | 1.00 | 44.15 | W |
| ATOM | 4476 | O | HOH | 116 | 40.508 | 27.337 | 28.107  | 1.00 | 45.88 | W |
| ATOM | 4477 | O | HOH | 117 | 41.210 | 12.812 | -1.190  | 1.00 | 66.16 | W |
| ATOM | 4478 | O | HOH | 118 | 23.723 | 30.084 | 26.100  | 1.00 | 20.00 | W |
| ATOM | 4479 | O | HOH | 119 | 0.869  | 28.565 | 2.785   | 1.00 | 20.00 | W |
| ATOM | 4480 | O | HOH | 120 | 15.469 | 15.123 | 22.821  | 1.00 | 20.00 | W |
| ATOM | 4481 | O | HOH | 122 | 12.470 | 22.800 | 11.398  | 1.00 | 20.00 | W |
| ATOM | 4482 | O | HOH | 123 | 41.506 | 25.423 | 15.397  | 1.00 | 20.00 | W |
| ATOM | 4483 | O | HOH | 124 | 37.626 | 28.216 | 31.136  | 1.00 | 20.00 | W |
| ATOM | 4484 | O | HOH | 125 | 48.566 | 37.385 | 16.630  | 1.00 | 20.00 | W |
| ATOM | 4485 | O | HOH | 126 | 1.496  | 22.085 | 13.272  | 1.00 | 20.00 | W |
| ATOM | 4486 | O | HOH | 127 | 34.698 | 24.986 | 24.965  | 1.00 | 20.00 | W |
| ATOM | 4487 | O | HOH | 128 | -2.903 | 37.363 | 6.990   | 1.00 | 20.00 | W |
| ATOM | 4488 | O | HOH | 129 | 12.491 | -3.414 | 25.110  | 1.00 | 20.00 | W |
| ATOM | 4489 | O | HOH | 130 | 5.176  | -10.899| 28.961  | 1.00 | 20.00 | W |
| ATOM | 4490 | O | HOH | 131 | 48.659 | 38.012 | 29.029  | 1.00 | 20.00 | W |
| ATOM | 4491 | O | HOH | 133 | 52.619 | 28.488 | 32.666  | 1.00 | 20.00 | W |
| ATOM | 4492 | O | HOH | 134 | 39.711 | 23.898 | 9.790   | 1.00 | 20.00 | W |
| ATOM | 4493 | O | HOH | 135 | 3.443  | 35.318 | -0.076  | 1.00 | 20.00 | W |
| ATOM | 4494 | O | HOH | 136 | 20.485 | 29.825 | -10.828 | 1.00 | 20.00 | W |
| ATOM | 4495 | O | HOH | 137 | 27.808 | 44.788 | 25.549  | 1.00 | 20.00 | W |

FIG. 3A-79

```
ATOM   4496  O   HOH   138     9.406  20.806  12.275  1.00 20.00    W
ATOM   4497  O   HOH   139    32.311  40.520  18.168  1.00 20.00    W
ATOM   4498  O   HOH   140    26.404  40.444   7.377  1.00 20.00    W
ATOM   4499  O   HOH   141    24.546  29.367  -7.098  1.00 20.00    W
ATOM   4500  O   HOH   142    64.483  32.976  23.998  1.00 20.00    W
ATOM   4501  O   HOH   143    59.735  33.731   8.443  1.00 20.00    W
END
```

|  |  | -5 | 1 | 10 |
|---|---|---|---|---|
| *B. subtillis* ACP |  | G P L G S | A D T L E | R V T K I |
| *E. coli* ACP |  |  | S T I E E | R V K K I |
| *Streptomyces coelicolor* A3(2) ACP | M A T L L T | T D D L R | R A L V E |

|  | 20 |  | 30 |  |
|---|---|---|---|---|
| I V D R L | G V D E A | D V K L E | A S F K E | D L G A D |
| I G E Q L | G V K Q E | E V T N N | A S F V E | D L G A D |
| C A G E T | D G T D L | S G D F L | D L R F E | D I G Y D |

| 40 |  | 50 |  | 60 |
|---|---|---|---|---|
| S L D V V | E L V M E | L E D E F | D M E I S | D E D A E |
| S L D T V | E L V M A | L E E E F | D T E I P | D E E A E |
| S L A L M | E T A A R | L E S R Y | G V S I P | D D V A G |

|  | 70 |  | 76 |
|---|---|---|---|
| K I A T V | G D A V N | Y I Q N Q | Q |
| K I T T V | Q A A I D | Y I N G H | Q A |
| R V D T P | R E L L D | L I N G A | L A E A A |

| | Atom No. | Atom Type | Residue | Res. No. | X | Y | Z | | |
|---|---|---|---|---|---|---|---|---|---|
| ATOM | 1 | N | GLY | -5 | 13.445 | 10.407 | 11.181 | 1.00 | 7.22 |
| ATOM | 2 | CA | GLY | -5 | 14.143 | 11.725 | 11.174 | 1.00 | 6.61 |
| ATOM | 3 | C | GLY | -5 | 14.807 | 11.951 | 9.811 | 1.00 | 5.70 |
| ATOM | 4 | O | GLY | -5 | 14.370 | 12.786 | 9.043 | 1.00 | 5.61 |
| ATOM | 5 | 1HA | GLY | -5 | 14.899 | 11.735 | 11.944 | 1.00 | 6.68 |
| ATOM | 6 | 2HA | GLY | -5 | 13.427 | 12.512 | 11.362 | 1.00 | 7.06 |
| ATOM | 7 | 1H | GLY | -5 | 13.304 | 10.082 | 10.204 | 1.00 | 7.45 |
| ATOM | 8 | 2H | GLY | -5 | 12.521 | 10.507 | 11.650 | 1.00 | 7.32 |
| ATOM | 9 | 3H | GLY | -5 | 14.022 | 9.712 | 11.696 | 1.00 | 7.59 |
| ATOM | 10 | N | PRO | -4 | 15.850 | 11.199 | 9.553 | 1.00 | 5.38 |
| ATOM | 11 | CA | PRO | -4 | 16.579 | 11.330 | 8.267 | 1.00 | 4.86 |
| ATOM | 12 | C | PRO | -4 | 15.735 | 10.796 | 7.104 | 1.00 | 4.19 |
| ATOM | 13 | O | PRO | -4 | 14.970 | 11.522 | 6.500 | 1.00 | 4.30 |
| ATOM | 14 | CB | PRO | -4 | 17.842 | 10.496 | 8.484 | 1.00 | 5.34 |
| ATOM | 15 | CG | PRO | -4 | 17.475 | 9.509 | 9.545 | 1.00 | 5.78 |
| ATOM | 16 | CD | PRO | -4 | 16.442 | 10.169 | 10.420 | 1.00 | 5.92 |
| ATOM | 17 | HA | PRO | -4 | 16.847 | 12.350 | 8.088 | 1.00 | 5.08 |
| ATOM | 18 | 1HB | PRO | -4 | 18.652 | 11.121 | 8.826 | 1.00 | 5.86 |
| ATOM | 19 | 2HB | PRO | -4 | 18.117 | 9.986 | 7.571 | 1.00 | 5.21 |
| ATOM | 20 | 1HG | PRO | -4 | 18.344 | 9.260 | 10.135 | 1.00 | 6.43 |
| ATOM | 21 | 2HG | PRO | -4 | 17.065 | 8.617 | 9.093 | 1.00 | 5.71 |
| ATOM | 22 | 2HD | PRO | -4 | 15.694 | 9.451 | 10.728 | 1.00 | 6.14 |
| ATOM | 23 | 1HD | PRO | -4 | 16.906 | 10.628 | 11.278 | 1.00 | 6.49 |
| ATOM | 24 | N | LEU | -3 | 15.866 | 9.543 | 6.782 | 1.00 | 3.93 |
| ATOM | 25 | CA | LEU | -3 | 15.072 | 8.976 | 5.655 | 1.00 | 3.68 |
| ATOM | 26 | C | LEU | -3 | 14.070 | 7.952 | 6.194 | 1.00 | 2.75 |
| ATOM | 27 | O | LEU | -3 | 13.707 | 7.972 | 7.353 | 1.00 | 2.91 |
| ATOM | 28 | CB | LEU | -3 | 16.012 | 8.295 | 4.657 | 1.00 | 4.75 |
| ATOM | 29 | CG | LEU | -3 | 15.555 | 8.610 | 3.231 | 1.00 | 5.69 |
| ATOM | 30 | CD1 | LEU | -3 | 16.304 | 9.840 | 2.715 | 1.00 | 6.59 |
| ATOM | 31 | CD2 | LEU | -3 | 15.856 | 7.414 | 2.324 | 1.00 | 6.39 |
| ATOM | 32 | HN | LEU | -3 | 16.487 | 8.977 | 7.275 | 1.00 | 4.25 |
| ATOM | 33 | HA | LEU | -3 | 14.537 | 9.772 | 5.159 | 1.00 | 3.87 |
| ATOM | 34 | 1HB | LEU | -3 | 15.991 | 7.227 | 4.812 | 1.00 | 4.81 |
| ATOM | 35 | 2HB | LEU | -3 | 17.018 | 8.662 | 4.803 | 1.00 | 5.14 |
| ATOM | 36 | HG | LEU | -3 | 14.493 | 8.808 | 3.229 | 1.00 | 5.59 |
| ATOM | 37 | 1HD1 | LEU | -3 | 16.849 | 10.297 | 3.527 | 1.00 | 6.91 |
| ATOM | 38 | 2HD1 | LEU | -3 | 15.596 | 10.550 | 2.313 | 1.00 | 6.87 |
| ATOM | 39 | 3HD1 | LEU | -3 | 16.995 | 9.542 | 1.940 | 1.00 | 6.92 |
| ATOM | 40 | 1HD2 | LEU | -3 | 15.148 | 7.394 | 1.509 | 1.00 | 6.75 |
| ATOM | 41 | 2HD2 | LEU | -3 | 15.774 | 6.501 | 2.894 | 1.00 | 6.70 |
| ATOM | 42 | 3HD2 | LEU | -3 | 16.857 | 7.504 | 1.929 | 1.00 | 6.55 |
| ATOM | 43 | N | GLY | -2 | 13.619 | 7.057 | 5.357 | 1.00 | 2.32 |
| ATOM | 44 | CA | GLY | -2 | 12.638 | 6.032 | 5.813 | 1.00 | 1.96 |
| ATOM | 45 | C | GLY | -2 | 11.651 | 5.742 | 4.682 | 1.00 | 1.44 |
| ATOM | 46 | O | GLY | -2 | 11.709 | 4.710 | 4.043 | 1.00 | 2.05 |
| ATOM | 47 | HN | GLY | -2 | 13.924 | 7.061 | 4.426 | 1.00 | 2.73 |
| ATOM | 48 | 1HA | GLY | -2 | 12.099 | 6.404 | 6.671 | 1.00 | 2.15 |
| ATOM | 49 | 2HA | GLY | -2 | 13.163 | 5.126 | 6.080 | 1.00 | 2.61 |
| ATOM | 50 | N | SER | -1 | 10.749 | 6.649 | 4.425 | 1.00 | 1.07 |
| ATOM | 51 | CA | SER | -1 | 9.760 | 6.434 | 3.331 | 1.00 | 0.77 |
| ATOM | 52 | C | SER | -1 | 9.611 | 7.726 | 2.524 | 1.00 | 0.80 |
| ATOM | 53 | O | SER | -1 | 8.568 | 8.007 | 1.971 | 1.00 | 1.03 |
| ATOM | 54 | CB | SER | -1 | 8.407 | 6.049 | 3.931 | 1.00 | 1.06 |
| ATOM | 55 | OG | SER | -1 | 7.911 | 7.134 | 4.704 | 1.00 | 1.57 |
| ATOM | 56 | HN | SER | -1 | 10.724 | 7.476 | 4.950 | 1.00 | 1.67 |
| ATOM | 57 | HA | SER | -1 | 10.104 | 5.641 | 2.683 | 1.00 | 0.86 |
| ATOM | 58 | 1HB | SER | -1 | 8.527 | 5.174 | 4.556 | 1.00 | 1.22 |
| ATOM | 59 | 2HB | SER | -1 | 7.709 | 5.826 | 3.140 | 1.00 | 1.21 |
| ATOM | 60 | HG | SER | -1 | 8.481 | 7.240 | 5.469 | 1.00 | 2.01 |
| ATOM | 61 | N | ALA | 1 | 10.648 | 8.520 | 2.454 | 1.00 | 0.84 |
| ATOM | 62 | CA | ALA | 1 | 10.567 | 9.797 | 1.687 | 1.00 | 0.86 |
| ATOM | 63 | C | ALA | 1 | 9.992 | 9.530 | 0.293 | 1.00 | 0.83 |
| ATOM | 64 | O | ALA | 1 | 8.843 | 9.816 | 0.019 | 1.00 | 0.87 |
| ATOM | 65 | CB | ALA | 1 | 11.967 | 10.400 | 1.556 | 1.00 | 0.91 |
| ATOM | 66 | HN | ALA | 1 | 11.478 | 8.281 | 2.909 | 1.00 | 1.01 |
| ATOM | 67 | HA | ALA | 1 | 9.930 | 10.484 | 2.212 | 1.00 | 0.92 |
| ATOM | 68 | 1HB | ALA | 1 | 12.031 | 11.295 | 2.156 | 1.00 | 1.45 |
| ATOM | 69 | 2HB | ALA | 1 | 12.158 | 10.645 | 0.521 | 1.00 | 1.12 |
| ATOM | 70 | 3HB | ALA | 1 | 12.700 | 9.684 | 1.898 | 1.00 | 1.48 |
| ATOM | 71 | N | ASP | 2 | 10.779 | 8.974 | -0.583 | 1.00 | 0.80 |
| ATOM | 72 | CA | ASP | 2 | 10.273 | 8.677 | -1.952 | 1.00 | 0.81 |
| ATOM | 73 | C | ASP | 2 | 9.341 | 7.469 | -1.879 | 1.00 | 0.76 |
| ATOM | 74 | O | ASP | 2 | 8.421 | 7.327 | -2.659 | 1.00 | 0.79 |
| ATOM | 75 | CB | ASP | 2 | 11.451 | 8.362 | -2.878 | 1.00 | 0.86 |
| ATOM | 76 | CG | ASP | 2 | 11.709 | 9.554 | -3.802 | 1.00 | 1.59 |
| ATOM | 77 | OD1 | ASP | 2 | 11.953 | 9.327 | -4.976 | 1.00 | 2.30 |

FIG. 5A-1

| | | | | | | | | |
|---|---|---|---|---|---|---|---|---|
| ATOM | 78 | CD2 | ASP | 2 | 11.658 | 10.674 | -3.321 | 1.00 | 2.20 |
| ATOM | 79 | HN | ASP | 2 | 11.697 | 8.745 | -0.338 | 1.00 | 0.81 |
| ATOM | 80 | HA | ASP | 2 | 9.732 | 9.531 | -2.331 | 1.00 | 0.85 |
| ATOM | 81 | 1HB | ASP | 2 | 11.219 | 7.492 | -3.473 | 1.00 | 1.31 |
| ATOM | 82 | 2HB | ASP | 2 | 12.333 | 8.168 | -2.285 | 1.00 | 1.14 |
| ATOM | 83 | N | THR | 3 | 9.573 | 6.601 | -0.933 | 1.00 | 0.73 |
| ATOM | 84 | CA | THR | 3 | 8.709 | 5.399 | -0.783 | 1.00 | 0.69 |
| ATOM | 85 | C | THR | 3 | 7.282 | 5.837 | -0.452 | 1.00 | 0.66 |
| ATOM | 86 | O | THR | 3 | 6.372 | 5.666 | -1.237 | 1.00 | 0.63 |
| ATOM | 87 | CB | THR | 3 | 9.253 | 4.534 | 0.355 | 1.00 | 0.71 |
| ATOM | 88 | OG1 | THR | 3 | 10.665 | 4.674 | 0.418 | 1.00 | 0.86 |
| ATOM | 89 | CG2 | THR | 3 | 8.895 | 3.070 | 0.110 | 1.00 | 0.75 |
| ATOM | 90 | HN | THR | 3 | 10.319 | 6.744 | -0.314 | 1.00 | 0.75 |
| ATOM | 91 | HA | THR | 3 | 8.708 | 4.830 | -1.699 | 1.00 | 0.68 |
| ATOM | 92 | HB | THR | 3 | 8.819 | 4.855 | 1.287 | 1.00 | 0.70 |
| ATOM | 93 | HG1 | THR | 3 | 10.946 | 4.453 | 1.309 | 1.00 | 1.08 |
| ATOM | 94 | 1HG2 | THR | 3 | 9.527 | 2.442 | 0.720 | 1.00 | 1.26 |
| ATOM | 95 | 2HG2 | THR | 3 | 9.046 | 2.830 | -0.932 | 1.00 | 1.33 |
| ATOM | 96 | 3HG2 | THR | 3 | 7.861 | 2.902 | 0.373 | 1.00 | 1.09 |
| ATOM | 97 | N | LEU | 4 | 7.086 | 6.404 | 0.709 | 1.00 | 0.68 |
| ATOM | 98 | CA | LEU | 4 | 5.721 | 6.862 | 1.118 | 1.00 | 0.68 |
| ATOM | 99 | C | LEU | 4 | 5.055 | 7.628 | -0.025 | 1.00 | 0.66 |
| ATOM | 100 | O | LEU | 4 | 4.006 | 7.254 | -0.507 | 1.00 | 0.66 |
| ATOM | 101 | CB | LEU | 4 | 5.838 | 7.776 | 2.340 | 1.00 | 0.73 |
| ATOM | 102 | CG | LEU | 4 | 4.566 | 7.670 | 3.182 | 1.00 | 0.77 |
| ATOM | 103 | CD1 | LEU | 4 | 4.435 | 6.250 | 3.730 | 1.00 | 1.60 |
| ATOM | 104 | CD2 | LEU | 4 | 4.643 | 8.660 | 4.346 | 1.00 | 1.36 |
| ATOM | 105 | HN | LEU | 4 | 7.842 | 6.528 | 1.317 | 1.00 | 0.71 |
| ATOM | 106 | HA | LEU | 4 | 5.119 | 6.006 | 1.370 | 1.00 | 0.67 |
| ATOM | 107 | 1HB | LEU | 4 | 5.970 | 8.797 | 2.016 | 1.00 | 0.83 |
| ATOM | 108 | 2HB | LEU | 4 | 6.688 | 7.473 | 2.933 | 1.00 | 0.83 |
| ATOM | 109 | HG | LEU | 4 | 3.708 | 7.900 | 2.567 | 1.00 | 1.32 |
| ATOM | 110 | 1HD1 | LEU | 4 | 3.887 | 5.642 | 3.027 | 1.00 | 2.12 |
| ATOM | 111 | 2HD1 | LEU | 4 | 3.907 | 6.274 | 4.672 | 1.00 | 2.07 |
| ATOM | 112 | 3HD1 | LEU | 4 | 5.418 | 5.829 | 3.880 | 1.00 | 2.15 |
| ATOM | 113 | 1HD2 | LEU | 4 | 4.357 | 8.163 | 5.261 | 1.00 | 1.85 |
| ATOM | 114 | 2HD2 | LEU | 4 | 3.974 | 9.486 | 4.160 | 1.00 | 1.90 |
| ATOM | 115 | 3HD2 | LEU | 4 | 5.654 | 9.030 | 4.438 | 1.00 | 1.95 |
| ATOM | 116 | N | GLU | 5 | 5.659 | 8.695 | -0.463 | 1.00 | 0.68 |
| ATOM | 117 | CA | GLU | 5 | 5.066 | 9.483 | -1.577 | 1.00 | 0.69 |
| ATOM | 118 | C | GLU | 5 | 4.786 | 8.555 | -2.760 | 1.00 | 0.64 |
| ATOM | 119 | O | GLU | 5 | 3.740 | 8.613 | -3.375 | 1.00 | 0.64 |
| ATOM | 120 | CB | GLU | 5 | 6.043 | 10.581 | -2.002 | 1.00 | 0.75 |
| ATOM | 121 | CG | GLU | 5 | 5.579 | 11.925 | -1.438 | 1.00 | 0.99 |
| ATOM | 122 | CD | GLU | 5 | 5.850 | 13.029 | -2.462 | 1.00 | 1.53 |
| ATOM | 123 | OE1 | GLU | 5 | 6.673 | 13.884 | -2.179 | 1.00 | 2.26 |
| ATOM | 124 | OE2 | GLU | 5 | 5.229 | 13.000 | -3.512 | 1.00 | 1.99 |
| ATOM | 125 | HN | GLU | 5 | 6.501 | 8.976 | -0.062 | 1.00 | 0.69 |
| ATOM | 126 | HA | GLU | 5 | 4.146 | 9.926 | -1.243 | 1.00 | 0.70 |
| ATOM | 127 | 1HB | GLU | 5 | 6.075 | 10.637 | -3.080 | 1.00 | 0.92 |
| ATOM | 128 | 2HB | GLU | 5 | 7.029 | 10.352 | -1.624 | 1.00 | 1.03 |
| ATOM | 129 | 1HG | GLU | 5 | 6.120 | 12.140 | -0.529 | 1.00 | 1.46 |
| ATOM | 130 | 2HG | GLU | 5 | 4.521 | 11.881 | -1.226 | 1.00 | 1.41 |
| ATOM | 131 | N | ARG | 6 | 5.709 | 7.688 | -3.071 | 1.00 | 0.62 |
| ATOM | 132 | CA | ARG | 6 | 5.489 | 6.744 | -4.201 | 1.00 | 0.60 |
| ATOM | 133 | C | ARG | 6 | 4.238 | 5.922 | -3.903 | 1.00 | 0.55 |
| ATOM | 134 | O | ARG | 6 | 3.258 | 5.972 | -4.619 | 1.00 | 0.57 |
| ATOM | 135 | CB | ARG | 6 | 6.707 | 5.815 | -4.337 | 1.00 | 0.61 |
| ATOM | 136 | CG | ARG | 6 | 6.411 | 4.687 | -5.334 | 1.00 | 0.59 |
| ATOM | 137 | CD | ARG | 6 | 5.997 | 5.283 | -6.680 | 1.00 | 0.64 |
| ATOM | 138 | NE | ARG | 6 | 6.941 | 4.821 | -7.736 | 1.00 | 0.73 |
| ATOM | 139 | CZ | ARG | 6 | 6.995 | 5.442 | -8.883 | 1.00 | 1.07 |
| ATOM | 140 | NH1 | ARG | 6 | 8.123 | 5.952 | -9.296 | 1.00 | 1.70 |
| ATOM | 141 | NH2 | ARG | 6 | 5.922 | 5.553 | -9.617 | 1.00 | 1.79 |
| ATOM | 142 | HN | ARG | 6 | 6.539 | 7.651 | -2.553 | 1.00 | 0.65 |
| ATOM | 143 | HA | ARG | 6 | 5.348 | 7.300 | -5.112 | 1.00 | 0.63 |
| ATOM | 144 | 1HB | ARG | 6 | 6.935 | 5.384 | -3.374 | 1.00 | 0.60 |
| ATOM | 145 | 2HB | ARG | 6 | 7.555 | 6.383 | -4.685 | 1.00 | 0.68 |
| ATOM | 146 | 1HG | ARG | 6 | 5.610 | 4.072 | -4.953 | 1.00 | 0.56 |
| ATOM | 147 | 2HG | ARG | 6 | 7.297 | 4.083 | -5.466 | 1.00 | 0.61 |
| ATOM | 148 | 1HD | ARG | 6 | 6.020 | 6.359 | -6.620 | 1.00 | 0.67 |
| ATOM | 149 | 2HD | ARG | 6 | 4.996 | 4.958 | -6.921 | 1.00 | 0.64 |
| ATOM | 150 | HE | ARG | 6 | 7.524 | 4.052 | -7.569 | 1.00 | 0.94 |
| ATOM | 151 | 1HH1 | ARG | 6 | 8.946 | 5.867 | -8.734 | 1.00 | 2.17 |
| ATOM | 152 | 2HH1 | ARG | 6 | 8.166 | 6.428 | -10.175 | 1.00 | 2.13 |
| ATOM | 153 | 1HH2 | ARG | 6 | 5.058 | 5.162 | -9.301 | 1.00 | 2.29 |
| ATOM | 154 | 2HH2 | ARG | 6 | 5.964 | 6.027 | -10.496 | 1.00 | 2.19 |

FIG. 5A-2

| | | | | | | | | |
|---|---|---|---|---|---|---|---|---|
| ATOM | 155 | N | VAL | 7 | 4.271 | 5.170 | -2.343 | 1.00 | 0.53 |
| ATOM | 156 | CA | VAL | 7 | 3.097 | 4.343 | -2.476 | 1.00 | 0.50 |
| ATOM | 157 | C | VAL | 7 | 1.864 | 5.236 | -2.365 | 1.00 | 0.50 |
| ATOM | 158 | O | VAL | 7 | 0.777 | 4.868 | -2.765 | 1.00 | 0.61 |
| ATOM | 159 | CB | VAL | 7 | 3.357 | 3.664 | -1.133 | 1.00 | 0.52 |
| ATOM | 160 | CG1 | VAL | 7 | 2.279 | 2.619 | -0.878 | 1.00 | 0.56 |
| ATOM | 161 | CG2 | VAL | 7 | 4.716 | 2.974 | -1.166 | 1.00 | 0.53 |
| ATOM | 162 | HN | VAL | 7 | 5.070 | 5.152 | -2.287 | 1.00 | 0.56 |
| ATOM | 163 | HA | VAL | 7 | 2.938 | 3.596 | -3.232 | 1.00 | 0.50 |
| ATOM | 164 | HB | VAL | 7 | 3.342 | 4.402 | -0.344 | 1.00 | 0.56 |
| ATOM | 165 | 1HG1 | VAL | 7 | 1.941 | 2.216 | -1.821 | 1.00 | 1.14 |
| ATOM | 166 | 2HG1 | VAL | 7 | 1.453 | 3.079 | -0.364 | 1.00 | 1.13 |
| ATOM | 167 | 3HG1 | VAL | 7 | 2.687 | 1.824 | -0.272 | 1.00 | 1.23 |
| ATOM | 168 | 1HG2 | VAL | 7 | 4.783 | 2.275 | -0.349 | 1.00 | 1.19 |
| ATOM | 169 | 2HG2 | VAL | 7 | 5.499 | 3.708 | -1.076 | 1.00 | 1.06 |
| ATOM | 170 | 3HG2 | VAL | 7 | 4.821 | 2.446 | -2.098 | 1.00 | 1.15 |
| ATOM | 171 | N | THR | 8 | 2.028 | 6.411 | -1.826 | 1.00 | 0.47 |
| ATOM | 172 | CA | THR | 8 | 0.871 | 7.335 | -1.689 | 1.00 | 0.49 |
| ATOM | 173 | C | THR | 8 | 0.287 | 7.613 | -3.071 | 1.00 | 0.47 |
| ATOM | 174 | O | THR | 8 | -0.913 | 7.667 | -3.250 | 1.00 | 0.50 |
| ATOM | 175 | CB | THR | 8 | 1.335 | 8.649 | -1.054 | 1.00 | 0.58 |
| ATOM | 176 | OG1 | THR | 8 | 1.898 | 8.384 | 0.223 | 1.00 | 0.63 |
| ATOM | 177 | CG2 | THR | 8 | 0.143 | 9.594 | -0.902 | 1.00 | 0.65 |
| ATOM | 178 | HN | THR | 8 | 2.915 | 6.685 | -1.514 | 1.00 | 0.50 |
| ATOM | 179 | HA | THR | 8 | 0.120 | 6.877 | -1.068 | 1.00 | 0.48 |
| ATOM | 180 | HB | THR | 8 | 2.077 | 9.112 | -1.685 | 1.00 | 0.60 |
| ATOM | 181 | HG1 | THR | 8 | 2.434 | 9.140 | 0.474 | 1.00 | 0.92 |
| ATOM | 182 | 1HG2 | THR | 8 | -0.152 | 9.961 | -1.874 | 1.00 | 1.18 |
| ATOM | 183 | 2HG2 | THR | 8 | 0.421 | 10.426 | -0.272 | 1.00 | 1.17 |
| ATOM | 184 | 3HG2 | THR | 8 | -0.683 | 9.062 | -0.453 | 1.00 | 1.30 |
| ATOM | 185 | N | LYS | 9 | 1.127 | 7.777 | -4.054 | 1.00 | 0.49 |
| ATOM | 186 | CA | LYS | 9 | 0.615 | 8.035 | -5.425 | 1.00 | 0.51 |
| ATOM | 187 | C | LYS | 9 | -0.093 | 6.777 | -5.919 | 1.00 | 0.46 |
| ATOM | 188 | O | LYS | 9 | -1.121 | 6.837 | -6.563 | 1.00 | 0.50 |
| ATOM | 189 | CB | LYS | 9 | 1.782 | 8.373 | -6.356 | 1.00 | 0.57 |
| ATOM | 190 | CG | LYS | 9 | 1.486 | 9.683 | -7.088 | 1.00 | 0.83 |
| ATOM | 191 | CD | LYS | 9 | 2.733 | 10.570 | -7.074 | 1.00 | 1.21 |
| ATOM | 192 | CE | LYS | 9 | 3.808 | 9.953 | -7.971 | 1.00 | 1.47 |
| ATOM | 193 | NZ | LYS | 9 | 4.135 | 10.898 | -9.075 | 1.00 | 2.31 |
| ATOM | 194 | HN | LYS | 9 | 2.091 | 7.718 | -3.890 | 1.00 | 0.53 |
| ATOM | 195 | HA | LYS | 9 | -0.083 | 8.857 | -5.402 | 1.00 | 0.54 |
| ATOM | 196 | 1HB | LYS | 9 | 1.909 | 7.580 | -7.077 | 1.00 | 0.71 |
| ATOM | 197 | 2HB | LYS | 9 | 2.686 | 8.480 | -5.774 | 1.00 | 0.75 |
| ATOM | 198 | 1HG | LYS | 9 | 0.676 | 10.198 | -6.594 | 1.00 | 1.43 |
| ATOM | 199 | 2HG | LYS | 9 | 1.208 | 9.469 | -8.110 | 1.00 | 1.41 |
| ATOM | 200 | 1HD | LYS | 9 | 3.110 | 10.646 | -6.065 | 1.00 | 1.82 |
| ATOM | 201 | 2HD | LYS | 9 | 2.479 | 11.554 | -7.440 | 1.00 | 1.93 |
| ATOM | 202 | 1HE | LYS | 9 | 3.441 | 9.026 | -8.387 | 1.00 | 1.92 |
| ATOM | 203 | 2HE | LYS | 9 | 4.696 | 9.759 | -7.388 | 1.00 | 1.77 |
| ATOM | 204 | 1HZ | LYS | 9 | 3.912 | 11.869 | -8.779 | 1.00 | 2.74 |
| ATOM | 205 | 2HZ | LYS | 9 | 3.575 | 10.653 | -9.918 | 1.00 | 2.83 |
| ATOM | 206 | 3HZ | LYS | 9 | 5.148 | 10.831 | -9.300 | 1.00 | 2.62 |
| ATOM | 207 | N | ILE | 10 | 0.451 | 5.634 | -5.608 | 1.00 | 0.43 |
| ATOM | 208 | CA | ILE | 10 | -0.176 | 4.364 | -6.036 | 1.00 | 0.44 |
| ATOM | 209 | C | ILE | 10 | -1.459 | 4.137 | -5.234 | 1.00 | 0.39 |
| ATOM | 210 | O | ILE | 10 | -2.527 | 3.977 | -5.787 | 1.00 | 0.43 |
| ATOM | 211 | CB | ILE | 10 | 0.809 | 3.227 | -5.777 | 1.00 | 0.48 |
| ATOM | 212 | CG1 | ILE | 10 | 2.071 | 3.447 | -6.615 | 1.00 | 0.57 |
| ATOM | 213 | CG2 | ILE | 10 | 0.167 | 1.902 | -6.165 | 1.00 | 0.53 |
| ATOM | 214 | CD1 | ILE | 10 | 3.198 | 2.559 | -6.086 | 1.00 | 0.73 |
| ATOM | 215 | HN | ILE | 10 | 1.276 | 5.610 | -5.084 | 1.00 | 0.45 |
| ATOM | 216 | HA | ILE | 10 | -0.409 | 4.410 | -7.085 | 1.00 | 0.48 |
| ATOM | 217 | HB | ILE | 10 | 1.069 | 3.207 | -4.729 | 1.00 | 0.47 |
| ATOM | 218 | 1HG1 | ILE | 10 | 2.370 | 4.483 | -6.548 | 1.00 | 0.65 |
| ATOM | 219 | 2HG1 | ILE | 10 | 1.866 | 3.197 | -7.646 | 1.00 | 0.65 |
| ATOM | 220 | 1HG2 | ILE | 10 | 0.064 | 1.856 | -7.238 | 1.00 | 1.15 |
| ATOM | 221 | 2HG2 | ILE | 10 | -0.806 | 1.829 | -5.704 | 1.00 | 1.10 |
| ATOM | 222 | 3HG2 | ILE | 10 | 0.791 | 1.090 | -5.825 | 1.00 | 1.22 |
| ATOM | 223 | 1HD1 | ILE | 10 | 3.988 | 3.178 | -5.689 | 1.00 | 1.17 |
| ATOM | 224 | 2HD1 | ILE | 10 | 3.585 | 1.952 | -6.991 | 1.00 | 1.28 |
| ATOM | 225 | 3HD1 | ILE | 10 | 2.815 | 1.919 | -5.305 | 1.00 | 1.36 |
| ATOM | 226 | N | ILE | 11 | -1.363 | 4.126 | -3.935 | 1.00 | 0.34 |
| ATOM | 227 | CA | ILE | 11 | -2.581 | 3.912 | -3.100 | 1.00 | 0.31 |
| ATOM | 228 | C | ILE | 11 | -3.628 | 4.971 | -3.443 | 1.00 | 0.33 |
| ATOM | 229 | O | ILE | 11 | -4.692 | 4.674 | -3.949 | 1.00 | 0.38 |
| ATOM | 230 | CB | ILE | 11 | -2.231 | 4.038 | -1.614 | 1.00 | 0.31 |
| ATOM | 231 | CG1 | ILE | 11 | -1.167 | 3.005 | -1.232 | 1.00 | 0.42 |

FIG. 5A-3

| | | | | | | | | |
|---|---|---|---|---|---|---|---|---|
| ATOM | 232 | CG2 | ILE | 11 | -3.490 | 3.793 | -0.782 | 1.00 | 0.37 |
| ATOM | 233 | CD1 | ILE | 11 | -0.869 | 3.106 | 0.267 | 1.00 | 0.43 |
| ATOM | 234 | HN | ILE | 11 | -0.492 | 4.260 | -3.510 | 1.00 | 0.36 |
| ATOM | 235 | HA | ILE | 11 | -2.985 | 2.933 | -3.294 | 1.00 | 0.32 |
| ATOM | 236 | HB | ILE | 11 | -1.859 | 5.033 | -1.417 | 1.00 | 0.33 |
| ATOM | 237 | 1HG1 | ILE | 11 | -0.263 | 3.194 | -1.791 | 1.00 | 0.58 |
| ATOM | 238 | 2HG1 | ILE | 11 | -1.531 | 2.016 | -1.458 | 1.00 | 0.69 |
| ATOM | 239 | 1HG2 | ILE | 11 | -3.237 | 3.817 | 0.267 | 1.00 | 1.09 |
| ATOM | 240 | 2HG2 | ILE | 11 | -3.903 | 2.826 | -1.031 | 1.00 | 1.07 |
| ATOM | 241 | 3HG2 | ILE | 11 | -4.218 | 4.561 | -0.996 | 1.00 | 1.08 |
| ATOM | 242 | 1HD1 | ILE | 11 | -0.273 | 2.259 | 0.572 | 1.00 | 0.99 |
| ATOM | 243 | 2HD1 | ILE | 11 | -1.797 | 3.109 | 0.820 | 1.00 | 1.22 |
| ATOM | 244 | 3HD1 | ILE | 11 | -0.328 | 4.018 | 0.466 | 1.00 | 1.12 |
| ATOM | 245 | N | VAL | 12 | -3.331 | 6.205 | -3.150 | 1.00 | 0.38 |
| ATOM | 246 | CA | VAL | 12 | -4.294 | 7.310 | -3.427 | 1.00 | 0.44 |
| ATOM | 247 | C | VAL | 12 | -4.862 | 7.187 | -4.844 | 1.00 | 0.48 |
| ATOM | 248 | O | VAL | 12 | -6.050 | 7.016 | -5.037 | 1.00 | 0.61 |
| ATOM | 249 | CB | VAL | 12 | -3.567 | 8.650 | -3.286 | 1.00 | 0.49 |
| ATOM | 250 | CG1 | VAL | 12 | -4.535 | 9.795 | -3.586 | 1.00 | 0.59 |
| ATOM | 251 | CG2 | VAL | 12 | -3.036 | 8.792 | -1.858 | 1.00 | 0.50 |
| ATOM | 252 | HN | VAL | 12 | -2.469 | 6.405 | -2.731 | 1.00 | 0.44 |
| ATOM | 253 | HA | VAL | 12 | -5.099 | 7.266 | -2.714 | 1.00 | 0.44 |
| ATOM | 254 | HB | VAL | 12 | -2.743 | 8.685 | -3.984 | 1.00 | 0.49 |
| ATOM | 255 | 1HG1 | VAL | 12 | -4.123 | 10.421 | -4.363 | 1.00 | 0.94 |
| ATOM | 256 | 2HG1 | VAL | 12 | -4.686 | 10.383 | -2.692 | 1.00 | 1.35 |
| ATOM | 257 | 3HG1 | VAL | 12 | -5.481 | 9.391 | -3.914 | 1.00 | 1.23 |
| ATOM | 258 | 1HG2 | VAL | 12 | -3.716 | 9.401 | -1.280 | 1.00 | 1.09 |
| ATOM | 259 | 2HG2 | VAL | 12 | -2.064 | 9.261 | -1.881 | 1.00 | 1.15 |
| ATOM | 260 | 3HG2 | VAL | 12 | -2.954 | 7.815 | -1.405 | 1.00 | 1.17 |
| ATOM | 261 | N | ASP | 13 | -4.023 | 7.287 | -5.833 | 1.00 | 0.45 |
| ATOM | 262 | CA | ASP | 13 | -4.502 | 7.193 | -7.244 | 1.00 | 0.50 |
| ATOM | 263 | C | ASP | 13 | -5.372 | 5.947 | -7.429 | 1.00 | 0.45 |
| ATOM | 264 | O | ASP | 13 | -6.222 | 5.898 | -8.296 | 1.00 | 0.49 |
| ATOM | 265 | CB | ASP | 13 | -3.296 | 7.112 | -8.184 | 1.00 | 0.57 |
| ATOM | 266 | CG | ASP | 13 | -3.751 | 7.364 | -9.623 | 1.00 | 1.25 |
| ATOM | 267 | OD1 | ASP | 13 | -2.914 | 7.729 | -10.432 | 1.00 | 1.87 |
| ATOM | 268 | OD2 | ASP | 13 | -4.927 | 7.187 | -9.892 | 1.00 | 1.93 |
| ATOM | 269 | HN | ASP | 13 | -3.073 | 7.433 | -5.648 | 1.00 | 0.46 |
| ATOM | 270 | HA | ASP | 13 | -5.081 | 8.068 | -7.484 | 1.00 | 0.55 |
| ATOM | 271 | 1HB | ASP | 13 | -2.851 | 6.132 | -8.115 | 1.00 | 0.87 |
| ATOM | 272 | 2HB | ASP | 13 | -2.569 | 7.859 | -7.899 | 1.00 | 0.86 |
| ATOM | 273 | N | ARG | 14 | -5.161 | 4.935 | -6.636 | 1.00 | 0.39 |
| ATOM | 274 | CA | ARG | 14 | -5.971 | 3.695 | -6.791 | 1.00 | 0.37 |
| ATOM | 275 | C | ARG | 14 | -7.082 | 3.633 | -5.736 | 1.00 | 0.32 |
| ATOM | 276 | O | ARG | 14 | -8.198 | 4.056 | -5.970 | 1.00 | 0.34 |
| ATOM | 277 | CB | ARG | 14 | -5.049 | 2.479 | -6.649 | 1.00 | 0.39 |
| ATOM | 278 | CG | ARG | 14 | -4.404 | 2.155 | -8.004 | 1.00 | 0.48 |
| ATOM | 279 | CD | ARG | 14 | -3.757 | 3.413 | -8.600 | 1.00 | 0.51 |
| ATOM | 280 | NE | ARG | 14 | -3.019 | 3.051 | -9.842 | 1.00 | 0.62 |
| ATOM | 281 | CZ | ARG | 14 | -1.795 | 3.466 | -10.019 | 1.00 | 0.95 |
| ATOM | 282 | NH1 | ARG | 14 | -0.833 | 2.603 | -10.203 | 1.00 | 1.69 |
| ATOM | 283 | NH2 | ARG | 14 | -1.532 | 4.744 | -10.014 | 1.00 | 1.63 |
| ATOM | 284 | HN | ARG | 14 | -4.465 | 4.986 | -5.949 | 1.00 | 0.37 |
| ATOM | 285 | HA | ARG | 14 | -6.417 | 3.685 | -7.774 | 1.00 | 0.42 |
| ATOM | 286 | 1HB | ARG | 14 | -5.625 | 1.630 | -6.314 | 1.00 | 0.38 |
| ATOM | 287 | 2HB | ARG | 14 | -4.279 | 2.697 | -5.923 | 1.00 | 0.37 |
| ATOM | 288 | 1HG | ARG | 14 | -5.160 | 1.788 | -8.682 | 1.00 | 0.51 |
| ATOM | 289 | 2HG | ARG | 14 | -3.648 | 1.395 | -7.866 | 1.00 | 0.53 |
| ATOM | 290 | 1HD | ARG | 14 | -3.071 | 3.841 | -7.885 | 1.00 | 0.50 |
| ATOM | 291 | 2HD | ARG | 14 | -4.525 | 4.136 | -8.836 | 1.00 | 0.50 |
| ATOM | 292 | HE | ARG | 14 | -3.453 | 2.500 | -10.526 | 1.00 | 0.87 |
| ATOM | 293 | 1HH1 | ARG | 14 | -1.035 | 1.623 | -10.207 | 1.00 | 2.25 |
| ATOM | 294 | 2HH1 | ARG | 14 | 0.105 | 2.921 | -10.340 | 1.00 | 2.08 |
| ATOM | 295 | 1HH2 | ARG | 14 | -2.269 | 5.405 | -9.874 | 1.00 | 2.17 |
| ATOM | 296 | 2HH2 | ARG | 14 | -0.594 | 5.062 | -10.150 | 1.00 | 2.01 |
| ATOM | 297 | N | LEU | 15 | -6.793 | 3.089 | -4.585 | 1.00 | 0.30 |
| ATOM | 298 | CA | LEU | 15 | -7.832 | 2.971 | -3.525 | 1.00 | 0.30 |
| ATOM | 299 | C | LEU | 15 | -8.196 | 4.357 | -2.977 | 1.00 | 0.31 |
| ATOM | 300 | O | LEU | 15 | -9.146 | 4.505 | -2.234 | 1.00 | 0.37 |
| ATOM | 301 | CB | LEU | 15 | -7.290 | 2.091 | -2.391 | 1.00 | 0.34 |
| ATOM | 302 | CG | LEU | 15 | -7.351 | 0.607 | -2.790 | 1.00 | 0.39 |
| ATOM | 303 | CD1 | LEU | 15 | -8.810 | 0.156 | -2.885 | 1.00 | 0.45 |
| ATOM | 304 | CD2 | LEU | 15 | -6.672 | 0.393 | -4.147 | 1.00 | 0.40 |
| ATOM | 305 | HN | LEU | 15 | -5.893 | 2.740 | -4.421 | 1.00 | 0.33 |
| ATOM | 306 | HA | LEU | 15 | -8.715 | 2.510 | -3.941 | 1.00 | 0.33 |
| ATOM | 307 | 1HB | LEU | 15 | -7.886 | 2.246 | -1.504 | 1.00 | 0.37 |
| ATOM | 308 | 2HB | LEU | 15 | -6.266 | 2.365 | -2.186 | 1.00 | 0.34 |

FIG. 5A-4

| | | | | | | | | |
|---|---|---|---|---|---|---|---|---|
| ATOM | 309 | HG | LEU | 15 | -6.843 | 0.017 | -2.039 | 1.00 | 0.46 |
| ATOM | 310 | 1HD1 | LEU | 15 | -8.986 | -0.644 | -2.180 | 1.00 | 1.16 |
| ATOM | 311 | 2HD1 | LEU | 15 | -9.013 | -0.197 | -3.886 | 1.00 | 1.04 |
| ATOM | 312 | 3HD1 | LEU | 15 | -9.459 | 0.987 | -2.658 | 1.00 | 1.03 |
| ATOM | 313 | 1HD2 | LEU | 15 | -6.598 | -0.665 | -4.349 | 1.00 | 1.06 |
| ATOM | 314 | 2HD2 | LEU | 15 | -5.684 | 0.826 | -4.127 | 1.00 | 1.08 |
| ATOM | 315 | 3HD2 | LEU | 15 | -7.258 | 0.867 | -4.920 | 1.00 | 1.10 |
| ATOM | 316 | N | GLY | 16 | -7.456 | 5.373 | -3.332 | 1.00 | 0.35 |
| ATOM | 317 | CA | GLY | 16 | -7.777 | 6.737 | -2.822 | 1.00 | 0.41 |
| ATOM | 318 | C | GLY | 16 | -9.065 | 7.239 | -3.474 | 1.00 | 0.47 |
| ATOM | 319 | O | GLY | 16 | -9.782 | 8.042 | -2.911 | 1.00 | 0.72 |
| ATOM | 320 | HN | GLY | 16 | -6.693 | 5.243 | -3.931 | 1.00 | 0.40 |
| ATOM | 321 | 1HA | GLY | 16 | -6.972 | 7.411 | -3.066 | 1.00 | 0.47 |
| ATOM | 322 | 2HA | GLY | 16 | -7.904 | 6.699 | -1.750 | 1.00 | 0.53 |
| ATOM | 323 | N | VAL | 17 | -9.364 | 6.771 | -4.656 | 1.00 | 0.45 |
| ATOM | 324 | CA | VAL | 17 | -10.606 | 7.220 | -5.348 | 1.00 | 0.66 |
| ATOM | 325 | C | VAL | 17 | -10.558 | 8.740 | -5.551 | 1.00 | 0.76 |
| ATOM | 326 | O | VAL | 17 | -10.142 | 9.222 | -6.586 | 1.00 | 0.89 |
| ATOM | 327 | CB | VAL | 17 | -11.826 | 6.835 | -4.504 | 1.00 | 0.86 |
| ATOM | 328 | CG1 | VAL | 17 | -13.099 | 7.397 | -5.144 | 1.00 | 1.16 |
| ATOM | 329 | CG2 | VAL | 17 | -11.930 | 5.310 | -4.433 | 1.00 | 1.06 |
| ATOM | 330 | HN | VAL | 17 | -8.771 | 6.123 | -5.089 | 1.00 | 0.44 |
| ATOM | 331 | HA | VAL | 17 | -10.671 | 6.737 | -6.310 | 1.00 | 0.75 |
| ATOM | 332 | HB | VAL | 17 | -11.717 | 7.235 | -3.507 | 1.00 | 1.21 |
| ATOM | 333 | 1HG1 | VAL | 17 | -13.187 | 8.447 | -4.908 | 1.00 | 1.72 |
| ATOM | 334 | 2HG1 | VAL | 17 | -13.958 | 6.868 | -4.759 | 1.00 | 1.62 |
| ATOM | 335 | 3HG1 | VAL | 17 | -13.048 | 7.272 | -6.215 | 1.00 | 1.56 |
| ATOM | 336 | 1HG2 | VAL | 17 | -11.288 | 4.942 | -3.646 | 1.00 | 1.40 |
| ATOM | 337 | 2HG2 | VAL | 17 | -11.624 | 4.884 | -5.377 | 1.00 | 1.46 |
| ATOM | 338 | 3HG2 | VAL | 17 | -12.952 | 5.028 | -4.225 | 1.00 | 1.47 |
| ATOM | 339 | N | ASP | 18 | -10.979 | 9.498 | -4.576 | 1.00 | 0.82 |
| ATOM | 340 | CA | ASP | 18 | -10.956 | 10.982 | -4.720 | 1.00 | 0.99 |
| ATOM | 341 | C | ASP | 18 | -9.777 | 11.555 | -3.930 | 1.00 | 0.95 |
| ATOM | 342 | O | ASP | 18 | -9.809 | 12.684 | -3.481 | 1.00 | 1.75 |
| ATOM | 343 | CB | ASP | 18 | -12.263 | 11.567 | -4.181 | 1.00 | 1.18 |
| ATOM | 344 | CG | ASP | 18 | -13.023 | 12.253 | -5.318 | 1.00 | 1.80 |
| ATOM | 345 | OD1 | ASP | 18 | -14.122 | 11.816 | -5.618 | 1.00 | 2.38 |
| ATOM | 346 | OD2 | ASP | 18 | -12.494 | 13.205 | -5.868 | 1.00 | 2.37 |
| ATOM | 347 | HN | ASP | 18 | -11.311 | 9.093 | -3.750 | 1.00 | 0.82 |
| ATOM | 348 | HA | ASP | 18 | -10.849 | 11.240 | -5.763 | 1.00 | 1.08 |
| ATOM | 349 | 1HB | ASP | 18 | -12.043 | 12.290 | -3.410 | 1.00 | 1.24 |
| ATOM | 350 | 2HB | ASP | 18 | -12.869 | 10.773 | -3.769 | 1.00 | 1.48 |
| ATOM | 351 | N | GLU | 19 | -8.735 | 10.787 | -3.758 | 1.00 | 0.64 |
| ATOM | 352 | CA | GLU | 19 | -7.554 | 11.288 | -2.998 | 1.00 | 0.62 |
| ATOM | 353 | C | GLU | 19 | -7.952 | 11.554 | -1.545 | 1.00 | 0.62 |
| ATOM | 354 | O | GLU | 19 | -8.124 | 12.685 | -1.134 | 1.00 | 0.75 |
| ATOM | 355 | CB | GLU | 19 | -7.048 | 12.585 | -3.635 | 1.00 | 0.77 |
| ATOM | 356 | CG | GLU | 19 | -6.935 | 12.402 | -5.149 | 1.00 | 1.61 |
| ATOM | 357 | CD | GLU | 19 | -6.329 | 13.661 | -5.772 | 1.00 | 2.10 |
| ATOM | 358 | OE1 | GLU | 19 | -7.074 | 14.420 | -6.371 | 1.00 | 2.44 |
| ATOM | 359 | OE2 | GLU | 19 | -5.130 | 13.846 | -5.639 | 1.00 | 2.74 |
| ATOM | 360 | HN | GLU | 19 | -8.729 | 9.880 | -4.129 | 1.00 | 1.15 |
| ATOM | 361 | HA | GLU | 19 | -6.771 | 10.545 | -3.023 | 1.00 | 0.58 |
| ATOM | 362 | 1HB | GLU | 19 | -6.078 | 12.830 | -3.230 | 1.00 | 0.89 |
| ATOM | 363 | 2HB | GLU | 19 | -7.741 | 13.386 | -3.419 | 1.00 | 1.28 |
| ATOM | 364 | 1HG | GLU | 19 | -7.917 | 12.234 | -5.566 | 1.00 | 2.13 |
| ATOM | 365 | 2HG | GLU | 19 | -6.302 | 11.553 | -5.363 | 1.00 | 2.05 |
| ATOM | 366 | N | ALA | 20 | -8.098 | 10.519 | -0.763 | 1.00 | 0.53 |
| ATOM | 367 | CA | ALA | 20 | -8.482 | 10.700 | 0.668 | 1.00 | 0.61 |
| ATOM | 368 | C | ALA | 20 | -8.820 | 9.337 | 1.269 | 1.00 | 0.58 |
| ATOM | 369 | O | ALA | 20 | -8.444 | 9.022 | 2.381 | 1.00 | 0.64 |
| ATOM | 370 | CB | ALA | 20 | -9.705 | 11.617 | 0.767 | 1.00 | 0.71 |
| ATOM | 371 | HN | ALA | 20 | -7.952 | 9.617 | -1.118 | 1.00 | 0.47 |
| ATOM | 372 | HA | ALA | 20 | -7.658 | 11.136 | 1.209 | 1.00 | 0.68 |
| ATOM | 373 | 1HB | ALA | 20 | -10.511 | 11.091 | 1.258 | 1.00 | 1.14 |
| ATOM | 374 | 2HB | ALA | 20 | -10.018 | 11.909 | -0.225 | 1.00 | 1.32 |
| ATOM | 375 | 3HB | ALA | 20 | -9.450 | 12.497 | 1.338 | 1.00 | 1.30 |
| ATOM | 376 | N | ASP | 21 | -9.531 | 8.527 | 0.536 | 1.00 | 0.54 |
| ATOM | 377 | CA | ASP | 21 | -9.906 | 7.180 | 1.043 | 1.00 | 0.58 |
| ATOM | 378 | C | ASP | 21 | -8.659 | 6.447 | 1.547 | 1.00 | 0.50 |
| ATOM | 379 | O | ASP | 21 | -8.733 | 5.602 | 2.418 | 1.00 | 0.53 |
| ATOM | 380 | CB | ASP | 21 | -10.544 | 6.378 | -0.094 | 1.00 | 0.64 |
| ATOM | 381 | CG | ASP | 21 | -12.062 | 6.564 | -0.065 | 1.00 | 0.76 |
| ATOM | 382 | OD1 | ASP | 21 | -12.679 | 6.398 | -1.105 | 1.00 | 1.29 |
| ATOM | 383 | OD2 | ASP | 21 | -12.582 | 6.869 | 0.995 | 1.00 | 1.52 |
| ATOM | 384 | HN | ASP | 21 | -9.821 | 8.807 | -0.352 | 1.00 | 0.53 |
| ATOM | 385 | HA | ASP | 21 | -10.614 | 7.287 | 1.847 | 1.00 | 0.70 |

FIG. 5A-5

```
ATOM    386  1HB ASP   21   -10.308   5.332   0.027  1.00  0.92
ATOM    387  2HB ASP   21   -10.156   6.726  -1.040  1.00  0.83
ATOM    388  N   VAL   22    -7.516   6.762   1.004  1.00  0.44
ATOM    389  CA  VAL   22    -6.263   6.084   1.445  1.00  0.41
ATOM    390  C   VAL   22    -6.097   6.233   2.960  1.00  0.48
ATOM    391  O   VAL   22    -6.123   7.325   3.493  1.00  0.64
ATOM    392  CB  VAL   22    -5.068   6.726   0.737  1.00  0.45
ATOM    393  CG1 VAL   22    -5.007   8.213   1.086  1.00  0.90
ATOM    394  CG2 VAL   22    -3.778   6.042   1.196  1.00  0.85
ATOM    395  HN  VAL   22    -7.481   7.445   0.302  1.00  0.45
ATOM    396  HA  VAL   22    -6.312   5.036   1.189  1.00  0.39
ATOM    397  HB  VAL   22    -5.179   6.612  -0.332  1.00  0.59
ATOM    398  1HG1 VAL  22    -4.269   8.699   0.465  1.00  1.54
ATOM    399  2HG1 VAL  22    -4.735   8.329   2.125  1.00  1.43
ATOM    400  3HG1 VAL  22    -5.973   8.663   0.915  1.00  1.37
ATOM    401  1HG2 VAL  22    -3.093   5.970   0.364  1.00  1.43
ATOM    402  2HG2 VAL  22    -4.006   5.051   1.561  1.00  1.32
ATOM    403  3HG2 VAL  22    -3.325   6.621   1.987  1.00  1.47
ATOM    404  N   LYS   23    -5.920   5.143   3.659  1.00  0.43
ATOM    405  CA  LYS   23    -5.745   5.225   5.138  1.00  0.54
ATOM    406  C   LYS   23    -4.981   3.996   5.638  1.00  0.62
ATOM    407  O   LYS   23    -5.383   2.870   5.424  1.00  1.44
ATOM    408  CB  LYS   23    -7.113   5.283   5.817  1.00  0.55
ATOM    409  CG  LYS   23    -7.843   6.559   5.396  1.00  0.67
ATOM    410  CD  LYS   23    -9.104   6.730   6.246  1.00  0.92
ATOM    411  CE  LYS   23    -9.214   8.183   6.713  1.00  1.09
ATOM    412  NZ  LYS   23   -10.431   8.342   7.558  1.00  1.65
ATOM    413  HN  LYS   23    -5.897   4.271   3.211  1.00  0.41
ATOM    414  HA  LYS   23    -5.187   6.117   5.382  1.00  0.69
ATOM    415  1HB LYS   23    -6.980   5.282   6.888  1.00  0.72
ATOM    416  2HB LYS   23    -7.694   4.422   5.525  1.00  0.65
ATOM    417  1HG LYS   23    -8.119   6.490   4.355  1.00  0.82
ATOM    418  2HG LYS   23    -7.192   7.410   5.541  1.00  0.94
ATOM    419  1HD LYS   23    -9.048   6.081   7.107  1.00  1.18
ATOM    420  2HD LYS   23    -9.972   6.473   5.657  1.00  1.22
ATOM    421  1HE LYS   23    -9.285   8.833   5.854  1.00  1.63
ATOM    422  2HE LYS   23    -8.339   8.443   7.290  1.00  1.47
ATOM    423  1HZ LYS   23   -10.842   9.284   7.401  1.00  2.08
ATOM    424  2HZ LYS   23   -10.173   8.239   8.561  1.00  2.13
ATOM    425  3HZ LYS   23   -11.129   7.615   7.303  1.00  2.14
ATOM    426  N   LEU   24    -3.886   4.211   6.311  1.00  0.81
ATOM    427  CA  LEU   24    -3.081   3.069   6.840  1.00  0.73
ATOM    428  C   LEU   24    -3.867   2.357   7.942  1.00  0.69
ATOM    429  O   LEU   24    -4.023   1.152   7.930  1.00  0.70
ATOM    430  CB  LEU   24    -1.776   3.606   7.434  1.00  0.87
ATOM    431  CG  LEU   24    -1.115   4.577   6.451  1.00  1.53
ATOM    432  CD1 LEU   24    -1.244   6.008   6.977  1.00  2.04
ATOM    433  CD2 LEU   24     0.368   4.229   6.308  1.00  2.10
ATOM    434  HN  LEU   24    -3.593   5.130   6.474  1.00  1.52
ATOM    435  HA  LEU   24    -2.859   2.370   6.040  1.00  0.66
ATOM    436  1HB LEU   24    -1.107   2.784   7.632  1.00  0.95
ATOM    437  2HB LEU   24    -1.992   4.121   8.358  1.00  1.14
ATOM    438  HG  LEU   24    -1.600   4.502   5.489  1.00  1.99
ATOM    439  1HD1 LEU  24    -2.173   6.437   6.635  1.00  2.68
ATOM    440  2HD1 LEU  24    -0.418   6.601   6.611  1.00  2.35
ATOM    441  3HD1 LEU  24    -1.228   5.998   8.057  1.00  2.28
ATOM    442  1HD2 LEU  24     0.656   3.547   7.094  1.00  2.39
ATOM    443  2HD2 LEU  24     0.957   5.132   6.383  1.00  2.56
ATOM    444  3HD2 LEU  24     0.539   3.768   5.348  1.00  2.54
ATOM    445  N   GLU   25    -4.358   3.097   8.899  1.00  0.74
ATOM    446  CA  GLU   25    -5.129   2.472  10.011  1.00  0.78
ATOM    447  C   GLU   25    -6.410   1.828   9.471  1.00  0.72
ATOM    448  O   GLU   25    -7.072   1.081  10.162  1.00  0.82
ATOM    449  CB  GLU   25    -5.498   3.546  11.037  1.00  0.86
ATOM    450  CG  GLU   25    -6.178   4.718  10.327  1.00  1.58
ATOM    451  CD  GLU   25    -7.020   5.505  11.333  1.00  2.17
ATOM    452  OE1 GLU   25    -6.443   6.063  12.251  1.00  2.77
ATOM    453  OE2 GLU   25    -8.229   5.535  11.167  1.00  2.66
ATOM    454  HN  GLU   25    -4.214   4.066   8.889  1.00  0.78
ATOM    455  HA  GLU   25    -4.522   1.717  10.488  1.00  0.83
ATOM    456  1HB GLU   25    -4.604   3.896  11.531  1.00  1.38
ATOM    457  2HB GLU   25    -6.174   3.126  11.769  1.00  1.27
ATOM    458  1HG GLU   25    -6.816   4.342   9.542  1.00  2.03
ATOM    459  2HG GLU   25    -5.425   5.366   9.901  1.00  2.22
ATOM    460  N   ALA   26    -6.772   2.107   8.246  1.00  0.60
ATOM    461  CA  ALA   26    -8.011   1.502   7.689  1.00  0.57
ATOM    462  C   ALA   26    -7.709   0.089   7.197  1.00  0.56
```

FIG. 5A-6

| | | | | | | | | |
|---|---|---|---|---|---|---|---|---|
| ATOM | 463 | O | ALA | 26 | -6.605 | -0.216 | 6.792 | 1.00 | 0.53 |
| ATOM | 464 | CB | ALA | 26 | -8.509 | 2.348 | 6.518 | 1.00 | 0.53 |
| ATOM | 465 | HN | ALA | 26 | -6.233 | 2.711 | 7.694 | 1.00 | 0.57 |
| ATOM | 466 | HA | ALA | 26 | -8.771 | 1.464 | 8.456 | 1.00 | 0.65 |
| ATOM | 467 | 1HB | ALA | 26 | -9.309 | 1.828 | 6.013 | 1.00 | 0.97 |
| ATOM | 468 | 2HB | ALA | 26 | -7.698 | 2.516 | 5.826 | 1.00 | 1.13 |
| ATOM | 469 | 3HB | ALA | 26 | -8.871 | 3.297 | 6.986 | 1.00 | 1.13 |
| ATOM | 470 | N | SER | 27 | -8.685 | -0.776 | 7.217 | 1.00 | 0.60 |
| ATOM | 471 | CA | SER | 27 | -8.452 | -2.165 | 6.738 | 1.00 | 0.63 |
| ATOM | 472 | C | SER | 27 | -8.524 | -2.201 | 5.205 | 1.00 | 0.55 |
| ATOM | 473 | O | SER | 27 | -8.406 | -3.247 | 4.599 | 1.00 | 0.58 |
| ATOM | 474 | CB | SER | 27 | -9.521 | -3.091 | 7.320 | 1.00 | 0.74 |
| ATOM | 475 | OG | SER | 27 | -8.923 | -3.952 | 8.281 | 1.00 | 1.33 |
| ATOM | 476 | HN | SER | 27 | -9.571 | -0.509 | 7.540 | 1.00 | 0.65 |
| ATOM | 477 | HA | SER | 27 | -7.474 | -2.496 | 7.059 | 1.00 | 0.65 |
| ATOM | 478 | 1HB | SER | 27 | -9.963 | -3.674 | 6.523 | 1.00 | 0.90 |
| ATOM | 479 | 2HB | SER | 27 | -10.287 | -2.504 | 7.799 | 1.00 | 0.89 |
| ATOM | 480 | HG | SER | 27 | -9.122 | -3.606 | 9.154 | 1.00 | 1.74 |
| ATOM | 481 | N | PHE | 28 | -8.716 | -1.070 | 4.570 | 1.00 | 0.50 |
| ATOM | 482 | CA | PHE | 28 | -8.791 | -1.056 | 3.083 | 1.00 | 0.47 |
| ATOM | 483 | C | PHE | 28 | -9.968 | -1.918 | 2.623 | 1.00 | 0.54 |
| ATOM | 484 | O | PHE | 28 | -9.838 | -2.735 | 1.735 | 1.00 | 0.67 |
| ATOM | 485 | CB | PHE | 28 | -7.492 | -1.620 | 2.506 | 1.00 | 0.44 |
| ATOM | 486 | CG | PHE | 28 | -6.555 | -0.491 | 2.148 | 1.00 | 0.38 |
| ATOM | 487 | CD1 | PHE | 28 | -6.241 | -0.238 | 0.807 | 1.00 | 1.15 |
| ATOM | 488 | CD2 | PHE | 28 | -5.990 | 0.296 | 3.158 | 1.00 | 1.29 |
| ATOM | 489 | CE1 | PHE | 28 | -5.363 | 0.800 | 0.478 | 1.00 | 1.15 |
| ATOM | 490 | CE2 | PHE | 28 | -5.114 | 1.335 | 2.826 | 1.00 | 1.28 |
| ATOM | 491 | CZ | PHE | 28 | -4.799 | 1.586 | 1.487 | 1.00 | 0.36 |
| ATOM | 492 | HN | PHE | 28 | -8.811 | -0.234 | 5.067 | 1.00 | 0.51 |
| ATOM | 493 | HA | PHE | 28 | -8.928 | -0.042 | 2.739 | 1.00 | 0.46 |
| ATOM | 494 | 1HB | PHE | 28 | -7.713 | -2.196 | 1.622 | 1.00 | 0.45 |
| ATOM | 495 | 2HB | PHE | 28 | -7.020 | -2.257 | 3.240 | 1.00 | 0.49 |
| ATOM | 496 | HD1 | PHE | 28 | -6.674 | -0.844 | 0.027 | 1.00 | 2.03 |
| ATOM | 497 | HD2 | PHE | 28 | -6.231 | 0.103 | 4.192 | 1.00 | 2.17 |
| ATOM | 498 | HE1 | PHE | 28 | -5.118 | 0.991 | -0.555 | 1.00 | 2.03 |
| ATOM | 499 | HE2 | PHE | 28 | -4.672 | 1.937 | 3.605 | 1.00 | 2.16 |
| ATOM | 500 | HZ | PHE | 28 | -4.122 | 2.387 | 1.232 | 1.00 | 0.38 |
| ATOM | 501 | N | LYS | 29 | -11.117 | -1.744 | 3.219 | 1.00 | 0.54 |
| ATOM | 502 | CA | LYS | 29 | -12.293 | -2.561 | 2.806 | 1.00 | 0.61 |
| ATOM | 503 | C | LYS | 29 | -13.555 | -2.051 | 3.508 | 1.00 | 0.65 |
| ATOM | 504 | O | LYS | 29 | -14.595 | -1.901 | 2.899 | 1.00 | 0.69 |
| ATOM | 505 | CB | LYS | 29 | -12.056 | -4.024 | 3.187 | 1.00 | 0.69 |
| ATOM | 506 | CG | LYS | 29 | -11.661 | -4.114 | 4.662 | 1.00 | 0.73 |
| ATOM | 507 | CD | LYS | 29 | -10.890 | -5.413 | 4.905 | 1.00 | 0.88 |
| ATOM | 508 | CE | LYS | 29 | -11.648 | -6.277 | 5.915 | 1.00 | 1.61 |
| ATOM | 509 | NZ | LYS | 29 | -11.118 | -7.669 | 5.873 | 1.00 | 2.16 |
| ATOM | 510 | HN | LYS | 29 | -11.205 | -1.081 | 3.935 | 1.00 | 0.55 |
| ATOM | 511 | HA | LYS | 29 | -12.423 | -2.487 | 1.738 | 1.00 | 0.63 |
| ATOM | 512 | 1HB | LYS | 29 | -11.262 | -4.430 | 2.578 | 1.00 | 0.71 |
| ATOM | 513 | 2HB | LYS | 29 | -12.962 | -4.589 | 3.021 | 1.00 | 0.77 |
| ATOM | 514 | 1HG | LYS | 29 | -12.550 | -4.105 | 5.275 | 1.00 | 0.81 |
| ATOM | 515 | 2HG | LYS | 29 | -11.037 | -3.270 | 4.920 | 1.00 | 0.71 |
| ATOM | 516 | 1HD | LYS | 29 | -9.910 | -5.183 | 5.295 | 1.00 | 1.44 |
| ATOM | 517 | 2HD | LYS | 29 | -10.789 | -5.951 | 3.974 | 1.00 | 1.05 |
| ATOM | 518 | 1HE | LYS | 29 | -12.698 | -6.284 | 5.666 | 1.00 | 2.05 |
| ATOM | 519 | 2HE | LYS | 29 | -11.515 | -5.871 | 6.907 | 1.00 | 2.21 |
| ATOM | 520 | 1HZ | LYS | 29 | -10.140 | -7.658 | 5.521 | 1.00 | 2.49 |
| ATOM | 521 | 2HZ | LYS | 29 | -11.709 | -8.246 | 5.240 | 1.00 | 2.47 |
| ATOM | 522 | 3HZ | LYS | 29 | -11.134 | -8.076 | 6.829 | 1.00 | 2.66 |
| ATOM | 523 | N | GLU | 30 | -13.475 | -1.789 | 4.784 | 1.00 | 0.68 |
| ATOM | 524 | CA | GLU | 30 | -14.675 | -1.297 | 5.518 | 1.00 | 0.78 |
| ATOM | 525 | C | GLU | 30 | -14.489 | 0.176 | 5.885 | 1.00 | 0.79 |
| ATOM | 526 | O | GLU | 30 | -15.443 | 0.895 | 6.108 | 1.00 | 0.96 |
| ATOM | 527 | CB | GLU | 30 | -14.863 | -2.118 | 6.795 | 1.00 | 0.91 |
| ATOM | 528 | CG | GLU | 30 | -13.616 | -1.990 | 7.672 | 1.00 | 1.39 |
| ATOM | 529 | CD | GLU | 30 | -13.876 | -2.645 | 9.030 | 1.00 | 1.76 |
| ATOM | 530 | OE1 | GLU | 30 | -14.797 | -2.217 | 9.705 | 1.00 | 2.17 |
| ATOM | 531 | OE2 | GLU | 30 | -13.148 | -3.563 | 9.372 | 1.00 | 2.28 |
| ATOM | 532 | HN | GLU | 30 | -12.628 | -1.921 | 5.259 | 1.00 | 0.68 |
| ATOM | 533 | HA | GLU | 30 | -15.548 | -1.404 | 4.891 | 1.00 | 0.79 |
| ATOM | 534 | 1HB | GLU | 30 | -15.015 | -3.155 | 6.538 | 1.00 | 1.32 |
| ATOM | 535 | 2HB | GLU | 30 | -15.724 | -1.750 | 7.336 | 1.00 | 1.25 |
| ATOM | 536 | 1HG | GLU | 30 | -13.383 | -0.946 | 7.817 | 1.00 | 1.81 |
| ATOM | 537 | 2HG | GLU | 30 | -12.784 | -2.481 | 7.187 | 1.00 | 1.80 |
| ATOM | 538 | N | ASP | 31 | -13.269 | 0.632 | 5.956 | 1.00 | 0.73 |
| ATOM | 539 | CA | ASP | 31 | -13.029 | 2.057 | 6.316 | 1.00 | 0.75 |

FIG. 5A-7

| | | | | | | | | |
|---|---|---|---|---|---|---|---|---|
| ATOM | 540 | C | ASP | 31 | -13.291 | 2.949 | 5.101 | 1.00 | 0.72 |
| ATOM | 541 | O | ASP | 31 | -14.213 | 3.714 | 5.084 | 1.00 | 0.77 |
| ATOM | 542 | CB | ASP | 31 | -11.580 | 2.233 | 6.772 | 1.00 | 0.76 |
| ATOM | 543 | CG | ASP | 31 | -11.555 | 2.867 | 8.164 | 1.00 | 0.98 |
| ATOM | 544 | OD1 | ASP | 31 | -11.051 | 3.971 | 8.281 | 1.00 | 1.57 |
| ATOM | 545 | OD2 | ASP | 31 | -12.042 | 2.237 | 9.088 | 1.00 | 1.51 |
| ATOM | 546 | HN | ASP | 31 | -12.511 | 0.037 | 5.777 | 1.00 | 0.77 |
| ATOM | 547 | HA | ASP | 31 | -13.694 | 2.341 | 7.119 | 1.00 | 0.83 |
| ATOM | 548 | 1HB | ASP | 31 | -11.059 | 2.874 | 6.077 | 1.00 | 0.84 |
| ATOM | 549 | 2HB | ASP | 31 | -11.094 | 1.268 | 6.806 | 1.00 | 0.92 |
| ATOM | 550 | N | LEU | 32 | -12.479 | 2.840 | 4.085 | 1.00 | 0.66 |
| ATOM | 551 | CA | LEU | 32 | -12.683 | 3.690 | 2.878 | 1.00 | 0.68 |
| ATOM | 552 | C | LEU | 32 | -13.430 | 2.898 | 1.801 | 1.00 | 0.66 |
| ATOM | 553 | O | LEU | 32 | -13.403 | 3.242 | 0.636 | 1.00 | 0.69 |
| ATOM | 554 | CB | LEU | 32 | -11.324 | 4.140 | 2.335 | 1.00 | 0.67 |
| ATOM | 555 | CG | LEU | 32 | -10.498 | 2.919 | 1.926 | 1.00 | 0.51 |
| ATOM | 556 | CD1 | LEU | 32 | -10.282 | 2.930 | 0.411 | 1.00 | 0.49 |
| ATOM | 557 | CD2 | LEU | 32 | -9.139 | 2.967 | 2.629 | 1.00 | 0.57 |
| ATOM | 558 | HN | LEU | 32 | -11.733 | 2.205 | 4.117 | 1.00 | 0.65 |
| ATOM | 559 | HA | LEU | 32 | -13.264 | 4.559 | 3.149 | 1.00 | 0.75 |
| ATOM | 560 | 1HB | LEU | 32 | -10.796 | 4.690 | 3.099 | 1.00 | 0.77 |
| ATOM | 561 | 2HB | LEU | 32 | -11.476 | 4.775 | 1.476 | 1.00 | 0.74 |
| ATOM | 562 | HG | LEU | 32 | -11.022 | 2.017 | 2.210 | 1.00 | 0.56 |
| ATOM | 563 | 1HD1 | LEU | 32 | -9.459 | 3.585 | 0.170 | 1.00 | 1.07 |
| ATOM | 564 | 2HD1 | LEU | 32 | -11.178 | 3.282 | -0.078 | 1.00 | 1.15 |
| ATOM | 565 | 3HD1 | LEU | 32 | -10.057 | 1.930 | 0.073 | 1.00 | 1.12 |
| ATOM | 566 | 1HD2 | LEU | 32 | -9.200 | 3.620 | 3.487 | 1.00 | 1.17 |
| ATOM | 567 | 2HD2 | LEU | 32 | -8.393 | 3.341 | 1.944 | 1.00 | 1.18 |
| ATOM | 568 | 3HD2 | LEU | 32 | -8.865 | 1.973 | 2.952 | 1.00 | 1.13 |
| ATOM | 569 | N | GLY | 33 | -14.103 | 1.843 | 2.178 | 1.00 | 0.69 |
| ATOM | 570 | CA | GLY | 33 | -14.856 | 1.035 | 1.172 | 1.00 | 0.74 |
| ATOM | 571 | C | GLY | 33 | -13.937 | 0.672 | 0.002 | 1.00 | 0.68 |
| ATOM | 572 | O | GLY | 33 | -13.951 | 1.310 | -1.031 | 1.00 | 0.89 |
| ATOM | 573 | HN | GLY | 33 | -14.117 | 1.583 | 3.122 | 1.00 | 0.71 |
| ATOM | 574 | 1HA | GLY | 33 | -15.692 | 1.609 | 0.803 | 1.00 | 0.82 |
| ATOM | 575 | 2HA | GLY | 33 | -15.219 | 0.130 | 1.639 | 1.00 | 0.79 |
| ATOM | 576 | N | ALA | 34 | -13.139 | -0.347 | 0.158 | 1.00 | 0.60 |
| ATOM | 577 | CA | ALA | 34 | -12.220 | -0.751 | -0.944 | 1.00 | 0.59 |
| ATOM | 578 | C | ALA | 34 | -12.385 | -2.246 | -1.225 | 1.00 | 0.74 |
| ATOM | 579 | O | ALA | 34 | -12.732 | -3.016 | -0.352 | 1.00 | 1.25 |
| ATOM | 580 | CB | ALA | 34 | -10.776 | -0.467 | -0.531 | 1.00 | 0.58 |
| ATOM | 581 | HN | ALA | 34 | -13.144 | -0.848 | 0.999 | 1.00 | 0.70 |
| ATOM | 582 | HA | ALA | 34 | -12.456 | -0.188 | -1.836 | 1.00 | 0.61 |
| ATOM | 583 | 1HB | ALA | 34 | -10.160 | -1.322 | -0.767 | 1.00 | 1.11 |
| ATOM | 584 | 2HB | ALA | 34 | -10.736 | -0.277 | 0.532 | 1.00 | 1.13 |
| ATOM | 585 | 3HB | ALA | 34 | -10.411 | 0.397 | -1.065 | 1.00 | 1.26 |
| ATOM | 586 | N | ASP | 35 | -12.137 | -2.664 | -2.435 | 1.00 | 0.85 |
| ATOM | 587 | CA | ASP | 35 | -12.278 | -4.109 | -2.766 | 1.00 | 0.96 |
| ATOM | 588 | C | ASP | 35 | -10.994 | -4.844 | -2.373 | 1.00 | 0.88 |
| ATOM | 589 | O | ASP | 35 | -9.903 | -4.405 | -2.673 | 1.00 | 1.15 |
| ATOM | 590 | CB | ASP | 35 | -12.518 | -4.270 | -4.268 | 1.00 | 1.06 |
| ATOM | 591 | CG | ASP | 35 | -14.012 | -4.465 | -4.529 | 1.00 | 1.59 |
| ATOM | 592 | OD1 | ASP | 35 | -14.343 | -5.156 | -5.479 | 1.00 | 2.24 |
| ATOM | 593 | OD2 | ASP | 35 | -14.801 | -3.920 | -3.775 | 1.00 | 2.05 |
| ATOM | 594 | HN | ASP | 35 | -11.856 | -2.027 | -3.126 | 1.00 | 1.21 |
| ATOM | 595 | HA | ASP | 35 | -13.112 | -4.525 | -2.220 | 1.00 | 1.09 |
| ATOM | 596 | 1HB | ASP | 35 | -11.976 | -5.131 | -4.630 | 1.00 | 1.23 |
| ATOM | 597 | 2HB | ASP | 35 | -12.173 | -3.385 | -4.784 | 1.00 | 1.26 |
| ATOM | 598 | N | SER | 36 | -11.115 | -5.959 | -1.703 | 1.00 | 0.89 |
| ATOM | 599 | CA | SER | 36 | -9.900 | -6.722 | -1.287 | 1.00 | 0.81 |
| ATOM | 600 | C | SER | 36 | -8.959 | -6.897 | -2.484 | 1.00 | 0.68 |
| ATOM | 601 | O | SER | 36 | -7.754 | -6.968 | -2.334 | 1.00 | 0.59 |
| ATOM | 602 | CB | SER | 36 | -10.318 | -8.098 | -0.765 | 1.00 | 0.98 |
| ATOM | 603 | OG | SER | 36 | -9.565 | -8.406 | 0.401 | 1.00 | 1.69 |
| ATOM | 604 | HN | SER | 36 | -12.006 | -6.296 | -1.471 | 1.00 | 1.17 |
| ATOM | 605 | HA | SER | 36 | -9.388 | -6.182 | -0.504 | 1.00 | 0.77 |
| ATOM | 606 | 1HB | SER | 36 | -10.138 | -8.842 | -1.529 | 1.00 | 1.34 |
| ATOM | 607 | 2HB | SER | 36 | -11.366 | -8.088 | -0.517 | 1.00 | 1.43 |
| ATOM | 608 | HG | SER | 36 | -9.931 | -9.204 | 0.789 | 1.00 | 1.97 |
| ATOM | 609 | N | LEU | 37 | -9.500 | -6.962 | -3.669 | 1.00 | 0.75 |
| ATOM | 610 | CA | LEU | 37 | -8.639 | -7.128 | -4.873 | 1.00 | 0.71 |
| ATOM | 611 | C | LEU | 37 | -7.830 | -5.851 | -5.100 | 1.00 | 0.58 |
| ATOM | 612 | O | LEU | 37 | -6.627 | -5.829 | -4.932 | 1.00 | 0.48 |
| ATOM | 613 | CB | LEU | 37 | -9.519 | -7.400 | -6.095 | 1.00 | 0.89 |
| ATOM | 614 | CG | LEU | 37 | -9.382 | -8.867 | -6.506 | 1.00 | 1.19 |
| ATOM | 615 | CD1 | LEU | 37 | -10.764 | -9.524 | -6.524 | 1.00 | 1.60 |
| ATOM | 616 | CD2 | LEU | 37 | -8.761 | -8.950 | -7.902 | 1.00 | 1.59 |

FIG. 5A-8

| | | | | | | | | | |
|---|---|---|---|---|---|---|---|---|---|
| ATOM | 617 | HN | LEU | 37 | -10.473 | -6.899 | -3.768 | 1.00 | 0.86 |
| ATOM | 618 | HA | LEU | 37 | -7.967 | -7.955 | -4.723 | 1.00 | 0.69 |
| ATOM | 619 | 1HB | LEU | 37 | -9.205 | -6.769 | -6.913 | 1.00 | 1.09 |
| ATOM | 620 | 2HB | LEU | 37 | -10.550 | -7.188 | -5.850 | 1.00 | 1.05 |
| ATOM | 621 | HG | LEU | 37 | -8.749 | -9.381 | -5.797 | 1.00 | 1.47 |
| ATOM | 622 | 1HD1 | LEU | 37 | -10.858 | -10.190 | -5.680 | 1.00 | 1.91 |
| ATOM | 623 | 2HD1 | LEU | 37 | -10.884 | -10.084 | -7.440 | 1.00 | 1.89 |
| ATOM | 624 | 3HD1 | LEU | 37 | -11.526 | -8.760 | -6.467 | 1.00 | 2.22 |
| ATOM | 625 | 1HD2 | LEU | 37 | -7.695 | -9.098 | -7.814 | 1.00 | 2.04 |
| ATOM | 626 | 2HD2 | LEU | 37 | -8.954 | -8.031 | -8.436 | 1.00 | 2.00 |
| ATOM | 627 | 3HD2 | LEU | 37 | -9.197 | -9.778 | -8.441 | 1.00 | 1.94 |
| ATOM | 628 | N | ASP | 38 | -8.484 | -4.788 | -5.481 | 1.00 | 0.65 |
| ATOM | 629 | CA | ASP | 38 | -7.766 | -3.500 | -5.725 | 1.00 | 0.59 |
| ATOM | 630 | C | ASP | 38 | -6.831 | -3.189 | -4.553 | 1.00 | 0.44 |
| ATOM | 631 | O | ASP | 38 | -5.759 | -2.645 | -4.727 | 1.00 | 0.41 |
| ATOM | 632 | CB | ASP | 38 | -8.788 | -2.371 | -5.872 | 1.00 | 0.69 |
| ATOM | 633 | CG | ASP | 38 | -9.146 | -2.193 | -7.348 | 1.00 | 1.07 |
| ATOM | 634 | OD1 | ASP | 38 | -8.496 | -1.395 | -8.003 | 1.00 | 1.42 |
| ATOM | 635 | OD2 | ASP | 38 | -10.063 | -2.859 | -7.799 | 1.00 | 1.84 |
| ATOM | 636 | HN | ASP | 38 | -9.453 | -4.837 | -5.607 | 1.00 | 0.78 |
| ATOM | 637 | HA | ASP | 38 | -7.188 | -3.576 | -6.631 | 1.00 | 0.63 |
| ATOM | 638 | 1HB | ASP | 38 | -8.367 | -1.452 | -5.492 | 1.00 | 0.71 |
| ATOM | 639 | 2HB | ASP | 38 | -9.679 | -2.618 | -5.312 | 1.00 | 0.85 |
| ATOM | 640 | N | VAL | 39 | -7.233 | -3.531 | -3.364 | 1.00 | 0.40 |
| ATOM | 641 | CA | VAL | 39 | -6.377 | -3.258 | -2.176 | 1.00 | 0.28 |
| ATOM | 642 | C | VAL | 39 | -5.035 | -3.973 | -2.332 | 1.00 | 0.23 |
| ATOM | 643 | O | VAL | 39 | -4.023 | -3.363 | -2.622 | 1.00 | 0.24 |
| ATOM | 644 | CB | VAL | 39 | -7.091 | -3.771 | -0.925 | 1.00 | 0.36 |
| ATOM | 645 | CG1 | VAL | 39 | -6.191 | -3.593 | 0.300 | 1.00 | 0.35 |
| ATOM | 646 | CG2 | VAL | 39 | -8.387 | -2.982 | -0.732 | 1.00 | 0.44 |
| ATOM | 647 | HN | VAL | 39 | -8.102 | -3.968 | -3.250 | 1.00 | 0.48 |
| ATOM | 648 | HA | VAL | 39 | -6.208 | -2.197 | -2.086 | 1.00 | 0.26 |
| ATOM | 649 | HB | VAL | 39 | -7.324 | -4.819 | -1.049 | 1.00 | 0.43 |
| ATOM | 650 | 1HG1 | VAL | 39 | -5.837 | -2.575 | 0.342 | 1.00 | 1.08 |
| ATOM | 651 | 2HG1 | VAL | 39 | -5.347 | -4.263 | 0.226 | 1.00 | 1.05 |
| ATOM | 652 | 3HG1 | VAL | 39 | -6.751 | -3.817 | 1.195 | 1.00 | 1.09 |
| ATOM | 653 | 1HG2 | VAL | 39 | -8.832 | -2.782 | -1.695 | 1.00 | 1.04 |
| ATOM | 654 | 2HG2 | VAL | 39 | -8.171 | -2.047 | -0.238 | 1.00 | 1.11 |
| ATOM | 655 | 3HG2 | VAL | 39 | -9.074 | -3.558 | -0.131 | 1.00 | 1.17 |
| ATOM | 656 | N | VAL | 40 | -5.016 | -5.259 | -2.138 | 1.00 | 0.27 |
| ATOM | 657 | CA | VAL | 40 | -3.738 | -6.006 | -2.270 | 1.00 | 0.28 |
| ATOM | 658 | C | VAL | 40 | -3.217 | -5.866 | -3.701 | 1.00 | 0.34 |
| ATOM | 659 | O | VAL | 40 | -2.029 | -5.932 | -3.947 | 1.00 | 0.39 |
| ATOM | 660 | CB | VAL | 40 | -3.967 | -7.479 | -1.937 | 1.00 | 0.33 |
| ATOM | 661 | CG1 | VAL | 40 | -2.616 | -8.175 | -1.764 | 1.00 | 0.39 |
| ATOM | 662 | CG2 | VAL | 40 | -4.763 | -7.582 | -0.633 | 1.00 | 0.36 |
| ATOM | 663 | HN | VAL | 40 | -5.841 | -5.731 | -1.902 | 1.00 | 0.33 |
| ATOM | 664 | HA | VAL | 40 | -3.011 | -5.593 | -1.585 | 1.00 | 0.29 |
| ATOM | 665 | HB | VAL | 40 | -4.517 | -7.950 | -2.738 | 1.00 | 0.37 |
| ATOM | 666 | 1HG1 | VAL | 40 | -2.571 | -9.038 | -2.410 | 1.00 | 1.10 |
| ATOM | 667 | 2HG1 | VAL | 40 | -2.501 | -8.487 | -0.736 | 1.00 | 1.06 |
| ATOM | 668 | 3HG1 | VAL | 40 | -1.822 | -7.489 | -2.023 | 1.00 | 1.10 |
| ATOM | 669 | 1HG2 | VAL | 40 | -4.781 | -6.617 | -0.146 | 1.00 | 0.94 |
| ATOM | 670 | 2HG2 | VAL | 40 | -4.295 | -8.304 | 0.019 | 1.00 | 1.11 |
| ATOM | 671 | 3HG2 | VAL | 40 | -5.773 | -7.893 | -0.851 | 1.00 | 1.14 |
| ATOM | 672 | N | GLU | 41 | -4.092 | -5.659 | -4.648 | 1.00 | 0.41 |
| ATOM | 673 | CA | GLU | 41 | -3.631 | -5.500 | -6.055 | 1.00 | 0.51 |
| ATOM | 674 | C | GLU | 41 | -2.789 | -4.231 | -6.151 | 1.00 | 0.51 |
| ATOM | 675 | O | GLU | 41 | -1.819 | -4.167 | -6.880 | 1.00 | 0.58 |
| ATOM | 676 | CB | GLU | 41 | -4.835 | -5.384 | -6.993 | 1.00 | 0.61 |
| ATOM | 677 | CG | GLU | 41 | -5.390 | -6.780 | -7.288 | 1.00 | 1.01 |
| ATOM | 678 | CD | GLU | 41 | -5.370 | -7.028 | -8.798 | 1.00 | 1.59 |
| ATOM | 679 | OE1 | GLU | 41 | -6.230 | -7.753 | -9.270 | 1.00 | 2.19 |
| ATOM | 680 | OE2 | GLU | 41 | -4.495 | -6.489 | -9.455 | 1.00 | 2.21 |
| ATOM | 681 | HN | GLU | 41 | -5.047 | -5.598 | -4.433 | 1.00 | 0.44 |
| ATOM | 682 | HA | GLU | 41 | -3.032 | -6.352 | -6.337 | 1.00 | 0.56 |
| ATOM | 683 | 1HB | GLU | 41 | -4.526 | -4.920 | -7.917 | 1.00 | 0.94 |
| ATOM | 684 | 2HB | GLU | 41 | -5.599 | -4.781 | -6.525 | 1.00 | 1.01 |
| ATOM | 685 | 1HG | GLU | 41 | -6.405 | -6.848 | -6.927 | 1.00 | 1.36 |
| ATOM | 686 | 2HG | GLU | 41 | -4.780 | -7.521 | -6.792 | 1.00 | 1.61 |
| ATOM | 687 | N | LEU | 42 | -3.149 | -3.219 | -5.409 | 1.00 | 0.45 |
| ATOM | 688 | CA | LEU | 42 | -2.365 | -1.956 | -5.447 | 1.00 | 0.46 |
| ATOM | 689 | C | LEU | 42 | -1.024 | -2.187 | -4.737 | 1.00 | 0.43 |
| ATOM | 690 | O | LEU | 42 | -0.009 | -1.626 | -5.098 | 1.00 | 0.52 |
| ATOM | 691 | CB | LEU | 42 | -3.180 | -0.825 | -4.778 | 1.00 | 0.46 |
| ATOM | 692 | CG | LEU | 42 | -2.874 | -0.710 | -3.279 | 1.00 | 0.87 |
| ATOM | 693 | CD1 | LEU | 42 | -1.690 | 0.235 | -3.071 | 1.00 | 1.15 |

FIG. 5A-9

| | | | | | | | | |
|---|---|---|---|---|---|---|---|---|
| ATOM | 694 | CD2 | LEU | 42 | -4.092 | -0.147 | -2.560 | 1.00 | 1.39 |
| ATOM | 695 | HN | LEU | 42 | -3.930 | -3.296 | -4.822 | 1.00 | 0.43 |
| ATOM | 696 | HA | LEU | 42 | -2.178 | -1.691 | -6.473 | 1.00 | 0.52 |
| ATOM | 697 | 1HB | LEU | 42 | -4.234 | -1.027 | -4.907 | 1.00 | 0.85 |
| ATOM | 698 | 2HB | LEU | 42 | -2.942 | 0.112 | -5.257 | 1.00 | 0.83 |
| ATOM | 699 | HG | LEU | 42 | -2.637 | -1.684 | -2.880 | 1.00 | 1.56 |
| ATOM | 700 | 1HD1 | LEU | 42 | -2.027 | 1.256 | -3.162 | 1.00 | 1.75 |
| ATOM | 701 | 2HD1 | LEU | 42 | -0.934 | 0.040 | -3.816 | 1.00 | 1.50 |
| ATOM | 702 | 3HD1 | LEU | 42 | -1.274 | 0.081 | -2.086 | 1.00 | 1.69 |
| ATOM | 703 | 1HD2 | LEU | 42 | -3.938 | -0.210 | -1.495 | 1.00 | 1.86 |
| ATOM | 704 | 2HD2 | LEU | 42 | -4.965 | -0.718 | -2.835 | 1.00 | 1.81 |
| ATOM | 705 | 3HD2 | LEU | 42 | -4.230 | 0.886 | -2.845 | 1.00 | 1.85 |
| ATOM | 706 | N | VAL | 43 | -1.026 | -3.011 | -3.726 | 1.00 | 0.34 |
| ATOM | 707 | CA | VAL | 43 | 0.229 | -3.290 | -2.979 | 1.00 | 0.35 |
| ATOM | 708 | C | VAL | 43 | 1.149 | -4.160 | -3.844 | 1.00 | 0.41 |
| ATOM | 709 | O | VAL | 43 | 2.345 | -4.208 | -3.638 | 1.00 | 0.46 |
| ATOM | 710 | CB | VAL | 43 | -0.110 | -4.011 | -1.669 | 1.00 | 0.32 |
| ATOM | 711 | CG1 | VAL | 43 | 1.073 | -3.915 | -0.702 | 1.00 | 0.36 |
| ATOM | 712 | CG2 | VAL | 43 | -1.335 | -3.350 | -1.025 | 1.00 | 0.28 |
| ATOM | 713 | HN | VAL | 43 | -1.861 | -3.449 | -3.455 | 1.00 | 0.30 |
| ATOM | 714 | HA | VAL | 43 | 0.727 | -2.357 | -2.756 | 1.00 | 0.37 |
| ATOM | 715 | HB | VAL | 43 | -0.326 | -5.049 | -1.875 | 1.00 | 0.33 |
| ATOM | 716 | 1HG1 | VAL | 43 | 1.436 | -4.906 | -0.477 | 1.00 | 1.09 |
| ATOM | 717 | 2HG1 | VAL | 43 | 0.754 | -3.433 | 0.211 | 1.00 | 1.03 |
| ATOM | 718 | 3HG1 | VAL | 43 | 1.863 | -3.336 | -1.156 | 1.00 | 1.03 |
| ATOM | 719 | 1HG2 | VAL | 43 | -1.282 | -3.460 | 0.048 | 1.00 | 1.02 |
| ATOM | 720 | 2HG2 | VAL | 43 | -2.234 | -3.823 | -1.392 | 1.00 | 1.08 |
| ATOM | 721 | 3HG2 | VAL | 43 | -1.352 | -2.300 | -1.278 | 1.00 | 1.03 |
| ATOM | 722 | N | MET | 44 | 0.604 | -4.832 | -4.826 | 1.00 | 0.49 |
| ATOM | 723 | CA | MET | 44 | 1.459 | -5.671 | -5.714 | 1.00 | 0.57 |
| ATOM | 724 | C | MET | 44 | 2.190 | -4.745 | -6.681 | 1.00 | 0.55 |
| ATOM | 725 | O | MET | 44 | 3.393 | -4.811 | -6.839 | 1.00 | 0.56 |
| ATOM | 726 | CB | MET | 44 | 0.586 | -6.657 | -6.495 | 1.00 | 0.68 |
| ATOM | 727 | CG | MET | 44 | 0.221 | -7.839 | -5.595 | 1.00 | 1.06 |
| ATOM | 728 | SD | MET | 44 | -0.272 | -9.247 | -6.619 | 1.00 | 1.46 |
| ATOM | 729 | CE | MET | 44 | 1.352 | -9.575 | -7.347 | 1.00 | 1.81 |
| ATOM | 730 | HN | MET | 44 | -0.359 | -4.771 | -4.990 | 1.00 | 0.55 |
| ATOM | 731 | HA | MET | 44 | 2.181 | -6.210 | -5.119 | 1.00 | 0.58 |
| ATOM | 732 | 1HB | MET | 44 | 1.130 | -7.017 | -7.355 | 1.00 | 1.17 |
| ATOM | 733 | 2HB | MET | 44 | -0.316 | -6.159 | -6.821 | 1.00 | 1.16 |
| ATOM | 734 | 1HG | MET | 44 | -0.598 | -7.559 | -4.949 | 1.00 | 1.57 |
| ATOM | 735 | 2HG | MET | 44 | 1.076 | -8.112 | -4.994 | 1.00 | 1.52 |
| ATOM | 736 | 1HE | MET | 44 | 2.110 | -9.511 | -6.578 | 1.00 | 2.32 |
| ATOM | 737 | 2HE | MET | 44 | 1.558 | -8.846 | -8.113 | 1.00 | 2.24 |
| ATOM | 738 | 3HE | MET | 44 | 1.357 | -10.565 | -7.783 | 1.00 | 2.15 |
| ATOM | 739 | N | GLU | 45 | 1.481 | -3.839 | -7.294 | 1.00 | 0.58 |
| ATOM | 740 | CA | GLU | 45 | 2.154 | -2.876 | -8.203 | 1.00 | 0.59 |
| ATOM | 741 | C | GLU | 45 | 3.160 | -2.100 | -7.359 | 1.00 | 0.51 |
| ATOM | 742 | O | GLU | 45 | 4.171 | -1.625 | -7.838 | 1.00 | 0.52 |
| ATOM | 743 | CB | GLU | 45 | 1.123 | -1.914 | -8.799 | 1.00 | 0.67 |
| ATOM | 744 | CG | GLU | 45 | 0.611 | -2.473 | -10.127 | 1.00 | 0.96 |
| ATOM | 745 | CD | GLU | 45 | 0.712 | -1.395 | -11.207 | 1.00 | 1.53 |
| ATOM | 746 | OE1 | GLU | 45 | 0.872 | -1.754 | -12.362 | 1.00 | 2.25 |
| ATOM | 747 | OE2 | GLU | 45 | 0.629 | -0.228 | -10.861 | 1.00 | 2.10 |
| ATOM | 748 | HN | GLU | 45 | 0.525 | -3.766 | -7.122 | 1.00 | 0.63 |
| ATOM | 749 | HA | GLU | 45 | 2.666 | -3.408 | -8.992 | 1.00 | 0.64 |
| ATOM | 750 | 1HB | GLU | 45 | 1.583 | -0.953 | -8.968 | 1.00 | 0.84 |
| ATOM | 751 | 2HB | GLU | 45 | 0.296 | -1.803 | -8.112 | 1.00 | 0.90 |
| ATOM | 752 | 1HG | GLU | 45 | -0.420 | -2.775 | -10.018 | 1.00 | 1.52 |
| ATOM | 753 | 2HG | GLU | 45 | 1.209 | -3.327 | -10.412 | 1.00 | 1.38 |
| ATOM | 754 | N | LEU | 46 | 2.885 | -1.998 | -6.085 | 1.00 | 0.49 |
| ATOM | 755 | CA | LEU | 46 | 3.802 | -1.295 | -5.167 | 1.00 | 0.49 |
| ATOM | 756 | C | LEU | 46 | 5.087 | -2.123 | -5.049 | 1.00 | 0.51 |
| ATOM | 757 | O | LEU | 46 | 6.184 | -1.602 | -5.102 | 1.00 | 0.55 |
| ATOM | 758 | CB | LEU | 46 | 3.094 | -1.150 | -3.803 | 1.00 | 0.53 |
| ATOM | 759 | CG | LEU | 46 | 4.097 | -0.970 | -2.657 | 1.00 | 0.73 |
| ATOM | 760 | CD1 | LEU | 46 | 3.689 | 0.231 | -1.809 | 1.00 | 1.49 |
| ATOM | 761 | CD2 | LEU | 46 | 4.097 | -2.224 | -1.783 | 1.00 | 0.80 |
| ATOM | 762 | HN | LEU | 46 | 2.070 | -2.405 | -5.727 | 1.00 | 0.51 |
| ATOM | 763 | HA | LEU | 46 | 4.026 | -0.325 | -5.568 | 1.00 | 0.52 |
| ATOM | 764 | 1HB | LEU | 46 | 2.502 | -2.034 | -3.619 | 1.00 | 0.70 |
| ATOM | 765 | 2HB | LEU | 46 | 2.441 | -0.291 | -3.836 | 1.00 | 1.00 |
| ATOM | 766 | HG | LEU | 46 | 5.085 | -0.809 | -3.058 | 1.00 | 1.40 |
| ATOM | 767 | 1HD1 | LEU | 46 | 2.900 | -0.058 | -1.131 | 1.00 | 1.92 |
| ATOM | 768 | 2HD1 | LEU | 46 | 3.340 | 1.025 | -2.452 | 1.00 | 2.10 |
| ATOM | 769 | 3HD1 | LEU | 46 | 4.540 | 0.573 | -1.245 | 1.00 | 1.98 |
| ATOM | 770 | 1HD2 | LEU | 46 | 3.701 | -3.056 | -2.347 | 1.00 | 1.41 |

FIG. 5A-10

```
ATOM    771  2HD2 LEU    46       3.483   -2.055   -0.911  1.00  1.46
ATOM    772  3HD2 LEU    46       5.108   -2.448   -1.474  1.00  1.30
ATOM    773  N    GLU    47       4.953   -3.411   -4.893  1.00  0.52
ATOM    774  CA   GLU    47       6.159   -4.272   -4.774  1.00  0.59
ATOM    775  C    GLU    47       7.005   -4.126   -6.044  1.00  0.63
ATOM    776  O    GLU    47       8.201   -4.333   -6.036  1.00  0.72
ATOM    777  CB   GLU    47       5.730   -5.737   -4.544  1.00  0.63
ATOM    778  CG   GLU    47       5.269   -6.406   -5.847  1.00  0.80
ATOM    779  CD   GLU    47       6.145   -7.629   -6.129  1.00  1.30
ATOM    780  OE1  GLU    47       6.898   -7.585   -7.088  1.00  1.82
ATOM    781  OE2  GLU    47       6.046   -8.588   -5.383  1.00  1.94
ATOM    782  HN   GLU    47       4.059   -3.808   -4.855  1.00  0.52
ATOM    783  HA   GLU    47       6.742   -3.941   -3.928  1.00  0.62
ATOM    784  1HB  GLU    47       4.915   -5.754   -3.836  1.00  0.82
ATOM    785  2HB  GLU    47       6.561   -6.291   -4.139  1.00  1.08
ATOM    786  1HG  GLU    47       5.351   -5.713   -6.665  1.00  1.31
ATOM    787  2HG  GLU    47       4.241   -6.717   -5.742  1.00  1.15
ATOM    788  N    ASP    48       6.385   -3.762   -7.136  1.00  0.61
ATOM    789  CA   ASP    48       7.146   -3.595   -8.406  1.00  0.68
ATOM    790  C    ASP    48       7.796   -2.208   -8.433  1.00  0.68
ATOM    791  O    ASP    48       8.818   -2.005   -9.059  1.00  0.77
ATOM    792  CB   ASP    48       6.192   -3.735   -9.594  1.00  0.71
ATOM    793  CG   ASP    48       6.564   -4.978  -10.404  1.00  1.07
ATOM    794  OD1  ASP    48       7.450   -4.875  -11.236  1.00  1.68
ATOM    795  OD2  ASP    48       5.956   -6.011  -10.179  1.00  1.70
ATOM    796  HN   ASP    48       5.416   -3.599   -7.119  1.00  0.58
ATOM    797  HA   ASP    48       7.913   -4.353   -8.468  1.00  0.72
ATOM    798  1HB  ASP    48       6.270   -2.861  -10.223  1.00  0.96
ATOM    799  2HB  ASP    48       5.179   -3.830   -9.231  1.00  0.93
ATOM    800  N    GLU    49       7.213   -1.252   -7.760  1.00  0.62
ATOM    801  CA   GLU    49       7.802    0.119   -7.752  1.00  0.64
ATOM    802  C    GLU    49       9.142    0.095   -7.021  1.00  0.67
ATOM    803  O    GLU    49      10.146    0.557   -7.526  1.00  0.73
ATOM    804  CB   GLU    49       6.854    1.089   -7.036  1.00  0.60
ATOM    805  CG   GLU    49       6.170    1.991   -8.065  1.00  0.73
ATOM    806  CD   GLU    49       5.346    1.135   -9.027  1.00  1.80
ATOM    807  OE1  GLU    49       4.143    1.059   -8.840  1.00  2.54
ATOM    808  OE2  GLU    49       5.931    0.570   -9.936  1.00  2.46
ATOM    809  HN   GLU    49       6.390   -1.435   -7.262  1.00  0.58
ATOM    810  HA   GLU    49       7.954    0.449   -8.766  1.00  0.68
ATOM    811  1HB  GLU    49       7.418    1.699   -6.345  1.00  0.65
ATOM    812  2HB  GLU    49       6.106    0.529   -6.493  1.00  0.54
ATOM    813  1HG  GLU    49       6.919    2.535   -8.621  1.00  1.00
ATOM    814  2HG  GLU    49       5.521    2.689   -7.555  1.00  0.99
ATOM    815  N    PHE    50       9.164   -0.432   -5.832  1.00  0.63
ATOM    816  CA   PHE    50      10.441   -0.479   -5.058  1.00  0.67
ATOM    817  C    PHE    50      11.064   -1.877   -5.159  1.00  0.70
ATOM    818  O    PHE    50      11.991   -2.201   -4.445  1.00  0.76
ATOM    819  CB   PHE    50      10.178   -0.152   -3.579  1.00  0.64
ATOM    820  CG   PHE    50       9.051    0.851   -3.455  1.00  0.60
ATOM    821  CD1  PHE    50       9.313    2.223   -3.550  1.00  1.31
ATOM    822  CD2  PHE    50       7.743    0.401   -3.246  1.00  1.23
ATOM    823  CE1  PHE    50       8.264    3.145   -3.434  1.00  1.27
ATOM    824  CE2  PHE    50       6.697    1.322   -3.132  1.00  1.25
ATOM    825  CZ   PHE    50       6.954    2.693   -3.224  1.00  0.56
ATOM    826  HN   PHE    50       8.339   -0.793   -5.444  1.00  0.58
ATOM    827  HA   PHE    50      11.130    0.247   -5.466  1.00  0.72
ATOM    828  1HB  PHE    50      11.073    0.261   -3.140  1.00  0.70
ATOM    829  2HB  PHE    50       9.908   -1.057   -3.056  1.00  0.63
ATOM    830  HD1  PHE    50      10.322    2.571   -3.710  1.00  2.14
ATOM    831  HD2  PHE    50       7.541   -0.657   -3.174  1.00  2.03
ATOM    832  HE1  PHE    50       8.465    4.203   -3.508  1.00  2.08
ATOM    833  HE2  PHE    50       5.691    0.975   -2.971  1.00  2.07
ATOM    834  HZ   PHE    50       6.140    3.401   -3.131  1.00  0.57
ATOM    835  N    ASP    51      10.567   -2.710   -6.036  1.00  0.72
ATOM    836  CA   ASP    51      11.141   -4.079   -6.167  1.00  0.76
ATOM    837  C    ASP    51      11.055   -4.800   -4.820  1.00  0.74
ATOM    838  O    ASP    51      12.001   -4.829   -4.059  1.00  0.80
ATOM    839  CB   ASP    51      12.605   -3.980   -6.601  1.00  0.84
ATOM    840  CG   ASP    51      12.699   -4.125   -8.120  1.00  1.18
ATOM    841  OD1  ASP    51      12.863   -5.243   -8.580  1.00  1.68
ATOM    842  OD2  ASP    51      12.603   -3.116   -8.799  1.00  1.85
ATOM    843  HN   ASP    51       9.819   -2.438   -6.606  1.00  0.74
ATOM    844  HA   ASP    51      10.584   -4.633   -6.908  1.00  0.78
ATOM    845  1HB  ASP    51      13.174   -4.767   -6.130  1.00  0.97
ATOM    846  2HB  ASP    51      13.004   -3.020   -6.304  1.00  1.23
ATOM    847  N    MET    52       9.926   -5.381   -4.521  1.00  0.75
```

FIG. 5A-11

| | | | | | | | | |
|---|---|---|---|---|---|---|---|---|
| ATOM | 348 | CA | MET | 52 | 9.776 | -6.100 | -3.224 | 1.00 | 0.77 |
| ATOM | 349 | C | MET | 52 | 9.189 | -7.490 | -3.477 | 1.00 | 0.81 |
| ATOM | 350 | O | MET | 52 | 8.891 | -7.855 | -4.597 | 1.00 | 0.96 |
| ATOM | 351 | CB | MET | 52 | 8.836 | -5.310 | -2.311 | 1.00 | 0.79 |
| ATOM | 852 | CG | MET | 52 | 9.638 | -4.687 | -1.164 | 1.00 | 0.87 |
| ATOM | 853 | SD | MET | 52 | 9.104 | -5.399 | 0.412 | 1.00 | 1.42 |
| ATOM | 854 | CE | MET | 52 | 7.774 | -4.220 | 0.750 | 1.00 | 0.79 |
| ATOM | 855 | HN | MET | 52 | 9.175 | -5.344 | -5.150 | 1.00 | 0.82 |
| ATOM | 856 | HA | MET | 52 | 10.742 | -6.196 | -2.752 | 1.00 | 0.83 |
| ATOM | 857 | 1HB | MET | 52 | 8.086 | -5.974 | -1.907 | 1.00 | 1.31 |
| ATOM | 858 | 2HB | MET | 52 | 8.355 | -4.528 | -2.881 | 1.00 | 1.31 |
| ATOM | 859 | 1HG | MET | 52 | 9.473 | -3.620 | -1.150 | 1.00 | 1.43 |
| ATOM | 860 | 2HG | MET | 52 | 10.689 | -4.887 | -1.310 | 1.00 | 1.41 |
| ATOM | 861 | 1HE | MET | 52 | 7.413 | -3.809 | -0.183 | 1.00 | 1.28 |
| ATOM | 862 | 2HE | MET | 52 | 8.147 | -3.422 | 1.371 | 1.00 | 1.42 |
| ATOM | 863 | 3HE | MET | 52 | 6.968 | -4.726 | 1.264 | 1.00 | 1.29 |
| ATOM | 864 | N | GLU | 53 | 9.019 | -8.269 | -2.444 | 1.00 | 0.83 |
| ATOM | 865 | CA | GLU | 53 | 8.449 | -9.634 | -2.625 | 1.00 | 0.88 |
| ATOM | 866 | C | GLU | 53 | 7.073 | -9.701 | -1.959 | 1.00 | 0.75 |
| ATOM | 867 | O | GLU | 53 | 6.675 | -10.722 | -1.434 | 1.00 | 1.16 |
| ATOM | 868 | CB | GLU | 53 | 9.379 | -10.664 | -1.981 | 1.00 | 1.11 |
| ATOM | 869 | CG | GLU | 53 | 10.817 | -10.410 | -2.437 | 1.00 | 1.59 |
| ATOM | 870 | CD | GLU | 53 | 11.667 | -11.653 | -2.170 | 1.00 | 2.23 |
| ATOM | 871 | OE1 | GLU | 53 | 12.056 | -11.847 | -1.030 | 1.00 | 2.86 |
| ATOM | 872 | OE2 | GLU | 53 | 11.914 | -12.391 | -3.110 | 1.00 | 2.66 |
| ATOM | 873 | HN | GLU | 53 | 9.264 | -7.956 | -1.548 | 1.00 | 0.90 |
| ATOM | 874 | HA | GLU | 53 | 8.350 | -9.846 | -3.679 | 1.00 | 0.99 |
| ATOM | 875 | 1HB | GLU | 53 | 9.079 | -11.657 | -2.280 | 1.00 | 1.43 |
| ATOM | 876 | 2HB | GLU | 53 | 9.321 | -10.578 | -0.905 | 1.00 | 1.51 |
| ATOM | 877 | 1HG | GLU | 53 | 11.225 | -9.573 | -1.891 | 1.00 | 1.92 |
| ATOM | 878 | 2HG | GLU | 53 | 10.824 | -10.188 | -3.495 | 1.00 | 2.01 |
| ATOM | 879 | N | ILE | 54 | 6.344 | -8.619 | -1.976 | 1.00 | 0.66 |
| ATOM | 880 | CA | ILE | 54 | 4.995 | -8.618 | -1.343 | 1.00 | 0.55 |
| ATOM | 881 | C | ILE | 54 | 4.059 | -9.539 | -2.125 | 1.00 | 0.67 |
| ATOM | 882 | O | ILE | 54 | 3.737 | -9.286 | -3.269 | 1.00 | 1.56 |
| ATOM | 883 | CB | ILE | 54 | 4.431 | -7.197 | -1.356 | 1.00 | 0.50 |
| ATOM | 884 | CG1 | ILE | 54 | 5.379 | -6.267 | -0.599 | 1.00 | 0.56 |
| ATOM | 885 | CG2 | ILE | 54 | 3.056 | -7.179 | -0.683 | 1.00 | 0.60 |
| ATOM | 886 | CD1 | ILE | 54 | 4.865 | -4.831 | -0.698 | 1.00 | 0.63 |
| ATOM | 887 | HN | ILE | 54 | 6.684 | -7.806 | -2.404 | 1.00 | 1.02 |
| ATOM | 888 | HA | ILE | 54 | 5.074 | -8.965 | -0.324 | 1.00 | 0.62 |
| ATOM | 889 | HB | ILE | 54 | 4.333 | -6.861 | -2.376 | 1.00 | 0.59 |
| ATOM | 890 | 1HG1 | ILE | 54 | 6.365 | -6.325 | -1.035 | 1.00 | 0.66 |
| ATOM | 891 | 2HG1 | ILE | 54 | 5.424 | -6.565 | 0.439 | 1.00 | 0.67 |
| ATOM | 892 | 1HG2 | ILE | 54 | 3.170 | -6.927 | 0.361 | 1.00 | 1.07 |
| ATOM | 893 | 2HG2 | ILE | 54 | 2.598 | -8.153 | -0.771 | 1.00 | 1.34 |
| ATOM | 894 | 3HG2 | ILE | 54 | 2.430 | -6.443 | -1.165 | 1.00 | 1.14 |
| ATOM | 895 | 1HD1 | ILE | 54 | 4.877 | -4.517 | -1.731 | 1.00 | 1.19 |
| ATOM | 896 | 2HD1 | ILE | 54 | 5.499 | -4.179 | -0.116 | 1.00 | 1.07 |
| ATOM | 897 | 3HD1 | ILE | 54 | 3.855 | -4.783 | -0.319 | 1.00 | 1.27 |
| ATOM | 898 | N | SER | 55 | 3.612 | -10.601 | -1.516 | 1.00 | 0.75 |
| ATOM | 899 | CA | SER | 55 | 2.690 | -11.530 | -2.223 | 1.00 | 0.77 |
| ATOM | 900 | C | SER | 55 | 1.252 | -11.225 | -1.801 | 1.00 | 0.82 |
| ATOM | 901 | O | SER | 55 | 1.012 | -10.432 | -0.913 | 1.00 | 1.54 |
| ATOM | 902 | CB | SER | 55 | 3.037 | -12.974 | -1.859 | 1.00 | 0.90 |
| ATOM | 903 | OG | SER | 55 | 3.508 | -13.649 | -3.019 | 1.00 | 1.56 |
| ATOM | 904 | HN | SER | 55 | 3.878 | -10.784 | -0.590 | 1.00 | 1.43 |
| ATOM | 905 | HA | SER | 55 | 2.789 | -11.393 | -3.290 | 1.00 | 0.80 |
| ATOM | 906 | 1HB | SER | 55 | 2.155 | -13.470 | -1.475 | 1.00 | 1.37 |
| ATOM | 907 | 2HB | SER | 55 | 3.807 | -12.983 | -1.106 | 1.00 | 1.08 |
| ATOM | 908 | HG | SER | 55 | 4.169 | -14.288 | -2.742 | 1.00 | 1.79 |
| ATOM | 909 | N | ASP | 56 | 0.292 | -11.846 | -2.428 | 1.00 | 0.77 |
| ATOM | 910 | CA | ASP | 56 | -1.127 | -11.584 | -2.058 | 1.00 | 0.74 |
| ATOM | 911 | C | ASP | 56 | -1.325 | -11.844 | -0.563 | 1.00 | 0.73 |
| ATOM | 912 | O | ASP | 56 | -2.253 | -11.349 | 0.043 | 1.00 | 1.00 |
| ATOM | 913 | CB | ASP | 56 | -2.043 | -12.510 | -2.861 | 1.00 | 0.90 |
| ATOM | 914 | CG | ASP | 56 | -2.969 | -11.672 | -3.745 | 1.00 | 1.56 |
| ATOM | 915 | OD1 | ASP | 56 | -3.948 | -11.161 | -3.227 | 1.00 | 2.33 |
| ATOM | 916 | OD2 | ASP | 56 | -2.682 | -11.555 | -4.926 | 1.00 | 2.15 |
| ATOM | 917 | HN | ASP | 56 | 0.504 | -12.482 | -3.143 | 1.00 | 1.31 |
| ATOM | 918 | HA | ASP | 56 | -1.372 | -10.556 | -2.279 | 1.00 | 0.69 |
| ATOM | 919 | 1HB | ASP | 56 | -2.637 | -13.105 | -2.184 | 1.00 | 1.33 |
| ATOM | 920 | 2HB | ASP | 56 | -1.443 | -13.160 | -3.481 | 1.00 | 1.28 |
| ATOM | 921 | N | GLU | 57 | -0.462 | -12.618 | 0.038 | 1.00 | 0.66 |
| ATOM | 922 | CA | GLU | 57 | -0.607 | -12.907 | 1.492 | 1.00 | 0.70 |
| ATOM | 923 | C | GLU | 57 | -0.097 | -11.718 | 2.310 | 1.00 | 0.59 |
| ATOM | 924 | O | GLU | 57 | -0.450 | -11.548 | 3.460 | 1.00 | 0.65 |

FIG. 5A-12

```
ATOM    925  CB   GLU   57       0.205 -14.154   1.846  1.00  0.82
ATOM    926  CG   GLU   57       1.654 -13.966   1.392  1.00  0.74
ATOM    927  CD   GLU   57       2.541 -15.013   2.066  1.00  1.01
ATOM    928  OE1  GLU   57       3.487 -14.621   2.730  1.00  1.45
ATOM    929  OE2  GLU   57       2.260 -16.190   1.907  1.00  1.65
ATOM    930  HN   GLU   57       0.280 -13.011  -0.467  1.00  0.78
ATOM    931  HA   GLU   57      -1.648 -13.080   1.721  1.00  0.79
ATOM    932  1HB  GLU   57      -0.218 -15.013   1.348  1.00  1.04
ATOM    933  2HB  GLU   57       0.179 -14.308   2.916  1.00  1.02
ATOM    934  1HG  GLU   57       1.993 -12.978   1.667  1.00  0.91
ATOM    935  2HG  GLU   57       1.711 -14.080   0.319  1.00  0.91
ATOM    936  N    ASP   58       0.735 -10.894   1.732  1.00  0.48
ATOM    937  CA   ASP   58       1.266  -9.722   2.486  1.00  0.43
ATOM    938  C    ASP   58       0.157  -8.688   2.683  1.00  0.40
ATOM    939  O    ASP   58      -0.414  -8.577   3.744  1.00  0.45
ATOM    940  CB   ASP   58       2.422  -9.090   1.708  1.00  0.42
ATOM    941  CG   ASP   58       3.751  -9.511   2.338  1.00  0.79
ATOM    942  OD1  ASP   58       3.790 -10.573   2.936  1.00  1.45
ATOM    943  OD2  ASP   58       4.706  -8.762   2.213  1.00  1.46
ATOM    944  HN   ASP   58       1.013 -11.047   0.805  1.00  0.51
ATOM    945  HA   ASP   58       1.622 -10.050   3.450  1.00  0.48
ATOM    946  1HB  ASP   58       2.335  -8.015   1.742  1.00  0.63
ATOM    947  2HB  ASP   58       2.389  -9.423   0.681  1.00  0.57
ATOM    948  N    ALA   59      -0.149  -7.932   1.665  1.00  0.41
ATOM    949  CA   ALA   59      -1.221  -6.889   1.775  1.00  0.43
ATOM    950  C    ALA   59      -2.458  -7.440   2.503  1.00  0.49
ATOM    951  O    ALA   59      -3.224  -6.695   3.082  1.00  0.53
ATOM    952  CB   ALA   59      -1.624  -6.444   0.370  1.00  0.54
ATOM    953  HN   ALA   59       0.331  -8.046   0.820  1.00  0.47
ATOM    954  HA   ALA   59      -0.840  -6.034   2.318  1.00  0.42
ATOM    955  1HB  ALA   59      -0.987  -6.927  -0.357  1.00  1.28
ATOM    956  2HB  ALA   59      -1.516  -5.375   0.288  1.00  1.06
ATOM    957  3HB  ALA   59      -2.651  -6.718   0.186  1.00  1.14
ATOM    958  N    GLU   60      -2.670  -8.728   2.471  1.00  0.55
ATOM    959  CA   GLU   60      -3.868  -9.300   3.154  1.00  0.68
ATOM    960  C    GLU   60      -3.558  -9.603   4.624  1.00  0.70
ATOM    961  O    GLU   60      -4.322  -9.271   5.508  1.00  0.80
ATOM    962  CB   GLU   60      -4.285 -10.591   2.448  1.00  0.79
ATOM    963  CG   GLU   60      -5.768 -10.515   2.079  1.00  1.03
ATOM    964  CD   GLU   60      -6.450 -11.838   2.431  1.00  1.32
ATOM    965  OE1  GLU   60      -5.791 -12.862   2.349  1.00  1.83
ATOM    966  OE2  GLU   60      -7.620 -11.806   2.776  1.00  1.97
ATOM    967  HN   GLU   60      -2.053  -9.317   1.991  1.00  0.54
ATOM    968  HA   GLU   60      -4.676  -8.591   3.103  1.00  0.75
ATOM    969  1HB  GLU   60      -4.122 -11.431   3.106  1.00  1.01
ATOM    970  2HB  GLU   60      -3.697 -10.716   1.551  1.00  0.99
ATOM    971  1HG  GLU   60      -5.867 -10.332   1.020  1.00  1.37
ATOM    972  2HG  GLU   60      -6.235  -9.711   2.629  1.00  1.60
ATOM    973  N    LYS   61      -2.455 -10.243   4.893  1.00  0.65
ATOM    974  CA   LYS   61      -2.114 -10.580   6.309  1.00  0.73
ATOM    975  C    LYS   61      -1.365  -9.417   6.968  1.00  0.70
ATOM    976  O    LYS   61      -1.291  -9.322   8.177  1.00  0.97
ATOM    977  CB   LYS   61      -1.230 -11.828   6.336  1.00  0.81
ATOM    978  CG   LYS   61      -1.407 -12.548   7.674  1.00  1.30
ATOM    979  CD   LYS   61      -1.016 -14.018   7.519  1.00  1.75
ATOM    980  CE   LYS   61       0.509 -14.139   7.498  1.00  2.14
ATOM    981  NZ   LYS   61       0.913 -15.427   8.131  1.00  2.62
ATOM    982  HN   LYS   61      -1.859 -10.512   4.166  1.00  0.59
ATOM    983  HA   LYS   61      -3.023 -10.776   6.858  1.00  0.85
ATOM    984  1HB  LYS   61      -0.197 -11.540   6.218  1.00  1.08
ATOM    985  2HB  LYS   61      -1.515 -12.488   5.530  1.00  1.02
ATOM    986  1HG  LYS   61      -2.439 -12.483   7.984  1.00  1.80
ATOM    987  2HG  LYS   61      -0.777 -12.083   8.419  1.00  1.76
ATOM    988  1HD  LYS   61      -1.418 -14.402   6.594  1.00  2.22
ATOM    989  2HD  LYS   61      -1.412 -14.585   8.348  1.00  2.08
ATOM    990  1HE  LYS   61       0.943 -13.316   8.047  1.00  2.32
ATOM    991  2HE  LYS   61       0.858 -14.115   6.477  1.00  2.47
ATOM    992  1HZ  LYS   61       1.131 -15.267   9.134  1.00  2.92
ATOM    993  2HZ  LYS   61       1.755 -15.800   7.647  1.00  2.99
ATOM    994  3HZ  LYS   61       0.135 -16.111   8.053  1.00  2.94
ATOM    995  N    ILE   62      -0.806  -8.537   6.187  1.00  0.57
ATOM    996  CA   ILE   62      -0.058  -7.386   6.767  1.00  0.54
ATOM    997  C    ILE   62      -0.962  -6.642   7.761  1.00  0.59
ATOM    998  O    ILE   62      -2.163  -6.577   7.587  1.00  1.32
ATOM    999  CB   ILE   62       0.397  -6.458   5.621  1.00  0.46
ATOM   1000  CG1  ILE   62       1.569  -5.596   6.093  1.00  0.56
ATOM   1001  CG2  ILE   62      -0.751  -5.549   5.150  1.00  0.67
```

FIG. 5A-13

| | | | | | | | | |
|---|---|---|---|---|---|---|---|---|
| ATOM | 1002 | CD1 | ILE | 62 | 2.130 | -4.818 | 4.903 | 1.00 | 0.60 |
| ATOM | 1003 | HN | ILE | 62 | -0.873 | -8.633 | 5.215 | 1.00 | 0.68 |
| ATOM | 1004 | HA | ILE | 62 | 0.811 | -7.758 | 7.291 | 1.00 | 0.62 |
| ATOM | 1005 | HB | ILE | 62 | 0.723 | -7.065 | 4.790 | 1.00 | 0.51 |
| ATOM | 1006 | 1HG1 | ILE | 62 | 2.343 | -6.230 | 6.500 | 1.00 | 0.74 |
| ATOM | 1007 | 2HG1 | ILE | 62 | 1.230 | -4.906 | 6.850 | 1.00 | 0.90 |
| ATOM | 1008 | 1HG2 | ILE | 62 | -0.534 | -5.178 | 4.159 | 1.00 | 1.33 |
| ATOM | 1009 | 2HG2 | ILE | 62 | -0.854 | -4.716 | 5.830 | 1.00 | 1.12 |
| ATOM | 1010 | 3HG2 | ILE | 62 | -1.672 | -6.112 | 5.129 | 1.00 | 1.31 |
| ATOM | 1011 | 1HD1 | ILE | 62 | 2.337 | -5.500 | 4.091 | 1.00 | 1.15 |
| ATOM | 1012 | 2HD1 | ILE | 62 | 3.042 | -4.318 | 5.195 | 1.00 | 1.18 |
| ATOM | 1013 | 3HD1 | ILE | 62 | 1.405 | -4.085 | 4.580 | 1.00 | 1.17 |
| ATOM | 1014 | N | ALA | 63 | -0.397 | -6.086 | 8.801 | 1.00 | 0.80 |
| ATOM | 1015 | CA | ALA | 63 | -1.231 | -5.352 | 9.802 | 1.00 | 0.75 |
| ATOM | 1016 | C | ALA | 63 | -2.146 | -4.363 | 9.078 | 1.00 | 0.75 |
| ATOM | 1017 | O | ALA | 63 | -3.285 | -4.165 | 9.451 | 1.00 | 1.33 |
| ATOM | 1018 | CB | ALA | 63 | -0.318 | -4.593 | 10.767 | 1.00 | 0.77 |
| ATOM | 1019 | HN | ALA | 63 | 0.572 | -6.151 | 8.926 | 1.00 | 1.44 |
| ATOM | 1020 | HA | ALA | 63 | -1.831 | -6.058 | 10.355 | 1.00 | 0.77 |
| ATOM | 1021 | 1HB | ALA | 63 | 0.683 | -4.995 | 10.708 | 1.00 | 1.10 |
| ATOM | 1022 | 2HB | ALA | 63 | -0.690 | -4.701 | 11.775 | 1.00 | 1.34 |
| ATOM | 1023 | 3HB | ALA | 63 | -0.302 | -3.546 | 10.500 | 1.00 | 1.30 |
| ATOM | 1024 | N | THR | 64 | -1.652 | -3.754 | 8.037 | 1.00 | 0.54 |
| ATOM | 1025 | CA | THR | 64 | -2.473 | -2.782 | 7.264 | 1.00 | 0.48 |
| ATOM | 1026 | C | THR | 64 | -1.699 | -2.346 | 6.020 | 1.00 | 0.41 |
| ATOM | 1027 | O | THR | 64 | -0.488 | -2.449 | 5.960 | 1.00 | 0.42 |
| ATOM | 1028 | CB | THR | 64 | -2.769 | -1.550 | 8.126 | 1.00 | 0.56 |
| ATOM | 1029 | OG1 | THR | 64 | -1.747 | -1.400 | 9.102 | 1.00 | 0.63 |
| ATOM | 1030 | CG2 | THR | 64 | -4.118 | -1.726 | 8.820 | 1.00 | 0.61 |
| ATOM | 1031 | HN | THR | 64 | -0.737 | -3.943 | 7.758 | 1.00 | 0.91 |
| ATOM | 1032 | HA | THR | 64 | -3.401 | -3.247 | 6.968 | 1.00 | 0.48 |
| ATOM | 1033 | HB | THR | 64 | -2.804 | -0.666 | 7.500 | 1.00 | 0.64 |
| ATOM | 1034 | HG1 | THR | 64 | -1.163 | -0.695 | 8.815 | 1.00 | 1.07 |
| ATOM | 1035 | 1HG2 | THR | 64 | -4.683 | -2.494 | 8.315 | 1.00 | 1.12 |
| ATOM | 1036 | 2HG2 | THR | 64 | -4.663 | -0.795 | 8.788 | 1.00 | 1.18 |
| ATOM | 1037 | 3HG2 | THR | 64 | -3.957 | -2.014 | 9.848 | 1.00 | 1.16 |
| ATOM | 1038 | N | VAL | 65 | -2.390 | -1.839 | 5.034 | 1.00 | 0.36 |
| ATOM | 1039 | CA | VAL | 65 | -1.712 | -1.363 | 3.791 | 1.00 | 0.31 |
| ATOM | 1040 | C | VAL | 65 | -0.527 | -0.472 | 4.188 | 1.00 | 0.36 |
| ATOM | 1041 | O | VAL | 65 | 0.546 | -0.542 | 3.619 | 1.00 | 0.38 |
| ATOM | 1042 | CB | VAL | 65 | -2.731 | -0.558 | 2.979 | 1.00 | 0.30 |
| ATOM | 1043 | CG1 | VAL | 65 | -2.031 | 0.276 | 1.901 | 1.00 | 0.37 |
| ATOM | 1044 | CG2 | VAL | 65 | -3.717 | -1.523 | 2.315 | 1.00 | 0.27 |
| ATOM | 1045 | HN | VAL | 65 | -3.363 | -1.754 | 5.118 | 1.00 | 0.37 |
| ATOM | 1046 | HA | VAL | 65 | -1.366 | -2.207 | 3.208 | 1.00 | 0.29 |
| ATOM | 1047 | HB | VAL | 65 | -3.265 | 0.098 | 3.647 | 1.00 | 0.37 |
| ATOM | 1048 | 1HG1 | VAL | 65 | -0.997 | -0.026 | 1.829 | 1.00 | 0.93 |
| ATOM | 1049 | 2HG1 | VAL | 65 | -2.084 | 1.321 | 2.168 | 1.00 | 1.10 |
| ATOM | 1050 | 3HG1 | VAL | 65 | -2.520 | 0.120 | 0.952 | 1.00 | 1.05 |
| ATOM | 1051 | 1HG2 | VAL | 65 | -4.569 | -1.669 | 2.962 | 1.00 | 0.98 |
| ATOM | 1052 | 2HG2 | VAL | 65 | -3.230 | -2.472 | 2.142 | 1.00 | 1.03 |
| ATOM | 1053 | 3HG2 | VAL | 65 | -4.046 | -1.111 | 1.373 | 1.00 | 1.06 |
| ATOM | 1054 | N | GLY | 66 | -0.722 | 0.356 | 5.177 | 1.00 | 0.41 |
| ATOM | 1055 | CA | GLY | 66 | 0.379 | 1.244 | 5.634 | 1.00 | 0.48 |
| ATOM | 1056 | C | GLY | 66 | 1.573 | 0.381 | 6.023 | 1.00 | 0.48 |
| ATOM | 1057 | O | GLY | 66 | 2.693 | 0.644 | 5.633 | 1.00 | 0.50 |
| ATOM | 1058 | HN | GLY | 66 | -1.593 | 0.384 | 5.624 | 1.00 | 0.41 |
| ATOM | 1059 | 1HA | GLY | 66 | 0.056 | 1.812 | 6.489 | 1.00 | 0.52 |
| ATOM | 1060 | 2HA | GLY | 66 | 0.659 | 1.914 | 4.834 | 1.00 | 0.49 |
| ATOM | 1061 | N | ASP | 67 | 1.342 | -0.670 | 6.771 | 1.00 | 0.48 |
| ATOM | 1062 | CA | ASP | 67 | 2.471 | -1.565 | 7.156 | 1.00 | 0.50 |
| ATOM | 1063 | C | ASP | 67 | 3.198 | -1.973 | 5.878 | 1.00 | 0.47 |
| ATOM | 1064 | O | ASP | 67 | 4.399 | -2.154 | 5.858 | 1.00 | 0.51 |
| ATOM | 1065 | CB | ASP | 67 | 1.930 | -2.806 | 7.866 | 1.00 | 0.51 |
| ATOM | 1066 | CG | ASP | 67 | 1.976 | -2.588 | 9.380 | 1.00 | 1.01 |
| ATOM | 1067 | OD1 | ASP | 67 | 2.765 | -3.253 | 10.031 | 1.00 | 1.56 |
| ATOM | 1068 | OD2 | ASP | 67 | 1.222 | -1.760 | 9.863 | 1.00 | 1.78 |
| ATOM | 1069 | HN | ASP | 67 | 0.429 | -0.877 | 7.061 | 1.00 | 0.48 |
| ATOM | 1070 | HA | ASP | 67 | 3.150 | -1.034 | 7.808 | 1.00 | 0.55 |
| ATOM | 1071 | 1HB | ASP | 67 | 2.536 | -3.662 | 7.609 | 1.00 | 0.76 |
| ATOM | 1072 | 2HB | ASP | 67 | 0.911 | -2.980 | 7.557 | 1.00 | 0.81 |
| ATOM | 1073 | N | ALA | 68 | 2.469 | -2.080 | 4.799 | 1.00 | 0.42 |
| ATOM | 1074 | CA | ALA | 68 | 3.108 | -2.431 | 3.504 | 1.00 | 0.41 |
| ATOM | 1075 | C | ALA | 68 | 4.102 | -1.322 | 3.182 | 1.00 | 0.45 |
| ATOM | 1076 | O | ALA | 68 | 5.221 | -1.563 | 2.769 | 1.00 | 0.49 |
| ATOM | 1077 | CB | ALA | 68 | 2.041 | -2.512 | 2.409 | 1.00 | 0.37 |
| ATOM | 1078 | HN | ALA | 68 | 1.504 | -1.901 | 4.839 | 1.00 | 0.40 |

FIG. 5A-14

| | | | | | | | | |
|---|---|---|---|---|---|---|---|---|
| ATOM | 1079 | HA | ALA | 68 | 3.624 | -3.374 | 3.592 | 1.00 | 0.42 |
| ATOM | 1080 | 1HB | ALA | 68 | 1.120 | -2.890 | 2.830 | 1.00 | 1.08 |
| ATOM | 1081 | 2HB | ALA | 68 | 2.377 | -3.177 | 1.627 | 1.00 | 1.05 |
| ATOM | 1082 | 3HB | ALA | 68 | 1.870 | -1.528 | 1.997 | 1.00 | 1.11 |
| ATOM | 1083 | N | VAL | 69 | 3.703 | -0.101 | 3.412 | 1.00 | 0.45 |
| ATOM | 1084 | CA | VAL | 69 | 4.620 | 1.040 | 3.169 | 1.00 | 0.50 |
| ATOM | 1085 | C | VAL | 69 | 5.814 | 0.870 | 4.119 | 1.00 | 0.56 |
| ATOM | 1086 | O | VAL | 69 | 6.964 | 0.971 | 3.730 | 1.00 | 0.62 |
| ATOM | 1087 | CB | VAL | 69 | 3.841 | 2.363 | 3.403 | 1.00 | 0.51 |
| ATOM | 1088 | CG1 | VAL | 69 | 4.347 | 3.137 | 4.631 | 1.00 | 0.55 |
| ATOM | 1089 | CG2 | VAL | 69 | 3.978 | 3.247 | 2.162 | 1.00 | 0.56 |
| ATOM | 1090 | HN | VAL | 69 | 2.805 | 0.058 | 3.773 | 1.00 | 0.43 |
| ATOM | 1091 | HA | VAL | 69 | 4.970 | 1.003 | 2.151 | 1.00 | 0.51 |
| ATOM | 1092 | HB | VAL | 69 | 2.796 | 2.128 | 3.548 | 1.00 | 0.51 |
| ATOM | 1093 | 1HG1 | VAL | 69 | 5.393 | 3.370 | 4.503 | 1.00 | 1.25 |
| ATOM | 1094 | 2HG1 | VAL | 69 | 4.218 | 2.531 | 5.516 | 1.00 | 0.95 |
| ATOM | 1095 | 3HG1 | VAL | 69 | 3.783 | 4.052 | 4.736 | 1.00 | 1.18 |
| ATOM | 1096 | 1HG2 | VAL | 69 | 4.964 | 3.687 | 2.139 | 1.00 | 1.18 |
| ATOM | 1097 | 2HG2 | VAL | 69 | 3.234 | 4.029 | 2.194 | 1.00 | 1.18 |
| ATOM | 1098 | 3HG2 | VAL | 69 | 3.829 | 2.648 | 1.277 | 1.00 | 1.13 |
| ATOM | 1099 | N | ASN | 70 | 5.534 | 0.571 | 5.358 | 1.00 | 0.57 |
| ATOM | 1100 | CA | ASN | 70 | 6.629 | 0.347 | 6.338 | 1.00 | 0.64 |
| ATOM | 1101 | C | ASN | 70 | 7.446 | -0.857 | 5.866 | 1.00 | 0.64 |
| ATOM | 1102 | O | ASN | 70 | 8.623 | -0.978 | 6.145 | 1.00 | 0.71 |
| ATOM | 1103 | CB | ASN | 70 | 6.031 | 0.053 | 7.716 | 1.00 | 0.67 |
| ATOM | 1104 | CG | ASN | 70 | 6.539 | 1.086 | 8.723 | 1.00 | 1.01 |
| ATOM | 1105 | OD1 | ASN | 70 | 5.774 | 1.617 | 9.504 | 1.00 | 1.73 |
| ATOM | 1106 | ND2 | ASN | 70 | 7.806 | 1.396 | 8.738 | 1.00 | 1.38 |
| ATOM | 1107 | HN | ASN | 70 | 4.600 | 0.468 | 5.635 | 1.00 | 0.56 |
| ATOM | 1108 | HA | ASN | 70 | 7.257 | 1.221 | 6.392 | 1.00 | 0.68 |
| ATOM | 1109 | 1HB | ASN | 70 | 6.330 | -0.934 | 8.035 | 1.00 | 0.87 |
| ATOM | 1110 | 2HB | ASN | 70 | 4.953 | 0.103 | 7.659 | 1.00 | 0.85 |
| ATOM | 1111 | 1HD2 | ASN | 70 | 8.423 | 0.967 | 8.108 | 1.00 | 1.81 |
| ATOM | 1112 | 2HD2 | ASN | 70 | 8.142 | 2.057 | 9.379 | 1.00 | 1.67 |
| ATOM | 1113 | N | TYR | 71 | 6.818 | -1.747 | 5.141 | 1.00 | 0.60 |
| ATOM | 1114 | CA | TYR | 71 | 7.529 | -2.950 | 4.629 | 1.00 | 0.62 |
| ATOM | 1115 | C | TYR | 71 | 8.618 | -2.519 | 3.646 | 1.00 | 0.66 |
| ATOM | 1116 | O | TYR | 71 | 9.677 | -3.110 | 3.577 | 1.00 | 0.74 |
| ATOM | 1117 | CB | TYR | 71 | 6.523 | -3.851 | 3.906 | 1.00 | 0.59 |
| ATOM | 1118 | CG | TYR | 71 | 6.898 | -5.299 | 4.100 | 1.00 | 0.61 |
| ATOM | 1119 | CD1 | TYR | 71 | 8.096 | -5.789 | 3.568 | 1.00 | 1.36 |
| ATOM | 1120 | CD2 | TYR | 71 | 6.046 | -6.153 | 4.811 | 1.00 | 1.33 |
| ATOM | 1121 | CE1 | TYR | 71 | 8.443 | -7.133 | 3.747 | 1.00 | 1.39 |
| ATOM | 1122 | CE2 | TYR | 71 | 6.393 | -7.497 | 4.990 | 1.00 | 1.38 |
| ATOM | 1123 | CZ | TYR | 71 | 7.592 | -7.987 | 4.459 | 1.00 | 0.77 |
| ATOM | 1124 | OH | TYR | 71 | 7.934 | -9.313 | 4.636 | 1.00 | 0.90 |
| ATOM | 1125 | HN | TYR | 71 | 5.870 | -1.621 | 4.930 | 1.00 | 0.57 |
| ATOM | 1126 | HA | TYR | 71 | 7.973 | -3.488 | 5.451 | 1.00 | 0.65 |
| ATOM | 1127 | 1HB | TYR | 71 | 6.526 | -3.618 | 2.851 | 1.00 | 0.61 |
| ATOM | 1128 | 2HB | TYR | 71 | 5.535 | -3.680 | 4.307 | 1.00 | 0.60 |
| ATOM | 1129 | HD1 | TYR | 71 | 8.751 | -5.130 | 3.018 | 1.00 | 2.21 |
| ATOM | 1130 | HD2 | TYR | 71 | 5.120 | -5.774 | 5.219 | 1.00 | 2.16 |
| ATOM | 1131 | HE1 | TYR | 71 | 9.368 | -7.512 | 3.337 | 1.00 | 2.24 |
| ATOM | 1132 | HE2 | TYR | 71 | 5.736 | -8.156 | 5.539 | 1.00 | 2.23 |
| ATOM | 1133 | HH | TYR | 71 | 8.247 | -9.653 | 3.794 | 1.00 | 0.96 |
| ATOM | 1134 | N | ILE | 72 | 8.361 | -1.496 | 2.878 | 1.00 | 0.64 |
| ATOM | 1135 | CA | ILE | 72 | 9.378 | -1.030 | 1.889 | 1.00 | 0.70 |
| ATOM | 1136 | C | ILE | 72 | 10.536 | -0.355 | 2.617 | 1.00 | 0.77 |
| ATOM | 1137 | O | ILE | 72 | 11.691 | -0.567 | 2.304 | 1.00 | 0.86 |
| ATOM | 1138 | CB | ILE | 72 | 8.753 | -0.013 | 0.930 | 1.00 | 0.67 |
| ATOM | 1139 | CG1 | ILE | 72 | 7.417 | -0.533 | 0.403 | 1.00 | 0.65 |
| ATOM | 1140 | CG2 | ILE | 72 | 9.699 | 0.228 | -0.249 | 1.00 | 0.76 |
| ATOM | 1141 | CD1 | ILE | 72 | 6.447 | 0.637 | 0.268 | 1.00 | 0.63 |
| ATOM | 1142 | HN | ILE | 72 | 7.496 | -1.039 | 2.947 | 1.00 | 0.61 |
| ATOM | 1143 | HA | ILE | 72 | 9.746 | -1.875 | 1.329 | 1.00 | 0.74 |
| ATOM | 1144 | HB | ILE | 72 | 8.594 | 0.919 | 1.454 | 1.00 | 0.65 |
| ATOM | 1145 | 1HG1 | ILE | 72 | 7.010 | -1.257 | 1.089 | 1.00 | 0.81 |
| ATOM | 1146 | 2HG1 | ILE | 72 | 7.566 | -0.991 | -0.563 | 1.00 | 0.80 |
| ATOM | 1147 | 1HG2 | ILE | 72 | 10.596 | 0.714 | 0.104 | 1.00 | 1.22 |
| ATOM | 1148 | 2HG2 | ILE | 72 | 9.211 | 0.859 | -0.978 | 1.00 | 1.24 |
| ATOM | 1149 | 3HG2 | ILE | 72 | 9.954 | -0.716 | -0.705 | 1.00 | 1.38 |
| ATOM | 1150 | 1HD1 | ILE | 72 | 5.439 | 0.287 | 0.424 | 1.00 | 1.17 |
| ATOM | 1151 | 2HD1 | ILE | 72 | 6.533 | 1.065 | -0.720 | 1.00 | 1.24 |
| ATOM | 1152 | 3HD1 | ILE | 72 | 6.686 | 1.389 | 1.007 | 1.00 | 1.22 |
| ATOM | 1153 | N | GLN | 73 | 10.235 | 0.467 | 3.579 | 1.00 | 0.76 |
| ATOM | 1154 | CA | GLN | 73 | 11.332 | 1.171 | 4.317 | 1.00 | 0.85 |
| ATOM | 1155 | C | GLN | 73 | 12.217 | 0.129 | 5.002 | 1.00 | 0.92 |

FIG. 5A-15

| | | | | | | | | |
|---|---|---|---|---|---|---|---|---|
| ATOM | 1156 | O | GLN | 73 | 13.399 | 0.333 | 5.193 | 1.00 | 1.03 |
| ATOM | 1157 | CB | GLN | 73 | 10.789 | 2.142 | 5.389 | 1.00 | 0.88 |
| ATOM | 1158 | CG | GLN | 73 | 9.338 | 2.558 | 5.107 | 1.00 | 1.08 |
| ATOM | 1159 | CD | GLN | 73 | 9.185 | 3.028 | 3.659 | 1.00 | 1.11 |
| ATOM | 1160 | OE1 | GLN | 73 | 10.158 | 3.203 | 2.953 | 1.00 | 2.07 |
| ATOM | 1161 | NE2 | GLN | 73 | 7.986 | 3.238 | 3.187 | 1.00 | 0.83 |
| ATOM | 1162 | HN | GLN | 73 | 9.295 | 0.622 | 3.803 | 1.00 | 0.71 |
| ATOM | 1163 | HA | GLN | 73 | 11.931 | 1.725 | 3.608 | 1.00 | 0.89 |
| ATOM | 1164 | 1HB | GLN | 73 | 11.411 | 3.025 | 5.409 | 1.00 | 1.16 |
| ATOM | 1165 | 2HB | GLN | 73 | 10.833 | 1.661 | 6.354 | 1.00 | 1.09 |
| ATOM | 1166 | 1HG | GLN | 73 | 9.061 | 3.362 | 5.773 | 1.00 | 1.61 |
| ATOM | 1167 | 2HG | GLN | 73 | 8.690 | 1.715 | 5.276 | 1.00 | 1.71 |
| ATOM | 1168 | 1HE2 | GLN | 73 | 7.203 | 3.095 | 3.760 | 1.00 | 1.17 |
| ATOM | 1169 | 2HE2 | GLN | 73 | 7.866 | 3.535 | 2.264 | 1.00 | 1.07 |
| ATOM | 1170 | N | ASN | 74 | 11.654 | -0.988 | 5.374 | 1.00 | 0.90 |
| ATOM | 1171 | CA | ASN | 74 | 12.463 | -2.044 | 6.046 | 1.00 | 1.01 |
| ATOM | 1172 | C | ASN | 74 | 13.479 | -2.616 | 5.054 | 1.00 | 1.06 |
| ATOM | 1173 | O | ASN | 74 | 14.494 | -3.163 | 5.438 | 1.00 | 1.18 |
| ATOM | 1174 | CB | ASN | 74 | 11.540 | -3.162 | 6.533 | 1.00 | 1.08 |
| ATOM | 1175 | CG | ASN | 74 | 11.703 | -3.336 | 8.044 | 1.00 | 1.31 |
| ATOM | 1176 | OD1 | ASN | 74 | 11.348 | -2.462 | 8.810 | 1.00 | 1.90 |
| ATOM | 1177 | ND2 | ASN | 74 | 12.230 | -4.436 | 8.509 | 1.00 | 1.80 |
| ATOM | 1178 | HN | ASN | 74 | 10.698 | -1.133 | 5.211 | 1.00 | 0.85 |
| ATOM | 1179 | HA | ASN | 74 | 12.985 | -1.615 | 6.888 | 1.00 | 1.07 |
| ATOM | 1180 | 1HB | ASN | 74 | 11.799 | -4.085 | 6.037 | 1.00 | 1.21 |
| ATOM | 1181 | 2HB | ASN | 74 | 10.515 | -2.906 | 6.308 | 1.00 | 1.26 |
| ATOM | 1182 | 1HD2 | ASN | 74 | 12.517 | -5.141 | 7.892 | 1.00 | 2.30 |
| ATOM | 1183 | 2HD2 | ASN | 74 | 12.338 | -4.556 | 9.476 | 1.00 | 2.08 |
| ATOM | 1184 | N | GLN | 75 | 13.216 | -2.493 | 3.782 | 1.00 | 1.08 |
| ATOM | 1185 | CA | GLN | 75 | 14.169 | -3.029 | 2.771 | 1.00 | 1.22 |
| ATOM | 1186 | C | GLN | 75 | 15.182 | -1.943 | 2.404 | 1.00 | 1.23 |
| ATOM | 1187 | O | GLN | 75 | 16.286 | -2.226 | 1.984 | 1.00 | 1.40 |
| ATOM | 1188 | CB | GLN | 75 | 13.399 | -3.456 | 1.520 | 1.00 | 1.31 |
| ATOM | 1189 | CG | GLN | 75 | 12.566 | -4.700 | 1.835 | 1.00 | 1.54 |
| ATOM | 1190 | CD | GLN | 75 | 13.222 | -5.927 | 1.200 | 1.00 | 1.98 |
| ATOM | 1191 | OE1 | GLN | 75 | 13.372 | -6.949 | 1.839 | 1.00 | 2.43 |
| ATOM | 1192 | NE2 | GLN | 75 | 13.622 | -5.869 | -0.041 | 1.00 | 2.55 |
| ATOM | 1193 | HN | GLN | 75 | 12.393 | -2.048 | 3.491 | 1.00 | 1.09 |
| ATOM | 1194 | HA | GLN | 75 | 14.689 | -3.881 | 3.183 | 1.00 | 1.35 |
| ATOM | 1195 | 1HB | GLN | 75 | 14.097 | -3.684 | 0.728 | 1.00 | 1.65 |
| ATOM | 1196 | 2HB | GLN | 75 | 12.747 | -2.654 | 1.207 | 1.00 | 1.73 |
| ATOM | 1197 | 1HG | GLN | 75 | 11.571 | -4.578 | 1.435 | 1.00 | 1.95 |
| ATOM | 1198 | 2HG | GLN | 75 | 12.511 | -4.834 | 2.906 | 1.00 | 1.75 |
| ATOM | 1199 | 1HE2 | GLN | 75 | 13.500 | -5.044 | -0.557 | 1.00 | 2.92 |
| ATOM | 1200 | 2HE2 | GLN | 75 | 14.042 | -6.650 | -0.457 | 1.00 | 2.94 |
| ATOM | 1201 | N | GLN | 76 | 14.815 | -0.700 | 2.563 | 1.00 | 1.14 |
| ATOM | 1202 | CA | GLN | 76 | 15.757 | 0.403 | 2.227 | 1.00 | 1.25 |
| ATOM | 1203 | C | GLN | 76 | 16.763 | 0.577 | 3.366 | 1.00 | 1.67 |
| ATOM | 1204 | O | GLN | 76 | 16.522 | 0.032 | 4.431 | 1.00 | 2.01 |
| ATOM | 1205 | CB | GLN | 76 | 14.974 | 1.704 | 2.037 | 1.00 | 1.23 |
| ATOM | 1206 | CG | GLN | 76 | 14.091 | 1.590 | 0.793 | 1.00 | 1.15 |
| ATOM | 1207 | CD | GLN | 76 | 14.345 | 2.786 | -0.126 | 1.00 | 1.58 |
| ATOM | 1208 | OE1 | GLN | 76 | 14.865 | 3.797 | 0.304 | 1.00 | 2.23 |
| ATOM | 1209 | NE2 | GLN | 76 | 14.000 | 2.713 | -1.382 | 1.00 | 1.97 |
| ATOM | 1210 | OXT | GLN | 76 | 17.757 | 1.252 | 3.155 | 1.00 | 2.36 |
| ATOM | 1211 | HN | GLN | 76 | 13.919 | -0.494 | 2.905 | 1.00 | 1.10 |
| ATOM | 1212 | HA | GLN | 76 | 16.283 | 0.163 | 1.315 | 1.00 | 1.55 |
| ATOM | 1213 | 1HB | GLN | 76 | 15.664 | 2.525 | 1.912 | 1.00 | 1.74 |
| ATOM | 1214 | 2HB | GLN | 76 | 14.355 | 1.881 | 2.905 | 1.00 | 1.68 |
| ATOM | 1215 | 1HG | GLN | 76 | 13.052 | 1.580 | 1.088 | 1.00 | 1.43 |
| ATOM | 1216 | 2HG | GLN | 76 | 14.326 | 0.675 | 0.269 | 1.00 | 1.35 |
| ATOM | 1217 | 1HE2 | GLN | 76 | 13.582 | 1.897 | -1.728 | 1.00 | 2.28 |
| ATOM | 1218 | 2HE2 | GLN | 76 | 14.159 | 3.474 | -1.979 | 1.00 | 2.36 |

END

CRYSTALS OF AN ACYL CARRIER PROTEIN SYNTHASE/ACYL CARRIER PROTEIN COMPLEX

This application is a divisional of U.S. patent application Ser. No. 09/770,834, filed Jan. 25, 2001, now U.S. Pat. No. 6,684,162, which claims the benefit of U.S. Provisional Application No. 60/202,466 filed May 8, 2000, the contents of both of which are herewith incorporated by reference.

FIELD OF THE INVENTION

The present invention relates to the crystal structure of the ACPS/ACP complex, as well as the three-dimensional solution structure of *B. subtilis* ACP. These structures are critical for the design and selection of potent and selective agents which interact with ACPS and ACP, and particularly, the design of novel antibiotics.

BACKGROUND OF THE INVENTION

Acyl Carrier Proteins (ACPs) play important roles in a number of biosynthetic pathways that are dependent upon acyl group transfers [1]. They are most often associated with the biosynthesis of fatty acids [2,3], but they are also utilized in the synthesis of polyketide antibiotics [4,5], non-ribosomal peptides [6,7], and of intermediates used in the synthesis of vitamins such as the protein-bound coenzymes, lipoic acid [8] and biotin [9]. The ACP in each of these pathways is composed of 80–100 residues and is either an integrated domain in a larger multi-functional protein (Type I synthase complex) or is a structurally independent protein that is part of a non-aggregated multi-enzyme system (Type II synthase complex). Type I synthases are found in mammals, fungi and certain *Mycobacteria* while type II ACPs are utilized by plants and most bacteria. The *Escherichia coli* ACP for fatty acid synthesis has been over-expressed [10] and purified [11,12], and the solution structure has been solved by NMR spectroscopy [13]. The fact that these proteins are essential for the maturation of the organism has led to their investigation as targets for the development of new anti-microbial agents [14–18].

ACPs require post-translational modification for activity. They are converted from an inactive apo-form to an active holo-form by the transfer of the 4'-phosphopantetheinyl (P-pant) moiety of coenzyme A to a conserved serine on the ACP. The β-hydroxy side chain of the serine residue serves as a nucleophilic group attacking the pyrophosphate linkage of CoA. Evidence now suggests [19] that each synthase that is dependent upon P-pant attachment for activation has its own partner enzyme responsible for this attachment.

The post-translational modification of the ACP subunit in the fatty acid synthase is performed by holo-[acyl carrier protein] synthase (hereinafter defined as "ACPS"; Enzyme Commission No. 2.7.8.7). The best characterized member of the ACPS family is the *E. coli* ACPS [20]. The enzyme produces holo-ACP by transferring the P-pant moiety to Ser-36 of the *E. coli* apo-ACP (SEQ ID NO:15) in a magnesium dependent reaction [20] as follows:

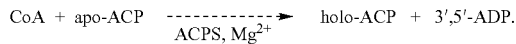

The over-expression and purification of the *E. coli* ACPS has been described [21] and this protein is classified as a member of a new enzyme superfamily, the phosphopantetheinyl transferases [19]. Based on the size of the proteins, the P-pant transferase superfamily can be roughly divided into two subgroups [22]. Enzymes responsible for modifying the peptidyl carrier protein subunits of non-ribosomal peptide synthetases are good examples for the first subgroup, which are usually ~230 amino acids in size. The structure of one of this subgroup enzymes, the surfactin synthetase activating enzyme Sfp, has been solved recently and it consists of a 2-fold intramolecular pseudosymmetry with the CoA binding site at the interface of the symmetrical fold [22]. ACPS and other enzymes transfering the P-pant group onto domains of the fatty acid synthases are usually smaller, about ~120 residues, and belong to the second subgroup of the P-pant transferase superfamily. The sequence homology between these two subgroups is rather low, about 12–22% between *E. coli* ACPS and *B. subtilis* Sfp, for example, although both have been shown to possess P-pant transferase activity. Alignment [19] of some of these proteins show that two regions, residues 5–13 and 54–65 (*E. coli* ACPS numbering), are highly conserved with five of the residues in these regions identical.

While numerous members of the phosphopantetheinyl transferase superfamily have been identified and sequenced, until the present invention, the crystal structure of ACPS complexed with halo-ACP, and the three dimensional structure of the ACPS/ACP active site has not been determined. Further, prior to the present invention, the solution structure of *B. subtilis* ACP had not been determined.

SUMMARY OF THE INVENTION

The present invention relates to a crystallized complex comprising an acyl carrier protein synthase (ACPS) and an acyl carrier protein (ACP) (hereinafter referred to as "ACPS-ACP complex"). The invention is further directed to the three dimensional structure of the ACPS-ACP complex, as determined using crystallographic analysis (with or without sedimentation analysis) of the ACPS-ACP complex. Particularly, the invention is directed to the three dimensional structure of the ACP binding site present in ACPS and other ACPS-like P-pant transferases, alone, and as complexed with ACP or other agents that interact with the ACP binding site of said transferases. In addition, the invention is directed to the ACPS binding site on ACP. Identification of the three dimensional structure of the ACP binding site on ACPS and the ACPS binding site on ACP will be valuable for the design of antibiotics and other agents that interfere with P-pant attachment, thereby preventing activation of corresponding carrier proteins.

The invention additionally provides a method for identifying an agent that interacts with any active site of an ACPS-ACP complex, comprising the steps of determining a putative active site of an ACPS-ACP complex from a three dimensional model of the ACPS-ACP complex, and performing various computer fitting analyses to identify an agent which interacts with the putative active site. Again, such agents may act as inhibitors or activators of ACPS-ACP complex activity, as determined by obtaining the identified agent, contacting the same with ACPS-ACP complex, and measuring the agent's effect on ACPS-ACP complex activity.

In addition, the invention provides a solution comprising *B. subtilis* ACP having a three dimensional structure defined by the structural coordinates of FIGS. 5 and 5A-1 to 5A-15, ± a root mean square deviation from the backbone atoms of said amino acids of not more than 1.5 Å. Also provided by the invention is any active site of *B. subtilis* ACP that is defined by the structural coordinates of FIGS. 5 and 5A-1 to 5A-15, ± a root mean square deviation from the backbone atoms of said amino acids of not more than 1.5 Å. Further, the present invention provides a method for identifying an agent that interacts with any active site of *B. subtilis* ACP, comprising the steps of determining a putative active site of ACP from a three dimensional model of the ACP, and performing various computer fitting analyses to identify an agent which interacts with the putative active site. Again, such agents may act as inhibitors or activators of ACP activity, as determined by obtaining the identified agent, contacting the same with ACP, and measuring the agent's effect on ACP activity.

Yet another aspect of the present invention is a method for identifying an activator or inhibitor of any molecule or molecular complex which comprises an ACP binding site, including any member of the ACPS-like P-pant transferases, comprising the steps of generating a three dimensional model of said molecule or molecular complex using the relative structural coordinates according to FIGS. 3 and 3A-1 to 3A-79 of residues Arg14, Met18, Arg21, Gln22, Arg24, Phe25, Arg28, Phe54, Glu58, Ile68, Gly69, Ala70, Ser73 and Phe74 from a first monomer of ACPS (SEQ ID NO:2), and residue Arg45 from a second monomer of ACPS (SEQ ID NO:2), or additionally, of residues Asp8, Ile9, Thr10, Glu11, Leu12, Ile15, Ala16, Ser17, Ala19, Gly20, Ala23, Ala26, Glu27, Ile29, Ala51, Lys57, Ser61, Lys62, Thr66, Gly67, Gln71, Leu72, Gln75, Asp76, Ile77 and Lys93 from the first monomer of ACPS (SEQ ID NO:2) and residues Leu41, Ser42, Lys44, Glu48, Gln83, Asn84, His105, Thr106 and Ala107 from the second monomer of ACPS (SEQ ID NO:2), in each case ± a root mean square deviation from the backbone atoms of said amino acids of not more than 1.5 Å, and then selecting or designing a candidate activator or inhibitor that interacts with said molecule or molecular complex using computer fitting analyses of interactions between the three dimensional model of the molecule or molecular complex and the candidate activator or inhibitor. The effect of the candidate activator or inhibitor may be evaluated by obtaining the candidate activator or inhibitor, contacting the same with the molecule or molecular complex, and measuring the effect of the candidate activator or inhibitor on molecular or molecular complex activity.

In addition, the present invention provides a method for identifying an activator or inhibitor of any molecule or molecular complex which comprises an ACPS binding site, comprising the steps of generating a three dimensional model of said molecule or molecular complex comprising an ACPS binding site using the relative structural coordinates according to FIGS. 3 and 3A-1 to 3A-79 or FIGS. 5 and 5A-1 to 5A-15 of residues Arg14, Lys29, Asp35, Ser36, Leu37, Asp38, Val40, Glu41, Val43, Met44, Glu47, Asp48, Ile54, Ser55, Asp56, Glu57 and Glu60, or additionally, of residues Asp13, Leu15, Phe28, Glu30, Asp31, Leu32, Gly33, Ala34, Val39, Leu42, Glu45, Leu46, Glu49, Met52, Glu53, Asp58, Ala59, and Lys61, according to the sequence set forth in SEQ ID NO:1, in each case ± a root mean square deviation from the backbone atoms of said amino acids of not more than 1.5 Å, and then selecting or designing a candidate activator or inhibitor that interacts with said molecule or molecular complex using computer fitting analyses of interactions between the three dimensional model of the molecule or molecular complex and the candidate activator or inhibitor. The effect of the candidate activator or inhibitor may be evaluated by obtaining the candidate activator or inhibitor, contacting the same with the molecule or molecular complex, and measuring the effect of the candidate activator or inhibitor on molecular or molecular complex activity. Also provided by the present invention are the activators or inhibitors selected or designed using the above-noted methods.

Still further, the present invention is directed to a method of determining the three dimensional structure of a molecule or molecular complex whose structure is unknown, comprising the steps of first obtaining crystals of the molecule or molecular complex whose structure is unknown, and then generating X-ray diffraction data from the crystallized molecule or molecular complex. The X-ray diffraction data from the molecule or molecular complex is compared with the known three dimensional structures determined from the ACPS-ACP crystals of the present invention, and molecular replacement analysis is used to conform the known three dimensional structures to the X-ray diffraction data from the crystallized molecule or molecular complex.

In addition, the present invention provides the ACP active site of an ACPS-like P-pant transferase, including, but not limited to, an ACPS, comprising the structural coordinates according to FIGS. 3 and 3A-1 to 3A-79 of residues Arg14, Met18, Arg21, Gln22, Arg24, Phe25, Arg28, Phe54, Glu58, Ile68, Gly69, Ala70, Ser73 and Phe74 from a first monomer of ACPS (SEQ ID NO:2), and residue Arg45 from a second monomer of ACPS (SEQ ID NO:2), in each case ± a root mean square deviation from the backbone atoms of said amino acids of not more than 1.5 Å. In another embodiment, the active site may include, in addition to the structural coordinates above, the relative the structural coordinates according to FIGS. 3 and 3A-1 to 3A-79 of residues Asp8, Ile9, Thr10, Glu11, Leu12, Ile15, Ala16, Ser17, Ala19, Gly20, Ala23, Ala26, Glu27, Ile29, Ala51, Lys57, Ser61, Lys62, Thr66, Gly67, Gln71, Leu72, Gln75, Asp76, Ile77 and Lys93 from one monomer of ACPS (SEQ ID NO:2) and residues Leu41, Ser42, Lys44, Glu48, Gln83, Asn84, His115, Thr106 and Ala107 from a second monomer of ACPS (SEQ ID NO:2), in each case ± a root mean square deviation from the backbone atoms of said amino acids of not more than 1.5 Å.

Finally, the present invention provides the ACPS active site of ACP (SEQ ID NO:1), comprising the structural coordinates according to FIGS. 3 and 3A-1 to 3A-79 or FIGS. 5 and 5A-1 to 5A-15 of residues Arg14, Lys29, Asp35, Ser36, Leu37, Asp38, Val40, Glu41, Val43, Met44, Glu47, Asp48, Ile54, Ser55, Asp56, Glu57 and Glu60, in each case ± a root mean square deviation from the backbone atoms of said amino acids of not more than 1.5 Å. In another embodiment, the active site may include, in addition to the structural coordinates above, the relative structural coordinates according to FIGS. 3 and 3A-1 to 3A-79 or FIGS. 5 and 5A-1 to 5A-15 of residues Asp13, Leu15, Phe28, Glu30, Asp31, Leu32, Gly33, Ala34, Val39, Leu42, Glu45, Leu46, Glu49, Met52, Glu53, Asp58, Ala59, and Lys61 according to the sequence set forth in SEQ ID NO:1, ± a root mean square deviation from the backbone atoms of said amino acids of not more than 1.5 Å.

BRIEF DESCRIPTION OF THE FIGURES

FIG. 1 depicts the amino acid sequences for the forms of ACP (SEQ ID NO:1) and ACPS (SEQ ID NO:2) used in the growth of ACP/ACPS complex crystals.

FIG. 2 illustrates the alignment of amino acid sequences for twelve members of the ACPS family, including the consensus sequence. Depicted are amino acid sequences for *Aquifex* (SEQ ID NO:3), *Chlamydophila* (SEQ ID NO:4), Helicobacter (SEQ ID NO:5), Staphylococcus (SEQ ID NO:6), Thermotoga (SEQ ID NO:7), Escherichia (SEQ ID NO:8), Rickettsia (SEQ ID NO:9), Streptomyces (SEQ ID NO:10), Treponema (SEQ ID NO:11), Bacillus (SEQ ID NO:12), Bradyrhizobium (SEQ ID NO:13), and Mycobacterium (SEQ ID NO:14).

FIGS. 3 and 3A-1 to 3A-79 provide the atomic structural coordinates for ACPS and ACP as derived by X-ray diffraction of an ACPS-ACP crystal. "Atom type" refers to the atom whose coordinates are being measured. "Residue" refers to the type of residue of which each measured atom is a part—i.e., amino acid, cofactor, ligand or solvent. The "x, y and z" coordinates indicate the Cartesian coordinates of each measured atom's location in the unit cell (Å). "Occ" indicates the occupancy factor. "B" indicates the "B-value", which is a measure of how mobile the atom is in the atomic structure ($Å^2$). "MOL" indicates the segment identification used to uniquely identify each molecule. Under "MOL", "A1", "B1" and "C1" refers to each molecule of ACPS (SEQ ID NO:2), "AP1", "AP2" and "AP3" refers to each molecule of ACP (SEQ ID NO:1), and "W" refers to water molecules.

FIG. 4 represents the sequence alignment of B. subtilis ACP (SEQ ID NO:1), E. coli ACP (SEQ ID NO:15), and Streptomyces coelicolor A3(2) ACP (SEQ ID NO:16).

FIGS. 5 and 5A-1 to 5A-15 provide the atomic structural coordinates for the restrained minimized mean structure of B. subtilis ACP (SEQ ID NO:1) as derived by NMR spectroscopy. "Atom type" refers to the atom whose coordinates are being measured. "Residue" refers to the type of residue of which each measured atom is a part—i.e., amino acid, cofactor, ligand or solvent. The "x, y and z" coordinates indicate the Cartesian coordinates of each measured atom's location (Å). The last column indicates the temperature factor field, representing the rms deviation of the 22 individual NMR structures about the restrained minimized mean structure. All non-protein atoms are listed as HETATM instead of atoms using PDB conventions.

DETAILED DESCRIPTION OF THE INVENTION

As used herein, the following terms and phrases shall have the meanings set forth below:

"ACPS" includes acyl carrier protein synthases as well as "ACPS-like" P-pant transferases. Acyl carrier protein synthases produce a holo-fatty acid synthase ACP by transferring the P-pant moiety to Ser-36 (or equivalent Serine) of an apo-fatty acid synthase ACP in a magnesium dependent reaction. "ACPS-like" P-pant transferases are those enzymes having P-pant transferase activity (i.e., that transfer the 4'-phosphopantetheinyl moiety of CoA to a conserved serine on the corresponding target molecule) which form homodimers and activate the ACP domains or subunits of fatty acid synthases, polyketide synthases or other enzymes.

As used herein, "ACP" is the carrier of fatty acids during fatty acid biosynthesis, is responsible for acyl group activation and includes a 4'phosphopantetheine (4'-PP) prosthetic group in which the 4'-PP moiety is attached through a phosphodiester linkage to a specific conserved serine residue. "ACP" also includes an active (holo) and inactive (apo) form where activation of ACP is mediated by Holo-acyl carier protein synthase (ACPS), and is preferably the active (holo) form.

Unless otherwise indicated, "protein" shall include a protein, protein domain, polypeptide or peptide.

"Structural coordinates" are the Cartesian coordinates corresponding to an atom's spatial relationship to other atoms in a molecule or molecular complex. Structural coordinates may be obtained using x-ray crystallography techniques or NMR techniques, or may be derived using molecular replacement analysis or homology modeling. Various software programs allow for the graphical representation of a set of structural coordinates to obtain a three dimensional representation of a molecule or molecular complex. The structural coordinates of the present invention may be modified from the original sets provided in FIGS. 3 and 3A-1 to 3A-79 or FIGS. 5 and 5A-1 to 5A-15 by mathematical manipulation, such as by inversion or integer additions or subtractions. As such, it is recognized that the structural coordinates of the present invention are relative, and are in no way specifically limited by the actual x, y, z coordinates of FIGS. 3 and 3A-1 to 3A-79 and FIGS. 5 and 5A-1 to 5A-15.

An "agent" shall include a protein, polypeptide, peptide, nucleic acid, including DNA or RNA, molecule, compound, antibiotic or drug.

"Root mean square deviation" is the square root of the arithmetic mean of the squares of the deviations from the mean, and is a way of expressing deviation or variation from the structural coordinates of ACPS and ACP described herein. The present invention includes all embodiments comprising conservative substitutions of the note amino acid residues resulting in same structural coordinates within the stated root mean square deviation.

It will be obvious to the skilled practitioner that the numbering of the amino acid residues in the various isoforms of ACPS, other ACPS-like P-pant transferases and ACP may be different than that set forth herein or may contain certain conservative amino acid substitutions that yield the same three dimensional structures as those defined in FIGS. 3 and 3A-1 to 3A-79 and FIGS. 5 and 5A-1 to 5A-15. Corresponding amino acids and conservative substitutions in other isoforms or analogues are easily identified by visual inspection of the relevant amino acid sequences or by using commercially available homology software programs (e.g., MODELLAR, MSI, San Diego, Calif.).

"Conservative substitutions" are those amino acid substitutions which are functionally equivalent to the substituted amino acid residue, either by way of having similar polarity, steric arrangement, or by belonging to the same class as the substituted residue (e.g., hydrophobic, acidic or basic) and includes substitutions having an inconsequential effect on the three dimensional structure of the ACPS-ACP complex, and the solution structure of B. subtilis ACP, with respect to the use of said structures for the identification and design of agents which interact with ACPS and ACP, for molecular replacement analyses and/or for homology modeling.

As used herein, an "active site" refers to a region of a molecule or molecular complex that, as a result of its shape and charge potential, favorably interacts or associates with another agent (including, without limitation, a protein, polypeptide, peptide, nucleic acid, including DNA or RNA, molecule, compound, antibiotic or drug) via various covalent and/or non-covalent binding forces.

As such, the active site of the ACPS-ACP complex may include both the actual site of ACP binding with ACPS, as well as accessory binding sites adjacent or proximal to the actual site of ACP binding that nonetheless may affect ACPS, ACPS-ACP or ACP activity upon interaction or association with a particular agent, either by direct interference with the actual site of ACP binding or by indirectly affecting the steric conformation or charge potential of the ACPS molecule and thereby preventing or reducing ACP binding to ACPS at the actual site of ACP binding. As used herein, an active site of ACPS-ACP also includes ACPS or ACPS analog residues which exhibit observable NMR perturbations in the presence of a binding ligand, such as ACP. While such residues exhibiting observable NMR perturbations may not necessarily be in direct contact with or immediately proximate to ligand binding residues, they may be critical to ACPS residues for rational drug design protocols.

The active site of ACP includes a region of ACP that, as a result of its shape and charge potential, favorably interacts or associates with another agent (including, without limitation, a protein, polypeptide, peptide, nucleic acid, including DNA or RNA, molecule, compound, antibiotic or drug) via various covalent and/or non-covalent binding forces. Preferably, the active site on ACP is the site of interaction with ACPS.

The present invention is directed to a crystallized ACPS-ACP complex that effectively diffracts X-rays for the determination of the structural coordinates of the ACPS-ACP complex. As used herein, the proteins used in the ACPS-ACP crystal complex of the present invention includes any ACPS or ACP protein (i.e., as used herein, any protein, polypeptide or peptide), isolated from any source (including, but not limited to, a protein isolated from *Aquifex, Chlamydophila, Helicobacter, Staphylococcus, Thermotoga, Escherichia, Rickettsia, Streptomyces, Treponema, Bacillus, Bradyrhizobium*, and *Mycobacterium*). In a preferred embodiment of the invention, ACPS and ACP are both cloned and isolated from *B. subtilis*, and overexpressed in a commercially available *E. coli* system.

The ACPS protein in the ACPS/ACP complex includes ACPS as well as proteins having ACPS-like P-pant transferase activity, including the consensus sequence shown in FIG. 2. More preferably, the ACPS protein or proteins having ACPS-like P-pant transferase activity, comprises the relative structural coordinates according to FIGS. 3 and 3A-1 to 3A-79 for the residues Arg14, Met18, Arg21, Gln22, Arg24, Phe25, Arg28, Arg45, Phe54, Glu58, Ile68, Gly69, Ala70, Ser73 and Phe74, or conservative substitutions thereof, and additionally, the residues Asp8, Ile9, Thr10, Glu11, Leu12, Ile15, Ala16, Ser17, Ala19, Gly20, Ala23, Ala26, Glu27, Ile29, Leu41, Ser42, Ala44, Glu48, Ala51, Lys57, Ser61, Lys62, Thr66, Gly67, Gln71, Leu72, Gln75, Asp76, Ile77, Gln83, Asn84, Lys93, His105, Thr106 and Ala107, or conservative substitutions thereof. The amino acid residues correspond to the sequence set forth in SEQ ID NO:2. More particularly, the ACPS protein or proteins having ACPS-like P-pant transferase activity include an ACP binding site defined using the relative structural coordinates according to FIGS. 3 and 3A-1 to 3A-79 of residues Arg14, Met18, Arg21, Gln22, Arg24, Phe25, Arg28, Phe54, Glu58, Ile68, Gly69, Ala70, Ser73 and Phe74 from a first monomer of ACPS (SEQ ID NO:2), and residue Arg45 from a second monomer of ACPS (SEQ ID NO:2), or additionally including the relative structural coordinates of residues Asp8, Ile9, Thr10, Glu11, Leu12, Ile15, Ala16, Ser17, Ala19, Gly20, Ala23, Ala26, Glu27, Ile29, Ala51, Lys57, Ser61, Lys62, Thr66, Gly67, Gln71, Leu72, Gln75, Asp76, Ile77 and Lys93 from the first monomer of ACPS (SEQ ID NO:2) and residues Leu41, Ser42, Ala44, Glu48, Gln83, Asn84, His105, Thr106 and Ala107 from the second monomer of ACPS (SEQ ID NO:2). In each case, the ± a root mean square deviation from the backbone atoms of the amino acids is not more than 1.5 Å, more preferably not more than 1.0 Å, and most preferably, not more than 0.5 Å.

The ACP protein in the ACPS/ACP complex includes ACP and proteins having ACP activity, and preferably comprises the relative structural coordinates accordingly to FIGS. 3 and 3A-1 to 3A-79 or FIGS. 5 and 5A-1 to 5A-15 for the residues Arg14, Lys29, Asp35, Ser36, Leu37, Asp38, Val40, Glu41, Val43, Met44, Glu47, Asp48, Ile54, Ser55, Asp56, Glu57 and Glu60, or conservative substitutions thereof, and additionally, the residues Asp13, Leu15, Phe28, Lys29, Glu30, Asp31, Leu32, Gly33, Ala34, Asp35, Ser36, Leu37, Asp38, Val39, Leu42, Glu45, Leu46, Glu49, Met52, Glu53, Asp58, Ala59 and Lys61, or conservative substitutions thereof, in each case ± a root mean square deviation from the backbone atoms of said amino acids of not more than 1.5 Å, or more preferably not more than 1.0 Å, or most preferably, not more than 0.5 Å. The amino acid residues correspond to the sequence set forth in SEQ ID NO:1.

The crystals of the present invention may take a wide variety of forms, all of which are included in the present invention. However, in a preferred embodiment of the present invention, the ACPS-ACP crystallized complex is characterized as being in rod-shape form with space group $C222_1$, and having unit cell parameters of a=78.46 Å, b=122.03 Å and c=136.77 Å, and consists of three molecules of ACPS and three molecules of ACP in an asymmetric unit.

Once a crystal or crystal complex of the present invention is grown, X-ray diffraction data can be collected by a variety of means in order to obtain the atomic coordinates of the crystallized molecule or molecular complex. With the aid of specifically designed computer software, such crystallographic data can be used to generate a three dimensional structure of the molecule or molecular complex. Various methods used to generate and refine the three dimensional structure of a crystallized molecule or molecular structure are well known to those skilled in the art, and include, without limitation, multiwavelength anomalous dispersion (MAD), multiple isomorphous replacement, reciprocal space solvent flattening, molecular replacement, and single isomorphous replacement with anomalous scattering (SIRAS).

The present invention is also directed to an ACP active site of an ACPS-like P-pant transferase, including the active site of ACPS, and comprising the structural coordinates according to FIGS. 3 and 3A-1 to 3A-79 of residues Arg14, Met18, Arg21, Gln22, Arg24, Phe25, Arg28, Phe54, Glu58, Ile68, Gly69, Ala70, Ser73 and Phe74 from one monomer of ACPS (SEQ ID NO:2), and residue Arg45 from a second monomer of ACPS (SEQ ID NO:2), in each case ± a root mean square deviation from the backbone atoms of said amino acids of not more than 1.5 Å, or more preferably not more than 1.0 Å, or most preferably, not more than 0.5 Å. Alternatively, the active site may include, in addition to the structural coordinates define above, the structural coordinates according to FIGS. 3 and 3A-1 to 3A-79 of residues Asp8, Ile9, Thr10, Glu11, Leu12, Ile15, Ala16, Ser17, Ala19, Gly20, Ala23, Ala26, Glu27, Ile29, Ala51, Lys57, Ser61, Lys62, Thr66, Gly67, Gln71, Leu72, Gln75, Asp76, Ile77 and Lys93 from the first monomer of ACPS (SEQ ID NO:2) and residues Leu41, Ser42, Lys44, Glu48, Gln83, Asn84, His105, Thr106 and Ala107 from the second monomer of ACPS (SEQ ID NO:2), in each case ± a root mean square deviation from the backbone atoms of said amino acids of not more than 1.5 Å, or more preferably not more than 1.0 Å, or most preferably, not more than 0.5 Å. Preferably, the ACP active site corresponds to the configuration of the ACPS molecule in its state of association or inactivation with an agent, and preferably, ACP.

In addition, the present invention provides the ACPS active site of an ACP that comprises the structural coordinates according to FIGS. 3 and 3A-1 to 3A-79 or FIGS. 5 and 5A-1 to 5A-15 of residues Arg14, Lys29, Asp35, Ser36, Leu37, Asp38, Val40, Glu41, Val43, Met44, Ser47, Asp48, Ile54, Ser55, Asp56, Glu57 and Glu60, ± a root mean square deviation from the backbone atoms of said amino acids of not more than 1.5 Å, or more preferably not more than 1.0 Å, or most preferably, not more than 0.5 Å. The amino acid residues are according to the sequence set forth in SEQ ID NO:1. Alternatively, the active site further includes, in addition to the coordinates defined above, the structural coordinates according to FIGS. 3 and 3A-1 to 3A-79 or FIGS. 5 and 5A-1 to 5A-15 of residues Asp13, Leu15, Phe28, Glu30, Asp31, Leu32, Gly33, Ala34, Val39, Leu42, Glu45, Leu46, Glu49, Met52, Glu53, Asp58, Ala59, and Lys61, ± a root mean square deviation from the backbone atoms of said amino acids of not more than 1.5 Å, or more preferably not more than 1.0 Å, or most preferably, not more than 0.5 Å. The amino acid residues are according to the sequence set forth in SEQ ID NO:1. Preferably, the ACPS active site corresponds to the configuration of the ACP molecule in its state of association or inactivation with an agent, and preferably, ACPS.

Another aspect of the present invention is directed to a method for identifying an agent that interacts with an active site of an ACPS-ACP complex, comprising the steps of determining an active site of the ACPS-ACP complex from a three dimensional model of the ACPS-ACP complex and performing computer fitting analyses to identify an agent which interacts with said active site. Computer fitting analyses utilize various computer software programs that evaluate the "fit" between the putative active site and the identified agent, by (a) generating a three dimensional model of the putative active site of a molecule or molecular complex using homology modeling or the atomic structural coordinates of the active site, and (b) determining the degree of association between the putative active site and the identified agent. Three dimensional models of the putative active site may be generated using any one of a number of methods known in the art, and include, but are not limited to, homology modeling as well as computer analysis of raw data generated using crystallographic or spectroscopy data. Computer programs used to generate such three dimensional models and/or perform the necessary fitting analyses include, but are not limited to: GRID (Oxford University, Oxford, UK), MCSS (Molecular Simulations, San Diego, Calif.), AUTODOCK (Scripps Research Institute, La Jolla, Calif.), DOCK (University of California, San Francisco, Calif.), Flo99 (Thistlesoft, Morris Township, N.J.), Ludi (Molecular Simulations, San Diego, Calif.), QUANTA (Molecular Simulations, San Diego, Calif.), Insight (Molecular Simulations, San Diego, Calif.), SYBYL (TRIPOS, Inc., St. Louis. Mo.) and LEAPFROG (TRIPOS, Inc., St. Louis, Mo.).

The effect of such an agent identified by computer fitting analyses on ACPS-ACP complex activity may be further evaluated by contacting the identified agent with the ACPS-ACP complex and measuring the effect of the agent on ACPS-ACP complex activity. Depending upon the action of the agent on the active site of ACPS-ACP complex, the agent may act either as an inhibitor or activator of ACPS-ACP complex activity. Enzymatic assays may be performed and the results analyzed to determine whether the agent is an inhibitor of ACPS-ACP complex activity (i.e., the agent may reduce or prevent binding affinity between ACPS and ACP, and thereby reduce the level or rate of ACPS-ACP activity compared to baseline), or an activator of ACPS-ACP activity (i.e., the agent may increase binding affinity between ACPS and ACP, and thereby increase the level or rate of ACPS activity compared to baseline). Further tests may be performed to evaluate the effect of the identified agent on bacterial or eukaryotic cell populations, wherein an inhibitor of ACPS-ACP activity inhibits cell viability or reproduction.

The present invention is not limited to identifying agents which interact with an active site of the ACPS-ACP complex, but also is directed to a method for identifying an activator or inhibitor of any molecule or molecular complex comprising an ACP binding site or an ACPS binding site. The candidate activator or inhibitor is selected or designed by performing computer fitting analyses of said candidate agent with the three dimensional model of the molecule or molecular complex comprising the active site. Once the candidate activator or inhibitor is obtained, it may be contacted with the molecule or molecular complex in order to measure the effect the candidate activator or inhibitor has on said molecule or molecular complex.

In this regard, a potential activator or inhibitor of a molecule or molecular complex comprising an ACP binding site, is obtained by (a) generating a three dimensional model of said molecule or molecular complex comprising an ACP binding site using the relative structural coordinates according to FIGS. 3 and 3A-1 to 3A-79 of residues Arg14, Met18, Arg21, Gln22, Arg24, Phe25, Arg28, Phe54, Glu58, Ile68, Gly69, Ala70, Ser73 and Phe74 from a first monomer of ACPS (SEQ ID NO:2), and residue Arg45 from a second monomer of ACPS (SEQ ID NO:2), and (b) selecting or designing a candidate activator or inhibitor by performing computer fitting analysis of the candidate activator or inhibitor with the three dimensional model generated in step (a). In another embodiment, the relative structural coordinates further include the relative structural coordinates according to FIGS. 3 and 3A-1 to 3A-79 of residues Asp8, Ile9, Thr10, Glu11, Leu12, Ile15, Ala16, Ser17, Ala19, Gly20, Ala23, Ala26, Glu27, Ile29, Ala51, Lys57, Ser61, Lys62, Thr66, Gly67, Gln71, Leu72, Gln75, Asp76, Ile77 and Lys93 from said first monomer of ACPS (SEQ ID NO:2) and residues Leu41, Ser42, Lys44, Glu48, Gln83, Asn84, His105, Thr106 and Ala107 from said second monomer of ACPS (SEQ ID NO:2). In each case, the ± a root mean square deviation from the backbone atoms of the amino acids is not more than 1.5 Å, preferably not more than 1.0 Å, and most preferably is not more than 0.5 Å.

A potential activator or inhibitor of a molecule or molecular complex comprising an ACPS binding site, may be obtained by (a) generating a three dimensional model of said molecule or molecular complex comprising an ACPS binding site using the relative structural coordinates according to FIGS. 3 and 3A-1 to 3A-79 or FIGS. 5 and 5A-1 to 5A-15 of residues Arg14, Lys29, Asp35, Ser36, Leu37, Asp38, Val40, Glu41, Val43, Met44, Glu47, Asp48, Ile54, Ser55, Asp56, Glu57 and Glu60, according to the sequence set forth in SEQ ID NO:1, and (b) selecting or designing a candidate activator or inhibitor by performing computer fitting analysis of the candidate activator or inhibitor with the three dimensional model generated in step (a). In another embodiment, the relative structural coordinates further include the relative structural coordinates according to FIGS. 3 and 3A-1 to 3A-79 or FIGS. 5 and 5A-1 to 5A-15 of residues Asp13, Leu15, Phe28, Glu30, Asp31, Leu32, Gly33, Ala34, Val39, Leu42, Glu45, Leu46, Glu49, Met52, Glu53, Asp58, Ala59, and Lys61 according to the sequence set forth in SEQ ID NO:1. In each case, the ± a root mean square deviation from the backbone atoms of the amino acids is not more than 1.5 Å, preferably not more than 1.0 Å, and most preferably is not more than 0.5 Å.

In addition, the invention provides a solution comprising *B. subtilis* ACP having a three dimensional structure defined by the structural coordinates of FIGS. 5 and 5A-1 to 5A-15, ± a root mean square deviation from the backbone atoms of said amino acids of not more than 1.5 Å, more preferably not more than 1.0 Å, and most preferably not more than 0.5 Å. Also provided by the invention is any active site of *B. subtilis* ACP that is defined by the structural coordinates of FIGS. 5 and 5A-1 to 5A-15, ± a root mean square deviation from the backbone atoms of said amino acids of not more than 1.5 Å, more preferably not more than 1.0 Å, and most preferably not more than 0.5 Å. In addition, the invention provides a method for identifying an agent that interacts with any active site of *B. subtilis* ACP, comprising the steps of determining a putative active site of ACP from a three dimensional model of the ACP, and performing various computer fitting analyses to identify an agent which interacts with the putative active site. Again, such agents may act as inhibitors or activators of ACP activity, as determined by obtaining the identified agent, contacting the same with ACP, and measuring the agent's effect on ACP activity. In the preferred embodiment, the three dimensional structure of *B. subtilis* ACP is defined by the relative structural coordinates of FIGS. 5 and 5A-1 to 5A-15, ± a root mean square deviation from the backbone atoms of said amino acids of not more than 1.5 Å, or more preferably not more than 1.0 Å, or most preferably, not more than 0.5 Å. The use of the NMR solution structure of ACP for the identification of inhibitor binding sites on ACP, for the determination of the solution structure of ACP-inhibitor complexes, and for inhibitor design, is described further below in Examples 3–5.

Various molecular analysis and rational drug design techniques are further disclosed in U.S. Pat. Nos. 5,834,228, 5,939,528 and 5,865,116, as well as in PCT Application No. PCT/US98/16879, published WO 99/09148, the contents of which are hereby incorporated by reference.

The present invention is also directed to the agents, activators or inhibitors identified using the foregoing methods. Such agents, activators or inhibitors may be a protein, polypeptide, peptide, nucleic acid, including DNA or RNA, molecule, compound, antibiotic or drug.

Finally, the present invention is further directed to a method for determining the three dimensional structure of a molecule or molecular complex whose structure is unknown, comprising the steps of obtaining crystals of the molecule or molecular complex whose structure is unknown and generating X-ray diffraction data from the crystallized molecule or molecular complex. The X-ray diffraction data from the molecule or molecular complex is then compared with the known three dimensional structure determined from the ACPS-ACP crystals of the present invention. Then, the known three dimensional structure determined from the crystals of the present invention is "conformed" using molecular replacement analysis to the X-ray diffraction data from the crystallized molecule or molecular complex. Alternatively, spectroscopic data or homology modeling may be used to generate a putative three dimensional structure for the molecule or molecular complex, and the putative structure is refined by conformation to the known three dimensional structure determined from the ACPS-ACP crystals of the present invention.

The present invention may be better understood by reference to the following non-limiting Examples. The following Examples are presented in order to more fully illustrate the preferred embodiments of the invention, and should in no way be construed as limiting the scope of the present invention.

EXAMPLE 1

Crystal Structure of ACPS/ACP Complex

1. Material and Methods

Crystallization of ACPS with ACP Purified ACP and ACPS were mixed at a 1:1.1 molar ratio and the mixture was loaded onto a gel filtration column. The resulting purified complex was dialyzed against a solution containing 50 mM Bis-Tris pH 6.4, 100 mM NaCl, 10 mM $MgCl_2$, and 10 mM DTT before concentrating the complex to ~10 mg/mL. Crystallization conditions for the ACP/ACPS complex were also determined using the sparse matrix screens available from both Hampton Research and Emerald Biostructures. Screens were set up with 2 μL drops at both 18° C. and 4° C. Optimization of a crystalline hit (0.2M Potassium Formate, 20% PEG 3350) gave diffraction quality rod shaped crystals. Crystals could be obtained between 0.15M and 0.3M Potassium Formate and between 15 and 23% PEG 3350. The rate of growth seriously affected the quality of crystals with the optimal crystals being formed between 8 and 12 days after setup. The crystals were grown with a 1:2 drop ratio of protein to well solution at 18° C. These crystals belonged to space group $C222_1$ with unit cell parameters a=78.46, b=122.03, c=136.77 Å and contained three molecules of ACPS and three molecules of ACP in the asymmetric unit.

Data Collection. Data from the ACP/ACPS complex crystals were collected using a R-Axis IV mounted on a Rigaku RUH2R rotating anode operating at 5 kW from a single crystal, cooled to −180° C. The data to 2.3 Å were collected for the ACP/ACPS complex crystal using one-degree oscillations. The data were processed using DENZO and Scalepack [23] and the statistics from refinement are given in Table 2.

Model Building and Refinement. The structure of the ACP/ACPS complex was solved by molecular replacement using the program AMORE[24], with the trimer of ACPS as found in the ACPS/CoA structure as the probe. Prior to refinement, 10% of the data were randomly selected and designated as a $R_{free}$ test set to monitor the progress of the refinement. The structure of the ACPS trimer was then rebuilt using the X-BUILD feature in Quanta utilizing a series of omit maps. During this rebuilding, extra density was found in each active site that sharpened after each cycle of rebuilding. When the ACPS molecules had been rebuilt, the NMR structure of the *B. subtilis* ACP was rotated into the density found in the active site. As a result of a large domain shift, a consequence of binding to ACPS, there were enough differences between the NMR structure and the X-Ray data that precluded using the NMR model as the starting point for refinement. Instead, the location of methionine 44 was noted from the NMR structure and the remainder of the ACP molecule was built into density using omit maps from that residue. Reference to the NMR structure as a source of secondary structure information allowed the structure of the three ACP molecules to be built into the electron density rapidly.

When roughly 80% of the ACP had been built into density, that ACP/ACPS model was then used as the initial model for refinement using the program CNS [25]. Following six cycles of refining and rebuilding the refinement converged with a model which contained 3 molecules of ACPS, 3 molecules of ACPS and 117 solvent molecules at an $R_{cryst}$ of 22.9% and $R_{free}$ of 28.0%. The refinement statistics are given in Table 3.

2. Results and Discussion

Needle-like crystals (0.1.times.0.1.times.0.5 mm) were grown using the hanging drop method from an equal molar solution of ACP and ACPS. These crystals belong to space group $C222_1$ with unit cell parameters a=78.46, b=122.03, c=136.77 Å and diffract to 2.3 Å using a R-Axis IV mounted on a Rigaku RUH2R rotating anode operating at 5 kW. These cell dimensions correspond to the asymmetric unit containing 3 molecules of ACPS and 3 molecules of ACP. The sequence of the ACP (SEQ ID NO:1) and ACPS (SEQ ID NO:2) used in obtaining these crystals is shown in FIG. 1. The phosphopantetheinyl group that is attached to the $O^\gamma$ of Ser-36 from ACP (SEQ ID NO:1) is not indicated in this figure.

The contacts between holo-ACP and ACPS are predominately hydrophilic in nature with almost all of the interactions occurring between helix α1 of ACPS and helix α2 of ACP. There are only two significant hydrophobic contacts and these both involve residues (Leu-37 and Met-44) from ACP (SEQ ID NO:1) protruding into hydrophobic pockets on ACP S. Leu-37 extends into a pocket formed by Met-18, Phe-25, Phe-54 and Ile-15 on ACP (SEQ ID NO:1) while Met-44 binds in a pocket formed by Phe-25 and the aliphatic portion of the side chains from Arg-28 and Gln-22. Table 1 details the hydrophilic interactions.

Examination of this structure suggests that a key residue in the binding of ACP to ACPS is Arg-14 from ACPS (SEQ ID NO:2). Arg-14 forms a salt bridge with the residue just before the reactive serine (Asp-35) of ACP (SEQ ID NO:1) and is involved in hydrogen bonding with Asp-38, two residues after the reactive serine. These interactions serve to position the ACP (SEQ ID NO:1) molecule so that one end of helix α2 from ACP (SEQ ID NO:1) is placed at the bottom of the active site and correctly orients Ser-36. As shown in FIG. 2, Arg-14 is conserved in all ACPS proteins except that from *Mycobacterium* in which it is an aspartic acid (SEQ ID NO:14). Another arginine, Arg-21, of ACPS (SEQ ID NO:2) forms a salt bridge with Glu-41 from ACP (SEQ ID NO:1). The other end of helix α2 is positioned by the interactions of Arg-24 and Gln-22 from ACPS (SEQ ID NO:2) with Asp-48 of ACP (SEQ ID NO:1). These interactions, along with the two hydrophobic "keys" described above, lock the ACP into place.

When the structure of ACPS/CoA and ACPS/ACP are superimposed (not shown), a loop consisting of residues 64 to 78 enlarges the active site by shifting 2 Å to accommodate helix α3 from ACP. Additionally, the dipole of the α2 helix of ACP is directed at the phosphate of the CoA that is to be transferred to ACP.

Since there is a significant rearrangement of ACP upon binding to ACPS and there are only limited interactions between the ACP and ACPS, it is not surprising that the B-values indicate the ACP molecules are very mobile. The average B of the main chain atoms of the three ACPS molecules is 40.1 Å³ while that of the three ACP molecules is 72.3 Å³.

TABLE 1

Hydrophilic Interactions between ACP and ACPS

| ACP Residue (SEQ ID NO:1) | ACPS Residue (SEQ ID NO:2) | Distance (Å) |
|---|---|---|
| Hydophilic | | |
| 9 LYS NZ | 308 GLU OE1 | 3.15* |
| 35 ASP OD1 | 214 ARG NH2 | 2.81 |
| 35 ASP OD2 | 214 ARG NH1 | 2.50 |
| 35 ASP OD2 | 214 ARG NH2 | 3.05 |
| 38 ASP OD1 | 214 ARG NH2 | 3.05 |
| 38 ASP OD2 | 214 ARG NH2 | 3.20 |
| 41 GLU GE1 | 221 ARG NH2 | 2.66 |
| 41 GLU OE2 | 221 ARG NE | 2.91 |
| 48 ASP OD1 | 224 ARG NH1 | 2.95 |
| 54 ILE O | 228 ARG NH2 | 2.60 |
| 56 ASP OD2 | 273 SER OG | 2.50 |
| 56 ASP OD2 | 274 PHE N | 2.85 |
| 60 GLU OE2 | 270 ALA N | 2.97 |

*denotes a symmetry related molecule

TABLE 2

Residues of ACPS from FIG. 1 that were modeled as alanine due to poor electron density beyond cβ for ACPS long chain residue

| Amino Acid | Chain A | Chain B | Chain C |
|---|---|---|---|
| Lys13 | Ala | Ala | Lys |
| Arg21 | Ala | Arg | Ala |
| Arg32 | Ala | Arg | Ala |
| Glu40 | Ala | Ala | Glu |
| Glu43 | Glu | Ala | Ala |
| Arg45 | Arg | Ala | Arg |
| Arg70 | Arg | Ala | Ala |
| Lys81 | Lys | Ala | Lys |
| Gln83 | Ala | Gln | Gln |
| Lys86 | Lys | Ala | Lys |
| Gln96 | Gln | Gln | Ala |
| Lys107 | Lys | Ala | Ala |

TABLE 3

Statistics for Data Collection, Phase Determination, and Refinement

|  | ACP/ACPS |
|---|---|
| Data Collection | |
| Wavelength (Å) | λ = 1.54 |
| resolution range (Å) | 15–2.3 |
| $R_{merge}{}^a$ | 5.7%(56.0) |
| % complete | 97.7(94.5) |
| total reflections | 270151 |
| unique reflections | 29694 |
| I/σ (I) | 26.6(3.5) |
| Model Refinement | |
| Maximum Resolution (Å) | 2.3 |
| $R_{work}{}^b$ (%) | 22.9 |
| $R_{free}$ (%) | 28.0 |
| <B value> (Å³) | 52.3 |
| R.m.s. Deviations from ideal geometry for | |
| Bonds (Å) | 0.0156 |
| Angles (°) | 1.80 |
| B values (Å²) | 2.054 |
| Non-hydrogen Protein Atoms | 6972 |
| Water Molecules | 117 |

TABLE 3-continued

Statistics for Data Collection, Phase Determination, and Refinement

| | ACP/ACPS |
|---|---|
| Ions | none |
| Other Molecules | none |

[a]$R_{merge} = ½I_h - <I_h> ½/I_h$, where $<I_h>$ is the average intensity over symmetry equivalents. Number in parentheses reflect statistics for the last shell
[b]$R_{work} = ½½F_{obs}½ - ½F_{calc}½/½F_{obs}½$, $R_{free}$ is equivalent to $R_{work}$, but calculated for a randomly chosen 5% (or 10%) of reflections omitted from the refinement process.

TABLE 4

Residues from ACPS (SEQ ID NO:2) which are within 4Å of ACP.

From one molecule of ACPS (SEQ ID NO:2):

Arg-14, Met-18, Arg-21, Gln-22, Arg-24, Phe-25, Arg-28, Phe-54, Glu-58, Ile-68, Gly-69, Ala-70, Ser-73, Phe-74

From a Second Molecule of ACPS (SEQ ID NO:2):

Arg-45

Residues from ACP (SEQ ID NO:1) which are within 4 Å of the ACPS dimer.

Arg-14, Lys-29, Asp-35, Ser-36, Leu-37, Asp-38, Val-40, Glu-41, Val-43, Met-44, Glu-47, Asp-48, Ile-54, Ser-55, Asp-56, Glu-57, Glu-60

TABLE 5

Residues from ACPS (SEQ ID NO:2) which are within 8Å of ACP.

From one molecule of ACPS (SEQ ID NO:2):

Asp-8, Ile-9, Thr-10, Glu-11, Leu-12, Arg-14, Ile-15, Ala-16, Ser-17, Met-18, Ala-19, Gly-20, Arg-21, Gln-22, Ala-23, Arg-24, Phe-25, Ala-26, Glu-27, Arg-28, Ile-29, Ala-51, Phe-54, Lys-57, Glu-58, Ser-61, Lys-62, Thr-66, Gly-67, Ile-68, Gly-69, Ala-70, Gln-71, Leu-72, Ser-73, Phe-74, Gln-75, Asp-76, Ile-77, Lys-93

From a Second Molecule of ACPS (SEQ ID NO:2):

Leu-41, Ser-42, Lys-44, Arg-45, Glu-48, Gln-83, Asn-84, His-105, Thr-106, Ala-107

Residues from ACP (SEQ ID NO:1) which are within 8 Å of the ACPS dimer.

Asp-13, Arg-14, Leu-15, Phe-28, Lys-29, Glu-30, Asp-31, Leu-32, Gly-33, Ala-34, Asp-35, Ser-36, Leu-37, Asp-38, Val-39, Val-40, Glu-41, Leu-42, Val-43, Met-44, Glu-45, Leu-46, Glu-47, Asp-48, Glu-49, Met-52, Glu-53, Ile-54, Ser-55, Asp-56, Glu-57, Asp-58, Ala-59, Glu-60, Lys-61

EXAMPLE 2

Determination of NMR Solution Structure of ACP

1. Material and Methods

B. subtilis ACP Sample Preparation. The uniform 15N and 13C-labeled B. subtilis ACP (SEQ ID NO:1) was cloned into pGEX-6P-1 vector and expressed in E. coli strain BL21DE3 (pLysS) similar to the conditions previously reported for expression of ACPS [26], except that 0.5 mM IPTG was used for induction. Purification was done using the following procedure. Typically, 20 grams of cell pellet expressing GST-ACP fusion protein was resuspended in 300 ml breaking buffer consisting of 50 mM Tris Cl (pH 8.0), 300 mM NaCl, 10 mM $MgCl_2$ and 2 mM of freshly prepared $MnCl_2$. Protease inhibitor tablets (Boehringer Mannheim GmbH, Mannheim, Germany), RNase H and DNase I (Sigma Chemical Co., St. Louis, Mo.) were added to the solution to prevent protease activity and to decrease viscosity of the solution. The cells were lysed by three passages through a Microfluidizer and the whole lysate was rocked at room temperature for one hour to enable the conversion of holo-ACP to apo-ACP by an endogenous ACP hydrolase from E. coli [27]. Once the incubation was finished, the lysate was centrifuged at 15,000 g for 20 minutes at 4° C. to remove the cell debris. Glutathione sepharose 4B resin (Amersham Pharmacia Biotech, Piscataway, N.J.) equilibrated with the same breaking buffer was added to the clear supernatant to a rough ratio of 1 ml resin slurry per 8 mg of GST fusion protein. The mixture was incubated at 4° C. for one hour by gentle rocking and centrifuged at 3,000 g for 10 minutes to remove excess supernatant prior to packing the resin into a suitable column. The column was then washed with 5 column volume of washing buffer containing 50 mM Tris Cl (pH 8.0), 10 mM $MgCl_2$, 5 mM DTT. The GST-ACP was eluted with wash buffer plus 60 mM freshly prepared reduced glutathione. The resulting GST-ACP solution was dialyzed overnight with Prescission Protease Cleavage buffer consisting of 50 mM Tris Cl (pH 8.0), 150 mM NaCl, 1 mM EDTA and 1 mM DTT. The fusion protein was cleaved with Prescission Protease (Amersham Pharmacia Biotech, Piscataway, N.J.) at room temperature for three hours at a ratio of 1U enzyme per 500 µg protein. The resulting protein mixture was loaded onto a MonoQ HR16/10 column (Amersham Pharmacia Biotech) equilibrated with 50 mM Tris Cl; pH 8.0, 150 mM NaCl and 10 mM $MgCl_2$.

NMR Data Collection. The NMR sample is a mixture of $^{15}N$-, $^{13}C$-double labeled Apo- and Holo-ACP in 50 mM Bis-Tris (pH 6.4), 100 mM NaCl, 10 mM $MgCl_2$ and 10 mM DTT with 0.02% $NaN_3$ in 5% $D_2O$/95% $H_2O$ solution. The protein concentration was <1 mM.

All spectra were recorded at 25° C. on Varian Unity[+] 600 spectrometer equipped with triple-resonance $^1H/^{13}C/^{15}N$ probe and an actively shielded z-gradient pulsed field accessories. 2D-$^1H$-$^{15}N$ HSQC and all triple-resonance 3D experiments were recorded with the enhanced-sensitivity pulsed field gradient approach [28]. This approach provides coherence transfer selection both to improve sensitivity and eliminate artifacts as well as for solvent suppression.

Data sets were typically processed and displayed on SGI workstation using the program packages NMRDraw and NMRPipe [29]. A skewed 600 phase-shifted sine-bell function and a single zero-filling was used in each of the all three dimensions prior to Fourier transformation. For triple-resonance 3D experiments, the time domain was extended by a factor of two using forward-backward linear prediction in the $^{15}N$ (t2) dimension and for constant-time $^1H$-$^{13}C$ correlation experiments, mirror image linear prediction was used prior to zero-filling to the double time-domain data points [30]. The programs PIPP and STAPP [31] were used for data analysis and semi-automatic assignments [30].

The complete assignments (>95%) of the $^1H$, $^{15}N$ and $^{13}C$ resonances were based on the following experiments: CBCA (CO)NNH, HNCACB, C(CC)TOCSY_NNH, H(CC) TOCSY_NNH, HAHB(CBCACO)NNH [28,32]. 2D $^{13}C$ (methyl)-1H HSQC and methyl relay experiments used for auxiliary methyl assignments of Ile, Val and Leu residues

[33–35]. Some ambiguous resonances were further confirmed by simultaneous $^{15}N/^{13}C$-edite-d NOESY [36].

B. subtilis ACP Structure Calculation. The NMR solution structure is based on interproton distance constraints converted from observed NOEs in both the $^{15}N$-edited NOESY [37,38] and simultaneous $^{15}N/^{13}C$-edited NOESY experiments [36]. The NOEs were classified as either strong (1.8–2.7 Å), medium (1.8–3.3 Å) or weak (1.8–5.5 Å) constraints. Φ and ψ torsion angle constraints were obtained from $^{15}N$, Hα, Cα and Cβ chemical shifts using the TALOS program [39]. Upper distance limits for distances involving methyl protons and non-stereospecifically assigned methylene protons were corrected appropriately for center averaging [40], and an additional 0.5 Å was added to upper distance limits for NOEs involving methyl protons [41,42].

The structures were calculated using the hybrid distance geometry-dynamical simulated annealing method of Nilges et al. (1988) [43] with minor modifications [44] using the program XPLOR [45], adapted to incorporate pseudopotential secondary $^{13}C\alpha/^{13}C\beta$ chemical shift restraints [46] and a conformational database potential [47,48]. The target function that is minimized during restrained minimization and simulated annealing comprises only quadratic harmonic terms for covalent geometry and secondary $^{13}C\alpha/^{13}C\beta$ chemical shift restraints, square-well quadratic potentials for the experimental distance and torsion angle restraints, and a quartic van der Waals term for non-bonded contacts. All peptide bonds were constrained to be planar and trans. There were no hydrogen-bonding, electrostatic or 6–12 Lennard-Jones empirical potential energy terms in the target function.

The structure of B. subtilis ACP was determined from a total of 1050 distance constraints comprising 337 intra-residue, 231 sequential, 188 medium, and 240 long range distance constraints, 54 hydrogen bond constraints and 92 torsion angles constraints comprised of 46 φ and 46 ψ dihedral constraints. The hydrogen bond constraints were based on the observation of slow exchanging NH protons in a $D_2O$ solution monitored by an $^1H$-$^{15}N$ HSQC spectrum.

The final ensemble of 22 structures contained no distance constraint violations greater than 0.2 Å and no torsion angle constraint violations greater than 2°. The NMR structures are well defined. This is evident by the atomic rms distribution of the 22 simulated annealing structures about the mean coordinate positions where the backbone and all atom rms is 0.45 Å and 0.93 Å, respectively. For residues only in secondary structure regions, the backbone and all atom rms is 0.35 Å and 0.84 Å, respectively. The B. subtilis ACP NMR structure is consistent with a good quality structure based on PROCHECK and Ramachandran analysis [49,50]. A Ramachandran plot of the minimized average structure shows a total of 83.1% of the residues are in the most favored region, 12.7% in the additional allowed, and 2.8% in the generously allowed regions with only one residue (Val 17) in a disallowed region (based on residues 6–81 of ACP). Val17 is located in a long loop between helices 1 and 2 that corresponds to a very flexible region of the protein. PROCHECK analysis indicates an overall G-factor of −0.23, a hydrogen bond energy of 0.9 and only 2 bad contacts.

2. Results and Discussion

Introduction. The biosynthesis of fatty acids consists of a series of reactions catalyzed by specific enzymatic activities [51]. The organization of the enzymatic activity is significantly different between eukaryotic cells and prokaryotic and plants cells. In eukaryotic cells large multifunctional enzymes exist with distinct domains associated with a particular function. Conversely, in prokaryotic and plant cells, the various enzymatic activities is associated with individual proteins that are loosely associated with each other. Acyl carrier protein (ACP) is a discrete small acid protein (9 KDa) in prokaryotic and plant cells that plays an essential role in fatty acid biosynthesis; whereas, ACP is a subunit of fatty acid synthetase (FAS) in animal tissue. ACP is the carrier of fatty acids during fatty acid biosynthesis in prokaryotic and plant cells and is responsible for acyl group activation [51–53].

A unique feature of ACP is the presence of the 4'-phosphopantetheine (P-pant) prosthetic group. The P-pant moiety is attached through a phosphodiester linkage to a specific conserved serine residue found in all ACPs. ACP exists in both an active (holo) and inactive (apo) form where activation of ACP is mediated by Holo-acyl carier protein synthase (ACPS). ACPS transfers the P-pant moiety from CoA to Ser-36 of Apo-ACP (SEQ ID NO:1) to produce holo-ACP and 3',5'-ADP in a $Mg^{+2}$-dependent reaction. During biosynthesis of a long-chain fatty acid, the fatty acid chain is attached to ACP via a thioester linkage to the terminal cysteamine thiol of the P-pant prosthetic group where the fatty acid chain is then elongated by the fatty acid synthetase system. A potential function of the P-pant prosthetic group is to act as a tether to transfer the growing fatty acid chains between the various enzymes or active sites in the FAS system.

ACP is a central component and plays a fundamental role in fatty acid and other biosynthetic pathways that require acyl transfer steps [54, 55–58]. The activation of ACP by ACPS is critical to this function where ACPS was identified as critical to the viability of E. coli [59,60]. Furthermore both ACP and ACPS are viable targets for a drug discovery program since the enzymes are essentially unique to prokaryotic cells. Since the activation of ACP is mediated by its interaction with ACPS, interfering with either the activity of ACPS or the binding interaction of ACPS with ACP may prove to be a valuable approach for developing novel antibiotics.

NMR Data. NMR data was collected on both the apo- and holo- forms of ACP. While the NMR spectra indicate distinct chemical shifts for the NH proton and amide-$^{15}N$ resonances for residues in the vicinity of the 4'-PP prosthetic group, the NMR data indicate that the structures for apo-ACP and holo-ACP are effectively identical.

Uniqueness of the B. subtilis ACP NMR Structure. Structures for E. coli and Streptomyces coelicolor A3(2) ACP were reported in the literature prior to initiation of our efforts on the structure determination of B. subtilis ACP [61–63]. Amino acid sequence alignments indicate that E. coli ACP is highly homologous to B. subtilis ACP where 53 of 76 residues are identical residue types (46) and identical residue classes (7). Comparison of Streptomyces coelicolor A3 (2) ACP with B. subtilis ACP indicate 38 of 76 residues are identical residue types (17) and identical residue classes (21). The overall sequence homology suggests that the three proteins should have a similar global fold (FIG. 4).

Comparison of the published structures for E. coli and Streptomyces coelicolor A3(2) ACP with B. subtilis ACP indicate similar secondary structure elements for the three proteins. The overall ACP structure consists of a four α-helical bundle where three helices are relatively long (6–15 residues) and one helix is short (0–6 residues). Despite the similarity in the secondary structure features the global fold for the three ACP structures is distinct. This is readily apparent by the superposition of the average-minimized three-dimensional structures for the three proteins (not shown). The atomic rms deviation of the Cα trace between E. coli and B. subtilis ACP is 2.32 Å. Similarly, the deviation of the Cα trace between *Streptomyces coelicolor* A3(2) and *B. subtilis* ACP is 2.31 Å. Although the previous structures of *E. coli* ACP and *Streptomyces coelicolor* A3(2) are of poor quality, the extremely large rms differences between *E. coli* ACP, *Streptomyces coelicolor* A3(2) and *B. subtilis* ACP indicate that each structure is relatively unique and that it would not be possible to predict the structure of *B. subtilis* ACP from the structures of *E. coli* ACP and *Streptomyces coelicolor* A3 (2).

The observed large rms deviations between the three ACPS structures are located mainly in the short α-helix 3 and the long loop region between α-helix 1 and 2. The short α-helix 3 is not present in some models of both *E. coli* and *Streptomyces coelicolor* A3(2) ACP and is not present in the average minimized *Streptomyces coelicolor* A3(2) ACP structure. Some of the observed differences between the *B. subtilis* ACP structure and both the *E. coli* and *Streptomyces coelicolor* A3(2) ACP structures result from unusual features of the *E. coli* and *Streptomyces coelicolor* A3(2) ACP structures. An example of an unusual feature is the presence of a large kink in α-helix 1 for *E. coli* ACP that results in this helix being extremely distorted. The observation of distinct structures for the three ACP proteins is unexpected given the reasonable sequence homology and the obvious fact that the proteins are functionally identical. A potential cause for the structural difference may be a function of the structure determination process instead of a difference that may be attributed to the origin of the proteins.

The available structural information for ACP has been obtained by NMR methodologies over a span of ~12 years. During this time-period NMR technology has been vastly improved resulting in the ability to obtain high-resolution structures of increasingly larger proteins [64–66]. As a result, the methodology applied to determining the *B. subtilis* ACP structure is inherently superior to the techniques used for the *E. coli* and *Streptomyces coelicolor* A3 (2) ACP structures. Invariably, the precision and accuracy of a protein structure determined by NMR is dependent on the number and reliability of the structural constraints interpreted from the NMR data [64,67]. The inherent reliability of the interpretation of the structural constraints is dependent on the number of available constraints. This relationship exists since a given structure has to be consistent with all the available constraints. So, the more constraints that are available for determining a structure the higher the likelihood that erroneous data will be identified by being inconsistent with the abundance of correct data. Additionally, the nature of the structural constraint is critical in relationship to the accuracy of the overall structure. Intra-residue constraints convey a localized structural effect usually contributing to the residues torsion angles whereas long-range inter-residue constraints will determine the overall fold of the protein. Therefore, a protein structure with an abundance of intra-residue constraints and a minimal number of long-range constraints will result in a relatively low-resolution structure.

The structures for *E. coli* and *Streptomyces coelicolor* A3(2) ACP were based on a minimal number of distance constraints, especially long-range distance constraints, relative to the *B. subtilis* ACP structure. *E. coli* ACP (SEQ ID NO:15) (77 residues) structure was based on a total of 478 distance constraints comprising 30H-bond distance constraints, 101 intra-residue distance constraints and 205 sequential, 87 short-range and 55 long-range inter-residue constraints. The average number of distance constraints was only 6.2 constraints per residue. Similarly, the *Streptomyces coelicolor* A3(2) ACP (SEQ ID NO:16) (86 residues) structure was based on a total of 747 distance constraints comprising 48H-bond distance constraints, 240 intra-residue constraints, 235 sequential, 131 short-range and 93 long-range distance constraints. The average number of distance constraints for *Streptomyces coelicolor* A3(2) ACP (SEQ ID NO:16) was only 8.7 constraints per residues. Conversely, our *B. subtilis* ACP (SEQ ID NO:1) (76 residues) structure is based on a total of 1050 distance constraints with an average of 13.8 constraints per residue. Similarly, the *B. subtilis* ACP structure is based on more $\phi$, $\psi$ dihedral angle constraints relative to both *E. coli* and *Streptomyces coelicolor* A3 (2) ACP. A total of $\phi$ and $\psi$, dihedral angle constraints were used for the *B. subtilis* ACP structure compared to 54 and 63 for the *E. coli* and *Streptomyces coelicolor* A3(2) ACP structures, respectively. In addition, the *B. subtilis* ACP structure was refined using both Cα/Cβ chemical shifts constraints and a conformational database potential which were not used for determining the *E. coli* and *Streptomyces coelicolor* A3 (2) ACP structures. In addition to the number of constraints, the quality of the ACP structures is also reflected by the rms difference between each structure in the ensemble relative to the average structure. Typically, a high resolution NMR structure exhibits a backbone rms of <0.5 Å [64]. As apparent in Table 6, the structures for *E. coli* and *Streptomyces coelicolor* A3(2) ACP have extremely high rms values suggestive of a low to poor quality structure, whereas, *B. subtilis* ACP conforms to a rms value consistent with a high quality structure.

TABLE 6

Atomic rms Differences (Å)[a]

|  | *E. coli* ACP | *Streptomyces coelicolor* A3(2) ACP[b] | *B. subtilis* ACP |
|---|---|---|---|
| All Residues |  |  |  |
| Backbone | 2.3 | 1.47 | 0.45 |
| All atoms | 3.3 | 1.84 | 0.93 |
| Secondary Structure |  |  |  |
| Backbone | N.D. | 1.01 | 0.35 |
| All atoms | N.D. | 1.45 | 0.84 |

[a]The NMR ensemble for the *E. coli*, *Streptomyces coelicolor* A3(2) and *B. subtilis* ACP structures consist of 7, 24 and 22; respectively.
[b]Only residues 5–86 were used for the rms.

There is additional evidence that indicates that the previous structural efforts related to ACP were problematic which may imply that the previous ACP structures may be inaccurate relative to the structure of *B. subtilis* ACP. The NMR structure for *E. coli* ACP was published in 1988, further modified in 1990 and finally released by the PDB in 1993 (PDB: 1ACP). In fact, two separate models for *E. coli* ACP were deposited in the PDB, where one model is described as "Not Energetically Ideal" and the authors suggest multiple conformers. Structural information for Spinach ACP and the nodulation protein NodF from *Rhizobium leguminosarum*, which shares homology with ACP were also published, but the NMR data was of too low a quality to determine and release a three dimensional structure [68,69]. These results clearly suggest an inherent technical difficulty that was encountered with the previous ACPs structures that was not a factor in the *B. subtilis* ACP structure.

The uniqueness of the three structures and more critically the inherent value and accuracy of the *B. subtilis* ACP was also apparent from the molecular replacement efforts for solving the X-ray structure of the *B. subtilis* ACP-ACPS complex. It was not possible to solve the X-ray structure of ACP in the *B. subtilis* ACP-ACPS complex using the *E. coli* ACP structure. A solution to the X-ray structure of ACP in the *B. subtilis* ACP-ACPS complex was only obtained when the NMR *B. subtilis* ACP structure was used as part of a molecular replacement approach.

EXAMPLE 3

Identification of Inhibitor Binding Sites on ACP

Inhibitors of the ACPS conversion of apo-ACP to holo-ACP were analyzed for direct binding to either ACP or ACPS by NMR. Inhibitor binding to ACP was monitored by chemical shift perturbations in a 2D $^1$H-$^{15}$N HSQC spectra. The observation of chemical shift perturbations in a 2D $^1$H-$^{15}$N HSQC spectra indicate both an interaction between ACP and the inhibitor and the location of the inhibitor binding site. The NMR assignments for free ACP was utilized to identify which residues have changed in the ACP-inhibitor complex. Further identification of the binding site was obtained by superimposing the perturbed residues onto the NMR structure of ACP. All of the residues that experience chemical shift changes in the presence of the inhibitor occur on a loop region corresponding to residues 53–56. This loop is spatially proximal to the conserved serine (S36) that is attached through a phosphodiester linkage to the 4'phosphopantetheine (P-pant) prosthetic group. The identification of the location of the P-pant prosthetic group was determined by chemical shift differences between the apo- and holo- forms of ACP. The proximal location of the potential inhibitor-binding site with the P-pant binding site suggests two possible mechanisms for inhibition of the ACP-ACPS activity. The activity of the inhibitor could be attributed to disruption of the binding of ACP with ACPS or it may sterically prevent the addition of the P-pant prosthetic group to ACP from CoA.

Specificity for the inhibitor to ACP is also monitored by its ability to bind ACPS. Inhibitor binding to ACPS was monitored by line-width changes in one-dimensional $^1$H titration studies. An effect of the large molecular-weight difference between ACPS and a small molecular inhibitor is the corresponding difference in the observable NMR linewidths. If the small molecule binds ACPS, it will demonstrate an apparent molecular weight similar to ACPS resulting in a dramatic increase in the NMR line-widths for the small molecule. Inhibitors identified to affect the ACP-ACPS activity have been shown to bind either ACP or ACPS.

EXAMPLE 4

Use of the A CP NMR Structure to Determine the Solution Structure of ACP-Inhibitor Complexes When an appropriate ACP inhibitor has been identified, a structure for the ACP complexed to the inhibitor may be determined from the following procedure.

NMR Data Collection. NMR sample preparation and data collection and processing were as described in Example 2, with the addition of the inhibitor in either a molar excess or a 1:1 molar ratio with ACP.

NMR Assignments. The assignments of the $^1$H, $^{15}$N, and $^{13}$C resonances of ACP in the ACP-inhibitor complex are based on a minimal set of experiments: 2D $^1$H-$^{15}$N HSQC, 3D $^{15}$N-edited NOESY [37,38], CBCA(CO)NH [30], C(CO)NH [71], HC(CO)NH, [71], HNHA [72] and HNCA [73].

The nearly complete resonance assignments for ACP provided the starting point for the assignments of ACP in the new inhibitor complex. Three important observations facilitated these assignments and provided a simple "boot-strap" approach using a minimal set of NMR experiments. First, as apparent by the chemical shift perturbations in a 2D $^1$H-$^{15}$N HSQC spectra, >90% of the ACP residues are unperturbed by the presence of the new inhibitor. In fact, for inhibitors that bind ACP in a similar manner the resonance assignments for ACP in the complex will be very comparable and greatly facilitate the assignment process. This indicates that the majority of the ACP structure is unaffected and that only residues in close proximity to the new inhibitor may incur a significant chemical shift change. Therefore, the backbone assignments of residues in the vicinity of the inhibitor may be obtained by following sequential NOE connectivities in the 3D $^{15}$N-edited NOESY spectra by starting with unaffected residues sequential to perturbed residues.

Second, while significant $^1$H and $^{15}$N chemical shift perturbations occur for residues in the vicinity of the inhibitor, the general NOE pattern may be intact. Simple comparison of the 3D $^{15}$N-edited NOESY spectra of ACP and the new complex may readily identify the sequential and intra-residue NOEs in the ACP:Inhibitor spectra. This provides a straight-forward approach to side-chain $^1$H assignments. Third, $^{13}$C chemical shifts generally do not incur any significant chemical shift perturbations even for residues in close proximity to the new inhibitor.

The resonance assignments and bound conformation of the inhibitor in ACP-inhibitor complex are based on the 2D $^{12}$C/$^{12}$C-filtered NOESY [74,75], 2D $^{12}$C/$^{12}$C-filtered TOCSY [74,75] and $^{12}$C/$^{12}$C-filtered COSY experiments [76]. The ACP-inhibitor NMR sample is composed of $^{13}$C/$^{15}$N labeled ACP and unlabeled inhibitor. Thus, traditional 2D-NOESY, COSY and TOCSY spectra of the inhibitor in the presence of ACP were determined from 2D $^{12}$C-filtering experiments [74–76] where only crosspeaks between protons attached to $^{12}$C carbons are observed. This efficiently filters all protein resonances and allows for the straight-forward analysis of the inhibitor spectrum.

The ACP-inhibitor structure is based on the following series of spectra: HNHA [72], HNHB [77], 3D long-range $^{13}$C-$^{13}$C correlation [78], coupled CT-HCACO [79,80], HACAHB-COSY [81], 3D $^{15}$N-[37,38] and $^{13}$C-edited NOESY [82,83], 3D $^{13}$C-edited/$^{12}$C-filtered NOESY [84], 2D $^{12}$C/$^{12}$C-filtered NOESY [74,75] and $^{15}$N-edited ROESY [85]. The $^{15}$N-edited NOESY, $^{13}$C-edited NOESY, 2D $^{12}$C/$^{12}$C-filtered NOESY, 3D $^{13}$C-edited/$^{12}$C-filtered NOESY and $^{15}$N-edited ROESY experiments were collected with 100 msec, 120 msec, 100 msec, 110 msec and 40 msec mixing times, respectively.

The ACP-inhibitor structure is based on the observed intermolecular and intramolecular NOEs from the inhibitor observed in the 3D $^{15}$N-edited NOESY [37,38], 2D $^{12}$C/$^{12}$C-filtered NOESY [74,75], 3D $^{13}$C-edited/$^{12}$C-filtered NOESY [84].

Structure Calculations. The structure calculations and distance restraints are used as described in Example 2 with the following modifications. The restraints used for the refinement of the ACP-inhibitor NMR structure are amended with the distance restraints observed between ACP and the inhibitor from the 3D $^{13}$C-edited/$^{12}$C-filtered NOESY and 3D $^{15}$N-edited NOESY experiments and the intra-molecular restraints observed for the inhibitor from the 2D $^{12}$C-filtered NOESY experiment. Additionally, the ACP NMR restraints are modified as appropriate for residues in the vicinity of the active site. This permits the structure of the ACP active site to be determined primarily by the observed inter-molecular NOEs between ACP and the inhibitor. Also, the ACP-inhibitor complex may be refined using the $^3J_{NH\alpha}$ coupling constants determined from the HNHA [72] experiment and secondary $^{13}C\alpha/^3C\beta$ chemical shift restraints from the assignments for the complex.

Generation of the bound conformation of the inhibitor followed the general procedure described for ACP in Example 2 with the following modifications. The bound conformation for the inhibitor is generated using QUANTA97 and CHARMM (Molecular Simulations Inc., San Diego) and the XPLOR topology and parameter files is generated using XPLOR2D [86]. Generation of the bound conformation of the inhibitor follows the following general procedure. The initial inhibitor structure is created using the QUANTA97 2D-sketcher application and is subjected to 500 steps of CHARMM minimization. NOE restraints were created using the CHARMM distance/dihedral constraint option. The NOE scaling constant is set to 500 and the structure is subject to an additional 500 steps of CHARMM minimization.

The starting ACP-inhibitor complex structure for the simulated-annealing protocol is then obtained by manually docking the bound conformation of the inhibitor into the NMR structure determined for ACP using QUANTA97. The inhibitor was then subjected to a 1000 steps of restrained CHARMM minimization using the inhibitor intramolecular and intermolecular NOE restraints while keeping coordinates for ACP fixed. This approach approximates the positioning of the inhibitor in the active site of ACP without distorting the ACP structure. The final structure is exported as a PDB file and used as the starting point for the standard XPLOR simulated annealing protocol where all residues in the structure are free to move.

EXAMPLE 5

Inhibitor Design

General. There are a number of computational software packages that may be used for the analysis of protein NMR structures. In this case, the software packages Sybyl v.6.4+ to v.6.5+ from Tripos Associates and QUANTA97 (Version 97.1003) an XPLOR (Version 3.840) from MSI were the packages used. Once the coordinates have been determined by NMR a number of steps may be taken as listed below:

1. The original coordinates are read into the software package and the three-dimensional structure is analyzed graphically. In addition, programs within QUANTA check for the correctness of the NMR coordinates with regard to features such as bond and atom types.

2. The modified (if necessary) structure is energy minimized using the QUANTA/CHARM until all the structural parameters are at their equilibrium/optimal values.

3. The energy minimized structure is superimposed against the original NMR structure to ensure there are no significant deviations between the original and minimized coordinates.

4. The protein-native ligand complex is analyzed, the interactions between the native ligand and the protein are identified. The uncomplexed structure binding site is compared to the complexed structure's binding site for areas which may be exploited by a potential inhibitor.

5. The final protein bound to the inhibitor is modified by removing the inhibitor so only the protein and a few residues of the natural ligand are left for analysis of the binding site cavity. The natural ligand residues are docked into the uncomplexed structure's binding site to be used as templates for SYBYL/UNITY database searching.

6. SYBYL/UNITY is used to create excluded volume and distance constrained queries for searching structural databases. Structures qualifying as 'hits' are screened for activity.

7. Once specific inhibitor-protein interactions are determined between new inhibitors and the protein structure, docking studies may be carried out between the different series of in-house inhibitors and ACP. This part gives the initial modeled complexes of new inhibitors with ACP.

To check for the integrity of the modeled new ACP-inhibitor complexes, different procedures may be used. In this case, constrained conformational analysis is carried out using molecular dynamics methods. In this modeling process, both protein and the complexed ligand are allowed to sample different 3D conformational states until the most favorable state is reached or found to exist between protein and inhibitor. The final structure as proposed by the molecular dynamics analysis is analyzed visually to make sure the modeled complex is in accord with known experimental SAR based on measured binding affinities.

REFERENCES (1) Magnuson, K., et al., Microbiological Reviews, 57:522–542 (1993).
(2) Lynen, F., Eur. J. Biochem., 112:431–442 (1980).
(3) Wakil, S. J., et al., Annu. Rev. Biochem., 52:537–579 (1983).
(4) B. Shen, B., et al., J. Bacteriol., 174:3818 (1992).
(5) Hopwood, D. A., and Sherman, D. H., Annu. Rev. Genet., 24:37–66 (1990).
(6) Kleinkauf, H., and Von Dohren, H., Eur. J. Biochem., 236:335–351 (1996).
(7) Marahiel, M. A., FEBS Lett., 307:40 (1992).
(8) White, R. H., Biochemistry, 19:9–15 (1980).
(9) Sanyal, I., et al., Am. Chem. Soc., 116:2637–2638 (1994).
(10) Rawlings, M. and J. E. J. Cronan, FASEB J., 2:A1559 (1988).
(11) Hill, R. B., et al., Protein Expression and Purification, 6:394–400 (1995).
(12) Rock, C. O. and J. E. J. Cronan, Anal. Biochem., 102:362–364 (1980).
(13) Holak, T. A., et al., Eur. J. Biochem., 175:9–15 (1988).
(14) Furukawa, H., et al., J. Bacteriol., 175:3723–3729 (1993).
(15) Bergler, H., et al., J. Biol. Chem., 269, 5493–5496 (1994).
(16) Banerjee, A., et al., Science, 263:227–230 (1994).
(17) Dessen, A., et al., Science, 267:1638–1641 (1995).
(18) Qumard, A., et al., Biochemistry, 34:8235–8241 (1995).
(19) Lambalot, R. H., et al., Chemistry & Biology, 3:923–936 (1996).
(20) Elovson, J. and Vagelos, P. R., J. Biol. Chem., 243:3603 (1968).
(21) Lambalot, R. H. and Walsh, C. T., J. Biol. Chem., 270:24658–24661 (1995).
(22) Reuter, K., et al., The EMBO Journal, 18:6823–6831 (1999).
(23) Otwinowski, Z. and W. Minor, Methods Enzymol., 276:307–326 (1997).
(24) Navaza, J., Acta Crystallogr., A50: 157–163 (1994).
(25) Brunger, A. T., et al., Acta Crystallographica, D54: 905–921 (1998).

(26) Lambalot, R. H., and Walsh, C. T., J. Biol. Chem., 270: 24658–61 (1995).
(27) Fischl, A. S., and Kennedy, E. P., J. Bacteriol., 172: 5445–9 (1990).
(28) Kay, L. E., Prog. Biophys. Molec. Biol., 63: 110–126 (1995).
(29) Delaglio, F., et al., J. Biomol. NMR, 6: 277–293 (1995).
(30) Zhu, G., and Bax, A., J. Magn. Reson., 100: 202–7 (1992).
(31) Garrett, D. S., et al., J. Magn. Reson., 95: 214–20 (1991).
(32) Muhandiram, D. R., and Kay, L. E., J. Magn. Reson., Ser. B, 103: 203–16 (1994).
(33) Grzesiek, S., et al., J. Biomol. Nmr, 3: 487–93 (1993).
(34) Bax, A., Max, D., and Zax, D., J. Am. Chem. Soc., 114: 6923–5 (1992).
(35) Bax, A., et al., J. Biomol. Nmr, 4: 787–97 (1994).
(36) Pascal, S. M., et al., J. Magn. Reson., Ser. B, 103: 197–201 (1994).
(37) Marion, D., et al., Biochemistry, 28: 6150–6 (1989).
(38) Zuiderweg, E. R. P., and Fesik, S. W., Biochemistry, 28: 2387–91 (1989).
(39) Cornilescu, G. et al., J. Biomol. NMR, 13: 289–302 (1999).
(40) Wuthrich, K., et al., J. Mol. Biol., 169: 949–961 (1983).
(41) Clore, G. M., et al., Biochemistry, 26: 8012–23 (1987).
(42) Wagner, G., et al., J. Mol. Biol, 196: 611–39 (1987).
(43) Nilges, M., et al., Protein Eng, 2: 27–38 (1988).
(44) Clore, G. M., et al., Biochemistry, 29: 1689–96 (1990).
(45) Brunger, A. T. X-PLOR Version 3.1 Manual, Yale University, New Haven, Conn. (1993).
(46) Kuszewski, J., et al., J. Magn. Reson., Ser. B, 106: 92–6 (1995).
(47) Kuszewski, J., et al., Protein Sci., 5: 1067–1080 (1996).
(48) Kuszewski, J., et al., J. Magn. Reson., 125: 171–177 (1997).
(49) Laskowski, R. A., et al., J. Appl. Cryst. 26, 283–291 (1993).
(50) Laskowski, R., et al., Biomol NMR, 8: 477–486 (1996).
(51) Wakil, S. J., et al., Annu. Rev. Biochem, 52: 537–79 (1983).
(52) Majerus, P. W., and Vagelos, P. R., Advan. Lipid Res, 5: 1–33 (1967).
(53) Prescott, D. J., and Vagelos, P. R., Advan. Enzymol. Relat. Areas Mol. Biol, 36: 269–311 (1972).
(54) Shen, B., et al., J. Bacteriol., 174: 3818–21 (1992).
(55) Baldwin, J. E., et al., J. Antibiot., 44: 241–8 (1991).
(56) Rusnak, F., et al., Biochemistry, 30: 2916–27 (1991).
(57) Geiger, O., et al., J. Bacteriol., 173: 2872–8 (1991).
(58) Issartel, J. P., et al., Nature, 351: 759–61 (1991).
(59) Takiff, H. E., et al., J. Bacteriol. 174: 1544–53 (1992).
(60) Lambalot, R. H., and Walsh, C. T., J. Biol. Chem., 270: 24658–61 (1995).
(61) Crump, M. P., et al., Biochemistry, 36: 6000–6008 (1997).
(62) Holak, T. A., et al., Biochemistry, 27: 6135–42 (1988).
(63) Holak, T. A., et al., FEBS Lett., 242: 218–24 (1989).
(64) Clore, G. M., and Gronenborn, A. M., Protein Science, 3:, 372–390 (1994).
(65) Arrowsmith, C. H., and Wu, Y. -S., Prog. Nucl. Magn. Reson. Spectrosc., 32: 277–286 (1998).
(66) Clore, G. M., and Gronenborn, A. M., Trends Biotechnol., 16: 22–34 (1998).
(67) Clore, G. M., et al., J. Mol. Biol., 231: 82–102 (1993).
(68) Ghose, R., et al., FEBS Lett., 388: 66–72 (1996).
(69) Oswood, M. C., et al., Proteins: Struct., Funct., Genet., 27: 131–143 (1997).
(70) Grzesiek, S., and Bax, A., J. Am. Chem. Soc, 114: 6291–3 (1992).
(71) Grzesiek, S., et al., J. Magn. Reson., Ser. B, 101: 114–19 (1993).
(72) Vuister, G. W., and Bax, A., J. Am. Chem. Soc, 115: 7772–7 (1993).
(73) Kay, L. E., et al., J. Magn. Reson, 89: 496–514 (1990).
(74) Petros, A. M., et al., FEBS Lett., 308: 309–14 (1992).
(75) Gemmecker, G, et al., J. Magn. Reson., 96: 199–204 (1992).
(76) Ikura, M., and Bax, A., J. Am. Chem. Soc., 114: 2433–40 (1992).
(77) Archer, S. J., et al., J. Magn. Reson., 95: 636–41 (1991).
(78) Bax, A., and Pochapsky, S. S., Journal of Magnetic Resonance, 99: 638–643 (1992).
(79) Powers, R., et al., J. Magn. Reson., 94: 209–13 (1991).
(80) Vuister, G. W., et al., J. Am. Chem. Soc, 114: 9674–5 (1992).
(81) Grzesiek, S., et al. J. Am. Chem. Soc, 117: 5312–15 (1995).
(82) Zuiderweg, E. R. P., et al., J. Magn. Reson, 86: 210–16 (1990).
(83) Ikura, M., et al., J. Magn. Reson, 86: 204–9 (1990).
(84) Lee, W., et al., FEBS Lett., 350: 87–90 (1994).
(85) Clore, G. M., et al., Biochemistry, 29: 5671–6 (1990).
(86) Kleywegt, G. J., and Jones, T. A., Methods Enzymol., 277: 208–230 (1997).

All publications mentioned herein above, whether to issued patents, pending applications, published articles, or otherwise, are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A crystallized complex comprising the acyl carrier protein synthase (ACPS) of SEQ ID NO:2 and the acyl carrier protein (ACP) of SEQ ID NO:1, wherein the crystallized complex belongs to space group C222$_1$.

2. The crystallized complex of claim 1, wherein ACPS comprises amino acid residues Arg14, Met18, Arg21, Gln22, Arg24, Phe25, Arg28, Arg45, Phe54, Glu58, Ile68, Gly69, Arg70, Ser73 and Phe74 of SEQ ID NO:2.

3. The crystallized complex of claim 2, wherein ACPS further comprises amino acid residues Asp8, Ile9, Thr10, Glu11, Leu12, Ile15, Ala16, Ser17, Ala19, Gly20, Lys23, Ala26, Glu27, Ile29, Leu41, Ser42, Lys44, Glu48, Ala51, Lys57, Ser61, Lys62, Thr66, Gly67, Gln71, Leu72, Gln75, Asp76, Ile-77, Gln83, Asn84, Lys93, His105, Thr106 and Ala107 of SEQ ID NO:2.

4. The crystallized complex of claim 1, wherein ACP comprises amino acid residues Arg14, Lys29, Asp35, Ser36, Leu37, Asp38, Val40, Glu41, Val43, Met44, Glu47, Asp48, Ile54, Ser55, Asp56, Glu57 and Glu60 of SEQ ID NO:1.

5. The crystallized complex of claim 1, wherein ACP further comprises amino acid residues Asp13, Leu15, Phe28, Glu30, Asp31, Leu32, Gly33, Ala34, Val39, Leu42, Glu45, Leu46, Glu49, Met52, Glu53, Asp58, Ala59, and Lys61 of SEQ ID NO:1.

6. The crystallized complex of claim 1, wherein the crystallized complex has unit cell parameters of a=78.46 Å, b=122.03 Å and c=136.77 Å.

7. The crystallized complex of claim 6, wherein the crystallized complex comprises three molecules of ACPS of SEQ ID NO:2 and three molecules of ACP of SEQ ID NO:1 in an asymmetric unit.

8. The crystallized complex of claim 1, wherein the crystallized complex has the structural coordinates set forth in FIGS. 3 and 3A-1 to 3A-79, ± a root mean square deviation from the backbone atoms of the amino acids listed in FIGS. 3 and 3A-1 to 3A-79 of not more than 1.5 Å.

9. The crystallized complex of claim 1, wherein ACPS comprises an active site defined by the structural coordinates according to FIGS. 3 and 3A-1 to 3A-79 of amino acid residues Arg14, Met18, Arg21, Gln22, Arg24, Phe25, Arg28, Phe54, Glu58, Ile68, Gly69, Arg70, SerR73 and Phe74 of SEQ ID NO:2 from a first monomer of ACPS, and residue ARG45 of SEQ ID NO:2 from a second monomer of ACPS, and in each case the structural coordinates are ± a root mean square deviation from the backbone atoms of said amino acids of not more than 1.5 Å.

10. The crystallized complex of claim 9, wherein the active site of ACPS further comprises the structural coordinates according to FIGS. 3 and 3A-1 to 3A-79 of amino acid residues Asp8, Ile9, Thr10, Glu11, Leu12, Ile15, Ala16, Ser17, Ala19, Gly20, -Lys23, Ala26, Glu27, Ile29, Ala51, Lys57, Ser61, Lys62, Thr66, Gly67, Gln71, Leu72, Gln75, Asp76, Ile77 and Lys93 of SEQ ID NO:2 from said first monomer of ACPS and residues Leu41, Ser42, Lys44, Glu48, Gln83, Asn84, His105, Thr106 and Ala107 of SEQ ID NO:2 from said second monomer of ACPS, and in each case the structural coordinates are ± a root mean square deviation from the backbone atoms of said amino acids of not more than 1.5 Å.

11. The crystallized complex of claim 1, wherein ACP comprises an active site comprising the structural coordinates according to FIGS. 3 and 3A-1 to 3A-79 of amino acid residues Arg14, Lys29, Asp35, Ser36, Leu37, Asp38, Val40, Glu41, Val43, Met44, Glu47, Asp48, Ile54, Ser55, Asp56, Glu57 and Glu60 of SEQ ID NO:1 ± a root mean square deviation from the backbone atoms of said amino acids of not more than 1.5 Å.

12. The crystallized complex of claim 11, wherein the active site of ACP further comprises the structural coordinates according to FIGS. 3 and 3A-1 to 3A-79 of amino acid residues Asp13, Leu15, Phe28, Glu30, Asp31, Leu32, Gly33, Ala34, Val39, Leu42, Glu45, Leu46, Glu49, Met52, Glu53, Asp58, Ala59, and Lys61 of SEQ ID NO:1, ± a root mean square deviation from the backbone atoms of said amino acids of not more than 1.5 Å.

13. The crystallized complex of claim 8, wherein the ± a root mean square deviation from the backbone atoms of said amino acids is not more than 1.0 Å.

14. The crystallized complex of claim 13, wherein the ± a root mean square deviation from the backbone atoms of said amino acids is not more than 0.5 Å.

15. The crystallized complex of claim 9, wherein the ± a root mean square deviation from the backbone atoms of said amino acids is not more than 1.0 Å.

16. The crystallized complex of claim 15, wherein the ± a root mean square deviation from the backbone atoms of said amino acids is not more than 0.5 Å.

17. The crystallized complex of claim 10, wherein the ± a root mean square deviation from the backbone atoms of said amino acids is not more than 1.0 Å.

18. The crystallized complex of claim 17, wherein the ± a root mean square deviation from the backbone atoms of said amino acids is not more than 0.5 Å.

19. The crystallized complex of claim 11, wherein the ± a root mean square deviation from the backbone atoms of said amino acids is not more than 1.0 Å.

20. The crystallized complex of claim 19, wherein the ± a root mean square deviation from the backbone atoms of said amino acids is not more than 0.5 Å.

21. The crystallized complex of claim 12, wherein the ± a root mean square deviation from the backbone atoms of said amino acids is not more than 1.0 Å.

22. The crystallized complex of claim 21, wherein the ± a root mean square deviation from the backbone atoms of said amino acids is not more than 0.5 Å.

* * * * *

UNITED STATES PATENT AND TRADEMARK OFFICE
CERTIFICATE OF CORRECTION

PATENT NO.          : 7,135,319 B2
APPLICATION NO. : 10/717138
DATED                  : November 14, 2006
INVENTOR(S)        : Kevin D. Parris et al.

It is certified that error appears in the above-identified patent and that said Letters Patent is hereby corrected as shown below:

On the Title page, item 73 Assignee, please add second Assignee:
--Millennium Pharmaceuticals, Inc., Cambridge, MA (US)--

Signed and Sealed this

Twentieth Day of November, 2007

JON W. DUDAS
*Director of the United States Patent and Trademark Office*

SEQUENCE LISTING

<160> NUMBER OF SEQ ID NOS: 16

<210> SEQ ID NO 1
<211> LENGTH: 81
<212> TYPE: PRT
<213> ORGANISM: Bacillus subtilis

<400> SEQUENCE: 1

```
Gly Pro Leu Gly Ser Ala Asp Thr Leu Glu Arg Val Thr Lys Ile Ile
1               5                   10                  15

Val Asp Arg Leu Gly Val Asp Glu Ala Asp Val Lys Leu Glu Ala Ser
            20                  25                  30

Phe Lys Glu Asp Leu Gly Ala Asp Ser Leu Asp Val Val Glu Leu Val
            35                  40                  45

Met Glu Leu Glu Asp Glu Phe Asp Met Glu Ile Ser Asp Glu Asp Ala
    50                  55                  60

Glu Lys Ile Ala Thr Val Gly Asp Ala Val Asn Tyr Ile Gln Asn Gln
65                  70                  75                  80

Gln
```

<210> SEQ ID NO 2
<211> LENGTH: 120
<212> TYPE: PRT
<213> ORGANISM: Bacillus subtilis

<400> SEQUENCE: 2

```
Ala Tyr Gly Ile Gly Leu Asp Ile Thr Glu Leu Lys Arg Ile Ala Ser
1               5                   10                  15

Met Ala Gly Arg Gln Lys Arg Phe Ala Glu Arg Ile Leu Thr Arg Ser
            20                  25                  30

Glu Leu Asp Gln Tyr Tyr Glu Leu Ser Glu Lys Arg Lys Asn Glu Phe
            35                  40                  45

Leu Ala Gly Arg Phe Ala Ala Lys Glu Ala Phe Ser Lys Ala Phe Gly
    50                  55                  60

Thr Gly Ile Gly Arg Gln Leu Ser Phe Gln Asp Ile Glu Ile Arg Lys
65                  70                  75                  80

Asp Gln Asn Gly Lys Pro Tyr Ile Ile Cys Thr Lys Leu Ser Gln Ala
            85                  90                  95

Ala Val His Val Ser Ile Thr His Thr Lys Glu Tyr Ala Ala Ala Gln
            100                 105                 110

Val Val Ile Glu Arg Leu Ser Ser
        115                 120
```

<210> SEQ ID NO 3
<211> LENGTH: 122
<212> TYPE: PRT
<213> ORGANISM: Aquifex sp.

<400> SEQUENCE: 3

```
Met Ile Gly Val Asp Ile Val Lys Asn Glu Arg Ile Lys Asp Ala Leu
1               5                   10                  15

Glu Arg Phe Gly Asp Lys Phe Leu Asp Arg Ile Tyr Thr Lys Arg Glu
            20                  25                  30

Leu Glu Tyr Cys Tyr Ala His Cys Asp Phe Leu Pro Cys Leu Ala Ala
            35                  40                  45

Arg Trp Ala Gly Lys Glu Ala Val Leu Lys Ala Phe Tyr Thr Glu Phe
    50                  55                  60

Lys Ile Phe Leu Arg Phe Lys Glu Ile Glu Ile Leu Gly Asn Arg Gly
65                  70                  75                  80

Arg Pro Pro Thr Val Val Ile Asn Arg Glu Gly Val Glu Glu Ile Leu
            85                  90                  95

Lys Asn Tyr Glu Val Ile Val Ser Leu Ser His Glu Arg Asp Tyr Ser
            100                 105                 110

Val Ala Val Ala Tyr Ile Lys Lys Lys Ser
```

<210> SEQ ID NO 4
<211> LENGTH: 122
<212> TYPE: PRT
<213> ORGANISM: Chlamydophila sp.

<400> SEQUENCE: 4

Met Glu Ile Ile His Ile Gly Thr Asp Ile Ile Glu Ile Ser Arg Ile
1               5                   10                  15

Arg Glu Ala Ile Ala Thr His Gly Asn Arg Leu Leu Asn Arg Ile Phe
            20                  25                  30

Thr Glu Ala Glu Gln Lys Tyr Cys Leu Glu Lys Thr Asp Pro Ile Pro
        35                  40                  45

Ser Phe Ala Gly Arg Phe Ala Gly Lys Glu Ala Val Ala Lys Ala Leu
    50                  55                  60

Gly Thr Gly Ile Gly Ser Val Val Ala Trp Lys Asp Ile Glu Val Phe
65                  70                  75                  80

Lys Val Ser His Gly Pro Glu Val Leu Leu Pro Ser His Val Tyr Ala
                85                  90                  95

Lys Ile Gly Ile Ser Lys Val Ile Leu Ser Ile Ser His Cys Lys Glu
            100                 105                 110

Tyr Ala Thr Ala Thr Ala Ile Ala Leu Ala
        115                 120

<210> SEQ ID NO 5
<211> LENGTH: 119
<212> TYPE: PRT
<213> ORGANISM: Helicobacter sp.

<400> SEQUENCE: 5

Met Ile Gly Ile Asp Ile Val Ser Ile Ala Arg Ile Glu Lys Cys Val
1               5                   10                  15

Lys Arg Phe Lys Met Lys Phe Leu Glu Arg Phe Leu Ser Pro Ser Glu
            20                  25                  30

Ile Val Leu Cys Lys Asp Lys Ser Ser Ile Ala Gly Phe Phe Ala
        35                  40                  45

Leu Lys Glu Ala Cys Ser Lys Ala Leu Gln Val Gly Ile Gly Lys Glu
    50                  55                  60

Leu Ser Phe Leu Asp Ile Lys Ile Ser Lys Ser Pro Lys Asn Ala Pro
65                  70                  75                  80

Leu Ile Thr Leu Ser Lys Glu Lys Met Asp Tyr Phe Asn Ile Gln Ser
                85                  90                  95

Leu Ser Ala Ser Ile Ser His Asp Ala Gly Phe Ala Ile Ala Val Val
            100                 105                 110

Val Val Ser Ser Ser Asn Glu
        115

<210> SEQ ID NO 6
<211> LENGTH: 119
<212> TYPE: PRT
<213> ORGANISM: Staphylococcus sp.

<400> SEQUENCE: 6

Met Ile His Gly Ile Gly Val Asp Leu Ile Glu Ile Asp Arg Ile Gln
1               5                   10                  15

Ala Leu Tyr Ser Lys Gln Pro Lys Leu Val Glu Arg Ile Leu Thr Lys
            20                  25                  30

```
Asn Glu Gln His Lys Phe Asn Asn Phe Thr His Glu Gln Arg Lys Ile
            35                  40                  45
Glu Phe Leu Ala Gly Arg Phe Ala Thr Lys Glu Ala Phe Ser Lys Ala
 50                  55                  60
Leu Gly Thr Gly Leu Gly Lys His Val Ala Phe Asn Asp Ile Asp Cys
 65                  70                  75                  80
Tyr Asn Asp Glu Leu Gly Lys Pro Lys Ile Asp Tyr Glu Gly Phe Ile
                85                  90                  95
Val His Val Ser Ile Ser His Thr Glu His Tyr Ala Met Ser Gln Val
                    100                 105                 110
Val Leu Glu Lys Ser Ala Phe
            115

<210> SEQ ID NO 7
<211> LENGTH: 169
<212> TYPE: PRT
<213> ORGANISM: Thermotoga sp.

<400> SEQUENCE: 7

Met Ile Val Gly Val Gly Ile Asp Val Leu Glu Val Glu Arg Val Pro
 1               5                  10                  15
Glu Lys Phe Ala Glu Arg Ile Leu Gly Glu Ser Glu Lys Arg Leu Phe
                20                  25                  30
Leu Thr Arg Lys Arg Arg Glu Phe Ile Ala Gly Arg Phe Ala Leu
            35                  40                  45
Lys Glu Ala Phe Phe Lys Ala Leu Gly Thr Gly Leu Asn Gly His Ser
 50                  55                  60
Phe Thr Asp Val Glu Phe Leu Glu Ser Asn Gly Lys Pro Val Leu Cys
 65                  70                  75                  80
Val His Lys Asp Phe Gly Phe Asn Tyr Ala His Val Ser Leu Ser
                85                  90                  95
His Asp Arg Phe Ala Val Ala Leu Val Val Leu Glu Lys Arg Lys Gly
                100                 105                 110
Asp Ile Ile Val Glu Gly Asp Glu Ser Phe Leu Arg Lys Arg Phe Glu
            115                 120                 125
Val Leu Glu Arg Ser Val Glu Gly Trp Glu Ile Glu Thr Ser Leu Pro
130                 135                 140
Pro Phe Thr Leu Lys Lys Leu Leu Glu Ser Ser Gly Cys Arg Leu Val
145                 150                 155                 160
Arg Tyr Gly Asn Ile Leu Ile Gly Glu
                165

<210> SEQ ID NO 8
<211> LENGTH: 126
<212> TYPE: PRT
<213> ORGANISM: Escherichia coli

<400> SEQUENCE: 8

Met Ala Ile Leu Gly Leu Gly Thr Asp Ile Val Glu Ile Ala Arg Ile
 1               5                  10                  15
Glu Ala Val Ile Ala Arg Ser Gly Asp Arg Leu Ala Arg Arg Val Leu
                20                  25                  30
Ser Asp Asn Glu Trp Ala Ile Trp Lys Thr His His Gln Pro Val Arg
            35                  40                  45
Phe Leu Ala Lys Arg Phe Ala Val Lys Glu Ala Ala Ala Lys Ala Phe
 50                  55                  60
```

```
Gly Thr Gly Ile Arg Asn Gly Leu Ala Phe Asn Gln Phe Glu Val Phe
 65                  70                  75                  80

Asn Asp Glu Leu Gly Lys Pro Arg Leu Arg Leu Trp Gly Glu Ala Leu
                 85                  90                  95

Lys Leu Ala Glu Lys Leu Gly Val Ala Asn Met His Val Thr Leu Ala
            100                 105                 110

Asp Glu Arg His Tyr Ala Cys Ala Thr Val Ile Ile Glu Ser
        115                 120                 125
```

<210> SEQ ID NO 9
<211> LENGTH: 126
<212> TYPE: PRT
<213> ORGANISM: Rickettsia sp.

<400> SEQUENCE: 9

```
Met Leu Ile Gly Val Gly Thr Asp Ile Val Gln Ile Pro Arg Ile Glu
  1               5                  10                  15

Lys Ile Leu Asn Ile Tyr Gln Glu Leu Phe Ala Lys Lys Ile Leu Ala
             20                  25                  30

Leu Lys Glu Leu Lys Gln Phe Thr Leu Leu Asn Lys Thr Asn His Ala
         35                  40                  45

Thr Phe Leu Ala Lys Arg Phe Ser Ala Lys Glu Ala Val Ser Lys Ala
 50                  55                  60

Phe Gly Val Gly Ile Gly Arg Gly Ile Asn Phe Lys Asp Ile Thr Ile
 65                  70                  75                  80

Leu Asn Asp Asn Leu Gly Lys Pro Thr Val Glu Ile Ser Ser His Tyr
                 85                  90                  95

Thr Asn Lys Leu Ala Pro Phe Asn Ile His Leu Ser Leu Ser Asp Asp
            100                 105                 110

Tyr Pro Ile Cys Ile Ala Phe Ala Ile Glu Ser Asn Cys
        115                 120                 125
```

<210> SEQ ID NO 10
<211> LENGTH: 123
<212> TYPE: PRT
<213> ORGANISM: Streptomyces sp.

<400> SEQUENCE: 10

```
Met Ser Ile Ile Gly Val Gly Ile Asp Val Ala Glu Val Glu Arg Phe
  1               5                  10                  15

Gly Ala Ala Leu Glu Arg Thr Pro Ala Leu Ala Gly Arg Leu Phe Leu
             20                  25                  30

Glu Ser Glu Leu Leu Pro Gly Gly Glu Arg Arg Gly Val Ala Ser
         35                  40                  45

Leu Ala Ala Arg Phe Ala Ala Lys Glu Ala Leu Ala Lys Ala Leu Gly
 50                  55                  60

Ala Pro Ala Gly Leu Leu Trp Thr Asp Ala Glu Val Trp Val Glu Ala
 65                  70                  75                  80

Gly Gly Arg Pro Arg Leu Arg Val Thr Gly Thr Val Ala Ala Arg Ala
                 85                  90                  95

Ala Glu Leu Gly Val Ala Ser Trp His Val Ser Leu Ser His Asp Ala
            100                 105                 110

Gly Ile Ala Ser Ala Val Val Ile Ala Glu Gly
        115                 120
```

<210> SEQ ID NO 11

```
<211> LENGTH: 125
<212> TYPE: PRT
<213> ORGANISM: Treponema sp.

<400> SEQUENCE: 11

Met Ile Ile Gly Val Gly Ile Asp Ile Val Glu Ile Glu Arg Phe Val
1               5                   10                  15

Ser Trp Thr His Asn Val Arg Leu Leu Arg Arg Phe Phe His Gln Glu
            20                  25                  30

Glu Ile Val Asp Phe Phe Lys Asn His Met Arg Ala Gln Phe Leu Ala
        35                  40                  45

Thr Arg Phe Ala Ala Lys Glu Ala Phe Gly Lys Ala Leu Gly Thr Gly
    50                  55                  60

Leu Arg Asn Met Glu Leu Arg Asn Ile Arg Val Cys Gln Asn Gly Trp
65                  70                  75                  80

Gly Lys Pro Arg Leu Glu Val Tyr Gly Ala Ala Gln Ala Met Leu Ala
                85                  90                  95

Ala Thr Gly Gly Thr His Ile Gln Val Ser Leu Thr His Glu Arg Glu
            100                 105                 110

Val Ala Ser Ala Ile Val Ile Glu Gly Pro Leu
        115                 120         125

<210> SEQ ID NO 12
<211> LENGTH: 121
<212> TYPE: PRT
<213> ORGANISM: Bacillus sp.

<400> SEQUENCE: 12

Met Ile Tyr Gly Ile Gly Leu Asp Ile Thr Glu Leu Lys Arg Ile Ala
1               5                   10                  15

Ser Met Ala Gly Arg Gln Lys Arg Phe Ala Glu Arg Ile Leu Thr Arg
            20                  25                  30

Ser Glu Leu Asp Gln Tyr Tyr Glu Leu Ser Glu Lys Arg Lys Asn Glu
        35                  40                  45

Phe Leu Ala Gly Arg Phe Ala Ala Lys Glu Ala Phe Ser Lys Ala Phe
    50                  55                  60

Gly Thr Gly Ile Gly Arg Gln Leu Ser Phe Gln Asp Ile Glu Ile Arg
65                  70                  75                  80

Lys Asp Gln Asn Gly Lys Pro Tyr Ile Ile Cys Thr Lys Leu Ser Gln
                85                  90                  95

Ala Ala Val His Val Ser Ile Thr His Thr Lys Glu Tyr Ala Ala Ala
            100                 105                 110

Gln Val Val Ile Glu Arg Leu Ser Ser
        115                 120

<210> SEQ ID NO 13
<211> LENGTH: 139
<212> TYPE: PRT
<213> ORGANISM: Bradyrhizobium sp.

<400> SEQUENCE: 13

Met Ile Ile Gly Ile Gly Ser Asp Leu Ile Asp Ile Thr Arg Val Gly
1               5                   10                  15

Lys Val Ile Glu Arg His Gly Glu Arg Phe Leu Asp Arg Ile Phe Thr
            20                  25                  30

Ala Ala Glu Arg Ala Lys Ala Glu Arg Arg Ala Lys Asn Glu Lys Met
        35                  40                  45
```

```
Val Val Ala Thr Tyr Ala Lys Arg Phe Ala Ala Lys Glu Ala Cys Ser
    50                  55                  60

Lys Ala Leu Gly Thr Gly Ile Arg Arg Gly Val Trp Trp Arg Asp Met
 65                  70                  75                  80

Gly Val Val Asn Leu Pro Gly Gly Arg Pro Thr Met Gln Leu Thr Gly
                 85                  90                  95

Gly Ala Leu Ala Arg Leu Gln Ala Leu Thr Pro Asp Gly Phe Glu Ala
                100                 105                 110

Arg Ile Asp Val Ser Ile Thr Asp Asp Trp Pro Leu Ala Gln Ala Phe
            115                 120                 125

Val Ile Ile Ser Ala Val Pro Leu Ala Lys Ser
            130                 135
```

```
<210> SEQ ID NO 14
<211> LENGTH: 130
<212> TYPE: PRT
<213> ORGANISM: Mycobacterium sp.

<400> SEQUENCE: 14

Met Gly Ile Val Gly Val Gly Ile Asp Leu Val Ser Ile Pro Asp Phe
 1               5                  10                  15

Ala Glu Gln Val Ser Gln Pro Gly Thr Val Phe Met Thr Ile Phe Thr
                20                  25                  30

Pro Gly Glu Arg Arg Asp Ala Ser Val Lys Ser Ser Ala Val Cys
                35                  40                  45

His Leu Ala Ala Arg Trp Ala Val Lys Glu Ala Ile Lys Ala Trp
     50                  55                  60

Ser Gly Ser Arg Phe Ala Gln Arg Pro Met Leu Pro Glu Asn Ile His
 65                  70                  75                  80

Arg Asp Ile Glu Val Val Asn Asp Met Trp Gly Arg Pro Arg Val Arg
                85                  90                  95

Leu Thr Gly Ala Ile Ala Lys His Leu Thr Asp Val Thr Ile His Val
                100                 105                 110

Ser Leu Thr His Glu Gly Asp Ile Ala Ala Val Val Ile Leu Glu
            115                 120                 125

Val Leu
    130
```

```
<210> SEQ ID NO 15
<211> LENGTH: 77
<212> TYPE: PRT
<213> ORGANISM: Escherichia coli

<400> SEQUENCE: 15

Ser Thr Ile Glu Glu Arg Val Lys Lys Ile Ile Gly Glu Gln Leu Gly
 1               5                  10                  15

Val Lys Gln Glu Glu Val Thr Asn Asn Ala Ser Phe Val Glu Asp Leu
                20                  25                  30

Gly Ala Asp Ser Leu Asp Thr Val Glu Leu Val Met Ala Leu Glu Glu
                35                  40                  45

Glu Phe Asp Thr Glu Ile Pro Asp Glu Glu Ala Glu Lys Ile Thr Thr
     50                  55                  60

Val Gln Ala Ala Ile Asp Tyr Ile Asn Gly His Gln Ala
 65                  70                  75
```

```
<210> SEQ ID NO 16
<211> LENGTH: 86
```

-continued

<212> TYPE: PRT
<213> ORGANISM: Streptomyces coelicolor

<400> SEQUENCE: 16

Met Ala Thr Leu Leu Thr Thr Asp Asp Leu Arg Arg Ala Leu Val Glu
1               5                   10                  15

Cys Ala Gly Glu Thr Asp Gly Thr Asp Leu Ser Gly Asp Phe Leu Asp
                20                  25                  30

Leu Arg Phe Glu Asp Ile Gly Tyr Asp Ser Leu Ala Leu Met Glu Thr
            35                  40                  45

Ala Ala Arg Leu Glu Ser Arg Tyr Gly Val Ser Ile Pro Asp Asp Val
        50                  55                  60

Ala Gly Arg Val Asp Thr Pro Arg Glu Leu Leu Asp Leu Ile Asn Gly
65                  70                  75                  80

Ala Leu Ala Glu Ala Ala
                85